United States Patent
Modlin et al.

(10) Patent No.: US 11,168,372 B2
(45) Date of Patent: Nov. 9, 2021

(54) COMPOSITIONS, METHODS AND KITS FOR DIAGNOSIS OF A GASTROENTEROPANCREATIC NEUROENDOCRINE NEOPLASM

(71) Applicant: Clifton Life Sciences LLC, Saint Kitts and Nevis (KN)

(72) Inventors: Irvin Mark Modlin, Woodbridge, CT (US); Mark Kidd, New Haven, CT (US); Ignat Drozdov, Warwick (GB)

(73) Assignee: Clifton Life Sciences LLC, Charlestown (KN)

( * ) Notice: Subject to any disclaimer, the term of this patent is extended or adjusted under 35 U.S.C. 154(b) by 0 days.

(21) Appl. No.: 16/528,864

(22) Filed: Aug. 1, 2019

(65) Prior Publication Data

US 2019/0345568 A1 Nov. 14, 2019

Related U.S. Application Data

(62) Division of application No. 14/855,229, filed on Sep. 15, 2015, now Pat. No. 10,407,730.

(60) Provisional application No. 62/050,465, filed on Sep. 15, 2014.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/112* (2013.01); *C12Q 2600/118* (2013.01); *C12Q 2600/158* (2013.01)

(58) Field of Classification Search
CPC ............ C12Q 1/6886; C12Q 2600/158; C12Q 2600/112; C12Q 2600/118; G01N 33/57407
See application file for complete search history.

(56) References Cited

U.S. PATENT DOCUMENTS 10,407,730 B2  9/2019  Modlin et al.

FOREIGN PATENT DOCUMENTS

| WO | WO 2009/150469 A2 | 12/2009 |
| WO | WO 2012/119013 A1 | 9/2012 |
| WO | WO 2005/020795 A2 | 3/2015 |

OTHER PUBLICATIONS

Modlin et al. Surgery. 2016. 159(1):336-347. (Year: 2016).*
Cwikla et al. J Clin Endocrinol Metab. 2015. 100(11):E1437-E1445. (Year: 2015).*
Banck, M. et al., "The genomic landscape of small intestine neuroendocrine tumors" *J Clin Invest* 2013; 123(6):2502-2508.
Boom, R. et al. (1990) "Rapid and Simple Method for Purification of Nucleic Acids" *J Clin Microbiol*, 28(3):495-503.
Cai, Y-C. et al., "Cytokeratin 7 and 20 and thyroid transcription factor 1 can help distinguish pulmonary from gastrointestinal carcinoid and pancreatic endocrine tumors," *Hum Pathol* 2001;32(10):1087-1093.
Chomczynski, P. (2006). "The single-step method of RNA isolation by acid guanidinium thiocyanate-phenol-chloroform extraction: twenty-something years on" *Nat Protoc*, 1(2):581-585.
Cohen, S.J. et al. "Isolation and characterization of circulating tumor cells in patients with metastatic colorectal cancer" *Clin Colorectal Cancer 2006*; 6(2):125-132.
Cristofanilli, M. et al., "Circulating tumor cells, disease progression, and survivalin in metastatic breast cancer", *N Engl J Med* 2004, 351(8):781-791.
Danila, D. et al. "Circulating tumor cell number and prognosis in progressive castration-resistant prostate cancer", *Clin Cancer Res* 2007; 13(23):7053-7058.
Dhawan, M. et al. (2010) "Application of committee kNN classifiers for gene expression profile classification" *Int J Bioinform Res Appl*, 6(4):344-352.
Drozdov, I. et al. (2010) "Genome-wide expression patterns in physiological cardiac hypertrophy" *BMC Genomics*, 11:557, 13 pages.
Evgeniou, T. et al. (1999) "Regularization Networks and Support Vector Machines" *Advances in Computational Math*, 13(1):1-53.
Freeman, T.C. et al. (Oct. 2007) "Construction, visualization, and clustering of transcription networks from microarray expression data" *PLoS Comput Biol*, 3(10):2032-2042.
Gabriel, K.R. (Dec. 1971) "The Biplot Graphic Display of Matrices with Application to Principal Component Analysis" *Biometrika*, 58(3):453-467.
Gallant, S.I. (Jun. 1990) "Perceptron-Based Learning Algorithms" *IEEE Transactions on Neural Networks*, 1(2):179-191.
Glotsos, D. et al. (2005) "Automated diagnosis of brain tumours astrocytomas using probabilistic neural network clustering and support vector machines" *Int J Neural Syst*, 15(1-2):1-11.
Godfrey, T.E. et al. (May 2000) "Quantitative mRNA Expression Analysis from Formalin-Fixed, Paraffin-Embedded Tissues Using 5' Nuclease Quantitative Reverse Transcription-Polymerase Chain Reaction" *Molec Diagnostics*, 2(2):84-91.
Hanahan, D and R.A. Weinberg (Mar. 4, 2011) "Hallmarks of cancer: The next generation" *Cell*, 144(5):646-674.
Hod, Y. (1992) "A Simplified Ribonuclease Protection Assay" *Biotechniques*, 13(6):852-853.

(Continued)

*Primary Examiner* — Joseph G. Dauner
(74) *Attorney, Agent, or Firm* — Cooley LLP; Ivor R. Elrifi; Matthew Pavao

(57) ABSTRACT

Methods are provided for diagnosing, detecting, or prognosticating a GEP-NEN based on the expression level score of biomarkers exhibiting differential expression in subjects having a GEP-NEN relative to a reference or control sample. The invention also provides compositions and kits comprising these biomarkers and methods of using these biomarkers in subsets or panels thereof to diagnose, classify, and monitor GEP-NEN and types of GEP-NEN. The methods and compositions provided herein may be used to diagnose or classify a subject as having a GEP-NEN, to distinguish between different stages of GEP-NENs, e.g., stable or progressive, to provide a measure of risk of developing a progressive GEP-NEN, and to gauge the completeness of treatments for GEP-NEN including, but not limited to surgery and somatostatin therapy.

18 Claims, 47 Drawing Sheets
Specification includes a Sequence Listing.

(56) References Cited

OTHER PUBLICATIONS

Hoshikawa et al. "Hypoxia induces different genes in the lungs of rat compared with mice" *Physical Genomics* 2003; 12:209-219.

Ji, S. and J. Ye (Oct. 2008) "Kernel Uncorrelated and Regularized Discriminant Analysis: A Theoretical and Computational Study" *IEEE Transactions on Knowledge and Data Engineering*, 20(10):1311-1321.

Kahan, L., "Medical devices; immunology and microbiology devices; classification of the immunomagnetic circulating cancer cell selection and enumeration system", Final rule. Department of Heath and Human Services. *Fed Regist* May 11, 2004; 69(91):26036-26038.

Kawarazaki, S. et al. (2010) "Conversion of a molecular classifier obtained by gene expression profiling into a classifier based on real-time PCR: a prognosis predictor for gliomas" *BMC Med Genomics*, 3:52, 8 pages.

Kidd, M. et al., "Isolation, Functional Characterization and transcriptome of the Mastomys ileal enterochromaffin cells," *Am J Physiol Gastrointest Liver Physiol* 2006; 291:G778-G791.

Kidd, M. et al. "Microsatellite instability and gene mutations in transforming growth factor-beta type II receptor are absent in small bowel carcinoid tumors" *Cancer* 2005; 103(2):229-236.

Kidd, M. et al. (2006) "The Role of Genetic Markers—Nap1L1,MAGE-D2, and MTA1—in Defining Small-Intestinal Carcinoid Neoplasia" *Ann Surg Oncol*, 13(2):253-262.

Kidd, M. et al. (2007) "GeneChip, geNorm, and Gastrointestinal tumors: novel reference genes for real-time PCR" *Physiol Genomics*, 30:363-370.

Kinross et al., "Metabonomic profiling: A Novel Approach in Neuroendocrine Neoplasias" *Surgery*, Dec. 1, 2013, vol. 154, No. 6, pp. 1185-1193.

Kohavi, R. (1995) "A Sudy of Cross-Validation and Bootstrap for Accuracy Estimation and Model Selection" *Proceedings of the Fourteenth International Joint Conference on Artificial Intelligence*, 2(12):1137-1143.

Lawlor, G, et al. (2011) "Increased Peripheral Blood GATA-3 Expression in Asymptomatic Patients With Active Ulcerative Colitis at Colonoscopy" *Gastroenterology*, 140(Suppl 1):S-842, Abstract Tu1827.

Lilien, R.H. et al. (2003) "Probabilistic Disease Classification of Expression-Dependent Proteomic Data from Mass Spectrometry of Human Serum" *J Comput Biol*, 10(6):925-946.

Markey, M.K. et al. (2002) "Perceptron error surface analysis: a case study in breast cancer diagnosis" *Comput Biol Med*, 32(2):99-109.

Mattfeldt, T. et al. (2003) "Classification of Prostatic Carcinoma with Artificial Neural Networks Using Comparative Genomic Hybridization and Quantitative Stereological Data" *Pathol Res Pract*, 199(12):773-784.

Mazzaglia, P.J. et al. (2007) "Laparoscopic radiofrequency ablation of neuroendocrine liver metastases: a 10-year experience evaluating predictors of survival" *Surgery*, 142(1):10-19.

Michiels, et al. (2007) "Interpretation of microarray data in cancer" *Br J Cancer*, 96(8):1155-1158.

Mimori, K. et al, "A large-scale study of MT1-MMP as a marker for isolated tumor cells in peripheral blood and bone marrow in gastric cancer cases," *Ann Surg Oncol* 2008; 15(10):2934-2942.

Modlin, I. et al. "The Identification of gut neuroendocrine tumor disease by multiple synchronous transcript analysis in blood", *Plos One* 2013, vol. 8, Issue 5, e63364 (12 pages).

Modlin I. et al. "The Identification of gut neuroendocrine tumor disease by multiple synchronous transcript analysis in blood", *Plos One* 2013, vol. 8, Issue 5, e63364, Supplementary Methods.

Modlin, I. et al., "The functional characterization of normal and neoplastic human enterochromaffin cells", *J Clin Endocrinol Metab* 2006; 91(6):2340-2348.

Noble, W.S. (Dec. 2006) "What is a support vector machine?" *Nat Biotechnol*, 24(12):1565-1567.

Parker, R.M.C. and N.M. Barnes (1999) "mRNA: Detection by In Situ and Northern Hypridization" *Methods in Molecular Biology*, 106:247-283.

Peng, H. et al. (Aug. 2005) "Feature Selection Based on Mutual Information: Criteria of Max-Dependency, Max-Relevance, and Min-Redundancy" *IEEE Transactions on Pattern Analysis and Machine Intelligence*, 27(8):1226-1238.

Picon, A. et al. (1998) "A subset of metastatic human colon cancers expresses elevated levels of transforming growth factor beta 1" *Cancer Epidemiol Biomarkers Prev*, 7(6):497-504.

Pima, I. and M. Aladjem (2004) "Regularized discriminant analysis for face recognition" *Pattern Recognition*, 37(9):1945-1948.

Pimentel, M. et al. (2011) "Validating a New Genomic Test for Irritable Bowel Syndrome" *Gastroenterology*, 140(Suppl 1):S-798, Abstract Tul329.

Pirooznia, M. et al. (2008) "A comparative study of different machine learning methods on microarray gene expression data" *BMC Genomics*, 9(Suppl 1):S13, 13 pages.

Ross, A.A. et al. "Detection and viability of tumor cells in peripheral blood stem cell collections from breast cancer patients using immunocytochemical and clonogenic assay techniques" *Blood* 1993; 82(9):2605-2610.

Schimmack et al., "The Clinical Implications and Biologic Relevance of Neurofilament Expression in Gastroenteropancreatic Neuroendocrine Neoplasms", May 15, 2012, Cancer, vol. 118, No. 10, pp. 2763-2775.

Sieuwerts, A.M. et al., "Molecular characterization of circulating tumor cells in large quantities of contaminating leukocytes by a multiplex real-time PCR," *Breast Cancer Res Treat* 2009; 118(3):455-468.

Simon et al. "Roadmap for Develping and Validating Therapeutically Relevant Genomic Classifiers" *Journal of Clinical Oncology* 2005; 23(29):7332-7341.

Specht, K. et al. (Feb. 2001) "Quantitative Gene Expression Analysis in Microdissected Archival Formalin-Fixed and Paraffin-Embedded Tumor Tissue" *Am J Pathol*, 158:419-429.

Tannapfel, A. et al., "BRAF gene mutations are rare events in gastroenteropancreatic neuroendocrine tumors," *Am J Clin Pathol* 2005; 123(2):256-260.

Urgard, E. et al. (2011) "Metagenes Associated with Survival in Non-Small Cell Lung Cancer" *Cancer Inform*, 10:175-183.

Van Eeden, S. et al. "Classification of low-grade neuroendocrine tumors of midgut and unknown origin" *Hum Pathol* 2002; 33(11):1126-1132.

Vandebriel, R.J. et al. (1998) "Altered cytokine (receptor) mRNA expression as a tool in immunotoxicology" *Toxicology*, 130(1):43-67.

Vandesompele, J. et al. (2002) "Accurate normalization of real-time quantitative RT-PCR data by geometric averaging of multiple internal control genes" *Genome Biol*, 3(7):research0034.1-0031.11.

Weis, J.H. et al. (Aug. 1992) "Detection of rare mRNAs via quantitative RT-PCT" *Trends in Genetics*, 8:263-264.

Whitehead et al. "Variation in tissue-specific gene expression among natural populations" *Genome Biology*, 2005; 6(2):Article R13.

Wong et al. "Real-time PCR for mRNA quantitation" *BioTechniques*, 2005; 39(1):1-11.

Yu, L. et al (2002) "TGF-beta receptor-activated p38 MAP kinase mediates Smad-independent TGF-beta responses" *EMBO J*, 21(14):3749-3759.

Zampetaki, A. et al. (2010) "Plasma MicroRNA Profiling Reveals Loss of Endothelial MiR-126 and Other MicroRNAs in Type 2 Diabetes" *Circ Res*, 107(6): 810-817.

Zhang, H. et al (2001) "Recursive Partitioning for Tumor Classification with Gene Expression Microarray Data" *Proc Natl Acad Sci USA*, 98(12):6730-6735.

Zikusoka, M.N. et al., "Molecular genetics of gastroenteropancreatic neuroendocrine tumors", *Cancer* 2005; 104:2292-2309.

\* cited by examiner

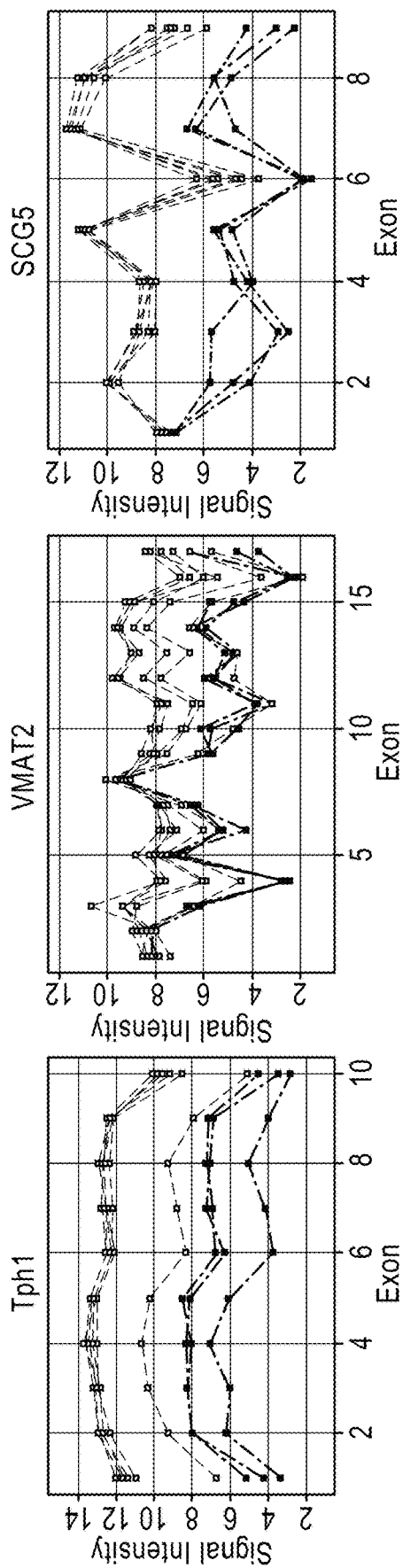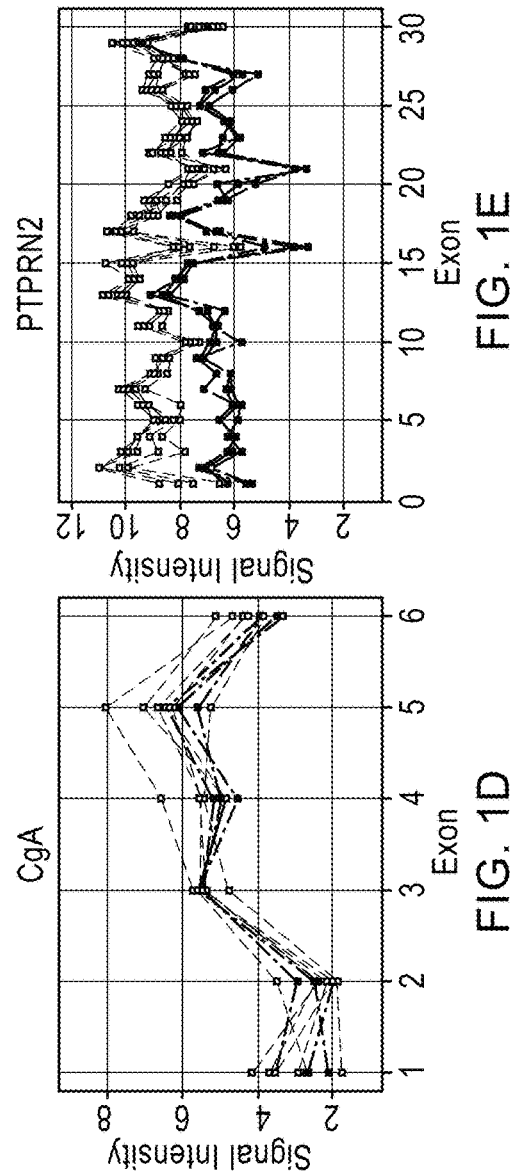
FIG. 1A  FIG. 1B  FIG. 1C  FIG. 1D  FIG. 1E

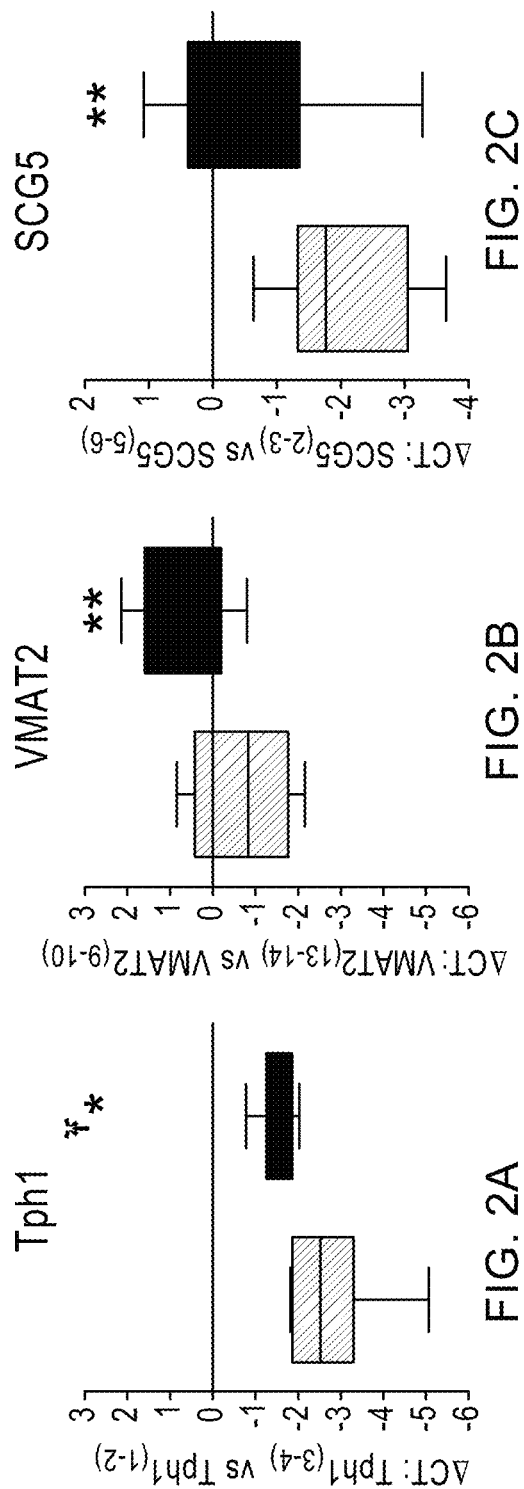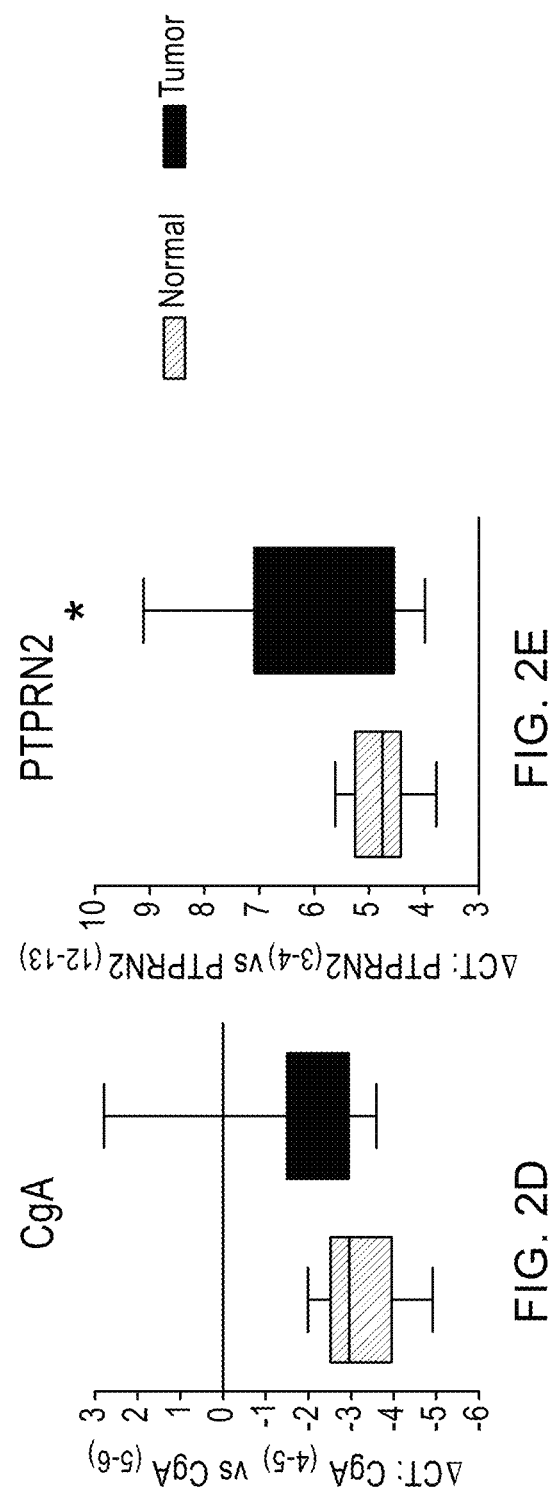
FIG. 2A  FIG. 2B  FIG. 2C  FIG. 2D  FIG. 2E

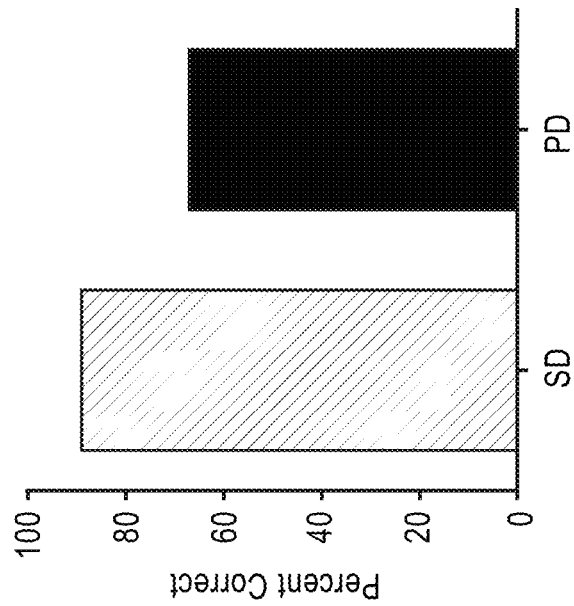
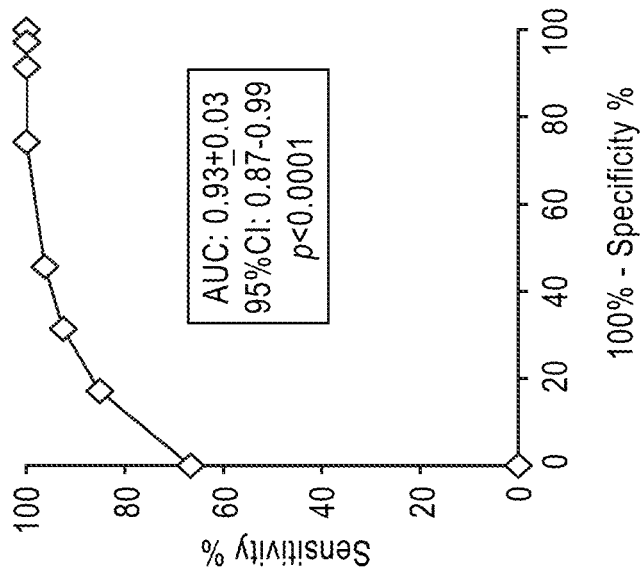
FIG. 7A
FIG. 7B

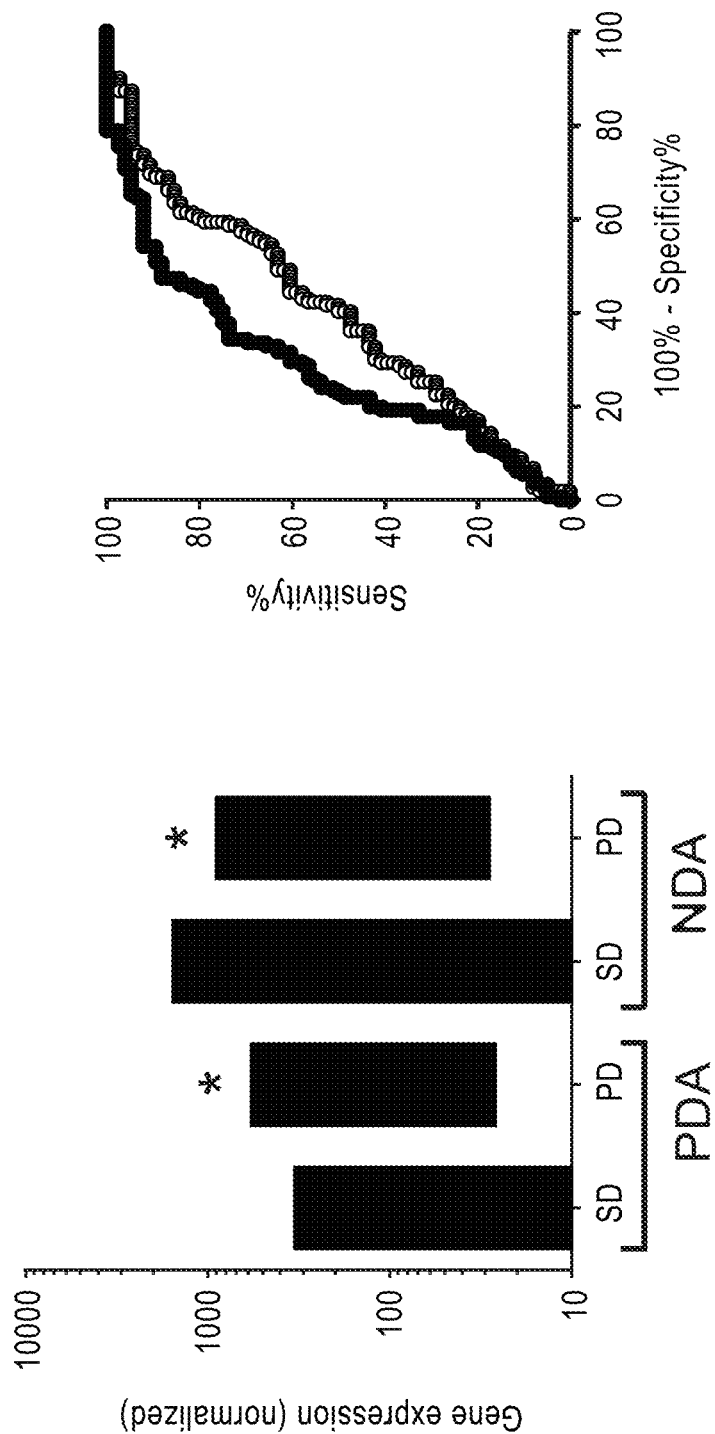

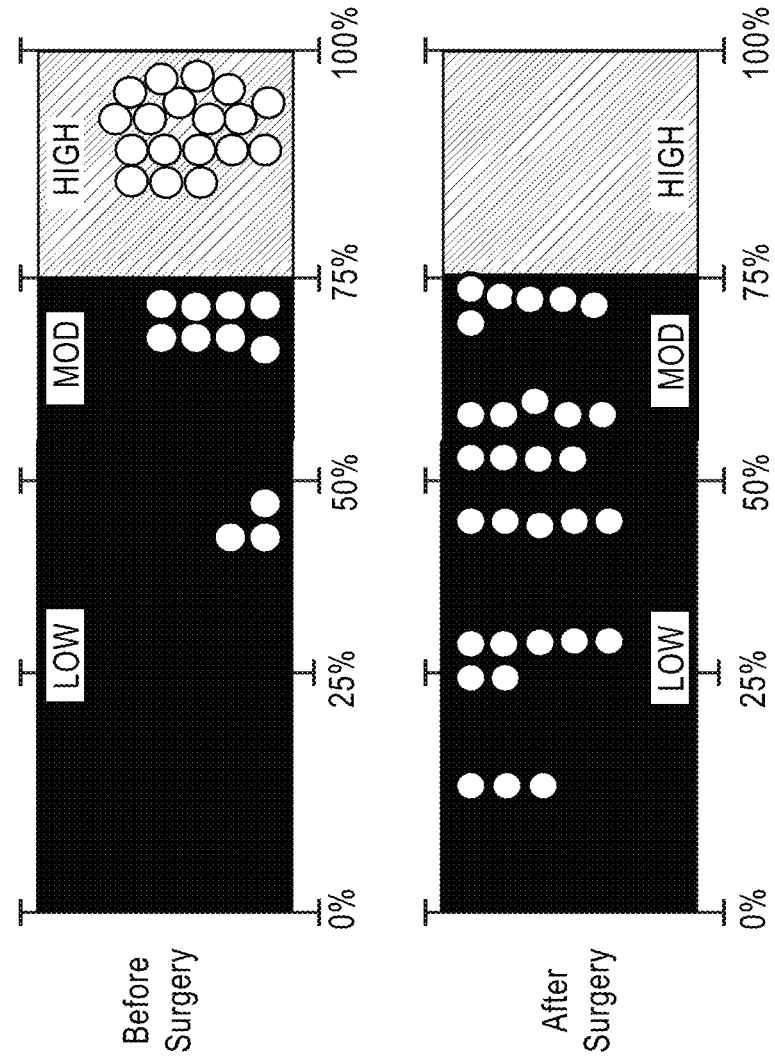
FIG. 24A Before Surgery
FIG. 24B After Surgery

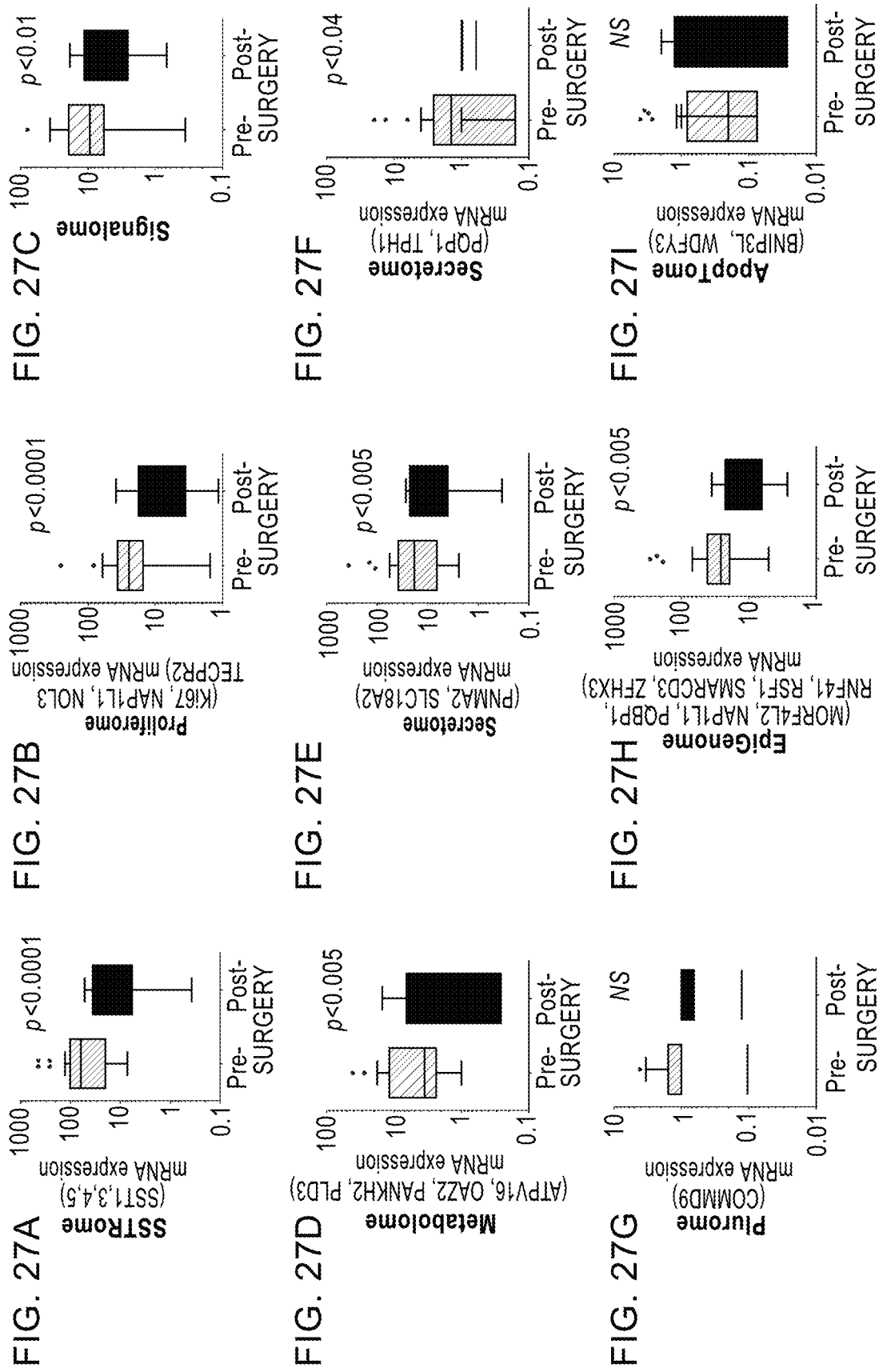

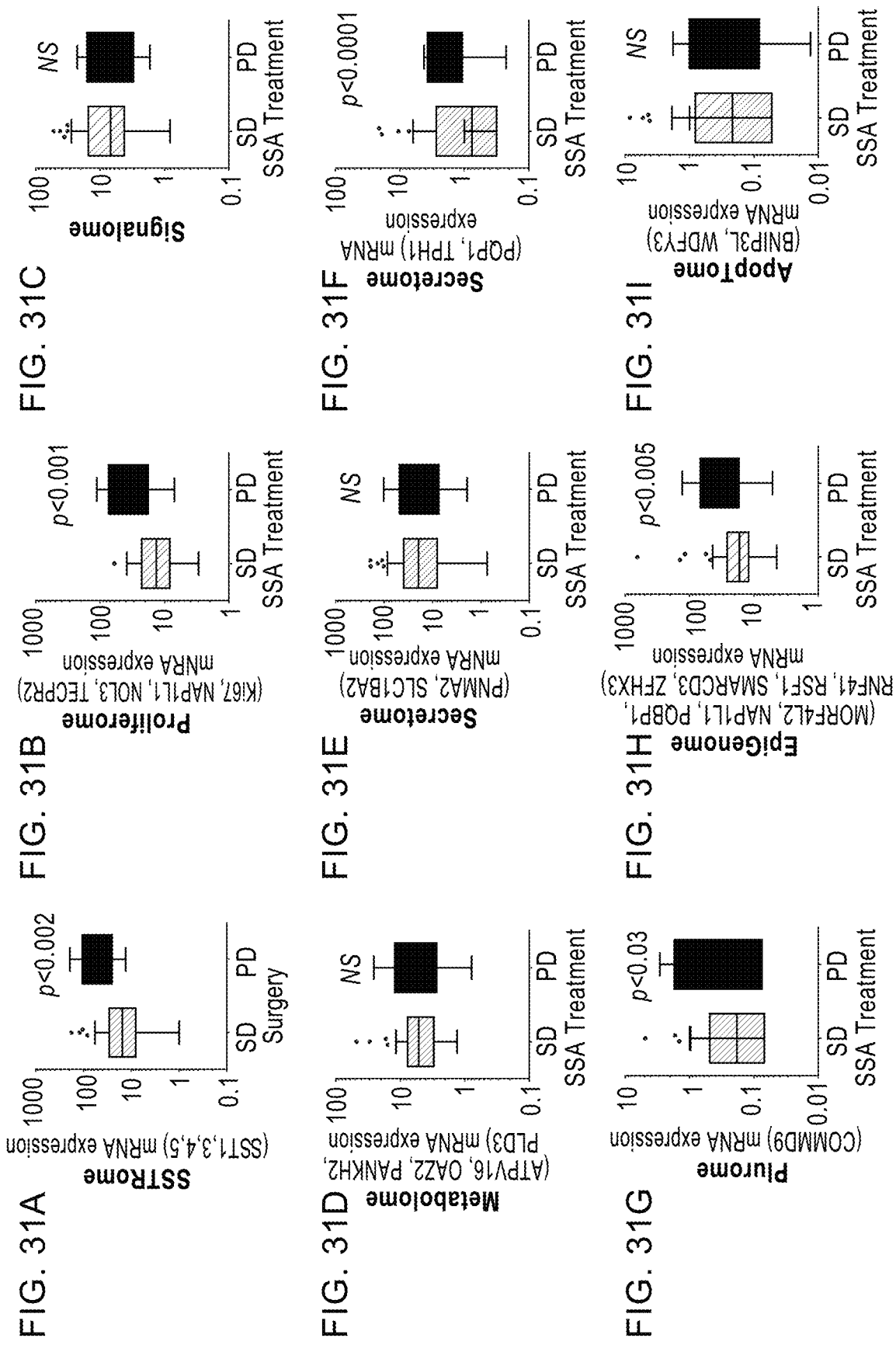

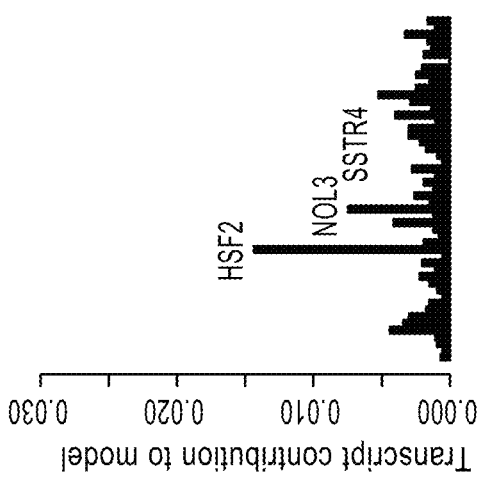
FIG. 38A Group 1
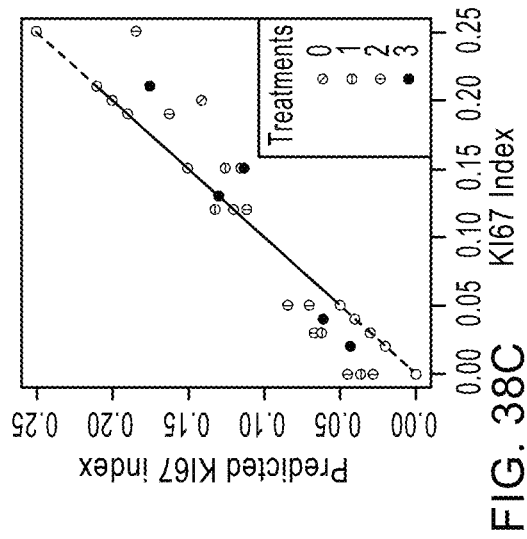
FIG. 38C
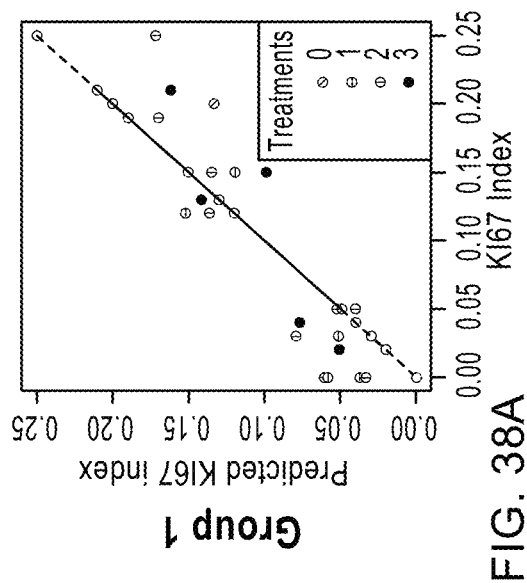
FIG. 38D
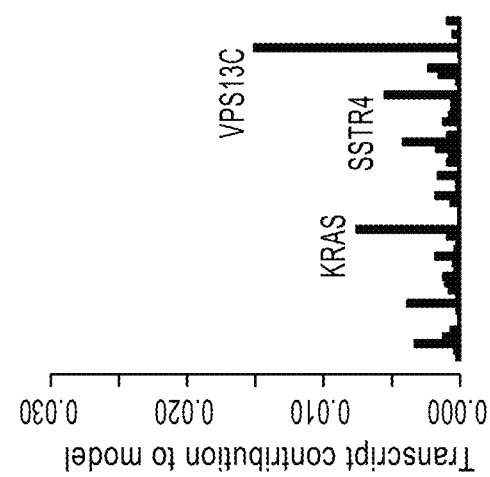
FIG. 38B Group 2
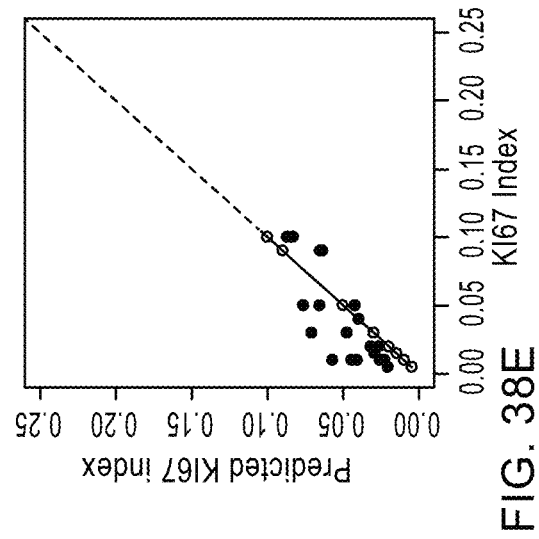
FIG. 38E
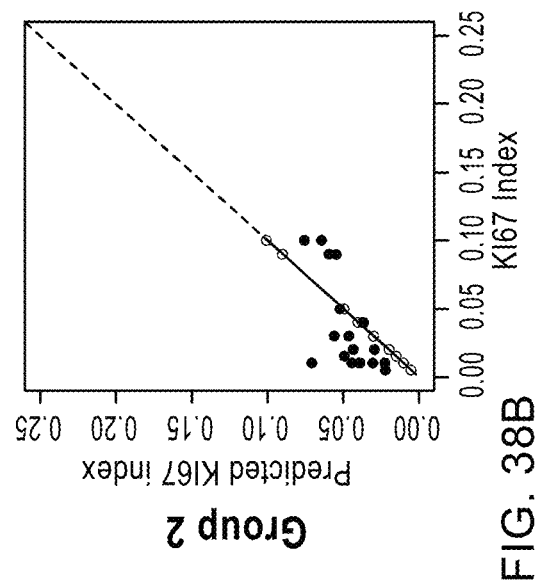
FIG. 38F

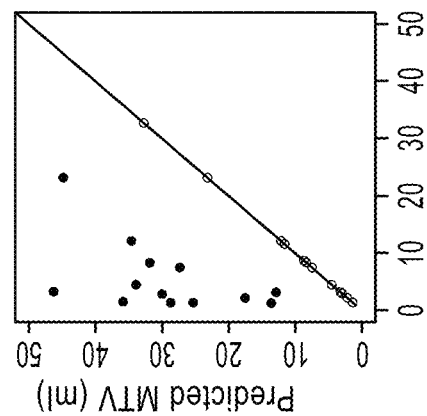
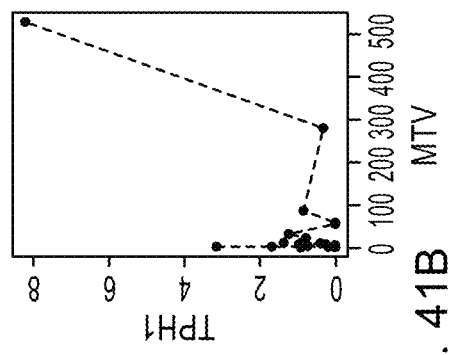
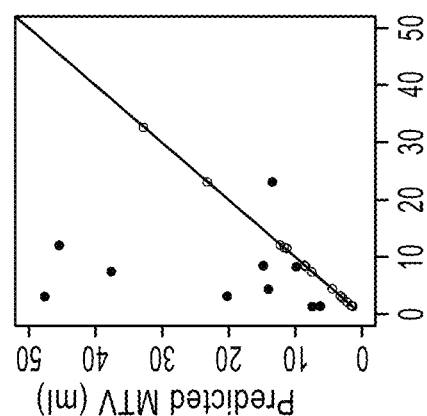
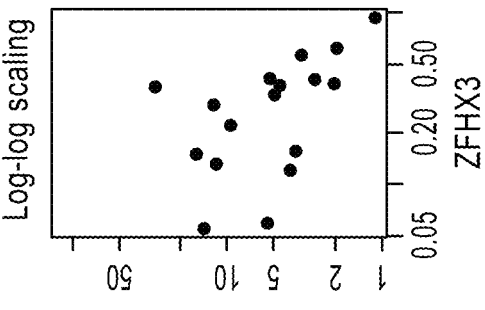
FIG. 41B
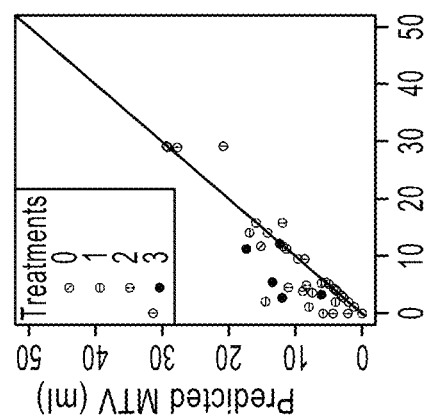
FIG. 41E
FIG. 41F
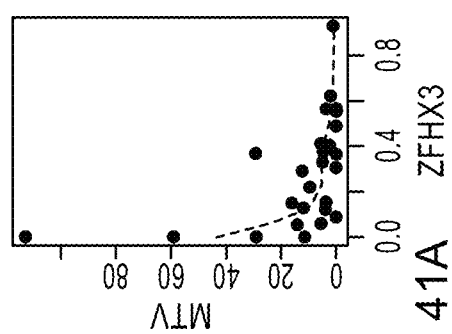
FIG. 41A
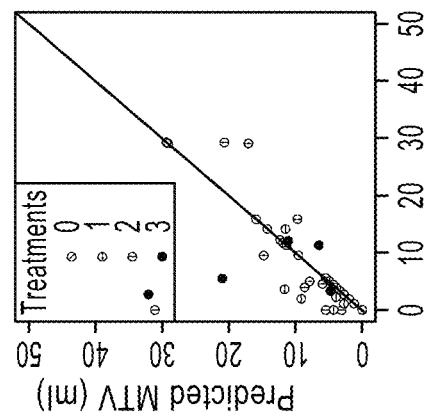
FIG. 41C
FIG. 41D

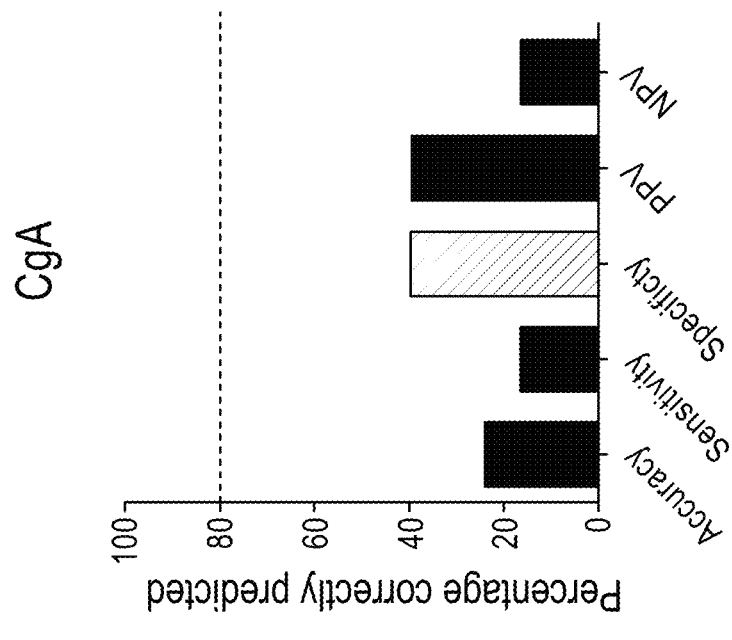
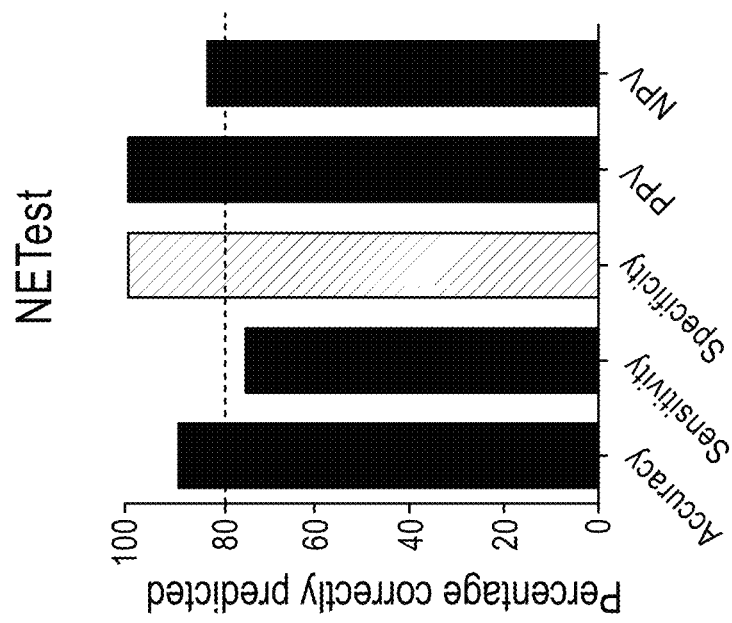
FIG. 46A
FIG. 46B

SEQUENCE LISTING

<160> NUMBER OF SEQ ID NOS: 52

<210> SEQ ID NO 1
<211> LENGTH: 6158
<212> TYPE: DNA
<213> ORGANISM: Homo sapiens

<400> SEQUENCE: 1

```
gtcttttgtc cctcggcgga caccgtttgc cagccaaagc tatgtctgcg cgctcaccga      60
cttcataggg tgccgaattc tttttccccc aggcttgcca tggctagtcg aggggctcgg     120
cagcgcctga agggcagcgg ggccagcagt ggggatacgg ccccggctgc ggacaagctg     180
cgggagctgc tgggcagccg agaggcgggc ggcgcggagc accggaccga gttatctggg     240
aacaaagcag gacaagtctg ggcacctgaa ggatctactg ctttcaagtg tctgctttca     300
gcaaggttat gtgctgctct cctgagcaac atctctgact gtgatgaaac attcaactac     360
tgggagccaa cacactacct catctatggg gaagggtttc agacttggga atattcccca     420
gcatatgcca ttcgctccta tgcttacctg ttgcttcatg cctggccagc tgcatttcat     480
gcaagaattc tacaaactaa taagattctt gtgttttact ttttgcgatg tcttctggct     540
tttgtgagct gtatttgtga actttacttt tacaaggctg tgtgcaagaa gtttgggttg     600
cacgtgagtc gaatgatgct agccttcttg gttctcagca ctggcatgtt ttgctcatca     660
tcagcattcc ttcctagtag cttctgtatg tacactacgt tgatagccat gactggatgg     720
tatatggaca agacttccat tgctgtgctg ggagtagcag ctggggctat cttaggctgg     780
ccattcagtg cagctcttgg tttacccatt gcctttgatt tgctggtcat gaaacacagg     840
tggaagagtt tcttttcattg gtcgctgatg gccctcatac tatttctggt gcctgtggtg     900
gtcattgaca gctactatta tgggaagttg gtgattgcac cactcaacat tgtttttgtat     960 aatgtcttta ctcctcatgg acctgatctt tatggtacag aaccctggta tttctattta    1020
attaatggat ttctgaattt caatgtagcc tttgctttgg ctctcctagt cctaccactg    1080
acttctctta tggaatacct gctgcagaga tttcatgttc agaatttagg ccaccgtat    1140
```

```
tggcttacct tggctccaat gtatatttgg tttataattt tcttcatcca gcctcacaaa    1200
gaggagagat ttcttttccc tgtgtatcca cttatatgtc tctgtggcgc tgtggctctc    1260
tctgcacttc agcacagttt tctgtacttc cagaaatgtt accactttgt gtttcaacga    1320
tatcgcctgg agcactatac tgtgacatcg aattggctgg cattaggaac tgtcttcctg    1380
tttgggctct tgtcattttc tcgctctgtg gcactgttca gaggatatca cgggcccctt    1440
gatttgtatc cagaatttta ccgaattgct acagacccaa ccatccacac tgtcccagaa    1500
ggcagacctg tgaatgtctg tgtgggaaaa gagtggtatc gatttcccag cagcttcctt    1560
cttcctgaca attggcagct tcagttcatt ccatcagagt tcagaggtca gttaccaaaa    1620
ccttttgcag aaggacctct ggccacccgg attgttccta ctgacatgaa tgaccagaat    1680
ctagaagagc catccagata tattgatatc agtaaatgcc attatttagt ggatttggac    1740
accatgagag aaacaccccg ggagccaaaa tattcatcca ataaagaaga atggatcagc    1800
ttggcctata gaccattcct tgatgcttct agatcttcaa agctgctgcg ggcattctat    1860
gtcccctccc tgtcagatca gtatacagtg tacgtaaact acaccatcct caaaccccgg    1920
aaagcaaagc aaatcaggaa gaaaagtgga ggttagcaac acacctgtgg ccccaaagga    1980
caaccatctt gttaactatt gattccagtg acctgactcc ctgcaagtca tcgcctgtaa    2040
catttgtaat aaaggtcttc tgacatgaat actggaatct gggtgctctg ggctagtcaa    2100
agtctatttc aaagtctaat caaagtcaca tttgctccct gtgtgtgtct ctgttctgca    2160
tgtaaacttt ttgcagctag gcagagaaag gccctaaagc acagatagat atattgctcc    2220
acatctcatt gttttttcctc tgttcaatta tttactagac cggagaagag cagaaccaac    2280
ttacaggaag aattgaaaat cctggtactg gatggctgtg ataagctgtt ctccacactc    2340
tggcctggca tctgagaact agcaagcctc tcttaggcca tatgggcttc tccaccaaag    2400
ctgtttggca gctcctagca gaccttctta ttgaaatcct catgctgaaa atgaacacag    2460
cctagttgcc aacccacatg tccttttcac ctccagcaag actaagcttc tttaaagcac    2520
ttcacaggac taggaccctg tcctggagct atctcaggaa aaaggtgacc atttgaggaa    2580
ctgtgaccta attttattat aatgatgcct ctaattttca tttcctttac aaccaactgt    2640
aactataagg ttgtattgct ttttttgttca gttttagcat gctatttttt gaattctaga    2700
ctcctccatg tgaagatatc aacagacaaa actacaactg tataggacat atttggagaa    2760
aattctatca attgatacat ttggatgaca tcacattttt aagtaatgta atctgaggcc    2820
attgctgagg aaattaagaa ttttcctttt tttttaacca cccccagtga aaaggatcag    2880
tgtatattta tagcacctat tttttagttc tgtctgttgt gaggcacatc ctgcatgggg    2940
cacttctagt caaataggca atgataagga cctaattaaa atgtgataag tgtatactat    3000
tactttaaaa gcctttacag tcagtacttc agtttacaag gcactttcac agcatctcgt    3060
ttgatcctca cagtcacaac atgtggtaga caaggcaggt gattttttatc cccatttttac    3120 agataaggaa acaggctgcg ggtggggagt gagggaggt aaagatagtt agttgcctaa    3180
ggtcacacag ccagtaagta atagagctgg gactggaacc caggtttcct tactctcatc    3240
tattgctcct ccatattcct cactcaacca tgaaaacatt acttgaaagg actgatgagg    3300
ttaaccagag acctaactga tattgtaact ttctattta aggaagaatt gtgtctgtat    3360
ttgagttctt tggagcctcc agtctgcctg tgtgttagac cagcacagca gtgctgtgtg    3420
atgcagcctg acctgtggca ggaaagtagt gcttctgttt ggaagtcatg ttcttttgca    3480
```

| | |
|---|---|
| gccacacagg atccaaatat cagtactatt cctgtagtca atctgggtc acattatagg | 3540 |
| tgccttattt ccctaagggt aactgatctg aatatctgca aataggatga atctattttt | 3600 |
| cagaagttcc atctttcatt tttctttttt tttttgagac agagtctcat tctgtcgccc | 3660 |
| atgctggagt gcagtggcgc gatctcggct cgctgcaacc tctgcctccc aggttgaagc | 3720 |
| aattctcatg cctcagccac ccgagtagct gggattacag gcatgcgcca tcatgcccag | 3780 |
| ctaatttatg tattttagt agagttggag tttcaccatg ttggccaggc tggtcttgga | 3840 |
| ctcctgacct caggtcatcc acccgcctca gcctcccaaa gtgctggtat tacaggcgtg | 3900 |
| agccaccgca cccagcccca tctttcattt tcaaagagaa gggcattcta ataggaactg | 3960 |
| gtgccaagag agaagaaaag aagtgataac agaagaaatg gctagttaca atattaaaaa | 4020 |
| gctcctcttt gagatctcct ctgcaggaat atcagacg gagttgaagc gctggagagg | 4080 |
| taataggtct agacagtaca gaacaataac tggggagtgt gtgaggatag actgggctcc | 4140 |
| cccttgcttg aaagatctct ggcatttaat tctcaattct tgattactat tttccagtgt | 4200 |
| aaaactagca catgatct gactacagga cagagaattt taagtgaaac atttgcctta | 4260 |
| cttgcagtaa taatgtgctg ttcttcacag tagctaaggc cctctatgtt tcccagaggt | 4320 |
| aaataagaat ccaggaatgg aggtccatct gtgatgaatg gcttttttct aatcaaagta | 4380 |
| gtataatgct gttttatctg ttttgtcatc ttgttttttt tttttttaa aaaacaaaa | 4440 |
| ccttaattat aatatagcgc aaagaaaggc caggactgat gcaggattc cttggaaata | 4500 |
| tcagttccta tcacttttaa aacctgattt tggatctctc tgttctatgt atgtctttag | 4560 |
| tgagagcaca atacatggca gaacgctgtg ccaaatgtta taggtaagga atatagaaat | 4620 |
| gaatgttttt tgttgtgaag gtgttttcat gtgatatttt ataaacacat tttaaaaaat | 4680 |
| ctccatcact ttttagtata ggaaggatag ctttgcctgg gaaaaacagt ttcaacacac | 4740 |
| ctgctcagag tagcagttct ccctcaaaaa agcagtgttc agcctgcact gactgttctg | 4800 |
| cttgccaaaa ggaggaagca tgcaagatac ttatttctcc atagattgtg gagtatagag | 4860 |
| ggatgtggga ctacagatta ttatttttt tccccgagac agagtcttgc tctgtcgccc | 4920 |
| aggttggaac acaatggcac gacctcagct cactgcaacc tctgtctccc gggttcaagc | 4980 |
| aattctcctg cttcagcctc ctgagtagct gggattacag gcacacacca ccaccgcact | 5040 |
| cagctaattt ttgtattttt agtagaggtg gggttttacc atgttggcca ggctggtctt | 5100 |
| aaactcctga ccttgtaatc atcccgcctc ggcctcctaa agtgctagga ttacaggcat | 5160 |
| gagccaccgc acccggccca gataattttt aatagccttt gatcatgggg tgagtgaggg | 5220 |
| agtaggtata cttggcaaat gcatggttct ctgatttcta gctctaaagc agccttatct | 5280 |
| gaatccccaa atcttgtgat gctgagtacc attactgaac cagtctgcac ggtaggcatc | 5340 |
| tgctaccaaa atttacctcc tacctggtag gtgtcatctg ataagaaaga agacaggtta | 5400 |
| ttttaatttt ttgagataat cacagaaaat tgcagcccat actctttatt accgaattca | 5460 |
| agtttggaaa tagacccttt gttttaaatc atgatgggtc tttatcccaa tcatttatct | 5520 |
| gggtcatttt tccaactttg gagttctagg aaagaacctt gaaaacctga tatgattctg | 5580 |
| cagcatgagg tctacggtga ccatttgggc aaagctccag tggcaatcat ttattgtgtt | 5640 |
| ttgcatttcc tgggatttat tgaaataaga attcactgtg attatgtagt cttctggcta | 5700 |
| gtatcaggca gctctgcttt taatttggtt aattttattt tctctgaaga gggagaagag | 5760 |
| gtacaattta atcttggcct ccacaagcat attaaagctc acgtgttaat cagtgcattc | 5820 |
| ttatgctcct acattaaatg ccttgggtaa atggataaat ggacatgtgc ccagctttaa | 5880 |

```
tttttttgc aacagaaaga tcagacttcc gtatggcatc gttggatttc agaggctttc   5940
tggtgtatct gtaaatctga atgttgcctt ctgccagtct gtataaccag gtgattcatg   6000
ctgcaaatga aatcaggaag cagtaaagtg ttaaagcaag agtattgtcc aattcacttg   6060
tcttcctgat ccttgtactt tatttcacgt gtcggtgttt acattacata cttatatttc   6120
ctgtgaaaga aagagttaaa taaattgtag cagtttga                          6158

<210> SEQ ID NO 2
<211> LENGTH: 2231
<212> TYPE: DNA
<213> ORGANISM: Homo sapiens

<400> SEQUENCE: 2
actgatatga ggaggcatag agatagacag cggttccttc caatagacgt gaagccgagg    60
ccggtatgag ccaatgcggt cgggaggcgg ggctcgggtg tgtgtggagg ggaccctgtg   120
gttagcagca gctatcgcag cgtcggatgt tcagagcagc agaagccggc gtcgtcggat   180
gttgtgttgc ccgccaccat gagctacaca ggctttgtcc aggatctgaa accactttg    240 cagtcgacat actcggatac cagcgctcag cccaccctgtg attatggata tggaacttgg   300
aactctggga caaatagagg ctacgagggc tatggctatg ctatggcta tggccaggat    360 aacaccacca actatgggta tggtatggcc acttcacact cttgggaaat gcctagctct    420
gacacaaatg caaacactag tgcctcgggt agcgccagtg ccgattccgt tttatccaga    480
attaaccagc gcttagatat ggtgccgcat ttggagacag acatgatgca aggaggcgtg    540
tacggctcag gtggagaaag gtatgactct tatgagtcct gcgactcgag ggccgtcctg    600
agtgagcgcg acctgtaccg gtcaggctat gactacagcg agcttgaccc tgagatggaa    660
atggcctatg agggccaata cgatgcctac cgcgaccagt tccgcatgcg tggcaacgac    720
accttcggtc ccagggcaca gggctgggcc cgggatgccc ggagcggccg gccaatggcc    780
tcaggctatg ggcgcatgtg ggaagacccc atgggggccc ggggccagtg catgtctggt    840
gcctctcggc tgccctccct cttctcccag aacatcatcc ccgagtacgg catgttccag    900
ggcatgcgag gtggggcgc cttcccgggc ggctcccgct ttggtttcgg gtttggcaat    960
ggcatgaagc agatgaggcg gacctggaag acctggacca cagccgactt ccgaaccaag   1020
aagaagaaga gaaagcaggg cggcagtcct gatgagccag atagcaaagc caccccgcacg   1080 gactgctcgg acaacagcga ctcagacaat gatgagggca ccgaggggga agccacagag   1140
ggccttgaag gcaccgaggc tgtggagaag ggctccagag tggacggaga ggatgaggag   1200
ggaaaagagg atgggagaga agaaggcaaa gaggatccag agaaggggc cctaaccacc   1260 caggatgaaa atgccagaca caagcgcaag ttgcaggcag caagaagag tcaggacaag   1320 cagaaaaagc ggcagcgaga ccgcatggtg gaaaggatcc agtttgtgtg ttctctgtgc   1380
aaataccgga ccttctatga ggacgagatg gccagccatc ttgacagcaa gttccacaag   1440 gaacactta agtacgtagg caccaagctc cctaagcaga cggctgactt tctgcaggag   1500
tacgtcacta acaagaccaa gaagacagag gagctccgaa aaccgtggga ggaccttgat   1560
ggcctcatcc agcaaatcta cagagaccag gatctgaccc aggaaattgc catggagcat   1620
tttgtgaaga aggtggaggc agcccattgt gcagcctgcg acctcttcat tcccatgcag   1680
tttgggatca tccagaagca tctgaagacc atggatcaca accggaaccg caggctcatg   1740
atggagcagt ccaagaagtc ctccctcatg gtggcccgca gtattctcaa caacaagctc   1800
```

| | |
|---|---|
| atcagcaaga agctggagcg ctacctgaag ggcgagaacc ctttcaccga cagccccgag | 1860 |
| gaggagaagg agcaggagga ggctgagggc ggtgccctgg acgaggggggc gcagggcgaa | 1920 |
| gcggcaggga tctcggaggg cgcagagggc gtgccggcgc agcctcccgt gccccagag | 1980 |
| ccagccccg gggccgtgtc gccgccaccg ccgccgcccc cagaggagga ggaggagggc | 2040 |
| gccgtgccct tgctgggagg ggcgctgcaa cgccagatcc gcggcatccc gggcctcgac | 2100 |
| gtggaggacg acgaggaggg cggcggggc gccccgtgac ccgagctcgg ggcgggcgga | 2160 |
| gcccgcgtgg ccgaagctgg aaaccaaacc taataaagtt ttcccatccc accaaaaaaa | 2220 |
| aaaaaaaaaa a | 2231 |

<210> SEQ ID NO 3
<211> LENGTH: 3791
<212> TYPE: DNA
<213> ORGANISM: Homo sapiens

<400> SEQUENCE: 3

| | |
|---|---|
| agaaggaggg cgtggtaata tgaagtcagt tccggttggt gtaaaacccc cggggcggcg | 60 |
| gcgaactggc tttagatgct tctgggtcgc ggtgtgctaa gcgaggagtc cgagtgtgtg | 120 |
| agcttgagag ccgcgcgcta gagcgacccg gcgaggggatg gcggccaccg ggaccgcggc | 180 |
| cgccgcagcc acgggcaggc tcctgcttct gctgctggtg gggctcacgg cgcctgcctt | 240 |
| ggcgctggcc ggctacatcg aggctcttgc agccaatgcc ggaacaggat ttgctgttgc | 300 |
| tgagcctcaa atcgcaatgt tttgtgggaa gttaaatatg catgtgaaca ttcagactgg | 360 |
| gaaatgggaa cctgatccaa caggcaccaa gagctgcttt gaaacaaaag aagaagttct | 420 |
| tcagtactgt caggagatgt atccagagct acagatcaca aatgtgatgg aggcaaacca | 480 |
| gcgggttagt attgacaact ggtgccggag ggacaaaaag caatgcaaga gtcgctttgt | 540 |
| tacacctttc aagtgtctcg tgggtgaatt tgtaagtgat gtcctgctag ttccagaaaa | 600 |
| gtgccagttt ttccacacaa agagcggatgga ggtgtgtgag aatcaccagc actggcacac | 660 |
| ggtagtcaaa gaggcatgtc tgactcaggg aatgaccttta tatagctacg gcatgctgct | 720 |
| cccatgtggg gtagaccagt tccatggcac tgaatatgtg tgctgccctc agacaaagat | 780 |
| tattggatct gtgtcaaaag aagaggaaga ggaagatgaa gaggaagagg aagaggaaga | 840 |
| tgaagaggaa gactatgatg tttataaaag tgaatttcct actgaagcag atctggaaga | 900 |
| cttcacagaa gcagctgtgg atgaggatga tgaggatgag gaaggaggg aggaagtggt | 960 |
| ggaggaccga gattactact atgacaccctt caaaggagat gactacaatg aggagaatcc | 1020 |
| tactgaaccc ggcagcgacg gcaccatgtc agacaaggaa attactcatg atgtcaaagc | 1080 |
| tgtctgctcc caggaggcga tgacggggcc ctgccgggcc gtgatgcctc gttggtactt | 1140 |
| cgacctctcc aagggaaagt gcgtgcgctt tatatatggt ggctgcggcg gcaacaggaa | 1200 |
| caattttgag tctgaggatt attgtatggc tgtgtgtaaa gcgatgattc ctccaactcc | 1260 |
| tctgccaacc aatgatgttg atgtgtattt cgagacctct gcagatgata atgagcatgc | 1320 |
| tcgcttccag aaggctaagg agcagctgga gattcggcac cgcaaccgaa tggacagggt | 1380 |
| aaagaaggaa tggaagagg cagagcttca agctaagaac ctcccaaag cagagaggca | 1440 |
| gactctgatt cagcacttcc aagccatggt taaagcttta gagaaggaag cagccagtga | 1500 |
| gaagcagcag ctggtggaga cccacctggc ccgagtggaa gctatgctga atgaccgccg | 1560 |
| tcggatggct ctggagaact acctggctgc cttgcagtct gacccgccac ggcctcatcg | 1620 |
| cattctccag gccttacggc gttatgtccg tgctgagaac aaagatcgct acatacccat | 1680 |

```
ccgtcattac cagcatgtgt tggctgttga cccagaaaag gcggcccaga tgaaatccca    1740
ggtgatgaca catctccacg tgattgaaga aaggaggaac caaagcctct ctctgctcta    1800
caaagtacct tatgtagccc aagaaattca agaggaaatt gatgagctcc ttcaggagca    1860
gcgtgcagat atggaccagt tcactgcctc aatctcagag acccctgtgg acgtccgggt    1920
gagctctgag gagagtgagg agatcccacc gttccacccc ttccaccct tcccagccct     1980 acctgagaac gaaggatctg gagtgggaga gcaggatggg ggactgatcg gtgccgaaga    2040
gaaagtgatt aacagtaaga ataaagtgga tgaaaacatg gtcattgacg agactctgga    2100
tgttaaggaa atgattttca atgccgagag agttggaggc ctcgaggaag agcgggaatc    2160
cgtgggccca ctgcgggagg acttcagtct gagtagcagt gctctcattg gcctgctggt    2220
catcgcagtg gccattgcca cggtcatcgt catcagcctg gtgatgctga ggaagaggca    2280
gtatggcacc atcagccacg ggatcgtgga ggttgatcca atgctcaccc cagaagagcg    2340
tcacctgaac aagatgcaga accatggcta tgagaacccc acctacaaat acctggagca    2400
gatgcagatt taggtggcag ggagcgcggc agccctggcg gagggatgca ggtgggccgg    2460
aagatcccac gattccgatc gactgccaag cagcagccgc tgccaggggc tgcgtctgac    2520
atcctgacct cctggactgt aggactatat aaagtactac tgtagaactg caatttccat    2580
tcttttaaat gggtgaaaaa tggtaatata acaatatatg atatataaac cttaaatgaa    2640
aaaaatgatc tattgcagat atttgatgta gttttctttt ttaaattaat cagaaacccc    2700
acttccattg tattgtctga cacatgctct caatatataa taaatgggaa atgtcgattt    2760
tcaataatag acttatatgc aggctgtcgt tccggttatg ttgtgtaagt caactcttca    2820
gcctcattca ctgtcctggc ttttatttaa agaaaaaaaa ggcagtattc ccttttttaaa    2880 tgagctttca ggaagttgct gagaaatggg gtggaatagg gaactgtaat ggccactgaa    2940
gcacgtgaga gaccctcgca aaatgatgtg aaaggaccag tttcttgaag tccagtgttt    3000
ccacggctgg ataccgtgt gtctccataa aagtcctgtc accaaggacg ttaaaggcat    3060
tttattccag cgtcttctag agagcttagt gtatacagat gagggtgtcc gctgctgctt    3120
tccttcggaa tccagtgctt ccacagagat tagcctgtag cttatatttg acattcttca    3180
ctgtctgttg tttacctacc gtagctttt accgttcact tcccttcca actatgtcca     3240 gatgtgcagg ctcctcctct ctggactttc tccaaaggca ctgaccctcg gcctctactt    3300
tgtcccctca cctccacccc ctcctgtcac cggccttgtg acattcactc agagaagacc    3360
acaccaagga ggcggccgct ggcccaggag agaacacggg gaggtttgtt tgtgtgaaag    3420
gaaagtagtc caggctgtcc ctgaaactga gtctgtggac actgtggaaa gctttgaaca    3480
attgtgtttt cgtcacagga gtctttgtaa tgcttgtaca gttgatgtcg atgctcactg    3540
cttctgcttt ttctttcttt ttattttaaa tctgaaggtt ctggtaacct gtggtgtatt    3600 tttatttttcc tgtgactgtt tttgttttgt tttttccttt tttcctcccc tttgacccta    3660
ttcatgtctc tacccactat gcacagatta aacttcacct acaaactcct taatatgatc    3720
tgtggagaat gtacacagtt taaacacatc aataaatact ttaacttcca ccgagaaaaa    3780
aaaaaaaaaa a                                                          3791
```

<210> SEQ ID NO 4
<211> LENGTH: 2562
<212> TYPE: DNA
<213> ORGANISM: Homo sapiens

```
<400> SEQUENCE: 4
cttgacagac gtgaccctga cccaataagg gtggaaggct gagtcccgca gagccaataa      60
cgagagtccg agaggcgacg gaggcggact ctgtgaggaa acaagaagag aggcccaaga     120
tggagacggc ggcggctgta gcggcgtgac aggagcccca tggcacctgc ccagccccac     180
ctcagcccat cttgacaaaa tctaaggctc catggagcca ccacggggcc ccctgccaa      240 tggggccgag ccatcccggg cagtgggcac cgtcaaagta tacctgccca acaagcaacg     300
cacggtggtg actgtccggg atggcatgag tgtctacgac tctctagaca aggccctgaa     360
ggtgcggggt ctaaatcagg actgctgtgt ggtctaccga ctcatcaagg gacgaaagac     420
ggtcactgcc tgggacacag ccattgctcc cctggatggc gaggagctca ttgtcgaggt     480
ccttgaagat gtcccgctga ccatgcacaa ttttgtacgg aagaccttct tcagcctggc     540
gttctgtgac ttctgcctta gtttctgtt ccatggcttc cgttgccaaa cctgtggcta      600
caagttccac cagcattgtt cctccaaggt ccccacagtc tgtgttgaca tgagtaccaa     660
ccgccaacag ttctaccaca gtgtccagga tttgtccgga ggctcagac agcatgaggc      720 tccctcgaac cgcccctga atgagttgct aaccccccag gtcccagcc ccgcaccca        780 gcactgtgac ccggagcact tccccttccc tgccccagcc aatgccccc tacagcgcat      840 ccgctccacg tccactccca acgtccatat ggtcagcacc acggccccca tggactccaa     900
cctcatccag ctcactggcc agagtttcag cactgatgct gccggtagta gaggaggtag     960
tgatggaacc ccccgggga gccccagccc agccagcgtg tcctcgggga ggaagtcccc    1020
acattccaag tcaccagcag agcagcgcga gcggaagtcc ttggccgatg acaagaagaa    1080
agtgaagaac ctggggtacc gggactcagg ctattactgg gaggtaccac ccagtgaggt    1140
gcagctgctg aagaggatcg ggacgggctc gtttggcacc gtgtttcgag gcggtggca     1200 tggcgatgtg gccgtgaagg tgctcaaggt gtcccagccc acagctgagc aggcccaggc    1260
tttcaagaat gagatgcagg tgctcaggaa gacgcgacat gtcaacatct tgctgtttat    1320
gggcttcatg acccggccgg gatttgccat catcacacag tggtgtgagg gctccagcct    1380
ctaccatcac ctgcatgtgg ccgacacacg cttcgacatg gtccagctca tcgacgtggc    1440
ccggcagact gcccagggca tggactacct ccatgccaag aacatcatcc accgagatct    1500
caagtctaac aacatcttcc tacatgaggg gctcacggtg aagatcggtg actttggctt    1560
ggccacagtg aagactcgat ggagcggggc ccagcccttg gagcagccct caggatctgt    1620
gctgtggatg gcagctgagg tgatccgtat gcaggacccg aaccctaca gcttccagtc     1680 agacgtctat gcctacgggg ttgtgctcta cgagcttatg actggctcac tgccttacag    1740
ccacattggc tgccgtgacc agattatctt tatggtgggc cgtggctatc tgtccccgga    1800
cctcagcaaa atctccagca actgccccaa ggccatgcgg cgcctgctgt ctgactgcct    1860
caagttccag cggaggagc ggcccctctt ccccagatc ctggccacaa ttgagctgct      1920
gcaacggtca ctccccaaga ttgagcggag tgcctcggaa ccctccttgc accgcaccca    1980
ggccgatgag ttgcctgcct gctactcag cgcagcccgc cttgtgcctt aggccccgcc    2040
caagccacca gggagccaat ctcagccctc acgccaagg agccttgccc accagccaat     2100
caatgttcgt ctctgccctg atgctgcctc aggatccccc attccccacc ctgggagatg    2160 aggggggtccc catgtgcttt tccagttctt ctggaattgg gggaccccg ccaaagactg    2220 agcccctgt ctcctccatc atttggtttc ctcttggctt tggggatact tctaaatttt     2280
gggagctcct ccatctccaa tggctgggat ttgtggcagg gattccactc agaacctctc    2340
```

| | | | |
|---|---|---|---|
| tggaatttgt | gcctgatgtg | ccttccactg | gattttgggg ttcccagcac cccatgtgga | 2400 |
| ttttgggggg | tccctttgt | gtctccccg | ccattcaagg actcctctct ttcttcacca | 2460 |
| agaagcacag | aattctgctg | ggcctttgct | tgtttaaaaa aaaaaaaaaa aaaaaaaaa | 2520 |
| aaaaaaaaaa | aaaaaaaaaa | aaaaaaaaaa | aaaaaaaaaa aa | 2562 |

<210> SEQ ID NO 5
<211> LENGTH: 2186
<212> TYPE: DNA
<213> ORGANISM: Homo sapiens

<400> SEQUENCE: 5

| | | | | |
|---|---|---|---|---|
| agcagtcacg | tgcctccgat | cacgtgaccg | gcgcctctgt cattctactg cggccgccct | 60 |
| ggcttccttc | tacctgtgcg | gccctcaacg | tctccttggt gcgggacccg cttcactttc | 120 |
| ggctcccgga | gtctccctcc | actgctcaga | cctctggacc tgacaggaga cgcctacttg | 180 |
| gctctgacgc | ggcgccccag | cccggctgtg | tccccggcgc cccggaccac cctccctgcc | 240 |
| ggctttgggt | gcgttgtggg | gtcccgagga | ttcgcgagat tgttgaaag acattcaaga | 300 |
| ttacgaagtt | tagatgacca | aaatggatat | ccgaggtgct gtggatgctg ctgtccccac | 360 |
| caatattatt | gctgccaagg | ctgcagaagt | tcgtgcaaac aaagtcaact ggcaatccta | 420 |
| tcttcaggga | cagatgattt | ctgctgaaga | ttgtgagttt attcagaggt ttgaaatgaa | 480 |
| acgaagccct | gaagagaagc | aagagatgct | tcaaactgaa ggcagccagt gtgctaaaac | 540 |
| atttataaat | ctgatgactc | atatctgcaa | agaacagacc gttcagtata tactaactat | 600 |
| ggtggatgat | atgctgcagg | aaaatcatca | gcgtgttagc attttctttg actatgcaag | 660 |
| atgtagcaag | aacactgcgt | ggccctactt | tctgccaatg ttgaatcgcc aggatccctt | 720 |
| cactgttcat | atggcagcaa | gaattattgc | caagttagca gcttggggaa aagaactgat | 780 |
| ggaaggcagt | gacttaaatt | actatttcaa | ttggataaaa actcagctga gttcacagaa | 840 |
| actgcgtggt | agcggtgttg | ctgttgaaac | aggaacagtc tcttcaagtg atagttcgca | 900 |
| gtatgtgcag | tgcgtggccg | ggtgtttgca | gctgatgctc cgggtcaatg agtaccgctt | 960 |
| tgcttgggtg | gaagcagatg | gggtaaattg | cataatggga gtgttgagta acaagtgtgg | 1020 |
| ctttcagctc | cagtatcaaa | tgattttttc | aatatggctc ctggcattca gtcctcaaat | 1080 |
| gtgtgaacac | ctgcggcgct | ataatatcat | tccagttctg tctgatatcc ttcaggagtc | 1140 |
| tgtcaaagag | aaagtaacaa | gaatcattct | tgcagcattt cgtaactttt tagaaaaatc | 1200 |
| aactgaaaga | gaaactcgcc | aagaatatgc | cctggctatg attcagtgca agttctgaa | 1260 |
| acagttggag | aacttggaac | agcagaagta | cgatgatgaa gatatcagcg aagatatcaa | 1320 |
| atttcttttg | gaaaaacttg | gagagagtgt | ccaggacctt agttcatttg atgaatacag | 1380 |
| ttcagaactt | aaatctggaa | ggttggaatg | gagtcctgtg cacaaatctg agaaattttg | 1440 |
| gagagagaat | gctgtgaggt | taaatgagaa | gaattatgaa ctcttgaaaa tcttgacaaa | 1500 |
| acttttggaa | gtgtcagatg | atccccaagt | cttagctgtt gctgctcacg atgttggaga | 1560 |
| atatgtgcgg | cattatccac | gaggcaaacg | ggtcatcgag cagctcggtg ggaagcagct | 1620 |
| ggtcatgaac | cacatgcatc | atgaagacca | gcaggtccgc tataatgctc tgctggccgt | 1680 |
| gcagaagctc | atggtgcaca | actgggaata | ccttggcaag cagctccagt ccgagcagcc | 1740 |
| ccagaccgct | gccgcccgaa | gctaagcctg | cctctgccct tccccctccgc ctcaatgcag | 1800 |
| aaccagtagt | gggagcactg | tgtttagagt | taagagtgaa cactgtttga ttttacttgg | 1860 |

| aatttcctct gttatatagc ttttcccaat gctaatttcc aaacaacaac aacaaaataa | 1920 |
| catgtttgcc tgttaagttg tataaaagta ggtgattctg tatttaaaga aaatattact | 1980 |
| gttacatata ctgcttgcaa tttctgtatt tattgttctc tggaaataaa tatagttatt | 2040 |
| aaaggattct cactccaaac atggcctctc tctttacttg gactttgaac aaaagtcaac | 2100 |
| tgttgtctct tttcaaacca aattgggaga attgttgcaa agtagtgaat ggcaaataaa | 2160 |
| tgttttaaaa tctatcgctc tatcaa | 2186 |

<210> SEQ ID NO 6
<211> LENGTH: 3505
<212> TYPE: DNA
<213> ORGANISM: Homo sapiens

<400> SEQUENCE: 6

| cgtcagggc aggggaggga cggcgcaggc gcagaaaagg gggcggcgga ctcggcttgt | 60 |
| tgtgttgctg cctgagtgcc ggagacggtc ctgctgctgc cgcagtcctg ccagctgtcc | 120 |
| gacaatgtcg tcccacctag tcgagccgcc gccgccctg cacaacaaca acaacaactg | 180 |
| cgaggaaaat gagcagtctc tgccccgcc ggccggcctc aacagttcct gggtggagct | 240 |
| acccatgaac agcagcaatg caatgataa tggcaatggg aaaaatgggg ggctggaaca | 300 |
| cgtaccatcc tcatcctcca tccacaatgg agacatggag aagattcttt tggatgcaca | 360 |
| acatgaatca ggacagagta gttccagagg cagttctcac tgtgacagcc cttcgccaca | 420 |
| agaagatggg cagatcatgt ttgatgtgga aatgcacacc agcagggacc atagctctca | 480 |
| gtcagaagaa gaagttgtag aaggagagaa ggaagtcgag gctttgaaga aaagtgcgga | 540 |
| ctgggtatca gactggtcca gtagacccga aaacattcca cccaaggagt tccacttcag | 600 |
| acaccctaaa cgttctgtgt ctttaagcat gaggaaaagt ggagccatga agaaggggg | 660 |
| tattttctcc gcagaatttc tgaaggtgtt cattccatct ctcttccttt ctcatgtttt | 720 |
| ggctttgggg ctaggcatct atattggaaa gcgactgagc acacccctctg ccagcaccta | 780 |
| ctgagggaaa ggaaaagccc ctggaaatgc gtgtgacctg tgaagtggtg tattgtcaca | 840 |
| gtagcttatt tgaacttgag accattgtaa gcatgaccca acctaccacc tgtttttac | 900 |
| atatccaatt ccagtaactc tcaaattcaa tattttattc aaactctgtt gaggcatttt | 960 |
| actaacctta taccctttt ggcctgaaga cattttagaa tttcctaaca gagtttactg | 1020 |
| ttgtttagaa atttgcaagg gcttcttttc cgcaaatgcc accagcagat tataaattttg | 1080 |
| tcagcaatgc tattatctct aattagtgcc accagactag acctgtatca ttcatggtat | 1140 |
| aaattttact cttgcaacat aactaccatc tctctcttaa aacgagatca ggttagcaaa | 1200 |
| tgatgtaaaa gaagctttat tgtctagttg ttttttttcc cccaagacaa aggcaagttt | 1260 |
| ccctaagttt gagttgatag ttattaaaaa gaaaacaaaa caaaaaaaaa aggcaaggca | 1320 |
| caacaaaaaa atatcctggg caataaaaaa aatatttaa accagctttg gagccacttt | 1380 |
| tttgtctaag cctcctaata gcgtcttta atttatagga ggcaaactgt ataaatgata | 1440 |
| ggtatgaaat agaataagaa gtaaaataca tcagcagatt tcatactag tatgttgtaa | 1500 |
| tgctgtcttt tctatggtgt agaatctttc tttctgataa ggaacgtctc aggcttagaa | 1560 |
| atatatgaaa ttgcttttg agattttgc gtgtgtgttt gatattttt acgataatta | 1620 |
| gctgcatgtg aatttttcat gaccttcttt acatttttta ttttttattt ctttattttt | 1680 |
| ttttctctaa gaagaggctt tggaatgagt tccaatttgt gatgttaata caggcttctt | 1740 |
| gttttaggaa gcatcaccta tactctgaag cctttaaact ctgaagagaa ttgtttcaga | 1800 |

```
gttattccaa gcacttgtgc aacttggaaa aacagacttg ggttgtggga acagttgaca    1860
gcgttctgaa aagatgccat ttgtttcctt ctgatctctc actgaataat gtttactgta    1920
cagtcttccc aaggtgattc ctgcgactgc aggcactggt catttctca tgtagctgtc     1980 ttttcagtta tggtaaactc ttaaagttca gaacactcaa cagattcctt cagtgatata    2040
cttgttcgtt catttctaaa atgtgaagct ttaggaccaa attgttagaa agcatcagga    2100
tgaccagtta tctcgagtag attttcttgg atttcagaac atctagcatg actctgaagg    2160
ataccacatg ttttatatat aaataattac tgtttatgat atagacattg atattgacta    2220
tttagagaac cgttgttaat tttaaaacta gcaatctata aagtgcacca ggtcaacttg    2280
aataaaaaca ctatgacaga caggtttgcc agtttgcaga aactaactct tttctcacat    2340
caacatttgt aaaattgatg tgttatagtg gaaaataaca tatagattaa acaaaatttt    2400
tatctttttt caagaatata gctggctatc tttaagaaag atgatatatc ctagttttga    2460
aagtaatttc cttttttctt tctagcattt gatgtctaaa taattttgga catctttttc    2520
ctagaccatg tttctgtctt actcttaaac ctggtaacac ttgatttgcc ttctataacc    2580
tatttatttc aagtgttcat atttgaattt cttgggaag aaagtaaatc tgatggctca     2640 ctgattttg aaaagcctga ataaaattgg aaagactgga aagttaggag aactgactag     2700
ctaaactgct acagtatgca atttctatta caattggtat tacaggggg aaaagtaaaa     2760 ttacacttta cctgaaagtg acttcttaca gctagtgcat tgtgctcttt ccaagttcag    2820
cagcagttct atcagtggtg ccactgaaac tgggtatatt tatgatttct ttcagcgtta    2880 aaagaaaca tagtgttgcc cttttctta aagcatcagt gaaattatgg aaaattactt      2940
aaaacgtgaa tacatcatca cagtagaatt tattatgaga gcatgtagta tgtatctgta    3000
gccctaacac atgggatgaa cgttttactg ctacacccag atttgtgttg aacgaaaaca    3060
ttgtggtttg gaaaggagaa ttcaacaatt aatagttgaa attgtgaggt taatgtttaa    3120
aaagctttac acctgtttac aatttgggga caaaaaggca ggcttcattt ttcatatgtt    3180
tgatgaaaac tggctcaaga tgtttgtaaa tagaatcaag agcaaaactg cacaaacttg    3240
cacattggaa agtgcaacaa gttcccgtga ttgcagtaaa aatatttact attctaaaaa    3300
aatgagaatt gaagacttag ccagtcagat aagtttttc atgaaccgt tgtggaaatt     3360 attggaatta actgagccaa agtgattatg cattcttcat ctattttagt tagcactttg    3420
tatcgttata tacagtttac aatacatgta taacttgtag ctataaacat tttgtgccat    3480
taaagctctc acaaaacttt aaaaa                                          3505

<210> SEQ ID NO 7
<211> LENGTH: 2949
<212> TYPE: DNA
<213> ORGANISM: Homo sapiens

<400> SEQUENCE: 7
cgcctccctt cccctcccc gcccgacagc ggccgctcgg gccccggctc tcggttataa      60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
```

```
ggaatctctg gggaacggaa ctgatttttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg gacactgat atttcctggc ttactggaga     720
agaattgcat gtggaagtgt tggagaatgt tccacttaca acacacaact tgtacgaaa     780 aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc caatgtgca tataaacaca atagaacctg tcaatattga    1200
tgacttgatt agagaccaag gatttcgtgg tgatggagga tcaaccacag gtttgtctgc   1260 tacccccct gcctcattac ctggctcact aactaacgtg aaagccttac agaaatctcc    1320
aggacctcag cgagaaagga agtcatcttc atcctcagaa acaggaatc gaatgaaaac    1380 acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta tgttaccca gtggtgtgag ggctccagct tgtatcacca    1680
tctccatatc attgagacca aatttgagat gatcaaactt atagatattg cacgacagac   1740
tgcacagggc atggattact acacgccaa gtcaatcatc cacagagacc tcaagagtaa    1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata    2340 tggtgcgttt cctgtccact gaaacaaatg agtgagagag ttcaggagag tagcaacaaa   2400
aggaaaataa atgaacatat gtttgcttat atgttaaatt gaataaaata ctctctttt    2460 ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca acttttgttg ccagctatca   2700
catgtccact agggactcca gaagaagacc ctacctatgc ctgtgtttgc aggtgagaag   2760
```

```
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                            2949

<210> SEQ ID NO 8
<211> LENGTH: 2260
<212> TYPE: DNA
<213> ORGANISM: Homo sapiens

<400> SEQUENCE: 8
cgcagccccg ttcctgccc gcacctctcc ctccacacct ccccgcaagc tgagggagcc      60
ggctccggcc tcggccagcc caggaaggcg ctcccacagc gcagtggtgg gctgaagggc    120
tcctcaagtg ccgccaaagt gggagcccag gcagaggagg cgccgagagc gagggagggc    180
tgtgaggact gccagcacgc tgtcacctct caatagcagc ccaaacagat taagacatgg    240
gagatgtaca agggcagccg tggggctggc aacagcttcg taatcctggc ttcctgcttt    300
ctgggtcaaa gccctggtgg tgtgttcttg atatcggtcc atctagtggc gttgtttgat    360
tcctcccacc ttgctgatca ttcgtagtgt agcccccaag gtgtggaata acccttaagc    420
ccttaccggg gtccttctgg actgagaatt gttgtaaagt aatactgctc aggtgaaaga    480
caacttgagt ggttaaatta ctgtcatgca aagcgactag atggttcagc tgattgcacc    540
tttagaagtt atgtggaacg aggcagcaga tcttaagccc cttgctctgt cacgcaggct    600
ggaatgcagt ggtggaatca tggctcacta cagccctgac ctcctgggcc cagagatgga    660
gtctcgctat tttgcccagg ttggtcttga acacctggct tcaagcagtc ctcctgcttt    720
tggcttcttg aagtgcttgg attacagtat ttcagtttta tgctctgcaa caagtttggc    780
catgttggag gacaatccaa aggtcagcaa gttggctact ggcgattgga tgctcactct    840
gaagccaaag tctattactg tgcccgtgga atccccagc tcccctctgg atgatacacc      900
ccctgaagac tccattcctt tggtcttttcc agaattagac cagcagctac agccctgcc     960 gccttgtcat gactccgagg aatccatgga ggtgttcaaa cagcactgcc aaatagcaga    1020
agaataccat gaggtcaaaa aggaaatcac cctgcttgag caaaggaaga aggagctcat    1080
tgccaagtta gatcaggcag aaaaggagaa ggtggatgct gctgagctgg ttcgggaatt    1140
cgaggctctg acggaggaga atcggacgtt gaggttggcc cagtctcaat gtgtggaaca    1200
actggagaaa cttcgaatac agtatcagaa gaggcagggc tcgtcctaac tttaaatttt    1260
tcagtgtgag catacgaggc tgatgactgc cctgtgctgg ccaaaagatt tttattttaa    1320
atgaatagtg agtcagatct attgcttctc tgtattaccc acatgacaac tgtctataat    1380
gagtttactg cttgccagct tctagcttga gagaagggat attttaaatg agatcattaa    1440
cgtgaaacta ttactagtat atgttttttgg agatcagaat tcttttccaa agatatatgt    1500 tttttttcttt tttaggaaga tatgatcatg ctgtacaaca gggtagaaaa tgataaaaat    1560
agactattga ctgacccagc taagaatcgt gggctgagca gagttaaacc atgggacaaa    1620
cccataacat gttcaccata gtttcacgta tgtgtatttt taaatttcat gcctttaata    1680
tttcaaatat gctcaaattt aaactgtcag aaacttctgt gcatgtattt atatttgcca    1740
gagtataaac tttatactc tgattttat ccttcaatga ttgattatac taagaataaa      1800
tggtcacata tcctaaaagc ttcttcatga aattattagc agaaaccatg tttgtaacca    1860
```

| | |
|---|---:|
| aagcacattt gccaatgcta actggctgtt gtaataataa acagataagg ctgcatttgc | 1920 |
| ttcatgccat gtgacctcac agtaaacatc tctgcctttg cctgtgtgtg ttctgggga | 1980 |
| gggggacat ggaaaaatat tgtttggaca ttacttgggt gagtgcccat gaaaacatca | 2040 |
| gtgaacttgt aactattgtt ttgttttgga tttaaggaga tgttttagat cagtaacagc | 2100 |
| taataggaat atgcgagtaa attcagaatt gaaacaattt ctccttgttc tacctatcac | 2160 |
| cacattttct caaattgaac tctttgttat atgtccattt ctattcatgt aacttctttt | 2220 |
| tcattaaaca tggatcaaaa ctgacaaaaa aaaaaaaaa | 2260 |

<210> SEQ ID NO 9
<211> LENGTH: 7680
<212> TYPE: DNA
<213> ORGANISM: Homo sapiens

<400> SEQUENCE: 9

| | |
|---|---:|
| ggggccgggg ggcggagcct tgcgggctgg agcgaaagaa tgcgggggct gagcgcagaa | 60 |
| gcggctcgag gctggaagag gatcttgggc gccgccagtc tttagcacca gttggtgtag | 120 |
| gagttgagac ctacttcaca gtagttctgt ggacaatcac aatgggaatc caaggagggt | 180 |
| ctgtcctgtt cgggctgctg ctcgtcctgg ctgtcttctg ccattcaggt catagcctgc | 240 |
| agtgctacaa ctgtcctaac ccaactgctg actgcaaaac agccgtcaat tgttcatctg | 300 |
| attttgatgc gtgtctcatt accaaagctg ggttacaagt gtataacaag tgttggaagt | 360 |
| ttgagcattg caatttcaac gacgtcacaa cccgcttgag ggaaaatgag ctaacgtact | 420 |
| actgctgcaa gaaggacctg tgtaacttta cgaacagct tgaaaatggt gggacatcct | 480 |
| tatcagagaa acagttctt ctgctggtga ctccattctt ggcagcagcc tggagccttc | 540 |
| atccctaagt caacaccagg agagcttctc ccaaactccc cgttcctgcg tagtccgctt | 600 |
| tctcttgctg ccacattcta aaggcttgat attttccaaa tggatcctgt tgggaaagaa | 660 |
| taaaattagc ttgagcaacc tggctaagat agagggggctc tgggagactt tgaagaccag | 720 |
| tcctgtttgc agggaagccc cacttgaagg aagaagtcta agagtgaagt aggtgtgact | 780 |
| tgaactagat tgcatgcttc ctcctttgct cttgggaaga ccagctttgc agtgacagct | 840 |
| tgagtgggtt ctctgcagcc ctcagattat ttttcctctg gctccttgga tgtagtcagt | 900 |
| tagcatcatt agtacatctt ggagggtgg ggcaggagta tatgagcatc ctctctcaca | 960 |
| tggaacgctt tcataaactt cagggatccc gtgttgccat ggaggcatgc caaatgttcc | 1020 |
| atatgtgggt gtcagtcagg gacaacaaga tccttaatgc agagctagag gacttctggc | 1080 |
| agggaagtgg ggaagtgttc cagatagcag ggcatgaaaa cttagagagg tacaagtggc | 1140 |
| tgaaaatcga gttttcctc tgtctttaaa ttttatatgg gctttgttat cttccactgg | 1200 |
| aaaagtgtaa tagcatacat caatggtgtg ttaaagctat ttccttgcct ttttttatt | 1260 |
| ggaatggtag gatatcttgg ctttgccaca cacagttaca gagtgaacac tctactacat | 1320 |
| gtgactggca gtattaagtg tgcttatttt aaatgttact ggtagaaagg cagttcaggt | 1380 |
| atgtgtgtat atagtatgaa tgcagtgggg acacccttg tggttacagt ttgagacttc | 1440 |
| caaaggtcat ccttaataac aacagatctg caggggtatg ttttaccatc tgcatccagc | 1500 |
| ctcctgctaa ctcctagctg actcagcata gattgtataa aatacctttg taacggctct | 1560 |
| tagcacactc acagatgttt gaggctttca gaagctcttc taaaaaatga tacacacctt | 1620 |
| tcacaagggc aaacttttc cttttccctg tgtattctag tgaatgaatc tcaagattca | 1680 |
| gtagacctaa tgacatttgt attttatgat cttggctgta tttaatggca taggctgact | 1740 |

```
tttgcagatg gaggaatttc ttgattaatg ttgaaaaaaa acccttgatt atactctgtt    1800
ggacaaaccg agtgcaatga atgatgcttt tctgaaaatg aaatataaca agtgggtgaa    1860
tgtggttatg gccgaaaagg atatgcagta tgcttaatgg tagcaactga aagaagacat    1920
cctgagcagt gccagctttc ttctgttgat gccgttccct gaacatagga aaatagaaac    1980
ttgcttatca aaacttagca ttaccttggt gctctgtgtt ctctgttagc tcagtgtctt    2040
tccttacatc aataggtttt ttttttttttt tttggcctga ggaagtactg accatgccca    2100
cagccaccgg ctgagcaaag aagctcattt catgtgagtt ctaaggaatg agaaacaatt    2160
ttgatgaatt taagcagaaa atgaatttct gggaactttt ttggggcgg ggggtgggg      2220 aattcagcca cactccagaa agccaggagt cgacagtttt ggaagcctct ctcaggattg    2280
agattctagg atgagattgg cttactgcta tcttgtgtca tgtacccact ttttggccag    2340
actacactgg gaagaaggta gtcctctaaa gcaaaatctg agtgccacta aatggggaga    2400
tggggctgtt aagctgtcca aatcaacaag ggtcatataa atggccttaa actttggggt    2460
tgctttctgc aaaaagttgc tgtgactcat gccatagaca aggttgagtg cctggaccca    2520
aaggcaatac tgtaatgtaa agacatttat agtactaggc aaacagcacc ccaggtactc    2580
caggccctcc tggctggaga gggctgtggc aatagaaaat tagtgccaac tgcagtgagt    2640
cagcctaggt taaatagaga gtgtaagagt gctggacagg aacctccacc ctcatgtcac    2700
atttcttcaa tgtgacccctt ctggcccctc tcctcctgac agcggaacaa tgactgcccc    2760
gataggtgag gctggaggaa gaatcagtcc tgtccttggc aagctcttca ctatgacagt    2820
aaaggctctc tgcctgctgc caaggcctgt gactttctaa cctggcctca cgctgggtaa    2880
gcttaaggta gaggtgcagg attagcaagc ccacctggct accaggccga cagctacatc    2940
ctccaactga ccctgatcaa cgaagaggga ttcatgtgtc tgtctcagtt ggttccaaat    3000
gaaaccaggg agcaggggag ttaggaatcg aacaccagtc atgcctactg gctctctgct    3060
cgagagccaa taccctgtgc cctccactca tctggattta caggaactgt catagtgttc    3120
agtattgggt ggtgataagc ccattggatt gtccccttgg ggggatgagc taggggtgca    3180
aggaacacct gatgagtaga taagtggagc tcatggtatt tcctgaaaga tgctaatcta    3240
tttgccaaac ttggtcttga atgtactggg ggcttcaagg tatgggtata ttttcttgt     3300 gtccttgcag ttagccccca tgtcttatgt gtgtcctgaa aaaataagag cctgcccaag    3360
actttgggcc tcttgacaga attaaccact tttatacatc tgagttctct tggtaagttc    3420
tttagcagtg ttcaaagtct actagctcgc attagtttct gttgctgcca acagatctga    3480
actaatgcta acagatcccc ctgagggatt cttgatgggc tgagcagctg gctggagcta    3540
gtactgactg acattcattg tgatgagggc agctttctgg tacaggattc taagctctat    3600
gttttatata catttttcatc tgtacttgca cctcacttta cacaagagga aactatgcaa    3660
agttagctgg atcgctcaag gtcacttagg taagttggca agtccatgct tcccactcag    3720
ctcctcaggt cagcaagtct acttctctgc ctattttgta tactctcttt aatatgtgcc    3780
tagctttgga aagtctagaa tgggtccctg gtgccttttt actttgaaga aatcagtttc    3840
tgcctctttt tggaaaagaa aacaaagtgc aattgttttt tactggaaag ttacccaata    3900
gcatgaggtg aacaggacgt agttaggcct tcctgtaaac agaaaatcat atcaaaacac    3960
tatcttccca tctgtttctc aatgcctgct acttcttgta gatatttcat ttcaggagag    4020
cagcagttaa acccgtggat tttgtagtta ggaacctggg ttcaaaccct cttccactaa    4080
```

```
ttggctatgt ctctggacaa gttttttttt ttttttttt ttaaaccctt tctgaactttt   4140
cactttctat gtctacctca aagaattgtt gtgaggcttg agataatgca tttgtaaagg   4200
gtctgccaga taggaagatg ctagttatgg atttacaagg ttgttaaggc tgtaagagtc   4260
taaaacctac agtgaatcac aatgcattta cccccactga cttggacata agtgaaaact   4320
agccagaagt ctcttttca aattacttac aggttattca atataaaatt tttgtaatgg   4380
ataatcttat ttatctaaac taaagcttcc tgtttataca cactcctgtt attctgggat   4440
aagataaatg accacagtac cttaatttct aggtgggtgc ctgtgatggt tcattgtagg   4500
taaggacatt ttctcttttt cagcagctgt gtaggtccag agcctctggg agaggagggg   4560
ggtagcatgc acccagcagg ggactgaact gggaaactca aggttctttt tactgtgggg   4620
tagtgagctg cctttctgtg atcggtttcc ctagggatgt tgctgttccc ctccttgcta   4680
ttcgcagcta catacaacgt ggccaacccc agtaggctga tcctatatat gatcagtgct   4740
ggtgctgact ctcaatagcc ccacccaagc tggctatagg tttacagata cattaattag   4800
gcaacctaaa atattgatgc tggtgttggt gtgacataat gctatggcca gaactgaaac   4860
ttagagttat aattcatgta ttagggttct ccagagggac agaattagta ggatatatgt   4920
atatatgaaa gggaggttat tagggagaac tggctcccac agttagaagg cgaagtcgca   4980
caataggccg tctgcaagct gggttagaga aagccagta gtggctcagc ctgagttcaa   5040
aaacctcaaa actggggaag ctgacagtgc agccagcctt cagtctgtgg ccaaaggccc   5100
aagagcccct ggcaaccaac ccactggtgc aagtcctaga ttccaaaggc tgaagaacct   5160
ggagtctgat gtccaagagc aggaagagtg aagaaagcc agaagactca gcaaacaagg   5220
tagacagtgt ctaccaccat agtggccata ccaaagaggc taccgattcc ttcctgctac   5280
ctggatccct gaagttgccc tggtctctgc accttctaaa cctagttctt aagagctttc   5340
cattacatga gctgtctcaa agccctccaa taaattctca gtgtaagctt ctgttgcttg   5400
tggacagaaa attctgacag acctacccta taagtgttac tgtcaggata acatgagaac   5460
gcacaacagt aagtggtcac taagtgttag ctacggttat tttgcccaag gtagcatggc   5520
tagttgatgc cggttgatgg ggcttaaacc cagctccctc atcttccagg cctctgtact   5580
ccctattcca ctaaactacc tctcaggttt atttttttaa attcttactc tgcaagtaca   5640
taggaccaca tttacctggg aaaacaagaa taaaggctgc tctgcatttt ttagaaactt   5700
ttttgaaagg gagatgggaa tgcctgcacc cccaagtcca gaccaacaca atggttaatt   5760
gagatgaata ataaaggaaa gactgttctg ggcttcccag aatagcttgg tccttaaatt   5820
gtggcacaaa caacctcctg tcagagccag cctcctgcca ggaagagggg taggagacta   5880
gaggccgtgt gtgcagcctt gccctgaagg ctagggtgac aatttggagg ctgtccaaac   5940
accctggcct ctagagctgg cctgtctatt tgaaatgccg gctctgatgc taatcggcga   6000
ccctcaggca agttacttaa ccttacatgc ctcagttttc tcatctggaa aatgagaacc   6060
ctaggtttag ggttgttaga aaagttaaat gagttaagac aagtgcctgg gacacagtag   6120
cctcttgtgt gtgtttatca ttatgtcctc agcaggtcgt agaagcagct tctcaggtgt   6180
gaggctggcg cgattatctg gagtgggttg gttttctag gatggacccc ctgctgcatt   6240
ttcctcattc atccaccagg gcttaatggg gaatcaagga atccatgtgt aactgtataa   6300
taactgtagc cacactccaa tgaccaccta ctagttgtcc ctggcactgc ttatacatat   6360
gtccatcaaa tcaatcctat gaagtagata ctgtcttcat tttatagatc agagacaatt   6420
ggggttcaga gagctgatgt gattttccca gggtcacaga gagtcccaga ttcaggcaca   6480
```

-continued

```
actcttgtat tccaagacac aaccactaca tgtccaaagg ctgcccagag ccaccgggca    6540
cggcaaattg tgacatatcc ctaaagaggc tgagcacctg gtcaggatct gatggctgac    6600
agtgtgtcca gatgcagagc tggagtgggg gaggggaagg ggggctcctt gggacagaga    6660
aggctttctg tgctttctct gaagggagca gtctgaggac caagggaacc cggcaaacag    6720
cacctcaggt actccaggcc ctcctggctg gagagggctg tggcaatgga aaattagtgc    6780
caactgcaat gagtcagcct cggttaaata gagagtgaag aatgctggac aggaacctcc    6840
accctcatgt cacatttctt cagtgtgacc cttctggccc ctctcctcct gacagcggaa    6900
caatgactgc cccgataggt gaggctggag gaagaatcag tcctgtcctt ggcaagctct    6960
tcactatgac agtaaaggct ctctgcctgc tgccaaggcc tgtgactttc taacctggcc    7020
tcacgctggg taagcttaag gtagaggtgc aggattagca agcccacctg gctaccaggc    7080
cgacagctac atcttttcaac tgaccctgat caacgaagag ggacttgtgt ctctcagttg    7140
gttccaaatg aaaccaggga gcaggggcgt taggaagctc caacaggatg gtacttaatg    7200
gggcatttga gtggagaggt aggtgacata gtgctttgga gcccagggag ggaaaggttc    7260
tgctgaagtt gaattcaaga ctgttctttc atcacaaact tgagtttcct ggacatttgt    7320
ttgcagaaac aaccgtaggg ttttgcctta acctcgtggg tttattatta cctcataggg    7380
actttgcctc ctgacagcag tttatggggtg ttcattgtgg cacttgagtt ttcttgcata    7440
cttgttagag aaaccaagtt tgtcatcaac ttcttatta accccctggc tataacttca    7500
tggattatgt tataattaag ccatccagag taaaatctgt ttagattatc ttggagtaag    7560
ggggaaaaaa tctgtaattt tttctcctca actagatata tacataaaaa atgattgtat    7620
tgcttcattt aaaaaatata acgcaaaatc tcttttcctt ctaaaaaaaa aaaaaaaaa    7680
```

<210> SEQ ID NO 10
<211> LENGTH: 2880
<212> TYPE: DNA
<213> ORGANISM: Homo sapiens

<400> SEQUENCE: 10

```
gcttccctgg gtgccacggt catgtgactt cggcaagatg gctgccctga cagcggagca      60
ttttgcagca ctccagagcc tgctcaagct gctccaggct ctgcaccgcc tcactaggct     120
ggtggcattc cgtgacctgt cctctgccga ggcaattctg gctctctttc cagaaaattt     180
ccaccaaaac ctcaaaaacc tgctgacaaa gatcatccta gaacatgtgt ctacttggag     240
aaccgaagcc caggcaaatc agatctctct gccacgcctg gtcgatctgg actggagagt     300
ggatatcaaa acctcctcag acagcatcag ccgcatggcc gtccccacct gcctgctcca     360
gatgaagatc caagaagatc ccagcctatg cggagacaaa ccctccatct cagctgtcac     420
cgtggagctg agcaaagaaa cactggacac catgttagat ggcctgggcc gcatccgaga     480
ccaactctct gccgtggcca gtaaatgatc cagccagctg ccaggccac tgccatgacc     540 cagctgctca tgagtgataa atgtctcccc atatgcaggc tgcccttgca gctgcagctg     600
acaacaggca ggatggtggg gacagcaggg ggctactgcc atccagaagt tacagttgga     660
ttgggaagaa gcagccagat ccccgctgt tctcactcat cttctttctc tttctgaagc     720
tggagagcag aagcccccat ctttgaaaag ctcctgagtg caacttaatt accaccatgg     780
cagggtgagg gaacatttgc atcgtcagct gcctctgcat agctgtttga gaaattcagg     840
cccaaatcat gcagcctatc caataagtaa gtttatttcc aacattagct ctaattagtt     900
```

| | |
|---|---:|
| catttccaat cccagaacac atggagggaa tcggacaggt gatgccagca gttcctgctc | 960 |
| ctctgtcagg gaagccaggc agagcccaca gagcatggtc catccagagt gttccctgag | 1020 |
| cccccctccac catactggaa cccctcttca gtgtaggaag tctgaaatgg gtgctaattc | 1080 |
| ccttcttcat gaaaccaggg ccctcttcct tcatctaatg cagccactcc taggtgaaga | 1140 |
| agtgggaata attggaaata aacaacagtt ctaaaacttc catgattttt gtagcttctt | 1200 |
| ttgtccccaa gttgaagctt ttggccagta ccttctctag ttttttaaaga tgatcccaac | 1260 |
| ttcctaattc ccagctaagc ccttgaccca tggtgtgaca tgaaatcagg caattgaatc | 1320 |
| gcaccacttt ctgtgttttc acctgttacg tagaacaaaa ggaagcaagg tggccaggcg | 1380 |
| caatggctca cgcctgtaat cccagcactt tgggaggccg aggcaggcag atcatgaggt | 1440 |
| caggagatcg agaccatggt gaaaccccat ctctactaaa aatacaaaaa attagctggg | 1500 |
| cgcggtggcg ggcatctgta gtcccagctc ctcgggaggc tgaggcagga aatggcgtg | 1560 |
| aacctgggag gcagagcttg cagtgagccg agatcgtgcc actgcactcc agtctgggtg | 1620 |
| acagagaagg actcgtctca aaaataaaa ataaataaaa aggaagcaag gctaatcatc | 1680 |
| agtatgtgct tgttacaaga gctatgatga aggcactcct tcgagtttaa ccaaatgaga | 1740 |
| tcatctctgt catgtgcctc acgcctcaca gggactccat gtgtgaagat tccccttca | 1800 |
| ctcaccagat catctccatg gcaacagctt gcagcctgct cttggagtgc tttgttttgg | 1860 |
| cagcttctct gctagtttgt gtatggagtg aatggaggag gtaaatccac agattaagaa | 1920 |
| tatgctgtca ggagtcaggc agccaaggtc agaagccagc tctgcttctc agtggtaagg | 1980 |
| tgcttgactt ctacatctca attttcaccc actttgtact ttttcctaa attaaatgag | 2040 |
| tataatagta gtacctactt gataggactt ttgtgaaaat taaatgatat aatgcaccta | 2100 |
| aaaacagtac tgttacaact aataggaaag gctttgatta ttaatggatg agagtagaaa | 2160 |
| gcttggtgca tttattgtct catctactat aacagagttg gtgtgagaat tagtattatc | 2220 |
| atcctccctt tattgaccag gaaaccagct cattgagatt gagtcatctg ctggtaaatg | 2280 |
| gtctcattaa gaggtggacc catatttctc tagctttctc tttacaacac aggactttgc | 2340 |
| aaggaacata taattctgtg actagcgcca tttggaaaat gttgaaactg aagtagagat | 2400 |
| gagagatctt acgtctgcct acccagtgag atacgaggaa ggtcaaggga aaaaaattc | 2460 |
| caagctcttc tttatctgct ataggaaatg aacattcaat tttttgcatg caacgacaag | 2520 |
| aggtcaagga ccccagaagc cagcccgcta cttccaagtt gagagcccct ggtcataccc | 2580 |
| tccagttgag ctcagatttg tcacaaattt acccctctcc tttccttcca ttccccatga | 2640 |
| cctgcagaga gagatgtcag ataccttcct cttggcctcc catgggcatc cataagaaac | 2700 |
| ttacttgaag caagaagccc agtataggtg tctgggcagt tggacatttc tctctagccag | 2760 |
| atctgtccga atagagccat ctgggtacat gacgcagagg gcatttgata aataactgga | 2820 |
| aaagtcaata atctttgct acccttcaaa aaaaaaaaaa aaaaaaaaa aaaaaaaaa | 2880 |

```
<210> SEQ ID NO 11
<211> LENGTH: 2358
<212> TYPE: DNA
<213> ORGANISM: Homo sapiens

<400> SEQUENCE: 11
```

| | |
|---|---:|
| aaactcacac aacaactctt ccccgctgag aggagacagc cagtgcgact ccaccctcca | 60 |
| gctcgacggc agccgccccg gccgacagcc ccgagacgca agcccggcgc gtcccggtcc | 120 |
| ccacctccga ccaccgccag cgctccaggc cccgccgctc cccgctcgcc gccaccgcgc | 180 |

```
cctccgctcc gcccgcagtg ccaaccatga ccgccgccag tatgggcccc gtccgcgtcg    240
ccttcgtggt cctcctcgcc ctctgcagcc ggccggccgt cggccagaac tgcagcgggc    300
cgtgccggtg cccggacgag ccggcgccgc gctgcccggc gggcgtgagc ctcgtgctgg    360
acggctgcgg ctgctgccgc gtctgcgcca agcagctggg cgagctgtgc accgagcgcg    420 accccctgcga cccgcacaag ggcctcttct gtgacttcgg ctccccggcc aaccgcaaga    480
tcggcgtgtg caccgccaaa gatggtgctc cctgcatctt cggtggtacg gtgtaccgca    540
gcggagagtc cttccagagc agctgcaagt accagtgcac gtgcctggac ggggcggtgg    600
gctgcatgcc cctgtgcagc atggacgttc gtctgcccag ccctgactgc cccttcccga    660
ggagggtcaa gctgcccggg aaatgctgcg aggagtgggt gtgtgacgag cccaaggacc    720
aaaccgtggt tgggcctgcc ctcgcggctt accgactgga agacacgttt ggcccagacc    780
caactatgat tagagccaac tgcctggtcc agaccacaga gtggagcgcc tgttccaaga    840
cctgtgggat gggcatctcc acccgggtta ccaatgacaa cgcctcctgc aggctagaga    900
agcagagccg cctgtgcatg gtcaggcctt gcgaagctga cctggaagag aacattaaga    960
agggcaaaaa gtgcatccgt actcccaaaa tctccaagcc tatcaagttt gagctttctg   1020
gctgcaccag catgaagaca taccgagcta aattctgtgg agtatgtacc gacggccgat   1080
gctgcacccc ccacagaacc accaccctgc cggtggagtt caagtgccct gacggcgagg   1140
tcatgaagaa gaacatgatg ttcatcaaga cctgtgcctg ccattacaac tgtcccggag   1200
acaatgacat ctttgaatcg ctgtactaca ggaagatgta cggagacatg gcatgaagcc   1260
agagagtgag agacattaac tcattagact ggaacttgaa ctgattcaca tctcattttt   1320
ccgtaaaaat gatttcagta gcacaagtta tttaaatctg tttttctaac tgggggaaaa   1380
gattcccacc caattcaaaa cattgtgcca tgtcaaacaa atagtctatc aaccccagac   1440
actggtttga agaatgttaa gacttgcag tggaactaca ttagtacaca gcaccagaat   1500
gtatattaag gtgtggcttt aggagcagtg ggagggtacc agcagaaagg ttagtatcat   1560
cagatagcat cttatacgag taatatgcct gctatttgaa gtgtaattga gaaggaaaat   1620
tttagcgtgc tcactgacct gcctgtagcc ccagtgacag ctaggatgtg cattctccag   1680
ccatcaagag actgagtcaa gttgttcctt aagtcagaac agcagactca gctctgacat   1740
tctgattcga atgacactgt tcaggaatcg gaatcctgtc gattagactg dacagcttgt   1800
ggcaagtgaa tttgcctgta acaagccaga ttttttaaaa tttatattgt aaatattgtg   1860
tgtgtgtgtg tgtgtgtata tatatatata tgtacagtta tctaagttaa tttaaagttg   1920
tttgtgcctt tttattttg tttttaatgc tttgatattt caatgttagc ctcaatttct   1980
gaacaccata ggtagaatgt aaagcttgtc tgatcgttca aagcatgaaa tggatactta   2040
tatggaaatt ctgctcagat agaatgacag tccgtcaaaa cagattgttt gcaaagggga   2100
ggcatcagtg tccttggcag gctgatttct aggtaggaaa tgtggtagcc tcacttttaa   2160
tgaacaaatg gcctttatta aaaactgagt gactctatat agctgatcag ttttttcacc   2220
tggaagcatt tgttctact ttgatatgac tgtttttcgg acagttatt tgttgagagt   2280 gtgaccaaaa gttacatgtt tgcacccttc tagttgaaaa taaagtgtat atttttctta   2340
taaaaaaaaa aaaaaaaa                                                 2358
```

<210> SEQ ID NO 12
<211> LENGTH: 4697
<212> TYPE: DNA

<213> ORGANISM: Homo sapiens

<400> SEQUENCE: 12

```
agacgctcgc ctggcagctg cgcacactcg gagcgccccg agcggcgcag atagggacgt    60
tggggctgtg ccccgcggcg cggcgcctgc cactgcgcag gcgcctcagg aagagctcgg   120
catcgcccct cttcctccag gtccccsttc cccgcaactt cccacgagtg ccaggtgccg   180
cgagcgccga gttccgcgca ttggaaagaa gcgaccgcgg cggctggaac cctgattgct   240
gtccttcaac gtgttcatta tgaagttatt agtaatactt ttgttttctg gacttataac   300
tggttttaga agtgactctt cctctagttt gccacctaag ttactactag tatcctttga   360
tggcttcaga gctgattatc tgaagaacta tgaatttcct catctccaga attttatcaa   420
agaaggtgtt ttggtagagc atgttaaaaa tgttttatc acaaaaacat ttccaaacca   480
ctacagtatt gtgacaggct gtatgaaga aagccatggc attgtggcta attccatgta   540
tgatgcagtc acaaagaaac acttttctga ctctaatgac aaggatcctt tttggtggaa   600
tgaggcagta cctatttggg tgaccaatca gcttcaggaa aacagatcaa gtgctgctgc   660
tatgtggcct ggtactgatg tacccattca cgataccatc tcttcctatt ttatgaatta   720
caactcctca gtgtcatttg aggaaagact aaataatatt actatgtggc taaacaattc   780
gaacccacca gtcaccttg caacactata ttgggaagaa ccagatgcaa gtggccacaa   840
atacggacct gaagataaag aaaacatgag cagagtgttg aaaaaaatag atgatcttat   900
cggtgactta gtccaaagac tcaagatgtt agggctatgg aaaatctta atgtgatcat   960
tacaagtgat catgggatga cccagtgttc tcaggacaga ctgataaacc tggattcctg  1020
catcgatcat tcatactaca ctcttataga tttgagccca gttgctgcaa tacttcccaa  1080
aataaataga acagagggttt ataacaaact gaaaaactgt agccctcata tgaatgttta  1140
tctcaaagaa gacattccta acagatttta ttaccaacat aatgatcgaa ttcagcccat  1200
tattttggtt gccgatgaag gctggacaat tgtgctaaat gaatcatcac aaaaattagg  1260
tgaccatggt tatgataatt cttttgccta gtatgcatcca tttctagctg cccacggacc  1320
tgcatttcac aaaggctaca agcatagcac aattaacatt gtggatattt atccaatgat  1380
gtgccacatc ctgggattaa accacatcc caataatggg acctttggtc atactaagtg  1440
cttgttagtt gaccagtggt gcattaatct cccagaagcc atcgcgattg ttatcggttc  1500
actcttggtg ttaaccatgc taacatgcct cataataatc atgcagaata gactttctgt  1560
acctcgtcca tttttctcgac ttcagctaca agaagatgat gatgatcctt taattgggtg  1620
acatgtgcta gggcttatac aaagtgtctt tgattaatca caaaactaag aatacatcca  1680
aagaatagtt ttgtaactat gaaaaagaat actttgaaag acaagaact tagactaagc  1740
atgttaaaat tattactttg ttttccttgt gttttgttc ggtgcatttg ctaataagat  1800
aacgctgacc atagtaaaat tgttagtaaa tcattaggta acatcttgtg gtaggaaatc  1860
attaggtaac atcaatccta actagaaata ctaaaaatgg cttttgagaa aaatacttcc  1920
tctgcttgta ttttgcgatg aagatgtgat acatctttaa atgaaaatat accaaaattt  1980
agtaggcatg ttttttctaat aaatttatat atttgtaaag aaaacaacag aaatcttat  2040
gcaatttgtg aattttgtat attagggagg aaaagcttcc tatattttta tatttacctt  2100
taattagttt gtatctcaag taccctcttg aggtaggaaa tgctctgtga tggtaaataa  2160
aattggagca gacagaaaag atatagcaaa tgaagaaata ttttaaggaa acctatttga  2220
aaaaaaagc aaagaccatt tgataaaagc ctgagttgtc accattatgt cttaagctgt  2280
```

```
tagtcttaaa gattattgtt aaaaaattca gaagaaaaga gagacaagtg ctcttctctc      2340
tatctatgct taatgccttt atgtaagtta cttagttgtt tgcgtgtgcc tgtgcaagtg      2400
tgtttgtgtg tggttgtgtg gacattatgt gatttactat ataaggaggt cagagatgga      2460
ctgtggccag gcttccacat tcctgaagca cacagatctc aggaaaggtt attttttgcac     2520 ttcatatttg tttactttct cctaactcac aagttaaaat cataacttaa tttcattaac      2580
ttttatcatt taactctctc atgtttgttg taacctgagg tatccaaatg ctacagaaaa      2640
atttatgacc caaatacaaa tctcaatttg actgggacag aatgaggaat ggagattttt      2700
gtatttatct ttgggacttt atgccttact ttttaggcta tagaatagtt aagaaatttt      2760
aaacaaaatt tagtatcttt tggtctttca caccattcat atgttaagtg cagaatagc       2820 cttagtgcta cctccacttt tttctccagt atttgcatca cagaaataat ccctctgttt      2880
aacatgtttg ttcagagcca agggtttatt gtgaagaact gtcatcctgc ctttgctagc      2940
tggtaccttc tagtaatcaa aattaatatg aagaaactag gttgtgacag actagattat      3000
atttagtagg ggaaaaattg ggctcaagaa ccattcatca gtacgtgaga caagcagtta      3060
atagtatgat ctttaaagtt ttgacaatat aaaataaact tggtaactgt tttacaaata      3120
taaaagtata ataaatatgc agcccagtta atatattgatt atctgtgatg gtaaagaaca     3180
acagtggtgc cagtcatcaa acatacagtg cgtcctattg agtcactgct aatttcttga      3240
gcctggtatt tgctgcctat tgtatttgtg gttgttgaga ggcattttca aaccctgtat      3300
aaataatcca tgctgttggt cataagttaa ctgtattaag aacagtaaaa taataaaaa       3360 ccaatagtac taattttgct ttaaaaaaat ttctaatttt tttcacataa aacaattatc      3420
ctaaaggtta atagttgatc gaaacagaat aatagaaaaa ttctacttta atttccatta      3480
aaaagcaaat agcattgaca catttaaagc ttttcattta aagtagtgga tgttttttgaa     3540 gtatctaaaa tagtagcaga atattttata cttggtcctt gcaatggtgt gagttttaat      3600
gattgcatta tcgtgattgg tggttatgag tttcagaaat ctatacttgg catccaactc      3660
atgagtggat tttatatagg atggaacagg aaggtatgtc ctgtcagtat cttaacccctt     3720 tcaacaagac atttacctat ttgtcttttcc ttacgttctc aaaatattaa ctcgaattgt      3780
aaattaagca aaaatttaaa aagtatatgt tgatgggaca agaagaatag tatttattta      3840
ataaaacata tattatattg aactatgtgt taattcattt gtatctttta aaaaattatc      3900
actgttaaag ccattgactc ctttagtaca ctgagaaaaa tcttatagta aaactagcct      3960
ttcacattaa ggttttggtg tgtattttgt taaataacta acatgctgct ctattttctg      4020
ggtgtagaaa gtatttggct ctaggaaaca tttacttgtt tgtgaaaaca atacccccaag     4080 gtaataggaa aagtttgagt taagtgtttt taattcagtc agtgaattca gaataagtac      4140
attcatgtat aacataggga cagttctgct gctgttattt atatgcaatt cttctggtaa      4200 atagcaaatag aataaaacat atttcaatgt ttgtgtatag gttttatatt attattccac     4260
taggaatggc ataagaattt atagataaat tcttgtaaca ttaaaggatt aaaatgtttt      4320
tacattgttt ttgggtgtct ccttcttgtg cccatatctg ataagcttta tggattattg      4380
catttaattc cttttatttg gagggtttta cttccttgtt aacatataaa gttataaatg      4440
aaggacaagg aggagatgga aaatgtgtat ttattgttaa ttcttaaaat agtgtgtaaa      4500
taaaataaca tcagtgtgct ttaaagaaat gtgtatgtag tgccttaatt taaattaaaa      4560
tatttttgac tgttacttga gttcagaatt aatgactttg ttcatgattt ttaaaatgtg      4620
```
tgtgaataaa atctaccaaa aaattcttac tgtaattatt aaatataaag ttcagtgtca    4680
aaaaaaaaaa aaaaaaa    4697

<210> SEQ ID NO 13
<211> LENGTH: 2448
<212> TYPE: DNA
<213> ORGANISM: Homo sapiens

<400> SEQUENCE: 13
accggcccgg ttccctctcc ggggagcggc ggcggacgcg cggctcccac ccctcccctc      60
tcacgggctc tcccctcccc agtgtggccg cgaccctacc ctctgcaagg cgatggcccg     120
cgccccgagc gcaggctagc gtgcctgggt gcccggccat gggctgtatc ggctctcgga     180
gcccggcggg tcaggcattt ctggggacca acagctggcc gaggctcagg gatagagacg     240
gctgctccag ctaaaggtga atgttggaga cacagtcgcg atgctgccca gtcccggcg      300 agccctaact atccaggaga tcgctgcgct ggccaggtcc tccctgcatg gtatttccca     360
ggtggtgaag gaccacgtga ccaagcctac cgccatggcc cagggccgag tggctcacct     420
cattgagtgg aagggctgga gcaagccgag tgactcacct gctgccctgg aatcagcctt     480
ttcctcctat tcagacctca gcgagggcga acaagaggct cgctttgcag caggagtggc     540
tgagcagttt gccatcgcgg aagccaagct ccgagcatgg tcttcggtgg atggcgagga     600
ctccactgat gactcctatg atgaggactt tgctggggga atggacacag acatggctgg     660
gcagctgccc ctggggccgc acctccagga cctgttcacc ggccaccggt tctcccggcc     720
tgtgcgccag ggctccgtgg agcctgagag cgactgctca cagaccgtgt ccccagacac     780
cctgtgctct agtctgtgca gcctggagga tgggttgttg gctcccggg ccggctggc      840 ctcccagctg ctgggcgatg agctgcttct cgccaaactg cccccagcc gggaaagtgc     900 cttccgcagc ctgggcccac tggaggccca ggactcactc tacaactcgc ccctcacaga     960
gtcctgcctt tccccgcgg aggaggagcc agcccctgc aaggactgcc agccactctg     1020
cccaccacta acgggcagct gggaacggca gcggcaagcc tctgacctgg cctcttctgg    1080
ggtggtgtcc ttagatgagg atgaggcaga gccagaggaa cagtgaccca catcatgcct    1140
ggcagtggca tgcatccccc ggctgctgcc aggggcagag cctctgtgcc caagtgtggg    1200
ctcaaggctc ccagcagagc tccacagcct agagggctcc tgggagcgct cgcttctccg    1260
tgtgtgtttt tgcatgaaag tgtttggaga ggaggcaggg gctgggctgg gggcgcatgt    1320
cctgccccca ctcccggggc ttgccggggg ttgcccgggg cctctggggc atggctacag    1380
ctgtggcaga cagtgatgtt catgttctta aaatgccaca cacacatttc ctcctcggat    1440
aatgtgaacc actaagggg ttgtgactgg gctgtgtgag ggtggggtgg gaggggccc      1500 agcaacccc cacctcccc atgcctctct cttctctgct tttcttctca cttccgagtc     1560
catgtgcagt gcttgataga atcaccccca cctggagggg ctggctcctg ccctcccgga    1620
gcctatgggt tgagccgtcc ctcaagggcc cctgcccagc tgggctcgtg ctgtgcttca    1680
ttcacctctc catcgtctct aaatcttcct cttttttcct aaagacagaa ggttttggt      1740 ctgttttttc agtcggatct tctcttctct gggaggcttt ggaatgatga aagcatgtac    1800
cctccaccct tttcctggcc ccctaatggg gcctgggccc tttcccaacc cctcctagga    1860
tgtgcgggca gtgtgctggc gcctcacagc cagccgggct gcccattcac gcagagctct    1920
ctgagcggga ggtggaagaa aggatggctc tggttgccac agagctggga cttcatgttc    1980
ttctagagag ggccacaaga gggccacagg ggtggccggg agttgtcagc tgatgcctgc    2040

```
tgagaggcag gaattgtgcc agtgagtgac agtcatgagg gagtgtctct tcttggggag    2100
gaaagaaggt agagcctttc tgtctgaatg aaaggccaag gctacagtac agggccccac    2160
cccagccagg gtgttaatgc ccacgtagtg gaggcctctg gcagatcctg cattccaagg    2220
tcactggact gtacgttttt atggttgtgg aagggtggg tggctttaga attaagggcc     2280
ttgtaggctt tggcaggtaa gagggcccaa ggtaagaacg agagccaacg ggcacaagca    2340
ttctatatat aagtggctca ttaggtgttt attttgttct atttaagaat ttgttttatt    2400
aaattaatat aaaaatcttt gtaaatctct aaaaaaaaaa aaaaaaa                  2448

<210> SEQ ID NO 14
<211> LENGTH: 5948
<212> TYPE: DNA
<213> ORGANISM: Homo sapiens

<400> SEQUENCE: 14
ggagcgggcc gagccgccac cgcggccgga gctgtcccct agccagaccc ggcgagacac    60
gagcggcggg agggaggcgg tggcgcgccc ggccccgccc gcccgaccaa gcgtcggacg    120
cggcccggcg ccgagccatg gagcctgagc cagtggagga ctgtgtgcag agcactctcg    180
ccgccctgta tccaccctt gaggcaacag cccccaccct gttgggccag gtgttccagg     240
tggtggagag gacttatcgg gaggacgcac tgaggtacac gctggacttc ctggtaccag    300
ccaagcacct gcttgccaag gtccagcagg aagcctgtgc caatacagtg ggattcctct    360
tcttccatga ggggtggccg ctctgcctgc atgaacaggt ggtggtgcag ctagcagccc    420
taccctggca actgctgcgc ccaggagact tctatctgca ggtggtgccc tcagctgccc    480
aagcaccccg actagcactc aagtgtctgg cccctggggg tggcgggtg caggaggttc     540 ctgtgcccaa tgaggcttgt gcctacctat tcacacctga gtggctacaa ggcatcaaca    600
aggaccggcc aacaggtcgc ctcagtacct gcctactgtc tgcgccctct gggattcagc    660
ggctgccctg ggctgagctc atctgtccac gatttgtgca caaagagggc ctcatggttg    720
gacatcagcc aagtacactg cccccagaac tgccctctgg acctccaggg cttcccagcc    780
ctccacttcc tgaggaggcg ctgggtaccc ggagtcctgg ggatgggcac aatgcccctg    840
tggaaggacc tgagggcgag tatgtggagc tgttagaggt gacgctgccc gtgaggggga    900
gcccaacaga tgctgaaggc tccccaggcc tctccagagt ccggacggta cccacccgca    960
agggcgctgg agggaagggc cgccaccgga gacaccgggc gtggatgcac cagaagggcc    1020
tggggcctcg gggccaggat ggagcacgcc caccggcga ggggagcagc accggagcct     1080
cccctgagtc tcccccagga gctgaggctg tcccagaggc agcagtcttg gaggtgtctg    1140
agcccccagc agaggctgtg ggagaagcct ccggatcttg ccccctgagg ccaggggagc    1200
ttagaggagg aggaggagga ggccagggg ctgaaggacc acctggtacc cctcggagaa     1260
caggcaaagg aaacagaaga agaagcgag ctgcaggtcg aggggctctt agccgaggag     1320
gggacagtgc cccactgagc cctggggaca aggaagatgc cagccaccaa gaagcccttg    1380
gcaatctgcc ctcaccaagt gagcacaagc ttccagaatg ccacctggtt aaggaggaat    1440
atgaaggctc agggaagcca gaatctgagc caaaagagct caaaacagca ggcgagaaag    1500
agcctcagct ctctgaagcc tgtgggccta cagaagaggg ggccggagag agagagctgg    1560
aggggccagg cctgctgtgt atggcaggac acacaggccc agaaggcccc ctgtctgaca    1620
ctccaacacc tccgctggag actgtgcagg aaggaaaagg ggacaacatt ccagaagagg    1680
```

```
cccttgcagt ctccgtctct gatcaccctg atgtagcttg ggacttgatg gcatctggat    1740
tcctcatcct gacgggaggg gtggaccaga gtgggcgagc tctgctgacc attaccccac    1800
cgtgccctcc tgaggagccc ccaccctccc gagacacgct gaacacaact cttcattacc    1860
tccactcact gctcaggcct gatctacaga cactgggggc gtccgtcctg ctggaccttc    1920
gtcaggcacc tccactgcct ccagcactca ttcctgcctt gagccaactt caggactcag    1980
gagatcctcc ccttgttcag cggctgctga ttctcattca tgatgacctt ccaactgaac    2040
tctgtggatt tcagggtgct gaggtgctgt cagagaatga tctgaaaaga gtggccaagc    2100
cagaggagct gcagtgggag ttaggaggtc acagggaccc ctctcccagt cactgggtag    2160
agatacacca ggaagtggta aggctatgtc gcctgtgcca aggtgtgctg ggctcggtac    2220
ggcaggccat tgaggagctg gagggagcag cagagccaga ggaagaggag gcagtgggaa    2280
tgcccaagcc actgcagaag gtgctggcag atccccggct gacggcactg cagagggatg    2340
gggggggccat cctgatgagg ctgcgctcca ctcccagcag caagctggag gccaaggcc    2400
cagctacact gtatcaggaa gtggacgagg ccattcacca gcttgtgcgc ctctccaacc    2460
tgcacgtgca gcagcaagag cagcggcagt gcctgcggcg actccagcag gtgttgcagt    2520
ggctctcggg cccaggggag gagcagctgg caagctttgc tatgcctggg gacaccttgt    2580
ctgccctgca ggagacagag ctgcgattcc gtgctttcag cgctgaggtc caggagcgcc    2640
tggcccaggc acgggaggcc ctggctctgg aggagaatgc cacctcccag aaggtgctgg    2700
atatctttga acagcggctg gagcaggttg agagtggcct ccatcgggcc ctgcggctac    2760
agcgcttctt ccagcaggca catgaatggg tggatgaggg cttttgctcgg ctggcaggag    2820
ctgggccggg tcgggaggct gtgctggctg cactggccct gcggcgggcc ccagagccca    2880
gtgccggcac cttccaggag atgcgggccc tggccctgga cctgggcagc cagcagccc    2940
tgcgagaatg gggccgctgc caggcccgct gccaagagct agagaggagg atccagcaac    3000
acgtgggaga ggaggcgagc ccacggggct accgacgacg gcgggcagac ggtgccagca    3060
gtggagggc ccagtggggg ccccgcagcc cctcgcccag cctcagctcc ttgctgctcc    3120
ccagcagccc tgggccacgg ccagcccccat cccattgctc cctggcccca tgtggagagg    3180
actatgagga gagggccct gagctggctc cagaagcaga gggcaggccc caagagctg    3240
tgctgatccg aggcctggag gtcaccagca ctgaggtggt agacaggacg tgctcaccac    3300
gggaacacgt gctgctgggc cgggctaggg ggccagacgg accctgggga gtaggcaccc    3360
cccggatgga gcgcaagcga agcatcagtg cccagcagcg gctggtgtct gagctgattg    3420
cctgtgaaca agattacgtg gccaccttga gtgagccagt gccaccccct gggcctgagc    3480
tgacgcctga acttcggggc acctgggctg ctgccctgag tgcccgggaa aggcttcgca    3540
gcttccaccg gacacacttt ctgcgggagc ttcagggctg cgccacccac cccctacgca    3600
ttggggcctg cttccttcgc cacggggacc agttcagcct ttatgcacag tacgtgaagc    3660
accgacacaa actggagaat ggtctggctg cgctcagtcc cttaagcaag ggctccatgg    3720
aggctggccc ttacctgccc cgagccctgc agcagcctct ggaacagctg actcggtatg    3780
ggcggctcct ggaggagctc ctgagggaag ctgggcctga gctcagttct gagtgccggg    3840
cccttgggc tgctgtacag ctgctccggg aacaagaggc ccgtggcaga gacctgctgg    3900
ccgtggaggc ggtgcgtggc tgtgagatag atctgaagga gcaggacag ctcttgcatc    3960
gagacccctt cactgtcatc tgtggccgaa agaagtgcct tcgccatgtc tttctcttcg    4020
agcatctcct cctgttcagc aagctcaagg gccctgaagg ggggtcagag atgtttgttt    4080
```

| | | |
|---|---|---|
| acaagcaggc ctttaagact gctgatatgg ggctgacaga aaacatcggg gacagcggac | 4140 | |
| tctgctttga gttgtggttt cggcggcggc gtgcacgaga ggcatacact ctgcaggcaa | 4200 | |
| cctcaccaga gatcaaactc aagtggacaa gttctattgc ccagctgctg tggagacagg | 4260 | |
| cagcccacaa caaggagctc cgagtgcagc agatggtgtc catgggcatt gggaataaac | 4320 | |
| ccttcctgga catcaaagcc cttggggagc ggacgctgag tgccctgctc actggaagag | 4380 | |
| ccgcccgcac ccgggcctcc gtggccgtgt catcctttga gcatgccggc ccctcccttc | 4440 | |
| ccggcctttc gccgggagcc tgctccctgc ctgcccgcgt cgaggaggag gcctgggatc | 4500 | |
| tggacgtcaa gcaaatttcc ctggcccag aaacacttga ctcttctgga gatgtgtccc | 4560 | |
| caggaccaag aaacagcccc agcctgcaac cccccaccc tgggagcagc actcccaccc | 4620 | |
| tggccagtcg agggatctta gggctatccc gacagagtca tgctcgagcc ctgagtgacc | 4680 | |
| ccaccacgcc tctgtgacct ggagaagatc cagaacttgc gtgcagcttc tcctctcagc | 4740 | |
| acactttggg ctgggatggc agtggggcat aatggagccc tgggcgatcg ctgaatttct | 4800 | |
| tccctctgct tcctggacac agaggaggtc taacgaccag agtattgccc tgccaccact | 4860 | |
| atctctagtc tccctagctt ggtgccttct cctgcaggag tcagagcagc acattgctt | 4920 | |
| gccttcatac cctggaggtg gggaagttat ccctcttccg gtgctttccc atcctgggcc | 4980 | |
| actgtatcca ggacatcact cccatgccag ccctccctgg cagcccatgt tctcctcttt | 5040 | |
| tctcaccccc tgactttccc tgagaagaat catctctgcc aggtcaactg gagtccctgg | 5100 | |
| tgactccatt ctgaggtgtc acaagcaatg aagctatgca aacaatagga gggtgtgaca | 5160 | |
| ggggaaccgt agactttata tatgtaatta ctgttattat aatactattg ttatattaaa | 5220 | |
| tgtatttact cacactttgc ctctaaggag ctagagtagt cctctggatt aaggtgataa | 5280 | |
| ataacttgag cactttccct caaccagccc ttaactagaa cacagaaaat aaaaccaaga | 5340 | |
| ctggaaggtc ccctctaccc ctcccaggcc cagagctagc tgactgtgta tgagcctggg | 5400 | |
| agaatgtgtc tcctccacag tggctcccag aggttccaca cactctctga agctccttct | 5460 | |
| cccacactgc acctactcct tgaggctgaa ctggtcacag acaaactggg atccagcaca | 5520 | |
| gtccagcagt tctcaaaatg aggtcctcag gccacagtgc gtgagaactt gcttggctgt | 5580 | |
| ttgttaaatg ctaattcttg ggccccatca gagctactgc atcgaaacct gggggtaaaa | 5640 | |
| cccaatattc tgcatttctt atcaaactct ttgggtgata actaagtgtc tgaagaggtg | 5700 | |
| actatttcct gacagaagga cccaaagagg gaagcaggac ataggtaggc agacagacac | 5760 | |
| agggccctgt gcctcaagac acctgtttat tggggacacg actctgcaat agggatgaca | 5820 | |
| ggaatcgtac caaaaatagc gacgtctaca gggcccctga tggggctaga agggtacagt | 5880 | |
| gccccccacc ctcaccccctt gtacaaaaat aaactctcac gcctatggac cagcaaaaaa | 5940 | |
| aaaaaaaa | 5948 | |

```
<210> SEQ ID NO 15
<211> LENGTH: 3851
<212> TYPE: DNA
<213> ORGANISM: Homo sapiens

<400> SEQUENCE: 15
```

| | | |
|---|---|---|
| ctctcccaac cgcctcgtcg cactcctcag gctgagagca ccgctgcact cgcggccggc | 60 | |
| gatgcgggac cccggcgcgg ccgctccgct ttcgtccctg ggcctctgtg ccctggtgct | 120 | |
| ggcgctgctg ggcgcactgt ccgcgggcgc cggggcgcag ccgtaccacg agagaagggg | 180 | |

-continued

```
catctccgtg ccggaccacg gcttctgcca gcccatctcc atcccgctgt gcacggacat    240
cgcctacaac cagaccatcc tgcccaacct gctgggccac acgaaccaag aggacgcggg    300
cctcgaggtg caccagttct acccgctggt gaaggtgcag tgttctcccg aactccgctt    360
tttcttatgc tccatgtatg cgcccgtgtg caccgtgctc gatcaggcca tcccgccgtg    420
tcgttctctg tgcgagcgcg cccgccaggg ctgcgaggcg ctcatgaaca agttcggctt    480
ccagtggccc gagcggctgc gctgcgagaa cttcccggtg cacggtgcgg gcagagatctg   540
cgtgggccag aacacgtcgg acggctccgg gggcccaggc ggcggcccca ctgcctaccc    600
taccgcgccc tacctgccgg acctgcccttcaccgcgctg cccccggggg cctcagatgg    660
caggggggcgt cccgccttcc ccttctcatg cccccgtcag ctcaaggtgc cccgtacct     720
gggctaccgc ttcctgggtg agcgcgattg tggcgcccg tgcgaaccgg gccgtgccaa      780
cggcctgatg tactttaagg aggaggagag gcgcttcgcc cgcctctggg tgggcgtgtg    840
gtccgtgctg tgctgcgcct cgacgctctt taccgttctc acctacctgg tggacatgcg    900
gcgcttcagc tacccagagc ggcccatcat cttcctgtcg ggctgctact tcatggtggc    960
cgtggcgcac gtggccggct ccttctaga ggaccgcgcc gtgtgcgtgg agcgcttctc     1020
ggacgatggc taccgcacgg tggcgcaggg caccaagaag gagggctgca ccatcctctt    1080
catggtgctc tacttcttcg gcatggccag ctccatctgg tgggtcattc tgtctctcac    1140
ttggttcctg gcggccggca tgaagtgggg ccacgaggcc atcgaggcca actcgcagta   1200
cttccacctg gccgcgtggg ccgtgcccgc cgtcaagacc atcactatcc tggccatggg    1260
ccaggtagac gggggacctgc tgagcggggt gtgctacgtt ggcctctcca gtgtggacgc    1320
gctgcggggc ttcgtgctgg cgcctctgtt cgtctacctc ttcataggca cgtccttctt     1380
gctgccgcgg ttcgtgtccc tcttccgtat ccgcaccatc atgaaacacg acggcaccaa    1440
gaccgagaag ctggagaagc tcatggtgcg catcggcgtc ttcagcgtgc tctacacagt    1500
gcccgccacc atcgtcctgg cctgctactt ctacgagcag gccttccgcg agcactggga    1560
gcgcacctgg ctcctgcaga cgtgcaagag ctatgccgtg ccctgcccgc ccggccactt    1620
cccgcccatg agccccgact tcaccgtctt catgatcaag tacctgatga ccatgatcgt    1680
cggcatcacc actggcttct ggatctggtc gggcaagacc ctgcagtcgt ggcgccgctt    1740
ctaccacaga cttagccaca gcagcaaggg ggagactgcg gtatgagccc cggcccctcc    1800
ccacctttcc caccccagcc ctcttgcaag aggagaggca cggtagggaa aagaactgct    1860
gggtgggggc ctgtttctgt aactttctcc ccctctactg agaagtgacc tggaagtgag    1920
aagttctttg cagatttggg gcgaggggtg atttggaaaa aagacctgg gtggaaagcg     1980
gtttggatga aaagatttca ggcaaagact gcaggaaga tgatgataac ggcgatgtga      2040
atcgtcaaag gtacgggcca gcttgtgcct aatagaaggt tgagaccagc agagactgct    2100
gtgagtttct cccggctccg aggctgaacg gggactgtga gcgatccccc tgctgcaggg    2160
cgagtggcct gtccagaccc ctgtgaggcc ccggaaaagg tacagccctg tctgcggtgg    2220
ctgctttgtt ggaaagaggg agggcctcct gcggtgtgct tgtcaagcag tggtcaaacc    2280
ataatctctt tcactggggg ccaaactgga gcccagatgg gttaatttcc agggtcagac    2340
attacggtct ctcctcccct gcccctccc gcctgttttt cctcccgtac tgctttcagg     2400
tcttgtaaaa taagcatttg gaagtcttgg gaggcctgcc tgctagaatc ctaatgtgag    2460
gatgcaaaag aaatgatgat aacatttga gataaggcca aggagacgtg gagtaggtat     2520
ttttgctact ttttcatttt ctggggaagg caggaggcag aaagacgggt gttttatttg    2580
```

```
gtctaatacc ctgaaaagaa gtgatgactt gttgcttttc aaaacaggaa tgcattttc      2640 cccttgtctt tgttgtaaga gacaaaagag gaaacaaaag tgtctccctg tggaaaggca      2700
taactgtgac gaaagcaact tttataggca aagcagcgca aatctgaggt ttcccgttgg      2760
ttgttaattt ggttgagata acattcctt tttaaggaaa agtgaagagc agtgtgctgt       2820
cacacaccgt taagccagag gttctgactt cgctaaagga aatgtaagag gttttgttgt      2880
ctgttttaaa taaatttaat tcggaacaca tgatccaaca gactatgtta aaatattcag      2940
ggaaatctct cccttcattt acttttttctt gctataagcc tatatttagg tttcttttct    3000 attttttct cccatttgga tcctttgagg taaaaaaaca taatgtcttc agcctcataa       3060
taaaggaaag ttaattaaaa aaaaaaagca aagagccatt ttgtcctgtt ttcttggttc      3120
catcaatctg tttattaaac atcatccata tgctgaccct gtctctgtgt ggttgggttg      3180
ggaggcgatc agcagatacc atagtgaacg aagaggaagg tttgaaccat gggccccatc      3240
tttaaagaaa gtcattaaaa gaaggtaaac ttcaaagtga ttctggagtt ctttgaaatg      3300
tgctggaaga cttaaattta ttaatcttaa atcatgtact ttttttctgt aatagaactc      3360
ggattctttt gcatgatggg gtaaagctta gcagagaatc atgggagcta accttatcc       3420 cacctttgac actaccctcc aatcttgcaa cactatcctg tttctcagaa cagttttaa       3480 atgccaatca tagagggtac tgtaaagtgt acaagttact ttatatatgt aatgttcact      3540
tgagtggaac tgctttttac attaaagtta aaatcgatct tgtgtttctt caaccttcaa      3600
aactatctca tctgtcagat ttttaaaact ccaacacagg ttttggcatc ttttgtgctg      3660
tatcttttaa gtgcatgtga aatttgtaaa atagagataa gtacagtatg tatattttgt      3720
aaatctccca tttttgtaag aaaatatata ttgtatttat acatttttac tttggatttt      3780
tgttttgttg gctttaaagg tctaccccac tttatcacat gtacagatca caaataaatt      3840
tttttaaata c                                                          3851

<210> SEQ ID NO 16
<211> LENGTH: 2394
<212> TYPE: DNA
<213> ORGANISM: Homo sapiens

<400> SEQUENCE: 16
gacgggccgg tacagcccgt gtcccgccc cgcgccatcg ctaggcgacg tgcgcttttg        60
ccgcgccgtg ctgcccgcga gggcagctga ggtggtggtg gcggccgcct tgtcgaggca      120
tcgcgcgccc gtgaagtgtt cgccgtcagt gctgttgggt gcctgagcc gcgtcccccg       180 tcccgaaaac tgtccttgac agtacttgcg cggcccaacg gccgccggcg ccccccgcgtc     240 tccatggcga cggcctttt ccctgcgagg accccggcgg cagggctgcc ccgcggcgcc      300
tgcttggcgc gacgctctag cggttaccgc tgcgggctgg ctgggcgtag tggggctgcg     360
cggctgccac ggagctagag ggcaagtgtg ctcggcccag cgtgcaggga acgcgggcgg     420
ccagacaacg ggctgggctc cggggcctgc ggcgcgggcg ctgagctggc agggcgggtc     480
ggggcgcggg ctgcatccgc atctcctcca tcgcctgcag taaggcggc cgcggcgagc      540 ctttgagggg aacgacttgt cggagcccta accagggta tctctgagcc tggtgggatc     600
cccggagcgt cacatcactt tccgatcact tcaaagtaca gcagaccgag gacacggttg     660
ttaccaagac caggctgttg ccttggaaga gcccagagcg tgtcaaggga gacagccaca     720
tcacgccaga aatacatgac agctggatta gccctgggag agggaggccc agatgtggga     780
```

-continued

| | |
|---|---|
| gctcagggga ggtgcagctc aacgtggagt ttggaggagg ctaccttgac ctttgaatgc | 840 |
| caagtgggag ccagccagat gaaagggtt aaaaactaat atttatatga cagaagaaaa | 900 |
| agatgtcatt ccgtaaagta acatcatca tcttggtcct ggctgttgct ctcttcttac | 960 |
| tggttttgca cctaacttc ctcagcttga gcagtttgtt aaggaatgag gttacagatt | 1020 |
| caggaattgt agggcctcaa cctatagact ttgtcccaaa tgctctccga catgcagtag | 1080 |
| atgggagaca agaggagatt cctgtggtca tcgctgcatc tgaagacagg cttgggggg | 1140 |
| ccattgcagc tataaacagc attcagcaca acactcgctc caatgtgatt ttctacattg | 1200 |
| ttactctcaa caatacagca gaccatctcc ggtcctggct caacagtgat tccctgaaaa | 1260 |
| gcatcagata caaaattgtc aattttgacc ctaaactttt ggaaggaaaa gtaaaggagg | 1320 |
| atcctgacca gggggaatcc atgaaacctt taacctttgc aaggttctac ttgccaattc | 1380 |
| tggttcccag cgcaaagaag gccatataca tggatgatga tgtaattgtg caaggtgata | 1440 |
| ttcttgccct ttacaataca gcactgaagc caggacatgc agctgcattt tcagaagatt | 1500 |
| gtgattcagc ctctactaaa gttgtcatcc gtggagcagg aaaccagtac aattacattg | 1560 |
| gctatcttga ctataaaaag gaaagaattc gtaagctttc catgaaagcc agcacttgct | 1620 |
| catttaatcc tggagttttt gttgcaaacc tgacggaatg gaaacgacag aatataacta | 1680 |
| accaactgga aaaatggatg aaactcaatg tagaagaggg actgtatagc agaaccctgg | 1740 |
| ctggtagcat cacaacacct cctctgctta tcgtatttta tcaacagcac tctaccatcg | 1800 |
| atcctatgtg gaatgtccgc caccttggtt ccagtgctgg aaaacgatat tcacctcagt | 1860 |
| ttgtaaaggc tgccaagtta ctccattgga atggacattt gaagccatgg ggaaggactg | 1920 |
| cttcatatac tgatgtttgg gaaaaatggt atattccaga cccaacaggc aaattcaacc | 1980 |
| taatccgaag atataccgag atctcaaaca taaagtgaaa cagaatttga actgtaagca | 2040 |
| agcatttctc aggaagtcct ggaagatagc atgcgtggga agtaacagtt gctaggcttc | 2100 |
| aatgcctatc ggtagcaagc catggaaaaa gatgtgtcag ctaggtaaag atgacaaact | 2160 |
| gccctgtctg gcagtcagct cccagacag actatagact ataaatatgt ctccatctgc | 2220 |
| cttaccaagt gttttcttac tacaatgctg aatgactgga agaagaact gatatggcta | 2280 |
| gttcagctag ctggtacaga taattcaaaa ctgctgttgg ttttaatttt gtaacctgtg | 2340 |
| gcctgatctg taaataaaac ttacattttt caataggtaa aaaaaaaaaa aaaa | 2394 |

<210> SEQ ID NO 17
<211> LENGTH: 4463
<212> TYPE: DNA
<213> ORGANISM: Homo sapiens

<400> SEQUENCE: 17

| | |
|---|---|
| gcagcgcgca ccgagccggc cgcgccgcgc ccgccgctct cgccgctttc gccgcggtct | 60 |
| cctcctctag cgcccgccgc ggccggtaaa tctcggctgg aggagcagcg gcggcccccg | 120 |
| agtcaacttt cattcccttt ttgcttctgc ctcaccattc tcttctcctc ctcgaaagat | 180 |
| ggctgtttgg agaagggga gaagttaaga ggtcgccagc gcggagcgaa ggagggcgcg | 240 |
| atagcctcag caggagcggg cggaggtttc tcctctgcca accctcctg gaccattgtc | 300 |
| agcagttgaa cgacaaaggc tgtgaatctg catcctagtc ttagcagtcc ctctgattct | 360 |
| catgatgagc tcacctgcac agcctgacct catgtggaac cttgtaccat gggtgctatt | 420 |
| ctgtggctgc tgtaggatct tcccagtgg ggtggctgga cgagagcagc tcttggctca | 480 |
| gcaaagaatg cacagtatga tcagctcagt ggatgtgaag tcagaagttc ctgtgggcct | 540 |

```
ggagcccatc tcacctttag acctaaggac agacctcagg atgatgatgc ccgtggtgga    600
ccctgttgtc cgtgagaagc aattgcagca ggaattactt cttatccagc agcagcaaca    660
aatccagaag cagcttctga tagcagagtt tcagaaacag catgagaact tgacacggca    720
gcaccaggct cagcttcagg agcatatcaa ggaacttcta gccataaaac agcaacaaga    780
actcctagaa aaggagcaga aactggagca gcagaggcaa gaacaggaag tagagaggca    840
tcgcagagaa cagcagcttc ctcctctcag aggcaaagat agaggacgag aaagggcagt    900
ggcaagtaca gaagtaaagc agaagcttca agagttccta ctgagtaaat cagcaacgaa    960
agacactcca actaatggaa aaaatcattc cgtgagccgc catcccaagc tctggtacac   1020
ggctgcccac cacacatcat tggatcaaag ctctccaccc cttagtggaa catctccatc   1080
ctacaagtac acattaccag gagcacaaga tgcaaaggat gatttccccc ttcgaaaaac   1140
tgaatcctca gtcagtagca gttctccagg ctctggtccc agttcaccaa caatgggcc    1200
aactggaagt gttactgaaa atgagacttc ggttttgccc cctacccctc atgccgagca   1260
aatggtttca cagcaacgca ttctaattca tgaagattcc atgaacctgc taagtcttta   1320
tacctctcct tctttgccca acattacctt ggggcttccc gcagtgccat cccagctcaa   1380
tgcttcgaat tcactcaaag aaaagcagaa gtgtgagacg cagacgctta ggcaaggtgt   1440
tcctctgcct gggcagtatg gaggcagcat cccggcatct tccagccacc ctcatgttac   1500
tttagaggga aagccaccca acagcagcca ccaggctctc ctgcagcatt tattattgaa   1560
agaacaaatg cgacagcaaa agcttcttgt agctggtgga gttcccttac atcctcagtc   1620
tcccttggca acaaaagaga gaatttcacc tggcattaga ggtacccaca aattgccccg   1680
tcacagaccc ctgaaccgaa cccagtctgc acctttgcct cagagcacgt tggctcagct   1740
ggtcattcaa cagcaacacc agcaattctt ggagaagcag aagcaatacc agcagcagat   1800
ccacatgaac aaaactgcttt cgaaatctat tgaacaactg aagcaaccag gcagtcacct   1860
tgaggaagca gaggaagagc ttcaggggga ccaggcgatg caggaagaca gagcgccctc   1920
tagtggcaac agcactagga gcgacagcag tgcttgtgtg gatgacacac tgggacaagt   1980
tggggctgtg aaggtcaagg aggaaccagt ggacagtgat gaagatgctc agatccagga   2040
aatggaatct ggggagcagg ctgcttttat gcaacaggta ataggcaaag atttagctcc   2100
aggatttgta attaaagtca ttatctgaac atgaaatgca ttgcaggttt ggtaaatgga   2160
tatgatttcc tatcagtttta tatttctcta tgatttgagt tcagtgttta aggattctac   2220
ctaatgcaga tatatgtata tatctatata gaggtctttc tatatactga tctctatata   2280
gatatcaatg tttcattgaa aatccactgg taaggaaata cctgttatac taaaattatg   2340
atacataata tctgagcagt taataggctt taaatttatc ccaaagcctg ctacaccaat   2400
tacttctaaa gaaaacaaat tcactgttat tttgagttta tgtgttgaga tcagtgactg   2460
ctggatagtc tcccagtctg atcaatgaag cattcgatta gttttttgatt ttttgcaaca   2520
tctagaattt aattttcaca tcactgtaca taatgtatca tactatagtc ttgaacactg   2580
ttaaaggtag tctgccccctt ccttcctctc tctttttta gttaagtaga aatgttctgg   2640
tcaccatgcc agtagtccta ggttattgtg taggttgcaa ttgaacatat taggaataca   2700
ggtggtttta aatatataga tgcaaattgc agcactactt taaatattag attatgtctc   2760
acatagcact gctcattta cttttatttt gtgtaatttg atgacactgt ctatcaaaaa   2820
agagcaaatg aagcagatgc aaatgttagt gagaagtaat gtgcagcatt atggtccaat   2880
```

```
cagatacaat attgtgtcta caattgcaaa aaacacagta acaggatgaa tattatctga   2940
tatcaagtca aaatcagttt gaaaagaagg tgtatcatat tttatattgt cactagaatc   3000
tcttaagtat aattccataa tgacatgggc ataaccgta acattctggc aaataacaat    3060
```
(Note: line 3060 in image reads "tcttaagtat aattccataa tgacatgggc atataccgta acattctggc aaataacaat")

```
cagatacaat attgtgtcta caattgcaaa aaacacagta acaggatgaa tattatctga   2940
tatcaagtca aaatcagttt gaaaagaagg tgtatcatat tttatattgt cactagaatc   3000
tcttaagtat aattccataa tgacatgggc atataccgta acattctggc aaataacaat   3060
tagaaaagat aggtttaaca aaaaattta  cttgtatata atgcaccttc aggaggacta   3120
tgtcctttga tgctataaaa tacaaacaac tttgaaggca acagaagaca ctgtttattc   3180
aagtcagttc tttgtcaggt tcctgctgtt ctcctacaga aaagtgattc tgtgagggtg   3240
aacaggaaat gccttgtgga aacaggaagt ccaagtgatt catgtactga ggaatgtagg   3300
aaaaaaaatc tgaggatagt gctttactct ttctgttttt aaagggcact ctatgaattg   3360
atttattgtc taagaaaata acaccacaag tagggaaatt gttacggaag cttttcactg   3420
gaacatttcc ttcatattcc ttttgtatat gtttacctg  ttttataggt ttacttttgt   3480
taagctagtt aaaggttcgt tgtattaaga cccctttaat atggataatc caaattgacc   3540
tagaatcttt gtgaggtttt ttctattaaa atatttatat ttctaaatcc gaggtatttc   3600
aaggtgtagt atcctatttc aaaggagata tagcagtttt gccaaatgta gacattgttc   3660
aactgtatgt tattggcacg tgttgtttac attttgctgt gacatttaaa aatatttctt   3720
taaaaatgtt actgctaaag atacattatc ctttttttaaa aagtctccat tcaaattaaa  3780
ttaacataac tagaagttag aaagtttaaa agttttccac ataatgaaag tccttctgat   3840
aatttgacaa atagctataa taggaacact ccctatcacc aacatatttt ggttagtata   3900
ttccttcata ttaaaatgac ttttttgtcag ttgttttgca ttaaaaatat ggcatgccta  3960
agataaaatt gtatattttt tccatctcat aaatattcat tttcttcaaa gtctttttc    4020
aatctcataa aaagggata gtgcatcttt taaaatacat tttatttggg gaggaacatg   4080
tggctgagca acttttgta  taatattact tcaaagatat gtaatcacaa acaaaaaaaa   4140
ctatttttta taatgtcatt tgagagagtt tcatcagtac agttggtgga cgttaattgt   4200
ttgaatttga tagtctttga atttaatcaa gaaactacct ggaaccagtg aaaaggaaag   4260
ctggacttaa ataatcttag aattaattga taaatgtctc ttttaaaatc tactgtattt   4320
attataattt acaccttga  aggtgatctc ttgttttgtg ttgtaaatat attgtttgta   4380
tgtttccctt cttgccttct gttataagtc tcttcctttc tcaaataaag tttttttaa    4440
aagaaaaaa  aaaaaaaaaa aaa                                           4463
```

<210> SEQ ID NO 18
<211> LENGTH: 2697
<212> TYPE: DNA
<213> ORGANISM: Homo sapiens

<400> SEQUENCE: 18

```
acttgtccgt cacgtgcggc cgcccggcct ctcggccttg ccgcgcgcct ggcggggttg     60
gggggcggg  gaccaagatc tgctgcgcct gcgttgtggg cgttctcggg gagctgctgc   120
cgtagctgcc gccgccgcta ccaccgcgtt cgggtgtaga atttggaatc cctgcgccgc   180
gttaacaatg aagcagagtt cgaacgtgcc ggctttcctc agcaagctgt ggacgcttgt   240
ggaggaaacc cacactaacg agttcatcac ctggagccag aatggccaaa gttttctggt   300
cttggatgag caacgatttg caaaagaaat tcttcccaaa tatttcaagc acaataatat   360
ggcaagcttt gtgaggcaac tgaatatgta tggtttccgt aaagtagtac atatcgactc   420
tggaattgta aagcaagaaa gagatggtcc tgtagaattt cagcatcctt acttcaaaca   480
aggacaggat gacttgttgg agaacattaa aaggaaggtt tcatcttcaa aaccagaaga   540
```

```
aaataaaatt cgtcaggaag atttaacaaa aattataagt agtgctcaga aggttcagat      600
aaaacaggaa actattgagt ccaggctttc tgaattaaaa agtgagaatg agtccctttg      660
gaaggaggtg tcagaattac gagcaaagca tgcacaacag caacaagtta ttcgaaagat      720
tgtccagttt attgttacat tggttcaaaa taaccaactt gtgagtttaa aacgtaaaag      780
gcctctactt ctaaacacta atggagccca aaagaagaac ctgtttcagc acatagtcaa      840
agaaccaact gataatcatc atcataaagt tccacacagt aggactgaag gtttaaagcc      900
aagggagagg atttcagatg acatcattat ttatgatgtt actgatgata atgcagatga      960
agaaaatatc ccagttattc cagaaactaa tgaggatgtt atatctgatc cctccaactg     1020
tagccagtac cctgatattg tcatcgttga agatgacaat gaagatgagt atgcacctgt     1080
cattcagagt ggagagcaga atgaaccagc cagagaatcc ctaagttcag gcagtgatgg     1140
cagcagccct ctcatgtcta gtgctgtcca gctaaatggc tcatccagtc tgacctcaga     1200
agatccagtg accatgatgg attccatttt gaatgataac atcaatcttt tgggaaaggt     1260
tgagctgttg gattatcttg acagtattga ctgcagttta gaggacttcc aggccatgct     1320
atcaggaaga caatttagca tagacccaga tctcctggtt gatcttttca ctagttctgt     1380
gcagatgaat cccacagatt acatcaataa tacaaaatct gagaataaag gattagaaac     1440
taccaagaac aatgtagttc agccagtttc ggaagaggga agaaaatcta aatccaaacc     1500
agataagcag cttatccagt ataccgcctt tccacttctt gcattcctcg atgggaaccc     1560
tgcttcttct gttgaacagg cgagtacaac agcatcatca gaagttttgt cctctgtaga     1620
taaacccata gaagttgatg agcttctgga tagcagccta gacccagaac caacccaaag     1680
taagcttgtt cgcctggagc cattgactga agctgaagct agtgaagcta cactgttta     1740 tttatgtgaa cttgctcctg cacctctgga tagtgatatg ccactttag atagctaaat     1800 ccccaggaag tggactttac atgtatatat tcatcaaaat gatgaactat ttatttaaa      1860 gtatcatttg gtactttttt tgtaaattgc tttgttttgt ttaatcagat actgtggaat     1920
aaaagcacct tttgcttttc tcactaacca cacactcttg cagagctttc aggtgttact     1980
cagctgcata gttacgcaga tgtaatgcac attattggcg tatctttaag ttggattcaa     2040
atggccattt ttctccaatt ttggtaaatt ggatatcttt tttttacaaa tacgaccatt     2100
aacctcagtt aaattttgt ttgttttcct gtttgatgct gtctatttgc attgagtgta     2160
agtcatttga actaatggta taactcctaa agctttctct gctccagtta ttttttattaa    2220 atattttca cttggcttat tttaaaact gggaacataa agtgcctgta tcttgtaaaa       2280
cttcatttgt ttcttttggt tcagagaagt tcatttatgt tcaaagacgt ttattcatgt     2340
tcaacaggaa agacaaagtg tacgtgaatg ctcgctgtct gatagggttc cagctccata     2400
tatatagaaa gatcgggggt gggatgggat ggagtgagcc ccatccagtt agttggacta     2460
gttttaaata aaggttttcc ggtttgtgtt ttttgaacc atactgttta gtaaaataaa      2520
tacaatgaat gttgagtact agtgtctgtt atgtgtcttc tttagaggtg acactcacat     2580
gaaacaattt tttcttctca taggaagcag tagctttaaa ctgtctgtgg ttcattattc     2640
tcaatatgaa tcataccaag atatttgtgc ctcatctcga aaatatattg tatattg        2697
```

<210> SEQ ID NO 19
<211> LENGTH: 11427
<212> TYPE: DNA
<213> ORGANISM: Homo sapiens

```
<400> SEQUENCE: 19
taccgggcgg aggtgagcgc ggcgccggct cctcctgcgg cggactttgg gtgcgacttg      60
acgagcggtg gttcgacaag tggccttgcg ggccggatcg tcccagtgga agagttgtaa     120
atttgcttct ggccttcccc tacggattat acctggcctt ccctacgga ttatactcaa      180
cttactgttt agaaaatgtg gcccacgaga cgcctggtta ctatcaaaag gagcgggtc      240
gacggtcccc actttcccct gagcctcagc acctgcttgt ttggaagggg tattgaatgt     300
gacatccgta tccagcttcc tgttgtgtca aaacaacatt gcaaaattga aatccatgag     360
caggaggcaa tattacataa tttcagttcc acaaatccaa cacaagtaaa tgggtctgtt     420
attgatgagc ctgtacggct aaaacatgga gatgtaataa ctattattga tcgttccttc     480
aggtatgaaa atgaaagtct tcagaatgga aggaagtcaa ctgaatttcc aagaaaaata     540
cgtgaacagg agccagcacg tcgtgtctca agatctagct tctcttctga ccctgatgag     600
agtgagggaa tacctttgaa aagaaggcgt gtgtcctttg gtgggcacct aagacctgaa     660
ctatttgatg aaaacttgcc tcctaatacg cctctcaaaa ggggagaagc cccaaccaaa     720
agaaagtctc tggtaatgca cactccacct gtcctgaaga aaatcatcaa ggaacagcct     780
caaccatcag gaaaacaaga gtcaggttca gaaatccatg tggaagtgaa ggcacaaagc     840
ttggttataa gccctccagc tcctagtcct aggaaaactc cagttgccag tgatcaacgc     900
cgtaggtcct gcaaaacagc ccctgcttcc agcagcaaat ctcagacaga ggttcctaag     960
agaggaggga gaaagagtgg caacctgcct tcaaagagag tgtctatcag ccgaagtcaa    1020
catgatattt tacagatgat atgttccaaa agaagaagtg gtgcttcgga agcaaatctg    1080
attgttgcaa aatcatgggc agatgtagta aaacttggtg caaaacaaac acaaactaaa    1140
gtcataaaac atggtcctca aaggtcaatg aacaaaaggc aaagaagacc tgctactcca    1200
aagaagcctg tgggcgaagt tcacagtcaa tttagtacag gccacgcaaa ctctccttgt    1260
accataataa tagggaaagc tcatactgaa aaagtacatg tgcctgctcg accctacaga    1320
gtgctcaaca acttcatttc aaccaaaaaa atggacttta aggaagatct ttcaggaata    1380
gctgaaatgt tcaagacccc agtgaaggag caaccgcagt tgacaagcac atgtcacatc    1440
gctatttcaa attcagagaa tttgcttgga aaacagtttc aaggaactga ttcaggagaa    1500
gaacctctgc tccccacctc agagagtttt ggaggaaatg tgttcttcag tgcacagaat    1560
gcagcaaaac agccatctga taatgctct gcaagccctc ccttaagacg gcagtgtatt    1620
agagaaaatg gaaacgtagc aaaaacgccc aggaacacct acaaaatgac ttctctggag    1680
acaaaaactt cagatactga gacagagcct tcaaaaacag tatccactgc aaacaggtca    1740
ggaaggtcta cagagttcag gaatatacag aagctacctg tggaaagtaa gagtgaagaa    1800
acaaatacag aaattgttga gtgcatccta aaaagaggtc agaaggcaac actactacaa    1860
caaaggagag aaggagagat gaaggaaata gaaagacctt ttgagacata taggaaaat     1920
attgaattaa aagaaaacga tgaaaagatg aaagcaatga gagatcaag aacttggggg    1980
cagaaatgtg caccaatgtc tgacctgaca gacctcaaga gcttgcctga tacagaactc    2040
atgaaagaca cggcacgtgg ccagaatctc ctccaaaccc aagatcatgc caaggcacca    2100
aagagtgaga aaggcaaaat cactaaaatg ccctgccagt cattacaacc agaaccaata    2160
aacacccccaa cacacacaaa acaacagttg aaggcatccc tggggaaagt aggtgtgaaa    2220
gaagagctcc tagcagtcgg caagttcaca cggacgtcag gggagaccac gcacacgcac    2280
agagagccag caggagatgg caagagcatc agaacgttta aggagtctcc aaagcagatc    2340
```

```
ctggacccag cagcccgtgt aactggaatg aagaagtggc caagaacgcc taaggaagag    2400
gcccagtcac tagaagacct ggctggcttc aaagagctct tccagacacc aggtccctct    2460
gaggaatcaa tgactgatga gaaaactacc aaaatagcct gcaaatctcc accaccagaa    2520
tcagtggaca ctccaacaag cacaaagcaa tggcctaaga gaagtctcag gaaagcagat    2580
gtagaggaag aattcttagc actcaggaaa ctaacaccat cagcagggaa agccatgctt    2640
acgcccaaac cagcaggagg tgatgagaaa gacattaaag catttatggg aactccagtg    2700
cagaaactgg acctggcagg aactttacct ggcagcaaaa gacagctaca gactcctaag    2760
gaaaaggccc aggctctaga agacctggct ggctttaaag agctcttcca gactcctggt    2820
cacaccgagg aattagtggc tgctggtaaa accactaaaa taccctgcga ctctccacag    2880
tcagacccag tggacacccc aacaagcaca aagcaacgac caagagaag tatcaggaaa     2940
```

```
aaaatactct gcaaatctcc gcaatcagac ccagcggaca ccccaacaaa cacaaagcaa    4740
cggcccaaga gaagcctcaa gaaagcagac gtagaggaag aattttttagc attcaggaaa    4800 ctaacaccat cagcaggcaa agccatgcac acgcctaaag cagcagtagg tgaagagaaa    4860
gacatcaaca catttgtggg gactccagtg gagaaactgg acctgctagg aaatttacct    4920
ggcagcaaga gacggccaca aactcctaaa gaaaaggcca aggctctaga agatctggct    4980
ggcttcaaag agctcttcca gacaccaggt cacactgagg aatcaatgac cgatgacaaa    5040
atcacagaag tatcctgcaa atctccacaa ccagacccag tcaaaacccc aacaagctcc    5100
aagcaacgac tcaagatatc cttggggaaa gtaggtgtga agaagaggt cctaccagtc    5160 ggcaagctca cacagacgtc agggaagacc acacagacac acagagagac agcaggagat    5220
ggaaagagca tcaaagcgtt taaggaatct gcaaagcaga tgctggaccc agcaaactat    5280
ggaactggga tggagaggtg gccaagaaca cctaaggaag aggcccaatc actagaagac    5340
ctggccggct tcaaagagct cttccagaca ccagaccaca ctgaggaatc aacaactgat    5400
gacaaaacta ccaaaatagc ctgcaaatct ccaccaccag aatcaatgga cactccaaca    5460
agcacaagga ggcggcccaa aacacctttg ggaaaaggg atatagtgga agagctctca    5520
gccctgaagc agctcacaca gaccacacac acagacaaag taccaggaga tgaggataaa    5580
ggcatcaacg tgttcaggga aactgcaaaa cagaaactgg acccagcagc aagtgtaact    5640
ggtagcaaga ggcagccaag aactcctaag ggaaaagccc aaccctaga agacttggct    5700 ggcttgaaag agctcttcca gacaccaata tgcactgaca agcccacgac tcatgagaaa    5760
actaccaaaa tagcctgcag atctccacaa ccagacccag tgggtacccc aacaatcttc    5820
aagccacagt ccaagagaag tctcaggaaa gcagacgtag aggaagaatc cttagcactc    5880
aggaaacgaa caccatcagt agggaaagct atggacacac ccaaaccagc aggaggtgat    5940
gagaaagaca tgaaagcatt tatgggaact ccagtgcaga aattggacct gccaggaaat    6000
ttacctggca gcaaaagatg gccacaaact cctaaggaaa aggcccaggc tctagaagac    6060
ctggctggct tcaaagagct cttccagaca ccaggcactg acaagcccac gactgatgag    6120
aaaactacca aaatagcctg caaatctcca caaccagacc cagtggacac cccagcaagc    6180
acaaagcaac ggcccaagag aaacctcagg aaagcagacg tagaggaaga atttttagca    6240
ctcaggaaac gaacaccatc agcaggcaaa gccatggaca caccaaaacc agcagtaagt    6300
gatgagaaaa atatcaacac atttgtggaa actccagtgc agaaactgga cctgctagga    6360
aatttacctg gcagcaagag acagccacag actcctaagg aaaaggctga ggctctagag    6420
gacctggttg gcttcaaaga actcttccag acaccaggtc acactgagga atcaatgact    6480
gatgacaaaa tcacagaagt atcctgtaaa tctccacagc cagagtcatt caaaacctca    6540
agaagctcca agcaaaggct caagataccc tggtgaaag tggacatgaa agaagagccc    6600
ctagcagtca gcaagctcac acggacatca ggggagacta cgcaaacaca cacagagcca    6660
acaggagata gtaagagcat caaagcgttt aaggagtctc caaagcagat cctgacccca    6720
gcagcaagtg taactggtag caggaggcag ctgagaactc gtaaggaaaa ggcccgtgct    6780
ctagaagacc tggttgactt caaagagctc ttctcagcac caggtcacac tgaagagtca    6840
atgactattg acaaaaacac aaaaattccc tgcaaatctc ccccaccaga actaacagac    6900
actgccacga gcacaaagag atgccccaag acacgtccca ggaaagaagt aaaagaggag    6960
ctctcagcag ttgagaggct cacgcaaaca tcagggcaaa gcacacacac acacaaagaa    7020
ccagcaagcg gtgatgaggg catcaaagta ttgaagcaac gtgcaaagaa gaaaccaaac    7080
```

```
ccagtagaag aggaacccag caggagaagg ccaagagcac ctaaggaaaa ggcccaaccc    7140
ctggaagacc tggccggctt cacagagctc tctgaaacat caggtcacac tcaggaatca    7200
ctgactgctg gcaaagccac taaaataccc tgcgaatctc ccccactaga agtggtagac    7260
accacagcaa gcacaaagag gcatctcagg acacgtgtgc agaaggtaca agtaaaagaa    7320
gagccttcag cagtcaagtt cacacaaaca tcaggggaaa ccacggatgc agacaaagaa    7380
ccagcaggtg aagataaagg catcaaagca ttgaaggaat ctgcaaaaca gacaccggct    7440
ccagcagcaa gtgtaactgg cagcaggaga cggccaagag cacccaggga aagtgcccaa    7500
gccatagaag acctagctgg cttcaaagac ccagcagcag gtcacactga gaatcaatg    7560
actgatgaca aaccactaa aatacccgtc aaatcatcac cagaactaga agacaccgca    7620
acaagctcaa agagacggcc caggacacgt gcccagaaag tagaagtgaa ggaggagctg    7680
ttagcagttg gcaagctcac acaaacctca ggggagacca cgcacaccga caaagagccg    7740
gtaggtgagg gcaaaggcac gaaagcattt aagcaacctg caaagcggaa gctgacgcga    7800
gaagatgtaa ttggcagcag gagacagcca agagcaccta aggaaaaggc caacccctg    7860
gaagatctgg ccagcttcca agagctctct caaacaccag gccacactga ggaactggca    7920
aatggtgctg ctgatagctt tacaagcgct ccaaagcaaa cacctgacag tggaaaacct    7980
ctaaaaatat ccagaagagt tcttcgggcc cctaaagtag aacccgtggg agacgtggta    8040
agcaccagag accctgtaaa atcacaaagc aaaagcaaca cttccctgcc cccactgccc    8100
ttcaagaggg gaggtggcaa agatggaagc gtcacgggaa ccaagaggct gcgctgcatg    8160
ccagcaccag aggaaattgt ggaggagctg ccagccagca agaagcagag ggttgctccc    8220
agggcaagag gcaaatcatc cgaacccgtg gtcatcatga agagaagttt gaggacttct    8280
gcaaaaagaa ttgaacctgc ggaagagctg aacagcaacg acatgaaaac caacaaagag    8340
gaacacaaat tacaagactc ggtccctgaa aataagggaa tatccctgcg ctccagacgc    8400
caaaataaga ctgaggcaga acagcaaata actgaggtct ttgtattagc agaaagaata    8460
gaaataaaca gaaatgaaaa gaagcccatg aagacctccc cagagatgga cattcagaat    8520
ccagatgatg gagcccggaa acccataccct agagacaaag tcactgagaa caaaaggtgc    8580
ttgaggtctg ctagacagaa tgagagctcc cagcctaagg tggcagagga gagcggaggg    8640
cagaagagtg cgaaggttct catgcagaat cagaaaggga aggagaagc aggaaattca    8700
gactccatgt gcctgagatc aagaaagaca aaaagccagc ctgcagcaag cactttggag    8760
agcaaatctg tgcagagagt aacgcggagt gtcaagaggt gtgcagaaaa tccaaagaag    8820
gctgaggaca atgtgtgtgt caagaaaata agaaccagaa gtcatagggga cagtgaagat    8880
atttgacaga aaaatcgaac tgggaaaaat ataataaagt tagttttgtg ataagttcta    8940
gtgcagtttt tgtcataaat tacaagtgaa ttctgtaagt aaggctgtca gtctgcttaa    9000
gggaagaaaa ctttggattt gctgggtctg aatcggcttc ataaactcca ctgggagcac    9060
tgctgggctc ctggactgag aatagttgaa caccggggc tttgtgaagg agtctgggcc    9120
aaggtttgcc ctcagctttg cagaatgaag ccttgaggtc tgtcaccacc cacagccacc    9180
ctacagcagc cttaactgtg acacttgcca cactgtgtcg tcgtttgttt gcctatgtcc    9240
tccagggcac ggtggcagga acaactatcc tcgtctgtcc caacactgag caggcactcg    9300
gtaaacacga atgaatggat gagcgcacgg atgaatggag cttacaagat ctgtctttcc    9360
aatggccggg ggcatttggt ccccaaatta aggctattgg acatctgcac aggacagtcc    9420
```

```
tattttttgat gtcctttcct ttctgaaaat aaagttttgt gctttggaga atgactcgtg    9480
agcacatctt tagggaccaa gagtgacttt ctgtaaggag tgactcgtgg cttgccttgg    9540
tctcttggga atacttttct aactagggtt gctctcacct gagacattct ccacccgcgg    9600
aatctcaggg tcccaggctg tgggccatca cgacctcaaa ctggctccta atctccagct    9660
ttcctgtcat tgaaagcttc ggaagtttac tggctctgct cccgcctgtt ttctttctga    9720
ctctatctgg cagcccgatg ccacccagta caggaagtga caccagtact ctgtaaagca    9780
tcatcatcct tggagagact gagcactcag caccttcagc cacgatttca ggatcgcttc    9840
cttgtgagcc gctgcctccg aaatctcctt tgaagcccag acatctttct ccagcttcag    9900
acttgtagat ataactcgtt catcttcatt tactttccac tttgcccct gtcctctctg     9960
tgttccccaa atcagagaat agcccgccat cccccaggtc acctgtctgg attcctcccc   10020
attcacccac cttgccaggt gcaggtgagg atggtgcacc agacagggta gctgtccccc   10080
aaaatgtgcc ctgtgcgggc agtgcccgtt ctccacgttt gttcccag tgtctggcgg    10140
ggagccaggt gacatcataa atacttgctg aatgaatgca gaaatcagcg gtactgactt   10200
gtactatatt ggctgccatg atagggttct cacagcgtca tccatgatcg taaggagaa    10260
tgacattctg cttgagggag ggaatagaaa ggggcaggga gggacatct gagggcttca    10320
cagggctgca aagggtacag ggattgcacc agggcagaac aggggagggt gttcaaggaa   10380
gagtggctct tagcagaggc actttggaag gtgtgaggca taaatgcttc cttctacgta   10440
ggccaacctc aaaactttca gtaggaatgt tgctatgatc aagttgttct aacactttag   10500
acttagtagt aattatgaac ctcacataga aaaatttcat ccagccatat gcctgtgagg   10560
tggaatattc tgtttagtag aaaaatcctt tagagttcag ctctaaccag aaatcttgct   10620
gaagtatgtc agcaccttt ctcaccctgg taagtacagt atttcaagag cacgctaagg    10680
gtggttttca ttttacaggg ctgttgatga tgggttaaaa atgttcattt aagggctacc   10740
cccgtgttta atagatgaac accttcta cacaaccctc cttggtactg ggggagggag     10800
agatctgaca aatactgccc attcccctag gctgactgga tttgagaaca aatacccacc   10860
catttccacc atggtatggt aacttctctg agcttcagtt tccaagtgaa tttccatgta   10920
ataggacatt cccattaaat acaagctgtt tttactttt cgcctcccag ggcctgtggg    10980
atctggtccc ccagcctctc ttgggctttc ttacactaac tctgtaccta ccatctcctg   11040
cctcccttag gcaggcacct ccaaccacca cacactccct gctgttttcc ctgcctggaa   11100
ctttccctcc tgccccacca agatcatttc atccagtcct gagctcagct taagggaggc   11160
ttcttgcctg tgggttccct cacccccatg cctgtcctcc aggctggggc aggttcttag   11220
tttgcctgga attgttctgt acctctttgt agcacgtagt gttgtggaaa ctaagccact   11280
aattgagttt ctggctcccc tcctgggggtt gtaagttttg ttcattcatg agggccgact   11340
gcatttcctg gttactctat cccagtgacc agccacagga gatgtccaat aaagtatgtg   11400
atgaaatggt cttaaaaaaa aaaaaa                                        11427

<210> SEQ ID NO 20
<211> LENGTH: 5765
<212> TYPE: DNA
<213> ORGANISM: Homo sapiens

<400> SEQUENCE: 20
tcctaggcgg cggccgcggc ggcggaggca gcagcggcgg cggcagtggc ggcggcgaag     60
gtggcggcgg ctcggccagt actcccggcc cccgccattt cggactggga gcgagcgcgg    120
```

```
cgcaggcact gaaggcggcg gcggggccag aggctcagcg gctcccaggt gcgggagaga      180
ggcctgctga aaatgactga atataaactt gtggtagttg gagctggtgg cgtaggcaag      240
agtgccttga cgatacagct aattcagaat cattttgtgg acgaatatga tccaacaata      300
gaggattcct acaggaagca agtagtaatt gatggagaaa cctgtctctt ggatattctc      360
gacacagcag gtcaagagga gtacagtgca atgagggacc agtacatgag gactggggag      420
ggctttcttt gtgtatttgc cataaataat actaaatcat ttgaagatat tcaccattat      480
agagaacaaa ttaaaagagt taaggactct gaagatgtac ctatggtcct agtaggaaat      540
aaatgtgatt tgccttctag aacagtagac acaaaacagg ctcaggactt agcaagaagt      600
tatggaattc cttttattga acatcagca aagacaagac agggtgttga tgatgccttc       660
tatacattag ttcgagaaat tcgaaaacat aaagaaaaga tgagcaaaga tggtaaaaag      720
aagaaaaaga agtcaaagac aaagtgtgta attatgtaaa tacaatttgt acttttttct      780
taaggcatac tagtacaagt ggtaattttt gtacattaca ctaaattatt agcatttgtt      840
ttagcattac ctaattttttt tcctgctcca tgcagactgt tagcttttac cttaaatgct      900
tattttaaaa tgacagtgga agttttttt tcctctaagt gccagtattc ccagagtttt       960
ggtttttgaa ctagcaatgc ctgtgaaaaa gaaactgaat acctaagatt tctgtcttgg     1020
ggtttttggt gcatgcagtt gattacttct tattttttctt accaattgtg aatgttggtg     1080
tgaaacaaat taatgaagct tttgaatcat ccctattctg tgttttatct agtcacataa     1140
atggattaat tactaattttc agttgagacc ttctaattgg ttttactga aacattgagg      1200 gaacacaaat ttatgggctt cctgatgatg attcttctag gcatcatgtc ctatagtttg     1260
tcatccctga tgaatgtaaa gttacactgt tcacaaaggt tttgtctcct ttccactgct     1320
attagtcatg gtcactctcc ccaaaatatt atattttttc tataaaaaga aaaaatgga      1380 aaaaaattac aaggcaatgg aaactattat aaggccattt ccttttcaca ttagataaat     1440
tactataaag actcctaata gcttttcctg ttaaggcaga cccagtatga atggggatt      1500 attatagcaa ccattttggg gctatatta catgctacta aattttttata ataattgaaa     1560 agattttaac aagtataaaa aattctcata ggaattaaat gtagtctccc tgtgtcagac     1620
tgctctttca tagtataact ttaaatcttt tcttcaactt gagtctttga agatagtttt     1680
aattctgctt gtgacattaa aagattattt gggccagtta tagcttatta ggtgttgaag     1740
agaccaaggt tgcaaggcca ggccctgtgt gaacctttga gctttcatag agagtttcac     1800
agcatggact gtgtccccac ggtcatccag tgttgtcatg cattggttag tcaaaatggg     1860
gagggactag ggcagtttgg atagctcaac aagatacaat ctcactctgt ggtggtcctg     1920
ctgacaaatc aagagcattg cttttgtttc ttaagaaaac aaactctttt ttaaaaatta     1980
cttttaaata ttaactcaaa agttgagatt ttggggtggt ggtgtgccaa gacattaatt     2040 tttttttaa acaatgaagt gaaaagttt tacaatctct aggttggct agttctctta       2100 acactggtta aattaacatt gcataaacac ttttcaagtc tgatccatat ttaataatgc     2160
tttaaaataa aaataaaaac aatccttttg ataaatttaa aatgttactt attttaaaat     2220
aaatgaagtg agatggcatg gtgaggtgaa agtatcactg gactaggaag aaggtgactt     2280
aggttctaga taggtgtctt ttaggactct gattttgagg acatcactta ctatccattt     2340
cttcatgtta aaagaagtca tctcaaactc ttagtttttt tttttacaa ctatgtaatt     2400 tatattccat ttacataagg atacacttat ttgtcaagct cagcacaatc tgtaaatttt     2460
```

```
taacctatgt tacaccatct tcagtgccag tcttgggcaa aattgtgcaa gaggtgaagt   2520
ttatatttga atatccattc tcgttttagg actcttcttc catattagtg tcatcttgcc   2580
tccctacctt ccacatgccc catgacttga tgcagtttta atacttgtaa ttcccctaac   2640
cataagattt actgctgctg tggatatctc catgaagttt tcccactgag tcacatcaga   2700
aatgccctac atcttatttc ctcagggctc aagagaatct gacagatacc ataaagggat   2760
ttgacctaat cactaatttt caggtggtgg ctgatgcttt gaacatctct ttgctgccca   2820
atccattagc gacagtagga tttttcaaac ctggtatgaa tagacagaac cctatccagt   2880
ggaaggagaa tttaataaag atagtgctga aagaattcct taggtaatct ataactagga   2940
ctactcctgg taacagtaat acattccatt gttttagtaa ccagaaatct tcatgcaatg   3000
aaaaatactt taattcatga agcttacttt ttttttttgg tgtcagagtc tcgctcttgt   3060
cacccaggct ggaatgcagt ggcgccatct cagctcactg caacctccat ctcccaggtt   3120
caagcgattc tcgtgcctcg gcctcctgag tagctgggat tacaggcgtg tgccactaca   3180
ctcaactaat ttttgtattt ttaggagaga cggggtttca ccctgttggc caggctggtc   3240
tcgaactcct gacctcaagt gattcaccca ccttggcctc ataaacctgt tttgcagaac   3300
tcatttattc agcaaatatt tattgagtgc ctaccagatg ccagtcaccg cacaaggcac   3360
tgggtatatg gtatccccaa acaagagaca taatcccggt ccttaggtag tgctagtgtg   3420
gtctgtaata tcttactaag gccttttggta tacgacccag agataacacg atgcgtattt   3480
tagttttgca aagaaggggt ttggtctctg tgccagctct ataattgttt tgctacgatt   3540
ccactgaaac tcttcgatca agctacttta tgtaaatcac ttcattgttt taaggaata   3600
aacttgatta tattgttttt ttatttggca taactgtgat tcttttagga caattactgt   3660
acacattaag gtgtatgtca gatattcata ttgacccaaa tgtgtaatat tccagttttc   3720
tctgcataag taattaaaat atacttaaaa attaatagtt ttatctgggt acaaataaac   3780
aggtgcctga actagttcac agacaaggaa acttctatgt aaaaatcact atgatttctg   3840
aattgctatg tgaaactaca gatctttgga acactgttta ggtagggtgt taagacttac   3900
acagtacctc gtttctacac agagaaagaa atggccatac ttcaggaact gcagtgctta   3960
tgaggggata tttaggcctc ttgaatttttt gatgtagatg ggcattttttt taaggtagtg   4020
gttaattacc tttatgtgaa cttttgaatggg tttaacaaaa gatttgtttt tgtagagatt   4080
ttaaagggg agaattctag aaataaatgt tacctaatta ttacagcctt aaagacaaaa   4140
atccttgttg aagtttttttt aaaaaaagct aaattacata gacttaggca ttaacatgtt   4200
tgtggaagaa tatagcagac gtatattgta tcatttgagt gaatgttccc aagtaggcat   4260
tctaggctct atttaactga gtcacactgc ataggaattt agaacctaac ttttataggt   4320
tatcaaaact gttgtcacca ttgcacaatt ttgtcctaat atatacatag aaactttgtg   4380
gggcatgtta agttacagtt tgcacaagtt catctcattt gtattccatt gattttttt   4440
ttcttctaaa catttttttct tcaaacagta tataactttt tttaggggat ttttttttag   4500
acagcaaaaa ctatctgaag atttccatttt gtcaaaaagt aatgatttct tgataattgt   4560
gtagtaatgt ttttttagaac ccagcagtta ccttaaagct gaatttatat ttagtaactt   4620
ctgtgttaat actggatagc atgaattctg cattgagaaa ctgaatagct gtcataaaat   4680
gaaactttct ttctaaagaa agatactcac atgagttctt gaagaatagt cataactaga   4740
ttaagatctg tgttttagtt taatagtttg aagtgcctgt ttgggataat gataggtaat   4800
ttagatgaat ttaggggaaa aaaaagttat ctgcagatat gttgagggcc catctctccc   4860
```

```
cccacacccc cacagagcta actgggttac agtgttttat ccgaaagttt ccaattccac    4920
tgtcttgtgt tttcatgttg aaaatacttt tgcattttc ctttgagtgc caatttctta    4980
ctagtactat ttcttaatgt aacatgttta cctggaatgt attttaacta tttttgtata    5040
gtgtaaactg aaacatgcac attttgtaca ttgtgctttc ttttgtggga catatgcagt    5100
gtgatccagt tgttttccat catttggttg cgctgaccta ggaatgttgg tcatatcaaa    5160
cattaaaaat gaccactctt ttaattgaaa ttaacttttta aatgtttata ggagtatgtg    5220
ctgtgaagtg atctaaaatt tgtaatattt ttgtcatgaa ctgtactact cctaattatt    5280
gtaatgtaat aaaatagtt acagtgacta tgagtgtgta tttattcatg aaatttgaac    5340
tgtttgcccc gaaatggata tggaatactt tataagccat agacactata gtataccagt    5400 gaatcttttta tgcagcttgt tagaagtatc ctttatttct aaaaggtgct gtggatatta    5460
tgtaaaggcg tgtttgctta aacttaaaac catatttaga agtagatgca aaacaaatct    5520
gcctttatga caaaaaaata ggataacatt atttatttat ttccttttat caaagaaggt    5580
aattgataca caacaggtga cttggttttta ggcccaaagg tagcagcagc aacattaata    5640
atggaaataa ttgaatagtt agttatgtat gttaatgcca gtcaccagca ggctatttca    5700
aggtcagaag taatgactcc atacatatta tttatttcta taactacatt taaatcatta    5760
ccagg                                                               5765
```

<210> SEQ ID NO 21
<211> LENGTH: 2202
<212> TYPE: DNA
<213> ORGANISM: Homo sapiens

<400> SEQUENCE: 21

```
cgtaaagaga ggccgggagc tgcccctaac cgaggcagca gcggacgtga gcgataatgg      60
cggatatgga ggatctcttc gggagcgacg ccgacagcga agctgagcgt aaagattctg     120
attctggatc tgactcagat tctgatcaag agaatgctgc ctctggcagt aatgcctctg     180
gaagtgaaag tgatcaggat gaaagaggtg attcaggaca accaagtaat aaggaactgt     240
ttggagatga cagtgaggac gagggagctt cacatcatag tggtagtgat aatcactctg     300
aaagatcaga caatagatca gaagcttctg agcgttctga ccatgaggac aatgaccect     360 cagatgtaga tcagcacagt ggatcagaag cccctaatga tgatgaagac gaaggtcata     420
gatcggatgg agggagccat cattcagaag cagaaggttc tgaaaaagca cattcagatg     480
atgaaaaatg gggcagagaa gataaaagtg accagtcaga tgatgaaaag atacaaaatt     540
ctgatgatga ggagagggca caaggatctg atgaagataa gctgcagaat tctgacgatg     600
atgagaaaat gcagaacaca gatgatgagg agaggcctca gctttccgat gatgagagac     660
aacagctatc tgaggaggaa aaggctaatt ctgatgatga acggccggta gcttctgata     720
atgatgatga gaaacagaat tctgatgatg aagaacaacc acagctgtct gatgaagaga     780
aaatgcaaaa ttctgatgat gaaaggccac aggcctcaga tgaagaacac aggcattcag     840
atgatgaaga ggaacaggat cataaatcag aatctgcaag aggcagtgat agtgaagatg     900
aagttttacg aatgaaacgc aagaatgcga ttgcatctga ttcagaagcg atagtgaca     960 ctgaggtgcc aaaagataat agtggaacca tggatttatt tggaggtgca gatgatatct    1020
cttcagggag tgatggagaa acaaaccac ctactccagg acagcctgtt gatgaaaatg    1080
gattgcctca ggatcaacag gaagaggagc caattcctga gaccagaata gaagtagaaa    1140
```

| | |
|---|---|
| tacccaaagt aaacactgat ttaggaaacg acttatattt tgttaaactg cccaactttc | 1200 |
| tcagtgtaga gcccagacct tttgatcctc agtattatga agatgaattt gaagatgaag | 1260 |
| aaatgctgga tgaagaaggt agaaccaggt taaaattaaa ggtagaaaat actataagat | 1320 |
| ggaggatacg ccgagatgaa gaaggaaatg aaattaaaga aagcaatgct cggatagtca | 1380 |
| agtggtcaga tggaagcatg tccctgcatt taggcaatga agtgtttgat gtgtacaaag | 1440 |
| ccccactgca gggcgaccac aatcatcttt ttataagaca aggtactggt ctacagggac | 1500 |
| aagcagtctt taaaacgaaa ctcaccttca gacctcactc tacggacagt gccacacata | 1560 |
| gaaagatgac tctgtcactt gcagataggt gttcaaagac acagaagatt agaatcttgc | 1620 |
| caatggctgg tcgtgatcct gaatgccaac gcacagaaat gattaagaaa gaagaagaac | 1680 |
| gtttgagggc ttccatacgt agggaatctc agcagcgccg aatgagagag aaacagcacc | 1740 |
| agcgggggct gagcgccagt tacctggaac ctgatcgata cgatgaggag gaggaaggcg | 1800 |
| aggagtccat cagcttggct gccattaaaa accgatataa aggggcatt cgagaggaac | 1860 |
| gagccagaat ctattcatca gacagtgatg agggatcaga agaagataaa gctcaaagat | 1920 |
| tactcaaagc aaagaaactt accagtgatg aggaaggtga accttccgga aagagaaaag | 1980 |
| cagaagatga tgataaagca aataaaaagc ataagaagta tgtgatcagc gatgaagagg | 2040 |
| aagaagatga tgattgaagt atgaaatatg aaaacatttt atatattta ttgtacagtt | 2100 |
| ataaatatgt aaacatgagt tattttgatt gaatgaatc gatttgcttt tgtgtaattt | 2160 |
| taattgtaat aaaacaattt aaaagcaaaa aaaaaaaaa aa | 2202 |

<210> SEQ ID NO 22
<211> LENGTH: 2047
<212> TYPE: DNA
<213> ORGANISM: Homo sapiens

<400> SEQUENCE: 22

| | |
|---|---|
| ttgattatgg aacattctaa aacttagaca agacgattgt gattggctga agggcatacg | 60 |
| ccctcctcca gggtgacgtg tctgcctatg gatatcagtt gccagagaaa cctggcttta | 120 |
| ctatggcggt tggaggaacg gcagtgatca cacgtcggct gctgggaaga tctggattct | 180 |
| cgtttcaggt caccatcaga aaagctaagt ttgctgtata gtgaggatca ggagatctga | 240 |
| tcctgattgc agaaccttcc ctgattacag aatcttggga ttgttgagag gattacatgt | 300 |
| aaagtaccag gacagtgcat ggcacatatg atttcacaaa agttcatctt cattgcagat | 360 |
| acctgccttt cttctaggt tgtatctccc acttcaccct tctagaccat cccagaagat | 420 |
| ctataagatt tcatctggga aatcactagg agttcttgga agggaaagaa ggaagattgt | 480 |
| tggttggaat aaaaacaggg ttgaatgagt tccagaaagc agggttctca acctcgtgga | 540 |
| cagcaatctg cagaagaaga gaacttcaaa aaaccaacta gaagcaacat gcagagaagt | 600 |
| aaaatgagag gggcctcctc aggaaagaag acagctggtc cacagcagaa aaatcttgaa | 660 |
| ccagctctcc caggaagatg gggtggtcgc tctgcagaga acccccttc aggatccgtg | 720 |
| aggaagacca gaaagaacaa gcagaagact cctggaaacg gagatggtgg cagtaccagc | 780 |
| gaagcacctc agccccctcg gaagaaaagg gcccgggcag accccactgt tgaaagtgag | 840 |
| gaggcgttta agaatagaat ggaggttaaa gtgaagattc ctgaagaatt aaaaccatgg | 900 |
| cttgttgagg actgggactt agttaccagg cagaagcagc tgtttcaact ccctgccaag | 960 |
| aaaaatgtag atgcaattct ggaggagtat gcaaattgca agaaatcgca gggaaatgtt | 1020 |
| gataataagg aatatgcggt taatgaagtt gtggcaggaa taaaagaata tttcaatgtg | 1080 |

-continued

```
atgttgggca ctcagctgct ctacaaattt gagaggcccc agtatgctga aatcctcttg      1140
gctcaccctg atgctccaat gtcccaggtt tatggagcac cacacctact gagattattt      1200
gtaagaattg gagcaatgtt ggcctatacg ccccttgatg agaaaagcct tgcattattg      1260
ttgggctatt tgcatgattt cctaaaatat ctggcaaaga attctgcatc tctctttact      1320
gccagtgatt acaaagtggc ttctgctgag taccaccgca aagccctgtg agcgtctaca      1380
gacagctcac cattttttgtc ctgtatctgt aaacactttt tgttcttagt cttttcttg      1440 taaaattgat gttctttaaa atcgttaatg tataacaggg cttatgtttc agtttgtttt      1500
ccgttctgtt ttaaacagaa aataaaagga gtgtaagctc cttttctcat ttcaaagttg      1560
ctaccagtgt atgcagtaat tagaacaaag aagaaacatt cagtagaaca ttttattgcc      1620
tagttgacaa cattgcttga atgctggtgg ttcctatccc tttgacacta cacaattttc      1680
taatatgtgt taatgctatg tgacaaaacg ccctgattcc tagtgccaaa ggttcaactt      1740
aatgtatata cctgaaaacc catgcatttg tgctcttttt tttttttat ggtgcttgaa       1800 gtaaaacagc ccatcctctg caagtccatc tatgttgttc ttaggcattc tatctttgct      1860
caaattgttg aaggatggtg atttgtttca tggttttgt atttgagtct aatgcacgtt       1920
ctaacatgat agaggcaatg cattattgtg tagccacggt tttctggaaa agttgatatt      1980
ttaggaattg tatttcagat cttaaataaa atttgtttct aaatttcaaa gcaaaaaaaa      2040
aaaaaaa                                                                2047

<210> SEQ ID NO 23
<211> LENGTH: 4451
<212> TYPE: DNA
<213> ORGANISM: Homo sapiens

<400> SEQUENCE: 23
aaaagatatg gtggggtgct taacagagga ggttagacac cggcgggaac cagaggagcc        60
caagcgcggc gcctgggcct cggggctgca ggagtcctcg gtgggggtat ggaggtcgcc       120
ggggaaggag gacggttcag ttgctaggca acccggcctg gacccgcctc tcgctcgcgt       180
tgctgggaga ctacaaggcc ggggagggg cggcgaaagg gccctacgtg ctgacgctaa       240
ttgtatatga gcgcgagcgg cgggctcttg ggtctttttt agcgccatct gctcgcggcg       300
ccgcctcctg ctcctcccgc tgctgctgcc gctgccgccc tgagtcactg cctgcgcagc       360
tccggccgcc tggctcccca tactagtcgc cgatatttgg agttcttaca acatggcaga      420
cattgacaac aaagaacagt ctgaacttga tcaagatttg gatgatgttg aagaagtaga       480
agaagaggaa actggtgaag aaacaaaact caaagcacgt cagctaactg ttcagatgat       540
gcaaaatcct cagattcttg cagcccttca agaaagactt gatggtctgg tagaaacacc       600
aacaggatac attgaaagcc tgcctagggt agttaaaaga cgagtgaatg ctctcaaaaa       660
cctgcaagtt aaatgtgcac agatagaagc caaattctat gaggaagttc acgatcttga       720
aaggaagtat gctgttctct atcagcctct atttgataag cgatttgaaa ttattaatgc       780
aatttatgaa cctacggaag aagaatgtga atggaaacca gatgaagaag atgagatttc       840
ggaggaattg aaagaaaagg ccaagattga agatgagaaa aagatgaag aaaaagaaga       900 ccccaaagga attcctgaat tttggttaac tgttttaag aatgttgact tgctcagtga       960
tatggttcag gaacacgatg aacctattct gaagcacttg aaagatatta agtgaagtt      1020 ctcagatgct ggccagccta tgagttttgt cttagaattt cactttgaac ccaatgaata      1080
```

```
ttttacaaat gaagtgctga caaagacata caggatgagg tcagaaccag atgattctga  1140
tcccttttct tttgatggac cagaaattat gggttgtaca gggtgccaga tagattggaa  1200
aaaaggaaag aatgtcactt tgaaaactat taagaagaag cagaaacaca agggacgtgg  1260
gacagttcgt actgtgacta aaacagtttc caatgactct ttctttaact tttttgcccc  1320
tcctgaagtt cctgagagtg gagatctgga tgatgatgct gaagctatcc ttgctgcaga  1380
cttcgaaatt ggtcactttt tacgtgagcg tataatccca agatcagtgt tatattttac  1440
tggagaagct attgaagatg atgatgatga ttatgatgaa gaaggtgaag aagcggatga  1500
ggaaggggaa gaagaaggag atgaggaaaa tgatccagac tatgacccaa gaaggatca  1560
aaacccagca gagtgcaagc agcagtgaag caggatgtat gtggccttga ggataacctg  1620
cactggtcta ccttctgctt ccctggaaag gatgaattta catcatttga caagcctatt  1680
ttcaagttat tgttgtttg tttgcttgtt tttgtttttg cagctaaaat aaaaatttca  1740
aatacaattt tagttcttac aagataatgt cttaattttg taccaattca ggtagaagta  1800
gaggcctacc ttgaattaag ggttatactc agttttaac acattgttga agaaaaggta  1860
ccagctttgg aacgagatgc tatactaata agcaagtgta aaaaaaaaa aaaaagagga  1920
agaaaatctt aagtgattga tgctgttttc ttttaaaaaa aaaaaaaaa attcatttc  1980
tttgggttag agctagagag aaggccccaa gcttctatgg tttcttctaa ttcttattgc  2040
ttaaagtatg agtatgtcac ttacccgtgc ttctgtttac tgtgtaatta aaatgggtag  2100
tactgtttac ctaactacct catggatgtg ttaaggcata ttgagttaaa tctcatataa  2160
tgtttctcaa tcttgttaaa agctcaaaat tttgggccta tttgtaatgc cagtgtgaca  2220
ctaagcattt tgttcacacc acgctttgat aactaaactg gaaaacaaag gtgttaagta  2280
cctctgttct ggatctgggc agtcagcact cttttagat ctttgtgtgg ctcctatttt  2340
tatagaagtg gagggatgca ctatttcaca aggtccaaga tttgttttca gatattttg  2400
atgactgtat tgtaaatact acagggatag cactatagta ttgtagtcat gagacttaaa  2460
gtggaaataa gactattttt gacaaaagat gccattaaat ttcagactgt agagccacat  2520
ttacaatacc tcaggctaat tactgttaat tttgggggttg aacttttttt tgacagtgag  2580
ggtggattat tggattgtca ttagaggaag gtctagattt cctgctctta ataaaattac  2640
attgaattga ttttagagg taatgaaaac ttccttctg agaagttagt gttaaggtct  2700
tggaatgtga acacattgtt tgtagtgcta tccattcctc tcctgagatt ttaacttact  2760
actgaaaatc cttaaccaat tataatagct ttttttcttt attttcaaaa tgatttcctt  2820
tgctttgatt agacactatg tgctttttt ttttaaccat agttcatcga aatgcagctt  2880
tttctgaact tcaaagatag aatcccattt taatgaact gaagtagcaa atcatctttt  2940
ttcattcttt aggaaatagc tattgccaaa gtgaaggtgt agataatacc tagtcttgtt  3000
acataaaggg gatgtggttt gcagaagaat tttctttata aaattgaagt tttaagggac  3060
gtcagtgttt atgccatttt tccagttcca aaatgattcc attccattct agaaatttga  3120
agtatgtaac ctgaaatcct taataaaatt tggatttaat tttataaaat gtactggtga  3180
tattttgggt gttttttttt aaatgaatgt atatacttt tttttgaaga gtggagagta  3240
gtgatgtcta gagggagcta ttttgtgctg aggccactat gttctgtaaa tatataattt  3300
taagagcaac ctcacaatcc ctgctaagtg gagtttatta tttgaagact aaaatggaat  3360
tccatagttc ctgataggtt atattctggg ttattattct gagttatcta caaacatttt  3420
tgagatttgt ctttacactc tgattgtagt ttccagcagc ccatgcacac tgccaagtaa  3480
```

```
gtctcatttt ttcctgttag aaatggtgaa atatcatata atcacttata aagaaaactg    3540
atatgaaaaa atttagagt tgtttgcttt atggtcactc aagtagggta agtgttccac     3600
aaattccaca agttgatagt ttaacatgga tgtctgaaag ccacatatat aatttcttag    3660
gattcttaaa ttagtaaatc tagcttactg aagcagtatt agcatcacta ttttagattg    3720
caaaaatacc ttaattgtgt ggaactggct tgtagagtgg tacttaagaa aaatgggatt    3780
ctacctctat ttctgtttta gcacacttaa tcaggaaagg atatattaac tttcataaaa    3840 atattttgt tgtgtgaata ggttaatgat atggtaaggc ccctaaaata actgaattaa     3900
ttgtttattg taattgtagg ccattcccat tattaaaaat aaagacaaaa cttgaagtaa    3960
ctgaaaatct tatcgtgcta tgtagaaata ttgaactaat attcaaatat ttgaatgctt    4020
tggtttcagg gattggttta aaattggagt cctttttat gggttagtct tacaaaaatt     4080 taagcccttta tattttgac tttaaatcaa aacaaatgtt attttaaatg tacagaatag    4140
attggtagtg cagaagagtg taagttcttc ataggagctt tagaaaagag aaatatgtgc    4200
taattcagtt tttttttaat ctgcactgta catatatact tggtaattat gagcttgatt    4260
ttgttttggg aaatatgtgt tcataattta ggtaatttgc tacttaaagc actaagtctc    4320
tgatacctga aaagtacatg taaatggtga tggtgaaata atactgcagt taacttaata   4380
gatgtatact ggtgattttt gtatgctgga ttaaaactcc agatattaaa atataacctg    4440
gataaaaagc c                                                         4451

<210> SEQ ID NO 24
<211> LENGTH: 1530
<212> TYPE: DNA
<213> ORGANISM: Homo sapiens

<400> SEQUENCE: 24
ggcattcaga gagtagatgc cagtcctggg aaaggcaggg gaggagagga gagccacggc      60
tgacgcttgg ggacagaagg aggagcctga ggaggagaca ggacagagcg tctggagagg     120
caggaggaca ccgagttccc cgtgttggcc tccaggtcct gtgcttgcgg agccgtccgg     180
cggctgggat cgagccccga caatgggcaa cgcgcaggag cggccgtcag agactatcga    240
ccgcgagcgg aaacgcctgg tcgagacgct gcaggcggac tcgggactgc tgttggacgc    300
gctgctggcg cggggcgtgc tcaccgggcc agagtacgag gcattggatg cactgcctga    360
tgccgagcgc agggtgcgcc gcctactgct gctggtgcag ggcaagggcg aggccgcctg    420
ccaggagctg ctacgctgtg cccagcgtac cgcgggcgcg ccggacccog cttgggactg    480 gcagcacgct accgggaccg cagctatgac cctccatgcc caggccactg gacgccggag    540
gcacccggct cggggaccac atgccccggg ttgcccagag cttcagaccc tgacgaggcc    600
gggggccctg agggctccga ggcggtgcaa tccgggaccc cggaggagcc agagccagag    660
ctggaagctg aggcctctaa agaggctgaa ccggagccgg agccagagcc agagctggaa    720
cccgaggctg aagcagaacc agagccggaa ctggagccag aaccggaccc agagcccgag    780
cccgacttcg aggaaaggga cgagtccgaa gattcctgaa ggccagagct ctgacaggcg    840
gtgccccgcc catgctggat aggacctggg atgctgctgg agctgaatcg gatgccacca    900
aggctcggtc cagcccagta ccgctggaag tgaataaact ccggagggtc ggacgggacc    960
tgggctctct ccacgattct ggctgtttgc ccaggaactt agggtgggta cctctgagtc   1020
ccagggacct gggcaggccc aagcccacca cgagcatcat ccagtcctca gccctaatct   1080
```

```
gcccttagga gtccaggctg caccctggag atcccaaacc tagcccccta gtgggacaag      1140
gacctgaccc tcctgcccgc atacacaacc catttcccct ggtgagccac ttggcagcat      1200
atgtaggtac cagctcaacc ccacgcaagt tcctgagctg aacatggagc aaggggaggg      1260
tgacttctct ccacataggg agggcttaga gctcacagcc ttgggaagtg agactagaag      1320
aggggagcag aaagggacct tgagtagaca aaggccacac acatcattgt cattactgtt      1380
ttaattgtct ggcttctctc tggactggga gctcagtgag gattctgacc agtgacttac      1440
acaaaaggcg ctctatacat attataatat attcgcttac taaatgaata aggactttcc      1500
aaaaaaaaaa aaaaaaaaaa aaaaaaaaaa                                       1530

<210> SEQ ID NO 25
<211> LENGTH: 2410
<212> TYPE: DNA
<213> ORGANISM: Homo sapiens

<400> SEQUENCE: 25
ggtgcagcct tacgccgctg acgcatcgcg cccaagatgg cggcgcggtc gtcgtcgggg        60
gtggcggcgg cagaggggggc ggcggccctg gcggcagcgg agacggcagc cgtgacggtg      120
gcagcggcgg cgcgggacct gggcctgggg aatgaggcg ccgcggcgg ccagcggcg         180 gagccgtgta gcggagaagc tccccctccc tgcttccctt ggccgagccg ggggcgcgcg      240
cgcacgcggc cgtccagagc gggctcccca cccctcgact cctgcgaccc gcaccgcacc      300
cccacccggg cccggaggat gatgaagctc aagtcgaacc agacccgcac ctacgacggc      360
gacggctaca agaagcgggc cgcatgcctg tgtttccgca gcgagagcga ggaggaggtg      420
ctactcgtga gcagtagtcg ccatccagac agatggattg tccctggagg aggcatggag      480
cccgaggagg agccaagtgt ggcagcagtt cgtgaagtct gtgaggaggc tggagtaaaa      540
gggacattgg gaagattagt tggaattttt gagaaccagg agaggaagca caggacgtat      600
gtctatgtgc tcattgtcac tgaagtgctg gaagactggg aagattcagt taacattgga      660
aggaagaggg aatggtttaa aatagaagac gccataaaag tgctgcagta tcacaaaccc      720
gtgcaggcat catattttga acattgagg caaggctact cagccaacaa tggcacccca      780
gtcgtggcca ccacatactc ggtttctgct cagagctcga tgtcaggcat cagatgactg      840
aagacttcct gtaagagaaa tggaaattgg aaactagact gaagtgcaaa tcttccctct      900
caccctggct cttttccactt ctcacaggcc tcctcttcca ataaggcat ggtgggcagc      960 aaagaaaggg tgtattgata atgttgctgt ttggtgttaa gtgatggggc ttttctcct      1020 gtttttattg agggtgggg ttgggtgtgt aatttgtaag tactttgtg catgatctgt      1080 ccctccctct tcccacccct gcagtcctct gaagagaggc caacagcctt ccctgcctt      1140 ggattctgaa gtgttcctgt ttgtcttatc ctggccctgg ccagacgttt tctttgattt      1200
ttaatttttt tttttatta aaagatacca gtatgagatg aaaacttcca ataatttgtc      1260
ctataatgtg ctgtacagtt cagtagagtg gtcactttca ctgcagtata catttatcta      1320
cacattatat atcggacata taatatgtaa ataaatgact tctagaaaga gaatttgtt      1380 taattttcta aggttttttt ctcttttaat ttgggcattt ctagaattga gagcctcaca      1440
attaacatac ctttttgttt tcgatgctag tggctgggca ggttgccctg tcctttctct      1500
atttcccagt cattgactgt agatatggga agagtttagc taccttcata gtgctcccag      1560
gactcatggc ctttccttct ttaagctgta tttccctgcc cagaaagaaa caggaagaaa      1620 cctttttttta tttttttatt ttttttaac caagcaagga gcaaatggcc tcagcccaga      1680
```

```
tctgtaaaaa caatgataga aattgaattc tgccccacat gttgacagta gagttggaac   1740
tggattcttg ggattactta tctaaaaaac tggagcatca ggtccatttc tgttctgctg   1800
gtttggaatc ttttccgtaa tgctatttat tgccaacaat ggcctctctt tgtgtccata   1860
tatgccttac accgtgctga cctgggtatc atccatgtgc tctgaagcat ccaactttac   1920
tttgcaggtg catcaatgta gtcctgtccc tgaactgagt aaccgtgttc ctgaaaagta   1980
cactagggaa attcacctgc ttgcttgtct ttgtattggc atggcacttg tgattgcacc   2040
atggagcatg ctcagagcta ttaaattggt ctcccatctc ccaccaggat atgaaaggtc   2100
catatgggag gccacgtaat cacttattac agtggttaca taatacactg gctcactgca   2160
gactctcttg tttttgata cagtttcgtg ctggcttcat tgccaattg tgttgtttag    2220 ttcggaagta agagggtctt gagattgagg ggtaggagg gctacactga ctgatccgtg    2280
gcttaagaca ggagattatc tctgtactcc agtggcatct ccttagccaa gatgtgaaat   2340
taaaatcata gttcgcctca tttaaaaatt ctaataaagc actcaaactt tgaaaaaaaa   2400
aaaaaaaaaa                                                          2410

<210> SEQ ID NO 26
<211> LENGTH: 1947
<212> TYPE: DNA
<213> ORGANISM: Homo sapiens

<400> SEQUENCE: 26
atgcagatga ggcactcggg ggcggggcgg cggcggcggc ggcggcggtg gcggccgggg    60
agggtcagtt ggaggcaggc gctcgctgag gcaaaaggag gcgctcggcc cgcggcctga   120
cagggactta gcccgcagag atcgaccccg cgcgcgtgac cccacaccca cccactcatc   180
catctatcca ctccctgcgc cgcctcctcc caccctgagc agagccgccg aggatgataa   240
acacccagga cagtagtatt ttgcctttga gtaactgtcc ccagtccag tgctgcaggc    300 acattgttcc agggcctctg tggtgctcct gatgcccctc acccactgtc gaagatcccc   360
ggtgggcgag gggcggcag ggatccttct ctctcagctc taatatataa ggacgagaag    420
ctcactgtga cccaggacct ccctgtgaat gatggaaaac ctcacatcgt ccacttccag   480
tatgaggtca ccgaggtgaa ggtctcttct tgggatgcag tcctgtccag ccagagcctg   540
tttgtagaaa tcccagatgg attattagct gatgggagca agaaggatt gttagcactg    600 ctagagtttg ctgaagagaa gatgaaagtg aactatgtct tcatctgctt caggaagggc   660
cgagaagaca gagctccact cctgaagacc ttcagcttct gggctttga gattgtacgt    720 ccaggccatc cctgtgtccc ctctcggcca gatgtgatgt tcatggttta tccctggac    780 cagaacttgt ccgatgagga ctaatagtca tagaggatgc tttacccaag agccacagtg   840
ggggaagagg ggaagttagg cagccctggg acagacgaga gggctcctcg ctgtctaggg   900
aaggacactg aggggctcag ggtgagggtt gcctattgtg ttctcggagt tgactcgttg   960
aaattgtttt ccataaagaa cagtataaac atattattca catgtaatca ccaatagtaa  1020
atgaagatgt ttatgaactg gcattagaag cttctctaaac tgcgctgtgt gatgtgttct  1080
atctagccta ggggaggaca ttgcctagag ggggagggac tgtctgggtt caggggcatg   1140
gcctggaggg ctggtgggca gcactgtcag gctcaggttt ccctgctgtt ggctttctgt   1200
tttggttatt aagacttgtg tattttcttt ctttgcttcc tgtcacccca ggggctcctg   1260
agtataggct tttcagtccc tgggcagtgt ccttgagttg ttttttgaca ctcttacctg   1320
```

-continued

| | |
|---|---|
| ggcttctctg tgtgcatttg cgtctggcct ggagtaagca ggtccgaccc ctccttcttt | 1380 |
| acagcttagt gttattctgg catttggtta agctggctta atctgtttaa tgttatcagt | 1440 |
| acattttaaa taggggcatt gaaatttact cccaccacca gggcttttt gggggatgcc | 1500 |
| tgggccttta aaacactagc caaactctaa ttaattctca aatcactgcc aggagttctt | 1560 |
| gctcctggct gcaggcccag gccccaaggt ctccttcttg gggtcacaaa cagcagtaag | 1620 |
| gaagaggaat atatagcaac tcagggcctg ggaattgtgg ggcaatccgt tcttagggac | 1680 |
| tggatacttc tggctggctg agtatagtac tagctgcctc cccaccaggt tccgagtagt | 1740 |
| gtctgagact ctgctctgca gggcctaggg tagcgctggg agtgtagaag tggcctgccc | 1800 |
| ttaactgttt tcactaaaca gcttttcta aggggagagc aaggggaga gatctagatt | 1860 |
| gggtgagggg gacggggatg tcagggaggc aagtgtgttg tgttactgtg tcaataaact | 1920 |
| gatttaaagt tgtgaaaaaa aaaaaaa | 1947 |

<210> SEQ ID NO 27
<211> LENGTH: 1712
<212> TYPE: DNA
<213> ORGANISM: Homo sapiens

<400> SEQUENCE: 27

| | |
|---|---|
| atgctggggg aggggctggc ggcctcgacg gcagctgcgg aactaggccg agggacaaag | 60 |
| gctaagtttt tccatggttt ggactggata tcggtgaaac tctggtcaag ctggtatatt | 120 |
| ttgaacccaa agacatcact gctgaagaag aagaggaaga agtggaaagt cttaaaagca | 180 |
| ttcggaagta cctgacctcc aatgtggctt atgggtctac aggcattcgg gacgtgcacc | 240 |
| tcgagctgaa ggacctgact ctgtgtggac gcaaaggcaa tctgcacttt atacgctttc | 300 |
| ccactcatga catgcctgct tttattcaaa tgggcagaga taaaaacttc tcgagtctcc | 360 |
| acactgtctt ttgtgccact ggaggtggag cgtacaaatt tgagcaggat tttctcacaa | 420 |
| taggtgatct tcagctttgc aaaactggat gaactagattg cttgatcaaa ggaatttttat | 480 |
| acattgactc agtcggattc aatggacggt cacagtgcta ttactttgaa aaccctgctg | 540 |
| attctgaaaa gtgtcagaag ttaccatttg atttgaaaaa tccgtatcct ctgcttctgg | 600 |
| tgaacattgg ctcaggggtt agcatcttag cagtatattc caaagataat tacaaacggg | 660 |
| tcacaggtac tagtcttgga ggaggaactt ttttggtct ctgctgtctt cttactggct | 720 |
| gtaccacttt tgaagaagct cttgaaatgg catctcgtgg agatagcacc aaagtggata | 780 |
| aactagtacg agatatttat ggagggact atgagaggtt tggactgcca ggctgggctg | 840 |
| tggcttcaag cttttggaaac atgatgagca aggagaagcg agaggctgtc agtaaagagg | 900 |
| acctggccag agcgactttg atcaccatca ccaacaacat tggctcaata gcaagaatgt | 960 |
| gtgcccttaa tgaaaacatt aaccaggtgg tatttgttgg aaatttcttg agaattaata | 1020 |
| cgatcgccat gcggcttttg gcatatgctt tggattattg gtccaagggg cagttgaaag | 1080 |
| cactttttc ggaacacgag ggttattttg gagctgttgg agcactcctt gagctgttga | 1140 |
| agatcccgtg atcattacct ggggaggggt tcctgaaacc ttccacaatg ggatctgtgg | 1200 |
| actttcattt ttttaagaga cttactcaat ttcatgactg tactacctga aacaaagtga | 1260 |
| gaaaggacag gtgtattttt ctaagtcatc aagataaatc cttaagaatt cagtctaaat | 1320 |
| tagcaaccag gaaggaaaaa tatattaaaa acaacaaaaa agtggcacat gtccaggcag | 1380 |
| tgtgaggatt tgctgtatat aagttgcctg cttttgtattt ttgaaatctc tgcatcactc | 1440 |
| attggaagtg cttctgaaga gagctgctct gtgttcagtt gactggtttt gtgtcctgtt | 1500 |

-continued

| | |
|---|---|
| tgaacttgct gaatgtaagg caggctacta tgcgttataa tctaatcaca atttgtcaat | 1560 |
| atggtcttgg caatcatctg tgcattactc tggtttgcat taagcctgtg tgtgaactta | 1620 |
| ctgtaaaaca tgttttattt caaggttctg caaaattaat tgggcaggtt aattgtgtac | 1680 |
| ctgaaactta acaagcagtt tttggaaggg ca | 1712 |

<210> SEQ ID NO 28
<211> LENGTH: 7332
<212> TYPE: DNA
<213> ORGANISM: Homo sapiens

<400> SEQUENCE: 28

| | |
|---|---|
| ggtgaatggg ctggtggtgc tcgctgctgc tgctgagagg aggaggagga tgaagagttg | 60 |
| ggcttgtttg tctcctacag tttctctcct gctgctctga ttccccctc ccgattccgg | 120 |
| cccggggcct gtgtgtgtcc ctcctggagg aggaggagga tccagttcct cccccaacc | 180 |
| ccctcctccc caccccccct tgcctgggga agaggaggaa agaaacagcc cagagagaga | 240 |
| gagagagaga gagtgagtga gagagagagg agaggagagg aggaggagga ggagggagaa | 300 |
| gggaacaacc taccatctta acacactaat atctaaaaag tgcgagaggc ccagagcagc | 360 |
| agcagaagca gcagcagcag ctccagcttc ttccctccct ccccatgaag aagagttccc | 420 |
| tcctcctcct cctcctgctt ctcctgctca gagttcctgc ctccagctgc caggggggac | 480 |
| agccagccag cagcaggagg ggggctagag agctgaagga gagccagttt ccccaaaatt | 540 |
| gctgcagtga aagaggagt ttgttactttt aaacagaggc tgaagaaact atagaattag | 600 |
| cagagaaagt ggagaaggta gaggatggag ttgcagactc tacaggaggc tcttaaagtg | 660 |
| gaaattcagg ttcaccagaa actggttgct caaatgaagc aggatccaca gaatgctgac | 720 |
| ttaaagaaac agcttcatga actccaagcc aaaatcacag ctttgagtga gaaacagaaa | 780 |
| agagtagttg aacagctacg gaagaacctg atagtaaagc aagaacaacc ggacaagttc | 840 |
| caaatacagc cattgccaca atctgaaaac aaactacaaa cagcacagca gcaaccacta | 900 |
| cagcaactac aacaacagca gcagtaccac caccaccacg cccagcagtc agctgcagcc | 960 |
| tctcccaacc tgactgcttc acagaagact gtaactacag cttctatgat taccacaaag | 1020 |
| acactacctc tcgtcttgaa agcagcaact gcgaccatgc ctgcctctgt ggtgggccag | 1080 |
| agacctacca ttgctatggt gaccgccatc aacagtcaga aggctgtgct cagcactgat | 1140 |
| gtgcagaaca caccagtcaa cctccagacg tctagtaagg tcactgggcc tggggcagag | 1200 |
| gctgtccaaa ttgtggcaaa aaacacagtc actctggttc aggcaacacc tcctcagccc | 1260 |
| atcaaagtac cacagtttat ccccctcct agactcactc cacgtccaaa ctttcttcca | 1320 |
| caggttcgac ccaagcctgt ggcccagaat aacattccta ttgccccagc accacctccc | 1380 |
| atgctcgcag ctcctcagct tatccagagg cccgtcatgc tgaccaagtt caccccaca | 1440 |
| acccttccca catcccagaa ttccatccac cccgtccgtg tcgtcaatgg gcagactgca | 1500 |
| accatagcca aaacgttccc catggcccag ctcaccagca ttgtgatagc tactccaggg | 1560 |
| accagactcg ctggacctca aactgtacag cttagcaagc caagtcttga aaaacagaca | 1620 |
| gttaaatctc acacagaaac agatgagaaa caaacagaga gccgcaccat caccccacct | 1680 |
| gctgcaccca aaccaaaacg ggaggagaac cctcagaaac ttgccttcat ggtgtctcta | 1740 |
| gggttggtaa cacatgacca tctagaagaa atccaaagca agaggcaaga gcgaaaaaga | 1800 |
| agaacaacag caaatccggt ctacagtgga gcagtctttg agccagagcg taagaagagt | 1860 |

```
gcagtgacat acctaaacag cacaatgcac cctgggaccc ggaagagagg tcgtcctcca    1920
aaatacaatg cagtgctggg gtttggagcc cttaccccaa catcccccca atccagtcat    1980
cctgactccc ctgaaaatga aaagacagag accacattca ctttccctgc acctgttcag    2040
cctgtgtccc tgcccagccc cacctccaca gacggtgata ttcatgagga ttttttgcagc   2100 gtttgcagaa aaagtggcca gttactgatg tgcgacacat gttcccgtgt atatcatttg    2160
gactgcttag acccccctct gaaaacaatt cccaagggca tgtggatctg tcccagatgt    2220
caggaccaga tgctgaagaa ggaagaagca attccatggc ctggaacttt agcaattgtt    2280
cattcctata ttgcctacaa agcagcaaaa gaagaagaga aacagaagtt acttaaatgg    2340
agttcagatt taaaacaaga acgagaacaa ctagagcaaa aggtgaaaca gctcagcaat    2400
tccataagta aatgcatgga aatgaagaac accatcctgg cccggcagaa ggagatgcac    2460
agctccctgg agaaggtaaa acagctgatt cgcctcatcc acggcatcga cctctccaaa    2520
cctgtagact ctgaggccac tgtggggcc atctccaatg cccggactg cacccccct     2580 gccaatgccg ccacctccac gccggcccct tccccctcct cccagagctg cacagcgaac    2640
tgtaaccagg gggaagagac taaataacag agccctcta ggagaagcca cgggatcccg     2700
gcggcaagga gaacagaaca ctgaagactc tagaaaagca aagccggatt tctggaaagt    2760
gcagaattct tttggttctt tggttccaga gagagagaag atgcttgtgc caggtggcac    2820
cagagtttgc caattgatcc ttcttattct gtgtgtacat gcaaagattg gaccatgtta    2880
catgaaatag tgccagctgg aggttctttg ccagcaccat gccaagtgaa ataatatatt    2940
tactctctct attatacacc agtgtgtgcc tgcagcagcc tccacagcca cgatgggttt    3000
gtttctgttt tcttgggtgg ggagcaggga cgggcggagg gaggagagca ggtttcagat    3060
ccttacttgc cgagccgttt gtttaggtag agaagacaag tccaaagagt gtgtgggctt    3120
tcctgtttct aaactttcgc tactataaaa ccaaaaaaag gaattgagat ttcaccaacc    3180
ccagtgccca gaagagggaa ggggagtggc tggagggagc aggggtggg acagtgtatc      3240 aaataagcag tatttaatca cctctggcgg gggcctcgtg caaggggaga ctgacaccaa    3300
gaacagccag taggttcttc tcccctgcac tctgctccct gcgcggtaac cccaccactc    3360
ctgaagcctg cccagtctcc ttccttccct gcttggtgag tcgcgcatct ccgtggttat    3420
cccgctgtct cctctccaag aacaagcaga gcccgggcca ctggcccttg cccaaggcag    3480
ggaagaagga tgtgtgtgtc caggaaggaa aaaaggtgg atcagtgatt ttacttgaaa     3540
acaagctcca tccctttttct atatttataa gaagagaaga tcttgagtga agcagcacgc    3600
gacccaggtg tgtgtgaatt gaatggagac gtttctttc tctttcttta attttttgttt    3660 ttgttctttt tttctttaag gaaagtttta ttttactgtt cattttactt tcttggtaac    3720
aaaaactaaa ataaggaata gaaaagctgt ttttcaggct gacagtccaa ttaagggtag    3780
ccaagacctt gcatggtaga gtaggaatca tagtgtcagt gaggtcccgt gagtctttgt    3840
gagtccttgt gtcatcgttc gggcactgtt tttttatgca agggcaaaaa tctttgtatc    3900
tggggaaaaa aaacttttttt ttaaattaaa aaggaaaata aaagatattg aggtcttcct    3960
agtgttactt aaattaagat caaggtaaga aacattgtaa aaaaaaatta caaaagtgct    4020
atttgtttcc taaaaacagt gatttctatt aaaaggtgt cagaactgga gaaaatgccg     4080
tgtagttata atttttttagc acagaccctg ctgatcacga tgacattttg ccgtgtgtgt    4140
gtctctagac tggtgggcca gtctccttga aggacagagg cggagctccc cacccttctc    4200
tctcctcaga aaagaccgtg ctctcttctt ggtgcaggga tcttgtctcc tgttgtgaag    4260
```

-continued

```
cccaaatgga agcgtggatg gtatcagggc cctacccgtg gtcttctcag attctgctag    4320
agcaaaaggc tggtgcctaa ataagatccc ttcctttggt gctgcttttg gtctttcagc    4380
caccagcatt atgagtgcct gggggacacc tccgagggaa ctggccagcg gagctctgtg    4440
gtgcgcacgc accctggccg tgacaggagg gtgcgggagt acaggctggc tgcatcagcc    4500
cttggtgctt agaacagagg aggagtgaca tgttttgagg gtacgtctct gagacagagc    4560
cccagcgtgg ccttcgctct gtcttgcctt tggggagagg tctgaagctc ccactccttt    4620
ctctgcctgt tggctccagg caccagaaat ttactccact ccacccaccc acaagcctcc    4680
tgggtgaccc tgggctagaa ttgctgcgct tgcctcggct tggccggttg tggcctctcc    4740
ttgagaaaac cagggttgtg aaagactcag accattctct catcttgcct tgtcagaagt    4800
aaattgtgtc agatttgtgc tctcgctgga gacctttgcc ccttgcgtgc ccctggccga    4860
tgggagggcg gtggaggctc tgtaccctgg ccctgctgga gcatctcccc caagcccact    4920
ccaggccctg ggaatggcca gagtctagga gaggtagaaa cgatcctatc agcttctctc    4980
ccacccaatt aggcccagag agacaaagac agatctgaaa gcaaatgcaa cagagaagag    5040
acacttctta gagtaaaatg tgtctcatct ctatcagcca tcgccttttca tcttcccagg    5100 ggcctcagaa gaaggaatta agttaggctg aacaggcctc agagttaggc cctggctgct    5160
tgattggctg agggggaaag agttcccttt tctcattcag aaaccaaggt gctgtgtcta    5220
gtcagggagc cttggagatg cctggactag ttggaggaat cgttggcaga ggatcagaga    5280
ccagcagcag gctgtctgcc ctgtctagag ctcttcccct caacttgtct gggcccatct    5340
gggggttgcc acacaacacc taacttacct tttcctgaaa gaagttggga aaccatcatc    5400
actagaggcc tttgctcaga gaggagctgc cttaggagtc ttgggtcgga ggacggggct    5460
aggaattgac cagggctttg cctgccgccc tcagcagtgt cgggtacatt ctgacctcgc    5520
ctgcagctgg gctgtggatt cttcctgaca ttcagatgtg agctgttttg ggagtcagct    5580
agtatggagt acgagatgca acccagcccc caaacctaca ttctgcactc aaattccaaa    5640
acactgcttt actgtaaaga agaggcccct ggcacccaat ctccctgtcc ttcactgtcc    5700
cctcagacct gggcggggag ggggggggc ctgtgaccac ctgagacata cgctcgtgac    5760
actgccccac cccagccacc tccacttgct tcctcctcct tccctccgct gctctttccc    5820
cacggcccag aatttagctg ctctgacagc cacttttgag accagctggc tttgtagtca    5880
cttcagagag ctggagcggc tgcccactgg gccctgactg ggagtcccct gccagctcct    5940
gatcaggcgc tgcgccctgg tggcagtgat gactgggagt cccctgccag ctcctgtcca    6000
ggcgctgcat cctggtaaca gtgaggccat gttgctgtca tctccacctc tgcattcttg    6060
ctgcctgtgt gtccttttc tttcatggag cctgctgggc cttgtctcac ctgtgctgag    6120
ctcctctggg gttttgattt cttccttcct tatcaggccc tttggggtaa gcctgctggt    6180
tgtacctgac ataggaggc agttagggc agtccctggt ggggccgccc tggcagcctc    6240
cagctggcac catcgtgtgc ctggtttccc tgcaacacct gcctctctgt ccctgctgct    6300
gcttggctca ggcccaacag gcagcgtgca tggaggtggt tacacacagc tgtttccgtg    6360
agggtgaccg tgtctgcagc acgcttccgt ctccgcatgc acggctgcct ctccagccac    6420
ctctgatact tctctcttgg ggccatcaga gcctcccttg ggctgtcacc tcccagctca    6480
cacacactct tcagtggttt cctctcttca ttctcttata gggcgtggtc cttcttattt    6540
atctaaaggg ctgaatttag gagacttttt acccaggggc aaaaggctct tagggtaatg    6600
```

| | |
|---|---:|
| agatggatgg tggcccaggt gcattttcca gggcctgggt tctccagatc ccgtggcttc | 6660 |
| tgttgagtgg aggcaacttt gctctgtgtg aacctcgccc ctgtccctct gccgggcacc | 6720 |
| cctggcagga agcaggactc ccatcctcac cctgacttag actgtcctct gagtcagctc | 6780 |
| ctctccaaga caggagtggg cagccctggg cagtcttctg gccccttgct aaagtgaggg | 6840 |
| gcaggaagct ggggctgccc tccagaaagc cggggtagga actctgaaaa atacctcctc | 6900 |
| taaacggaag cagggctctc cagttccact tggcgccccc tcccacaagg cccttcctcc | 6960 |
| ctgaggaccc caccccccta cccctt ccc agcagccttt ggaccctcac ctctctccgg | 7020 |
| tgtccgtggg tcctcagccc agggtgagct gcagtcaggc gggatgggac gggcaggcca | 7080 |
| gaggtcagcc agctcctagc agagaagagc cagccagacc ccaaccctgt ctcttgtcca | 7140 |
| tgcccttgt gatttcagtc ttggtagact tgtatttgga gttttgtgct tcaaagtttt | 7200 |
| tgttttgtt tgtttggttt ttgttttgag ggggtggggg gggatacaga gcagctgatc | 7260 |
| aatttgtatt tatttatttt aacatttta c taaataaagc caaataaagc ctctcaaaaa | 7320 |
| aaaaaaaaaa aa | 7332 |

```
<210> SEQ ID NO 29
<211> LENGTH: 14135
<212> TYPE: DNA
<213> ORGANISM: Homo sapiens

<400> SEQUENCE: 29
```

| | |
|---|---:|
| gcactgcagc gccagcgtcc gagcgggcgg ccgagctccc ggagcggcct ggccccgagc | 60 |
| cccgagcggg cgtcgctcag cagcaggtcg cggccgcagc cccatccagc cccgcgcccg | 120 |
| ccatgccgtc cgcgggcccc gcctgagctg cggcctccgc gcgcgggcgg gcctggggac | 180 |
| ggcgggggcca tgcgcgcgct gccctaacga tgccgcccgc cgcgcccgcc cgcctggcgc | 240 |
| tggccctggg cctgggcctg tggctcgggg cgctggcggg gggccccggg cgcggctgcg | 300 |
| ggccctgcga gccccctgc ctctgcggcc cagcgcccgg cgccgcctgc cgcgtcaact | 360 |
| gctcgggccg cgggctgcgg acgctcggtc ccgcgctgcg catccccgcg gacgccacag | 420 |
| cgctagacgt ctcccacaac ctgctccggg cgctggacgt tgggctcctg gcgaacctct | 480 |
| cggcgctggc agagctggat ataagcaaca acaagatttc tacgttagaa gaaggaatat | 540 |
| ttgctaattt atttaattta agtgaaataa acctgagtgg gaaccgtttt gagtgtgact | 600 |
| gtggcctggc gtggctgccg cgatgggcgg aggagcagca ggtgcgggtg gtgcagcccg | 660 |
| aggcagccac gtgtgctggg cctggctccc tggctgccca gcctctgctt ggcatcccct | 720 |
| tgctggacag tggctgtggt gaggagtatg tcgcctgcct ccctgacaac agctcaggca | 780 |
| ccgtggcagc agtgtccttt tcagctgccc acgaaggccc gcttcagcca gaggcctgca | 840 |
| gcgccttctg cttctccacc ggccagggcc tgcagccct ctcggagcag ggctggtgcc | 900 |
| tgtgtgggc ggcccagccc tccagtgcct cctttgcctg cctgtccctc tgctccggcc | 960 |
| ccccgccacc tcctgccccc acctgtaggg gccccaccct cctccagcac gtcttccctg | 1020 |
| cctccccagg ggccaccctg gtggggcccc acggacctct ggcctctggc cagctagcag | 1080 |
| ccttccacat cgctgccccg ctccctgtca ctgccacacg ctgggacttc ggagacggct | 1140 |
| ccgccgaggt ggatgccgct gggccggctg cctcgcatcg ctatgtgctg cctgggcgct | 1200 |
| atcacgtgac ggccgtgctg gccgtggggg ccggctcagc cctgctgggg acagacgtgc | 1260 |
| aggtggaagc ggcacctgcc gccctggagc tcgtgtgccc gtcctcggtg cagagtgacg | 1320 |
| agagccttga cctcagcatc cagaaccgcg gtggttcagg cctggaggcc gcctacagca | 1380 |

```
tcgtggccct gggcgaggag ccggcccgag cggtgcaccc gctctgcccc tcggacacgg   1440
agatcttccc tggcaacggg cactgctacc gcctggtggt ggagaaggcg gcctggctgc   1500
aggcgcagga gcagtgtcag gcctgggccg gggccgccct ggcaatggtg gacagtcccg   1560
ccgtgcagcg cttcctggtc tcccgggtca ccaggagcct agacgtgtgg atcggcttct   1620
cgactgtgca gggggtggag gtgggcccag cgccgcaggg cgaggccttc agcctggaga   1680
gctgccagaa ctggctgccc ggggagccac acccagccac agccgagcac tgcgtccggc   1740
tcgggcccac cgggtggtgt aacaccgacc tgtgctcagc gccgcacagc tacgtctgcg   1800
agctgcagcc cggaggccca gtgcaggatg ccgagaacct cctcgtggga gcgcccagtg   1860
gggacctgca gggaccccctg acgcctctgg cacagcagga cggcctctca gccccgcacg   1920
agcccgtgga ggtcatggta ttcccggggcc tgcgtctgag ccgtgaagcc ttcctcacca   1980
cggccgaatt tgggacccag gagctccggc ggcccgccca gctgcggctg caggtgtacc   2040
ggctcctcag cacagcaggg accccggaga acggcagcga gcctgagagc aggtccccgg   2100
acaacaggac ccagctggcc cccgcgtgca tgccagggg acgctggtgc cctggagcca   2160
acatctgctt gccgctggac gcctcctgcc acccccaggc ctgcgccaat ggctgcacgt   2220
cagggccagg gctacccggg gccccctatg cgctatggag agagttcctc ttctccgttc   2280
ccgcggggcc ccccgcgcag tactcggtca ccctccacgg ccaggatgtc ctcatgctcc   2340
ctggtgacct cgttggcttg cagcacgacg ctggccctgg cgcctcctg cactgctcgc   2400
cggctccccgg ccaccctggt ccccaggccc cgtacctctc cgccaacgcc tcgtcatggc   2460
tgccccactt gccagcccag ctggagggca cttgggcctg ccctgcctgt gccctgcggc   2520
tgcttgcagc cacggaacag ctcaccgtgc tgctgggctt gaggcccaac cctggactgc   2580
ggctgcctgg gcgctatgag gtccgggcag aggtgggcaa tggcgtgtcc aggcacaacc   2640
tctcctgcag ctttgacgtg gtctccccag tggctgggct gcgggtcatc taccctgccc   2700
cccgcgacgg ccgcctctac gtgcccacca acggctcagc cttggtgctc caggtggact   2760
ctggtgccaa cgccacggcc acggctcgct ggcctggggg cagtgtcagc gcccgctttg   2820
agaatgtctg ccctgccctg gtggccacct tcgtgcccgg ctgccctgg gagaccaacg   2880
ataccctgtt ctcagtggta gcactgccgt ggctcagtga gggggagcac gtggtggacg   2940
tggtggtgga aaacagcgcc agccgggcca acctcagcct gcgggtgacg gcggaggagc   3000
ccatctgtgg cctccgcgcc acgcccagcc ccgaggcccg tgtactgcag ggagtcctag   3060
tgaggtacag ccccgtggtg gaggccggct cggacatggt cttccggtgg accatcaacg   3120
acaagcagtc cctgaccttc agaacgtgg tcttcaatgt catttatcag agcgcggcgg   3180
tcttcaagct ctcactgacg gcctccaacc acgtgagcaa cgtcaccgtg aactacaacg   3240
taaccgtgga gcggatgaac aggatgcagg tctgcaggt ctccacagtg ccggccgtgc   3300
tgtccccccaa tgccacgcta gcactgacgg cgggcgtgct ggtggactcg gccgtggagg   3360
tggccttcct gtggaccttt ggggatgggg agcaggccct ccaccagttc cagcctccgt   3420
acaacgagtc cttcccggtt ccagacccct cggtggccca ggtgctggtg gagcacaatg   3480
tcatgcacac ctacgctgcc ccaggtgagt acctcctgac cgtgctggca tctaatgcct   3540
tcgagaacct gacgcagcag gtgcctgtga gcgtgcgcgc ctccctgccc tccgtggctg   3600
tgggtgtgag tgacgcgtc ctggtggccg gccgcccgt caccttctac ccgcacccgc   3660
tgccctcgcc tgggggtgtt ctttacacgt gggacttcgg ggacggctcc cctgtcctga   3720
```

```
cccagagcca gccggctgcc aaccacacct atgcctcgag gggcacctac cacgtgcgcc   3780
tggaggtcaa caacacggtg agcggtgcgg cggcccaggc ggatgtgcgc gtctttgagg   3840
agctccgcgg actcagcgtg gacatgagcc tggccgtgga gcagggcgcc ccgtggtgg    3900
tcagcgccgc ggtgcagacg ggcgacaaca tcacgtggac cttcgacatg ggggacggca   3960
ccgtgctgtc gggcccggag gcaacagtgg agcatgtgta cctgcgggca cagaactgca   4020
cagtgaccgt gggtgcggcc agccccgccg gccacctggc ccggagcctg cacgtgctgg   4080
tcttcgtcct ggaggtgctg cgcgttgaac ccgccgcctg catccccacg cagcctgacg   4140
cgcggctcac ggcctacgtc accgggaacc cggcccacta cctcttcgac tggaccttcg   4200
gggatggctc ctccaacacg accgtgcggg ggtgcccgac ggtgacacac aacttcacgc   4260
ggagcggcac gttcccctg cgctggtgc tgtccagccg cgtgaacagg gcgcattact   4320
tcaccagcat ctgcgtggag ccagaggtgg gcaacgtcac cctgcagcca gagaggcagt   4380
ttgtgcagct cggggacgag gcctggctgg tggcatgtgc ctggcccccg ttcccctacc   4440
gctacacctg ggactttggc accgaggaag ccgcccccac ccgtgccagg ggccctgagg   4500
tgacgttcat ctaccgagac ccaggctcct atcttgtgac agtcaccgcg tccaacaaca   4560
tctctgctgc caatgactca gccctggtgg aggtgcagga gcccgtgctg gtcaccagca   4620
tcaaggtcaa tggctccctt gggctggagc tgcagcagcc gtacctgttc tctgctgtgg   4680
gccgtgggcg ccccgccagc tacctgtggg atctggggga cggtgggtgg ctcgagggtc   4740
cggaggtcac ccacgcttac aacagcacag gtgacttcac cgttagggtg gccggctgga   4800
atgaggtgag ccgcagcgag gcctggctca atgtgacggt gaagcggcgc gtgcggggc    4860
tcgtcgtcaa tgcaagccgc acggtggtgc ccctgaatgg gagcgtgagc ttcagcacgt   4920
cgctggaggc cggcagtgat gtgcgctatt cctgggtgct ctgtgaccgc tgcacgccca   4980
tccctggggg tcctaccatc tcttacacct tccgctccgt gggcaccttc aatatcatcg   5040
tcacggctga gaacgaggtg ggctccgccc aggacagcat cttcgtctat gtcctgcagc   5100
tcatagaggg gctgcaggtg gtgggcggtg ccgctactt ccccaccaac cacacggtac    5160
agctgcaggc cgtggttagg gatggcacca acgtctccta cagctggact gcctggaggg   5220
acaggggccc ggccctggcc ggcagcggca aaggcttctc gctcaccgtg ctcgaggccg   5280
gcacctacca tgtgcagctg cgggccacca acatgctggg cagcgcctgg gccgactgca   5340
ccatggactt cgtggagcct gtggggtggc tgatggtggc cgcctccccg aacccagctg   5400
ccgtcaacac aagcgtcacc ctcagtgccg agctggctgg tggcagtggt gtcgtataca   5460
cttggtcctt ggaggagggg ctgagctggg agacctccga gccatttacc acccatagct   5520
tccccacacc cggcctgcac ttggtcacca tgacggcagg gaaccgcctg gctcagccaa   5580
acgccaccgt ggaagtggat gtgcaggtgc ctgtgagtgg cctcagcatc agggccagcg   5640
agcccggagg cagcttcgtg gcggccgggt cctctgtgcc cttttggggg cagctggcca   5700
cgggcaccaa tgtgagctgg tgctgggctg tgcccgcgg cagcagcaag cgtggccctc   5760
atgtcaccat ggtcttcccg gatgctggca ccttctccat ccggctcaat gcctccaacg   5820
cagtcagctg gtctcagcc acgtacaacc tcacggcgga ggagcccatc gtgggcctgg    5880
tgctgtgggc cagcagcaag gtggtggcgc ccgggcagct ggtccatttt cagatcctgc   5940
tggctgccgg ctcagctgtc accttccgcc tgcaggtcgg cggggccaac ccgaggtgc    6000
tccccggggcc ccgtttctcc cacagcttcc ccgcgtcgg agaccacgtg gtgagcgtgc   6060
ggggcaaaaa ccacgtgagc tgggcccagg cgcaggtgcg catcgtggtg ctggaggccg   6120
```

```
tgagtgggct gcaggtgccc aactgctgcg agcctggcat cgccacgggc actgagagga   6180
acttcacagc ccgcgtgcag cgcggctctc gggtcgccta cgcctggtac ttctcgctgc   6240
agaaggtcca gggcgactcg ctggtcatcc tgtcgggccg cgacgtcacc tacacgcccg   6300
tggccgcggg gctgttggag atccaggtgc gcgccttcaa cgccctgggc agtgagaacc   6360
gcacgctggt gctggaggtt caggacgccg tccagtatgt ggccctgcag agcggcccct   6420
gcttcaccaa ccgctcggcg cagtttgagg ccgccaccag ccccagcccc cggcgtgtgg   6480
cctaccactg ggactttggg gatgggtcgc cagggcagga cacagatgag cccagggccg   6540
agcactccta cctgaggcct ggggactacc gcgtgcaggt gaacgcctcc aacctggtga   6600
gcttcttcgt ggcgcaggcc acggtgaccg tccaggtgct ggcctgccgg gagccggagg   6660
tggacgtggt cctgcccctg caggtgctga tgcggcgatc acagcgcaac tacttggagg   6720
cccacgttga cctgcgcgac tgcgtcacct accagactga gtaccgctgg gaggtgtatc   6780
gcaccgccag ctgccagcgg ccggggcgcc cagcgcgtgt ggccctgccc ggcgtggacg   6840
tgagccggcc tcggctggtg ctgccgcggc tggcgctgcc tgtgggcac tactgctttg     6900
tgtttgtcgt gtcatttggg gacacgccac tgacacagag catccaggcc aatgtgacgg   6960
tggcccccga gcgcctggtg cccatcattg agggtggctc ataccgcgtg tggtcagaca   7020
cacgggacct ggtgctggat gggagcgagt cctacgaccc caacctggag gacggcgacc   7080
agacgccgct cagtttccac tgggcctgtg tggcttcgac acagagggag gctggcgggt   7140
gtgcgctgaa ctttgggccc cgcgggagca gcacggtcac cattccacgg gagcggctgg   7200
cggctggcgt ggagtacacc ttcagcctga ccgtgtggaa ggccggccgc aaggaggagg   7260
ccaccaacca gacggtgctg atccggagtg gccgggtgcc cattgtgtcc ttggagtgtg   7320
tgtcctgcaa ggcacaggcc gtgtacgaag tgagccgcag ctcctacgtg tacttggagg   7380
gccgctgcct caattgcagc agcggctcca agcgagggcg gtgggctgca cgtacgttca   7440
gcaacaagac gctggtgctg gatgagacca ccacatccac gggcagtgca ggcatgcgac   7500
tggtgctgcg gcggggcgtg ctgcgggacg gcgagggata caccttcacg ctcacggtgc   7560
tgggccgctc tggcgaggag gagggctgcg cctccatccg cctgtccccc aaccgcccgc   7620
cgctgggggg ctcttgccgc ctcttccac tgggcgctgt gcacgccctc accaccaagg    7680
tgcacttcga atgcacgggc tggcatgacg cggaggatgc tggcgcccg ctggtgtacg     7740
ccctgctgct gcggcgctgt cgccagggcc actgcgagga gttctgtgtc tacaagggca   7800
gcctctccag ctacgagcc gtgctgcccc cgggtttcag gccacacttc gaggtgggcc    7860
tggccgtggt ggtgcaggac cagctgggag ccgctgtggt cgccctcaac aggtctttgg   7920
ccatcaccct cccagagccc aacggcagcg caacgggct cacagtctgg ctgcacgggc    7980
tcaccgctag tgtgctccca gggctgctgc ggcaggccga tccccagcac gtcatcgagt   8040
actcgttggc cctggtcacc gtgctgaacg agtacgagcg ggccctggac gtggcggcag   8100
agcccaagca cgagcggcag caccgagccc agatacgcaa gaacatcacg gagactctgg   8160
tgtccctgag ggtccacact gtggatgaca tccagcagat cgctgctgcg ctggcccagt   8220
gcatggggcc cagcagggag ctcgtatgcc gctcgtgcct gaagcagacg ctgcacaagc   8280
tggaggccat gatgctcatc ctgcaggcag agaccaccgc gggcaccgtg acgccaccg    8340
ccatcggaga cagcatcctc aacatcacag gagacctcat ccacctggcc agctcggacg   8400
tgcgggcacc acagccctca gagctgggag ccgagtcacc atctcggatg gtggcgtccc   8460
```

```
aggcctacaa cctgacctct gccctcatgc gcatcctcat gcgctcccgc gtgctcaacg    8520
aggagcccct gacgctggcg ggcgaggaga tcgtggccca gggcaagcgc tcggacccgc    8580
ggagcctgct gtgctatggc ggcgcccag  ggcctggctg ccacttctcc atccccgagg    8640
ctttcagcgg ggccctggcc aacctcagtg acgtggtgca gctcatcttt ctggtggact    8700
ccaatccctt tcccttggc  tatatcagca actacaccgt ctccaccaag gtggcctcga    8760
tggcattcca gacacaggcc ggcgcccaga tccccatcga gcggctggcc tcagagcgcg    8820
ccatcaccgt gaaggtgccc aacaactcgg actgggctgc ccggggccac cgcagctccg    8880
ccaactccgc caactccgtt gtggtccagc cccaggcctc cgtcggtgct gtggtcaccc    8940
tggacagcag caaccctgcg gccgggctgc atctgcagct caactatacg ctgctggacg    9000
gccactacct gtctgaggaa cctgagcccc cctggcagt  ctaccacac  tcggagcccc    9060
ggcccaatga gcacaactgc tcggctagca ggaggatccg cccagagtca ctccagggtg    9120
ctgaccaccg gccctacacc ttcttcattt ccccggggag cagagaccca gcggggagtt    9180
accatctgaa cctctccagc cacttccgct ggtcggcgct gcaggtgtcc gtgggcctgt    9240
acacgtccct gtgccagtac ttcagcgagg aggacatggt gtggcggaca gaggggctgc    9300
tgcccctgga ggagacctcg ccccgccagg ccgtctgcct cacccgccac ctcaccgcct    9360
tcggcgccag cctcttcgtg cccccaagcc atgtccgctt tgtgtttcct gagccgacag    9420
cggatgtaaa ctacatcgtc atgctgacat gtgctgtgtg cctggtgacc tacatggtca    9480
tggccgccat cctgcacaag ctggaccagt ggatgccag  ccggggccgc gccatcccttt   9540
tctgtgggca gcggggccgc ttcaagtacg agatcctcgt caagacaggc tggggccggg    9600
gctcaggtac cacggcccac gtgggcatca tgctgtatgg ggtggacagc cggagcggcc    9660
accggcacct ggacgcgac  agagccttcc accgcaacag cctggacatc ttccggatcg    9720
ccaccccgca cagcctgggt agcgtgtgga agatccgagt gtggcacgac aacaaagggc    9780
tcagccctgc ctggttcctg cagcacgtca tcgtcaggga cctgcagacg gcacgcagcg    9840
ccttcttcct ggtcaatgac tggctttcgg tggagacgga ggccaacggg ggcctggtgg    9900
agaaggaggt gctggccgcg agcgacgcag ccttttgcg  cttccggcgc ctgctggtgg    9960
ctgagctgca gcgtggcttc tttgacaagc acatctggct ctccatatgg gaccggccgc   10020
ctcgtagccg tttcactcgc atccagaggg ccacctgctg cgttctcctc atctgcctct   10080
tcctgggcgc caacgccgtg tggtacgggg ctgttggcga ctctgcctac agcacggggc   10140
atgtgtccag gctgagcccg ctgagcgtcg acacagtcgc tgttggcctg gtgtccagcg   10200
tggttgtcta tcccgtctac ctggccatcc tttttctctt ccggatgtcc cggagcaagg   10260
tggctgggag cccgagcccc acacctgccg ggcagcaggt gctggacatc gacagctgcc   10320
tggactcgtc cgtgctggac agctccttcc tcacgttctc aggcctccac gctgaggcct   10380
ttgttggaca gatgaagagt gacttgtttc tggatgattc taagagtctg gtgtgctggc   10440
cctccggcga gggaacgctc agttggccgg acctgctcag tgacccgtcc attgtgggta   10500
gcaatctgcg gcagctggca cggggccagg cgggccatgg gctgggccca gaggaggacg   10560
gcttctccct ggccagcccc tactcgcctg ccaaatcctt tcagcatca  gatgaagacc   10620
tgatccagca ggtccttgcc gaggggtca  gcagcccagc ccctacccaa gacacccaca   10680
tggaaacgga cctgctcagc agcctgtcca gcactcctgg ggagaagaca gagacgctgg   10740
cgctgcagag gctggggag  ctgggccac  ccagcccagg cctgaactgg gaacagcccc   10800
aggcagcgag gctgtccagg acaggactgg tggagggtct gcggaagcgc ctgctgccgg   10860
```

```
cctggtgtgc ctccctggcc cacgggctca gcctgctcct ggtggctgtg gctgtggctg   10920
tctcagggtg ggtgggtgcg agcttccccc cgggcgtgag tgttgcgtgg ctcctgtcca   10980
gcagcgccag cttcctggcc tcattcctcg gctgggagcc actgaaggtc ttgctggaag   11040
ccctgtactt ctcactggtg gccaagcggc tgcacccgga tgaagatgac accctggtag   11100
agagcccggc tgtgacgcct gtgagcgcac gtgtgccccg cgtacggcca ccccacggct   11160
ttgcactctt cctggccaag gaagaagccc gcaaggtcaa gaggctacat ggcatgctgc   11220
ggagcctcct ggtgtacatg cttttctgc tggtgaccct gctggccagc tatggggatg   11280
cctcatgcca tgggcacgcc taccgtctgc aaagcgccat caagcaggag ctgcacagcc   11340
gggccttcct ggccatcacg cggtctgagg agctctggcc atggatggcc cacgtgctgc   11400
tgccctacgt ccacgggaac cagtccagcc cagagctggg gccccacgg ctgcggcagg   11460
tgcggctgca ggaagcactc tacccagacc ctcccggccc cagggtccac acgtgctcgg   11520
ccgcaggagg cttcagcacc agcgattacg acgttggctg ggagagtcct cacaatggct   11580
cggggacgtg ggcctattca gcgccggatc tgctgggggc atggtcctgg ggctcctgtg   11640
ccgtgtatga cagcggggc tacgtgcagg agctgggcct gagcctggag gagagccgcg   11700
accggctgcg cttcctgcag ctgcacaact ggctggacaa caggagccgc gctgtgttcc   11760
tggagctcac gcgctacagc ccggccgtgg ggctgcacgc cgccgtcacg ctgcgcctcg   11820
agttcccggg ggccggccgc gccctggccg ccctcagcgt ccgccccttt gcgctgcgcc   11880
gcctcagcgc gggcctctcg ctgcctctgc tcacctcggt gtgcctgctg ctgttcgccg   11940
tgcacttcgc cgtggccgag gcccgtactt ggcacaggga agggcgctgg cgcgtgctgc   12000
ggctcggagc ctgggcgcgg tggctgctgg tggcgctgac ggcggccacg gcactggtac   12060
gcctcgccca gctgggtgcc gctgaccgcc agtggacccg tttcgtgcgc ggccgccgc   12120
gccgcttcac tagcttcgac caggtggcgc agctgagctc cgcagccgt ggcctggcgg   12180
cctcgctgct cttcctgctt ttggtcaagg ctgcccagca gctacgcttc gtgcgccagt   12240
ggtccgtctt tggcaagaca ttatgccgag ctctgccaga gctcctgggg gtcaccttgg   12300
gcctggtggt gctcggggta gcctacgccc agctggccat cctgctcgtg tcttcctgtg   12360
tggactccct ctggagcgtg gcccaggccc tgttggtgct gtgccctggg actgggctct   12420
ctaccctgtg tcctgccgag tcctggcacc tgtcaccct gctgtgtgtg gggctctggg   12480
cactgcggct gtggggcgcc ctacggctgg gggctgttat tctccgctgg cgctaccacg   12540
ccttgcgtgg agagctgtac cggccggcct gggagcccca ggactacgag atggtggagt   12600
tgttcctgcg caggctgcgc ctctggatgg gcctcagcaa ggtcaaggag ttccgccaca   12660
aagtccgctt tgaagggatg gagccgctgc cctctcgctc ctccaggggc tccaaggtat   12720
ccccggatgt gccccaccc agcgctggct ccgatgcctc gcacccctcc acctcctcca   12780
gccagctgga tgggctgagc gtgagcctgg gccggctggg gacaaggtgt gagcctgagc   12840
cctcccgcct ccaagccgtg ttcgaggccc tgctcaccca gtttgaccga ctcaaccagg   12900
ccacagagga cgtctaccag ctggagcagc agctgcacag cctgcaaggc cgcaggagca   12960
gccgggcgcc cgccggatct tcccgtgcc atccccggg cctgcggcca gcactgccca   13020
gccgccttgc ccgggccagt cggggtgtgg acctggccac tggccccagc aggacacccc   13080
ttcgggccaa gaacaaggtc caccccagca gcacttagtc ctccttcctg gcgggggtgg   13140
gccgtggagt cggagtggac accgctcagt attactttct gccgctgtca aggccgaggg   13200
```

| | |
|---|---:|
| ccaggcagaa tggctgcacg taggttcccc agagagcagg caggggcatc tgtctgtctg | 13260 |
| tgggcttcag cactttaaag aggctgtgtg gccaaccagg acccagggtc ccctccccag | 13320 |
| ctcccttggg aaggacacag cagtattgga cggtttctag cctctgagat gctaatttat | 13380 |
| ttccccgagt cctcaggtac agcgggctgt gcccggcccc accccctggg cagatgtccc | 13440 |
| ccactgctaa ggctgctggc ttcagggagg gttagcctgc accgccgcca ccctgcccct | 13500 |
| aagttattac ctctccagtt cctaccgtac tccctgcacc gtctcactgt gtgtctcgtg | 13560 |
| tcagtaattt atatggtgtt aaaatgtgta tattttgta tgtcactatt ttcactaggg | 13620 |
| ctgaggggcc tgcgcccaga gctggcctcc cccaacacct gctgcgcttg gtaggtgtgg | 13680 |
| tggcgttatg gcagcccggc tgctgcttgg atgcgagctt ggccttgggc cggtgctggg | 13740 |
| ggcacagctg tctgccaggc actctcatca ccccagaggc cttgtcatcc tcccttgccc | 13800 |
| caggccaggt agcaagagag cagcgcccag gcctgctggc atcaggtctg ggcaagtagc | 13860 |
| aggactaggc atgtcagagg accccagggt ggttagagga aaagactcct cctgggggct | 13920 |
| ggctcccagg gtggaggaag gtgactgtgt gtgtgtgtgt gtgcgcgcgc gcacgcgcga | 13980 |
| gtgtgctgta tggcccaggc agcctcaagg ccctcggagc tggctgtgcc tgcttctgtg | 14040 |
| taccacttct gtgggcatgg ccgcttctag agcctcgaca ccccccaac ccccgcacca | 14100 |
| agcagacaaa gtcaataaaa gagctgtctg actgc | 14135 |

<210> SEQ ID NO 30
<211> LENGTH: 2207
<212> TYPE: DNA
<213> ORGANISM: Homo sapiens

<400> SEQUENCE: 30

| | |
|---|---:|
| gcatcctctc accgccggaa gctgaactga ctcgtccgcg gccgctctac cccaacaggc | 60 |
| cgccaccagc gagagtgcgg ccataaccat cacgtgaccg cccaccgaca ccagcgagag | 120 |
| tgcagtcgta accgtcacgt gaccgccac cgtcggcccg cgctcccct ccgcccgaag | 180 |
| ctagcaagcg gcgcggccaa tgagaaaggc gcatgcctgg ccccgccgg cctgcagtct | 240 |
| agccgtagtg cgcctgcgcg cggctaggag ggccgtcag gcggggatac agcctggaag | 300 |
| gtaatgcatg tccatggtac acaaattcac aagtttggag accctgacac acccaccttc | 360 |
| tcacctgggc tctgcgtatc ccccagcctt gagggaagat gaagcctaaa ctgatgtacc | 420 |
| aggagctgaa ggtgcctgca gaggagcccg ccaatgagct gcccatgaat gagattgagg | 480 |
| cgtggaaggc tgcggaaaag aaagcccgct gggtcctgct ggtcctcatt ctggcggttg | 540 |
| tgggcttcgg agccctgatg actcagctgt ttctatggga atacggcgac ttgcatctct | 600 |
| ttgggcccaa ccagcgccca gcccctgct atgacccttg cgaagcagtg ctggtggaaa | 660 |
| gcattcctga gggcctggac ttccccaatg cctccacggg gaaccccttc accagccagg | 720 |
| cctggctggg cctgctcgcc ggtgcgcaca gcagcctgga catcgcctcc ttctactgga | 780 |
| ccctcaccaa caatgacacc cacacgcagg agccctctgc ccagcagggt gaggaggtcc | 840 |
| tccggcagct gcagaccctg caccaaaagg gcgtgaacgt ccgcatcgct gtgagcaagc | 900 |
| ccagcgggcc ccagccacag gcggacctgc aggctctgct gcagagcggt gcccaggtcc | 960 |
| gcatggtgga catgcagaag ctgacccatg gcgtcctgca taccaagttc tgggtggtgg | 1020 |
| accagaccca cttctacctg gcagtgccaa acatggactg gcgttcactg acccaggtca | 1080 |
| aggagctggg cgtggtcatg tacaaactgc agctgcctgg tcgagacctg accaagatct | 1140 |
| ttgaggccta ctggttcctg ggccaggcag gcagctccat cccatcaact ggccccggt | 1200 |

```
tctatgacac ccgctacaac caagagacac caatggagat ctgcctcaat ggaacccctg   1260
ctctggccta cctggcgagt gcgcccccac ccctgtgtcc aagtggccgc actccagacc   1320
tgaaggctct actcaacgtg gtggacaatg cccggagttt catctacgtc gctgtcatga   1380
actacctgcc cactctggag ttctcccacc ctcacaggtt ctggcctgcc attgacgatg   1440
ggctgcggcg ggccacctac gagcgtggcg tcaaggtgcg cctgctcatc agctgctggg   1500
gacactcgga gccatccatg cgggccttcc tgctctctct ggctgccctg cgtgacaacc   1560
atacccactc tgacatccag gtgaaactct ttgtggtccc cgcggatgag gcccaggctc   1620
gaatcccata tgcccgtgtc aaccacaaca agtacatggt gactgaacgc gccacctaca   1680
tcggaacctc caactggtct ggcaactact tcacggagac ggcgggcacc tcgctgctgg   1740
tgacgcagaa tggagggggc ggcctgcgga gccagctgga ggccattttc ctgagggact   1800
gggactcccc ttacagccat gaccttgaca cctcagctga cagcgtgggc aacgcctgcc   1860
gcctgctctg aggcccgatc cagtgggcag gccaaggcct gctgggcccc cgcggaccca   1920
ggtgctctgg gtcacggtcc ctgtccccgc gccccgcttc tgtctgccc cattgtggct   1980 cctcaggctc tctccctgc tctcccacct tacctccac ccccaccggc ctgacgctgt   2040
ggccccggga cccagcagag ctgggggagg gatcagcccc caaagaaatg ggggtgcatg   2100
ctgggcctgg cccctggcc cacccccact ttccagggca aaaagggccc agggttataa   2160
taagtaaata acttgtctgt acagcctgaa aaaaaaaaa aaaaaa                  2207

<210> SEQ ID NO 31
<211> LENGTH: 4846
<212> TYPE: DNA
<213> ORGANISM: Homo sapiens

<400> SEQUENCE: 31
gagcggtgct caggggaggg ctggagggga gggaaggaga gagagagggg agggcggcac     60
cgcccctagc cccgcgctcc ggaagtgaag cggccagacc accagctaat ggatgcggag    120
cggagggccc gctgaccgct ctccgcgcct ggagcagctt ggcttggctg gagctaagag    180
ccagacacac cactgtgtgg aggtgggtga tgtcttcctg tgctaaaagg tgaataaata    240
agctcctcac ctctcgcgga acactcggga acacatcaac aggggtccaa gccgccctgc    300
tgggaggctt ctcttcaaga gttctgggtc ccagagtgga aggcattttc ccatcaactg    360
gagagagacg aaacatcaga gaccaggagg ctgtggagaa agcagctgtc ccaggtgcct    420
caactatcag agaagggtca gcgtcacgtg gctgccagca tctttgagaa atcactggc    480 aatcggactt cagagctgcg ggcacaggtg tggttagaac tgagatacga cctgcccacc    540
tgggtcaggc ctaaagacaa gaagtcctga gttcttgcca ctgagtaggc cagggtcatt    600
tgtccagaaa actttgtgac tgtctttgag tgacctagtc tgggacccat tcattggtgg    660
gttctaaggt tagaagctca tccaggatat tttcaatatt aagtcagtgc atagctgcac    720
cactaacaaa ttggtgcctg tagagtcaga gtgggtcaat tcttaggaca atggcgctgg    780
cactgttaga ggactggtgc aggataatga gtgtggatga gcagaagtca ctgatggtta    840
cggggatacc ggcggacttt gaggaggctg agattcagga ggtccttcag gagactttaa    900
agtctctggg caggtataga ctgcttggca agatattccg gaagcaggag aatgccaatg    960
ctgtcttact agagcttctg gaagatactg atgtctcggc cattcccagt gaggtccagg   1020 gaaaggggg tgtctggaag gtgatcttta agaccccctaa tcaggacact gagtttcttg   1080
```

```
aaagattgaa cctgtttcta gaaaaagagg ggcagacggt ctcgggtatg tttcgagccc    1140
tggggcagga gggcgtgtct ccagccacag tgccctgcat ctcaccagaa ttactggccc    1200
atttgttggg acaggcaatg gcacatgcgc ctcagcccct gctacccatg agataccgga    1260
aactgcgagt attctcaggg agtgctgtcc cagcccaga ggaagagtcc tttgaggtct     1320
ggttggaaca ggccacggag atagtcaaag agtggccagt aacagaggca gaaaagaaaa    1380
ggtggctggc ggaaagcctg cggggccctg ccctggacct catgcacata gtgcaggcag    1440
acaacccgtc catcagtgta gaagagtgtt tggaggcctt taagcaagtg tttgggagcc    1500
tagagagccg caggacagcc caggtgaggt atctgaagac ctatcaggag gaaggagaga    1560
aggtctcagc ctatgtgtta cggctagaaa ccctgctccg gagagcggtg gagaaacgcg    1620
ccatccctcg gcgtattgcg gaccaggtcc gcctggagca ggtcatggct ggggccactc    1680
ttaaccagat gctgtggtgc cggcttaggg agctgaagga tcagggcccg ccccccagct    1740
tccttgagct aatgaaggta atacgggaag aagaggagga agaggcctcc tttgagaatg    1800
agagtatcga gagccagag gaacgagatg gctatggccg ctggaatcat gagggagacg    1860
actgaaaacc acctggggc aggacccaca gccagtgggc taagaccttt aaaaaatttt     1920
tttctttaat gtatgggact gaaatcaaac catgaaagcc aattattgac cttccttcct    1980
tccttccttc cctcccttcc tccttctctc cttctctcct cctctctcct ctcctctcct    2040
ctctttcctt ccttccttcc ttttttcttt ttctctttct tctttatttc ttgggtctca    2100
ctctcatcac ccaggctaga gtgcagtggc acaaaatct cggctcactg cagccttgac     2160
ttcccaggct caggctcagg tgatcctcac accttagcct cccaagtacc tgggactaca    2220
ggcacgcacc accatgccta gctattcttt tgtattttg tagagacag ggttttgctg      2280
tgttgctcag gctggtctgg aaccctagg ctcaaatgat gtgcccaact cggcctccca     2340
aagtgctggg attacaggca tgaaccgcca tgcctggccc ttgatttttc ttttaagaa     2400
aaaaatatct aggagtttct tagaccctat gtagattatt aatgaacaaa agattaaact    2460
ccaaatatta aatagtaagc ctgaaggaat ctgaaacact tgtacttcca attttcttta    2520
aataatccca aatagaccag aattggccca taccatagaa gaaagaattg gcagtcaaaa    2580
aaaaaaatac cttttgtaat gtttgaaaaa taaagctgtt tgacttgtca ggtgttttcc    2640
tttctcaaat cagcaaattc tctctgagtg cctggctttg tgagacactg tacaaggagt    2700
tacaagacta cagctataac ctgcagttga gcagttataa acctacaaaa tgggccctgc    2760
cctcagagag gttccagtct agatgaggag ctgatctaga caggtaaaag gctaactaac    2820
cctttgtgta aataagttca tcaccccagt aaaagtgtca tcacccagtg aataggacca    2880
cctctgcctg cagattttg ttgttgttgt tgtcattgtt gttgttgttt aacctggga     2940
agtgttcttc ctgcctttct gctaggtgtc agatagatgg tcccagagct aggtgctgtg    3000
tcaggccctg aagacacaga tgactcaacc taagctttac tttccagagg tccacagcct    3060
gagaggtgtc cccaaagaaa gggggacatg aggggactgc atgcttgaga gcagggttgt    3120
ttagggcagg tttggattta gtgagcaggc tggtttgctt agagaaggct tttagtggca    3180
acaaaggatg aagaggagag aaaaggaact cacatttatt gagggcctac tgtgtgcaaa    3240
gtgtttcatg tatatctcat tgaatgtata cagccaccct gttgtggtat aattttgctc    3300
tttataaaga gaaagaccga agctcagatg agttaagtgg tctcctcaac accaaaatgc    3360
caagaagtga tggagcctag acagaagccc agaactttct gactcacact agtccatcct    3420
ctaccatcac gatgactttc aaattgtgct ctgcagttct gcagattttc tagcagtgcc    3480
```

| | | |
|---|---|---|
| atctccaaaa tgtgttttaa actctttatt tttttaatta ttattagtat tattttgaga | 3540 |
| ctgagtcttg ctctatcacc caggctggag tgcagtggtg caatctcagc tcactgcaac | 3600 |
| ctccgcctcc caggttcaag cgatttcgtg cctcagcctc ccgagtagct gggattacag | 3660 |
| gcacccacca ccacgcccag ctaattttg tattttagt agaaatgggg tttcaccatg | 3720 |
| ttggccaggc tggtctcgaa ctcctgacct caagtgatcc actcacctcg gcctcccaaa | 3780 |
| gtgctgggat tacaggtgtg agccaccatg cctgggctaa actctttaag tctctagtaa | 3840 |
| atgcagctag attcaaatgg gctgataacc aaattttaac acatcagcat tcaccaccag | 3900 |
| gtttactttt attttcagat tggctcattt tgtgcagacc ttagagcaaa gtttcctta | 3960 |
| tggtatctgt gtacgtatcc aaacttcttt taattgttca cagattttaa aagcggtagc | 4020 |
| accacatggt tgtgtagatc agacctgtgt atttagatca gacctgtgta tcacgtaagt | 4080 |
| gtgtgagtgc agtgcagatg agcaccattt agttatatgt gctaggcaaa tctccaacac | 4140 |
| agttgatgtg tagtcttgtg gtagatttgt gcatactgta agcaaattgc ttagcttctc | 4200 |
| tagacatcag tttccacatc tgaaaaataa gaagatgaga gtacacggtt gttatgaaca | 4260 |
| aatgacttaa tgcttttaa gcacgttgca tgacatctgg aacacagaaa gccctcaata | 4320 |
| cattgaagct cttaggattt tcacgatgtt cctgtctgct caatgcatgc tttctttatt | 4380 |
| gttctgacag ttgtgtggta acaagctaat atgcttccag ttgacttcca gtctaccctg | 4440 |
| gtgttagaaa ccgtttcatc tcttattgta aatttgagtg cttgttgttt tttatatttg | 4500 |
| tgatgactct tccagcagtt gttgacaatt gttagaggtt tgactttaa ataattactt | 4560 |
| attttttctg attgtggttc agtttaactg aagaatatcc tgagattgta agaaaagcat | 4620 |
| tttttaaaag gtatcacttg tgatcattta tctttctaaa ttctattttt aatactgttc | 4680 |
| caccaaagtg atgcagtggt taccatgaca ccctaatttc atgtgttttt gtatttatga | 4740 |
| aaatagtttc attgtcattt attggcggta tacaaagtaa aatgttataa atgtgaagtt | 4800 |
| ataaaataaa tatatgctaa taaaatcctg agtttttctg tttcct | 4846 |

<210> SEQ ID NO 32
<211> LENGTH: 1014
<212> TYPE: DNA
<213> ORGANISM: Homo sapiens

<400> SEQUENCE: 32

| | |
|---|---|
| tgcctcctga gcgtagtcca gttactttca ggctcgggga gtgaaggcct cgttgagaga | 60 |
| aggtctcatt cggtgttttg ggaagagagt cgtgtgggcc caggtctgtc tgctatcagc | 120 |
| tatgccgctg cccgttgcgc tgcagacccg cttggccaag agaggcatcc tcaaacatct | 180 |
| ggagcctgaa ccagaggaag agatcattgc cgaggactat gacgatgatc ctgtggacta | 240 |
| cgaggccacc aggttggagg gcctaccacc aagctggtac aaggtgttcg acccttcctg | 300 |
| cgggctccct tactactgga atgcagacac agaccttgta tcctggctct ccccacatga | 360 |
| ccccaactcc gtggttacca aatcggccaa gaagctcaga agcagtaatg cagatgctga | 420 |
| agaaaagttg gaccggagcc atgacaagtc ggacaggggc catgacaagt cggaccgcag | 480 |
| ccatgagaaa ctagacaggg gccacgacaa gtcagaccgg ggccacgaca gtctgacag | 540 |
| ggatcgagag cgtggctatg acaaggtaga cagagagaga gagcgagaca gggaacggga | 600 |
| tcgggaccgc gggtatgaca aggcagaccg ggaagagggc aaagaacggc gccaccatcg | 660 |
| ccgggaggag ctggctccct atcccaagag caagaaggca gtaagccgaa aggatgaaga | 720 |

| | | | | |
|---|---|---|---|---|
| gttagacccc | atggacccta | gctcatactc | agacgccccc | cggggcacgt | ggtcaacagg | 780 |
| actccccaag | cggaatgagg | ccaagactgg | cgctgacacc | acagcagctg | ggcccctctt | 840 |
| ccagcagcgg | ccgtatccat | ccccaggggc | tgtgctccgg | gccaatgcag | aggcctcccg | 900 |
| aaccaagcag | caggattgaa | gcttcggcct | ccctggccct | gggttaaaat | aaaagctttc | 960 |
| tggtgatcct | gcccaccaaa | aaaaaaaaa | aaaaaaaa | aaaaaaaaaa | aaaa | 1014 |

<210> SEQ ID NO 33
<211> LENGTH: 3291
<212> TYPE: DNA
<213> ORGANISM: Homo sapiens

<400> SEQUENCE: 33

| | | | | | | |
|---|---|---|---|---|---|---|
| agaatcggag | agccggtggc | gtcgcaggtc | gggaggacga | gcaccgagtc | gagggctcgc | 60 |
| tcgtctgggc | cgcccgagag | tcttaatcgc | gggcgcttgg | gccgccatct | tagatggcgg | 120 |
| gagtaagagg | aaaacgattg | tgaggcggga | acggctttct | gctgcctttt | ttgggccccg | 180 |
| aaaagggtca | gctggccggg | ctttgggcg | cgtgccctga | ggcgcggagc | gcgtttgcta | 240 |
| cgatgcgggg | gctgctcggg | gctccgtccc | ctgggctggg | gacgcgccga | atgtgaccgc | 300 |
| ctcccgctcc | ctcacccgcc | gcggggagga | ggagcgggcg | agaagctgcc | gccgaacgac | 360 |
| aggacgttgg | ggcggcctgg | ctccctcagg | tttaagaatt | gtttaagctg | catcaatgga | 420 |
| gcacatacag | ggagcttgga | agacgatcag | caatggtttt | ggattcaaag | atgccgtgtt | 480 |
| tgatggctcc | agctgcatct | ctcctacaat | agttcagcag | tttggctatc | agcgccgggc | 540 |
| atcagatgat | ggcaaactca | cagatccttc | taagacaagc | aacactatcc | gtgttttctt | 600 |
| gccgaacaag | caaagaacag | tggtcaatgt | gcgaaatgga | atgagcttgc | atgactgcct | 660 |
| tatgaaagca | ctcaaggtga | ggggcctgca | accagagtgc | tgtgcagtgt | tcagacttct | 720 |
| ccacgaacac | aaaggtaaaa | agcacgcttt | agattggaat | actgatgctg | cgtctttgat | 780 |
| tggagaagaa | cttcaagtag | atttcctgga | tcatgttccc | ctcacaacac | acaactttgc | 840 |
| tcggaagacg | ttcctgaagc | ttgccttctg | tgacatctgt | cagaaattcc | tgctcaatgg | 900 |
| atttcgatgt | cagacttgtg | gctacaaaat | tcatgagcac | tgtagcacca | agtacctac | 960 |
| tatgtgtgtg | gactggagta | acatcagaca | actcttattg | tttccaaatt | ccactattgg | 1020 |
| tgatagtgga | gtcccagcac | taccttcttt | gactatgcgt | cgtatgcgag | agtctgtttc | 1080 |
| caggatgcct | gttagttctc | agcacagata | ttctacacct | cacgccttca | ccttaacac | 1140 |
| ctccagtccc | tcatctgaag | gttccctctc | ccagaggcag | aggtcgacat | ccacacctaa | 1200 |
| tgtccacatg | gtcagcacca | ccctgcctgt | ggacagcagg | atgattgagg | atgcaattcg | 1260 |
| aagtcacagc | gaatcagcct | caccttcagc | cctgtccagt | agcccaaca | atctgagccc | 1320 |
| aacaggctgg | tcacagccga | aaaccccgt | gccagcacaa | agagagcggg | caccagtatc | 1380 |
| tgggacccag | gagaaaaaca | aaattaggcc | tcgtggacag | agagattcaa | gctattattg | 1440 |
| ggaaatagaa | gccagtgaag | tgatgctgtc | cactcggatt | gggtcaggct | cttttggaac | 1500 |
| tgtttataag | ggtaaatggc | acggagatgt | tgcagtaaag | atcctaaagg | ttgtcgaccc | 1560 |
| aaccccagag | caattccagg | ccttcaggaa | tgaggtggct | gttctgcgca | aaacacggca | 1620 |
| tgtgaacatt | ctgcttttca | tggggtacat | gacaaaggac | aacctggcaa | ttgtgaccca | 1680 |
| gtggtgcgag | ggcagcagcc | tctacaaaca | cctgcatgtc | caggagacca | gtttcagat | 1740 |
| gttccagcta | attgacattg | cccggcagac | ggctcaggga | atggactatt | tgcatgcaaa | 1800 |
| gaacatcatc | catagagaca | tgaaatccaa | caatatattt | ctccatgaag | gcttaacagt | 1860 |

```
gaaaattgga gattttggtt tggcaacagt aaagtcacgc tggagtggtt ctcagcaggt    1920
tgaacaacct actggctctg tcctctggat ggccccagag gtgatccgaa tgcaggataa    1980
caacccattc agtttccagt cggatgtcta ctcctatggc atcgtattgt atgaactgat    2040
gacgggggag cttccttatt ctcacatcaa caaccgagat cagatcatct tcatggtggg    2100
ccgaggatat gcctccccag atcttagtaa gctatataag aactgcccca agcaatgaa     2160 gaggctggta gctgactgtg tgaagaaagt aaaggaagag aggcctcttt tccccagat     2220 cctgtcttcc attgagctgc tccaacactc tctaccgaag atcaaccgga gcgcttccga    2280
gccatccttg catcgggcag cccacactga ggatatcaat gcttgcacgc tgaccacgtc    2340
cccgaggctg cctgtcttct agttgacttt gcacctgtct tcaggctgcc aggggaggag    2400
gagaagccag caggcaccac ttttctgctc cctttctcca gaggcagaac acatgttttc    2460
agagaagctg ctgctaagga ccttctagac tgctcacagg gccttaactt catgttgcct    2520
tcttttctat ccctttgggc cctgggagaa ggaagccatt tgcagtgctg gtgtgtcctg    2580
ctccctcccc acattcccca tgctcaaggc ccagccttct gtagatgcgc aagtggatgt    2640
tgatggtagt acaaaaagca ggggcccagc cccagctgtt ggctacatga gtatttagag    2700
gaagtaaggt agcaggcagt ccagccctga tgtggagaca catgggattt tggaaatcag    2760
cttctggagg aatgcatgtc acaggcggga cttcttcag agagtggtgc agcgccagac     2820
attttgcaca taaggcacca aacagcccag gactgccgag actctggccg cccgaaggag    2880
cctgctttgg tactatggaa cttttcttag gggacacgtc ctcctttcac agcttctaag    2940
gtgtccagtg cattgggatg gttttccagg caaggcactc ggccaatccg catctcagcc    3000
ctctcaggga gcagtcttcc atcatgctga attttgtctt ccaggagctg ccctatggg     3060 gcggggccgc agggccagcc ttgtttctct aacaaacaaa caaacaaaca gccttgtttc    3120
tctagtcaca tcatgtgtat acaaggaagc caggaataca ggttttcttg atgatttggg    3180 ttttaattt gttttattg cacctgacaa aatacagtta tctgatggtc cctcaattat       3240
gttattttaa taaataaat taaatttagg tgtaaaaaaa aaaaaaaaa a                3291
```

<210> SEQ ID NO 34
<211> LENGTH: 5216
<212> TYPE: DNA
<213> ORGANISM: Homo sapiens

<400> SEQUENCE: 34

```
gatgtcccag gggtattggg gcgggggggtt gaaataactg gggttcagga ggagggatgg     60
tggtagagat aaaaatgtga gaagggagca gcactggcga ggagtcggga gagtactcct    120
gattgtgaca tcacattcat cccctgggcg atggagcttg tcactgggaa ggaatactca    180
gtcggagaat agccaacaag atgggttact gggagaatct cttcagtggc actgagtgga    240
ggcatcaggg ggtggagcc ttgtgaacag ggaacctgcc ccccaacact tggaaggacc      300
tgggtttcag tgatgagaca tggggtatga tgtaacccgt ttccagggg atgttgacga     360 agatcttatc tgccctattt gcagtggagt cttggaggag ccagtacagg cacctcattg    420
tgaacatgct ttctgcaacg cctgcatcac ccagtggttc tctcagcaac agacatgtcc    480
agtggaccgt agtgttgtga cggtcgccca tctgcgccca gtacctcgga tcatgcggaa    540
catgttgtca aagctgcaga ttgcctgtga caacgctgtg ttcggctgta gtgccgttgt    600
ccggcttgac aacctcatgt ctcacctcag cgactgtgag cacaacccga agcggcctgt    660
```

-continued

```
gacctgtgaa cagggctgtg gcctggagat gcccaaagat gagctgccca accataactg    720
cattaagcac ctgcgctcag tggtacagca gcagcagaca cgcatcgcag agctggagaa    780
gacgtcagct gaacacaaac accagctggc ggagcagaag cgagacatcc agctgctaaa    840
ggcatacatg cgtgcaatcc gcagtgtcaa ccccaacctt cagaacctgg aggagacaat    900
tgaatacaac gagatcctag agtgggtgaa ctcccttcag ccagcaagag tgacccgctg    960
gggagggatg atctcgactc ctgatgctgt gctccaggct gtaatcaagc gctccctggt   1020
ggagagtggc tgtcctgctt ctattgtcaa cgagctgatt gaaaatgccc acgagcgtag   1080
ctggccccag ggtctggcca cactagagac tagacagatg aaccgacgct actatgagaa   1140
ctacgtggcc aagcgcatcc ctggcaagca ggctgttgtc gtgatggcct gtgagaacca   1200
gcacatgggg gatgacatgg tgcaagagcc aggccttgtc atgatatttg cgcatggcgt   1260
ggaagagata taagagaact cgactggcta tcaggaagag atggaaatca gaaaatccca   1320
tcactccagc agctgggacc tgagtcctac ccaccattct taatactgtg gcttatacct   1380
gagccacaca tctccctgcc cttctggcac tgaagggcct tggggtagtt tgctcagcct   1440
ttcaggtggg aaacccagat ttcctccctt tgccatattc ccctaaaatg tctataaatt   1500
atcagtctgg gtgggaaagc ccccacctcc atccattttc ctgcttaggg tccctggttc   1560
cagttatttt cagaaagcac aaagagattc aatttccctg gaggatcagg acagaggaag   1620
gaatctctaa tcgtccctct cctccaaaac cagggaatca gagcagtcag gctgttgac   1680 tctaagcagc agacatcctg aagaaatggt aagggtggag ccaaatctct agaaataagt   1740
agtgaggccg ttaattggcc atcactgatg gcccttaggg aaagactgga cctctgtgcc   1800
aagcagtatc cctgttcagc ccaccttaaa ggtgtaggca cccactgggt ctaccagtat   1860
gcaggttggg atactgaaaa ttccagatg agctcttctt tcctacaagt tttcataatt   1920
agggaatgcc agggtttagg gtaggggtta atctgttggg ggttgatgtg tttagcaaga   1980
agctactcct agcttttgct aaaatatggt tggcactgcc tcttgtggca caggccataa   2040

tgttccata gacccctctc tagccctgtg actgtagtta gttactttga taattttctt   2100

tggccattgt ttgtttatat ttcacaaact ccacctactg cccccccccc тcттттттттт   2160 aagaatggcc tgatcatggc tatctcagcc acattgttgg caatttaatt tatttacttc   2220
cttttttttt tttaagaaa ggaaaaaaga aaaaaaatc aaacttgaaa cтттттcтттт   2280 gatgttccta ttgtgggggt tctggatagg gtgggacagg gatgggggtg tgttttatat   2340

тттттccтттт tcagcacaac cтттggcтттт aatataggaa gagccaaggg agtcctcggc   2400

tgaacttacg atatctgccc caaacctctg taaccccaac tgaaatgagg agcttcctct   2460
cttcctgtga aggatatgac agtccagcat cgatgcctgt gccctctgga aaaatttcct   2520
cctagcccct ccagggcctt atcataaaac tctggattta gagtattcat tttgaaggca   2580 acтccccсттт cсccaagтттт ccttggagct gtatagctgg gttctaagct tcaccatgca   2640
aatcagaaat tttatctcta agtacaggct gtgccgtgtc tcacccacac ccccctgggg   2700
acttcagttc catttcaggt tacctggggt ataccttgat ccctagagtg actggcagag   2760

taagagaagg ggagagataa taggtgtgat tattttaata tggaggtggg agtgtggttg   2820
gagatagaaa ggctcctccc caccatgtaa tggcttcctc tcagaatttt attccaggct   2880
agcttgctgc aggtctgggt agttggatca tggctccact gggattgggg tggaaagctt   2940
gaggggagta gggttccagc tctgggacat tgtgctcagg aatttgaaaa cgctgctata   3000
cttactctgg ttactacatt tcttccactc ccсттттcccc тacстgccттт aaccaaggct   3060
```

```
catactgtcc tgtccttacc ctcagatgga gccaggaagc tcagtgaaag gcttccctac    3120
cctttgcact agtgtctctg caggttgctg gttgtgttgt atgtgctgtt ccatggtgtt    3180
gactgcacta ataataaacc ttttactcaa ctctctaaat tcttcagcat tactcccttt    3240
cttgagaagg tttcccctct gcttttgcct ttctctcacc ttaattccct ttcttcctta    3300
ctttgttacc taccttatc ttagtgctaa cttctctttc aggaggatgt ctgggagtag    3360
tgtgcacttc acagctgctt tcccatgtac cctcctgcat tcttccctcc tatctcctgt    3420
tctgtagcag ccaaagctct ctagtgatct gaactgtgtg cttcccaggg tctgccttta    3480
tcctaaattc catgtcttcc ctgagtggtc ctgagttttt gggataattt ctacagaaga    3540
tatgtatata tcttttcct ttgtcccaca agcaactttg ctttagaatc tagaattcct    3600
ttgcaggcag agaagtctct acctcccagt gtttcctagc taagaacgta atgtgagga    3660
gggaaatgta cttgcagagg tttcataatt atttacttat aaaaatagtc ttcatagccg    3720
ggcgcggtgg ctcacgcctg taatcccagc actttgggag gccgaggtgg gtggatcaca    3780
aggtcaggag ttcgagacca tcctggctaa cacagtgaaa ccccgtctct actaaaaata    3840
caaaaaatta gccgggcgtg gtggcaggca cctgtagtcc cagctactta ggaggctgag    3900
gcaggagaat ggcgtgaacc cgggaggcag agcttgcagt gagcagagat tgggccactg    3960
cattccagcc tgggcgacag agcaaggctc cgtctaaaaa aaaaaaaaa aaaaaaagtc    4020
ttcataggcc gggcacggtg gctcacgtct gtaatcccag cactttggga ggccaaggtg    4080
ggtggatcac aacgtcagga gatcgagacc atcctggcta acatggtgaa accctgtctc    4140
tactaaaaat ataaataaat tagccggaca ggcgcctgtc ctcccagcta ctcaggaggc    4200
tgaggcagga gaatggtgtg aacctgggag gcggagcttg cagtgagctg agatcacgcc    4260
actgcactcc agcctgggca acagagcaag actccgtctc aaaaaaaaaa aaaaaaaac    4320
cagtcttcat aagtatttgc tgctaccttt ccctgtcata agaaaaagga tagccagaca    4380
tggtgggacg ccactatgat cccagctcct tggaaggcta aggcacaaga atcgcttgaa    4440
cctgggaggt ggaggttgca gtgagctgag atcatgccac tgcactccag cctggtgaca    4500
gagcaagagc ctgtctcaaa aaaaaaaag aaaagaaaag aaaaagggat atcttttcct    4560
cctcccagaa gtttgtttta aatttgagca tttatcatgc acctgatgta aacctaatag    4620
tactcttgat actctagtgg cttgaaaaaa aaaaaaagg catttctgtg ctgagtctgc    4680
gcttctatgc acacaaggta tgtttataaa atactgataa gcatgtcaca gtatagagca    4740
taagaggcaa tgtatgtatc ctagtgacat tagcagtgct tttccccct taaactcctt    4800
taaaattact tttagaactt gctgctcatt cttgtgaatg ttatgaatgg tgtcatattg    4860
tccttttaca gaagatacga ttttttagaaa caaatattca ttgaatgtct gccctgtgag    4920
atactcacta gagtgaacat gaggaggctt atgtagcaaa atggcaccta cctgcaaaga    4980
acttagtccc taatggagat gaatatataa taagggatca taaatgtgct aagtggattt    5040
actagtaata tgtgagccaa ggacgataaa gctcctgatt ctgatgggta tcaggaaagg    5100
cttttcagga agtgttactt gttataggtc agaggtcagc aaactacagg ttacaacccc    5160
actgcctgct tttgtaaaaa actttattgg aatacagtta tgcccacttg tttata         5216
```

<210> SEQ ID NO 35
<211> LENGTH: 5138
<212> TYPE: DNA
<213> ORGANISM: Homo sapiens

```
<400> SEQUENCE: 35
gatccgcaga ggagcccact tgagagcgcc tcctgtcgtc tgtaaggttg ccttgccatc      60
cctcggcacc ccaacttccc ccgccccccc atcgcctcct cctccatcct ccagttcaaa     120
atggcgacgg cggcggcagc ggcggcggtg atggctcctc cgggctgccc gggttcgtgc     180
cccaacttcg ccgtagtctg ctccttcttg gagcgctacg ggccgctgct agacctgcct     240
gagttgccgt tccctgagct ggagcgggtg ctgcaggcgc cgccgccgga cgtcggcaac     300
ggagaagtac caaaagaatt ggtggagctc catttgaagc tgatgaggaa aattggcaaa     360
tctgttactg cagacagatg ggaaaaatat ttgatcaaga tatgccaaga gtttaacagt     420
acctgggcat gggagatgga agaagggc tatcttgaaa tgagtgttga atgcaaacta      480
gcactcttaa agtaccctg tgagtgtcag tttgatgaca atctcaaatt caagaatatt     540
attaatgagg aggatgccga tactatgcgt ctccagccaa ttggtcgaga caagatggc      600 ctcatgtact ggtaccaatt ggatcaagat cacaatgtca gaatgtacat agaagaacaa     660
gatgatcaag atggctcttc atggaaatgc attgtcagaa tcgaaacga gttggctgag      720 actcttgcac tcctgaaagc acaaattgat cctgtactat tgaaaactc tagccaacaa      780 gacaactctt ctcgggaaag tcccagctta gaggatgagg agactaaaaa agaggaagaa     840
acacctaaac aagaggaaca gaaagaaagt gaaagatga aaagtgagga gcagcctatg     900
gatttagaaa accgttctac agccaatgtt ctagaagaga ctactgtgaa aaagaaaaaa     960
gaagatgaaa aggaacttgt gaaactgcca gtcatagtga agctagaaaa accttttgcca   1020 gaaaatgaag aaaaaaagat tatcaaagaa gaaagtgatt ccttcaagga aaatgtcaaa   1080
cccattaaag ttgaggtgaa ggaatgtaga gcagatccta agataccaa agtagcatg     1140 gagaagccag tggcacagga gcctgaaagg atcgaatttg gtggcaatat taatcttct    1200 cacgaaatta ctgagaaatc tactgaagaa actgagaaac ttaaaaatga ccagcaggcc   1260
aagataccac taaaaaaacg agaaattaaa ctgagtgatg attttgacag tccagtcaag   1320
ggacctttgt gtaaatcagt tactccaaca aaagagtttt tgaaagatga aataaaacaa    1380
gaggaagaga cttgtaaaag gatctctaca atcactgctt ggttcatga agggaaacag    1440 ctggtaaatg gagaagttag tgatgaaagg gtagctccaa atttaagac agaaccaata    1500 gagacaaagt tttatgagac aaaggaagag agctatagcc cctctaagga cagaaatatc   1560
atcacggagg gaaatggaac agagtcctta aattctgtca taacaagtat gaaaacaggt   1620
gagcttgaga agaaaacagc cccttttgagg aaagatgcag atagttcaat atcagtctta   1680
gagatccata gtcaaaaagc acaaatagag gaacccgatc ctccagaaat ggaaacttct    1740
cttgattctt ctgagatggc aaaagatctc tcttcaaaaa ctgctttatc ttccaccgag    1800
tcgtgtacca tgaaaggtga agagaagtct cccaaaacta gaaggataa gcgcccacca    1860 atcctagaat gtcttgaaaa gttagagaag tccaaaaaga cttttcttga taaggacgca   1920
caaagattga gtccaatacc agaagaagtt ccaaagagta ctctagagtc agaaaagcct   1980
ggctctcctg aggcagctga aacttctcca ccatctaata tcattgacca ctgtgagaaa   2040
ctagcctcag aaaaagaagt ggtagaatgc cagagtacaa gtactgttgg tggccagtct   2100
gtgaaaaaag tagacctaga aaccctaaaa gaggattctg agttcacaaa ggtagaaatg   2160
gataatctgg acaatgccca gacctctggc atagaggagc cttctgagac aaagggttct   2220
atgcaaaaaa gcaaattcaa atataagttg gttcctgaag aagaaccac tgcctcagaa    2280 aatacagaga taacctctga aaggcagaaa gagggcatca aattaacaat caggatatca   2340
```

```
agtcggaaaa agaagcccga ttctcccccc aaagttctag aaccagaaaa caagcaagag    2400
aagacagaaa aggaagagga gaaaacaaat gtgggtcgta ctttaagaag atctccaaga    2460
atatctagac ccactgcaaa agtggctgag atcagagatc agaaagctga taaaaaaaga    2520
ggggaaggag aagatgaggt ggaagaagag tcaacagctt tgcaaaaaac tgacaaaaag    2580
gaaattttga aaaatcaga gaaagataca aattctaaag taagcaaggt aaaacccaaa     2640
ggcaaagttc gatggactgg ttctcggaca cgtggcagat ggaaatattc cagcaatgat    2700
gaaagtgaag ggtctggcag tgaaaaatca tctgcagctt cagaagagga ggaagaaaag    2760
gaaagtgaag aagccatcct agcagatgat gatgaaccat gcaaaaaatg tggccttcca    2820
aaccatcctg agctaattct tctgtgtgac tcttgcgata gtggatacca tactgcctgc    2880
cttcgccctc ctctgatgat catcccagat ggagaatggt tctgcccacc ttgccaacat    2940
aaactgctct gtgaaaaatt agaggaacag ttgcaggatt tggatgttgc cttaaagaag    3000
aaagagcgtg ccgaacgaag aaaagaacgc ttggtgtatg ttggtatcag tattgaaaac    3060
atcattcctc cacaagagcc agacttttct gaagatcaag aagaaaagaa aaagattca    3120
aaaaaatcca aagcaaactt gcttgaaagg aggtcaacaa gaacaaggaa atgtataagc    3180
tacagatttg atgagtttga tgaagcaatt gatgaagcta ttgaagatga catcaaagaa    3240
gccgatggag gaggagttgg ccgaggaaaa gatatctcca ccatcacagg tcatcgtggg    3300
aaagacatct ctactatttt ggatgaagaa agaaagaaa ataaacgacc ccagagggca    3360
gctgctgctc gaaggaagaa acgccggcga ttaaatgatc tggacagtga tagcaacctg    3420
gatgaagaag agagcgagga tgaattcaag atcagtgatg gatctcaaga tgagtttgtt    3480
gtgtctgatg aaaacccaga tgaaagtgaa gaagatccgc catctaatga tgacagtgac    3540
actgactttt gtagccgtag actgaggcga caccccctctc ggccaatgag gcagagcagg    3600
cgtttgcgaa gaaagacccc aaagaaaaaa tattccgatg atgatgaaga ggaggaatct    3660
gaggagaata gtagagactc tgaaagtgac ttcagtgatg attttagtga tgatttgta    3720
gaaactcggc gaaggcggtc aaggagaaat cagaaaagac aaattaacta caaagaagac    3780
tcagaaagtg acggttccca gaagagtttg cgacgtggta agaaataag gcgagtacac    3840
aagcgaagac tttccagctc agagagtgaa gagagctatt tgtccaagaa ctctgaagat    3900
gatgagctag ctaaagaatc aaagcggtca gttcgaaagc ggggccgaag cacagacgag    3960
tattcagaag cagatgagga ggaggaggaa gaggaaggca aaccatcccg caaacggcta    4020
caccggattg agacgtgatga ggaggagagt tgtgacaatg ctcatggaga tgcaaatcag    4080
cctgcccgtg acagccagcc tagggtcctg ccctcagaac aagagagcac caagaagccc    4140
taccggatag aaagtgatga ggaagaggac tttgaaaatg taggcaaagt ggggagccca    4200
ttggactata gcttagtgga cttaccttca accaatggac agagccctgg caaagccatt    4260
gagaacttga ttggcaagcc tactgagaag tctcagaccc ccaaggacaa cagcacagcc    4320
agtgcaagcc tagcctccaa tgggacaagt ggtgggcagg aggcaggagc accagaagag    4380
gaggaagatg agcttttgag agtgactgac cttgttgatt atgtctgtaa cagtgaacag    4440
ttataagact tttttttccat ttttgtgcta atttattcca cggtagctct cacaccagcg    4500
ggccagttat taaaagctgt ttaattttc ctagaaaact ccactacaga atgactttta    4560
gaagaaaaat ttcaacaaat cctgaagtct tctgtgaag tgaccagttc tgaactttga    4620
agataaataa ttgctgtaaa ttccttttga ttttcttttt ccaggttcat ggtccttggt    4680
```

-continued

| | |
|---|---|
| aatttcattc atggaaaaaa atcttattat aataacaaca aagatttgta tatttttgac | 4740 |
| tttatatttc ctgagctctc ctgactttgt gaaaagggt ggatgaaaat gcattccgaa | 4800 |
| tctgtgaggg cccaaaacag aatttagggg tgggtgaaag cacttgtgct ttagcttttt | 4860 |
| catattaaat atatattata tttaaacatt catggcatag atgatgattt acagacaatt | 4920 |
| taaaagttca agtctgtact gttacagttt gagaattgta gataacatca tacataagtc | 4980 |
| atttagtaac agcctttgtg aaatgaactt gtttactatt ggagataacc acacttaata | 5040 |
| aagaagagac agtgaaagta ccatcataat taacctaaat ttttgttata gcagagtttc | 5100 |
| ttgtttaaaa aaaataaaa tcatctgaaa agcaaaaa | 5138 |

<210> SEQ ID NO 36
<211> LENGTH: 2288
<212> TYPE: DNA
<213> ORGANISM: Homo sapiens

<400> SEQUENCE: 36

| | |
|---|---|
| cgcgcgctgc agtgccttcc ccacctcggc cccgcccgcc ccgccgagc cgagcaccag | 60 |
| ggcggcggcg gcggcggcgg cggcggcggc ggctggagca gcccgggagg aggaggcggc | 120 |
| gagaatggca gcgcgtcgt gggcgcggcg gagatgagcg cccgcgaccc cgggcccagg | 180 |
| gcggcacagc cggagtgggc gggggtcccg atgcaggccc gagggggggcc atggggcagg | 240 |
| tcctgccggt cttcgcccac tgcaaagaag ctccgtctac agcctcctca actcctgatt | 300 |
| ccacagaagg agggaacgac gactctgatt ttcgagagct gcacacagcc cggaattct | 360 |
| cagaggagga cgaggaggag accacgtcgc aggactgggg cacccccgg gagctgacct | 420 |
| tctcctacat cgcctttgat ggtgtagtgg gctccggggg ccgcagggat tcaactgccc | 480 |
| gccgccccg cccccaggc cgctcagtct cggaaccacg agaccagcac cctcagccca | 540 |
| gcctgggcga cagcttggag agcatcccca gcctgagcca atccccggag cctggacgac | 600 |
| ggggtgatcc tgcacaccgcg cctccatccg agcgccctct ggaagacctg aggcttcggt | 660 |
| tggaccatct gggctgggtg gcccggggaa cgggatccgg ggaggactct ccaccagca | 720 |
| gctccacccc gctggaagac gaagaacccc aagaacccaa cagattggag acaggagaag | 780 |
| ctggggaaga actggaccta cgactccgac ttgctcagcc ctcatcgccc gaggtcttga | 840 |
| ctccccagct cagtccgggc tctgggacac cccaggccgg tactccgtcc ccatcccgat | 900 |
| cgcgagattc gaactctggg cccgaagagc cattgctgga agaggaagaa aagcagtggg | 960 |
| ggccactgga gcgagagcca gtaagggggac agtgcctcga tagcacggac caattagaat | 1020 |
| tcacggtgga gccacgcctt ctaggaacag ctatggaatg gttaaagaca tcattgctttt | 1080 |
| tggctgttta caagacggtt ccaattttgg aattgtcccc acctctgtgg acagccattg | 1140 |
| gctgggtcca aaggggcccc accccccta ctcctgtcct ccgggttcta ctgaagtggg | 1200 |
| caaaatcccc gagaagcagc ggtgtcccca gcctctcact cggagccgat atggggagta | 1260 |
| aagtggcgga cctgctgtac tggaaggaca cgaggacgtc aggagtggtc ttcacaggcc | 1320 |
| tgatggtctc cctcctctgc ctcctgcact ttagcatcgt gtccgtggcc gcgcacttgg | 1380 |
| ctctgttgct gctctgcggc accatctctc tcagggttta ccgcaaagtg ctgcaggccg | 1440 |
| tgcaccgggg ggatggagcc aacccttcc aggcctacct ggatgtggac ctcacccctga | 1500 |
| ctcgggagca gacggaacgt tgtcccacc agatcacctc ccgcgtggtc tcggcggcca | 1560 |
| cgcagctgcg gcacttcttc ctggtagaag acctcgtgga ttcccctcaag ctggccctcc | 1620 |
| tcttctacat cttgaccttc gtgggtgcca tcttcaatgg tttgactctt ctcattctgg | 1680 |

-continued

| | |
|---|---|
| gagtgattgg tctattcacc atccccctgc tgtaccggca gcaccaggct cagatcgacc | 1740 |
| aatatgtggg gttggtgacc aatcagttga gccacatcaa agctaagatc cgagctaaaa | 1800 |
| tcccagggac cggagccctg gcctctgcag cagccgcagt ctccggatcc aaagccaaag | 1860 |
| ccgaatgaga acggtgtctc tgcccgcagg acgcctgccc ccagccccg cagccctctg | 1920 |
| gcccctcca tctcttgtcc gttcccaccc accccctcc tcggcccgag ccttttcccg | 1980 |
| gtgggtgtca ggatcactcc cactagggac tctgcgctaa ttacctgagc gaccaggact | 2040 |
| acatttccca agaggctctg ctccaggagt ccaggaaaga cgaggcacct tggccgcggg | 2100 |
| gcctgctggg acttgtagtt gcctagacag ggcaccaccc tgcacttccg gacccgccgc | 2160 |
| tggaggcgcc gtgaggcgtt ggtgtctcct ggatgctact agccccaacg ccggggcttt | 2220 |
| gcatggggcc caggggaggc ctgagcttgg atttacactg taataaagac tcctgtggaa | 2280 |
| aacccgag | 2288 |

<210> SEQ ID NO 37
<211> LENGTH: 1700
<212> TYPE: DNA
<213> ORGANISM: Homo sapiens

<400> SEQUENCE: 37

| | |
|---|---|
| agcaggactc agaggggaga gttggaggaa aaaaaaggc agaaaaggga aagaagagg | 60 |
| aagagagaga gagagtgaga ggagccgctg agcccacccc gatggccgcg acgaagttg | 120 |
| ccggaggggc cgcaaagcc acgaaaagca aactttttga gtttctggtc catggggtgc | 180 |
| gccccgggat gccgtctgga gcccggatgc cccaccaggg ggcgcccatg ggcccccgg | 240 |
| gctccccgta catgggcagc cccgccgtgc gacccggcct ggcccccgcg ggcatggagc | 300 |
| ccgcccgcaa gcgagcagcg ccccgcccg ggcagagcca ggcacagagc cagggccagc | 360 |
| cggtgcccac cgcccccgcg cggagccgca gtgccaagag gaggaagatg gctgacaaaa | 420 |
| tcctccctca aaggattcgg gagctggtcc ccgagtccca ggcttacatg gacctcttgg | 480 |
| catttgagag gaaactggat caaaccatca tgcggaagcg ggtggacatc caggaggctc | 540 |
| tgaagaggcc catgaagcaa agcggaagc tgcgactcta tatctccaac acttttaacc | 600 |
| ctgcgaagcc tgatgctgag gattccgacg gcagcattgc ctcctgggag ctacgggtgg | 660 |
| aggggaagct cctggatgat cccagcaaac agaagcggaa gttctcttct tcttcaaga | 720 |
| gtttggtcat cgagctggac aaagatcttt atggccctga caaccacctc gttgagtggc | 780 |
| atcggacacc cacgacccag gagacggacg gcttccaggt gaaacggcct ggggacctga | 840 |
| gtgtgcgctg cacgctgctc ctcatgctgg actaccagcc tccccagttc aaactggatc | 900 |
| cccgcctagc ccggctgctg gggctgcaca cacagagccg ctcagccatt gtccaggccc | 960 |
| tgtggcagta tgtgaagacc aacaggctgc aggactccca tgacaaggaa tacatcaatg | 1020 |
| gggacaagta tttccagcag atttttgatt gtccccggct gaagttttct gagattcccc | 1080 |
| agcgcctcac agccctgcta ttgcccctg acccaattgt catcaaccat gtcatcagcg | 1140 |
| tggacccttc agaccagaag aagacggcgt gctatgacat tgacgtggag gtggaggagc | 1200 |
| cattaaaggg gcagatgagc agcttcctcc tatccacggc caaccagcag gagatcagtg | 1260 |
| ctctggacag taagatccat gagacgattg agtccataaa ccagctcaag atccagaggg | 1320 |
| acttcatgct aagcttctcc agagacccca aaggctatgt ccaagacctg ctccgctccc | 1380 |
| agagccggga cctcaaggtg atgacagatg tagccggcaa ccctgaagag gagcgccggg | 1440 |

| | |
|---|---:|
| ctgagttcta ccaccagccc tggtcccagg aggccgtcag tcgctacttc tactgcaaga | 1500 |
| tccagcagcg caggcaggag ctggagcagt cgctggttgt gcgcaacacc taggagccca | 1560 |
| aaaataagca gcacgacgga actttcagcc gtgtcccggg ccccagcatt ttgccccggg | 1620 |
| ctccagcatc actcctctgc caccttgggg tgtggggctg gattaaaagt cattcatctg | 1680 |
| acaaaaaaaa aaaaaaaaa | 1700 |

<210> SEQ ID NO 38
<211> LENGTH: 1935
<212> TYPE: DNA
<213> ORGANISM: Homo sapiens

<400> SEQUENCE: 38

| | |
|---|---:|
| acaatagcga ctcactggac ccagcccttg gcaacggcct ggcgacggtt tccctgctgc | 60 |
| tgcagccccc gtcggctcct cttttccagt cctccactgc cggggctggg cccggccgcg | 120 |
| ggaaggaccg aagggggatac agcgtgtccc tgcggcggct gcaagaggac taagcatgga | 180 |
| tggcagccgg agagtcagag caacctctgt ccttcccaga tatggtccac cgtgcctatt | 240 |
| taaaggacac ttgagcacca aaagtaatgc tgcagtagac tgctcggttc cagtaagcgt | 300 |
| gagtaccagc ataaagtatg cagaccaaca acgaagagag aaactcaaaa aggaattagc | 360 |
| acaatgtgaa aaagagttca aattaactaa aactgcaatg cgagccaatt ataaaaataa | 420 |
| ttccaagtca cttttaata ccttacaaaa gccctcaggc gaaccgcaaa ttgaggatga | 480 |
| catgttaaaa gaagaaatga atggattttc atcctttgca aggtcactag taccctcttc | 540 |
| agagagacta cacctaagtc tacataaatc cagtaaagtc atcacaaatg gtcctgagaa | 600 |
| gaactccagt tcctccccgt ccagtgtgga ttatgcagcc tccgggcccc ggaaactgag | 660 |
| ctctggagcc ctgtatggca gaaggccag aagcacattc ccaaattccc accggtttca | 720 |
| gttagtcatt tcgaaagcac ccagtgggga tcttttggat aaacattctg aactcttttc | 780 |
| taacaaacaa ttgccattca ctcctcgcac tttaaaaaca gaagcaaaat ctttcctgtc | 840 |
| acagtatcgc tattatacac ctgccaaaag aaaaaaggat tttacagatc aacggataga | 900 |
| agctgaaacc cagactgaat taagctttaa atctgagttg gggacagctg agactaaaaa | 960 |
| catgacagat tcagaaatga acataaagca ggcatctaat tgtgtgacat atgatgccaa | 1020 |
| agaaaaaata gctcctttac ctttagaagg gcatgactca acatgggatg agattaagga | 1080 |
| tgatgctctt cagcattcct caccaagggc aatgtgtcag tattccctga gccccttc | 1140 |
| aactcgtaaa atctactctg atgaagaaga actgttgtat ctgagtttca ttgaagatgt | 1200 |
| aacagatgaa attttgaaac ttggtttatt ttcaaacagg ttttagaac gactgttcga | 1260 |
| gcgacatata aaacaaaata aacatttgga ggaggaaaaa atgcgccacc tgctgcatgt | 1320 |
| cctgaaagta gacttaggct gcacatcgga ggaaaactcg gtaaagcaaa atgatgttga | 1380 |
| tatgttgaat gtatttgatt ttgaaaaggc tgggaattca gaaccaaatg aattaaaaaa | 1440 |
| tgaaagtgaa gtaacaattc agcaggaacg tcaacaatac caaaaggctt tggatatgtt | 1500 |
| attgtcggca ccaaaggatg agaacgagat attcccttca ccaactgaat ttttcatgcc | 1560 |
| tatttataaa tcaaagcatt cagaaggggt tataattcaa caggtgaatg atgaaacaaa | 1620 |
| tcttgaaact tcaactttgg atgaaaatca tccaagtatt tcagacagtt taacagatcg | 1680 |
| ggaaacttct gtgaatgtca ttgaaggtga tagtgaccct gaaaaggttg agatttcaaa | 1740 |
| tggattatgt ggtcttaaca catcacccctc ccaatctgtt cagttctcca gtgtcaaagg | 1800 |
| cgacaataat catgacatgg agttatcaac tcttaaaatc atggaaatga gcattgagga | 1860 |

```
ctgcccttg gatgtttaat cttcattaat aaatacctca aatggccagt aactcaaaaa    1920
aaaaaaaaaa aaaaa                                                    1935

<210> SEQ ID NO 39
<211> LENGTH: 4343
<212> TYPE: DNA
<213> ORGANISM: Homo sapiens

<400> SEQUENCE: 39
tggtcatcgc acggcggcag ctcctcacct ggatttagaa gagctggcgt ccccgcccgc      60
ccaagccttt aaactctcgt ctgccagaac ccgccaactc tccaggctta gggccagttt    120
ccgcgattct aagagtaatt gcgtgggcac ctgtgctggg gccaggcgca aagaagggag    180
ttggtctgcg cgaagatcgt caacctgcta acagaccgca catgcacttt gcaccgacca    240
tctacgtctc agtctggagg ttgcgcactt tggctgctga cgcgctggtg gtgcctatta    300
atcatttacc agtccagagc cgcgccagtt aatggctgtg ccgtgcggtg ctcccacatc    360
ctggcctctc ctctccacgg tcgcctgtgc ccgggcaccc cggagctgca aactgcagag    420
cccaggcaac cgctgggctg tgcgccccgc cggcgccggt aggagccgcg ctccccgcag    480
cggttgcgct ctacccggag gcgctgggcg gctgtgggct gcaggcaagc ggtcgggtgg    540
ggagggaggg cgcaggcggc gggtgcgcga ggagaaagcc ccagccctgg cagccccact    600 ggccccctc agctgggatg ttccccaatg gcaccgcctc ctctccttcc tcctctccta    660
gccccagccc gggcagctgc ggcgaaggcg gcggcagcag gggccccggg gccggcgctg    720
cggacggcat ggaggagcca gggcgaaatg cgtcccagaa cgggaccttg agcgagggcc    780
agggcagcgc catcctgatc tctttcatct actccgtggt gtgcctggtg gggctgtgtg    840
ggaactctat ggtcatctac gtgatcctgc gctatgccaa gatgaagacg gccaccaaca    900
tctacatcct aaatctggcc attgctgatg agctgctcat gctcagcgtg cccttcctag    960
tcacctccac gttgttgcgc cactggccct tcggtgcgct gctctgccgc ctcgtgctca    1020
gcgtggacgc ggtcaacatg ttcaccagca tctactgtct gactgtgctc agcgtggacc    1080
gctacgtggc cgtggtgcat cccatcaagg cggcccgcta ccgccggccc accgtggcca    1140
aggtagtaaa cctgggcgtg tgggtgctat cgctgctcgt catcctgccc atcgtggtct    1200
tctctcgcac cgcggccaac agcgacggca cggtggcttg caacatgctc atgccagagc    1260
ccgctcaacg ctggctggtg ggcttcgtgt tgtacacatt tctcatgggc ttcctgctgc    1320
ccgtgggggc tatctgcctg tgctacgtgc tcatcattgc taagatgcgc atggtggccc    1380
tcaaggccgg ctggcagcag cgcaagcgct cggagcgcaa gatcacctta atggtgatga    1440
tggtggtgat ggtgtttgtc atctgctggg tgccttccta cgtggtgcag ctggtcaacg    1500
tgtttgctga gcaggacgac gccacggtga gtcagctgtc ggtcatcctc ggctatgcca    1560
acagctgcgc caaccccatc ctctatgcct ttctctcaga caacttcaag cgctcttttcc    1620 aacgcatcct atgcctcagc tggatggaca acgccgcgga ggagccggtt gactattacg    1680
ccaccgcgct caagagccgt gcctacagtg tggaagactt ccaacctgag aacctggagt    1740
ccggcggcgt cttccgtaat ggcacctgca cgtcccggat cacgacgctc tgagcccggg    1800
ccacgcaggg gctctgagcc cgggccacgc aggggccctg agccaaaaga ggggagaat    1860 gagaagggaa ggccgggtgc gaaagggacg gtatccaggg cgccagggtg ctgtcgggat    1920
aacgtggggc taggacactg acagcctttg atggaggaac ccaagaaagg cgcgcgacaa    1980
```

-continued

```
tggtagaagt gagagctttg cttataaact gggaaggctt tcaggctacc ttttctggg       2040
tctcccactt tctgttcctt cctccactgc gcttactcct ctgaccctcc ttctattttc      2100
cctaccctgc aacttctatc cttctcttccg caccgtcccg ccagtgcaga tcacgaactc     2160
attaacaact cattctgatc ctcagcccct ccagtcgtta tttctgtttg tttaagctga     2220
gccacggata ccgccacggg tttccctcgg cgttagtccc tagccgcgcg gggccgctgt     2280
ccaggttctg tctggtgccc ctactggagt cccgggaatg accgctctcc ctttgcgcag     2340
ccctaccttta aggaaagttg gacttgagaa agatctaagc agctggtctt ttctcctact    2400
cttgggtgaa ggtgcatctt tccctgcctc ccctgtccc cctctcgccg cccgccgcc       2460
accaccactc tcactccacc cagagtagag ccaggtgctt agtaaaatag gtcccgcgct     2520
tcgaactcca ggctttctgg agttcccacc caagccctcc tttggagcaa agaaggagct    2580
gagaacaagc cgaatgagga gttttttataa gattgcgggg tcggagtgtg ggcgcgtaat   2640
aggaatcacc ctcctactgc gcgttttcaa agaccaagcg ctgggcgctc ccgggccgcg    2700
cgtctgcgtt aggcagggca gggtagtgca gggcacacct tccccggggt tcggggttcg    2760
gggttcggtt gcagggctgc agcccgcctt ggctttctcc ctcacccaag tttccggagg    2820
agccgaccta aaagtaacaa tagataaggt ttcctgctcc agtgtatctc aaaagaccgg    2880
gcgccagggg cgggggacct agggcgacgt cttcagagtc cgccagtgtt ggcggtgtcg   2940
ccgcaacctg caggctcccg agtgggggcct gcctggtctc tagaggggttg ctgccttca   3000
agcggtgcct aagaagttat tttcttgttt aacatatata tttattaatt tatttgtcgt    3060
gttggaaaat gtgtctctgc tttccttttc tctgcttgcc tagccccagg tcttttcttt    3120
gggaccctgg gggcgggcat ggaagtggaa gtaggggcaa gctcttgccc cactccctgg   3180
ccatctcaac gcctctcctc aatgctgggc cctcttatct catcctttcc tctagctttt    3240
ctattttga ttgtgttgag tgaagtttgg agatttttca tactttttctt actatagtct    3300
cttgtttgtc ttattaggat aatacataaa tgataatgtg ggttatcctc ctctccatgc   3360
acagtggaaa gtcctgaact cctggctttc caggagacat atataggga acatcaccct    3420
atatataatt tgagtgtata tatatttata tatgatgt ggacatatgt atacttatct    3480
tgctccattg tcatgagtcc atgagtctaa gtatagccac tgatggtgac aggtgtgagt   3540
ctggctggaa cactttcagt ttcaggagtg caagcagcac tcaaacctgg agctgaggaa   3600
tctaattcag acagagactt taatcactgc tgaagatgcc cctgctccct ctgggttcca   3660
gcagaggtga ttcttacata tgatccagtt aacatcatca cttttttttga ggacattgaa  3720
agtgaaataa tttgtgtctg tgtttaatat taccaactac attggaagcc tgagcagggc   3780
gaggaccaat aatttttaatt atttatattt cctgtattgc tttagtatgc tggcttgtac  3840
atagtaggca ctaaatacat gtttgttggt tgattgttta agccagagtg tattacaaca   3900
atctggagat actaaatctg gggttctcag gttcactcat tgacatgata tacaatggtt   3960
aaatcacta ttgaaaaata cgttttgtgt atatttgctt caacaacttt gtgctttcct    4020
gaaagcagta accaagagtt aagatatccc taatgttttg cttaaactaa tgaacaaata   4080
tgctttgggt cataaatcag aaagtttaga tctgtccctt aataaaaata tatattacta   4140
ctcctttgga aaatagattt ttaatggtta agaactgtga aatttacaaa tcaaaatctt    4200
aatcattatc cttctaagag gatacaaatt tagtgctctt aacttgttac cattgtaata   4260
ttaactaaat aaacagatgt attatgctgt taaaaaaaaa aaaaaaaaaa aaaaaaaaaa    4320
aaaaaaaaaa aaaaaaaaaa aaa                                            4343
```

<210> SEQ ID NO 40
<211> LENGTH: 4171
<212> TYPE: DNA
<213> ORGANISM: Homo sapiens

<400> SEQUENCE: 40

| | | | | | |
|---|---|---|---|---|---|
| ctgcatctct | ccctctcacc | cgtgtctcct | ctcctctctt | tccttctcgt | cttctccctg | 60 |
| tcacgcatct | ctcatcactc | ccctcattc | tgcctttcct | cctactcacg | gtctcctctc | 120 |
| cctctccctc | tctctctctc | ccctccctc | tttctctctc | tctctctttc | tccacctcct | 180 |
| cccgaccccc | tttcccctct | atttctattg | gcttctgtgt | cccttgctcc | cctcttctct | 240 |
| tcctcaccct | gggaagcttc | tccccctat | ccttgcccct | gcccccccag | gatgtgtcct | 300 |
| ggagatgggg | ggtgacgtac | caggctctgg | ttgggaagtc | agggccggag | accagatggg | 360 |
| agaggctctg | tggacagccg | tggccgaggg | cctgggaggg | aacctgagcc | cgcaagcggt | 420 |
| ctagaagtgg | gtgccttgtg | ggaccctag | ttaggagtgc | cctgggggca | cctggggact | 480 |
| gggcagggag | aggggacagc | agaatgataa | ccagcctggc | ggcaaggagg | gaagccctca | 540 |
| ccccatggga | aggcaaatag | ctgactgctg | accaccctcc | cctcagccat | ggacatgctt | 600 |
| catccatcat | cggtgtccac | gacctcagaa | cctgagaatg | cctcctcggc | ctggcccca | 660 |
| gatgccaccc | tggcaacgt | gtcggcgggc | ccaagcccgg | cagggctggc | cgtcagtggc | 720 |
| gttctgatcc | ccctggtcta | cctggtggtg | tgcgtggtgg | gcctgctggg | taactcgctg | 780 |
| gtcatctatg | tggtcctgcg | gcacacggcc | agcccttcag | tcaccaacgt | ctacatcctc | 840 |
| aacctggcgc | tggccgacga | gctcttcatg | ctggggctgc | ccttcctggc | cgcccagaac | 900 |
| gccctgtcct | actggccctt | cggctccctc | atgtgccgcc | tggtcatggc | ggtggatggc | 960 |
| atcaaccagt | tcaccagcat | attctgcctg | actgtcatga | gcgtggaccg | ctacctggcc | 1020 |
| gtggtacatc | ccacccgctc | ggcccgctgg | cgcacagctc | cggtggcccg | cacggtcagc | 1080 |
| gcggctgtgt | gggtggcctc | agccgtggtg | gtgctgcccg | tggtggtctt | ctcgggagtg | 1140 |
| ccccgcggca | tgagcacctg | ccacatgcag | tgggcccgagc | cggcggcggc | ctggcgagcc | 1200 |
| ggcttcatca | tctacacggc | cgcactgggc | ttcttcgggc | cgctgctggt | catctgcctc | 1260 |
| tgctacctgc | tcatcgtggt | gaaggtgcgc | tcagctgggc | gccgggtgtg | ggcaccctcg | 1320 |
| tgccagcggc | ggcggcgctc | cgaacgcagg | gtcacgcgca | tggtggtggc | cgtggtggcg | 1380 |
| ctcttcgtgc | tctgctggat | gcccttctac | gtgctcaaca | tcgtcaacgt | ggtgtgccca | 1440 |
| ctgcccgagc | agcctgcctt | ctttgggctc | tacttcctgg | tggtggcgct | gccctatgcc | 1500 |
| aacagctgtg | ccaaccccat | cctttatggc | ttcctctcct | accgcttcaa | gcagggcttc | 1560 |
| cgcagggtcc | tgctgcggcc | ctcccgccgt | gtgcgcagcc | aggagcccac | tgtggggccc | 1620 |
| ccggagaaga | ctgaggagga | ggatgaggag | gaggaggatg | gggaggagag | caggagggg | 1680 |
| ggcaagggga | aggagatgaa | cggccgggtc | agccagatca | cgcagcctgg | caccagcggg | 1740 |
| caggagcggc | cgcccagcag | agtggccagc | aaggagcagc | agctcctacc | ccaagaggct | 1800 |
| tccactgggg | agaagtccag | cacgatgcgc | atcagctacc | tgtagggggcc | tggggaaagc | 1860 |
| caggatggcc | cgaggaagag | gcagaagccg | tgggtgtgcc | tagggcctac | ttcccaaggt | 1920 |
| gccacaggcc | catgatggga | tgttgagggg | cctggacttt | gatgctattg | ctgccaggtc | 1980 |
| ttgctgtgtg | accttgggta | ggttgcttct | actctctggg | ccttgttttc | tcctctgtga | 2040 |
| ctcagggata | ggagtcatca | gcctggatga | gctatgtcag | atgagaggtt | tggagggcac | 2100 |

| | | | | |
|---|---|---|---|---|
| tgttgctggg | ctgacctggc | tgagcaggca | aaaggtgggt | gcagactggc | ctcccccag | 2160 |
| ggatggagtg | tcttggggca | tcaactagaa | tcttggccct | cagagggata | aaccaaggcc | 2220 |
| aggatttctt | gggctcagag | tcaggaacac | aggagctgct | gggggctggg | ctggaaacct | 2280 |
| aaacagaaga | aagcctaacc | cggtgggagg | agtgggcag | aaatggtcag | gccccagatc | 2340 |
| agctccctcc | cctcgactgt | gaggccttgg | accagctctg | ctcctctcta | ggcctcaggc | 2400 |
| ttcacctggg | taaaacccaa | caacctctac | acccttttgg | cccaggcagt | caatgctgga | 2460 |
| ggtcctgtgc | tcctggacgg | gaagagcagg | tgaatttcct | gctcatggaa | gcgaatgaag | 2520 |
| tccagcttca | gggtctctca | ctgcctgggc | ttttgcaagg | ccctgcatct | acttttgtac | 2580 |
| ttgtcatttt | gtattcgttt | tcttaaagag | ggacctcgaa | ctgcataagc | ttaggccacc | 2640 |
| caaagcctgg | ctctgcccct | gctgaggtca | gccacccaat | ccccaaggaa | gctcatgttg | 2700 |
| ggtcttatgg | ctggagtagg | ggcccccggg | ggttcccagg | tcttttgagg | gcttccaggc | 2760 |
| acctccttgt | aggaagggcc | atccctgttc | ctctccttgt | gacccatatt | ctcccttcct | 2820 |
| ggagaccgag | acagggaccc | agcccatgag | gactggcatg | gaaaggcaga | gtgtctgaag | 2880 |
| agcgctgtga | ggagaaggaa | gaggaaggga | gaagaggaag | aggaaggaga | aggaaggaga | 2940 |
| agacaagggg | gaaggggag | gatgaggagg | gggaaggaga | agtacagatc | tgtttcctgg | 3000 |
| agccgtcttt | ggcccccctg | ggctgagctc | agtggtagca | tctgtgaacc | tgagttgccg | 3060 |
| acaacagccc | cacccaacca | gtactgaggg | aaggacacga | tcaggtgga | acagccaggg | 3120 |
| tgcaatggca | aatgcacaga | gtacagacag | gcacagggcc | tgcgtccctg | aggggcctca | 3180 |
| gagtgctgcc | aagagggctc | aggccttaat | aaagccctag | ggtggagctg | gctaccaggg | 3240 |
| acattgggag | gactggggag | ctccctcccc | atgctctatc | atcctggaga | ctacaggtcg | 3300 |
| ggaggcccag | ggaagacaag | aagaggctga | agtgggactg | tggagggga | ccatggggag | 3360 |
| cagccaccat | ccaaggctgg | gcctagactc | cctcccagag | atggtccctc | agagctgtgg | 3420 |
| tgaggctggc | cctgggaggg | tgagaccccc | ggtgaaatcc | ttccgcttcc | ccacccctg | 3480 |
| cagagggcag | gggtcctcag | ggaaagcaca | ggaaccagac | ttttggagac | ttggatcttc | 3540 |
| agcacacctc | agggtcctgg | gctggcattg | gccttccggg | cctcaatttc | cccatcaaca | 3600 |
| aatggagatg | aatcccagct | tggctgcctc | ctgggatcta | acgagaaaat | gagtcatgtg | 3660 |
| aggtaacttc | caggctcact | gcaatgggta | cggtggggtg | tatcagatta | taaagtgggg | 3720 |
| gtgccctcct | cacccccagg | cttggcctat | accccctct | ccatcaagtg | gcctctctgt | 3780 |
| gtctgtcctt | tggggtgagg | acactgtagg | ccatgagaaa | tggcagttg | gggggtcaga | 3840 |
| ggccaagggt | tagggaggca | gggcttgggg | agagtgtggg | accatcagaa | gagaaggaag | 3900 |
| tttacaaaac | cacattttgt | gtggagatgg | aggctggagg | cccggccctg | ggacttggtc | 3960 |
| tggggtttct | tgaggaagat | ctgagggtcc | aagggaggaa | ggatgccctg | gccttctggc | 4020 |
| cttctctggc | tgatcctgcc | ttcttgctgc | ctaggacagg | agagtaatgt | cctagaatgg | 4080 |
| tccctgggag | gccagttagg | aaacccttg | ctgcttctgt | ctctagctct | tgtcaataaa | 4140 |
| gacggtgaca | cctgaaaaaa | aaaaaaaaaa | a | | | 4171 |

<210> SEQ ID NO 41
<211> LENGTH: 1258
<212> TYPE: DNA
<213> ORGANISM: Homo sapiens

<400> SEQUENCE: 41

| | | | | | |
|---|---|---|---|---|---|
| ccgagctctc | tggcgcagcg | ctagctccgc | cgcgctcagc | tgccctgcgc | cggcacccct | 60 |

-continued

| | |
|---|---|
| ggtcatgagc gcccctcga cgctgccccc cggggcgag aagggctgg ggacggcctg | 120 |
| gccctctgca gccaatgcca gtagcgctcc ggcggaggcg gaggaggcgg tggcggggcc | 180 |
| cggggacgcg cggcggcgg gcatggtcgc tatccagtgc atctacgcgc tggtgtgcct | 240 |
| ggtggggctg gtgggcaacg ccctggtcat cttcgtgatc cttcgctacg ccaagatgaa | 300 |
| gacggctacc aacatctacc tgctcaacct ggccgtagcc gacgagctct tcatgctgag | 360 |
| cgtgcccttc gtggcctcgt cggccgccct gcgccactgg cccttcggct ccgtgctgtg | 420 |
| ccgcgcggtg ctcagcgtcg acggcctcaa catgttcacc agcgtcttct gtctcaccgt | 480 |
| gctcagcgtg gaccgctacg tggccgtggt gcaccctctg cgcgcggcga cctaccggcg | 540 |
| gcccagcgtg gccaagctca tcaacctggg cgtgtggctg gcatccctgt tggtcactct | 600 |
| ccccatcgcc atcttcgcag acaccagacc ggctcgcggc ggccaggccg tggcctgcaa | 660 |
| cctgcagtgg ccacacccgg cctggtcggc agtcttcgtg gtctacactt tcctgctggg | 720 |
| cttcctgctg cccgtgctgg ccattggcct gtgctacctg ctcatcgtgg caagatgcg | 780 |
| cgccgtggcc ctgcgcgctg gctggcagca gcgcaggcgc tcggagaaga aaatcaccag | 840 |
| gctggtgctg atggtcgtgg tcgtctttgt gctctgctgg atgcctttct acgtggtgca | 900 |
| gctgctgaac ctcttcgtga ccagccttga tgccaccgtc aaccacgtgt cccttatcct | 960 |
| tagctatgcc aacagctgcg ccaaccccat tctctatggc ttcctctccg acaacttccg | 1020 |
| ccgattcttc cagcgggttc tctgcctgcg ctgctgcctc ctggaaggtg ctggaggtgc | 1080 |
| tgaggaggag cccctggact actatgccac tgctctcaag agcaaaggtg gggcagggtg | 1140 |
| catgtgcccc ccactcccct gccagcagga agccctgcaa ccagaacccg gccgcaagcg | 1200 |
| catccccctc accaggacca ccaccttctg aggagccctt cccctaccca ccctgcgt | 1258 |

<210> SEQ ID NO 42
<211> LENGTH: 2674
<212> TYPE: DNA
<213> ORGANISM: Homo sapiens

<400> SEQUENCE: 42

| | |
|---|---|
| atgcctgcat gtgctggttc agggactcac caccctggcg tcctcccttc ttctcttgca | 60 |
| gagcctgacg cacccagggg ctgccgccat ggagcccctg ttcccagcct ccacgcccag | 120 |
| ctggaacgcc tcctcccgg gggctgcctc tggaggcggt gacaacagga cgctggtggg | 180 |
| gccggcgccc tcggcagggg cccggcggt gctggtgccc gtgctgtacc tgctggtgtg | 240 |
| tgcggccggg ctgggcggga acacgctggt catctacgtg gtgctgcgct cgccaagat | 300 |
| gaagaccgtc accaacatct acattctcaa cctggcagtg gccgacgtcc tgtacatgct | 360 |
| ggggctgcct ttcctggcca cgcagaacgc gcgtcccttc tggcccttcg gcccgtcct | 420 |
| gtgccgcctg gtcatgacgc tggacggcgt caaccagttc accagtgtct tctgcctgac | 480 |
| agtcatgagc gtggaccgct acctggcagt ggtgcacccg ctgagctcgg cccgctggcg | 540 |
| ccgcccgcgt gtggccaagc tggcgagcgc cgcggcctgg gtcctgtctc tgtgcatgtc | 600 |
| gctgccgctc ctggtgttcg cggacgtgca ggagggcgt acctgcaacg ccagctggcc | 660 |
| ggagcccgtg ggctgtgggg cgccgtcttc atcatctac acggccgtgc tgggcttctt | 720 |
| cgcgccgctg ctggtcatct gcctgtgcta cctgctcatc gtggtgaagg tgagggcggc | 780 |
| gggcgtgcgc gtgggctgcg tgcggcgcg ctcggagcgg aaggtgacgc gcatggtgtt | 840 |
| ggtggtggtg ctggtgtttg cgggatgttg gctgcccttc ttcaccgtca acatcgtcaa | 900 |

```
cctggccgtg gcgctgcccc aggagcccgc ctccgccggc ctctacttct tcgtggtcat    960
cctctcctac gccaacagct gtgccaaccc cgtcctctac ggcttcctct ctgacaactt   1020
ccgccagagc ttccagaagg ttctgtgcct ccgcaagggc tctggtgcca aggacgctga   1080
cgccacggag ccgcgtccag acaggatccg gcagcagcag gaggccacgc cacccgcgca   1140
ccgcgccgca gccaacgggc ttatgcagac cagcaagctg tgagagtgca ggcgggggt    1200
gggcggcccc gtgtcacccc caggagcgga ggttgcactg cggtgacccc cacccatgac   1260
ctgccagtca ggatgctccc cggcggtggt gtgaggacga agctggctga agccaggctg   1320
gggtagacac agggcagtag gttccccacc gtgaccgacc atcccctcta accgtctgcc   1380
acacagcggg ggctcccggg aggtagggga ggtggccaga ccggtggggg gctccgccat   1440
gccgtgcaag tgctcaggc cgcctcaccc tccatctggc cccagcccat gccggccttc   1500
cctctgggga gcgacttttc cagaaggccg gccaggcgag agggtcttcc tgacggcgga   1560
gctgacctgc ccggcccacc agctgcatgt cagctccgag ccaccgggtc cccgtccaag   1620
gctgctctgc taagttaaag acacccgaaa gcgcttgact caggtccccg gagtccctgg   1680
ccagggcccc agccctcgc ttgccctgca ctgtgtggac tctggggatg caggtgtaag   1740
gggagtgtgg ctgggcagcc cctggtcagc cagggtcacg cctgtcctgg ggccccacc    1800
ctgctgcccg acacccccca tgggaggctg cgggcggcag ttgctgtctc agagagggga   1860
gtgtgggggc ttgggcgctg gcctagccag gggcgaggtg gggaggcggc tggtgcagag   1920
gagagctggg ggctgaggtt ggggtgaagg ctgcagccct ccaggctgct gggggtgcag   1980
atggctgtgc cgtgctgaga ttggctctgt ctggaggggt ccagtgtggg gtgcctgagg   2040
gcactaggga gaggtgctcc tgctgcagga ggacctgagg gtcagggctt ggagaggaca   2100
gggaacctgc ggccgtctct tctgctttgg ggcaggggct ctggcccggg agagggaacg   2160
gggacaggag cagaggacgg tcatccaggc gcagcgggga gctgctcccc aggccacagc   2220
agacagcact gctgagaggc agcggccgcg cgggtgacgc aaatggcagg ccctgggaat   2280
cccgccgcct cccacctaga attgtcctac ctcccccacc ccaaacacca gcttttcctg   2340
gcgcccagg cccagaacgt gggcccgag agccttgctg ggtctctgg ggcaccttgg    2400
ccttgctctg aggctggaag gagaaggacc agggtgcggc atcactcggc ctcagggacc   2460
cctctgccct gcccagcact ggccccgacc cgtgctcccg ccgtctgccc agagcaggac   2520
ctcaacctcc tggagggcac agggagcggc tgagtgggca caaatcctgg caggagaaag   2580
gcccaggctg aggccaggcc tgggaaacat ccaagcagtg aggacacgcg tgtttgacaa   2640
ctgctcccct gaataaatgc gaggataaat gttt                              2674
```

<210> SEQ ID NO 43
<211> LENGTH: 4427
<212> TYPE: DNA
<213> ORGANISM: Homo sapiens

<400> SEQUENCE: 43

```
cccccggcgg agccagctgc tgctcttcgg tgctggcccc ggtgccggcc ccgttgccca     60
gggaacaggc tcccggcagc ccccgcggcc cggagtccat cccgcctcct ccggcccggc    120
ggggccgacg agtccggagg ggctgccgcg ggagccccca ggtttcccta gatgacaaat    180
aaacattcct tttcctgcgt gaagatagtc tgtggaaacc ttggccatgg catcgatatc    240
agagcctgtt acattcagag agttctgccc gttgtactat ctcctcaatg ccattccgac    300
aaagatccag aagggtttcc gctctatcgt ggtctatctc acggccctcg acaccaacgg    360
```

-continued

```
ggactacatc gcggtgggca gcagcatcgg catgctctat ctgtactgcc ggcacctcaa    420
ccagatgagg aagtacaact ttgagcggaa gacggaatct atcactgtgg tgaagctgct    480
gagctgcttt gatgacctgg tggcagcagg cacagcctct ggcagggttg cagtttttca    540
acttgtatct tcattgccag ggagaaataa acagcttcgg agatttgatg tcactggtat    600
tcacaaaaat agcattacag ctctggcttg gagccccaat ggaatgaaat tgttctctgg    660
agatgacaaa ggcaaaattg tttattcttc tctggatcta gaccagggggc tctgtaactc    720 ccagctggtg ttggaggagc catcttccat tgtgcagctg gattatagcc agaaagtgct    780
gctggtctct actctgcaaa gaagtctgct cttttacact gaagaaaagt ctgtaaggca    840
aattggaaca caaccaagga aaagtactgg gaaatttggt gcttgtttta taccaggact    900
ctgtaagcaa agtgatctaa ccttgtatgc gtcacggccc gggctccggc tatggaaggc    960
tgatgtccac gggactgttc aagccacgtt tatcttaaaa gatgcttttg ccgggggagt   1020
caagcctttt gaactgcacc cgcgtctgga atcccccaac agtggaagtt gcagcttacc   1080
tgagaggcac ctggggcttg tttcatgttt cttttcaagaa ggctgggtgc tgagttggaa   1140
tgaatatagt atctatctcc tagacacagt caaccaggcc acagttgctg gtttggaagg   1200
atccggtgat attgtgtctg tttcgtgcac agaaaatgaa atattttttct tgaaaggaga   1260 taggaacatt ataagaattt caagcaggcc tgaaggatta acatcaacag tgagagatgg   1320
tctggagatg tctggatgct cagagcgtgt ccacgtgcag caagcggaga agctgccagg   1380
ggccacagtt tctgagacga ggctcagagg ctcttccatg gccagctccg tggccagcga   1440
gccaaggagc aggagcagct cgctcaactc caccgacagc ggctccgggc tcctgccccc   1500
tgggctccag gccaccctg agctgggcaa gggcagccag cccctgtcac agagattcaa   1560
cgccatcagc tcagaggact tgaccagga gcttgtcgtg aagcctatca agtgaaaaag   1620
gaagaagaag aagaagaaga cagaaggtgg aagcaggagc acctgtcaca gctccctgga   1680
atcgacaccc tgctccgaat ttcctgggga cagtccccag tccttgaaca cagacttgct   1740
gtcgatgacc tcaagtgtcc tgggcagtag cgtggatcag ttaagtgcag agtctccaga   1800
ccaggaaagc agcttcaatg gtgaagtgaa cggtgtccca caggaaaata ctgaccccga   1860
aacgtttaat gtcctggagg tgtcaggatc aatgcctgat tctctggctg aggaagatga   1920
cattagaact gaaatgccac actgtcacca tgcacatggg cgggagctgc tcaatggagc   1980
gagggaagat gtgggaggca gtgatgtcac gggactcgga gatgagccgt gtcctgcaga   2040
tgatggacca aatagcacac agttacccctt ccaagaacag acagctctc ctggggcgca   2100 tgatggggaa gacatccaac ccattggccc ccaaagcact ttttgtgaag tccccctcct   2160
gaactcactc actgtgcctt ccagcctcag ctgggcccca gtgctgaac agtggctgcc   2220 tgggaccaga gctgatgaag gcagccccgt ggagcccagc caagagcagg acatcctaac   2280
cagcatggag gcctctggcc acctcagcac aaatctctgg catgctgtca ctgatgatga   2340
cacaggtcag aaagaaatac ccatttctga acgtgtcttg gggagtgtgg gaggacagct   2400
gactccggtc tctgccttgg cagccagcac tcacaagccc tggcttgagc agcctccacg   2460
ggatcagaca ttgacgtcca gcgatgagga ggacatctat gcccacgggc ttccttcttc   2520
atcctcagag acgagtgtga cagagctcgg acctagttgc tcccagcagg acctgagccg   2580
gctgggtgca gaggacgccg gctgctcaa gccagatcag tttgcagaaa gctggatggg   2640
ctactcgggt cccggctatg gcatcctcag cttggtggtc tccgagaagt atatctggtg   2700
```

-continued

| | | | |
|---|---|---|---|
| cctggactac | aaaggcggcc | tgttctgcag | cgcgttgccg ggcgccgggc tgcgctggca | 2760 |
| gaagtttgaa | gatgctgtcc | agcaggtggc | agtctcgccc tcaggagccc ttctctggaa | 2820 |
| gattgaacag | aaatctaacc | gggcttttgc | ttgtgggaaa gtcaccatca aggggaagcg | 2880 |
| gcactggtac | gaagccctgc | cccaggcagt | gtttgtggcc ctgagcgatg acacggcctg | 2940 |
| gatcatcagg | accagtgggg | acctatactt | gcagacaggt ctgagcgtgg atcgcccttg | 3000 |
| tgccagagcc | gtaaaggtgg | actgtcccta | cccgctgtcc cagatcacag cccgaacaa | 3060 |
| tgtggtgtgg | gcgctgacag | agcagagggc | cctcctgtac cgggagggcg tgagcagctt | 3120 |
| ctgtccggaa | ggcgagcagt | ggaagtgtga | cattgtcagc gaaaggcaag ctttagaacc | 3180 |
| cgtctgcata | acgctcgggg | atcagcagac | tctctgggcc ctggacatcc atgggaacct | 3240 |
| gtggttcaga | actggcatta | tttccaagaa | gccccaagga gatgacgacc attggtggca | 3300 |
| agtgagcatc | acggactatg | tggtgtttga | ccagtgcagc ttatttcaga cgataatcca | 3360 |
| tgccactcac | tcggtggcca | cagcagccca | agccccgta gaaaaggtgg cagataagct | 3420 |
| gcgcatggcg | ttttggtccc | agcagcttca | gtgccagcca agccttctcg gggtcaataa | 3480 |
| cagcggtgtc | tggatctcct | cgggcaagaa | tgaattccac gtcgctaagg gaagtctcat | 3540 |
| aggcacctac | tggaatcatg | tggttccccg | tgggacagct tctgctacaa aatgggcctt | 3600 |
| tgtgttggct | tctgcagctc | ccacgaagga | aggaagcttc ctgtggctgt gccagagcag | 3660 |
| caaggacctg | tgcagcgtca | gcgcccgag | cgcacagtcg cggccctcca cggtgcagct | 3720 |
| gcctcccgaa | gccgagatgc | gcgcctatgc | cgcctgccag gatgcgctgt gggcgctgga | 3780 |
| cagcctcggc | caggtgttca | tcaggacgct | ctccaagagc tgccccacgg gcatgcactg | 3840 |
| gaccaggctg | gacctctccc | agctaggagc | tgtaaaattg acaagcttgg catgtggaaa | 3900 |
| tcagcacatc | tgggcctgtg | attccagggg | tggagtttac ttccgtgtag ggactcagcc | 3960 |
| tctcaatccc | agtctcatgc | ttccagcctg | gataatgatt gagccacctg tccaggtaag | 4020 |
| cagaagttag | ctggtggaac | tcactcttca | gtaagacaga aactgtgagg atgctggtac | 4080 |
| tgggaaaaag | gatctgcaca | gcctctagag | gcctcccagc aaatgcgggg agccatgccc | 4140 |
| ccagggtcta | cacactctcg | ttcatcaaca | tcacaactgg aattcgggat tgtgaagtt | 4200 |
| tagagctgaa | cagactgtta | cagattatga | gtcaacacgt atattttctc tttcaaaata | 4260 |
| ataatatttc | gttttttgact | ttttactaag | tgaatattat tttttaaatc tgcctatata | 4320 |
| ttggaacctc | tattttataa | taataatgat | aataaatcag tacccagaag tataaagaag | 4380 |
| gtaaagttac | ctttgaaaaa | aaaaaaaaaa | aaaaaaaaaa aaaaaaa | 4427 |

<210> SEQ ID NO 44
<211> LENGTH: 1815
<212> TYPE: DNA
<213> ORGANISM: Homo sapiens

<400> SEQUENCE: 44

| | | | |
|---|---|---|---|
| ttttagagaa | ttactccaaa | ttcatcatga | ttgaagacaa taaggagaac aaagaccatt | 60 |
| ccttagaaag | ggaagagca | agtctcattt | tttccttaaa gaatgaagtt ggaggactta | 120 |
| taaaagccct | gaaaatcttt | caggagaagc | atgtgaatct gttacatatc gagtcccgaa | 180 |
| aatcaaaaag | aagaaactca | gaatttgaga | ttttttgttga ctgtgacatc aacagagaac | 240 |
| aattgaatga | tattttttcat | ctgctgaagt | ctcataccaa tgttctctct gtgaatctac | 300 |
| cagataattt | tactttgaag | gaagatggta | tggaaactgt tccttggttt ccaaagaaga | 360 |
| tttctgacct | ggaccattgt | gccaacagag | ttctgatgta tggatctgaa ctagatgcag | 420 |

```
accatcctgg cttcaaagac aatgtctacc gtaaacgtcg aaagtatttt gcggacttgg      480
ctatgaacta taaacatgga daccccattc caaaggttga attcactgaa gaggagatta      540
agacctgggg aaccgtattc caagagctca acaaactcta cccaacccat gcttgcagag      600
agtatctcaa aaacttacct ttgctttcta aatattgtgg atatcgggag ataatatcc       660 cacaattgga agatgtctcc aactttttaa aagagcgtac aggttttcc atccgtcctg       720 tggctggtta cttatcacca agagatttct tatcaggttt agcctttcga gttttcact       780 gcactcaata tgtgagacac agttcagatc ccttctatac ccagagccga gatacctgcc     840
atgaactctt aggtcatgtc ccgcttttgg ctgaacctag ttttgcccaa ttctcccaag     900
aaattggctt ggcttctctt ggcgcttcag aggaggctgt caaaaactg caacgtgct      960 acttttcac tgtggagttt ggtctatgta aacaagatgg acagctaaga gtctttggtg    1020
ctggcttact ttcttctatc agtgaactca acatgcact ttctggacat gccaaagtaa   1080 agcccttga tcccaagatt acctgcaaac aggaatgtct tatcacaact tttcaagatg   1140
tctactttgt atctgaaagt tttgaagatg caaaggagaa gatgagagaa tttaccaaaa   1200
caattaagcg tccatttgga gtgaagtata atccatatac acggagtatt cagatcctga   1260
aagacaccaa gagcataacc agtgccatga atgagctgca gcatgatctc gatgttgtca   1320
gtgatgccct tgctaaggtc agcaggaagc cgagtatcta acagtagcca gtcatccagg   1380
aacatttgag catcaattcg gaggtctggg ccatctcttg ctttccttga cacctgatc    1440 ctggagggac agcatcttct ggccaaacaa tattatcgaa ttccactact taaggaatca  1500 ctagtcttg aaaatttgta cctggatatt ctatttacca cttattttt tgtttagttt    1560 tattctttt ttttttggt agcagcttta atgagacaat ttatatacca tacaagccac     1620
tgaccaccca ttttaatag agaagttgtt tgacccaata gatagatcta atctcagcct   1680
aactctattt tccccaatcc tccttgagta aaatgaccct ttaggatcgc ttagaataac   1740
ttgaggagta ttatggcgct gactcatatt gttacctaag atcccttat ttctaaagta    1800 tctgttactt attgc                                                     1815
```

<210> SEQ ID NO 45
<211> LENGTH: 1305
<212> TYPE: DNA
<213> ORGANISM: Homo sapiens

<400> SEQUENCE: 45

```
ggccacccgc agaacagagc ttccgggacc cacgcctcgt ttgcactggg tgctggacag      60
ccgacgcaac tacaaatggg gcggagcttt cggcactgga gcagctaatt tgcatatagg     120
aatgaggtgc ggctcggctt ccatgggcct aatttacaga tagggcggta tttctgcccc    180
ttaaccgaaa gtgggataca gaggacgacg gtgttaggcg cctgtgtagg agtaaaatgt    240
gtttattttg cattcaacga gagctcctgc attgcagcta ttttgcatat gatttgcatc    300
ttacgaagaa tttgtggcaa aaaaagctg ggcgtgcgcc gtaggaacct cctgctgaga    360
cgcttccggt agcggcgcgt gacccgacag gtctttcacc tacctacctc agctcccaca    420
aacacgagaa gttccagcaa gttcgccact tccggttctc ctggctatcc aatagcatcg    480
agaggagcat ccccggaagt gaggcagcgg aggacgacct ttttccggtt ccggcctggc    540
gagagtttgt gcggcgacat gaaactgctt acccacaatc tgctgagctc gcatgtgcgg    600
ggggtggggt cccgtggctt cccctgcgc ctccaggcca ccgaggtccg tatctgccct    660
```

| | |
|---|---|
| gtggaattca acccccaactt cgtggcgcgt atgatacccta aagtggagtg gtcggcgttc | 720 |
| ctggaggcgg ccgataactt gcgtctgatc caggtgccga aagggccggt tgagggatat | 780 |
| gaggagaatg aggagtttct gaggaccatg caccacctgc tgctggaggt ggaagtgata | 840 |
| gagggcaccc tgcagtgccc ggaatctgga cgtatgttcc ccatcagccg cgggatcccc | 900 |
| aacatgctgc tgagtgaaga ggaaactgag agttgattgt gccaggcgcc agttttttctt | 960 |
| gttatgactg tgtattttttg ttgatctata ccctgttttcc gaattctgcc gtgtgtatcc | 1020 |
| ccaaccccttg acccaatgac accaaacaca gtgttttttga gctcggtatt atatattttt | 1080 |
| ttctcattaa aggtttaaaa ccaaaagcgg tttctcttttg cagcaaatat acattaaaat | 1140 |
| agagtctctg tacagccaag ggctctgggc cctggcttgc cccatgtccc tgcgcctccc | 1200 |
| tggccaaacc caaaaataaa tatagtgtta ttgctctgca gggcatagag gcagtgctct | 1260 |
| cctaccccct gaggaggctc gttgggagct gatggggaag ccctg | 1305 |

<210> SEQ ID NO 46
<211> LENGTH: 2770
<212> TYPE: DNA
<213> ORGANISM: Homo sapiens

<400> SEQUENCE: 46

| | |
|---|---|
| cacacacaca catacacaga atcctcagat aacaggaggc aataaatcca acagcacatc | 60 |
| cacgttcaga gaacagtgtc cctgctgtct tgctaacagc tgccaatacc tcactgagtg | 120 |
| cctcacacca acatgggctc caagtgagtt tccttcgtct gggcagactc cctcccctct | 180 |
| tccataaagg ctgcaggaga cctgtagctg tcacaggacc ttccctaaga gcccgcaggg | 240 |
| gaagactgcc ccagtccggc catcaccatg ctccggacca ttctggatgc tccccagcgg | 300 |
| ttgctgaagg aggggagagc gtcccggcag ctggtgctgg tggtggtatt cgtcgctttg | 360 |
| ctcctggaca acatgctgtt tactgtggtg gtgccaattg tgcccacctt cctatatgac | 420 |
| atggagttca aagaagtcaa ctcttctctg cacctcggcc atgccggaag ttccccacat | 480 |
| gccctcgcct ctcctgcctt ttccaccatc ttctccttct tcaacaacaa caccgtggct | 540 |
| gttgaagaaa gcgtacctag tggaatagca tggatgaatg acactgccag caccatccca | 600 |
| cctccagcca ctgaagccat ctcagctcat aaaaacaact gcttgcaagg cacaggtttc | 660 |
| ttggaggaag agattacccg ggtcgggggtt ctgtttgctt caaaggctgt gatgcaactt | 720 |
| ctggtcaacc cattcgtggg ccctctcacc aacaggattg gatatcatat ccccatgttt | 780 |
| gctggctttg ttatcatgtt tctctccaca gttatgtttg cttttttctgg gacctatact | 840 |
| ctactctttg tggcccgaac ccttcaaggc attggatctt cattttcatc tgttgcaggt | 900 |
| cttgaatgc tggccagtgt ctacactgat gaccatgaga gaggacgagc catgggaact | 960 |
| gctctggggg gcctggcctt ggggttgctg gtgggagctc cctttggaag tgtaatgtac | 1020 |
| gagtttgttg ggaagtctgc acccttcctc atcctggcct tcctggcact actggatgga | 1080 |
| gcactccagc tttgcatcct acagccttcc aaagtctctc ctgagagtgc caaggggact | 1140 |
| cccctctttta tgcttctcaa agacccttac atcctggtgg ctgcagggtc catctgcttt | 1200 |
| gccaacatgg gggtggccat cctggagccc acactgccca tctggatgat gcagaccatg | 1260 |
| tgctccccca gtggcagct gggtctagct ttcttgcctg ccagtgtgtc ctacctcatt | 1320 |
| ggcaccaacc tctttggtgt gttggccaac aagatgggtc ggtggctgtg ttccctaatc | 1380 |
| gggatgctgg tagtaggtac cagcttgctc tgtgttcctc tggctcacaa tattttttggt | 1440 |
| ctcattggcc ccaatgcagg gcttggcctt gccataggca tggtggattc ttctatgatg | 1500 |

```
cccatcatgg ggcacctggt ggatctacgc cacacctcgg tgtatgggag tgtctacgcc      1560
atcgctgatg tggcttttg catgggcttt gctataggtc catccaccgg tggtgccatt      1620
gtaaaggcca tcggttttcc ctggctcatg tcatcactg gggtcatcaa catcgtctat      1680
gctccactct gctactacct gcggagcccc ccggcaaagg aagagaagct tgctattctg      1740
agtcaggact gccccatgga gacccggatg tatgcaaccc agaagcccac gaaggaattt      1800
cctctggggg aggacagtga tgaggagcct gaccatgagg agtagcagca gaaggtgctc      1860
cttgaattca tgatgcctca gtgaccacct cttcctgg gaccagatca ccatggctga      1920
gcccacggct cagtgggctt cacatacctc tgcctgggaa tcttctttcc tcccctccca      1980
tggacactgt ccctgatact cttctcacct gtgtaacttg tagctcttcc tctatgcctt      2040
ggtgccgcag tggcccatct tttatgggaa gacagagtga tgcaccttcc cgctgctgtg      2100
aggttgatta aacttgagct gtgacgggtt ctgcaagggg tgactcattg catagaggtg      2160
gtagtgagta atgtgcccct gaaccagtg gggtgactga caagcctctt taatctgttg      2220
cctgattttc tctggcatag tcccaacaga tcggaagagt gttaccctct tttcctcaac      2280
gtgttctttc ccgggttttc ccagccgagt tgagaaaatg ttctcagcat tgtcttgctg      2340
ccaaatgcca gcttgaagag ttttgttttg ttttttttca tttattttt ttttaataa      2400 agtgagtgat ttctgtgg ctaaatctag agctgctaaa agggcttac cctcagtgaa      2460 aagtgtcttc tattttcatt atctttcaga aacaggagcc catttctctt ctgctggagt      2520
tattgacatt ctcctgacct ccctgtgtg ttcctacctt ttctgaacct cttagactct      2580
tagaaataaa agtagaagaa agacagaaaa aataactgat tagacccaag atttcatggg      2640
aagaagttaa aagaaactgc cttgaaatcc ctcctgattg tagatttcct aacaggaggg      2700
gtgtaatgtg acattgttca tacttgctaa taaatacatt attgcctaat tcaaaaaaaa      2760
aaaaaaaaa                                                              2770

<210> SEQ ID NO 47
<211> LENGTH: 3885
<212> TYPE: DNA
<213> ORGANISM: Homo sapiens

<400> SEQUENCE: 47
agagccggac gggtaaaact gagcggcggc ggcggggcgc tggggcggag actgcgaccc        60
ggagccgccc ggactgacgg agcccactgc ggtgcgggcg ttggcgcggg cacggaggac       120
ccgggcaggc atcgcaagcg accccgagcg gagccccgga gccatggccc tgagcgagct       180
ggcgctggtc cgctggctgc aggagagccg ccgctcgcgg aagctcatcc tgttcatcgt       240
gttcctggcg ctgctgctgg acaacatgct gctcactgtc gtggtcccca tcatcccaag       300
ttatctgtac agcattaagc atgagaagaa tgctacagaa atccagacgg ccaggccagt       360
gcacactgcc tccatctcag acagcttcca gagcatcttc tcctattatg ataactcgac       420
tatggtcacc gggaatgcta ccagagacct gacacttcat cagaccgcca cacagcacat       480
ggtgaccaac gcgtccgctg ttccttccga ctgtcccagt gaagacaaag acctcctgaa       540
tgaaaacgtg caagttggtc tgttgtttgc ctcgaaagcc accgtccagc tcatcaccaa       600
ccctttcata ggactactga ccaacagaat tggctatcca attcccatat ttgcgggatt       660
ctgcatcatg tttgtctcaa caattatgtt tgccttctcc agcagctatg ccttcctgct       720
gattgccagg tcgctgcagg gcatcggctc gtcctgctcc tctgtggctg ggatgggcat       780
```

```
gcttgccagt gtctacacag atgatgaaga gagaggcaac gtcatgggaa tcgccttggg     840
aggcctggcc atgggggtct tagtgggccc cccttcggg agtgtgctct atgagtttgt      900
ggggaagacg gctccgttcc tggtgctggc cgccctggta ctcttggatg gagctattca    960
gctctttgtg ctccagccgt cccggggtgca gccagagagt cagaagggga cacccctaac   1020
cacgctgctg aaggacccgt acatcctcat tgctgcaggc tccatctgct ttgcaaacat    1080
gggcatcgcc atgctggagc cagccctgcc catctggatg atggagacca tgtgttcccg    1140
aaagtggcag ctgggcgttg ccttcttgcc agctagtatc tcttatctca ttggaaccaa    1200 tattttgg   atacttgcac acaaaatggg gaggtggctt tgtgctcttc tgggaatgat    1260
aattgttgga gtcagcattt tatgtattcc atttgcaaaa acatttatg gactcatagc     1320 tccgaacttt ggagttggtt ttgcaattgg aatggtggat tcgtcaatga tgcctatcat    1380
gggctacctc gtagacctgc ggcacgtgtc cgtctatggg agtgtgtacg ccattgcgga    1440
tgtggcattt tgtatggggt atgctatagg tccttctgct ggtggtgcta ttgcaaaggc    1500
aattggattt ccatggctca tgacaattat tgggataatt gatattcttt ttgcccctct    1560
ctgctttttt cttcgaagtc cacctgccaa agaagaaaaa atggctattc tcatggatca    1620
caactgccct attaaaacaa aaatgtacac tcagaataat atccagtcat atccgatagg    1680
tgaagatgaa gaatctgaaa gtgactgaga tgagatcctc aaaaatcatc aaagtgttta   1740
attgtataaa acagtgtttc cagtgacaca actcatccag aactgtctta gtcataccat    1800
ccatccctgg tgaaagagta aaaccaaagg ttattatttc ctttccatgg ttatggtcga    1860
ttgccaacag ccttataaag aaaaagaagc ttttctaggg gtttgtataa atagtgttga    1920
aactttattt tatgtatttta attttattaa atatcataca atatatttttg atgaaatagg   1980 tattgtgtaa atctataaat atttgaatcc aaaccaaata taattttta acttacatta      2040 acaaacattt gggcaaaaat catattggta atgagtgttt aaaattaaag cacacattat    2100
ctctgagact cttccaacaa agagaaacta gaatgaagtc tgaaaaacag aatcaagtaa    2160
gacagcatgt tatatagtga cactgaatgt tatttaactt gtagttacta tcaatatatt    2220
tatgcgttaa acagctagtt ctctcaagtg tagaggacaa gaacttgtgt cagttatctt    2280
ttgaatccat aaatcttagc tggcattagt tttctatgta atcacctacc tagagagagt    2340
tgtaaattat atgttaacat gttatctggt tggcagcaaa cactaaagcc aataaaggaa    2400
aaacagtaaa tgttccgaaa gcagagaaaa gcaaccaaac atattgttat gaactaaaag    2460
ctttcccttt aagatgcata cttgtcttac tggatgaaga aaattgaggg tacatgtacc    2520
ttatactgtc aaggttgttt aaacatgata aggttaatcg ccatctactt caagttttag    2580
aaaaggaaac aagaagctga aaacagctgc tctgacttta atatctgact atatctttga    2640
tctgtttgca ggtcatccaa gtgttttcta ggaatatatt tatttaggt tgtctgaaac     2700 tactattttt tagactcctg aaagttgttc acatcaatgt gaagacaaat tttaatgaa    2760 aatgaagaat gaaattatgt cttgaatcat atattaagaa gtaaaaataa tagtgatcag    2820
gcagaaaaga aaaatggaac atctaaaaat gtatgtgcta actatatcat ccagtgtgca    2880
gtgttgtgta ttttttctaag catgacaaca ttgatgtgcc ttttcagtgt aacagcaaat   2940
actgttagtg aacattgtca atttatgtca ttttgttaag agatatgact ggagtgtgca    3000
gtgtggaatg tctctaatac tacttgtgaa tcctgcagtt ctataatcat aaacaaaaat    3060
tactagtttt cgttaagcta agattgtgtt tgtgttaact tcgacatcaa ggagcaaaga    3120
actttagaac agactcctca atcttgtgac tttcttattc tctaggaaag taacacttcg    3180
```

| | |
|---|---|
| tttcatgaag cttttctgtg gggcttcgat tatttcaagt ctggtttcta agtgcagtgt | 3240 |
| gtttgaagca aacgaacttc caactcactt atttggcatt gggcaacttg ccaagtctg | 3300 |
| ccactttgga agatggctct ggaggaaact ctcatatggc taaaaaggca ggctagtttc | 3360 |
| ttacttctac aggggtagag ccttaaaaaa gaacgtgcta caaattggtt ctctttgagg | 3420 |
| gtttctggtt ctccctgccc ccaataccat atactttatt gcaattttat ttttgccttt | 3480 |
| acggctctgt gtctttctgc aagaaggcct ggcaaaggta tgcctgctgt tggtccctcg | 3540 |
| ggataagata aaatataaat aaaaccttca gaactgtttt ggagcaaaag atagcttgta | 3600 |
| cttgggaaa aaaattctaa gttctttat atgactaata ttcttggtta gcaagactgg | 3660 |
| aaagaggtgt ttttttaaaa tgtacatacc agaacaaaga acatacagct ctctgaacat | 3720 |
| ttatttttg aacagaggtg gttttatgt ttggacctgg taatacagat acaaaaactt | 3780 |
| taatgaggta gcaatgaata ttcaactgtt tgactgctaa gtgtatctgt ccatatttta | 3840 |
| gcaagtttac ttaataaatc ttctgaacca tgaaaaaaaa aaaaa | 3885 |

<210> SEQ ID NO 48
<211> LENGTH: 14607
<212> TYPE: DNA
<213> ORGANISM: Homo sapiens

<400> SEQUENCE: 48

| | |
|---|---|
| ccggaggggc tgtcatttgc agcgctggtc gcagccctca gctgcgccgg gcggttccgg | 60 |
| ctcctccctc tccttgtgcc tcagcgccac catggtgctg gagtcggtgg tcgcggactt | 120 |
| gctgaaccgc ttcctggggg actatgtgga gaacctgaac aagtcccagc tgaagctggg | 180 |
| catctggggc ggaaatgtgg ctttagataa tctacagata aaagaaaatg ccctgagtga | 240 |
| attggatgtt ccttttaaag tcaaggctgg ccaaattgat aaattaactt tgaagattcc | 300 |
| ttggaagaac ctttatggag aagcagttgt tgcgaccctg aaggattat acctgcttgt | 360 |
| tgtccctgga gcaagtatta agtatgatgc tgtaaaagaa gaaaaatcct tgcaggatgt | 420 |
| taaacagaaa gagctatccc gaattgaaga agcccttcaa aaagcagcag aaaaaggcac | 480 |
| acattcaggg gagttcatat atggcttgga gaactttgtt tacaaggaca tcaagcctgg | 540 |
| acgtaaacgt aaaaagcaca aaaaacattt taagaaacct tttaaaggtc ttgatcgttc | 600 |
| aaaagataag ccaaaagaag ccaaaaagga tacatttgtg gaaaaattgg caactcaagt | 660 |
| aataaaaaat gtacaagtaa aaatcacaga tattcacatt aaatatgaag atgatgtcac | 720 |
| tgatccaaag cggcctcttt catttggtgt cacactggga gagcttagtc tactgactgc | 780 |
| aaatgaacac tggactccat gcatattaaa tgaagcagac aaaattatat acaagcttat | 840 |
| acgacttgat agtcttagcg cctactggaa tgtaaattgc agcatgtctt accagagatc | 900 |
| aagggaacag attttggatc agctgaaaaa tgaaattctt acaagtggaa atatacccc | 960 |
| aaattatcaa tacattttcc agccaatatc agcctctgca aaactctaca tgaatccta | 1020 |
| tgcagaatca gagctcaaaa cgcccaaact ggattgcaac atagaaatac aaaatattgc | 1080 |
| cattgaactg accaaacctc agtacttaag tatgattgac cttttggagt cagtggatta | 1140 |
| tatggttagg aatgcgcctt ataggaaata caagccttat ttaccacttc ataccaatgg | 1200 |
| tcgacgatgg tggaaatatg caattgattc tgttcttgaa gttcatataa gaaggtatac | 1260 |
| acagatgtgg tcatggagta acataaaaaa gcacaggcag ttactcaaga gttataaaat | 1320 |
| tgcctacaaa aacaagttaa cacagtctaa agtctcagaa gaaatacaga agaaattca | 1380 |

```
ggacttggag aagactctag atgttttta  cataatttta gcaaggcaac aagcacaagt  1440
tgaggtgatt cggtctgggc aaaaattaag gaaaaagtct gctgacacag gcgagaaacg  1500
tggaggctgg tttagtgggt tgtggggtaa gaaagagtct aagaaaaagg acgaagaatc  1560
attgattcct gaaactattg atgaccttat gactccagag gaaaaagata aactcttcac  1620
tgccattggt tatagtgaga gtacccacaa cctaacttta cctaagcagt atgttgccca  1680
tattatgacc ctgaagttag taagcacctc tgttacgata agagaaaaca agaatattcc  1740
agaaatacta aaaattcaga taattggcct gggcactcaa gtatctcagc gaccaggagc  1800
acaagcactt aaggtagaag cgaaattaga acactggtat ataacaggtt tgagacagca  1860
ggatattgtg ccatcacttg tggcttcaat tggtgacact acatcatcct tgcttaaaat  1920
taaatttgaa accaatccgg aggatagtcc tgctgaccag actctgattg ttcagtccca  1980
gcctgtggag gtcatctatg atgctaaaac tgtcaatgca gtggttgaat tctttcaatc  2040
aaataaggga ttggatcttg agcaaataac atcagcaaca ttgatgaagc tggaagaaat  2100
taaggagaga acagctacag gacttacaca tattattgaa actcgaaaag tccttgattt  2160
aaggataaat ctgaagcctt cttatctagt agttccacag acgggtttcc accatgaaaa  2220
gtcagatctt ctgattttag attttggtac atttcagctc aacagtaaag atcaaggttt  2280
acagaagact actaattcat ctctggaaga aataatggat aaggcatatg acaagtttga  2340
tgttgaaata aaaaatgtac aactactttt tgcaagagca gaggaaacct ggaaaaagtg  2400
tcgatttcag catccatcaa ctatgcatat attgcaaccc atggatattc atgttgagtt  2460
ggctaaggcc atggtagaaa aagacattag aatggccaga tttaaagtgt caggaggact  2520
tcctttgatg catgtgagaa tttctgacca gaagatgaaa gatgtgctat atttgatgaa  2580
cagtatacct ttgccacaga aatcatcagc ccagtctcca gagagacagg tatcctcaat  2640
tcctattatt tcaggtggta caaaaggtct acttggtact tcactattgc tagacactgt  2700
ggaatcagag tctgatgatg agtattttga tgctgaagat ggagaaccac agacttgtaa  2760
aagtatgaaa ggatcagaac ttaaaaaagc tgcagaggtc ccaaatgagg agctcatcaa  2820
tcttctactc aagtttgaaa ttaaagaagt gattttggaa tttactaaac agcagaaaga  2880
agaagataca attctagtat ttaatgttac tcagttagga acagaggcca caatgagaac  2940
atttgactta actgtggtat cttatttaaa gaaaatcagc ttggattatc atgaaattga  3000
aggatccaaa aggaagcccc ttcacttgat tagctcttct gacaaacctg gattagatct  3060
tttgaaagtg gagtatatta aggctgataa gaatggacct agttttcaaa ctgcttttgg  3120
aaaaactgaa caaacagtta aggtggcctt ttcatcttta aatctgttgc tgcaaacaca  3180
agctcttgtc gcttctatta attacctcac aaccattatt ccatctgatg atcaaagcat  3240
aagtgttgct aaggaggtac aaatttcaac tgaaaaacaa caaaaaaatt caactctgcc  3300
aaaagcgatt gtatcctcca gagatagtga cattattgat ttcaggctat ttgccaagtt  3360
gaatgctttc tgtgtcattg tttgcaacga aaagaacaat atcgccgaaa tcaagattca  3420
aggactggat tcctcccttt ctctccagtc aagaaagcag tcacttttg cccgactaga  3480
aaatattatt gtcacagatg ttgatccaaa gacagttcat aagaaagctg tgtcaataat  3540
gggaaatgaa gttttccgtt ttaatttgga tttgtatcca gatgctactg aggggattt  3600
gtatactgac atgtccaaag tggatggtgt gctgtctctg aatgttggct gtattcagat  3660
tgtctatctt cataaaattcc ttatgtcact tctgaacttc ctgaataatt tccagacagc  3720
caaagagtct ctgagtgctg ccactgccca ggctgcagaa agggctgcca caagtgtgaa  3780
```

```
agatcttgcc cagaggagtt ttcgtgtttc catcaatatt gatttgaaag caccggttat    3840
agtcatccca cagtcttcta tttccaccaa tgcagtagtg gtagatcttg ggttaatcag    3900
agttcataat cagttcagtc tggtgtctga tgaagactac ttaaatcctc cagtaattga    3960
tagaatggat gtgcagctaa caaagcttac actttatagg acagtgatcc agccaggcat    4020
ctaccatcct gatattcagc tgttgcaccc aattaacttg gaatttcttg taaatcggaa    4080
tctagctgca tcttggtacc acaaggtgcc tgttgtggaa attaaaggac atcttgattc    4140
aatgaatgtt agtctaaatc aagaagatct taatctttta tttaggatac taacagaaaa    4200
tctctgtgag ggtactgaag acttggataa agtgaaacca agagtacaag agacaggtga    4260
aattaaagag ccccttgaaa tctctatatc acaagatgta catgattcaa aaaatacttt    4320
aacaactgga gtggaagaaa ttaggtctgt agacatcatt aatatgctgc tgaattttga    4380
aattaaagag gttgtggtta ctttgatgaa aaaatcagaa aagaaaggaa ggcctttaca    4440
tgagctaaat gtcctgcaac ttggaatgga agctaaagtt aaaacctatg acatgactgc    4500
taaagcttat ctaaaaaaaa ttagtatgca gtgctttgat ttcactgact ctaaagggga    4560
acctcttcac attattaact cttctaatgt gactgacgaa ccccttctga aaatgttact    4620
gacaaaggca gacagtgatg gaccagaatt taaaactatt catgacagta ccaaacagag    4680
actgaaggtt tcatttgcat ccttagactt agtacttcat ttggaagctt tactttcctt    4740
catggatttt ttatcatctg ctgctccatt ctctgagcct tcctcttctg agaaggaatc    4800
cgagctgaaa ccacttgtgg gggagtccag aagtatcgct gtcaaagctg tatccagcaa    4860
catttcccaa aaggatgtgt tgatttaaaa gatcacagct gaattaaatg catttaatgt    4920
cttttgtctgt gatcagaagt gtaacattgc agatattaaa atacatggaa tggatgcctc    4980
tatttctgtg aagcctaagc agactgatgt gtttgccaga cttaaagata ttatagttat    5040
gaatgtagat ttgcagtcca ttcacaaaaa ggctgtctct atttttggga tgaagtcctt    5100
taggttccaa ctgactcttt atccagatgc cacagaagga gaggcctatg ctgatatgtc    5160
caaagtagac ggcaaactta gttttaaagt gggttgtatt cagattgttt atgttcataa    5220
attcttcatg tctcttttga acttcctcaa caatttccaa actgctaaag aagctttgag    5280
tacagccaca gtccaggctg cagaaagagc tgcttccagc atgaaagact ggctcaaaa    5340
gagtttccgc cttttgatgg atattaattt gaaagcacca gttattatta ttcctcagtc    5400
ttcagtatca cctaatgctg ttatagcaga tctgggttta atcagagttg aaaacaagtt    5460
tagcttggtt cctatggaac attattctct tcctccagtc attgataaaa tgaacatcga    5520
actcactcag ttgaagctgt caagaactat tttgcaggct agcttgccac aaaatgacat    5580
tgaaatttta aaaccagtca acatgctttt gtccatacag cgaaacttag cagcagcatg    5640
gtatgtgcaa attccaggga tggagataaa aggaaaacta aaacctatgc aggttgctct    5700
cagtgaagat gacttgacag ttttaatgaa aattttgcta gaaaatcttg gagaagcttc    5760
ctcacaacca agccctacac agtctgtgca ggagactgta agagtgagaa agttgatgt    5820
ttcaagtgta cctgaccatc tcaaagaaca agaagattgg acagactcaa agctctctat    5880
gaaccagatt gtcagtctcc aatttgactt tcactttgaa tctcttttcca ttatccttta    5940
taacaatgat atcaaccagg aatctggagt tgcatttcat aatgacagtt ccaacttgg    6000
tgaactcaga ctcatctta tggcctcctc agggaagatg tttaaggatg gctcaatgaa    6060
tgtcagcgtt aaacttaaga catgcaccct tgatgatctc agagaaggaa ttgagagagc    6120
```

```
aacatcgaga atgattgaca gaaagaatga ccaagataac aacagttcta tgattgatat     6180
aagttacaaa caagacaaaa atggaagtca aattgatgct gttcttgaca agctgtatgt     6240
atgtgccagt gtggaatttc tgatgactgt ggcagatttc tttatcaaag ctgtgcctca     6300
gagtccagaa aatgtggcaa aagaaacaca gattttacca agacagactg ccacagggaa     6360
ggtcaagata gagaaagatg actctgttag accaaatatg actttaaagg ccatgatcac     6420
agatccagaa gtggtatttg ttgccagcct gacaaaggct gatgctcctg ctctgacagc     6480
ctcgtttcag tgcaaccttt ctctgtcaac atccaaactc gaacagatga tggaagcttc     6540
tgtgagagat ctgaaagtgc tcgcttgccc ttttctcaga gaaagagag ggaaaaacat     6600 taccacagtc ttgcagccct gttctttatt tatggaaaaa tgtacgtggg cttcaggaaa     6660
gcaaaatata atatattatgg ttaaagaatt tataattaag atttcaccca taattcttaa     6720
tactgtgttg acaatcatgg ctgcattgtc tccaaaaaca aaagaagatg gatccaaaga     6780
tacgtctaag gaaatggaaa atctttgggg tatcaaatcg attaatgatt ataacacttg     6840
gtttcttggt gttgacacgg caacagaaat aacgaaagc ttcaaaggca ttgaacattc     6900
actgatagag gaaaattgtg gtgttgttgt agaatccatt caagttacct tagaatgtgg     6960
ccttggacat cgaactgtac ctttattatt ggcagagtct aagttttcag gaaatattaa     7020
aaattggact tctctaatgg ctgctgttgc tgacgtgaca ctacaggtgc actattacaa     7080
tgagatccat gctgtctggg agccactgat tgagagagtg gaggggaaga acaatggaa     7140 tttaaggctt gatgtaaaga agaacccagt tcaggataaa agtttgctgc caggagatga     7200
ttttattcct gagccacaaa tggcaattca tatttcttca ggaaatacaa tgaatataac     7260
aatatccaaa agttgtctta atgttttcaa caatttagca aaaggttttt cagagggcac     7320
tgcttctact tttgactact cttaaagga cagagctcct tttacggtaa aaaatgctgt     7380
aggtgttccc attaaggtga agcccaattg taatctcaga gtaatgggct ccctgagaa     7440 aagtgatatt tttgatgttg atgctggcca gaatttggaa ctggagtatg ccagcatggt     7500
accttcaagt caagggaacc tatctatatt gagccgtcaa gaaagctcct tcttcactct     7560
gaccattgta cctcatggat atacagaagt tgcaaatatc cctgtggcca gacctggacg     7620
gcgattgtat aatgtacgga atcccaatgc cagtcattct gactctgtct tggtacaaat     7680
tgatgcaact gaagggaata aagtaattac ccttcgctct cctctacaga tcaaaaacca     7740
tttctccatt gcatttatca tctataaatt tgttaagaat gttaagctat ggagcgcat     7800 tgggatagcc agacctgaag aggagttcca tgttcctta gattcatata gatgtcaatt     7860
gtttatccag ccagctggaa tcttagagca tcagtacaaa gaatctacca cttatatttc     7920
ctggaaggaa gaacttcata ggagcaggga agtcagatgc atgttgcagt gtccatcagt     7980
agaagtcagc ttcttacctc tcatagtgaa tacagttgct ctgcctgatg aattgagcta     8040
catatgtaca catggggaag actgggatgt agcttacatt attcatcttt atccttctct     8100
cactttgcgg aatcttctcc catattccct aagatattta cttgagggaa cagcagaaac     8160
tcatgagctg gcagaaggca gtactgctga tgttctgcat tcgagaatca gtggtgaaat     8220
aatgaaatta gtcctggtga ataccaggg caaaaactgg aatggacatt ccgcatacg     8280 tgatacacta ccagaattct ttcctgtgtg ttttttcttct gactccacag aagtgacgac     8340
agtcgacctg tcagtccacg tcaggagaat tggcagccgg atggtgctgt ctgtctttag     8400
tccctattgg ttaatcaaca agactacccg ggttctccag tatcgttcag aagatattca     8460
tgtgaaacat ccagctgatt tcagggatat tatttttattt tctttcaaga agaagaacat     8520
```

```
ttttactaaa aataaggtac aattaaaaat ttcaaccagt gcctggtcca gtagtttctc    8580
attggataca gtgggaagtt atgggtgtgt gaagtgtcct gccaacaata tggagtacct    8640
ggttggtgtt agcatcaaaa tgagcagttt caacctttca cgaatagtta ccctgactcc    8700
cttttgtacc attgcaaaca agtcatcatt agaactagaa gttggcgaga ttgcatctga    8760
tggctcaatg ccaactaata aatggaacta tattgcttct tcagagtgcc ttccattttg    8820
gccagaaagt ttgtcaggca aactttgtgt gagagtggtg ggctgtgaag gatcttccaa    8880
accattcttt tataaccgac aggataatgg cactttattg agcttagaag atctgaatgg    8940
gggtatcttg gtggatgtaa acactgccga acattcaact gtcataactt tttctgatta    9000
ccatgaggga tctgcacctg ccttgataat gaaccataca ccatgggaca tcctcacata    9060
caaacagagt gggtcaccag aagaaatggt cttgctgcca agacaggctc gacttttttgc    9120 ctgggcagat cctactggta ccagaaaact tacatggaca tatgcagcaa atgttgggga    9180
acatgatctg ttaaaggatg gatgtggaca gtttccatat gatgcaaaca tccagataca    9240
ctgggtatca tttctggatg ggcgccagag agttttgctt ttcaccgatg atgttgcctt    9300
ggtttccaaa gcactgcagg cagaagaaat ggaacaggct gattatgaaa taaccttgtc    9360
tctccacagt cttgggcttt cactggttaa caatgaaagc aagcaggaag tttcctatat    9420
tgggataacc agttctggtg ttgtttggga ggtgaaacca aagcagaaat ggaagccatt    9480
tagtcaaaag cagataatct tattggaaca atcctatcag aaacatcaaa tatcaagaga    9540
ccatggctgg attaagctag ataataattt tgaggtcaat tttgataaag atccaatgga    9600
aatgcgcctc cctattcgta gccctattaa acgagacttt ttatcaggaa ttcagattga    9660
atttaagcag tcttctcacc agagaagttt aagggccagg ttgtactggc ttcaggttga    9720
taatcagtta ccaggtgcaa tgttccctgt tgtatttcat cctgttgccc ctccaaaatc    9780
tattgcttta gattcagagc ccaagccttt cattgatgtg agtgtcatca caagatttaa    9840
tgagtacagt aaagtcttac agttcaagta ttttatggtc ctcattcagg aaatggcctt    9900
aaaaattgat caagggtttc taggagctat tattgcactg tttacccccaa caacagaccc    9960 tgaagctgaa agaagacgga caaagttaat ccaacaagat attgatgctc taaatgcaga   10020
attaatggag acttcaatga ctgatatgtc aattcttagt ttctttgaac atttccatat   10080
ttctcctgtg aagttgcatt tgagtttgtc tttgggttcc ggaggtgaag aatcagacaa   10140
agaaaaacag gaaatgtttg cagttcattc tgtcaacttg ctgttgaaaa gcataggtgc   10200
tactctgact gatgtggatg acctatatt caaacttgct tattatgaaa ttcgatatca   10260
gttctacaag agagatcagc ttatatggag tgttgttagg cattacagtg aacagttctt   10320
gaaacagatg tatgtcctg tattgggggtt agatgtactt ggaaaccat ttggattaat   10380 tagaggtctg tctgaaggag ttgaagcttt attctatgaa cccttccagg gtgctgttca   10440
aggccctgaa gaatttgcag aggggttagt gattggagtg agaagcctct ttggacacac   10500
agtaggtggt gcagcaggag ttgtatctcg aatcaccggt tctgttggga aaggtttggc   10560
agcaattaca atggacaagg aatatcagca aaaagaaga gaaagttga gtcgacagcc   10620 cagagatttt ggagacagcc tggccagagg aggaaagggc tttctgcgag gagttgttgg   10680
tggagtgact ggaataataa caaaacctgt ggaaggtgcc aaaaaggaag gagctgctgg   10740
attcttaaaa ggaattggaa aagggcttgt gggtgctgtg gcccgtccaa ctggtggaat   10800
cgtagatatg gccagtagta ccttccaagg cattcagagg gcagcagaat caactgagga   10860
```

```
agtatctagc ctccgtcccc ctcgcctgat ccatgaagat ggcatcattc gtccttatga   10920
cagacaggaa tctgagggct ctgacttact tgagcaagaa ctggaaatac aggaataaat   10980
gtttcctaaa ctactacttg atttcatcct taaaaatcaa aacaaactgt ggtgttaatt   11040
gactgtgtgt gaattccatt gtcaatttta atgaaatttt ctttaaaact ctcacctcca   11100
tctgaacttt tcatagtagt gggattgact acaaataaaa acttgtggta ttcctggtaa   11160
tactgtccag aaataagaga ttagtataaa atattaaagg atgcagagaa tcagctctct   11220
tctgcgttta atagatgaaa gcctttattg agctcagaag cagatactgt tactatcatt   11280
tcgaaaattt tatcttatgg tgttcatgtg catttcaggt aaaattgaaa acaggacaa   11340 ttattatgtc caattaatat gtttatgttt gtgagtcttg atgatggaat tacatagctt   11400
tctgtttcac aaatggctct aaatttgctt aagttacggg actattaccc ggagcatctg   11460
ctttaataat tgaattgtca gttgctctga gcctgccctt agacctcaag taataaatag   11520
ttggcacatg aattttgagg atatgtttcc tcttccctct ttttcctatt taacccctgg   11580
gtactgttgc taaataaatg atagccattt tataattatg ttatatacat tttcagcctt   11640
tagcatttct gcttttcaaa aattgaatct ccttgttggt tatgcttatt tcataattat   11700
tagttttaat taatgtagat agaagttgaa catgtaatta ggcaaattgc tgtgtggcac   11760
ttgaatacat agatttcttt attttcaaaa accaaccttt tgcttttaaa tccttagaga   11820
gggtttatta tcttagagaa aaaataatta taatcattat ttttgaaatt agtatcctct   11880
taattctcaa cataagttat gtttcaattt ctttttttg taataaatga tggaaatgtt   11940
taacaatgtc ttatctagca actttcatgc ttctcctcag aaatgaagcc aaagtataaa   12000
cttagattta atgtgttgta tatttgaaga gaatgaaact attaacatat aattgttcag   12060
ttggattatg tattttaagg attgcagtta tcaaaataat aaattgaatg ttttatgttt   12120 aaccactta agaagaaag actgacatcc aaaaaccagc gtgtgctaga tatacaaagg   12180
aaattacttc tgtccttaag ggaccaagta taacaaaaca tgtaactgtt aaaagtagct   12240
gacaaacctt tcttgtgcct agataaattta gcattggcaa aaatgtcacc acatgcagtt   12300
ttctaggaga gtcaagcaca ataactaat tcaagatgct gacttaaatc atctccaata   12360
gttacccttc ctgagattct aaagtaacaa ttttaatt tactggtat attgctgttt   12420 tactgagact tactttaag aaccctgta acttaagatt ttttcttaat tgttttgttt   12480
agctctgtta ttaatttttt ccttgtgata tctttttata actctctgtc aaaaagcaca   12540
aaacttcaag aaactttaa ttatttgtc tgaacatata atcttgtctg atttcttagt   12600
ttttattaag atatcagaca acttttaaaa ctttagtgca ttattataat tactggaaga   12660 aaagaatga ttatacacta atgagaggac ttggtagttt ttgtcgtgga tgtcaagtgt   12720
gggcatggat aattgaaata tttaggctat ttcattcttt gcccatcttg ctgtgatcag   12780
ttagttgggt aaaaatattt attgattatt tagactgtac tggatataca aaagaagcct   12840
tctgtcctta agggaccgag taaaacaaaa catggaaata ttaaagagta ttagagtata   12900 aagtatatc tttttagccc tttgtaatat ggccaaattc taaataattt atttggggat   12960
cttttgatcc tcatgttcct ttttctccta agtactactt tgtattcttt aatatgcagc   13020
tttgagagtt actgaatcat atattatatt tccatgagat gtactattct acttatcctc   13080
taatcttcat atatatatac acacacacat atatatacac atacatatat acacacgtac   13140
atatatgtac acatacagat atacatacac acaaacacat atatacacac atacatatac   13200
acacatatat atacacatac aaatatacac atatatacac atacatatat atacacacat   13260
```

```
acaaatatac ccatatgtac acatacatat atacacatac atatatacac acacatatac    13320
acacatatat acgcaaacat acacatattt acacatacat atatacatac attatatgta    13380
tgtatatata gtcatttaat actcattttg gttcacatac ttatgatcat gcaacgttta    13440
aaacagcatt tcttgctttt tagttttagt tatattttc catgttctta gaaatgcctc     13500
attaacattt ttaattcttg tattgccatc tattgaggtg acattacatt gtgttttat    13560 ctcgtcttaa ttcatgacat taaattattc tactaacagt aataatgctg taataaacat    13620
cattatagat tttgcttttt tatatcttgt ttgcttttc atatttcctt agaatttact    13680
tgaaaaaatt gaattactgg gtaaagggct tttgcaaagt attgttaaat tcctcgagtt    13740 gcattttgg aaaggggacg tgaatatttt atcaactaat ttggtctccc tgctgccatt    13800
agtgactgaa tatcttaatc tgaatctcag agtgtagtgg gttttagta gtgctgaaga    13860 caagttttct aaagtgtatt atggtgataa attatatttt aaaaactgtc aatggcttga    13920
agcacaatag cctaataact aacgaaaata catacaagat agaaagtggg tagtatttct    13980
tgtacttgca tttcagatct aaatatttta acatatttaa atttcaagct gcagataaat    14040
gcattacatt attaaattca tttcccattt tctctttgaa gaaattaagg caaaagtgtt    14100
aaaagatttt aactaattcg cacaagtgaa ttgtgaaaca agtagctatt gctgtgaaat    14160
ctgcactcct ctctgagact cattctgaag atgagatccc agttctttgt ggattcctct    14220
tccttattca tggcttttg caattgtcaa ggaatgacta ggtaccaagc aactttaaaa    14280
aatgtatatt taagcattga aataatatca aatgtgatt ctctgcttgt ggttatattg    14340
attatattat ccttttaata atattggcat tatattcttg gtcgtaaaat gtcaaggtct    14400
tatttattca gtatatttat gttctgtatt ttcatatata ttatctattt tcagccatgc    14460
attatatata atgtcagtaa tagtatttca ttagcattca ttataaaaaa actcgttttt    14520
aatatttgac taattcaagt cacagtactt ttgagatagc tgaaaaggaa aataaatgtg    14580
ttttaatgtg ctactaaaaa aaaaaaa                                        14607
```

<210> SEQ ID NO 49
<211> LENGTH: 14329
<212> TYPE: DNA
<213> ORGANISM: Homo sapiens

<400> SEQUENCE: 49

```
gcggccgcag aatcgagctc gggccccggc ccccggcccg cggcgcgggg ctcccgggcc      60
ccgccgcgga cgtcgcgccg gtcgccccctt ccccgtagcc cgtgcgccct cggcgcggag    120
ccccggcccg ccgcggtccc gtctcctggg cctgtcccgc ccgcgccctc gccggccct     180 caggtataat acttctccac gtctgcttca ggaagaaagt gcctgccatt cttatcattt    240
ctaagcaggt tcatgccagc ccagaacaga gaatcagctg gagcccagat ttcaagtttt    300
gagtaaaata ccttcaagcg aatgggccct attgtgctca cacattcaga acctgttacc    360
caaggaattc cctaaagaat tagaagtgcg tctcaccaac cagccaagat gaacatggtg    420
aagaggatca tggggcggcc gaggcaggag gagtgcagcc cacaagacaa cgccttagga    480
ctgatgcacc tccgccggct cttcacggag ttgtgccatc ctccccggca catgactcag    540
aaggaacaag aagagaaact gtatatgatg ctgccagtgt ttaacagggt ttttggaaat    600
gctccgccga atacaatgac agaaaaattt tctgatcttc tgcagttcac aacacaagtc    660
tcacgactaa tggtgacaga aattcgaagg agagcatcaa acaaatccac agaggctgca    720
```

```
agtcgggcca tagttcagtt cctagagatt aatcagagtg aagaagccag tagaggctgg    780
atgcttctaa cgacaattaa tttgttagct tcctctggtc agaaaaccgt ggactgcatg    840
acaacaatgt cagtgccttc caccctggtt aaatgtttat atctgttttt tgaccttcca    900
catgtgcctg aggcagttgg aggtgcacag aatgagctac ctctagcaga acgtcgagga    960
ctactccaga aagttttgt acagatctta gtgaaactgt gcagttttgt ttccctgcg    1020
gaggagctgg ctcagaaaga tgatctccag cttctattca gtgcaataac ctcttggtgc   1080
cctccctata acctgccttg agaaagagt gctggagaag tcctcatgac catatctcgt    1140
catggtctta gtgtcaatgt agtgaagtat attcatgaga aagagtgttt atctacatgt   1200
gttcagaata tgcagcaatc agatgacctg tctcccctag aaattgtcga aatgtttgct   1260
gggcttctt gtttcctcaa agattccagc gatgtttccc aaacacttct ggatgattt    1320
cggatatggc aaggatataa ttttctttgt gatctcttgc ttagattgga caagcaaaa    1380
gaggcagaat ccaaagatgc cttgaaagat ctggttaatc tgataacttc cctaacaaca   1440
tatggtgtca gtgaactaaa accagctggt attaccacag gggcacccttt ttattgcct   1500
ggatttgcag tacctcagcc tgcaggcaaa ggtcacagtg tgagaaacgt ccaggccttt   1560
gcagttcttc agaatgcatt tttaaaagca aaaaccagct tccttgccca aatcatcctt   1620
gatgctatca aaatattta catggctgac aatgccaatt acttcatcct agagtcacag    1680
cacacattgt cacagtttgc agagaagatt tctaaactcc cagaagtaca aaacaaatac   1740
tttgagatgc tggagtttgt tgttttagc ttaaattata taccttgtaa agaacttatt   1800
agtgtcagta tcctcttaaa atctagctct tcttatcact gtagcattat tgcaatgaaa   1860
acacttctta gtttacaag acatgactac atatttaaag acgtgttcag ggaggttggc    1920
cttttggagg tcatggtaaa ccttttgcat aaatatgctg ccctgttgaa ggatccaact   1980
caggcactaa atgaacaagg ggactcaaga aataatagtt cagttgaaga ccaaaaacac   2040
ctggctttat tggttatgga gaccttgaca gtgcttcttc aaggatcaaa cacaaatgca   2100
ggaattttc gagaatttgg aggtgcaaga tgtgcacata atatagtaaa gtaccctcaa   2160
tgccggcagc atgccttgat gactatccaa cagctggtgc tctccccaaa tggggacgat   2220
gacatgggca ctctcctggg gctaatgcat tcagccccac cgacggaatt gcagttgaag   2280
actgatatt taagggccct cctgtcggtc cttcgagaaa gccatcgttc aagaacagtt   2340
tttaggaaag ttggaggatt tgtgtacatt acatccttgc tcgttgctat ggaaagatct   2400
ttgagctgtc cacccaagaa tggctgggag aaagtgaacc agaatcaagt gtttgaactt   2460
cttcacactg tgttctgcac gttgactgca gcaatgcgct atgagccagc caactctcat   2520
ttcttcaaaa cagagattca gtatgagaag ttggcagatg ctgttcgatt tcttggctgc   2580
ttctcagacc taagaaaat aagcgccatg aatgtcttcc cctcaaatac acagccattt   2640
caaagacttt tagaggaaga tgtaatctca atagaatcag tgtcacccac gttacggcac   2700
tgcagtaaac ttttattta tctttacaaa gtagccacag attcttttga cagtcgtgca   2760
gaacagatcc ctccttgcct gacaagtgag tcttctctcc cctctccttg gggtacacca   2820
gctttgtcca ggaaaggca tgcatatcat tctgtttcaa ctcccctgt ttaccctcct    2880
aaaaatgttg ccgacctgaa actacatgtg acaacttcat ctctgcagag ttctgatgca   2940
gtcatcattc atcctggagc catgcttgcc atgctggacc tactggcctc tgttgggtca   3000
gtgacacagc cagaacatgc tttggatctt caacttgccg tggcaaatat tttacaatcc   3060
ctggtgcaca cagaaaggaa ccagcaagtc atgtgtgaag ctggtcttca tgcacgactg   3120
```

```
ctgcagaggt gcagtgctgc attggctgat gaggaccact cactgcaccc gccctgcag    3180 cggatgtttg aacgattagc ctctcaggct ctggaaccca tggtgttgag ggagttttta    3240
cgtttggcaa gtcctttaaa ttgtggtgcc tgggacaaaa aactgctaaa acaatatagg    3300
gtccacaaac caagttcact gagttatgaa ccagaaatga aagtagtat gatcacatct    3360 ctggaaggtc tgggtactga taatgttttt agcttacatg aagataacca ttaccggata    3420
agcaagagcc tggtaaaatc tgcggaagga agtactgtac ccctgaccag ggtgaagtgt    3480
ctggtctcca tgacaacccc acatgacatc agacttcatg ggtcatcagt tactccagct    3540
tttgttgaat tgacacatc acttgaaggg tttggatgtc ttttttttgcc cagtttggcc    3600 cctcataatg ctcctacaaa taataccgtc acaacaggtc ttattgatgg ggctgtggtc    3660
agtggcattg ttctggtga aagattcttc cctcctccct ccggcttaag ttactctagc    3720
tggttttgta ttgaacattt tagttctcct ccaaataacc accctgtcag acttcttact    3780
gttgtgcgcc gagcaaattc ttctgagcaa cattacgtgt gccttgcaat agttctatca    3840
gcaaaagacc gatctctgat tgtttccacc aaagaggaac tcctccaaaa ttatgttgat    3900 gatttagtg aagagtcctc attttatgaa attctcccat gctgtgctcg ctttcgatgt    3960
ggagagctta tcattgaggg acagtggcat catttggtcc tggtaatgag caaaggcatg    4020
ttgaaaaaca gtactgcagc cctttatatt gatggacagc ttgttaacac tgtaaagctt    4080
cattatgtcc acagtactcc aggggggttca ggttcggcaa atccaccagt ggtgagcacg    4140
gtctatgcct acattggtac tccacctgcc aacgccaaa ttgcctcatt ggttttggcgc    4200 ctgggaccca cacattttct agaagaagtt ttaccttctt caaatgttac taccatttat    4260
gaacttggac caaattatgt tggaagcttt caggctgtat gtatgccatg taaagatgca    4320
aaatccgaag gggtggtgcc atccctgtg tcattagtac cagaggagaa agtgtcattt    4380
ggcctctatg cactctctgt gtcgtctcta acagtggcaa gaatccggaa agtgtataac    4440
aaattggata gcaaagccat tgctaagcag ttaggcattt cctcacatga aatgccact    4500 cctgtgaagt tgatacacaa ttcagcagga catcttaatg gatctgcacg gacaattggg    4560
gccgctctga ttggatactt gggagtaaga acatttgtcc ctaagcctgt tgccactact    4620
ttgcagtacg ttggtggagc tgcagccatc ctgggcctgg tggccatggc ctctgatgtg    4680
gaagggttat atgcagcagt caaggccctg gtttgtgtgg tcaagagtaa cccactagcc    4740
agcaaagaaa tggaaagaat caagggctac cagttgctgg caatgttgct taagaagaaa    4800
cgttcccttc ttaacagcca catcctccat ctaacttttt ctttggtggg aactgttgat    4860
agtggacatg agacctccat tattccaaat tcaactgctt tccaggacct cctctgtgat    4920
tttgaagtct ggctccatgc accatatgaa cttcatcttt ccttatttga acactttatt    4980
gaactgctca cagagtccag tgaagcctca aagaatgcca aattaatgag agaattccag    5040
ttaatcccaa agctgctcct gactcttcga gatatgtctt tatcccagcc tactattgct    5100
gctattagta atgtcctgag cttcttactg caaggttttc ctagcagcaa tgatctgctc    5160
agatttgggc agtttatttc ttctactttg ccaacctttg cggtttgtga gaaatttgta    5220 gtaatgaaa taaataatga agagaagctt gacactggaa ctgaagagga gtttggaggt    5280
cttgtatcag ctaatcttat acttttgagg aacagacttc tggatatctt gctaaaacta    5340
atttatacat ctaaagaaaa gacaagcatt aatttgcaag cttgtgaaga actggtgaag    5400
acactgggtt ttgactggat catgatgttt atggaggaac acttacattc caccacagtt    5460
```

```
acagcagcca tgaggattct tgttgtccta ctaagtaatc agtctattct catcaagttt    5520
aaagaaggac tcagtggtgg aggatggctt gaacagacag attctgtctt aactaataag    5580
attggaactg tattaggatt caacgtgggc agaagtgctg gtgggagatc gacggtcagg    5640
gagattaacc gagatgcttg tcattttcct ggttttccag tccttcagtc attccttcct    5700
aaacacacta atgtccctgc cctctatttt ctcctcatgg ccttgtttct gcagcagcca    5760
gttagtgagc tgcctgagaa cctgcaggtc agtgtgcctg tcatcagctg ccggagtaag    5820
cagggttgcc agtttgattt ggattccatt tggacattca tctttggagt tcctgcctcc    5880
agcggaactg tggtctcttc tatccataac gtatgcacag aagctgtttt tttattattg    5940
ggaatgctcc gcagcatgct gacttcacct tggcaatcag aagaagaggg atcttggctc    6000
cgagaatatc ctgtgaccct gatgcagttc ttcagatatt tgtatcacaa cgtgccagac    6060
cttgcctcca tgtggatgag ccctgacttc ctgtgtgcat agcagccac cgtcttcccc    6120
ttcaatattc gcccttactc agagatggtg actgaccttg atgatgaagt tggatctcca    6180
gcagaagagt ttaaagcgtt tgcagcagac acagggatga acaggagcca atcagagtac    6240
tgcaatgtgg gcaccaagac atatctgacc aatcacccgg ctaaaaagtt cgttttgac    6300
ttcatgcggg tcttaatcat agacaacctc tgtctcactc ctgccagcaa gcaaactcca    6360
ctaattgatc ttttgttgga ggcttcccct gaaaggtcta caagaactca gcaaaaagaa    6420
tttcaaactt acattttgga tagcgtgatg gaccatttgc ttgcagctga tgtgttatta    6480
ggggaagatg catctctgcc tattaccagt ggaggaagct accaggtatt ggtgaacaat    6540
gtgttttatt tcacacagcg tgtggtggac aagctttggc aaggcatgtt caacaaagaa    6600
tctaaacttc ttatagattt tataattcaa ctaattgcac agtcaaagag aagatcacag    6660
ggattgtcac tggatgcagt gtatcattgc ctcaatagga ccatcttgta ccagttctca    6720
cgggcacaca aaccgttcc tcagcaagta gctctgcttg attcactcag ggtcctcact    6780
gtaaacagaa acttgatcct gggacctggg aaccatgacc aagaattcat tagctgtctg    6840
gcccactgct tgataaatct acatgttgga agcaacgtgg atggatttgg actggaagca    6900
gaagcccgca tgaccacatg gcacattatg atcccctcgg acattgaacc agatggtagt    6960
tacagccaag atattagtga agggcgtcag cttctcataa aagctgtcaa cagagtttgg    7020
actgaactga tacatagtaa gaaacaagtc ttagaggaac ttttcaaagt aactctacct    7080
gtgaatgaaa ggggccacgt ggacatagct acagcaaggc cactcattga agaagctgcc    7140
ctgaagtgct ggcagaatca tttggcccat gaaaagaaat gcataagtcg aggagaagct    7200
ttagcgccca ccacacagtc caaattatcc cgtgtcagca gtggctttgg tctttccaag    7260
ttaacaggat caagaaggaa tcgaaaagaa agtggtctta ataaacacag tcttccacc    7320
caggagattt cgcagtggat gtttactcac attgctgttg ttcgtgactt agtagataca    7380
caatataaag aatatcagga gcgtcagcag aatgccctga gtacgtgac agaagagtgg    7440
tgtcagatcg agtgcgagct gttgagggag cgggggctgt ggggccctcc catcggctcc    7500
cacctcgaca gtggatgct ggagatgaca gaagggccct gcaggatgag gaaaaagatg    7560
gtgcgaaatg atatgtttta taaccattac ccttacgtgc cagaaactga gcaagagaca    7620
aatgtggcgt ctgagatccc aagtaaacag cctgagacac ccgatgatat tcctcaaaag    7680
aaacctgctc gatatagaag agccgtaagt tatgacagta aagagtacta catgcgactg    7740
gcctctggca atcccgccat tgtccaagac gccattgtgg agagttcaga aggtgaagct    7800
gctcagcaag aaccagagca tggggaagac actattgcta aagtcaaagg tttggtcaag    7860
```

```
cctcctctaa aacgctcccg atctgcacct gatggaggag atgaggagaa ccaggagcag   7920
ctacaagacc agattgctga gggcagctcc atagaagagg aggagaaaac agataatgct   7980
accttactgc gcctgttaga ggaaggagaa aagatccaac acatgtaccg ctgtgctcga   8040
gtccagggcc tagataccag tgaggggctc cttcttttg gtaaagagca ttttatgtg    8100 attgatggat ttaccatgac agcaaccagg gaaataagag atattgaaac cttacctcca   8160
aatatgcatg agcctattat tcctagagga gccaggcaag gccctagtca actcaagaga   8220
acatgcagca tttttgcata tgaagatatc aaggaagttc ataaaggag atatctcctg    8280 cagcctattg ctgtggaagt tttctctgga gatggacgga attacctcct tgcttttcag   8340
aaaggaatca gaaacaaagt ctatcaaagg ttttggctg tagtgccatc tctaacggac    8400
agttcagaat ctgtatctgg gcaacgacca aacacgagtg tggagcaggg atctgggtta   8460
cttagcactt tggttggaga gaagtctgtg actcagagat gggagagagg tgaaatcagc   8520
aacttccaat atttgatgca tttgaacact ttggctggca gatcatataa tgatctcatg   8580
cagtatcctg tcttccccctg gatccttgca gattatgact cagaggaggt ggatcttact   8640
aatcccaaga cgtttagaaa cctggctaag ccaatgggag cacaaacaga tgaacgatta   8700
gctcagtata agaagcggta taaagactgg gaggatccta atggagaaac tcctgcatac   8760
cactatggga cccactattc atctgcaatg attgtggcct catacctgt aaggatggag     8820 cctttcacac agatattctt aaggctacag gtggccact ttgacctggc tgaccggatg     8880
tttcacagtg tgcgcgaggc ctggtattca gcgtcaaagc acaatatggc agatgtaaaa   8940
gaacttatcc cagagttctt ttatttacca gaattcctgt tcaattccaa caactttgat   9000
ctaggctgta acaaaatgg caccaagctt ggagatgtta ccttccacc ctgggcaaaa     9060 ggggacccac gagaattcat cagagtccat cgtgaggctt ggagtgtga ttacgtgagt    9120 gcccatctac atgagtggat tgacttaatc ttcggttata aacagcaagg ccctgctgca   9180
gtagaagctg taaatgtctt ccatcatctt ttttatgagg gtcaagtgga tatctacaac   9240
atcaatgacc cactaaagga gacagccaca attgggttca ttaataactt cggtcagatc   9300
cctaaacagt tatttaaaaa acctcatcca ccaaagcgag tgagaagtcg actcaatgga   9360
gacaatgcag gaatctctgt cctaccagga tctacaagtg acaagatctt ttttcatcat   9420
ctagacaact tgaggccttc tctaacacct gtaaagaaac tcaaagaacc tgtaggacaa   9480
atcgtatgta cagataaagg tattcttgcg gtggaacaga ataaggttct tatcccacca   9540
acctggaata aaacttttgc ttggggctat gcagacctca gttgcagact gggaacctat   9600
gagtcagaca aggccatgac tgtttatgaa tgcttgtctg agtggggcca gattctctgt   9660
gcaatctgcc ccaaccccaa gctggtcatc acgggtggaa caagcacggt tgtgtgtgtg   9720
tgggagatgg gcacctccaa agaaaaggcc aagaccgtca ccctcaaaca ggccttactg   9780
ggccacactg ataccgtcac ctgcgccaca gcatcattag cctatcacat aattgtcagt   9840
gggtcccgtg atcgaacctg tatcatttgg gatttgaaca aactgtcatt tctaacccag   9900
cttcgagggc atcgagctcc agtttctgct ctttgtatca atgaattaac aggggacatt   9960
gtgtcctgcg ctggcacata tccccatgtg tggagcatca atgggaaccc tatcgtgagt  10020
gtcaacacgt tcacaggtag gagccagcag atcatctgct gctgcatgtc ggagatgaac  10080
gaatgggaca cgcagaacgt catagtgaca ggacactcag atgagtggt tcggttttgg   10140 agaatggaat ttttgcaagt tcctgaaaca ccagctcctg agcctgctga agtcctagaa   10200
```

```
atgcaggaag actgtccaga agcacaaata gggcaggaag cccaagacga ggacagcagt    10260
gattcagaag cagatgagca gagcatcagc caggacccta aggacactcc aagccaaccc    10320
agcagcacca gccacaggcc ccgggcagcc tcctgccgcg caacagccgc ctggtgtact    10380
gacagtggct ctgacgactc cagacgctgg tccgaccagc tcagtctaga tgagaaagac    10440
ggcttcatat ttgtgaacta ttcagagggc cagaccagag cccatctgca gggccccctt    10500
agccaccccc accccaatcc cattgaggtg cggaattaca gcagattgaa acctgggtac    10560
cgatgggaac ggcagctggt gttcaggagt aagctgacta tgcacacagc cttttgatcga   10620 aaggacaatg cacacccagc tgaggtcact gccttgggca tctccaagga tcacagtagg    10680
atcctcgttg gtgacagtcg aggccgagtt ttcagctggt ctgtgagtga ccagccaggc    10740
cgttctgctg ctgatcactg ggtgaaggat gaaggtggtg acagctgctc aggctgctcg    10800
gtgaggtttt cactcacaga agacgacac cattgcagga actgtggtca gctcttctgc     10860
cagaagtgca gtcgctttca atctgaaatc aaacgcttga aaatctcatc cccggtgcgt    10920
gtttgtcaga actgttatta taacttacag catgagagag gttcagaaga tgggcctcga    10980
aattgttgaa gattcaacaa gctgagtgga gaccatggtc tgtagacccc ttcccgattc    11040
tcctgtccca gcttggaagg cattgaaaac agtctccgtt tacacatctc ttcataccac    11100
gtgtttgaag tgttaaaatt caaagggatc attgaataaa acgggtgtag agtacaggaa    11160
tggggcagac gcgattcagg tgaacagcac aagaagaata tgaggtggtt cctaggagca    11220
acactttcga cctccagttc tccctgatga cagtagctgt ctccaagaga aaaatcctca    11280
cttattaact ctctttcttt gcatctcatt tttatagagc tactcatcct tatttggaaa    11340
aaccaacaac aaaaaaggct tttagaaaat ggttgtaaat ctgacttctt tgcaagtaac    11400
tatgtatatt gtaaatagat ataaaaggcc ttttttctaa ataaggactt aactgcctgt    11460
aacatgaaac ttcaaactaa accactaact caatgaacta cttatggttt gtctgacatc    11520
cctcacttac caattaatta taaatatgtt ttttttaaatc cccaaagaca ttatctgtgg    11580 tcttttttttc ctttcaagct cagcctgtgt gcctgatgtc atttctttca agttgcccac    11640
agtatctcca cttaaactag gctagtaacc aaaataatgt ggaccttctt taggaaacag    11700
tgtgggagaa taggagtcca gccgtaagat aaactggaaa tatttgggcg tcttgtacct    11760
ggctacgcac cacctcagtg ttgttcctac ataaacaggg ccccttttaa acttgtatgt    11820
ggactgctgt ttggtcaaag aataccttct tagcattgca gaaaggtggt cagatgacca    11880
gtgtagtgca ggaaacagcc ctgtctcaac taatggaaat atatttgcat gtaacccaaa    11940
attagcttat cttgcataga acataataag tatgtgtctt tggtgacact aatgttctac    12000
tatagcttat tttcaaacaa ggggtaaaaa aaggaaagaa agaagtgtac agaattaaca    12060
tataaacttt gttgtaaaac tgaatcatgt cagaactgct taaaattaac ctttaccatt    12120
taatgtcatc tacctgaaaa cagtgagatt tatactgtat caatgtctat ttttttgttt    12180
ttgctatgaa tataattaca gtattttaat atttagttat ttaatttgtt ctactagttg    12240
gatacagaac acacaaatcc aggggatta aagctggaag gggctaagag attagtttac      12300
agagaaaagg cttggtggtg ggatttttt aaatgtgtgt tatgtacata tatatatata       12360
tataatatat attaaaaatg aaacaattaa tctagatttt aacattttca gaaacttagt    12420
gataacatta tgaacaattc taaaagcccct gtgatttgaa aaatatagaa tcattaatgg    12480
cccaagatag gccttcacac cttcacaggt gcgaaaggaa aggccttcac accctcacag    12540
aggcatcatg caaaggacag cggctttggc ttttccaatt ttccatcttt aggccctggt    12600
```

```
gagaggcaca cttatgcact aaaatgcaca tatatgcaca tgcattcaaa aataggcatt    12660
tggtacaatg gtgatcttgt acctgatggg ctgaaaccag cttaagaaca aatttgttct    12720
tcctgatatg ataactaggt ctccaagaga aaatagaaag gctgctttag tgccttacgc    12780
ttactaaatt taaatctttc tttacctggg tttgagccta cagtctattt atgattacat    12840
atcaaaattg attaaaacac ttccatttct aaagttcaa atatacttgt taataaaagg     12900
attatcggca ttaatacttt aatttaaaga aaagttgtgt tctgttttcc tttctgtgtc    12960
ttactccccc cacactctcc ctcccccatc accatcttca attctaataa ataatgctga    13020
tgttcaacag ttgcagaaat tgtgctatta tgtaactgtg ggccttgccc ctgtctggcc    13080
ctctagatga tttgtagcag tgttattcta cacttttaa aagaagcgtc ctccttttgt     13140
ccatgaatca tgtttacccc atacccagtg gcagaggtgt tctttaaaga cttgaatata    13200
tgaatgtgtg tgtgtagtta cttaaaggtt attcctcttt gtaataggaa actatatggg    13260
atgaacactt ttaaactttc cgacacaact tccattacta actttctaac agaacttcca    13320
taactagaag gtggaaacca aaaccctcat ggtagtattt cctctggcag ctggtgctgt    13380
gggcaactgt tttgttcaat cgggtttctt ttcttttgc ctctaatgca gaaatcaaca     13440
gaatcactca cacatacaag tacactcaca tacataaact aattatttct ctggatatct    13500
ttctgtgttc catgtaaatt tatttaccaa catctattgt caacatgtac atctaccttn    13560
gtatggtctg cattctttt ctgagagtac ctcatagggc tcctgcctga tctttgtagt     13620
ttgttcattc atccatccac ctgttcattt gttcatccat gtattctaac atttctatgt    13680
agtgtgcaac tctaatgtca tgcttttgaa gaagagaata gctgcccata gcagccatcc    13740
gtctggataa tagcaaaaca ctctagataa gttattttgc acttcttat gtataaagtt     13800 ggtagaaact tatttttgct ttgtatcatt taaatacatt ttgttttggt aaatgaactg    13860
tgtataaaat atttatgccg ttaaaactgt ttttagaaag tatttttaat ttcagcaagt    13920
ttggttactt gttgcatgac tcttaacaca gctgactttt tgtgtcagtg caatgtatat    13980 ttttgtcct gttattaact tgtaagcccct agtaatggcc aattattgt acagcaacag     14040 aagtaaattg aagatactgg ctaagactgg attgattgtg gactttata ctatattgca     14100 gaaaccaata tctgtttctt ggtggttatg taaaagacct gaagaattac tatctagtgt    14160
gcagtctgtg atatctgaat gttcattgta tatttgtctc tgatgcaaaa aggtagagta    14220
acacaattac aatacatgat taaatgcaat agtccaggta cttaagtaat ttttttttca    14280
tttcaaataa atacctatt accaccaaaa gaaagaaaaa aaaaaaaaa                 14329
```

<210> SEQ ID NO 50
<211> LENGTH: 12778
<212> TYPE: DNA
<213> ORGANISM: Homo sapiens

<400> SEQUENCE: 50

```
cgcggcccga gcgcctcttt tcgggattaa aagcgccgcc agctcccgcc gccgccgccg      60
tcgccagcag cgccgctgca gccgccgccg ccggagaagc aaccgctggg cggtgagatc     120
cccctagaca tgcggctcgg gggcgggcag ctggtgtcag aggagctgat gaacctgggc     180
gagagcttca tccagaccaa cgacccgtcg ctgaagctct ccagtgcgc cgtctgcaac     240 aagttcacga cggacaacct ggacatgctg ggcctgcaca tgaacgtgga gcgcagcctg    300
tcggaggacg agtggaaggc ggtgatgggg gactcatacc agtgcaagct ctgccgctac    360
```

```
aacacccagc tcaaggccaa cttccagctg cactgcaaga cagacaagca cgtgcagaag      420
taccagctgg tggcccacat caaggagggc ggcaaggcca acgagtggag gctcaagtgt      480
gtggccatcg gcaaccccgt gcacctcaag tgcaacgcct gtgactacta caccaacagc      540
ctggagaagt gcggctgca cacggtcaac tccaggcacg aggccagcct gaagttgtac      600
aagcacctgc agcagcatga gagtggtgta aaggtgaga gctgctacta ccactgcgtt      660
ctgtgcaact actccaccaa ggccaagctc aacctcatcc agcatgtgcg ctccatgaag      720
caccagcgaa gcgagagcct gcgaaagctg cagcggctgc agaagggcct tccagaggag      780
gacgaggacc tggggcagat cttcaccatc cgcaggtgcc cctccacgga cccgaagaa      840 gccattgaag atgttgaagg acccagtgaa acagctgctg atccagagga gcttgctaag      900
gaccaagagg gcggagcatc gtccagccaa gcagagaagg agctgacaga ttctcctgca      960
acctccaaac gcatctcctt cccaggtagc tcagagtctc ccctctcttc gaagcgacca     1020
aaaacagctg aggagatcaa accggagcag atgtaccagt gtccctactg caagtacagt     1080
aatgccgatg tcaaccggct ccgggtgcat gccatgacgc agcactcggt gcaacccatg     1140
cttcgctgcc ccctgtgcca ggacatgctc aacaacaaga tccacctcca gctgcacctc     1200
acccacctcc acagcgtggc acctgactgc gtggagaagc tcattatgac ggtgaccacc     1260
cctgagatgg tgatgccaag cagcatgttc ctcccagcag ctgttccaga tcgagatggg     1320
aattccaatt tggaagaggc aggaaagcag cctgaaacct cagaggatct gggaaagaac     1380
atcttgccat ccgcaagcac agagcaaagc ggagatttga accatcccc tgctgaccca     1440 ggctctgtga gagaagactc aggcttcatc tgctggaaga aggggtgcaa ccaggttttc     1500
aaaacttctg ctgcccttca gacgcatttt aatgaagtgc atgccaagag gcctcagctg     1560
ccggtgtcag atcgccatgt gtacaagtac cgctgtaatc agtgtagcct ggccttcaag     1620
accattgaaa agttgcagct ccattctcag taccatgtga tcagagctgc caccatgtgc     1680
tgtctttgtc agcgcagttt ccgaactttc caggctctga agaagcacct tgagacaagc     1740
cacctggagc tgagtgaggc tgacatccaa cagctttatg gtggcctgct ggccaatggg     1800
gacctcctgg caatgggaga ccccactctg cagaggacc ataccataat tgttgaggaa     1860
gacaaggagg aagagagtga cttggaagat aaacagagcc aacgggcag tgactctggg     1920 tcagtacaag aagactcggg ctcagagcca aagagagctc tgcctttcag aaaaggtccc     1980
aattttacta tggaaaagtt cctagaccct tctcgccctt acaagtgtac cgtctgcaag     2040
gaatctttca ctcaaaagaa tatcctgcta gtacactaca attctgtctc ccacctgcat     2100
aagttaaaga gagcccttca agaatcagca accggtcagc cagaacccac cagcagccca     2160
gacaacaaac ctttttaagtg taacacttgt aatgtggcct acagccagag ttccactctg     2220
gagatccata tgaggtctgt gttacatcaa accaaggccc gggcagccaa gctggaggct     2280
gcaagtggca gcagcaatgg gactgggaac agcagcagta tttccttgag ctcctccacg     2340
ccaagtcctg tgagcaccag tggcagtaac acctttacca cctccaatcc aagcagtgct     2400
ggcattgctc caagctctaa cttactaagc caagtgccca ctgagagtgt agggatgcca     2460
cccctgggga tcctattgg tgccaacatt gcttcccctt cagagcccaa agaggccaat     2520
cggaagaaac tggcagatat gattgcatcc aggcagcagc aacaacagca gcagcaacag     2580
caacaacaac aacaacaaca acaacaacaa gcacaaacgc tggcccaggc ccaggctcaa     2640
gttcaagctc acctgcagca ggagctgcag caacaggctg ccctgatcca gtctcagctg     2700
tttaacccca ccctccttcc tcacttcccc atgacaactg agaccctgct gcaactacag     2760
```

-continued

```
cagcagcagc acctcctctt cccttfctac atccccagtg ctgagttcca gcttaacccc    2820
gaggtgagct tgccagtgac cagtggggca ctgacactga ctgggacagg cccaggcctg    2880
ctggaagatc tgaaggctca ggttcaggtc ccacagcaga gccatcagca gatcttgccg    2940
cagcagcagc agaaccaact ctctatagcc cagagtcact ctgccctcct tcagccaagc    3000
cagcaccccg aaaagaagaa caaattggtc atcaaagaaa aggaaaaaga aagccagaga    3060
gagagggaca gcgccgaggg gggagagggc aacaccggtc cgaaggaaac actgccagat    3120
gccttgaagg ccaaagagaa gaaagagttg gcaccagggg gtggttctga gccttccatg    3180
ctccctccac gcattgcttc agatgccaga gggaacgcca ccaaggccct gctggagaac    3240
tttggctttg agttggtcat ccagtataat gagaacaagc agaaggtgca gaaaaagaat    3300
gggaagactg accagggaga gaacctggaa aagctcgagt gtgactcctg cggcaagttg    3360
ttttccaaca tcttgatttt aaagagtcat caagagcacg ttcatcagaa ttactttcct    3420
ttcaaacagc tcgagaggtt tgccaaacag tacagagacc actacgataa actgtaccca    3480
ctgaggcccc agaccccaga gccaccacca cctccccctc caccccctcc accccacctt    3540
ccggcagcgc gcctcagcc ggcgtccaca ccagccatcc ccgcatcagc ccacccatc    3600 acctcaccta caattgcacc ggcccagcca tcagtgccgc tcacccagct ctccatgccg    3660
atggagctgc ccatcttctc gccgctgatg atgcagacga tgccgctgca gaccttgccg    3720
gctcagctac ccccgcagct gggacctgtg gagcctctgc ctgcggacct ggcccaactc    3780
taccagcatc agctcaatcc aaccctgctc cagcagcaga acaagaggcc tcgcaccagg    3840
atcacagatg atcagctccg agtcttgcgg caatattttg acattaacaa ctccccccagt    3900 gaagagcaaa taaagagat ggcagacaag tccgggttgc cccagaaagt gatcaagcac    3960
tggttcagga acactctctt caaagagagg cagcgtaaca aggactcccc ttacaacttc    4020
agtaatcctc ctatcaccag cctggaggag ctcaagattg actccgcgcc ccttcgccg    4080 gaacctccaa agcaggagta ctggggaagc aagaggtctt caagaacaag gtttacggac    4140
taccagctga gggtcttaca ggacttcttc gatgccaatg cttacccaaa ggatgatgaa    4200
tttgagcaac tctctaattt actgaacctt ccaaccccgag tgatagtggt gtggtttcag    4260
aatgcccgac agaaggccag gaagaattat gagaatcagg gagagggcaa agatggagag    4320
cggcgtgagc ttacaaatga tagatacatt cgaacaagca acttgaacta ccagtgcaaa    4380
aaatgtagcc tggtgtttca gcgcatctt gatctcatca agcaccagaa gaagctgtgt    4440
tacaaggatg aggatgagga ggggcaggac gacagccaaa atgaggattc catggatgcc    4500
atggaaatcc tgacgcctac cagctcatcc tgcagtaccc cgatgccctc acaggcttac    4560
agcgccccag caccatcagc caataataca gcttcctccg cttcttgca gcttacagcg    4620 gaggctgagg aactggccac cttcaattca aaaacagagg caggcgatga gaaaccaaag    4680
ctggcggaag ctcccagtgc acagccaaac caaacccaag aaaagcaagg acaaccaaag    4740
ccagagctgc agcagcaaga gcagcccgag cagaagacca cactccccca gcagaagctc    4800
ccccagctgt tgtccctgcc ttcgttgcca cagcctcctc cacaagcgcc cctccacag    4860 tgcccttac cccagtcgag ccccagtcct tcccagctct cccacctgcc cctcaagccc    4920
ctccacacat caactcctca acagctcgca aacctacctc ctcagctaat ccctaccag    4980 tgtgaccagt gtaagttggc atttccgtca tttgagcact ggcaggagca tcagcagctc    5040
cacttcctga gcgcgcagaa ccagttcatc cacccccagt ttttggacag gtccctggat    5100
```

```
atgcctttca tgctctttga tcccagtaac ccactcctgg ccagccagct gctctctggg   5160
gccatacctc agattccagc aagctcagcc acttctcctt caactccaac ctccacaatg   5220
aacactctca agaggaagct ggaggaaaag gccagtgcaa gccctggcga aaacgacagt   5280
gggacaggag gagaagagcc tcagagagac aagcgtttga gaacaaccat cacaccggaa   5340
caactagaaa ttctctacca gaagtatcta ctggattcca atccgactcg aaagatgttg   5400
gatcacattg cacacgaggt gggcttgaag aaacgtgtgg tacaagtctg gtttcagaac   5460
acccgagctc gggaaaggaa aggacagttc cgggctgtag gccagcgca ggcccacagg   5520
agatgccctt tttgcagagc gctcttcaaa gccaagactg ctcttgaggc tcatatccgg   5580
tcccgtcact ggcatgaagc caagagagct ggctacaacc taactctgtc tgcgatgctc   5640
ttagactgtg atgggggact ccagatgaaa ggagatattt ttgacggaac tagcttttcc   5700
cacctacccc caagcagtag tgatggtcag ggtgtccccc tctcacctgt gagtaaaacc   5760
atggaattgt cacccagaac tcttctaagc ccttcctcca ttaaggtgga agggattgaa   5820
gactttgaaa gccccctccat gtcctcagtt aatctaaact ttgaccaaac taagctggac   5880
aacgatgact gttcctctgt caacacagca atcacagata ccacaactgg agacgagggc   5940
aacgcagata acgacagtgc aacgggaata gcaactgaaa ccaaatcctc ttctgcaccc   6000
aacgaagggt tgaccaaagc ggccatgatg gcaatgtctg agtatgaaga tcggttgtca   6060
tctggtctgg tcagcccggc cccgagcttt tatagcaagg aatatgacaa tgaaggtaca   6120
gtggactaca gtgaaaccctc aagccttgca gatccctgct ccccgagtcc tggtgcgagt   6180
ggatctgcag gcaaatctgg tgacagcgga gatcggcctg gcagaaacg ttttcgcact   6240
caaatgacca atctgcagct gaaggtcctc aagtcatgct ttaatgacta caggacaccc   6300
actatgctag aatgtgaggt cctgggcaat gacattggac tgccaaagag agtcgttcag   6360
gtctggttcc agaatgcccg ggcaaaagaa aagaagtcca agttaagcat ggccaagcat   6420
tttggtataa accaaacgag ttatgaggga cccaaaacag agtgcacttt tgtgtggcatc   6480
aagtacagcg ctcggctgtc tgtacgtgac catatctttt cccaacagca tatctccaaa   6540
gttaaagaca ccattggaag ccagctggac aaggagaaag aatactttga cccagccacc   6600
gtacgtcagt tgatggctca acaagagttg gaccggatta aaaaggccaa cgaggtcctt   6660
ggactggcag ctcagcagca agggatgttt gacaacaccc ctcttcaggc ccttaacctt   6720
cctacagcat atccagcgct ccagggcatt cctcctgtgt tgctcccggg cctcaacagc   6780
ccctccttgc caggctttac tccatccaac acagctttaa cgtctcctaa gccgaacttg   6840
atgggtctgc ccagcacaac tgttccttcc cctggcctcc ccacttctgg attaccaaat   6900
aaaccgtcct cagcgtcgct gagctcccca accccagcac aagccacgat ggcgatgggc   6960
cctcagcaac ccccccagca gcagcagcag cagcagcaac cacaggtgca gcagcctccc   7020
ccgccgccag cagcccagcc gccacccaca ccacagctcc cactgcaaca gcagcagcaa   7080
cgcaaggaca aagacagtga gaaagtaaag gagaaggaaa aggcacacaa agggaagggg   7140
gaacccctgc ctgtccccaa gaaggagaaa ggagaggccc ccacggcaac tgcagccacg   7200
atctcagccc cgctgccccac catggagtat gcggtagacc ctgcacagct gcaggccctg   7260
caggccgcgt tgacttcgga ccccacagca ttgctcacaa gccagttcct tccttacttt   7320
gtaccaggct tttctcctta ttatgctccc cagatccctg gcgccctgca gagcgggtac   7380
ctgcagccta tgtatggcat ggaaggcctg ttccctaca gccctgcact gtcgcaggcc   7440
ctgatggggc tgtccccagg ctccctactg cagcagtacc agcaatacca gcagagtctg   7500
```

```
caggaggcaa ttcagcagca gcagcagcgg caactacagc agcagcagca gcaaaaagtg    7560
cagcagcagc agcccaaagc aagccaaacc ccagtccccc ccggggctcc ttccccagac    7620
aaagaccctg ccaaagaatc ccccaaacca gaagaacaga aaacacccc ccgtgaggtg    7680 tccccctcc tgccgaaact ccctgaagag ccagaagcag aaagcaaaag tgcggactcc    7740
ctctacgacc ccttcattgt tccaaaggtg cagtacaagt tggtctgccg caagtgccag    7800
gcgggcttca gcgacgagga ggcagcgagg agccacctga agtccctctg cttcttcggc    7860
cagtctgtgg tgaacctgca agagatggtg cttcacgtcc ccaccggcgg cggcggcggt    7920
ggcagtggcg gcggcggcgg cggtggcggc ggcggcggcg gcggcggctc gtaccactgc    7980
ctggcgtgcg agagcgcgct ctgtggggag gaagctctga gtcaacatct cgagtcggcc    8040
ttgcacaaac acagaacaat cacgagagca gcaagaaacg ccaaagagca ccctagttta    8100
ttacctcact ctgcctgctt ccccgatcct agcaccgcat ctacctcgca gtctgccgct    8160
cactcaaacg cagccccc tccccgtcg gccgccgccc cctcctccgc ttcccccac    8220 gcctccagga agtcttggcc gcaagtggtc tcccgggctt cggcagcgaa gccccttct    8280 tttcctcctc tctcctcatc ttcaacggtt acctcaagtt catgcagcac ctcaggggtt    8340
cagccctcga tgccaacaga cgactattcg gaggagtctg acacggatct cagccaaaag    8400
tccgacggac cggcgagccc ggtggagggt cccaaagacc ccagctgccc caaggacagt    8460
ggtctgacca gtgtaggaac ggacaccttc agattgtaag ctttgaagat gaacaataca    8520
aacaaatgaa tttaaataca aaattaata acaaaccaat ttcaaaaata gactaactgc    8580
aattccaaag cttctaacca aaaacaaaa aaaaaaaaa aagaaaaaa aagaaaaagc    8640 gtgggttgtt ttcccatata cctatctatg ccggtgattt tacattcttg tcttttttctt    8700 ttcttttaat attaaaaaaa aaaaaaagc cctaaccctg ttacattgtg tccttttgaa    8760
ggtactattg gtctgggaaa cagaagtccg cagggcctcc ctaatgtctt tggagcttaa    8820
accccttgta tatttgcccc ttttcaataa acgccccacg ctgatagcac agaggagccc    8880
ggcatgcact gtatgggaaa gcagtccacc ttgttacagt tttaaatttc ttgctatctt    8940
agcattcaga taccaatggc ttgctaaaag aaaaaaagaa atgtaatgtc tttttattct    9000
caggtcaatc gctcacactt tgttttcaga atcattgttt tatatattat tgttttttca    9060 gtttttttt ttttttttgt tccagaaaag attttttgtt ttgttaactt aaaaatgggc    9120
agaaagtatt caagaaaaac aatgtgaact gctttagctt tctggggatt tttaaggata    9180
gcttttctgc tgaagccaat ttcaagggga aagttaagc actccacttt tcaaaaaaaa    9240
aaaaaaataa taacccacac acacaaagag tgttgaggac ttgtagctta aaaaaaataa    9300
gttttaaaaa ctgactttct gtatttatga tagatatgac cattttttggt gttgagtaga    9360 ttgttgcatt ggaaatgaac tgaagcagta tggtagattt aaaaggaaaa aaaaaaaaaa    9420
accttttgtg tacatttagc tttttgtatg gtccagctga cagctcctca tttgatgttg    9480
tcttgttcat tcctagcaga tgatagattg caatccgttg attcgcctaa gcttttctcc    9540
ccttgtccct taattccact ttctctttct tgtcccttaa ttccactttc tctttccttc    9600
tcccacctcc cgtcctataa tctcccactt aaggtagctg ccttcatttc ttagagggag    9660
ctgcagaatt atttataaa actaaagaaa gaatttcaag ggattctagg ggtcattagg    9720
atcctcacag attattttttg gttggggagt tgaaacttttt taaaggcata taattctagt    9780
tacctgtgtc tgttagcttt gtgcatttat tttttatttta tccttctttt ggcttttttt    9840
```

```
tctttgtacc ccttctttc ctccttgttt ggtaggagct tcaaatattc tttttttttc    9900
tatactaaag gatttgtttc catttgtgta attggctgtg tacttttctt ttctaaaaaa    9960
agttttggt tagggatttg gttttggtt ttgtgtttgt ttttctttc ctctctcaga     10020
aaaaaaatt tcatgcttta aataaaatcc aaagacacac cctttcactg ctgatgcaga    10080
aaaaagggaa agggttcttg ttacttgaga atttgtttct gatttaaaca aacaagactt   10140
agtttaataa agaaagaga aaacaaaag attcccaggt tgttatgtgc ttcttctgca    10200
agcagagagg caaatgttaa tgacaattcc atataccaaa agacacattt tttacttcaa   10260
agttttgtcc ttgtgttagg cagtctgagc agcgagtgat ccagagcgca gccaacaaag   10320
cagcagatag cagtgtacag aaagcaaaaa aggaactgta tgtgaggcac ttgtttctgt   10380
taatatccat attcctgtta acacacaccc tttctcatgt aaaaagaaaa ataaataaat   10440
ggtctgaact ttgaaaactt tgtgctgcta aaacatagat tttggagaca aataaataga   10500
tgctttgctg tttcactttc atagctaaac atcaacagaa accatctccc cttgccccca   10560
aagtgtgaaa tccttcttcc cttcgttttc ttccttatgt ttcaaaaggg aactttgaag   10620
actgtgaata caggttccat tggtcacctt tcgggcttct ttccccagtg ctgaagccac   10680
tcatcgactt tgcaaaagac tggagcattc caagatctga aaatggattt tttttctttt   10740
tttctttttt agccgggact atttttatttt tatgaatttg tttttagttt aatgaaatag   10800
tagatcctga aatgttgtac atatttctaa ctaggctgat gcacagtgca aattcctttt   10860
ttaattgttt ttttttaagta gaaatactaa agaaagaata ccatctaact attcatacca   10920
gtatccagtt gtagcataag gtgtcaaaag caagtacgca aaacatttac tgttttaaca   10980
agctatttcc ttttaacaag aaatcttgta tttcttcctg tgtttgagat gaacattttt   11040
aaattttaaa gttgtacagt ttttttgtttt ccattatttt atcttgtttg taactctatg   11100
aaatatatat atatatattt tttgccattt aactgttgta tgttactctg tgtctgtacc   11160
atatagaaaa aaaattgttt ttgtttttgg ttctctatgt gatatcagtt aacaatgtaa   11220
cactagcttt acctgtcaaa ttctgctagg tcttctctga aaacgttgtt tttaaaaatg   11280
atattgcttg gtaatagtgc aatttctatc cttttccctc cccccctcaac ttttaagttc   11340
ttttctttat aattttgctg ccccctccct gatggtttgg gttttttgttt ttgttttttgt  11400
tttttttttt catggagcta ctatgccatc ctccctctgt gaggcagagt gactgtcagt   11460
gttttgttat gccatgcctt gagctgtggg tgtttggcga caataaggtg gttgaataga   11520
ttggctgagc acacttccac ccacctagtg ttctcagagg ggttatgtga ttgtttcaac   11580
ctggagtggg ttgcacccctt aatgctttcc tctgcaacta aaccgccac atatatgttc    11640
attgaaaaaa gtaagaataa ttctcagcac taacccagaa gtagcaaagc agtcagtgat   11700
ggtgaacatt agaggtcaaa catgagttag atgtttgtgg gctgacagcc atcgtggcta   11760
tgaccagtac tatttacaaa gcatgaattc actacaatgc tcaactgttt gtttagcttt   11820
atctcacttg gggaatttat tcctgtctgc tgcattgtag gtagctgggt aggatatatt   11880
tccacttgct ttttaaatta gttcttcacc tccattgaca ctcgtttttt ggttttctcc   11940
ctatagtgtg ggtggtgct agacaccagt ctgacccaca gaatgggagt tatttcatcc   12000
atctttcctc catccttcca aaaccacat atctacacaa ggaaaaattt aatacatcta    12060
ggaattttttt tttaattac aagctattta aagagatgaa tgtggccaaa gttttacaca   12120
attgaaaata aagtaaaaca gacggcatgt gtttaaacct gagtttatca ggcatggcag   12180
gaagttgcag gagagagagg cagtgaccca agccagtgca cttgatgttc atggacatat   12240
```

| | | | |
|---|---|---|---|
| atttttttta | aataataaat | taaaacattt | taaatagaag cataaattga gttgtttgtt | 12300 |
| ggcgctgaga | tactgcccac | tgtgaaacaa | agctttgact agttttttgt ttgtttactt | 12360 |
| tcttcagggg | ggaggggggc | aagtttgggt | aggaagaaa gcataaatga acgtgaccct | 12420 |
| gaggtgaaga | ggtatatgaa | cagcctttgc | aatgtacaaa agaaaaaaa aacaaaaaac | 12480 |
| aacaaaaaaa | atagagcaag | tgaaaccaaa | aatgatgttc ttggtgtttt tctataatgt | 12540 |
| agtcttgtta | gctttttttgt | tactgtaaca | atgctgatct cgaactgtac caaaatacat | 12600 |
| ggagactaac | aaacagaacc | acatggaact | ttcaaactga aaaaaaaatt tgtcacaaaa | 12660 |
| actttgttgt | catagttaag | ttgattgtag | atggtaattg aatatactcc tttgaaaata | 12720 |
| tttcatcaag | tatgtttcct | gctcattgtg | atacattaaa aaaaaaatat gagcaaaa | 12778 |

<210> SEQ ID NO 51
<211> LENGTH: 4826
<212> TYPE: DNA
<213> ORGANISM: Homo sapiens

<400> SEQUENCE: 51

| | | | | |
|---|---|---|---|---|
| gggcgcgggc | agctctgcgt | ccgaagctgc | tccgacgccg tcgctgggac caagatggac | 60 |
| ctcccggcgc | tgctccccgc | cccgactgcg | cgcggagggc aacatggcgg cggccccggc | 120 |
| ccgctccgcc | gagccccagc | gccgctcggc | gcgagcccg cgccgccg cctgctactg | 180 |
| gtgcggggcc | ctgaagatgg | cgggccaggg | gcgcggcccg gggaggcctc cgggccaagc | 240 |
| ccgccgcccg | ccgaggacga | cagcgacggc | gactcttct tggtgctgct ggaagtgccg | 300 |
| cacggcggcg | ctgccgccga | ggctgccgga | tcacaggagg ccgagcctgg ctcccgtgtc | 360 |
| aacctggcga | gccgccccga | gcagggcccc | agcggcccgg ccgccccccc cggccctggc | 420 |
| gtagccccgg | cgggcgccgt | caccatcagc | agccaggacc tgctggtgcg tctcgaccgc | 480 |
| ggcgtcctcg | cgctgtctgc | gccgcccggc | cccgcaaccg cgggcgccgc cgctccccgc | 540 |
| cgcgcgcccc | aggcctccgg | ccccagcacg | cccggctacc gctgccccga gccgcagtgc | 600 |
| gcgctggcct | tcgccaagaa | gcaccagctc | aaggtgcacc tgctcacgca cggcggcgt | 660 |
| cagggccggg | ggcccttcaa | gtgcccactg | gagggctgtg gttgggcctt cacaacgtcc | 720 |
| tacaagctca | gcggcacct | gcagtcgcac | gacaagctgc ggcccttcgg ctgtccagtg | 780 |
| ggcggctgtg | gcaagaagtt | cactacggtc | tataacctca aggcgcacat gaagggccac | 840 |
| gagcaggaga | gcctgttcaa | gtgcgaggtg | tgcgccgagc gcttccccac gcacgccaag | 900 |
| ctcagctccc | accagcgcag | ccacttcgag | cccgagcgcc cttacaagtg tgactttccc | 960 |
| ggctgtgaga | agacatttat | cacagtgagt | gccctgtttt cccataaccg agcccacttc | 1020 |
| agggaacaag | agctcttttc | ctgctccttt | cctgggtgca gcaagcagta tgataaagcc | 1080 |
| tgtcggctga | aaattcacct | gcggagccat | acaggtgaaa gaccatttat ttgtgactct | 1140 |
| gacagctgtg | gctggacctt | caccagcatg | tccaaacttc taaggcacag aaggaaacat | 1200 |
| gacgatgacc | ggaggtttac | ctgccctgtc | gagggctgtg gaaatcatt caccagagca | 1260 |
| gagcatctga | aaggcacag | cataacccac | ctaggcacaa agccgttcga gtgtcctgtg | 1320 |
| gaaggatgtt | gcgcgaggtt | ctccgctcgt | agcagtctgt acattcactc taagaaacac | 1380 |
| gtgcaggatg | tgggtgctcc | gaaaagccgt | tgcccagttt ctacctgcaa cagactcttc | 1440 |
| acctccaagc | acagcatgaa | ggcgcacatg | gtcagacagc acagccggcg ccaagatctc | 1500 |
| ttacctcagc | tagaagctcc | gagttctctt | actcccagca gtgaactcag cagcccaggc | 1560 |

```
caaagtgagc tcactaacat ggatcttgct gcactcttct ctgacacacc tgccaatgct   1620
agtggttctg caggtgggtc ggatgaggct ctgaactccg gaatcctgac tattgacgtc   1680
acttctgtga gctcctctct gggagggaac ctccctgcta ataatagctc cctagggccg   1740
atggaacccc tggtcctggt ggcccacagt gatattcccc aagcctggga cagccctctg   1800
gttctcggga cagcagccac ggttctgcag cagggcagct tcagtgtgga tgacgtgcag   1860
actgtgagtg caggagcatt aggctgtctg gtggctctgc ccatgaagaa cttgagtgac   1920
gacccactgg ctttgacctc caatagtaac ttagcagcac atatcaccac accgacctct   1980
tcgagcaccc cccgagaaaa tgccagtgtc ccggaactgc tggctccaat caaggtggag   2040
ccggactcgc cttctcgccc aggagcagtt gggcagcagg aaggaagcca tgggctgccc   2100
cagtccacgt tgcccagtcc agcagagcag acggtgcccc aggacacaga gctcagtgca   2160
ggcactggca acttctattt ggtatgaagc actctattca gtcaccacca tataggtcac   2220
ttctctcata ctcggtcttg aggatattct ggattaatcc tttctatgca gacgtttctg   2280
gtttacaaaa ggacgcagcc ctggactaca agtctgaaac tgacaagttc ttatgacctt   2340
gacaaatcac cttaacccat ctgagcctta aattctcatt tatttcctgc ataaggagat   2400
ttggctaaat gctttctgag gtcctttgga gtcctgtggc tccatggtaa tgtgctcctt   2460
tccttgaaga ttgggggttt tgtaatgttg agatactttg cctctatgct tgtcagctca   2520
tgaccagtcc tagaagagga gtcgagacat aagccacctt cagaggttca atggaaactt   2580
taaaaccata ccaaactctt tttttaaaatt agaattaaca agaaaaaaaa aaagggtggg   2640
gtttatgagc cttagttctt ggaggattat aagagtactt ccccagtttt gaggctggac   2700
agttaatata ctttatatca attatacatt taatataatt taatttaaaa taatttaaag   2760
attcttagga gatagtctga ctttcctgac ctagatggga atgatcagat agggatttt    2820 tttgtggcac aggctaaatt tgatggtgac atttatattg ttgagaatgt tacatcttat   2880
tttaccacaa cttttaaaaa atgttacatc ttttgcagta ggatcagttg tgaggcacat   2940
agtagctgag gctccatgga gccacctttc atttctttca gtcagagagg aggacagtct   3000
ctgtctctgc atttctggtg tcttgcttgt cggtggcaga gccatgcttg ccggcatttg   3060
cttaggcggc catagtagtt gctaagtgta caggtgactg ggcagggatg ggaggtggcc   3120
acaggtcaga gacaagtgct cagtcagtcc ctggtgccag gactgtgtgc ctcggtgcct   3180
tgggaaatgg aagctccctg gtgcagctgc agctgtgggt ggaggtagag aagccagcaa   3240
gaccttggtc ttaaccccgt gttcattttc ttgctagctg tgtgacgttg ggctacctcg   3300
cttctctgag tacaaatggt gtgtggtgaa tgggtcccag gtatgctacg agctttgagg   3360
gctgctcttt ttctcttcat agcgataagt gttaaactgt cttccttagg aaacgttcac   3420
agacttgcaa cagctgatgt cctctgagta ctgtctgact ccctcaggca agttcctgaa   3480
ttcagtacca tcattattat ttttgtgtaa gactttgaca aagtatagcc cctgccacca   3540
gagcagcctg tacagtgggt ctctaaggtg ggacctgccc cgggcctgcc atgcacgtgt   3600
gtgaaacagc gtgaaaagtg tcgcggtaag gtgaccctgg gttacccagg caaggctcgg   3660
tgtttgtttc agaaagcaga gaagtatgta attgatttta aagtttctg tttaaaatat    3720 ttggctatgt tttagactat gaaggaatga actttgcttc tctggataag aaagtcacat   3780
acattgttcc agctccaagt tgttcggcc ctcgccacaa gtggatgtag cgtttggccc    3840
tttgtgtgcc ttgctggtga ctctggtttt gggagctcgg atatgtccca gaagcaggct   3900
tatggcactt ctgtagctcc cttgctaccc ttcctttgtg tctagataag tgactgacat   3960
```

```
gcttttcttt ggtctcagga aagtgggggc tcagcaagaa ctgattaccg agccattcaa    4020
ctagccaagg aaaaaaagca gagaggagcg gggagcaatg caggtgaggc cgtgtgtgct    4080
gcagccggac gagcaagggc ctgagggttc tctgtcactg ttactggcag aagaaacaca    4140
gcaggtgttt ctgtgctctt ggttttactt ttctgttcag aatacccttt tatcaactcc    4200
ttagttttat ttgaacttaa gggaaaaaat tagtaacaaa attcccagca tcagtatgaa    4260
catattttat ttgcctaaac aagctttgtg aaagttaagc gttcaaacac cagtgtcagt    4320
tacctggaag gctactaagg taaataagca aagcaggcca gttgtcagga aagcagagat    4380
tgtgcctggt gctgaatggc cttggggcct gatcttggca tggcagagac ctggggactg    4440
ccactgtccc caggtacgtg tacatggagc caaactgtgt gtcctgtggc attgtcagag    4500
ttatgttgaa atcttatttg aaaatgttag caacttactt gcattttttaa agaccaaaca    4560 agagctggta acctatggcc tcaagcatct gtccttccta aaaatggaat agtgggatgt    4620
agtgcttaat ggaaactgct aaatcttttt ctaaaaacta acagtggatt tttaaaatat    4680
attgtttttt gtgtatttca tttgtccttt gtatttatct aaaagggttg atatgatttt    4740
atatcttgct ctctattcct aatagtatta tgacttctta tttaaaataa ataacaattg    4800
ccggttttct gttaaaaaaa aaaaaa                                         4826
```

<210> SEQ ID NO 52
<211> LENGTH: 4344
<212> TYPE: DNA
<213> ORGANISM: Homo sapiens

<400> SEQUENCE: 52

```
gttggcagag cagttgtcct ggatggcgga gccttgggtt ccgggggcct gggacctgca      60 actcttttcta caagatatca agttattcta gtacaaccat ataataaat aatacctgaa     120 gtctcagtgt aacatggaca attaacagtg atgacagata aatacagacg catggggatc     180
aaatactagg caaaacgctt tttaaaagtg tatcaggctt ttaagaaaca ctgcaggatc     240
ctgtctatct taatgctgat agagctcagc taaaaattta ggaggttcta gtattcttca    300
tggctgaagc tgagagagtc tgaaaccctg atgcttaagc tccattctag atcatagctc    360
caactccttc aggatataag gaaaagagat tatattttcca caatgataga tctttggttg   420
tacaggtttc ccaatgagtg gatcatgatg accgtattgt agggacttgc catagtatgg    480
ctgcttcccg atctactcgt gttacaagat caacagtggg gttaaacggc ttggatgaat    540 cttttttgtgg tagaaacttta aggaatcgta gcattgcgca tcctgaagaa atctcttcta   600
attctcaagt acgatcaaga tcaccaaaga agagaccaga gcctgtgcca attcagaaag    660
gaaataataa tgggagaacc actgatttaa acagcagag tacccgagaa tcatgggtaa     720
gccctaggaa aagaggactt tcttcttcag aaaaggataa catagaaagg caggctatag    780
aaaattgtga gagaaggcaa acagaacctg tttcaccagt tttaaaaaga attaagcgtt    840
gtcttagatc tgaagcacca aacagttcag aagaagattc tcctataaaa tcagacaagg    900
agtcagtaga acagaggagt acagtagtgg acaatgatgc agattttcaa gggactaaac    960
gagcttgtcg atgtcttata ctggatgatt gtgagaaaag ggaaattaaa aaggtgaatg   1020
tcagtgagga agggccactt aattctgcag tagttgaaga atcacaggc tatttggctg    1080 tcaatggtgt tgatgacagt gattcagctg ttataaactg tgatgactgt cagcctgatg   1140
ggaacactaa acaaaatagc attggttcct atgtgttaca ggaaaaatca gtagctgaaa   1200
```

```
atggggatac ggatacccaa acttcaatgt tccttgatag taggaaggag gacagttata    1260
tagaccataa ggtgccttgc acagattcac aagtgcaggt caagttggag gaccacaaaa    1320
tagtaactgc ctgcttgcct gtggaacatg ttaatcagct gactactgag ccagctacag    1380 ggccctttc tgaaactcag tcatctttaa gggattctga ggaggaagta gatgtggtgg     1440
gagatagcag tgcctcaaaa gagcagtgta aagaaaacac caataacgaa ctggacacaa    1500
gtcttgagag tatgccagcc tccggagaac ctgaaccatc tcctgttcta gactgtgttt    1560
cagctcaaat gatgtcttta tcagaacctc aagaacatcg ttatactctg agaacctcac    1620
cacgaagggc agcccctacc agaggtagtc ccactaaaaa cagttctcct tacagagaaa    1680
atggacaatt tgaggagaat aatcttagtc ctaatgaaac aaatgcaact gttagtgata    1740
atgtaagtca atctcctaca aatcctggtg aaatttctca aaatgaaaaa gggatatgtt    1800
gtgactctca aaataatgga agtgaaggag taagtaaacc accctcagag gcaagactca    1860
atattggaca tttgccatct gccaaagaga gtgccagtca gcacattaca gaagaggaag    1920
atgatgatcc tgatgtttat tactttgaat cagatcatgt ggcactgaaa cacaacaaag    1980
attatcagag actattacag acgattgctg tactcgaggc tcagcgttct caagcagtcc    2040
aagaccttga agtttaggc aggcaccaga gagaagcact gaaaaatccc attggatttg     2100
tggaaaaact ccagaagaag gctgatattg ggcttccata tccacagaga gttgttcaat    2160
tgcctgagat cgtatgggac caatataccc atagccttgg gaattttgaa agagaattta    2220
aaaatcgtaa aagacatact agaagagtta agctagtttt tgataaagta ggtttacctg    2280
ctagaccaaa aagtccttta gatcctaaga aggatggaga gtcccttca tattctatgt      2340 tgcctttgag tgatggtcca gaaggctcaa gcagtcgtcc tcagatgata agaggacgct    2400
tgtgtgatga taccaaaacct gaaacattta accagttgtg gactgttgaa gaacagaaaa   2460
agctggaaca gctactcatc aaataccctc ctgaagaagt agaatctcga cgctggcaga    2520
agatagcaga tgaattgggc aacaggacag caaaacaggt tgccagccga gtacagaagt    2580
atttcataaa gctaactaaa gctggcattc cagtaccagg cagaacacca aacttatata    2640
tatactccaa aaagtcttca acaagcagac gacagcaccc tcttaataag catctctta    2700 agccttccac tttcatgact tcacatgaac cgccagtgta tatggatgaa gatgatgacc    2760
gatcttgttt tcatagccac atgaacactg ctgttgaaga tgcatcagat gacgaaagta    2820
ttcctatcat gtataggaat ttacctgaat ataaagaact attacagtttt aaaaagttaa   2880 agaagcagaa acttcagcaa atgcaagctg aaagtggatt tgtgcaacat gtgggctta    2940 agtgtgataa ctgtggcata gaacccatcc agggtgttcg gtggcattgc caggattgtc    3000
ctccagaaat gtctttggat ttctgtgatt cttgttcaga ctgtctacat gaaacagata    3060
ttcacaagga agatcaccaa ttagaaccta tttataggtc agagacattc ttagacagag    3120
actactgtgt gtctcaggc accagttaca attaccttga cccaaactac tttccagcaa    3180
acagatgaca tggaagagaa catcatttac tagtcctctt caacacatag caatggtatc    3240
attgttaatt atgtgcacag tttggaaaga ttctctgctt tcccagaaat gacactcaca    3300
gcatgagagc ttcctgagtg ttctcgtcaa gtacagctct gcaccgttgt ggctctagat    3360
cactgttcag cagctgaaca ttcctggtga gcaaaggttt ccctggtgaa ttttcacca     3420 ctgcgtttta ggtggtgatc ttaaatgggt gagatggaac gagagcacac attaaagaga    3480
gagtaaattc caaaggtttc aaagaacttg gtcataaata tgataatgag aagacaaagt    3540
atttatatta aaacagtttta gtagccttca gttttgtgaa aatagttttc agcacagaaa    3600
```

```
ctgacttctt tagacaaagt tttaaccaat gatggtgttt gcttctagga tatacacttt    3660
aaaagaactc actgtcccag tggtggtcat tgatggcctt tagtaaattg gagctgctta    3720
atcatattga tatctaattt cttttaacca caatgaattg tccttaatta ccaacagtga    3780
agcactacag gaggcaactg tggcattgct tccttaacca gctcatggtg tgtgaatgtt    3840
ataaaattgt cactcagata tattttttaa atgtaatgtt ataaagatg atcatgtgat     3900 gtgtacaaac tatggtgaaa agtgccagtg gtagtaactg tgtaaagttt ctaattcaca    3960
acattaattc ctttaaaata cacagccttc tgcctctgta tttggagttg tcagtacaac    4020
tcatcaaaga aaactgccta atataaaaat catatatatg gtaataattt ccctcttttg    4080
tagtctgcac aagatccata aaagattgta tttttattac tatttaaaca agtgattaaa    4140
tttagtctgc acagtgagca agggttcaca tgcattcttt tatactgctg gattttgttg    4200
tgcatcattt aaaacatttt gtatgtttct tcttatctgt gtatacagta tgttcttgaa    4260
tgatgttcat ttgtcaggag aactgtgaga aataaactat gtggatactg tctgtttata   4320
ttaaaagaaa aaaaaaaaaa aaaa                                           4344
```

COMPOSITIONS, METHODS AND KITS FOR DIAGNOSIS OF A GASTROENTEROPANCREATIC NEUROENDOCRINE NEOPLASM

CROSS REFERENCE TO RELATED APPLICATIONS

This application is a divisional of U.S. patent application Ser. No. 14/855,229, filed on Sep. 15, 2015. U.S. patent application Ser. No. 14/855,229 claims the priority to, and the benefit of, U.S. Provisional Application Ser. No. 62/050,465, filed on Sep. 15, 2014. The contents of each of the aforementioned applications are incorporated by reference in their entireties.

SEQUENCE LISTING

The Sequence Listing associated with this application is provided in text format in lieu of a paper copy, and is hereby incorporated by reference into the specification. The name of the text file containing the Sequence Listing is CLSL-001-D01US-SEQ.txt. The text file is 291 KB, was created on Aug. 1, 2019, and is being submitted electronically via EFS-Web.

BACKGROUND OF THE INVENTION

Gastroenteropancreatic (GEP) neuroendocrine neoplasm (GEP-NEN), also referred to as Gastroenteropancreatic Neuroendocrine Tumor and Neuroendocrine Tumor (NET), is the second most prevalent malignant tumor in the gastrointestinal (GI) tract in the U.S. Incidence and prevalence have increased between 100 and 600 percent in the U.S. over the last thirty years, with no significant increase in survival.

Heterogeneity and complexity of GEP-NENs has made diagnosis, treatment, and classification difficult. These neoplasms lack several mutations commonly associated with other cancers and microsatellite instability is largely absent. See Tannapfel A, Vomschloss S, Karhoff D, et al., "BRAF gene mutations are rare events in gastroenteropancreatic neuroendocrine tumors," *Am J Clin Pathol* 2005; 123(2): 256-60; Banck M, Kanwar R, Kulkarni A A, et al., "The genomic landscape of small intestine neuroendocrine tumors," *J Clin Invest* 2013; 123(6):2502-8; Zikusoka M N, Kidd M, Eick G, et al., Molecular genetics of gastroenteropancreatic neuroendocrine tumors. *Cancer* 2005; 104:2292-309; Kidd M, Eick G, Shapiro M D, et al. Microsatellite instability and gene mutations in transforming growth factor-beta type II receptor are absent in small bowel carcinoid tumors," *Cancer* 2005; 103(2):229-36.

Individual histopathologic subtypes as determined from tissue resources e.g., biopsy, associate with distinct clinical behavior, yet there is no definitive, generally accepted pathologic classification or prediction scheme, hindering treatment assessment and follow-up.

Existing diagnostic and prognostic approaches for GEP-NENs include imaging (e.g., CT or MRI), histology, measurements of circulating hormones and proteins associated with NENs e.g., chromogranin A and detection of some gene products. Available methods are limited, for example, by low sensitivity and/or specificity, inability to detect early-stage disease, or exposure to radiation risk. GEP-NENs often go undiagnosed until they are metastatic and often untreatable. In addition, follow-up is difficult, particularly in patients with residual disease burden.

There is a need for specific and sensitive methods and agents for the detection of GEP-NEN, including stable and progressive GEP-NEN, for example, for use in diagnosis, prognosis, prediction, staging, classification, treatment, monitoring, and risk assessment, and for investigating and understanding molecular factors of pathogenesis, malignancy, and aggressiveness of this disease. For example, such methods and agents are needed that can be repeatedly and directly collected with low risk exposure e.g., non-invasive peripheral blood test, be performed simply, rapidly, and at relatively low cost.

The present application overcomes the above-noted problems by providing novel compositions, methods, and kits for accurately diagnosing, detecting, and monitoring the presence of GEP-NENs and/or the types or stage of GEP-NEN in circulating peripheral blood samples. The described embodiments furthermore may be used to identify a level of risk for a patient to develop a progressive GEP-NEN, and/or to determine the risk of residual or reoccurring progressive GEP-NEN in a post-surgery or post-somatostatin treated human patient. In addition, it can be used as a prognostic for predicting response to therapy e.g., peptide receptor radiotherapy (PRRT).

SUMMARY OF THE INVENTION

In one aspect, the present invention relates to gastroenteropancreatic neuroendocrine neoplasm (GEP-NEN) biomarkers measured in circulating blood, the detection of which may be used in diagnostic, prognostic and predictive methods. Among the provided objects are GEP-NEN biomarkers, feature subsets and panels of the biomarkers, agents for binding and detecting the biomarkers, kits and systems containing such agents, and methods and compositions for detecting the biomarkers, for example, in biological samples e.g., blood, as well as prognostic, predictive, diagnostic, and therapeutic uses thereof.

Provided are agents, sets of agents, and systems containing the agents for GEP-NEN prognosis, detection and diagnosis. Typically, the systems include a plurality of agents (e.g., set of agents), where the plurality specifically binds to and/or detects a plurality of GEP-NEN biomarkers in a panel of GEP-NEN biomarkers. The agents may be isolated polypeptides or polynucleotides which specifically bind to one or more GEP-NEN biomarkers. For example, provided are sets of isolated polynucleotides and polypeptides that bind to a panel of GEP-NEN biomarkers, and methods and uses of the same.

Also provided are prognostic, diagnostic, and predictive methods and uses of the agents, compositions, systems, and kits for GEP-NEN and associated conditions, syndromes and symptoms. For example, provided are methods and uses for detection, diagnosis, classification, prediction, therapeutic monitoring, prognosis, or other evaluation of GEP-NEN or an outcome, stage or level of aggressiveness or risk thereof, or associated condition. In some embodiments, the methods are performed by determining the presence, absence, expression levels, or expression profile of a GEP-NEN biomarker, more typically a plurality of GEP-NEN biomarkers, such as a feature subset chosen from a panel of biomarkers, and/or comparing such information with normal or reference expression levels or profiles or standards. Thus, in some embodiments, the methods are carried out by obtaining a biological test sample and detecting the presence, absence, expression level score, or expression profile of a GEP-NEN biomarker as described herein. For example, the methods can be performed with any of the systems of agents, e.g., polynucleotides or polypeptides, provided herein. For example, the methods generally are carried out using one or more of the provided systems.

Provided are methods, agents and compositions for detection of and distinguishing between a number of different GEP-NEN types or stages. Exemplary GEP-NEN types and stages include stable disease (SD) and progressive (highly active) disease (PD).

In one aspect, the provided methods and compositions may be used to specifically and sensitively detect different stages of GEP-NENs, such as GEP-NENs in a stable disease (SD) or progressive disease (PD) states; in some aspects, the methods and compositions may be used to predict disease progression, treatment response, and metastasis. Methods and compositions provided herein are useful for diagnosis, prognosis, prediction, staging, classification, treatment, monitoring, assessing risk, and investigating molecular factors associated with GEP-NEN disease.

Provided are such methods capable of being carried out quickly, simply, and at relatively low cost, as compared to other diagnostic and prognostic methods.

Provided are methods and compositions that are useful for defining gene expression-based classification of GEP-NENs, and thus are useful for allowing the prediction of malignancy and metastasis, such as in early stage disease or using histologically negative samples, providing accurate staging, facilitating rational therapy, and in developing large validated clinical datasets for GEP-NEN-specific therapeutics.

The GEP-NEN biomarkers may include a subset of biomarkers, the expression of which is different in or is associated with the presence or absence of GEP-NEN, or is different in or is associated with a particular classification, stage, aggressiveness, severity, degree, metastasis, symptom, risk, treatment responsiveness or efficacy, or associated syndrome. The subset of GEP-NEN biomarkers typically includes at least 22 GEP-NEN biomarkers. In some embodiments, the subset of biomarkers includes at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers, or includes at or about 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 GEP-NEN biomarkers.

For example, in some aspects, the subset of biomarkers includes at least 22, or at least 38, or at least 51 biomarkers. In a particular example, the subset contains at least 22 biomarkers, or about 22 biomarkers, or 22 biomarkers, chosen from a panel of 38 biomarkers. In some embodiments, the subset of biomarkers includes at least 22, 23, 24, 25, 26, 27, 28, 29, 30, 31, 32, 33, 34, 35, 36, 37, or 38 biomarkers chosen from a panel of 38 biomarkers.

Because the systems, methods, and kits contain a plurality of agents that specifically bind to or hybridize to the biomarkers in the panel, the number of biomarkers generally relates to the number of agents in a particular system. For example, among the provided methods is a method that contains at least 22 binding agents, which specifically hybridizes to or binds to a subset of at least 22 GEP-NEN biomarkers, respectively.

In some aspects, the subset of biomarkers includes at least 22, 23, 24, 25, 26, 27, 28, 29, 30, 31, 32, 33, 34, 35, 36, 37, and/or all of the following group of gene products, including polynucleotides (e.g. 38 transcripts) and polypeptides: PNMA2, NAP1L1, FZD7, SLC 18A2/VMAT2, NOL3, SSTR5, TPH1, RAF1, RSF1, SSTR3, SSTR1, CD59, ARAF, APLP2, KRAS, MORF4L2, TRMT 112, MK167/ KI67, SSTR4, CTGF, SPATA7, ZFHX3, PHF21A, SLC 18A 1 N/VMAT 1, ZZZ3, TECPR2, ATP6V 1H, OAZ2, PANK2, PLD3, PQBP 1, RNF41, SMARCD3, BNIP3L, WDFY3, COMMD9, BRAF, and/or GLT8DI gene products.

In a particular example, the subset of 22 biomarkers includes PNMA2, NAP1L1, FZD7, SLC18A2, NOL3, SSTR5, TPH1, RAF1, RSF1, SSTR3, SSTR1, CD59, ARAF, APLP2, KRAS, MORF4L2, TRMT112, MKI67, SSTR4, CTGF, SPATA7, and ZFHX3 gene products.

Among the provided methods, agents, and systems are those that are able to classify or detect a GEP-NEN in a human blood sample. In some embodiments, the provided systems and methods can identify or classify a GEP-NEN in a human blood sample. In some examples, the systems can provide such information with a specificity, sensitivity, and/or accuracy of at least 75%, 80%, 85%, 90%, 91%, 92%, 93%, 94%, 95%, 96%, 97%, 98° %, 99%0 or 100%, e.g., at least 80%.

In some embodiments, the system can predict treatment responsiveness to, or determine whether a patient has become clinically stable following, or is responsive or non-responsive to, a GEP-NEN treatment, such as a surgical intervention or drug therapy (for example, somatostatin analog therapy). In some cases, the methods and systems do so with a specificity, sensitivity, and/or accuracy of at least 75%, 80%, 85%, 90%, 91%, 92%, 93%, 94%, 95%, 96%, 97%, 98%, 99% or 100%, e.g., with at least 90% accuracy. In some cases, it can differentiate between treated and untreated GEP-NEN with a specificity, sensitivity, and/or accuracy of at least 75%, 80%, 85%, 90%, 91%, 92%, 93%, 94%, 95%, 96%, 97%, 98%, 99% or 100%, e.g., with a sensitivity and specificity of at least 85%.

In some cases, the system can determine diagnostic or prognostic information regarding a subject previously diagnosed with GEP-NEN, for example, whether the subject has a stable disease (SD) or progressive disease (PD) state of GEP-NEN, or is in complete remission, for example, would be clinically categorized as having stable disease, progressive disease, or being in complete remission.

In some embodiments, the agents for detecting the biomarkers, e.g., the sets of polynucleotide or polypeptide agents, and uses thereof, are capable of distinguishing between the presence and absence of GEP-NEN in a biological sample, between GEP-NEN and mucosal samples and GEP-NEN samples, and/or between specific classes or subtypes of GEP-NENs, for example, between aggressive (high activity) and benign (low activity) GEP-NEN samples, In one aspect, the system is able to classify or detect a GEP-NEN in a human blood sample or human saliva sample. In one aspect, the human sample is whole blood or nucleic acid or protein prepared from whole blood, without first sorting or enriching for any particular population of cells. In one aspect, the system includes agents that bind to biomarkers in a subset of at least 22 GEP-NEN biomarkers.

In some embodiments, in addition to the agents that bind the GEP-NEN biomarkers, the provided systems contain one or more agents that bind to gene products for use in normalization or as controls, for example, housekeeping gene products include ALG9 gene products, In some embodiments, the methods include selecting a subset of at least 22 biomarkers chosen from a panel of 38 biomarkers useful in generating a classifier for GEP-NEN and different stages of GEP-NEN.

In some embodiments, the methods further include contacting a test sample from the human patient with a plurality of agents specific to the biomarkers in the subset.

The biological test sample used with the methods can be any biological sample, such as tissue, biological fluid, or other sample, including blood samples, such as plasma, serum, whole blood, buffy coat, or other blood sample, tissue, saliva, serum, urine, or semen sample. In some aspects, the sample is obtained from blood. Often, the test sample is taken from a GEP-NEN patient.

The agents can be any agents for detection of biomarkers, and typically are isolated polynucleotides or isolated polypeptides or proteins, such as antibodies, for example, those that specifically hybridize to or bind to a subset or panel of GEP-NEN biomarkers including at least 22 GEP-NEN biomarkers.

In some embodiments, the methods are performed by contacting the test sample with one of the provided agents, more typically with a plurality of the provided agents, for example, one of the provided systems, such as a set of polynucleotides that specifically bind to the subset of GEP-NEN biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the GEP-NEN biomarkers, such as expression levels thereof, includes detecting the presence, absence, or amount of RNA. In one example, the RNA is detected by PCR or by hybridization.

In one aspect, the polynucleotides include sense and antisense primers, such as a pair of primers that is specific to each of the GEP-NEN biomarkers in the subset of biomarkers. In one aspect of this embodiment, the detection of the GEP-NEN biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of GEP-NEN biomarkers, and detecting products of the amplification. In some embodiments, the GEP-NEN biomarkers include mRNA, cDNA, or protein.

In some embodiments, the methods further include determining a mathematically-derived expression level score of biomarkers selected in the subset in the test sample. This is the MAARC-NET score (Multi-Analyte Risk Classification for NETs). It has two scales 0-8 and the percentage-derivatives scaled to 100% i.e., 0-100%.

The mathematically-derived MAARC-NET score is the product of a classifier built from predictive classification algorithms, e.g. support vector machines (SVM), linear discriminant analysis (LDA), K-nearest neighbor (KNN) and/or naïve Bayes (NB). In some examples, the classifier is generated from a combination of SVM, LDA, KNN, and NB classification algorithms and a 10-fold cross-validation design.

In some embodiments, the methods further include a step of determining a mathematically-derived expression level score of biomarkers in the subset in a normal or reference sample, typically carried out prior to the normalization and comparing steps.

The normal or reference sample may be from a healthy patient or a patient who has GEP-NEN. Where the test sample is from a patient with GEP-NEN, the normal or reference sample or level may be from the same or a different patient. For example, the normal or reference sample may be from the GEP-NEN patient from a tissue, fluid or cell not expected to contain GEP-NEN or GEP-NEN cells. On another aspect, the normal or control sample is from the GEP-NEN patient before or after therapeutic intervention, such as after surgery or chemical intervention.

In another aspect, the reference or normal sample is from a tissue or fluid that corresponds to the GEP-NEN or metastasis of the test sample, from a healthy individual, such as normal enterochromaffin cell (EC) preparation or small intestinal (SI) sample, or normal liver, lung, bone, blood, saliva, or other bodily fluid, tissue, or biological sample. In another embodiment, the test sample is from a metastasis, plasma, or whole blood or other fluid of a GEP-NEN patient and the reference sample is from primary tumor or fluorescent activated cell (FAC)-sorted tumor cells.

In other aspects, the test sample is from blood and the test biological sample is from the GEP-NEN patient after treatment and the reference sample is from the same GEP-NEN patient as the test biological sample, prior to treatment; the reference sample is from a tissue or fluid not containing GEP-NEN cells; the reference sample is from a healthy individual; the reference sample is from a cancer other than GEP-NEN; the reference sample is from an EC cell or SI tissue; the test biological sample is from a metastatic GEP-NEN and the reference sample is from a non-metastatic GEP-NEN; or the reference sample is from a GEP-NEN of a different classification compared to the GEP-NEN patient from which the test biological sample is obtained.

In one aspect, the test biological sample is from a GEP-NEN patient prior to treatment and the normal or reference sample is from the GEP-NEN patient after treatment. In another aspect, the normal or reference sample is from a non-metastatic tissue of the GEP-NEN patient.

In some cases, a normalization step is performed to normalize the level of expression score of the biomarkers in the subset in the test sample to the level of expression score of the biomarkers in the subset in the reference sample.

In some cases, a comparison step is performed to determine whether there is a difference, such as a significant difference, between the normalized expression level score and a predetermined cut-off value or score threshold. Certain predetermined cut-off values or score thresholds are indicative of different stages of GEP-NEN, while others are indicative of different levels of risk, i.e. low, intermediate, or high, for developing a progressive GEP-NEN.

In one aspect, the methods include comparing the normalized expression level score with a predetermined cutoff value chosen to exclude a control or reference sample, wherein a normalized expression level above the predetermined cutoff value is indicative of a GEP-NEN, wherein the cutoff value is about 2 (on a scale of 0-8, or 13.4% on a scale of 0-100%).

In another aspect, the methods include comparing the normalized expression level score with a predetermined cutoff value chosen to exclude a non-progressive GEP-NEN, wherein a normalized expression level above the predetermined cutoff value of 5 (on a scale of 0-8, or 43.4% on a scale of 0-100%) is indicative of progressive GEP-NEN.

In another aspect, the methods further include identifying the level of risk for a human patient to develop progressive GEP-NEN, wherein a normalized expression level score below about 5 (or 43.4%) is indicative of a low level of risk for developing a progressive GEP-NEN, a normalized expression level score between about 5 and 7 (43.4%-63.4%) is indicative of an intermediate level of risk for developing progressive GEP-NEN, and a normalized expression level score between about 7 and 8 (>63.4%) is indicative of a high level of risk for developing progressive GEP-NEN.

In some cases, a subsequent determination is performed for the actual expression level (not mathematically-derived expression level score) of individual genes, where identifying the intermediate level of risk for developing progressive GEP-NEN further includes determining a first state of intermediate risk, wherein the normalized expression level score between a non-progressive reference sample and the test sample is about 5 (43.4%), the normalized expression level of SMARCD3 is below a first threshold value, and the expression level of TPH1 is below a second threshold value.

In other cases, identifying the intermediate level of risk for developing progressive GEP-NEN further includes determining a second state of intermediate risk, wherein the normalized expression level score between a non-progressive reference sample and the test sample is about 6 (52.7%), the normalized expression level of VMAT1 is equal to or above 0, and the expression level of PHF21A is equal to or above a first threshold value.

In some cases, identifying the intermediate level of risk for developing progressive GEP-NEN further includes determining a third state of intermediate risk, wherein the normalized expression level score between a non-progressive reference sample and the test sample is about 7 (63.4%), the expression level of VMAT1 is equal to or above 0, and the expression level of PHF21A is equal to or below a first threshold value.

In other cases, identifying the high level of risk for developing progressive GEP-NEN further includes determining the normalized expression level score of ZZZ3, wherein the expression level score of ZZZ3 is equal to or less than 14.

Also provided are methods and uses of the provided biomarkers, agents, systems and detection methods for use in determining the risk of residual or reoccurring progressive GEP-NEN in a post-surgery human patient. In such cases, the level of risk for residual or reoccurring progressive GEP-NEN in the post-surgical test sample is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8>63.4%) is indicative of a high level of risk.

In some cases, identifying the level of risk for residual or reoccurring progressive GEP-NEN further includes determining an elevated expression level score of gene products in at least one gene cluster as determined between a pre-surgical test sample from the patient and the post-surgical test sample.

In some embodiments, the at least one gene cluster includes the proliferome, signalome, secretome I and II, plurome, epigenome, plurome, SSTRome, and combinations thereof.

In other embodiments, the at least one gene cluster includes the PD cluster, the ND cluster, the TD cluster, and the ID cluster. The PD cluster includes the proliferome, signalome, secretome II, plurome, and epigenome. The ND cluster includes the ARAF1, BRAF, KRAS, RAF1, Ki67, NAP1L1, NOL3, GLT8D1, PLD3, PNMA2, VMAT2, TPH1, FZD7, MORF4L2, and ZFHX3. The TD cluster includes the Secretome (I), the Plurome, and the SSTRome. The ID cluster includes the Proliferome, secretome (II), plurome, and epigenome.

In other embodiments, determining the elevated expression of gene products in at least one gene cluster includes evaluating a plurality of gene cluster algorithms including the PDA, NDA, TDA, and IDA algorithms.

In some embodiments, the methods further include treating the patient based on the indication of intermediate or high level of risk for residual or recurring progressive GEP-NEN by one of surgery or therapy.

Also provided are methods and uses of the provided biomarkers, agents, systems and detection methods for use in determining the risk of residual or reoccurring progressive GEP-NEN in a post-somatostatin analog treated patient. In such cases, the level of risk for somatostatin treatment failure is identified, wherein a normalized expression level score below about 5 (43.4%) is indicative of a low level of risk, a normalized expression level score between about 5 and 7 (43.4-63.4%) is indicative of an intermediate level of risk, and a normalized expression level score between about 7 and 8 (>63.4%) is indicative of a high level of risk.

The methods may further include determining the difference in expression level score in at least one of the SSTRome and Proliferome gene clusters between a pre-therapy test sample from the human patient and the post-therapy test sample, wherein an increased level of expression score is indicative of increased risk for residual or reoccurring progressive GEP-NEN.

In some cases, a somatostatin analog is administered to the human patient-based on the indication of intermediate or high level of risk for residual or recurring progressive GEP-NEN and an increased level of expression in at least one of the SSTRome and Proliferome gene clusters.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 1A-1E are graphs showing differential exon expression in a marker gene panel inferred from an Affymetrix Human Exon 1.0 ST array in neuroendocrine tumor (NET) tissue relative to normal intestinal mucosa controls. RMA-normalized exon expressions of (FIG. 1A) Tph1, (FIG. 1B) VMAT2, (FIG. 1C) SCG5, (FIG. 1D) CgA, and (FIG. 1E) PTPRN2 were visualized in normal (green) and tumor (samples).

FIGS. 2A-2E are graphs showing the validation of alternative splicing in marker genes by Reverse transcriptase polymerase chain reaction (RT-PCR). Marker genes (FIG. 2A) Tph1, (FIG. 2B) VMAT2, (FIG. 2C) SCG5, (FIG. 2D) CgA, and (FIG. 2E) PTPRN2 were differentially expressed in NET samples relative to normal mucosa controls.

(FIG. 4A) Frequency distribution for the 0-4 score in the controls, SD and PD; (FIG. 4B) Frequency distribution using a 0-8 score in the same sample set; (FIG. 4C) Correlation assessment for each of the two scores in (FIG. 4A) and (FIG. 4B).

In FIG. 5A, NETs had a significantly elevated score compared to controls, where values for PD were higher than SD. In FIG. 5B, a ROC curve of controls versus GEP-NETS is shown, wherein the AUC was >0.98, $p<0.0001$. *$p<0.05$ vs. controls, #$p<0.05$ vs. SD (2-tailed Mann-Whitney U-test).

(FIG. 6B) a frequency distribution graph for the 0-8 score in SD and PD. #$p<0.0001$ vs. SD (2-tailed Mann-Whitney U-test).

FIGS. 7A-7B are (FIG. 7A) a graph of ROC of SD versus PD NETs with an AUC of >0.93, $p<0.0001$ and (FIG. 7B) a graph of the percentage of SD and PD NETs correctly called using a cut-off score of >7.

FIG. 14A shows a delineation of tumor (adenocarcinoma) derived hallmarks from Hanahan D, Weinberg R A: Hallmarks of cancer: the next generation. *Cell* 2011, 144(5): 646-674. FIG. 14B shows NET hallmark based on the Hanahan and Weinberg classification.

FIGS. 20A-20B are graphs showing (FIG. 20A) normalized gene expression of PDA and NDA gene cluster algorithms in the combined set, and (FIG. 20B) a ROC analysis curve of PDA and NDA for differentiating SD from PD, where *$p<0.05$ vs. SD.

FIGS. 24A-24B are illustrations showing differences in the NETest nomogram in (FIG. 24A) pre-surgical therapy conditions and (FIG. 24B) post-surgical therapy conditions.

FIGS. 27A-27I are graphs showing the differences in NETest score for gene-derived clusters, (FIG. 27A) SSTRome, (FIG. 27B) Proliferome, (FIG. 27C) Signalome, (FIG. 27D) Metabolome, (FIG. 27E) Secretome, (FIG. 27F) Secretome, (FIG. 27G) Plurome, (FIG. 27H) EpiGenome, and (FIG. 27I) ApopTome, in pre- and post-surgery conditions.

FIGS. 31A-31I are graphs showing the differences in gene-derived clusters, specifically (FIG. 31A) SSTrome, (FIG. 31B) Proliferome, (FIG. 31C) Signalome, (FIG. 31D) Metabolome, (FIG. 31E) Secretome, (FIG. 31F) Secretome, (FIG. 31G) Plurome, (FIG. 31H) EpiGenome, and (FIG. 31I) ApopTome, in stably treated patients (SD) and SSA treatment failure (equivalent of PD conditions).

FIGS. 38A-38F are graphs including predicted Ki67 index versus Ki67 index in (FIGS. 38A-38B) SSTRome, (FIGS. 38C-38E) All genes, and (FIGS. 38D-38F) high relevant genes (KRAS, SSTR4, and VPS13C).

(FIG. 40A) and (FIG. 40C)) and all genes (Group II: (FIG. 40B) and (FIG. 40D)).

FIGS. 41A-41F are graphs modeling MTV (molecular tumor volume—a measure of the tumor burden) in individual genes (FIGS. 41A-41B), SSTRome (FIGS. 41C-41E), and all genes (FIGS. 41D-41F).

(FIG. 44C) change in CgA level versus clinical status at 6M FuP.

FIGS. 46A-46B shows the accuracy of the NETest Score versus CgA for treatment responses.

DETAILED DESCRIPTION OF THE INVENTION

Figure 3:
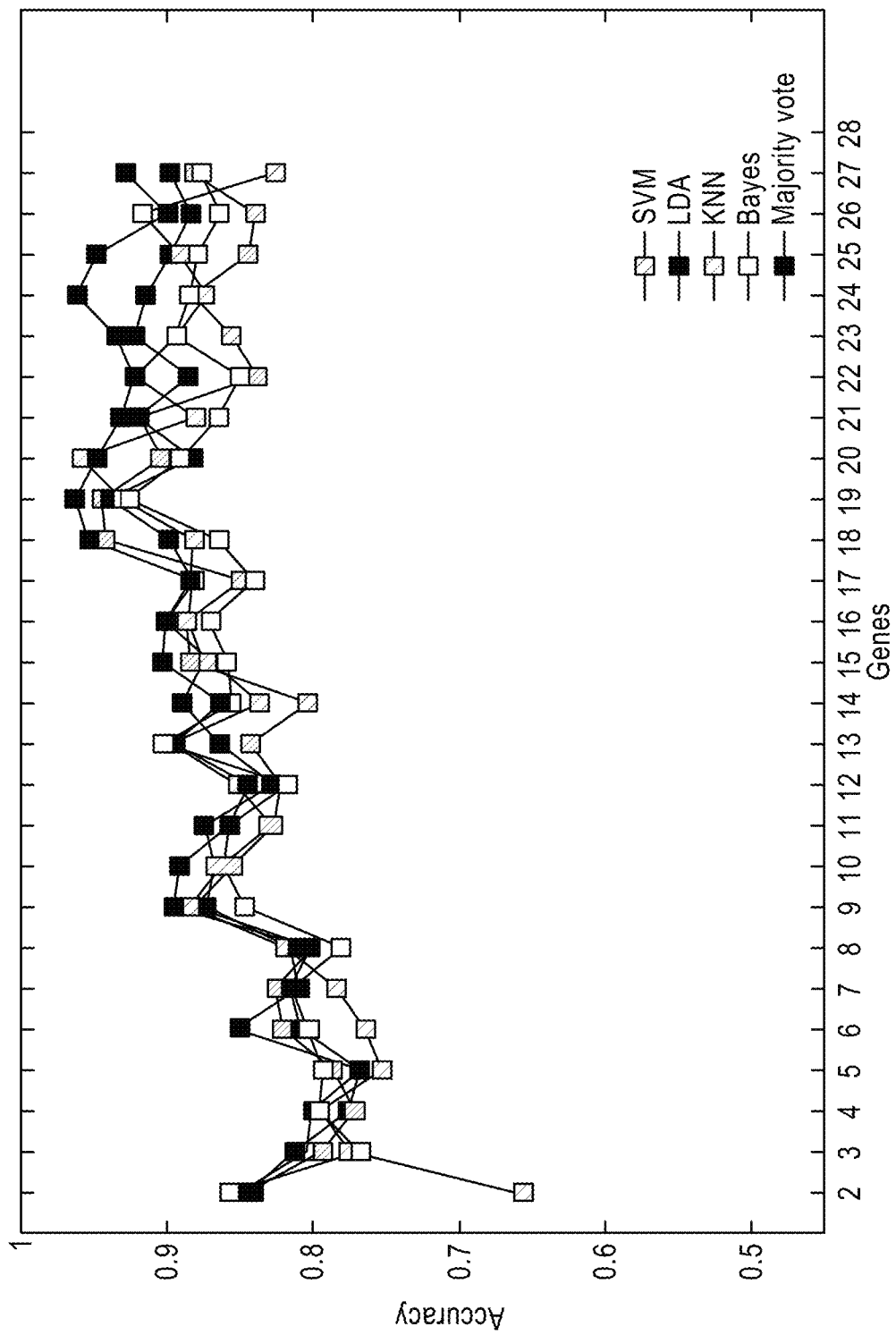
FIG. 3 is a line graph showing the prediction accuracy of four classification algorithms (SVM, LDA, KNN, and Bayes) using sequential addition of up to 22 significantly up-regulated genes (p<0.05) in GEP-NET samples obtained using the results of 10-fold cross validation.

Three-quarters of all human genes undergo alternative splicing. Identifying and defining cancer-specific splice variants is therefore advantageous for the development of biomarker assays. The described embodiments derive from the surprising discovery that particular cancer-specific splice variants of NET marker genes can be used to maximize the difference between neoplasia and normal samples in biomarker diagnostic methods.

The present invention provides a method for detecting a gastroenteropancreatic neuroendocrine neoplasm (GEP-NEN) in a subject in need thereof, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%.

The score is based on a "majority vote" strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naïve Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN.

The at least 22 biomarkers can include APLP2, ARAF, CD59, CTGF, FZD7, KRAS, MKI67/KI67, MORF4L2, NAP1L1, NOL3, PNMA2, RAF1, RSF1, SLC18A2/VMAT2, SMARCD3, SPATA7, SSTR1, SSTR3, SSTR4, SSTR5, TPH1, TRMT112, and ZFHX3.

The methods can further include determining the presence of a progressive GEP-NEN in the subject when the normalized expression level is equal to or higher than the predetermined cutoff value, wherein the predetermined cutoff value is 5 on a scale of 0-8, or less than 55% on a scale of 0-100%.

The methods can further include identifying a level of risk for the subject to develop a progressive GEP-NEN the method further including identifying a low level of risk for developing a progressive GEP-NEN when the normalized expression level is less than a predetermined cutoff value of 5 on a scale of 0-8, or less than 55% on a scale of 0-100%; identifying an intermediate level of risk for developing a progressive GEP-NEN when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk for developing a progressive GEP-NEN when the normalized expression level is equal to or greater than a predetermined cutoff value of 7 on a scale of 0-8, or equal to or greater than 75% on a scale of 0-100%.

The biomarker can be RNA, cDNA, or protein. When the biomarker is RNA, the RNA can be reverse transcribed to produce cDNA (such as by RT-PCR, and the produced cDNA expression level is detected. The expression level of the biomarker can be detected by forming a complex between the biomarker and a labeled probe or primer. When the biomarker is RNA or cDNA, the RNA or cDNA detected by forming a complex between the RNA or cDNA and a labeled nucleic acid probe or primer. The complex between the RNA or cDNA and the labeled nucleic acid probe or primer can be a hybridization complex. When the biomarker is protein, the protein can be detected by forming a complex between the protein and a labeled antibody. The label can be any label for example a fluorescent label, chemiluminescence label, radioactive label, etc.

The test sample can be any biological fluid obtained from the subject. Preferably, the test sample is blood, serum, plasma or neoplastic tissue. The reference sample can be any biological fluid obtained from a subject not having, showing symptoms of or diagnosed with a neoplastic disease. Preferably, the reference sample is blood, serum, plasma or non-neoplastic tissue.

The subject in need thereof can be a subject diagnosed with a GEP-NEN, a subject having at least one GEP-NEN symptom or a subject having a predisposition or familial history for developing a GEP-NEN. The subject can be any mammal. Preferably, the subject is human. The terms subject and patient are used interchangeably herein.

The methods can further include treating a subject identified as having an intermediate level or high level of risk for developing a progressive GEP-NEN with surgery or drug therapy. The drug therapy can be somatostatin analog treatment or peptide receptor radiotherapy therapy (PRRT). The methods can further include treating a subject identified as having a low level of risk for developing a progressive GEP-NEN with regular or periodic monitoring over at least a six month period, a twelve month period, an eighteen month period or twenty four month period.

The present invention also provides a method for differentiating stable and progressive GEP-NEN in a subject comprising determining that the normalized expression level of the at least 22 biomarkers from the test sample from the subject is equal to or greater than a predetermined cutoff value of 5 and less than a predetermined cutoff value of 6, according to the methods of the present invention; detecting an expression level of SMARCD3 and TPH1 from the test sample and from a reference sample by contacting the test sample and the reference sample with a plurality of agents specific to detect the expression of SMARCD3 and the expression of TPH1; normalizing the expression level of SMARCD3 and TPH1 in the test sample to the expression level of SMARCD3 and TPH1 in the reference sample; comparing the normalized expression level of SMARCD3 and TPH1 in the test sample with a first and a second predetermined cutoff value, respectively; and determining the presence of stable GEP-NEN in the subject when the normalized expression level of SMARCD3 is greater than the first predetermined cutoff value and the expression level of TPH1 is equal to or greater than the second predetermined cutoff value, or determining the presence of progressive GEP-NEN in the subject when the normalized expression level of SMARCD3 is equal to or less than the first predetermined cutoff value and the expression level of TPH1 is less than the second predetermined cutoff value wherein the first predetermined cutoff value is 1.3 on a scale of 0-8 and wherein the second predetermined cutoff value is 4 on a scale of 0-8.

The first predetermined cutoff value of 1.3 corresponds to 12% on a scale of 0-100% and wherein the second predetermined cutoff value of 4 corresponds to 41% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 6 and less than a predetermined cutoff value of 7, according to the methods of the present invention; detecting an expression level of VMAT1 and PHF21A from the test sample and from a reference sample by contacting the test sample and reference sample with a plurality of agents specific to detect the expression of VMAT1 and the expression of PHF21A, normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is less than the second predetermined cutoff value, or determining the presence of progressive GEP-NEN in the subject when the normalized expression level of VMAT1 is equal to or greater than the first predetermined cutoff value and the expression level of PHF21A is equal to or greater than the second predetermined cutoff value wherein the first predetermined cutoff value is 0 on a scale of 0-8 and wherein the second predetermined cutoff value is 1.2 on a scale of 0-8.

The first predetermined cutoff value of 0 corresponds to 0% on a scale of 0-100% and wherein the second predetermined cutoff value of 1.2 corresponds to 8% on a scale of 0-100%.

The present invention also provides a method for differentiating stable and progressive GEP-NEN in a subject comprising determining that the normalized expression level of the at least 22 biomarkers from the test sample from the subject is equal to or greater than a predetermined cutoff value of 7 and less than a predetermined cutoff value of 8, according to the methods of the present invention; detecting an expression level of VMAT1 and PHF21A from the test sample and a reference sample by contacting the test sample and the reference sample with a plurality of agents specific to detect the expression of VMAT1 and the expression of PHF21A; normalizing the expression level of VMAT1 and PHF21A in the test sample to the expression level of VMAT1 and PHF21A in the reference sample; comparing the normalized expression level of VMAT1 and PHF21A in the test sample with a first and a second predetermined cutoff value, respectively; and determining the presence of stable GEP-NEN in the subject when the normalized expression level of VMAT1 is equal to or greater than the first predetermined cutoff value and the expression level of PHF21A is greater than the second predetermined cutoff value, or determining the presence of progressive GEP-NEN in the subject when the normalized expression level of VMAT1 is equal to or greater than the first predetermined cutoff value and the expression level of PHF21A is equal to or less than the second predetermined cutoff value wherein the first predetermined cutoff value is 0 on a scale of 0-8 and wherein the second predetermined cutoff value is 1 on a scale of 0-8.

The first predetermined cutoff value of 0 corresponds to 0% on a scale of 0-100% and wherein the second predetermined cutoff value of 1 corresponds to 7% on a scale of 0-100%.

The present invention also provides a method for differentiating stable and progressive GEP-NEN in a subject comprising determining that the normalized expression level of the at least 22 biomarkers from the test sample from the subject is equal to a predetermined cutoff value of 8, according to the methods of the present invention; detecting an expression level of ZZZ3 from the test sample and a reference sample by contacting the test sample and the reference sample with at least one agent specific to detect the expression of ZZZ3; normalizing the expression level of ZZZ3 in the test sample to the expression level of ZZZ3 in the reference sample; comparing the normalized expression level of ZZZ3 in the test sample with a predetermined cutoff value; and determining the presence of progressive GEP-NEN in the subject when the normalized expression level of ZZZ3 is equal to or less than the predetermined cutoff value, wherein the predetermined cutoff value is 1 on a scale of 0-8.

The predetermined cutoff value of 1 corresponds to 18% on a scale of 0-100%.

The methods of the present invention further include determining the expression level of each of 16 biomarkers from a test sample from the subject and a reference sample by contacting the test sample and the reference sample with a plurality of agents specific to detect the expression of each of the 16 biomarkers, wherein the 16 biomarkers comprise Ki67, NAP1L1, NOL3, TECPR2, ARAF1, BRAF, KRAS, RAF1, PQBP1, TPH1, COMMD9, MORF4L2, RNF41, RSF1, SMARCD3, and ZFHX3; summing the expression level of each of the 16 biomarkers of the test sample to generate a progressive diagnostic I total test value and summing the expression level of each of the 16 biomarkers of the reference sample to generate a progressive diagnostic I total reference value, wherein an increased value of the progressive diagnostic I total test value compared to the progressive diagnostic I total reference value indicates the presence of progressive GEP-NEN in the subject.

The methods of the present invention further include determining the expression level of each of 15 biomarkers from a test sample from the subject and a reference sample by contacting the test sample and the reference sample with a plurality of agents specific to detect the amount of each of the 15 biomarkers, wherein the 15 biomarkers comprise ARAF1, BRAF, KRAS, RAF1, Ki67, NAP1L1, NOL3, GLT8D1, PLD3, PNMA2, VMAT2, TPH1, FZD7, MORF4L2 and ZFHX3; averaging the expression level of each of the 15 biomarkers of the test sample to generate a progressive diagnostic II test value and averaging the expression level of each of the 15 biomarkers of the reference sample to generate a progressive diagnostic II reference value, wherein an increased value of the progressive diagnostic II test value compared to the progressive diagnostic II reference value indicates the presence of progressive GEP-NEN in the subject.

The methods of the present invention further include determining the expression level of each of 7 biomarkers from a test sample from the subject and a reference sample by contacting the test sample and the reference sample with a plurality of agents specific to detect the amount of each of the 7 biomarkers, wherein the 7 biomarkers comprise PNMA2, VMAT2, COMMD9, SSTR1, SSTR3, SSTR4, and SSTR5; summing the expression level of each of the 7 biomarkers of the test sample to generate a progressive diagnostic III total test value and summing the expression level of each of the 7 biomarkers of the reference sample to generate a progressive diagnostic III total reference value, wherein an increased value of the progressive diagnostic III total test value compared to the progressive diagnostic III total reference value indicates the presence of progressive GEP-NEN in the subject.

The methods of the present invention further include determining the expression level of each of 11 biomarkers from a test sample from the subject and a reference sample by contacting the test sample and the reference sample with a plurality of agents specific to detect the amount of each of the 11 biomarkers, wherein the 11 biomarkers comprise Ki67, NAP1L1, NOL3, TECPR2, PQBP1, TPH1, MORF4L2, RNF41, RSF1, SMARCD3, and ZFHX3; summing the expression level of each of the 11 biomarkers of the test sample to generate a progressive diagnostic IV total test value and summing the expression level of each of the 11 biomarkers of the reference sample to generate a progressive diagnostic IV total reference value, wherein an increased value of the progressive diagnostic IV total test value compared to the progressive diagnostic IV total reference value indicates the presence of progressive GEP-NEN in the subject.

The present invention also provides a method for determining the risk of relapsing or reoccurring progressive GEP-NEN in a post-surgery subject, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; identifying an absence of risk of relapsing or reoccurring progressive GEP-NEN post-surgery when the normalized expression level is less than a predetermined cutoff value of 2 on a scale of 0-8, or less than 0% on a scale of 0-100%; identifying a low level of risk of relapsing or reoccurring progressive GEP-NEN post-surgery when the normalized expression level is less than a predetermined cutoff value of 5 on a scale of 0-8, or less than 55% on a scale of 0-100%; identifying an intermediate level of risk of relapsing or reoccurring progressive GEP-NEN post-surgery when the normalized expression level is equal to or greater than a predetermined cutoff value of 5 and less than a predetermined cutoff value of 7 on a scale of 0-8, or equal to or greater than 55% and less than 75% on a scale of 0-100%; or identifying a high level of risk of relapsing or reoccurring progressive GEP-NEN post-surgery when the normalized expression level is equal to or greater than a predetermined cutoff value of 7 on a scale of 0-8, or equal to or greater than 75% on a scale of 0-100%.

The present invention also provides a method for determining the risk of relapsing or reoccurring progressive GEP-NEN in a subject treated with somatostatin, including determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; when a GEP-NEN is present, determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise Ki67, NAP1L1, NOL3, TECPR2, SSTR1, SSTR2, SSTR4, and SSTR5; summing the expression level of each of the 8 biomarkers of the test sample to generate a progressive diagnostic V total test value and summing the expression level of each of the 8 biomarkers of the reference sample to generate a progressive diagnostic V total reference value, wherein an increased value of the progressive diagnostic V total test value compared to the progressive diagnostic V total reference value indicates the presence of relapsing or reoccurring progressive GEP-NEN in the subject.

The present invention also provides a method for determining a response of a peptide receptor radionucleotide therapy (PRRT) of a GEP-NEN in a subject in need thereof, including determining the expression level of each of 8 biomarkers from a test sample from the subject and a reference sample by contacting the test sample and the reference sample with a plurality of agents specific to detect the expression of each of the 8 biomarkers, wherein the 8 biomarkers comprise ARAF1, BRAF, KRAS, RAF1, ATP6V1H, OAZ2, PANK2, PLD3; normalizing the expression level of the 8 biomarkers in the test sample to the expression level of the 8 biomarkers in the reference sample; comparing the normalized expression level of the 8 biomarkers in the test sample with a predetermined cutoff value; determining the presence of a PRRT-responsive GEP-NEN in the subject when the normalized expression level of the 8 biomarkers is greater than a predetermined cutoff value, wherein the predetermined cutoff value is 5.9 on a scale of 0-8.

The present invention also provides a method for determining a response of a peptide receptor radionucleotide therapy (PRRT) of a GEP-NEN in a subject in need thereof, including (a) following a first cycle of PRRT therapy: determining the expression level of at least 22 biomarkers from a first cycle test sample from the subject by contacting the first cycle test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the first cycle test sample to the expression level of the at least 22 biomarkers in the reference sample; (b) following a second cycle of PRRT therapy, determining the expression level of at least 22 biomarkers from a second cycle test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the second cycle test sample to the expression level of the at least 22 biomarkers in the reference sample; (c) determining a ratio of change of the normalized expression levels from (a) to the normalized expression levels from (b); (d) determining the presence of a PRRT-responsive GEP-NEN when the ratio of change is greater than a pre-PRRT therapy cutoff value, wherein the pre-PRRT therapy cutoff value is 1 on a scale of 0-8.

The present invention also provides a method for determining a progression of a GEP-NEN in a subject in need thereof, including determining the expression level of ZFHX3 from a test sample from the subject by contacting the test sample with an agent specific to detect the expression of ZFHX3; determining the expression level of ZFHX3 from a reference sample by contacting the reference sample with an agent specific to detect the expression of ZFHX3; normalizing the expression level of ZFHX3 in the test sample to the expression level of ZFHX3 in the reference sample; comparing the normalized expression level of ZFHX3 in the test sample with a predetermined cutoff value; determining the progression of a GEP-NEN in the subject when the normalized expression level is equal to or greater than the predetermined cutoff value, wherein the predetermined cutoff value is 0.5 on a scale of 0-8.

The present invention also provides a method for predicting tumor proliferation of a GEP-NEN in a subject in need thereof, including (a) determining the expression level of at least 22 biomarkers from a test sample from the subject by contacting the test sample with a plurality of agents specific to detect the expression of the at least 22 biomarkers, wherein the 22 biomarkers are selected from the group consisting of APLP2, ARAF, ATP6V1H, BNIP3L, BRAF, CD59, COMMD9, CTGF, FZD7, GLT8D1, KRAS, MKI67/KI67, MORF4L2, NAP1L1, NOL3, OAZ2, PANK2, PHF21A, PLD3, PNMA2, PQBP1, RAF1, RNF41, RSF1, SLC18A1/VMAT1, SLC18A2/VMAT2, SMARCD3, SPATA7, SSTR1, SSTR3, SSTR4, SSTR5, TECPR2, TPH1, TRMT112, WDFY3, ZFHX3 and ZZZ3; determining the expression level of the at least 22 biomarkers from a reference sample by contacting the reference sample with a plurality of agents specific to detect the expression of the at least 22 biomarkers; normalizing the expression level of the at least 22 biomarkers in the test sample to the expression level of the at least 22 biomarkers in the reference sample; comparing the normalized expression level of the at least 22 biomarkers in the test sample with a predetermined cutoff value; determining the presence of a GEP-NEN in the subject when the normalized expression level is equal to or greater than the predetermined cutoff value or determining the absence of a GEP-NEN in the subject when the normalized expression level is below the predetermined cutoff value, wherein the predetermined cutoff value is 2 on a MAARC-NET scoring system scale of 0-8, or 0% on a scale of 0-100%; (b) when a GEP-NEN is present, determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise KRAS, SSTR4 and VPS13C; summing the expression level of each of the 3 biomarkers of the test sample to generate a progressive diagnostic VI total test value and summing the expression level of each of the 3 biomarkers of the reference sample to generate a progressive diagnostic VI total reference value, wherein an increased value of the progressive diagnostic VI total test value compared to the progressive diagnostic VI total reference value indicates the presence of tumor proliferation of a GEP-NEN in the subject.

The method wherein (b) further includes determining the expression level of each of 3 biomarkers from a test sample from the subject and a reference sample by contacting the test sample and the reference sample with a plurality of agents specific to detect the expression of each of the 3 biomarkers, wherein the 3 biomarkers comprise SSTR1, SSTR2 and SSTR5; summing the expression level of each of the 3 biomarkers of the test sample to generate a progressive diagnostic VII total test value and summing the expression level of each of the 3 biomarkers of the reference sample to generate a progressive diagnostic VII total reference value, wherein an increased value of the progressive diagnostic VII total test value compared to the progressive diagnostic VII total reference value indicates the presence of tumor proliferation of a GEP-NEN in the subject.

As used herein, the term "GEP-NEN biomarker" and "NET biomarker" refer synonymously to a biological molecule, such as a gene product, the expression or presence of which (e.g., the expression level or expression profile) on its own or as compared to one or more other biomarkers (e.g., relative expression) differs (i.e., is increased or decreased) depending on the presence, absence, type, class, severity, metastasis, location, stage, prognosis, associated symptom, outcome, risk, likelihood or treatment responsiveness, or prognosis of GEP-NEN disease, or is associated positively or negatively with such factors of the prediction thereof.

As used herein, the term "polynucleotide" or nucleic acid molecule means a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees and temperatures for washing in 0.1×SSC/0.1% SDS are above 55 degrees C., and most preferably to stringent hybridization conditions.

The term "blood biopsy" refers to a diagnostic study of the blood to determine whether a patient presenting with symptoms has a condition that may be classified as either benign (low activity) or malignant (high activity/metastatic).

The term "classifying" as used herein with regard to different types or stages of GEP-NEN refers to the act of compiling and analyzing expression data for using statistical techniques to provide a classification to aid in diagnosis of a stage or type of GEP-NEN.

The term "classifier" as used herein refers to an algorithm that discriminates between disease states with a predetermined level of statistical significance. A two-class classifier is an algorithm that uses data points from measurements from a sample and classifies the data into one of two groups. A multi-class classifier is an algorithm that uses data points from measurements from a sample and classifies the data into one of multiple groups. The "classifier" maximizes the probability of distinguishing a randomly selected cancer sample from a randomly selected benign sample, i.e., the area under a curve (AUC) of receiver operating characteristic (ROC) curve.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression.

The term "condition" as used herein refers generally to a disease, event, or change in health status.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

The term "disease prevalence" refers to the number of all new and old cases of a disease or occurrences of an event during a particular period. Prevalence is expressed as a ratio in which the number of events is the numerator and the population at risk is the denominator.

The term "disease incidence" refers to a measure of the risk of developing some new condition within a specified period of time; the number of new cases during some time period, it is better expressed as a proportion or a rate with a denominator.

The term "stable disease" refers to a diagnosis for the presence of GEP-NEN, however GEP-NEN has been treated and remains in a stable condition, i.e. one that that is not progressive, as determined by imaging data and/or best clinical judgment.

The term "progressive disease" refers to a diagnosis for the presence of a highly active state of GEP-NEN, i.e. one has not been treated and is not stable or has been treated and has not responded to therapy, or has been treated and active disease remains, as determined by imaging data and/or best clinical judgment.

The term "expression level score" or "NETest score" refers to the output of a mathematically-derived classifier algorithm generated from the combination of classification algorithms, i.e. SVM, LDA, KNN, and Bayes. This score ranges between 0 and 100%. The expression level score from a test sample, once compared to the expression level score for a reference or control sample, may be used to diagnose the presence of GEP-NEN, the different stages of GEP-NEN, predict the risk of contracting a stage of GEP-NEN, or determines the risk of recurrence of GEP-NEN in post-therapy human patients. Distinctions between GEP-NEN disease states are based on pre-determined expression level score thresholds and/or ranges as further defined in the present application.

Diagnosis and prognosis of GEP-NEN has been difficult, in part due to the prosaic symptoms and syndromes of the disease, such as carcinoid syndrome, diarrhea, flushing, sweating, bronchoconstriction, gastrointestinal bleeding, cardiac disease, intermittent abdominal pain, which often remain silent for years. Available diagnostic methods include anatomical localization, such as by imaging, e.g., X-ray, gastrointestinal endoscopy, abdominal computed tomography (CT), combined stereotactic radiosurgery (SRS)/CT, and MRI, and detection of some gene products e.g., chromogranin A. Known methods are limited, for example by low specificity and/or sensitivity and/or in the ability to detect early-stage disease.

Detection of single biomarkers has not been entirely satisfactory, for example, to identify malignancy in human blood samples and to predict complex outcomes like fibrosis and metastasis. See Michiels S, Koscielny S, Hill C, "Interpretation of microarray data in cancer," Br J Cancer 2007; 96(8): 1155-8. Limitations in available methods have contributed to difficulties in pathological classification, staging, and prediction, treatment developing and monitoring therapeutic effects. Among the embodiments provided herein are methods and compositions that address these limitations.

In one aspect, the present application relates to the detection and identification of GEP-NEN biomarkers and panels of such biomarkers, for example, in biological samples. Provided are methods and compositions (e.g., agents, such as polynucleotides), for detecting, determining expression levels of, and recognizing or binding to the biomarkers, in biological samples, typically blood samples.

Also provided are models and biomathematical algorithms, e.g., supervised learning algorithms, and methods using the same, for prediction, classification, and evaluation of GEP-NEN and associated outcomes, for example, predicting degree of risk, responsiveness to treatment, metastasis or aggressiveness, and for determining GEP-NEN subtype.

Detection of the biomarkers using the provided embodiments is useful for improving GEP-NEN diagnostics and prognostics, and to inform treatment protocols. In some aspects, detection of the biomarkers and/or expression levels by the provided embodiments confirms or indicates the presence, absence, stage, class, location, sub-type, aggressiveness, malignancy, metastasis, prognosis, or other outcome of GEP-NEN, or a GEP-NEN cell, such as a circulating GEP-NEN cell (CNC). The provided methods and compositions may be used for tumor localization, and for predicting or detecting metastases, micrometastases, and small lesions, and/or for determining degree of risk, likelihood of recurrence, treatment responsiveness or remission, and informing appropriate courses of treatment. For example, detecting the biomarkers, e.g., in circulation may be used to detect early-stage and primary GEP-NENs (e.g., to identify GEP-NEN disease or metastases in a patient previously deemed "negative" by another approach, such as anatomic localization).

The provided methods and compositions may be used for designing, implementing, and monitoring treatment strategies, including patient-specific treatment strategies. In one example, detected expression levels of the GEP-NEN biomarkers serve as surrogate markers for treatment efficacy, e.g., to monitor the effects of surgical therapy, e.g., removal of tumors, targeted medical therapy, e.g., inhibition of tumor secretion/proliferation, and other therapeutic approaches, by detecting remission or recurrence of tumors, even in the form of small micrometastases. The methods also may be used in evaluating clinical symptoms and outcomes, and for histological grading and molecular characterization of GEP-NENs.

The provided biomarkers including GEP-NEN biomarkers, and subsets and panels of the same. Among the provided GEP-NEN biomarkers are gene products, such as DNA, RNA, e.g., transcripts, and protein, which are differentially expressed in GEP-NEN disease, and/or in different stages or sub-types of GEP-NEN, or in different GEP-NEN tumors, such as gene products differentially expressed in metastatic versus non-metastatic tumors, tumors with different degrees of aggressiveness, high versus low-risk tumors, responsive versus non-responsive tumors, tumors exhibiting different pathological classifications and/or likelihood of response to particular courses of treatment, as well as those associated with features of GEP-NEN disease, stage, or type, or with neuroendocrine cells or related cell-types.

For example, the biomarkers include gene products whose expression is associated with or implicated in tumorogenicity, metastasis, or hormone production, or a phenotype of primary or metastatic GEP-NEN, such as adhesion, migration, proliferation, apoptosis, metastasis, and hormone secretion, and those associated with neoplasia or malignancy in general.

Among the biomarkers are GEP-NEN cell secretion products, including hormones and amines, e.g., gastrin, ghrelin, pancreatic polypeptide, substance P, histamine, and serotonin, and growth factors such as tumor growth factor-beta (TGF-β) and connective tissue growth factor (CTGF), which are detectable in the circulation. Secretion products can vary with tumor sub-type and origin.

In one example, the biomarkers are gene products associated with regulatory genotypes (i.e., adhesion, migration, proliferation, apoptosis, metastasis, and/or hormone secretion) that underlay various GEP-NEN subtypes, stages, degrees of aggressiveness, or treatment responsiveness.

A total of 51 differentially expressed biomarker genes have been discovered for the diagnosis, prognosis, and/or monitoring of GEP-NENs. Further details regarding the 51 differentially expressed GEP-NEN biomarkers as well as the housekeeping gene, ALG9, are found in TABLE 1.

TABLE 1

GEP-NEN Biomarker/Houskeeper Sequence Information

| Gene Name | RefSeq Accession | Sequence | SEQ ID NO: |
|---|---|---|---|
| ALG9 | NM_024740.2 | GTCTTTTGTCCCTCGGCGGACACCGTTTGCCAGCCAAAGC TATGTCTGCGCGCTCACCGACTTCATAGGGTGCCGAATTC TTTTTTCCCCAGGCTTGCCATGGCTAGTCGAGGGGCTCGG CAGCGCCTGAAGGGCAGCGGGGCCAGCAGTGGGGATACGG CCCCGGCTGCGGACAAGCTGCGGGAGCTGCTGGGCAGCCG AGAGGCGGGCGGCGCGGAGCACCGGACCGAGTTATCTGGG AACAAAGCAGGACAAGTCTGGGCACCTGAAGGATCTACTG CTTTCAAGTGTCTGCTTTCAGCAAGGTTATGTGCTGCTCT CCTGAGCAACATCTCTGACTGTGATGAAACATTCAACTAC TGGGAGCCAACACACTACCTCATCTATGGGGAAGGGTTTC AGACTTGGGAATATTCCCCAGCATATGCCATTCGCTCCTA TGCTTACCTGTTGCTTCATGCCTGGCCAGCTGCATTTCAT GCAAGAATTCTACAAACTAATAAGATTCTTGTGTTTTACT TTTTGCGATGTCTTCTGGCTTTTGTGAGCTGTATTTGTGA ACTTTACTTTTACAAGGCTGTGTGCAAGAAGTTTGGGTTG CACGTGAGTCGAATGATGCTAGCCTTCTTGGTTCTCAGCA CTGGCATGTTTTGCTCATCATCAGCATTCCTTCCTAGTAG CTTCTGTATGTACACTACGTTGATAGCCATGACTGGATGG TATATGGACAAGACTTCCATTGCTGTGCTGGGAGTAGCAG CTGGGGCTATCTTAGGCTGGCCATTCAGTGCAGCTCTTGG TTTACCCATTGCCTTTGATTTGCTGGTCATGAAACACAGG TGGAAGAGTTTCTTTCATTGGTCGCTGATGGCCCTCATAC TATTTCTGGTGCCTGTGGTGGTCATTGACAGCTACTATTA TGGGAAGTTGGTGATTGCACCACTCAACATTGTTTTGTAT AATGTCTTTACTCCTCATGGACCTGATCTTTATGGTACAG AACCCTGGTATTTCTATTTAATTAATGGATTTCTGAATTT CAATGTAGCCTTTGCTTTGGCTCTCCTAGTCCTACCACTG ACTTCTCTTATGGAATACCTGCTGCAGAGATTTCATGTTC AGAATTTAGGCCACCCGTATTGGCTTACCTTGGCTCCAAT GTATATTTGGTTTATAATTTTCTTCATCCAGCCTCACAAA GAGGAGAGATTTCTTTTCCCTGTGTATCCACTTATATGTC TCTGTGGCGCTGTGGCTCTCTCTGCACTTCAGCACAGTTT | 1 |

TABLE 1-continued

GEP-NEN Biomarker/Houskeeper Sequence Information

| Gene Name | RefSeq Accession | Sequence | SEQ ID NO: |
|---|---|---|---|
| | | TCTGTACTTCCAGAAATGTTACCACTTTGTGTTTCAACGA | |
| | | TATCGCCTGGAGCACTATACTGTGACATCGAATTGGCTGG | |
| | | CATTAGGAACTGTCTTCCTGTTTGGGCTCTTGTCATTTTC | |
| | | TCGCTCTGTGGCACTGTTCAGAGGATATCACGGGCCCCTT | |
| | | GATTTGTATCCAGAATTTTACCGAATTGCTACAGACCCAA | |
| | | CCATCCACACTGTCCCAGAAGGCAGACCTGTGAATGTCTG | |
| | | TGTGGGAAAAGAGTGGTATCGATTTCCCAGCAGCTTCCTT | |
| | | CTTCCTGACAATTGGCAGCTTCAGTTCATTCCATCAGAGT | |
| | | TCAGAGGTCAGTTACCAAAACCTTTTGCAGAAGGACCTCT | |
| | | GGCCACCCGGATTGTTCCTACTGACATGAATGACCAGAAT | |
| | | CTAGAAGAGCCATCCAGATATATTGATATCAGTAAATGCC | |
| | | ATTATTTAGTGGATTTGGACACCATGAGAGAAACACCCCG | |
| | | GGAGCCAAAATATTCATCCAATAAAGAAGAATGGATCAGC | |
| | | TTGGCCTATAGACCATTCCTTGATGCTTCTAGATCTTCAA | |
| | | AGCTGCTGCGGGCATTCTATGTCCCCTTCCTGTCAGATCA | |
| | | GTATACAGTGTACGTAAACTACACCATCCTCAAACCCCGG | |
| | | AAAGCAAAGCAAATCAGGAAGAAAAGTGGAGGTTAGCAAC | |
| | | ACACCTGTGGCCCCAAAGGACAACCATCTTGTTAACTATT | |
| | | GATTCCAGTGACCTGACTCCCTGCAAGTCATCGCCTGTAA | |
| | | CATTTGTAATAAAGGTCTTCTGACATGAATACTGGAATCT | |
| | | GGGTGCTCTGGGCTAGTCAAAGTCTATTTCAAAGTCTAAT | |
| | | CAAAGTCACATTTGCTCCCTGTGTGTGTCTCTGTTCTGCA | |
| | | TGTAAACTTTTTGCAGCTAGGCAGAGAAAGGCCCTAAAGC | |
| | | ACAGATAGATATATTGCTCCACATCTCATTGTTTTTCCTC | |
| | | TGTTCAATTATTTACTAGACCGGAGAAGAGCAGAACCAAC | |
| | | TTACAGGAAGAATTGAAAATCCTGGTACTGGATGGCTGTG | |
| | | ATAAGCTGTTCTCCACACTCTGGCCTGGCATCTGAGAACT | |
| | | AGCAAGCCTCTCTTAGGCCATATGGGCTTCTCCACCAAAG | |
| | | CTGTTTGGCAGCTCCTAGCAGACCTTCTTATTGAAATCCT | |
| | | CATGCTGAAAATGAACACAGCCTAGTTGCCAACCCACATG | |
| | | TCCTTTTCACCTCCAGCAAGACTAAGCTTCTTTAAAGCAC | |
| | | TTCACAGGACTAGGACCCTGTCCTGGAGCTATCTCAGGAA | |
| | | AAAGGTGACCATTTGAGGAACTGTGACCTAATTTTTATTAT | |
| | | AATGATGCCTCTAATTTTCATTTCCTTTACAACCAACTGT | |
| | | AACTATAAGGTTGTATTGCTTTTTTGTTCAGTTTTAGCAT | |
| | | GCTATTTTTGAATTCTAGACTCCTCCATGTGAAGATATC | |
| | | AACAGACAAAACTACAACTGTATAGGACATATTTGGAGAA | |
| | | AATTCTATCAATTGATACATTTGGATGACATCACATTTTT | |
| | | AAGTAATGTAATCTGAGGCCATTGCTGAGGAAATTAAGAA | |
| | | TTTTCCTTTTTTTTTAACCACCCCAGTGAAAAGGATCAG | |
| | | TGTATATTTATAGCACCTATTTTTTAGTTCTGTCTGTTGT | |
| | | GAGGCACATCCTGCATGGGGCACTTCTAGTCAAATAGGCA | |
| | | ATGATAAGGACCTAATTAAAATGTGATAAGTGTATACTAT | |
| | | TACTTTAAAAGCCTTTACAGTCAGTACTTCAGTTTACAAG | |
| | | GCACTTTCACAGCATCTCGTTTGATCCTCACAGTCACAAC | |
| | | ATGTGGTAGACAAGGCAGGTGATTTTTATCCCCATTTTAC | |
| | | AGATAAGGAAACAGGCTGCGGGTGGGGAGTGAGGGGAGGT | |
| | | AAAGATAGTTAGTTGCCTAAGGTCACACAGCCAGTAAGTA | |
| | | ATAGAGCTGGGACTGGAACCCAGGTTTCCTTACTCTCATC | |
| | | TATTGCTCCTCCATATTCCTCACTCAACCATGAAAACATT | |
| | | ACTTGAAAGGACTGATGAGGTTAACCAGAGACCTAACTGA | |
| | | TATTGTAACTTTCTATTTTAAGGAAGAATTGTGTCTGTAT | |
| | | TTGAGTTCTTTGGAGCCTCCAGTCTGCCTGTGTGTTAGAC | |
| | | CAGCACAGCAGTGCTGTGTGATGCAGCCTGACCTGTGGCA | |
| | | GGAAAGTAGTGCTTCTGTTTGGAAGTCATGTTCTTTTGCA | |
| | | GCCACACAGGATCCAAATATCAGTACTATTCCTGTAGTCA | |
| | | ATCTGGGGTCACATTATAGGTGCCTTATTTCCCTAAGGGT | |
| | | AACTGATCTGAATATCTGCAAATAGGATGAATCTATTTTT | |
| | | CAGAAGTTCCATCTTTCATTTTTCTTTTTTTTTTGAGAC | |
| | | AGAGTCTCATTCTGTCGCCCATGCTGGAGTGCAGTGGCGC | |
| | | GATCTCGGCTCGCTGCAACCTCTGCCTCCCAGGTTGAAGC | |
| | | AATTCTCATGCCTCAGCCACCCGAGTAGCTGGGATTACAG | |
| | | GCATGCGCCATCATGCCCAGCTAATTTATGTATTTTTAGT | |
| | | AGAGTTGGAGTTTCACCATGTTGGCCAGGCTGGTCTTGA | |
| | | CTCCTGACCTCAGGTCATCCACCCGCCTCAGCCTCCCAAA | |
| | | GTGCTGGTATTACAGGCGTGAGCCACCGCACCCAGCCCCA | |
| | | TCTTTCATTTTCAAAGAGAAGGGCATTCTAATAGGAACTG | |
| | | GTGCCAAGAGAGAAGAAAAGAAGTGATAACAGAAGAAATG | |
| | | GCTAGTTACAATATTAAAAAGCTCCTCTTTGAGATCTCCT | |
| | | CTGCAGGAATATCAGAGACGGAGTTGAAGCGCTGGAGAGG | |
| | | TAATAGGTCTAGACAGTACAGAACAATAACTGGGAGTGT | |
| | | GTGAGGATAGACTGGGCTCCCCCTTGCTTGAAAGATCTCT | |
| | | GGCATTTAATTCTCAATTCTTGATTACTATTTTCCAGTGT | |
| | | AAAACTAGCACATATGATCTGACTACAGGACAGAGAATTT | |
| | | TAAGTGAAACATTTGCCTTACTTGCAGTAATAATGTGCTG | |

TABLE 1-continued

GEP-NEN Biomarker/Houskeeper Sequence Information

| Gene Name | RefSeq Accession | Sequence | SEQ ID NO: |
|---|---|---|---|
| | | TTCTTCACAGTAGCTAAGGCCCTCTATGTTTCCCAGAGGT<br>AAATAAGAATCCAGGAATGGAGGTCCATCTGTGATGAATG<br>GCTTTTTTCTAATCAAAGTAGTATAATGCTGTTTTATCTG<br>TTTTGTCATCTTGTTTTTTTTTTTTTAAAAAAACAAAA<br>CCTTAATTATAATATAGCGCAAAGAAAGGCCAGGACTGAT<br>GCAGGGATTCCTTGGAAATATCAGTTCCTATCACTTTTAA<br>AACCTGATTTTGGATCTCTCTGTTCTATGTATGTCTTTAG<br>TGAGAGCACAATACATGGCAGAACGCTGTGCCAAATGTTA<br>TAGGTAAGGAATATAGAAATGAATGTTTTTTGTTGTGAAG<br>GTGTTTTCATGTGATATTTTATAAACACATTTTAAAAAAT<br>CTCCATCACTTTTTAGTATAGGAAGGATAGCTTTGCCTGG<br>GAAAAACAGTTTCAACACACCTGCTCAGAGTAGCAGTTCT<br>CCCTCAAAAAAGCAGTGTTCAGCCTGCACTGACTGTTCTG<br>CTTGCCAAAAGGAGGAAGCATGCAAGATACTTATTTCTCC<br>ATAGATTGTGGAGTATAGAGGGATGTGGGACTACAGATTA<br>TTATTTTTTTCCCCGAGACAGAGTCTTGCTCTGTCGCCC<br>AGGTTGGAACACAATGGCACGACCTCAGCTCACTGCAACC<br>TCTGTCTCCCGGGTTCAAGCAATTCTCCTGCTTCAGCCTC<br>CTGAGTAGCTGGGATTACAGGCACACACCACCACCGCACT<br>CAGCTAATTTTTGTATTTTTAGTAGAGGTGGGGTTTTACC<br>ATGTTGGCCAGGCTGGTCTTAAACTCCTGACCTTGTAATC<br>ATCCCGCCTCGGCCTCCTAAAGTGCTAGGATTACAGGCAT<br>GAGCCACCGCACCCGGCCCAGATAATTTTTAATAGCCTTT<br>GATCATGGGGTGAGTGAGGGAGTAGGTATACTTGGCAAAT<br>GCATGGTTCTCTGATTTCTAGCTCTAAAGCAGCCTTATCT<br>GAATCCCCAAATCTTGTGATGCTGAGTACCATTACTGAAC<br>CAGTCTGCACGGTAGGCATCTGCTACCAAAATTTACCTCC<br>TACCTGGTAGGTGTCATCTGATAAGAAAGAAGACAGGTTA<br>TTTTAATTTTTTGAGATAATCACAGAAAATTGCAGCCCAT<br>ACTCTTTATTACCGAATTCAAGTTTGGAAATAGACCCTTT<br>GTTTTAAATCATGATGGGTCTTTATCCCAATCATTTATCT<br>GGGTCATTTTTCCAACTTTGGAGTTCTAGGAAAGAACCTT<br>GAAAACCTGATATGATTCTGCAGCATGAGGTCTACGGTGA<br>CCATTTGGGCAAAGCTCCAGTGGCAATCATTTATTGTGTT<br>TTGCATTTCCTGGGATTTATTGAAATAAGAATTCACTGTG<br>ATTATGTAGTCTTCTGGCTAGTATCAGGCAGCTCTGCTTT<br>TAATTTGGTTAATTTTATTTTCTCTGAAGAGGGAGAAGAG<br>GTACAATTTAATCTTGGCCTCCACAAGCATATTAAAGCTC<br>ACGTGTTAATCAGTGCATTCTTATGCTCCTACATTAAATG<br>CCTTGGGTAAATGGATAAATGGACATGTGCCCAGCTTTAA<br>TTTTTTTTGCAACAGAAAGATCAGACTTCCGTATGGCATC<br>GTTGGATTTCAGAGGCTTTCTGGTGTATCTGTAAATCTGA<br>ATGTTGCCTTCTGCCAGTCTGTATAACCAGGTGATTCATG<br>CTGCAAATGAAATCAGGAAGCAGTAAAGTGTTAAAGCAAG<br>AGTATTGTCCAATTCACTTGTCTTCCTGATCCTTGTACTT<br>TATTTCACGTGTCGGTGTTTACATTACATACTTATATTTC<br>CTGTGAAAGAAAGAGTTAAATAAATTGTAGCAGTTTGA | |
| AKAP8L | NM_014371.3 | ACTGATATGAGGAGGCATAGAGATAGACAGCGGTTCCTTC<br>CAATAGACGTGAAGCCGAGGCCGGTATGAGCCAATGCGGT<br>CGGGAGGCGGGGCTCGGGTGTGTGTGGAGGGGACCCTGTG<br>GTTAGCAGCAGCTATCGCAGCGTCGGATGTTCAGAGCAGC<br>AGAAGCCGGCGTCGTCGGATGTTGTGTTGCCCGCCACCAT<br>GAGCTACACAGGCTTTGTCCAGGGATCTGAAACCACTTTG<br>CAGTCGACATACTCGGATACCAGCGCTCAGCCCACCTGTG<br>ATTATGGATATGGAACTTGGAACTCTGGGACAAATAGAGG<br>CTACGAGGGCTATGGCTATGGCTATGGCTATGGCCAGGAT<br>AACACCACCAACTATGGGTATGGTATGGCCACTTCACACT<br>CTTGGGAAATGCCTAGCTCTGACACAAATGCAAACACTAG<br>TGCCTCGGGTAGCGCCAGTGCCGATTCCGTTTTATCCAGA<br>ATTAACCAGCGCTTAGATATGGTGCCGCATTTGGAGACAG<br>ACATGATGCAAGGAGGCGTGTACGGCTCAGGTGGAGAAAG<br>GTATGACTCTTATGAGTCCTGCGACTCGAGGGCCGTCCTG<br>AGTGAGCGCGACCTGTACCGGTCAGGCTATGACTACAGCG<br>AGCTTGACCCTGAGATGGAAATGGCCTATGAGGGCCAATA<br>CGATGCCTACCGCGACCAGTTCCGCATGCGTGGCAACGAC<br>ACCTTCGGTCCCAGGGCACAGGGCTGGGCCCGGGATGCCC<br>GGAGCGGCCGGCCAATGGCCTCAGGCTATGGGCGCATGTG<br>GGAAGACCCCATGGGGGCCCGGGGCCAGTGCATGTCTGGT<br>GCCTCTCGGCTGCCCTCCCTCTTCTCCCAGAACATCATCC<br>CCGAGTACGGCATGTTCCAGGGCATGCGAGGTGGGGGCGC<br>CTTCCCGGGCGGCTCCCGCTTTGGTTTCGGGTTTGGCAAT<br>GGCATGAAGCAGATGAGGCGGACCTGGAAGACCTGGACCA<br>CAGCCGGACTTCCGAACCAAGAAGAAGAAGAGAAAGCAGGG<br>CGGCAGTCCTGATGAGCCAGATAGCAAAGCCACCCGCACG | 2 |

TABLE 1-continued

GEP-NEN Biomarker/Houskeeper Sequence Information

| Gene Name | RefSeq Accession | Sequence | SEQ ID NO: |
|---|---|---|---|
| | | GACTGCTCGGACAACAGCGACTCAGACAATGATGAGGGCA<br>CCGAGGGGAAGCCACAGAGGGCCTTGAAGGCACCGAGGC<br>TGTGGAGAAGGGCTCCAGAGTGGACGGAGAGGATGAGGAG<br>GGAAAAGAGGATGGGAGAGAAGAAGGCAAAGAGGATCCAG<br>AGAAGGGGGCCCTAACCACCCAGGATGAAAATGGCCAGAC<br>CAAGCGCAAGTTGCAGGCAGGCAAGAAGAGTCAGGACAAG<br>CAGAAAAAGCGGCAGCGAGACCGCATGGTGGAAAGGATCC<br>AGTTTGTGTGTTCTCTGTGCAAATACCGGACCTTCTATGA<br>GGACGAGATGGCCAGCCATCTTGACAGCAAGTTCCACAAG<br>GAACACTTTAAGTACGTAGGCACCAAGCTCCCTAAGCAGA<br>CGGCTGACTTTCTGCAGGAGTACGTCACTAACAAGACCAA<br>GAAGACAGAGGAGCTCCGAAAAACCGTGGAGGACCTTGAT<br>GGCCTCATCCAGCAAATCTACAGAGACCAGGATCT<u>GACCC<br>AGGAAATTGCCATGGAGCATTTTGTGAAGAAGGTGGAGGC<br>AGCCCATTGTGCAGCCTGCGACCTCTTCATTCCCATGCAG</u><br>TTTGGGATCATCCAGAAGCATCTGAAGACCATGGATCACA<br>ACCGGAACCGCAGGCTCATGATGGAGCAGTCCAAGAAGTC<br>CTCCCTCATGGTGGCCCGCAGTATTCTCAACAACAAGCTC<br>ATCAGCAAGAAGCTGGAGCGCTACCTGAAGGGCGAGAACC<br>CTTTCACCGACAGCCCCGAGGAGGAGAAGGAGCAGGAGGA<br>GGCTGAGGGCGGTGCCCTGGACGAGGGGCGCAGGGCGAA<br>GCGGCAGGGATCTCGGAGGGCGCAGAGGGCGTGCCGGCGC<br>AGCCTCCCGTGCCCCCAGAGCCAGCCCCCGGGGCCGTGTC<br>GCCGCCACCGCCGCCGCCCCCAGAGGAGGAGGAGGAGGGC<br>GCCGTGCCCTTGCTGGGAGGGGCGCTGCAACGCCAGATCC<br>GCGGCATCCCGGGCCTCGACGTGGAGGACGACGAGGAGGG<br>CGGCGGGGGCGCCCCGTGACCCGAGCTCGGGCGGGCGGA<br>GCCCGCGTGGCCGAAGCTGGAAACCAAACCTAATAAAGTT<br>TTCCCATCCCACCAAAAAAAAAAAAAAAAAA | |
| APLP2 | NM_001142276.1 | AGAAGGAGGGCGTGGTAATATGAAGTCAGTTCCGGTTGGT<br>GTAAAACCCCCGGGGCGGCGGCGAACTGGCTTTAGATGCT<br>TCTGGGTCGCGGTGTGCTAAGCGAGGAGTCCGAGTGTGTG<br>AGCTTGAGAGCCGCGCGCTAGAGCGACCCGGCGAGGGATG<br>GCGGCCACCGGGACCGCGGCCGCCGCAGCCACGGGCAGGC<br>TCCTGCTTCTGCTGCTGGTGGGGCTCACGGCGCCTGCCTT<br>GGCGCTGGCCGGCTACATCGAGGCTCTTGCAGCCAATGCC<br>GGAACAGGATTTGCTGTTGCTGAGCCTCAAATCGCAATGT<br>TTTGTGGGAAGTTAAATATGCATGTGAACATTCAGACTGG<br>GAAATGGGAACCTGATCCAACAGGCACCAAGAGCTGCTTT<br>GAAACAAAAGAAGAAGTTCTTCAGTACTGTCAGGAGATGT<br>ATCCAGAGCTACAGATCACAAATGTGATGGAGGCAAACCA<br>GCGGGTTAGTATTGACAACTGGTGCCGGAGGGACAAAAAG<br>CAATGCAAGAGTCGCTTTGTTACACCTTTCAAGTGTCTCG<br>TGGGTGAATTTGTAAGTGATGTCCTGCTAGTTCCAGAAAA<br>GTGCCAGTTTTTCCACAAAGAGCGGATGGAGGTGTGTGAG<br>AATCACCAGCACTGGCACACGGTAGTCAAAGAGGCATGTC<br>TGACTCAGGGAATGACCTTATATAGCTACGGCATGCTGCT<br>CCCATGTGGGGTAGACCAGTTCCATGGCACTGAATATGTG<br>TGCTGCCCTCAGACAAAGATTATTGGATCTGTGTCAAAAG<br>AAGAGGAAGAGGAAGATGAAGAGGAAGAGGAAGAGGAAGA<br>TGAAGAGGAAGACTATGATGTTTATAAAAGTGAATTTCCT<br>ACTGAAGCAGATCTGGAAGACTTCACAGAAGCAGCTGTGG<br>ATGAGGATGATGAGGATGAGGAAGAAGGGGAGGAAGTGGT<br>GGAGGACCGAGATTACTACTATGACACCTTCAAAGGAGAT<br>GACTACAATGAGGAGAATCCTACTGAACCCGGCAGCGACG<br>GCACCATGTCAGACAAGGAAATTACTCATGATGTCAAAGC<br>TGTCTGCTCCCAGGAGGCGATGACGGGGCCCTGCCGGGCC<br>GTGATGCCTCGTTGGTACTTCGACCTCTCCAAGGGAAAGT<br>GCGTGCGCTTTATATATGGTGGCTGCGGCGGCAACAGGAA<br>CAATTTTGAGTCTGAGGATTATTGTATGGCTGTGTGTAAA<br>GCGATGATTCCTCCAACTCCTCTGCCAACCAATGATGTTG<br>ATGTGTATTTCGAGACCTCTGCAGATGATAATGAGCATGC<br>TCGCTTCCAGAAGGCTAAGGAGCAGCTGGAGATTCGGCAC<br>CGCAACCGAATGGACAGGGTAAAGAAGGAATGGGAAGAGG<br>CAGAGCTTCAAGCTAAGAACCTCCCCAAAGCAGAGAGGCA<br>GACTCTGATTCAGCACTTCCAAGCCATGGTTAAAGCTTTA<br>GAGAAGGAAGCAGCCAGTGAGAAGCAGCAGCTGGTGGAGA<br>CCCACCTGGCCCGAGTGGAAGCTATGCTGAATGACCGCCG<br>TCGGATGGCTCTGGAGAACTACCTGGCTGCCTTGCAGTCT<br>GACCCGCCACGGCCTCATCGCATTCTCCAGGCCTTACGGC<br>GTTATGTCCGTGCTGAGAACAAAGATCGCTTACATACCAT<br>CCGTCATTACCAGCATGTGTTGGCTGTTGACCCAGAAAAG<br>GCGGCCCAGATGAAATCCCAGGTGATGACACATCTCCACG<br>TGATTGAAGAAGGAGGAACCAAAGCCTCTCTCTGCTCTA | 3 |

TABLE 1-continued

GEP-NEN Biomarker/Houskeeper Sequence Information

| Gene Name | RefSeq Accession | Sequence | SEQ ID NO: |
|---|---|---|---|
| | | CAAAGTACCTTATGTAGCCCAAGAAATTCAAGAGGAAATT<br>GATGAGCTCCTTCAGGAGCAGCGTGCAGATATGGACCAGT<br>TCACTGCCTCAATCTCAGAGACCCCTGTGGACGTCCGGGT<br>GAGCTCTGAGGAGAGTGAGGAGATCCCACCGTTCCACCCC<br>TTCCACCCCTTCCCAGCCCTACCTGAGAACGAAGGATCTG<br>GAGTGGGAGAGCAGGATGGGGGACTGAT<u>CGGTGCCGAAGA</u><br><u>GAAAGTGATTAACAGTAAGAATAAAGTGGATGAAAACATG</u><br><u>GTCATTGACGAGACTCTGGATGTTAAGGAAATGATTTTCA</u><br><u>ATGCCGAGAGAGT</u>TGGAGGCCTCGAGGAAGAGCGGGAATC<br>CGTGGGCCCACTGCGGGAGGACTTCAGTCTGAGTAGCAGT<br>GCTCTCATTGGCCTGCTGGTCATCGCAGTGGCCATTGCCA<br>CGGTCATCGTCATCAGCCTGGTGATGCTGAGGAAGAGGCA<br>GTATGGCACCATCAGCCACGGGATCGTGGAGGTTGATCCA<br>ATGCTCACCCCAGAAGAGCGTCACCTGAACAAGATGCAGA<br>ACCATGGCTATGAGAACCCCACCTACAAATACCTGGAGCA<br>GATGCAGATTTAGGTGGCAGGGAGCGCGGCAGCCCTGGCG<br>GAGGGATGCAGGTGGGCCGGAAGATCCCACGATTCCGATC<br>GACTGCCAAGCAGCAGCCGCTGCCAGGGGCTGCGTCTGAC<br>ATCCTGACCTCCTGGACTGTAGGACTATATAAAGTACTAC<br>TGTAGAACTGCAATTTCCATTCTTTTAAATGGGTGAAAAA<br>TGGTAATATAACAATATATGATATATAAACCTTAAATGAA<br>AAAAATGATCTATTGCAGATATTTGATGTAGTTTTCTTTT<br>TTAAATTAATCAGAAACCCCACTTCCATTGTATTGTCTGA<br>CACATGCTCTCAATATATAATAAATGGGAAATGTCGATTT<br>TCAATAATAGACTTATATGCAGGCTGTCGTTCCGGTTATG<br>TTGTGTAAGTCAACTCTTCAGCCTCATTCACTGTCCTGGC<br>TTTTTATTTAAAGAAAAAAAAGGCAGTATTCCCTTTTTAAA<br>TGAGCTTTCAGGAAGTTGCTGAGAAATGGGGTGGAATAGG<br>GAACTGTAATGGCCACTGAAGCACGTGAGAGACCCTCGCA<br>AAATGATGTGAAAGGACCAGTTTCTTGAAGTCCAGTGTTT<br>CCACGGCTGGATACCTGTGTGTCTCCATAAAAGTCCTGTC<br>ACCAAGGACGTTAAAGGCATTTTATTCCAGCGTCTTCTAG<br>AGAGCTTAGTGTATACAGATGAGGGTGTCCGCTGCTGCTT<br>TCCTTCGGAATCCAGTGCTTCCACAGAGATTAGCCTGTAG<br>CTTATATTTGACATTCTTCACTGTCTGTTGTTTACCTACC<br>GTAGCTTTTTACCGTTCACTTCCCCTTCCAACTATGTCCA<br>GATGTGCAGGCTCCTCCTCTCTGGACTTTCTCCAAAGGCA<br>CTGACCCTCGGCCTCTACTTTGTCCCCTCACCTCCACCCC<br>CTCCTGTCACCGGCCTTGTGACATTCACTCAGAGAAGACC<br>ACACCAAGGAGGCGGCCGCTGGCCCAGGAGAGAACACGGG<br>GAGGTTTGTTTGTGTGAAAGGAAAGTAGTCCAGGCTGTCC<br>CTGAAACTGAGTCTGTGGACACTGTGGAAAGCTTTGAACA<br>ATTGTGTTTTCGTCACAGGAGTCTTTGTAATGCTTGTACA<br>GTTGATGTCGATGCTCACTGCTTCTGCTTTTTCTTTCTTT<br>TTATTTTAAATCTGAAGGTTCTGGTAACCTGTGGTGTATT<br>TTTATTTTCCTGTGACTGTTTTTGTTTTGTTTTTTTCCTT<br>TTTCCTCCCCTTTGACCCTATTCATGTCTCTACCCACTAT<br>GCACAGATTAAACTTCACCTACAAACTCCTTAATATGATC<br>TGTGGAGAATGTACACAGTTTAAACACATCAATAAATACT<br>TTAACTTCCACCGAGAAAAAAAAAAAAAAAA | |
| ARAF1 | NM_001654.4 | CTTGACAGACGTGACCCTGACCCAATAAGGGTGGAAGGCT<br>GAGTCCCGCAGAGCCAATAACGAGAGTCCGAGAGGCGACG<br>GAGGCGGACTCTGTGAGGAAACAAGAAGAGAGGCCCAAGA<br>TGGAGACGGCGGCGGCTGTAGCGGCGTGACAGGAGCCCCA<br>TGGCACCTGCCCAGCCCCACCTCAGCCCATCTTGACAAAA<br>TCTAAGGCTCCATGGAGCCACCACGGGGCCCCCCTGCCAA<br>TGGGGCCGAGCCATCCCGGGCAGTGGGCACCGTCAAAGTA<br>TACCTGCCCAACAAGCAACGCACGGTGGTGACTGTCCGGG<br>ATGGCATGAGTGTCTACGACTCTCTAGACAAGGCCCTGAA<br>GGTGCGGGGTCTAAATCAGGACTGCTGTGTGGTCTACCGA<br>CTCATCAAGGGACGAAAGACGGTCACTGCCTGGGACACAG<br>CCATTGCTCCCCTGGATGGCGAGGAGCTCATTGTCGAGGT<br>CCTTGAAGATGTCCCGCTGACCATGCACAATTTTGTACGG<br>AAGACCTTCTTCAGCCTGGCGTTCTGTGACTTCTGCCTTA<br>AGTTTCTGTTCCATGGCTTCCGTTGCCAAACCTGTGGCTA<br>CAAGTTCCACCAGCATTGTTCCTCCAAGGTCCCCACAGTC<br>TGTGTTGACATGAGTACCAACCGCCAACAGTTCTACCACA<br>GTGTCCAGGATTTGTCCGGAGGCTCCAGACAGCATGAGGC<br>TCCCTCGAACCGCCCCCTGAATGAGTTGCTAACCCCCAG<br>GGTCCCAGCCCCCGCACCCAGCACTGTGACCCGGAGCACT<br>TCCCCTTCCCTGCCCCAGCCAATGCCCCCTACAGCGCAT<br>CCGCTCCACGTCCACTCCCAACGTCCATATGGTCAGCACC<br>ACGGCCCCCATGGACTCCAACCTCATCCAGCTCACTGGCC<br>AGAGTTTCAGCACTGATGCTGCCGGTAGTAGAGGAGGTAG | 4 |

TABLE 1-continued

GEP-NEN Biomarker/Housekeeper Sequence Information

| Gene Name | RefSeq Accession | Sequence | SEQ ID NO: |
|---|---|---|---|
| | | TGATGGAACCCCCGGGGGAGCCCCAGCCCAGCCAGCGTG TCCTCGGGGAGGAAGTCCCCACATTCCAAGTCACCAGCAG AGCAGCGCGAGCGGAAGTCCTTGGCCGATGACAAGAAGAA AGTGAAGAACCTGGGGTACCGGGACTCAGGCTATTACTGG GAGGTACCACCCAGTGAGGTGCAGCTGCTGAAGAGGATCG GGACGGGCTCGTTTGGCACCGTGTTTCGAGGGCGGTGGCA TGGCGATGTGGCCGTGAAGGTGCTCAAGGTGTCCCAGCCC ACAGCTGAGCAGGCCCAGGCTTTCAAGAATGAGATGCAGG TGCTCAGGAAGACGCGACATGTCAACATCTTGCTGTTTAT GGGCTTCATGACCCGGCCGGGATTTGCCATCATCACACAG TGGTGTGAGGGCTCCAGCCTCTACCATCACCTGCATGTGG CCGACACACGCTTCGACATGGTCCAGCTCATCGACGTGGC CCGGCAGACTGCCCAGGGCATGGACTACCTCCATGCCAAG AACATCATCCACCGAGATCTCAAGTCTAACAACATCTTCC TACATGAGGGGCTCACGGTGAAGATCGGTGACTTTGGCTT GGCCACAGTGAAGACTCGATGGAGCGGGGCCCAGCCCTTG GAGCAGCCCTCAGGATCTGTGCTGTGGATGGCAGCTGAGG TGATCCGTATGCAGGACCCGAACCCCTACAGCTTCCAGTC AGACGTCTATGCCTACGGGGTTGTGCTCTACGAGCTTATG ACTGGCTCACTGCCTTACAGCCACATTGGCTGCCGTGACC AGATTATCTTTATGGTGGGCCGTGGCTATCTGTCCCCGGA CCTCAGCAAAATCTCCAGCAACTGCCCCAAGGCCATGCGG CGCCTGCTGTCTGACTGCCTCAAGTTCCAGCGGGAGGAGC GGCCCCTCTTCCCCCAGATCCTGGCCACAATTGAGCTGCT GCAACGGTCACTCCCCAAGATTGAGCGGAGTGCCTCGGAA CCCTCCTTGCACCGCACCCAGGCCGATGAGTTGCCTGCCT GCCTACTCAGCGCAGCCCGCCTTGTGCCTTAGGCCCCGCC CAAGCCACCAGGGAGCCAATCTCAGCCCTCCACGCCAAGG AGCCTTGCCCACCAGCCAATCAATGTTCGTCTCTGCCCTG ATGCTGCCTCAGGATCCCCCATTCCCCACCCTGGGAGATG AGGGGGTCCCCATGTGCTTTTCCAGTTCTTCTGGAATTGG GGGACCCCCGCCAAAGACTGAGCCCCCTGTCTCCTCCATC ATTTGGTTTCCTCTTGGCTTTGGGGATACTTCTAAATTTT GGGAGCTCCTCCATCTCCAATGGCTGGGATTTGTGGCAGG GATTCCACTCAGAACCTCTCTGGAATTTGTGCCTGATGTG CCTTCCACTGGATTTTGGGGTTCCCAGCACCCCATGTGGA TTTTGGGGGGTCCCTTTTGTGTCTCCCCCGCCATTCAAGG ACTCCTCTCTTTCTTCACCAAGAAGCACAGAATTCTGCTG GGCCTTTGCTTGTTTAAAAAAAAAAAAAAAAAAAAAAAAA AA | |
| ATP6V1H | NM_015941.3 | AGCAGTCACGTGCCTCCGATCACGTGACCGGCGCCTCTGT CATTCTACTGCGGCCGCCCTGGCTTCCTTCTACCTGTGCG GCCCTCAACGTCTCCTTGGTGCGGGACCCGCTTCACTTTC GGCTCCCGGAGTCTCCCTCCACTGCTCAGACCTCTGGACC TGACAGGAGACGCCTACTTGGCTCTGACGCGGCGCCCCAG CCCGGCTGTGTCCCCGGCGCCCCGGACCACCCTCCCTGCC GGCTTTGGGTGCGTTGTGGGGTCCCGAGGATTCGCGAGAT TTGTTGAAAGACATTCAAGATTACGAAGTTTAGATGACCA AAATGGATATCCGAGGTGCTGTGGATGCTGCTGTCCCCAC CAATATTATTGCTGCCAAGGCTGCAGAAGTTCGTGCAAAC AAAGTCAACTGGCAATCCTATCTTCAGGGACAGATGATTT CTGCTGAAGATTGTGAGTTTATTCAGAGGTTTGAAATGAA ACGAAGCCCTGAAGAGAAGCAAGAGATGCTTCAAACTGAA GGCAGCCAGTGTGCTAAAACATTTATAAATCTGATGACTC ATATCTGCAAAGAACAGACCGTTCAGTATATACTAACTAT GGTGGATGATATGCTGCAGGAAAATCATCAGCGTGTTAGC ATTTTCTTTGACTATGCAAGATGTAGCAAGAACACTGCGT GGCCCTACTTTCTGCCAATGTTGAATCGCCAGGATCCCTT CACTGTTCATATGGCAGCAAGAATTATTGCCAAGTTAGCA GCTTGGGGAAAAGAACTGATGGAAGGCAGTGACTTAAATT ACTATTTCAATTGGATAAAAACTCAGCTGAGTTCACAGAA ACTGCGTGGTAGCGGTGTTGCTGTTGAAACAGGAACAGTC TCTTCAAGTGATAGTTCGCAGTATGTGCAGTGCGTGGCCG GGTGTTTGCAGCTGATGCTCCGGGTCAATGAGTACCGCTT TGCTTGGGTGGAAGCAGATGGGGTAAATTGCATAATGGGA GTGTTGAGTAACAAGTGTGGCTTTCAGCTCCAGTATCAAA TGATTTTTTCAATATGGCTCCTGGCATTCAGTCCTCAAAT GTGTGAACACCTGCGGCGCTATAATATCATTCCAGTTCTG TCTGATATCCTTCAGGAGTCTGTCAAAGAGAAAGTAACAA GAATCATTCTTGCAGCATTTCGTAACTTTTTAGAAAAATC AACTGAAAGAGAAACTCGCCAAGAATATGCCCTGGCTATG ATTCAGTGCAAAGTTCTGAAACAGTTGGAGAACTTGGAAC AGCAGAAGTACGATGATGAAGATATCAGCGAAGATATCAA ATTTCTTTTGGAAAAACTTGGAGAGAGTGTCCAGGACCTT | 5 |

TABLE 1-continued

GEP-NEN Biomarker/Houskeeper Sequence Information

| Gene Name | RefSeq Accession | Sequence | SEQ ID NO: |
|---|---|---|---|
| | | AGTTCATTTGATGAATACAGTTCAGAACTTAAATCTGGAA<br>GGTTGGAATGGAGTCCTGTGCACAAATCTGAGAAATTTTG<br>GAGAGAGAATGCTGTGAGGTTAAATGAGAAGAATTATGAA<br>CTCTTGAAAATCTTGACAAAACTTTTGGAAGTGTCAGATG<br>ATCCCCAAGTCTTAGCTGTTGCTGCTCACGATGTTGGAGA<br>ATATGTGCGGCATTATCCACGAGGCAAACGGGTCATCGAG<br>CAGCTCGGTGGGAAGCAGCTGGTCATGAAC<u>CACATGCATC</u><br><u>ATGAAGACCAGCAGGTCCGCTATAATGCTCTGCTGGCCGT</u><br><u>GCAGAAGCTCATGGTGCACAACTGGGAATACCTTGGCAAG</u><br><u>CAGCTCCAGTCC</u>GAGCAGCCCCAGACCGCTGCCGCCCGAA<br>GCTAAGCCTGCCTCTGGCCTTCCCCTCCGCCTCAATGCAG<br>AACCAGTAGTGGGAGCACTGTGTTTAGAGTTAAGAGTGAA<br>CACTGTTTGATTTTACTTGGAATTTCCTCTGTTATATAGC<br>TTTTCCCAATGCTAATTTCCAAACAACAACAACAAAATAA<br>CATGTTTGCCTGTTAAGTTGTATAAAAGTAGGTGATTCTG<br>TATTTAAAGAAAATATTACTGTTACATATACTGCTTGCAA<br>TTTCTGTATTTATTGTTCTCTGGAAATAAATATAGTTATT<br>AAAGGATTCTCACTCCAAACATGGCCTCTCTCTTTACTTG<br>GACTTTGAACAAAAGTCAACTGTTGTCTCTTTTCAAACCA<br>AATTGGGAGAATTGTTGCAAAGTAGTGAATGGCAAATAAA<br>TGTTTTAAAATCTATCGCTCTATCAA | |
| BNIP3L | NM_004331.2 | CGTCAGGGGCAGGGGAGGGACGGCGCAGGCGCAGAAAAGG<br>GGGCGGCGGACTCGGCTTGTTGTGTTGCTGCCTGAGTGCC<br>GGAGACGGTCCTGCTGCTGCCGCAGTCCTGCCAGCTGTCC<br>GACAATGTCGTCCCACCTAGTCGAGCCGCCGCCGCCCCTG<br>CACAACAACAACAACAACTGCGAGGAAAATGAGCAGTCTC<br>TGCCCCCGCCGGCCGGCCTCAACAGTTCCTGGGTGGAGCT<br>ACCCCATGAACAGCAGCAATGGCAATGATAATGGCAATGGG<br>AAAAATGGGGGCTGGAACACGTACCATCCTCATCCTCCA<br>TCCACAATGGAGACATGGAGA<u>AGATTCTTTTGGATGCACA</u><br><u>ACATGAATCAGGAC</u>AGAGTAGTTCCAGAGGCAGTTCTCAC<br>TGTGACAGCCCTTCGCCACAAGAAGATGGGCAGATCATGT<br>TTGATGTGGAAATGCACACCAGCAGGGACCATAGCTCTCA<br>GTCAGAAGAAGAAGTTGTAGAAGGAGAGAAGGAAGTCGAG<br>GCTTTGAAGAAAAGTGCGGACTGGGTATCAGACTGGTCCA<br>GTAGACCCGAAAACATTCCACCCAAGGAGTTCCACTTCAG<br>ACACCCTAAACGTTCTGTGTCTTTAAGCATGAGGAAAAGT<br>GGAGCCATGAAGAAGGGGGTATTTTCTCCGCAGAATTTC<br>TGAAGGTGTTCATTCCATCTCTCTTCCTTTCTCATGTTTT<br>GGCTTTGGGGCTAGGCATCTATATTGGAAAGCGACTGAGC<br>ACACCCTCTGCCAGCACCTACTGAGGGAAAGGAAAAGCCC<br>CTGGAAATGCGTGTGACCTGTGAAGTGGTGTATTGTCACA<br>GTAGCTTATTTGAACTTGAGACCATTGTAAGCATGACCCA<br>ACCTACCACCCTGTTTTTACATATCCAATTCCAGTAACTC<br>TCAAATTCAATATTTTATTCAAACTCTGTTGAGGCATTTT<br>ACTAACCTTATACCCTTTTTGGCCTGAAGACATTTTAGAA<br>TTTCCTAACAGAGTTTACTGTTGTTTAGAAATTTGCAAGG<br>GCTTCTTTTCCGCAAATGCCACCAGCAGATTATAATTTTG<br>TCAGCAATGCTATTATCTCTAATTAGTGCCACCAGACTAG<br>ACCTGTATCATTCATGGTATAAATTTTACTCTTGCAACAT<br>AACTACCATCTCTCTCTTAAAACGAGATCAGGTTAGCAAA<br>TGATGTAAAAGAAGCTTTATTGTCTAGTTGTTTTTTTCC<br>CCCAAGACAAAGGCAAGTTTCCCTAAGTTTGAGTTGATAG<br>TTATTAAAAGAAAACAAAACAAAAAAAAAGGCAAGGCA<br>CAACAAAAAAATATCCTGGGCAATAAAAAAAATATTTTAA<br>ACCAGCTTTGGAGCCACTTTTTTGTCTAAGCCTCCTAATA<br>GCGTCTTTTAATTTATAGGAGGCAAACTGTATAAATGATA<br>GGTATGAAATAGAATAAGAAGTAAAATACATCAGCAGATT<br>TTCATACTAGTATGTTGTAATGCTGTCTTTTCTATGGTGT<br>AGAATCTTTCTTTCTGATAAGGAACGTCTCAGGCTTAGAA<br>ATATATGAAATTGCTTTTGAGATTTTTGCGTGTGTGTTT<br>GATATTTTTTACGATAATTAGCTGCATGTGAATTTTTCAT<br>GACCTTCTTTACATTTTTTATTTTTATTTCTTATTTTT<br>TTTTCTCTAAGAAGAGGCTTTGGAATGAGTTCCAATTTGT<br>GATGTTAATACAGGCTTCTTGTTTTAGGAAGCATCCACCTA<br>TACTCTGAAGCCTTTAAACTCTGAAGAGAATTGTTTCAGA<br>GTTATTCCAAGCACTTGTGCAACTTGGAAAAACAGACTTG<br>GGTTGTGGGAACAGTTGACAGCGTTCTGAAAAGATGCCAT<br>TTGTTTCCTTCTGATCTCTCACTGAATAATGTTTACTGTA<br>CAGTCTTCCCAAGGTGATTCCTGCGACTGCAGGCACTGGT<br>CATTTTCTCATGTAGCTGTCTTTTCAGTTATGGTAAACTC<br>TTAAAGTTCAGAACACTCAACAGATTCCTTCAGTGATATA<br>CTTGTTCGTTCATTTCTAAAATGTGAAGCTTTAGGACCAA<br>ATTGTTAGAAAGCATCAGGATGACCAGTTATCTCGAGTAG | 6 |

TABLE 1-continued

GEP-NEN Biomarker/Houskeeper Sequence Information

| Gene Name | RefSeq Accession | Sequence | SEQ ID NO: |
|---|---|---|---|
| | | ATTTTCTTGGATTTCAGAACATCTAGCATGACTCTGAAGG<br>ATACCACATGTTTTATATATAAATAATTACTGTTTATGAT<br>ATAGACATTGATATTGACTATTTAGAGAACCGTTGTTAAT<br>TTTAAAACTAGCAATCTATAAAGTGCACCAGGTCAACTTG<br>AATAAAAACACTATGACAGACAGGTTTGCCAGTTTGCAGA<br>AACTAACTCTTTTCTCACATCAACATTTGTAAAATTGATG<br>TGTTATAGTGGAAAATAACATATAGATTAAACAAAATTTT<br>TATCTTTTTTCAAGAATATAGCTGGCTATCTTTAAGAAAG<br>ATGATATATCCTAGTTTTGAAAGTAATTTTCTTTTTTCTT<br>TCTAGCATTTGATGTCTAAATAATTTTGGACATCTTTTTC<br>CTAGACCATGTTTCTGTCTTACTCTTAAACCTGGTAACAC<br>TTGATTTGCCTTCTATAACCTATTTATTTCAAGTGTTCAT<br>ATTTGAATTTCTTTGGGAAGAAAGTAAATCTGATGGCTCA<br>CTGATTTTTGAAAAGCCTGAATAAAATTGGAAAGACTGGA<br>AAGTTAGGAGAACTGACTAGCTAAACTGCTACAGTATGCA<br>ATTTCTATTACAATTGGTATTACAGGGGGGAAAAGTAAAA<br>TTACACTTTACCTGAAAGTGACTTCTTACAGCTAGTGCAT<br>TGTGCTCTTTCCAAGTTCAGCAGCAGTTCTATCAGTGGTG<br>CCACTGAAACTGGGTATATTTATGATTTCTTTCAGCGTTA<br>AAAAGAAACATAGTGTTGCCCTTTTTCTTAAAGCATCAGT<br>GAAATTATGGAAAATTACTTAAAACGTGAATACATCATCA<br>CAGTAGAATTTATTATGAGAGCATGTAGTATGTATCTGTA<br>GCCCTAACACATGGGATGAACGTTTTACTGCTACACCCAG<br>ATTTGTGTTGAACGAAAACATTGTGGTTTGGAAAGGAGAA<br>TTCAACAATTAATAGTTGAAATTGTGAGGTTAATGTTTAA<br>AAAGCTTTACACCTGTTTACAATTTGGGGACAAAAAGGCA<br>GGCTTCATTTTTCATATGTTTGATGAAAACTGGCTCAAGA<br>TGTTTGTAAATAGAATCAAGAGCAAAACTGCACAAACTTG<br>CACATTGGAAAGTGCAACAAGTTCCCGTGATTGCAGTAAA<br>AATATTTACTATTCTAAAAAAATGAGAATTGAAGACTTAG<br>CCAGTCAGATAAGTTTTTTCATGAACCCGTTGTGGAAATT<br>ATTGGAATTAACTGAGCCAAAGTGATTATGCATTCTTCAT<br>CTATTTTAGTTAGCACTTTGTATCGTTATATACAGTTTAC<br>AATACATGTATAACTTGTAGCTATAAACATTTTGTGCCAT<br>TAAAGCTCTCACAAAACTTTAAAAA | |
| BRAF | NM_004333.4 | CGCCTCCCTTCCCCCTCCCCGCCCGACAGCGGCCGCTCGG<br>GCCCCGGCTCTCGGTTATAAGATGGCGGCGCTGAGCGGTG<br>GCGGTGGTGGCGGCGCGGAGCCGGGCCAGGCTCTGTTCAA<br>CGGGGACATGGAGCCCGAGGCCGGCGCCGGCGCCGGCGCC<br>GCGGCCTCTTCGGCTGCGGACCCTGCCATTCCGGAGGAGG<br><u>TGTGGAATATCAAACAAATGATTAAGTTGACACAGGAACA</u><br>TATAGAGGCCCTATTGGACAAATTTGGTGGGGAGCATAAT<br>CCACCATCAATATATCTGGAGGCCTATGAAGAATACACCA<br>GCAAGCTAGATGCACTCCAACAAAGAGAACAACAGTTATT<br>GGAATCTCTGGGGAACGGAACTGATTTTTCTGTTTCTAGC<br>TCTGCATCAATGGATACCGTTACATCTTCTTCCTCTTCTA<br>GCCTTTCAGTGCTACCTTCATCTCTTTCAGTTTTTCAAAA<br>TCCCACAGATGTGGCACGGACAACCCCAAGTCACCACAA<br>AAACCTATCGTTAGAGTCTTCCTGCCCAACAAACAGAGGA<br>CAGTGGTACCTGCAAGGTGTGGAGTTACAGTCCGAGACAG<br>TCTAAAGAAAGCACTGATGATGAGAGGTCTAATCCCAGAG<br>TGCTGTGCTGTTTACAGAATTCAGGATGGAGAGAAGAAAC<br>CAATTGGTTGGGACACTGATATTTCCTGGCTTACTGGAGA<br>AGAATTGCATGTGGAAGTGTTGGAGAATGTTCCACTTACA<br>ACACACAACTTTGTACGAAAAACGTTTTTCACCTTAGCAT<br>TTTGTGACTTTTGTCGAAAGCTGCTTTTTCCAGGGTTTCCG<br>CTGTCAAACATGTGGTTATAAATTTCACCAGCGTTGTAGT<br>ACAGAAGTTCCACTGATGTGTGTTAATTATGACCAACTTG<br>ATTTGCTGTTTGTCTCCAAGTTCTTTGAACACCACCCAAT<br>ACCACAGGAAGAGGCGTCCTTAGCAGAGACTGCCCTAACA<br>TCTGGATCATCCCCTTCCGCACCCGCCTCGGACTCTATTG<br>GGCCCCAAATTCTCACCAGTCCGTCTCCTTCAAAATCCAT<br>TCCAATTCCACAGCCCTTCCGACCAGCAGATGAAGATCAT<br>CGAAATCAATTTGGGCAACGAGACCGATCCTCATCAGCTC<br>CCAATGTGCATATAAACACAATAGAACCTGTCAATATTGA<br>TGACTTGATTAGAGACCAAGGATTTCGTGGTGATGGAGGA<br>TCAACCACAGGTTTGTCTGCTACCCCCCTGCCTCATTAC<br>CTGGCTCACTAACTAACGTGAAAGCCTTACAGAAATCTCC<br>AGGACCTCAGCGAGAAAGGAAGTCATCTTCATCCTCAGAA<br>GACAGGAATCGAATGAAAACACTTGGTAGACGGGACTCGA<br>GTGATGATTGGGAGATTCCTGATGGGCAGATTACAGTGGG<br>ACAAAGAATTGGATCTGGATCATTTGGAACAGTCTACAAG<br>GGAAAGTGGCATGGTGATGTGGCAGTGAAAATGTTGAATG<br>TGACAGCACCTACACCTCAGCAGTTACAAGCCTTCAAAAA | 7 |

TABLE 1-continued

GEP-NEN Biomarker/Houskeeper Sequence Information

| Gene Name | RefSeq Accession | Sequence | SEQ ID NO: |
|---|---|---|---|
| | | TGAAGTAGGAGTACTCAGGAAAACACGACATGTGAATATC<br>CTACTCTTCATGGGCTATTCCACAAAGCCACAACTGGCTA<br>TTGTTACCCAGTGGTGTGAGGGCTCCAGCTTGTATCACCA<br>TCTCCATATCATTGAGACCAAATTTGAGATGATCAAACTT<br>ATAGATATTGCACGACAGACTGCACAGGGCATGGATTACT<br>TACACGCCAAGTCAATCATCCACAGAGACCTCAAGAGTAA<br>TAATATATTTCTTCATGAAGACCTCACAGTAAAAATAGGT<br>GATTTTGGTCTAGCTACAGTGAAATCTCGATGGAGTGGGT<br>CCCATCAGTTTGAACAGTTGTCTGGATCCATTTTGTGGAT<br>GGCACCAGAAGTCATCAGAATGCAAGATAAAAATCCATAC<br>AGCTTTCAGTCAGATGTATATGCATTTGGAATTGTTCTGT<br>ATGAATTGATGACTGGACAGTTACCTTATTCAAACATCAA<br>CAACAGGGACCAGATAATTTTTATGGTGGGACGAGGATAC<br>CTGTCTCCAGATCTCAGTAAGGTACGGAGTAACTGTCCAA<br>AAGCCATGAAGAGATTAATGGCAGAGTGCCTCAAAAAGAA<br>AAGAGATGAGAGACCACTCTTTCCCCAAATTCTCGCCTCT<br>ATTGAGCTGCTGGCCCGCTCATTGCCAAAAATTCACCGCA<br>GTGCATCAGAACCCTCCTTGAATCGGGCTGGTTTCCAAAC<br>AGAGGATTTTAGTCTATATGCTTGTGCTTCTCCAAAAACA<br>CCCATCCAGGCAGGGGGATATGGTGCGTTTCCTGTCCACT<br>GAAACAAATGAGTGAGAGAGTTCAGGAGAGTAGCAACAAA<br>AGGAAAATAAATGAACATATGTTTGCTTATATGTTAAATT<br>GAATAAAATACTCTCTTTTTTTTAAGGTGAACCAAAGAA<br>CACTTGTGTGGTTAAAGACTAGATATAATTTTTCCCCAAA<br>CTAAAATTTATACTTAACATTGGATTTTTAACATCCAAGG<br>GTTAAAATACATAGACATTGCTAAAAATTGGCAGAGCCTC<br>TTCTAGAGGCTTTACTTTCTGTTCCGGGTTTGTATCATTC<br>ACTTGGTTATTTTAAGTAGTAAACTTCAGTTTCTCATGCA<br>ACTTTTGTTGCCAGCTATCACATGTCCACTAGGGACTCCA<br>GAAGAAGACCCTACCTATGCCTGTGTTTGCAGGTGAGAAG<br>TTGGCAGTCGGTTAGCCTGGGTTAGATAAGGCAAACTGAA<br>CAGATCTAATTTAGGAAGTCAGTAGAATTTAATAATTCTA<br>TTATTATTCTTAATAATTTTTCTATAACTATTTCTTTTTA<br>TAACAATTTGGAAAATGTGGATGTCTTTTATTTCCTTGAA<br>GCAATAAACTAAGTTTCTTTTTATAAAAA | |
| C21ORF7 | NM_020152.3 | CGCAGCCCCGGTTCCTGCCCGCACCTCTCCCTCCACACCT<br>CCCCGCAAGCTGAGGGAGCCGGCTCCGGCCTCGGCCAGCC<br>CAGGAAGGCGCTCCCACAGCGCAGTGGTGGGCTGAAGGGC<br>TCCTCAAGTGCCGCCAAAGTGGGAGCCCAGGCAGAGGAGG<br>CGCCGAGAGCGAGGGAGGGCTGTGAGGACTGCCAGCACGC<br>TGTCACCTCTCAATAGCAGCCCAAACAGATTAAGACATGG<br>GAGATGTACAAGGGCAGCCGTGGGGCTGGCAACAGCTTCG<br>TAATCCTGGCTTCCTGCTTTCTGGGTCAAAGCCCTGGTGG<br>TGTGTTCTTGATATCGGTCCATCTAGTGGCGTTGTTTGAT<br>TCCTCCCACCTTGCTGATCATTCGTAGTGTAGCCCCCAAG<br>GTGTGGAATAACCCTTAAGCCCTTACCGGGGTCCTTCTGG<br>ACTGAGAATTGTTGTAAAGTAATACTGCTCAGGTGAAAGA<br>CAACTTGAGTGGTTAAATTACTGTCATGCAAAGCGACTAG<br>ATGGTTCAGCTGATTGCACCTTTAGAAGTTATGTGGAACG<br>AGGCAGCAGATCTTAAGCCCCTTGCTCTGTCACGCAGGCT<br>GGAATGCAGT<u>GGTGGAATCATGGCTCACTACAGCCCTGAC</u><br><u>CTCCTGGGCCCAGAGATGGAGTCTCGCTATTTTGCCCAGG</u><br><u>TTGGTC</u>TTGAACACCTGGCTTCAAGCAGTCCTCCTGCTTT<br>TGGCTTCTTGAAGTGCTTGGATTACAGTATTTCAGTTTTA<br>TGCTCTGCAACAAGTTTGGCCATGTTGGAGGACAATCCAA<br>AGGTCAGCAAGTTGGCTACTGGCGATTGGATGCTCACTCT<br>GAAGCCAAAGTCTATTACTGTGCCCGTGGAAATCCCCAGC<br>TCCCCTCTGGATGATACACCCCCTGAAGACTCCATTCCTT<br>TGGTCTTTCCAGAATTAGACCAGCAGCTACAGCCCCTGCC<br>GCCTTGTCATGACTCCGAGGAATCCATGGAGGTGTTCAAA<br>CAGCACTGCCAAATAGCAGAAGAATACCATGAGGTCAAAA<br>AGGAAATCACCCTGCTTGAGCAAAGGAAGAAGGAGCTCAT<br>TGCCAAGTTAGATCAGGCAGAAAAGGAGAAGGTGGATGCT<br>GCTGAGCTGGTTCGGGAATTCGAGGCTCTGACGGAGGAGA<br>ATCGGACGTTGAGGTTGGCCCAGTCTCAATGTGTGGAACA<br>ACTGGAGAAACTTCGAATACAGTATCAGAAGAGGCAGGGC<br>TCGTCCTAACTTTAAATTTTTCAGTGTGAGCATACGAGGC<br>TGATGACTGCCCTGTGCTGGCCAAAAGATTTTTATTTTAA<br>ATGAATAGTGAGTCAGATCTATTGCTTCTCTGTATTACCC<br>ACATGACAACTGTCTATAATGAGTTTACTGCTTGCCAGCT<br>TCTAGCTTGAGAGAAGGGATATTTTAAATGAGATCATTAA<br>CGTGAAACTATTACTAGTATATGTTTTTGGAGATCAGAAT<br>TCTTTTTCCAAAGATATATGTTTTTTTCTTTTTTAGGAAGA<br>TATGATCATGCTGTACAACAGGGTAGAAAATGATAAAAAT | 8 |

TABLE 1-continued

GEP-NEN Biomarker/Houskeeper Sequence Information

| Gene Name | RefSeq Accession | Sequence | SEQ ID NO: |
|---|---|---|---|
| | | AGACTATTGACTGACCCAGCTAAGAATCGTGGGCTGAGCA<br>GAGTTAAACCATGGGACAAACCCATAACATGTTCACCATA<br>GTTTCACGTATGTGTATTTTTAAATTTCATGCCTTTAATA<br>TTTCAAATATGCTCAAATTTAAACTGTCAGAAACTTCTGT<br>GCATGTATTTATATTTGCCAGAGTATAAACTTTTATACTC<br>TGATTTTTATCCTTCAATGATTGATTATACTAAGAATAAA<br>TGGTCACATATCCTAAAAGCTTCTTCATGAAATTATTAGC<br>AGAAACCATGTTTGTAACCAAAGCACATTTGCCAATGCTA<br>ACTGGCTGTTGTAATAATAAACAGATAAGGCTGCATTTGC<br>TTCATGCCATGTGACCTCACAGTAAACATCTGCCTTTG<br>CCTGTGTGTGTTCTGGGGGAGGGGGGACATGGAAAAATAT<br>TGTTTGGACATTACTTGGGTGAGTGCCCATGAAAACATCA<br>GTGAACTTGTAACTATTGTTTTGTTTTGGATTTAAGGAGA<br>TGTTTTAGATCAGTAACAGCTAATAGGAATATGCGAGTAA<br>ATTCAGAATTGAAACAATTTCTCCTTGTTCTACCTATCAC<br>CACATTTTCTCAAATTGAACTCTTTGTTATATGTCCATTT<br>CTATTCATGTAACTTCTTTTTCATTAAACATGGATCAAAA<br>CTGACAAAAAAAAAAAAAAA | |
| CD59 | NM_203331.2 | GGGGCCGGGGGGCGGAGCCTTGCGGGCTGGAGCGAAAGAA<br>TGCGGGGGCTGAGCGCAGAAGCGGCTCGAGGCTGGAAGAG<br>GATCTTGGGCGCCGCCAGTCTTTAGCACCAGTTGGTGTAG<br>GAGTTGAGACCTACTTCACAGTAGTTCTGTGGACAATCAC<br>AATGGGAATCCAAGGAGGGTCTGTCCTGTTCGGGCTGCTG<br>CTCGTCCTGGCTGTCTTCTGCCATTCAGGTCATAGCCTGC<br>AGTGCTACAACTGTCCTAACCCAACTGCTGACTGCAAAAC<br>AGCCGTCAATTGTTCATCTGATTTTGATGCGTGTCTCATT<br>ACCAAAGCTGGGTTACAAGTGTATAACAAGTGTTGGAAGT<br>TTGAGCATTGCAATTTCAACGACGTCACAACCCGCTTGAG<br>GGAAAATGAGCTAACGTACTACTGCTGCAAGAAGGACCTG<br>TGTAACTTTAACGAACAGCTTGAAAATGGTGGGACATCCT<br>TATCAGAGAAAACAGTTCTTCTGCTGGTGACTCCATTTCT<br>GGCAGCAGCCTGGAGCCTTCATCCCTAAGTCAACACCAGG<br>AGAGCTTCTCCCAAACTCCCCGTTCCTGCGTAGTCCGCTT<br>TCTCTTGCTGCCACATTCTAAAGGCTTGATATTTTCCAAA<br>TGGATCCTGTTGGGAAAGAATAAAATTAGCTTGAGCAACC<br>TGGCTAAGATAGAGGGGCTCTGGGAGACTTTGAAGACCAG<br>TCCTGTTTGCAGGGAAGCCCCACTTGAAGGAAGAAGTCTA<br>AGAGTGAAGTAGGTGTGACTTGAACTAGATTGCATGCTTC<br>CTCCTTTGCTCTTGGGAAGACCAGCTTTGCAGTGACAGCT<br>TGAGTGGGTTCTCTGCAGCCCTCAGATTATTTTTCCTCTG<br>GCTCCTTGGATGTAGTCAGTTAGCATCATTAGTACATCTT<br>TGGAGGGTGGGGCAGGAGTATATGAGCATCCTCTCTCACA<br>TGGAACGCTTTCATAAACTTCAGGGATCCCGTGTTGCCAT<br>GGAGGCATGCCAAATGTTCCATATGTGGGTGTCAGTCAGG<br>GACAACAAGATCCTTAATGCAGAGCTAGAGGACTTCTGGC<br>AGGGAAGTGGGGAAGTGTTCCAGATAGCAGGGCATGAAAA<br>CTTAGAGAGGTACAAGTGGCTGAAAATCGAGTTTTTCCTC<br>TGTCTTTAAATTTTATATGGGCTTTGTTATCTTCCACTGG<br>AAAAGTGTAATAGCATACATCAATGGTGTGTTAAAGCTAT<br>TTCCTTGCCTTTTTTTATTGGAATGGTAGGATATCTTGG<br>CTTTGCCACACACAGTTACAGAGTGAACACTCTACTACAT<br>GTGACTGGCAGTATTAAGTGTGCTTATTTTAAATGTTACT<br>GGTAGAAAGGCAGTTCAGGTATGTGTGTATATAGTATGAA<br>TGCAGTGGGGACACCCTTTGTGGTTACAGTTTGAGACTTC<br>CAAAGGTCATCCTTAATAACAACAGATCTGCAGGGGTATG<br>TTTTACCATCTGCATCCAGCCTCCTGCTAACTCCTAGCTG<br>ACTCAGCATAGATTGTATAAAATACCTTTGTAACGGCTCT<br>TAGCACACTCACAGATGTTTGAGGCTTTCAGAAGCTCTTC<br>TAAAAAATGATACACACCTTTCACAAGGGCAAACTTTTTC<br>CTTTTCCCTGTGTATTCTAGTGAATGAATCTCAAGATTCA<br>GTAGACCTAATGACATTTGTATTTTATGCATCTTGGCTGTA<br>TTTAATGGCATAGGCTGACTTTTGCAGATGGAGGAATTTC<br>TTGATTAATGTTGAAAAAAAACCCTTGATTATACTCTGTT<br>GGACAAACCGAGTGCAATGAATGATGCTTTTCTGAAAATG<br>AAATATAACAAGTGGGTGAATGTGGTTATGGCCGAAAAGG<br>ATATGCAGTATGCTTAATGGTAGCAACTGAAAGAAGACAT<br>CCTGAGCAGTGCCAGCTTTCTTCTGTTGATGCCGTTCCCT<br>GAACATAGGAAAATAGAAACTTGCTTATCAAACTTAGCA<br>TTACCTTGGTGCTCTGTGTCTCTGTTAGCTCAGTGTCTT<br>TCCTTACATCAATAGGTTTTTTTTTTTTTTTGGCCTGA<br>GGAAGTACTGACCATGCCCACAGCCACCGGCTGAGCAAAG<br>AAGCTCATTTCATGTGAGTTCTAAGGAATGAGAAACAATT<br>TTGATGAATTTAAGCAGAAAATGAATTTCTGGGAACTTTT<br>TTGGGGGCGGGGGGTGGGGAATTCAGCCACACTCCAGAA | 9 |

TABLE 1-continued

GEP-NEN Biomarker/Houskeeper Sequence Information

| Gene Name | RefSeq Accession | Sequence | SEQ ID NO: |
|---|---|---|---|
| | | AGCCAGGAGTCGACAGTTTTGGAAGCCTCTCTCAGGATTG<br>AGATTCTAGGATGAGATTGGCTTACTGCTATCTTGTGTCA<br>TGTACCCACTTTTTGGCCAGACTACACTGGGAAGAAGGTA<br>GTCCTCTAAAGCAAAATCTGAGTGCCACTAAATGGGGAGA<br>TGGGGCTGTTAAGCTGTCCAAATCAACAAGGGTCATATAA<br>ATGGCCTTAAACTTTGGGGTTGCTTTCTGCAAAAAGTTGC<br>TGTGACTCATGCCATAGACAAGGTTGAGTGCCTGGACCCA<br>AAGGCAATACTGTAATGTAAAGACATTTATAGTACTAGGC<br>AAACAGCACCCCAGGTACTCCAGGCCCTCCTGGCTGGAGA<br>GGGCTGTGGCAATAGAAAATTAGTGCCAACTGCAGTGAGT<br>CAGCCTAGGTTAAATAGAGAGTGTAAGAGTGCTGGACAGG<br>AACCTCCACCCTCATGTCACATTTCTTCAATGTGACCCTT<br>CTGGCCCCTCTCCTCCTGACAGCGGAACAATGACTGCCCC<br>GATAGGTGAGGCTGGAGGAAGAATCAGTCCTGTCCTTGGC<br>AAGCTCTTCACTATGACAGTAAAGGCTCTCTGCCTGCTGC<br>CAAGGCCTGTGACTTTCTAACCTGGCCTCACGCTGGGTAA<br>GCTTAAGGTAGAGGTGCAGGATTAGCAAGCCCACCTGGCT<br>ACCAGGCCGACAGCTACATCCTCCAACTGACCCTGATCAA<br>CGAAGAGGGATTCATGTGTCTGTCTCAGTTGGTTCCAAAT<br>GAAACCAGGGAGCAGGGGAGTTAGGAATCGAACACCAGTC<br>ATGCCTACTGGCTCTCTGCTCGAGAGCCAATACCCTGTGC<br>CCTCCACTCATCTGGATTTACAGGAACTGTCATAGTGTTC<br>AGTATTGGGTGGTGATAAGCCCATTGGATTGTCCCCTTGG<br>GGGGATGAGCTAGGGGTGCAAGGAACACCTGATGAGTAGA<br>TAAGTGGAGCTCATGGTATTTCCTGAAAGATGCTAATCTA<br>TTTGCCAAACTTGGTCTTGAATGTACTGGGGGCTTCAAGG<br>TATGGGTATATTTTCTTGTGTCCTTGCAGTTAGCCCCCA<br>TGTCTTATGTGTGTCCTGAAAAAATAAGAGCCTGCCCAAG<br>ACTTTGGGCCTCTTGACAGAATTAACCACTTTTATACATC<br>TGAGTTCTCTTGGTAAGTTCTTTAGCAGTGTTCAAAGTCT<br>ACTAGCTCGCATTAGTTTCTGTTGCTGCCAACAGATCTGA<br>ACTAATGCTAACAGATCCCCCTGAGGGATTCTTGATGGGC<br>TGAGCAGCTGGCTGGAGCTAGTACTGACTGACATTCATTG<br>TGATGAGGGCAGCTTTCTGGTACAGGATTCTAAGCTCTAT<br>GTTTTATATACATTTTCATCTGTACTTGCACCTCACTTTA<br>CACAAGAGGAAACTATGCAAAGTTAGCTGGATCGCTCAAG<br>GTCACTTAGGTAAGTTGGCAAGTCCATGCTTCCCACTCAG<br>CTCCTCAGGTCAGCAAGTCTACTTCTCTGCCTATTTTGTA<br>TACTCTCTTTAATATGTGCCTAGCTTTGGAAAGTCTAGAA<br>TGGGTCCCTGGTGCCTTTTTACTTTGAAGAAATCAGTTTC<br>TGCCTCTTTTTGGAAAAGAAAACAAAGTGCAATTGTTTTT<br>TACTGGAAAGTTACCCAATAGCATGAGGTGAACAGGACGT<br>AGTTAGGCCTTCCTGTAAACAGAAAATCATATCAAAACAC<br>TATCTTCCCATCTGTTTCTCAATGCCTGCTACTTCTTGTA<br>GATATTTCATTTCAGGAGAGCAGCAGTTAAACCCGTGGAT<br>TTTGTAGTTAGGAACCTGGGTTCAAACCCTCTTCCACTAA<br>TTGGCTATGTCTCTGGACAAGTTTTTTTTTTTTTTTTTT<br>TTAAACCCTTTCTGAACTTTCACTTTCTATGTCTACCTCA<br>AAGAATTGTTGTGAGGCTTGAGATAATGCATTTGTAAGG<br>GTCTGCCAGATAGGAAGATGCTAGTTATGGATTTACAAGG<br>TTGTTAAGGCTGTAAGAGTCTAAAACCTACAGTGAATCAC<br>AATGCATTTACCCCCACTGACTTGGACATAAGTGAAAACT<br>AGCCAGAAGTCTCTTTTTCAAATTACTTACAGGTTATTCA<br>ATATAAAATTTTTGTAATGGATAATCTTATTTATCTAAAC<br>TAAAGCTTCCTGTTTATACACACTCCTGTTATTCTGGGAT<br>AAGATAAATGACCACAGTACCTTAATTTCTAGGTGGGTGC<br>CTGTGATGGTTCATTGTAGGTAAGGACATTTTCTCTTTTT<br>CAGCAGCTGTGTAGGTCCAGAGCCTCTGGGAGAGGAGGGG<br>GGTAGCATGCACCCAGCAGGGGACTGAACTGGGAAACTCA<br>AGGTTCTTTTTACTGTGGGGTAGTGAGCTGCCTTTCTGTG<br>ATCGGTTTCCCTAGGGATGTTGCTGTTCCCCTCCTTGCTA<br>TTCGCAGCTACATACAACGTGGCCAACCCCAGTAGGCTGA<br>TCCTATATATGATCAGTGCTGGTGCTGACTCTCAATAGCC<br>CCACCCAAGCTGGCTATAGGTTTACAGATACATTAATTAG<br>GCAACCTAAAATATTGATGCTGGTGTTGGTGTGACATAAT<br>GCTATGGCCAGAACTGAAACTTAGAGTTATAATTCATGTA<br>TTAGGGTTCTCCAGAGGGACAGAATTAGTAGGATATATGT<br>ATATATGAAAGGGAGGTTATTAGGGAGAAACTGGCTCCCAC<br>AGTTAGAAGGCGAAGTCGCACAATAGGCCGTCTGCAAGCT<br>GGGGTTAGAGAGAAGCCAGTAGTGGCTCAGCCTGAGTTCAA<br>AAACCTCAAAACTGGGGAAGCTGACAGTGCAGCCAGCCTT<br>CAGTCTGTGGCCAAAGGCCCAAGAGCCCCTGGCAACCAAC<br>CCACTGGTGCAAGTCCTAGATTCCAAAGGCTGAAGAACCT<br>GGAGTCTGATGTCAAGAGCAGGAAGAGTGGAAGAAAGCC<br>AGAAGACTCAGCAAACAAGGTAGACAGTGTCTACCACCAT | |

TABLE 1-continued

GEP-NEN Biomarker/Houskeeper Sequence Information

| Gene Name | RefSeq Accession | Sequence | SEQ ID NO: |
|---|---|---|---|
| | | AGTGGCCATACCAAAGAGGCTACCGATTCCTTCCTGCTAC<br>CTGGATCCCTGAAGTTGCCCTGGTCTCTGCACCTTCTAAA<br>CCTAGTTCTTAAGAGCTTTCCATTACATGAGCTGTCTCAA<br>AGCCCTCCAATAAATTCTCAGTGTAAGCTTCTGTTGCTTG<br>TGGACAGAAAATTCTGACAGACCTACCCTATAAGTGTTAC<br>TGTCAGGATAACATGAGAACGCACAACAGTAAGTGGTCAC<br>TAAGTGTTAGCTACGGTTATTTTGCCCAAGGTAGCATGGC<br>TAGTTGATGCCGGTTGATGGGGCTTAAACCCAGCTCCCTC<br>ATCTTCCAGGCCTCTGTACTCCCTATTCCACTAAACTACC<br>TCTCAGGTTTATTTTTTAAATTCTTACTCTGCAAGTACA<br>TAGGACCACATTTACCTGGGAAAACAAGAATAAAGGCTGC<br>TCTGCATTTTTTAGAAACTTTTTTGAAAGGGAGATGGGAA<br>TGCCTGCACCCCCAAGTCCAGACCAACACAATGGTTAATT<br>GAGATGAATAATAAAGGAAAGACTGTTCTGGGCTTCCCAG<br>AATAGCTTGGTCCTTAAATTGTGGCACAAACAACCTCCTG<br>TCAGAGCCAGCCTCCTGCCAGGAAGAGGGGTAGGAGACTA<br>GAGGCCGTGTGTGCAGCCTTGCCCTGAAGGCTAGGGTGAC<br>AATTTGGAGGCTGTCCAAACACCCTGGCCTCTAGAGCTGG<br>CCTGTCTATTTGAAATGCCGGCTCTGATGCTAATCGGCGA<br>CCCTCAGGCAAGTTACTTAACCTTACATGCCTCAGTTTTC<br>TCATCTGGAAAATGAGAACCCTAGGTTTAGGGTTGTTAGA<br>AAAGTTAAATGAGTTAAGACAAGTGCCTGGGACACAGTAG<br>CCTCTTGTGTGTGTTTATCATTATGTCCTCAGCAGGTCGT<br>AGAAGCAGCTTCTCAGGTGTGAGGCTGGCGCGATTATCTG<br>GAGTGGGTTGGGTTTTCTAGGATGGACCCCCTGCTGCATT<br>TTCCTCATTCATCCACCAGGGCTTAATGGGGAATCAAGGA<br>ATCCATGTGTAACTGTATAATAACTGTAGCCACACTCCAA<br>TGACCACCTACTAGTTGTCCCTGGCACTGCTTATACATAT<br>GTCCATCAAATCAATCCTATGAAGTAGATACTGTCTTCAT<br>TTTATAGATCAGAGACAATTGGGGTTCAGAGAGCTGATGT<br>GATTTTCCCAGGGTCACAGAGAGTCCCAGATTCAGGCACA<br>ACTCTTGTATTCCAAGACACAACCACTACATGTCCAAAGG<br>CTGCCCAGAGCCACCGGGCACGGCAAATTGTGACATATCC<br>CTAAAGAGGCTGAGCACCTGGTCAGGATCTGATGGCTGAC<br>AGTGTGTCCAGATGCAGAGCTGGAGTGGGGAGGGGAAGG<br>GGGGCTCCTTGGGACAGAGAAGGCTTTCTGTGCTTTCTCT<br>GAAGGGAGCAGTCTGAGGACCAAGGGAACCCGGCAAACAG<br>CACCTCAGGTACTCCAGGCCCTCCTGGCTGGAGAGGGCTG<br>TGGCAATGGAAAATTAGTGCCAACTGCAATGAGTCAGCCT<br>CGGTTAAATAGAGAGTGAAGAATGCTGGACAGGAACCTCC<br>ACCCTCATGTCACATTTCTTCAGTGTGACCCCTTCTGGCCC<br>CTCTCCTCCTGACAGCGGAACAATGACTGCCCCGATAGGT<br>GAGGCTGGAGGAAGAATCAGTCCTGTCCTTGGCAAGCTCT<br>TCACTATGACAGTAAAGGCTCTCTGCCTGCTGCCAAGGCC<br>TGTGACTTTCTAACCTGGCCTCACGCTGGGTAAGCTTAAG<br>GTAGAGGTGCAGGATTAGCAAGCCCACCTGGCTACCAGGC<br>CGACAGCTACATCTTTCAACTGACCCTGATCAACGAAGAG<br>GGACTTGTGTCTCTCAGTTGGTTCCAAATGAAACCAGGGA<br>GCAGGGGCGTTAGGAAGCTCCAACAGGATGGTACTTAATG<br>GGGCATTTGAGTGGAGAGGTAGGTGACATAGTGCTTTGGA<br>GCCCAGGGAGGGAAAGGTTCTGCTGAAGTTGAATTCAAGA<br>CTGTTCTTTCATCACAAACTTGAGTTTCCTGGACATTTGT<br>TTGCAGAAACAACCGTAGGGTTTTGCCTTAACCTCGTGGG<br>TTTATTATTACCTCATAGGGACTTTGCCTCCTGACAGCAG<br>TTTATGGGTGTTCATTGTGGCACTTGAGTTTTCTTGCATA<br>CTTGTTAGAGAAACCAAGTTTGTCATCAACTTCTTATTTA<br>ACCCCCTGGCTATAACTTCATGGATTATGTTATAATTAAG<br>CCATCCAGAGTAAAATCTGTTTAGATTATCTTGGAGTAAG<br>GGGGAAAAAATCTGTAATTTTTTCTCCTCAACTAGATATA<br>TACATAAAAAATGATTGTATTGCTTCATTTAAAAAATATA<br>ACGCAAATCTCTTTTCCTTCTAAAAAAAAAAAAAAAAAAA | |
| COMMD9 | NM_001101653.1 | GCTTCCCTGGGTGCCACGGTCATGTGACTTCGGCAAGATG<br>GCTGCCCTGACAGCGGAGCATTTTGCAGCACTCCAGAGCC<br>TGCTCAAGCTGCTCCAGGCTCTGCACCGCCTCACTAGGCT<br>GGTGGCATTCCGTGACCTGTCCTCTGCCGAGGCAATTCTG<br>GCTCTCTTTCCAGAAAATTTCCACCAAAAC<u>CTCAAAAACC</u><br><u>TGCTGACAAAGATCATCCTAGAACATGTGTCTACTTGGAG</u><br><u>AACCGAAGCCCAGGCAAATCAGATCTCTCTGCCACGCCTG</u><br>GTCGATCTGGACTGGAGAGTGGATATCAAAACCTCCTCAG<br>ACAGCATCAGCCGCATGGCCGTCCCCACCTGCCTGCTCCA<br>GATGAAGATCCAAGAGATCCCAGCCTATGCGGAGACAAA<br>CCCTCCATCTCAGCTGTCACCGTGGAGCTGAGCAAAGAAA<br>CACTGGACACCATGTTAGATGGCTGGGCCGCATCCGAGA<br>CCAACTCTCTGCCGTGGCCAGTAAATGATCCAGCCAGCTG | 10 |

TABLE 1-continued

GEP-NEN Biomarker/Houskeeper Sequence Information

| Gene Name | RefSeq Accession | Sequence | SEQ ID NO: |
|---|---|---|---|
| | | CCAGGGCCACTGCCATGACCCAGCTGCTCATGAGTGATAA ATGTCTCCCCATATGCAGGCTGCCCTTGCAGCTGCAGCTG ACAACAGGCAGGATGGTGGGGACAGCAGGGGGCTACTGCC ATCCAGAAGTTACAGTTGGATTGGGAAGAAGCAGCCAGAT CCCCCGCTGTTCTCACTCATCTTCTTTCTCTTTCTGAAGC TGGAGAGCAGAAGCCCCCATCTTTGAAAAGCTCCTGAGTG CAACTTAATTACCACCATGGCAGGGTGAGGGAACATTTGC ATCGTCAGCTGCCTCTGCATAGCTGTTTGAGAAATTCAGG CCCAAATCATGCAGCCTATCCAATAAGTAAGTTTATTTCC AACATTAGCTCTAATTAGTTCATTTCCAATCCCAGAACAC ATGGAGGGAATCGGACAGGTGATGCCAGCAGTTCCTGCTC CTCTGTCAGGGAAGCCAGGCAGAGCCCACAGAGCATGGTC CATCCAGAGTGTTCCCTGAGCCCCCTCCACCATACTGGAA CCCCTCTTCAGTGTAGGAAGTCTGAAATGGGTGCTAATTC CCTTCTTCATGAAACCAGGGCCCTCTTCCTTCATCTAATG CAGCCACTCCTAGGTGAAGAAGTGGGAATAATTGGAAATA AACAACAGTTCTAAAACTTCCATGATTTTTGTAGCTTCTT TTGTCCCCAAGTTGAAGCTTTTGGCCAGTACCTTCTCTAG TTTTTAAAGATGATCCCAACTTCCTAATTCCCAGCTAAGC CCTTGACCCATGGTGTGACATGAAATCAGGCAATTGAATC GCACCACTTTCTGTGTTTTCACCTGTTACGTAGAACAAAA GGAAGCAAGGTGGCCAGGCGCAATGGCTCACGCCTGTAAT CCCAGCACTTTGGGAGGCCGAGGCAGGCAGATCATGAGGT CAGGAGATCGAGACCATGGTGAAACCCCATCTCTACTAAA AATACAAAAAATTAGCTGGGCGCGGTGGCGGGCATCTGTA GTCCCAGCTCCTCGGGAGGCTGAGGCAGGAGAATGGCGTG AACCTGGGAGGCAGAGCTTGCAGTGAGCCGAGATCGTGCC ACTGCACTCCAGTCTGGGTGACAGAGAAGGACTCGTCTCA AAAAATAAAATAAATAAAAAGGAAGCAAGGCTAATCATC AGTATGTGCTTGTTACAAGAGCTATGATGAAGGCACTCCT TCGAGTTTAACCAAATGAGATCATCTCTGTCATGTGCCTC ACGCCTCACAGGGACTCCATGTGTGAAGATTCCCCCTTCA CTCACCAGATCATCTCCATGGCAACAGCTTGCAGCCTGCT CTTGGAGTGCTTTGTTTTGGCAGCTTCTCTGCTAGTTTGT GTATGGAGTGAATGGAGGAGGTAAATCCACAGATTAAGAA TATGCTGTCAGGAGTCAGGCAGCCAAGGTCAGAAGCCAGC TCTGCTTCTCAGTGGTAAGGTGCTTGACTTCTACATCTCA ATTTTCACCCACTTTGTACTTTTTTCCTAAATTAAATGAG TATAATAGTAGTACCTACTTGATAGGACTTTTGTGAAAAT TAAATGATATAATGCACCTAAAAACAGTACTGTTACAACT AATAGGAAAGGCTTTGATTATTAATGGATGAGAGTAGAAA GCTTGGTGCATTTATTGTCTCATCTACTATAACAGAGTTG GTGTGAGAATTAGTATTATCATCCTCCCTTTATTGACCAG GAAACCAGCTCATTGAGATTGAGTCATCTGCTGGTAAATG GTCTCATTAAGAGGTGGACCCATATTTCTCTAGCTTTCTC TTTACAACACAGGACTTTGCAAGGAACATATAATTCTGTG ACTAGCGCCATTTGGAAAATGTTGAAACTGAAGTAGAGAT GAGAGATCTTACGTCTGCCTACCCAGTGAGATACGAGGAA GGTCAAGGGAAAAAAAATTCCAAGCTCTTCTTTATCTGCT ATAGGAAATGAACATTCAATTTTTTGCATGCAACGACAAG AGGTCAAGGACCCCAGAAGCCAGCCCGCTACTTCCAAGTT GAGAGCCCCTGGTCATACCCTCCAGTTGAGCTCAGATTTG TCACAAATTTACCCCTCTCCTTTCCTTCCATTCCCCATGA CCTGCAGAGAGATGTCAGATACCTTCCTCTTGGCCTCC CATGGGCATCCATAAGAAACTTACTTGAAGCAAGAAGCCC AGTATAGGTGTCTGGGCAGTTGGACATTTCCTCTAGCCAG ATCTGTCCGAATAGAGCCATCTGGGTACATGACGCAGAGG GCATTTGATAAATAACTGGAAAAGTCAATAAATCTTTGCT ACCCTTCAAAAAAAAAAAAAAAAAAAAAAAAAAAAAAA | |
| CTGF | NM_001901.2 | AAACTCACACAACAACTCTTCCCCGCTGAGAGGAGACAGC CAGTGCGACTCCACCCTCCAGCTCGACGGCAGCCGCCCCG GCCGACAGCCCCGAGACGACAGCCCCGGCGCGTCCCGGTCC CCACCTCCGACCACCGCCAGCGCTCCAGGCCCCGCCGCTC CCCGCTCGCCGCCACCGCGCCCTCCGCTCCGCCCGCAGTG CCAACCATGACCGCCGCCAGTATGGGCCCCGTCCGCGTCG CCTTCGTGGTCCTCCTCGCCCTCTGCAGCCGGCCGGCCGT CGGCCAGAACTGCAGCGGGCCGTGCCGGTGCCCGGACGAG CCGGCGCCGCGCTGCCCGGCGGGCGTGAGCCTCGTGCTGG ACGGCTGCGGCTGCTGCCGCGTCTGCGCCAAGCAGCTGGG CGAGCTGTGCACCGAGCGCGACCCCTGCGACCCGCACAAG GGCCTCTTCTGTGACTTCGGCTCCCCGGCCAACCGCAAGA TCGGCGTGTGCACCGCCAAAGATGGTGCTCCCTGCATCTT CGGTGGTACGGTGTACCGCAGCGGAGAGTCCTTCCAGAGC AGCTGCAAGTACCAGTGCACGTGCCTGGACGGGGCGGTGG | 11 |

TABLE 1-continued

GEP-NEN Biomarker/Houskeeper Sequence Information

| Gene Name | RefSeq Accession | Sequence | SEQ ID NO: |
|---|---|---|---|
| | | GCTGCATGCCCCTGTGCAGCATGGACGTTCGTCTGCCCAG CCCTGACTGCCCCTTCCCGAGGAGGGTCAAGCTGCCCGGG AAATGCTGCGAGGAGTGGGTGTGTGACGAGCCCAAGGACC AAACCGTGGTTGGGCCTGCCCTCGCGGCTTACCGACTGGA AGACACGTTTGGCCCAGACCCAACTATGATTAGAGCCAAC TGCCTGGTCCAGACCACAGAGTGGAGCGCCTGTTCCAAGA CCTGTGGGATGGGCATCTCCACCCGGGTTACCAATGACAA CGCCTCCTGCAGGCTAGAGAAGCAGAGCCGCCTGTGCATG GTCAGGCCTTGCGAAGCTGACCTGGAAGAGAACATTAAGA AGGGCAAAAGTGCATCCGTACTCCCAAAATCTCCAAGCC TATCAAGTTTGAGCTTTCTGGCTGCACCAGCATGAAGACA TACCGAGCTAAATTCTGTGGAGTATGTACCGACGGCCGAT GCTGCACCCCCACAGAACCACCACCCTGCCGGTGGAGTT CAAGTGCCCTGACGGCGAGGTCATGAAGAAGAACATGATG TTCATCAAGACCTGTGCCTGCCATTACAACTGTCCCGGAG ACAATGACATCTTTGAATCGCTGTACTACAGGAAGATGTA CGGAGACATGGCATGAAGCCAGAGAGTGAGAGACATTAAC TCATTAGACTGGAACTTGAACTGATTCACATCTCATTTTT CCGTAAAAATGATTTCAGTAGCACAAGTTATTTAAATCTG TTTTTCTAACTGGGGGAAAAGATTCCCACCCAATTCAAAA CATTGTGCCATGTCAAACAAATAGTCTATCAACCCCAGAC ACTGGTTTGAAGAATGTTAAGACTTGACAGTGGAACTACA TTAGTACACAGCACCAGAATGTATATTAAGGTGTGGCTTT AGGAGCAGTGGGAGGGTACCAGCAGAAAGGTTAGTATCAT CAGATAGCATCTTATACGAGTAATATGCCTGCTATTTGAA GTGTAATTGAGAAGGAAAATTTTAGCGTGCTCACTGACCT GCCTGTAGCCCCAGTGACAGCTAGGATGTGCATTCTCCAG CCATCAAGAGACTGAGTCAAGTTGTTCCTTAAGTCAGAAC AGCAGACTCAGCTCTGACATTCTGATTCGAATGACACTGT TCAGGAATCGGAATCCTGTCGATTAGACTGGACAGCTTGT GGCAAGTGAATTTGCCTGTAACAAGCCAGATTTTTTAAAA TTTATATTGTAAATATTGTGTGTGTGTGTGTGTGTGTATA TATATATATATGTACAGTTATCTAAGTTAATTTAAAGTTG TTTGTGCCTTTTTATTTTTGTTTTTAATGCTTTGATATTT CAATGTTAGCCTCAATTTCTGAACACCATAGGTAGAATGT AAAGCTTGTCTGATCGTTCAAAGCATGAAATGGATACTTA TATGGAAATTCTGCTCAGATAGAATGACAGTCCGTCAAAA CAGATTGTTTGCAAAGGGGAGGCATCAGTGTCCTTGGCAG GCTGATTTCTAGGTAGGAAATGTGGTAGCCTCACTTTTAA TGAACAAATGGCCTTTATTAAAAACTGAGTGACTCTATAT AGCTGATCAGTTTTTTCACCTGGAAGCATTTGTTTCTACT TTGATATGACTGTTTTTCGGACAGTTTATTTGTTGAGAGT GTGACCAAAAGTTACATGTTTGCACCTTTCTAGTTGAAAA TAAAGTGTATATTTTTCTATAAAAAAAAAAAAAAAA | |
| ENPP4 | NM_014936.4 | AGACGCTCGCCTGGCAGCTGCGCACACTCGGAGCGCCCCG AGCGGCGCAGATAGGGACGTTGGGGCTGTGCCCCGCGGCG CGGCGCCTGCCACTGCGCAGGCGCCTCAGGAAGAGCTCGG CATCGCCCCTCTTCCTCCAGGTCCCCCTTCCCCGCAACTT CCCACGAGTGCCAGGTGCCGCGAGCGCCGAGTTCCGCGCA TTGGAAAGAAGCGACCGCGGCGGCTGGAACCCTGATTGCT GTCCTTCAACGTGTTCATTATGAAGTTATTAGTAATACTT TTGTTTTCTGGACTTATAACTGGTTTTAGAAGTGACTCTT CCTCTAGTTTGCCACCTAAGTTACTACTAGTATCCTTTGA TGGCTTCAGAGCTGATTATCTGAAGAACTATGAATTTCCT CATCTCCAGAATTTTATCAAAGAAGGTGTTTTGGTAGAGC ATGTTAAAAATGTTTTTATCACAAAAACATTTCCAAACCA CTACAGTATTGTGACAGGCTTGTATGAAGAAAGCCATGGC ATTGTGGCTAATTCCATGTATGATGCAGTCACAAAGAAAC ACTTTTCTGACTCTAATGACAAGGATCCTTTTTGGTGGAA TGAGGCAGTACCTATTTGGGTGACCAATCAGCTTCAGGAA AACAGATCAAGTGCTGCTATGTGGCCTGGTACTGATG TACCCATTCACGATACCATCTCTTCCTATTTTATGAATTA CAACTCCTCAGTGTCATTTGAGGAAAGACTAAATAATATT ACTATGTGGCTAAACAATTCGAACCCACCAGTCACCTTTG CAACACTATATTGGGAAGAACCAGATGCAAGTGGCCACAA ATACGGACCTGAAGATAAAGAAAACATGAGCAGAGTGTTG AAAAAAATAGATGATCTTATCGGTGACTTAGTCCAAAGAC TCAAGATGTTAGGGCTATGGGAAAATCTTAATGTGATCAT TACAAGTGATCATGGGATGACCCAGTGTTCTCAGGACAGA CTGATAAACCTGGATTCCTGCATCGATCATTCATACTACA CTCTTATAGATTTGAGCCCAGTTGCTGCAATACTTCCCAA AATAAATAGAACAGAGGTTTATAACAAACTGAAAAACTGT AGCCCTCATATGAATGTTTATCTCAAAGAAGACATTCCTA ACAGATTTATTACCAACATAATGATCGAATTCAGCCCAT | 12 |

TABLE 1-continued

GEP-NEN Biomarker/Houskeeper Sequence Information

| Gene Name | RefSeq Accession | Sequence | SEQ ID NO: |
|---|---|---|---|
| | | TATTTTGGTTGCCGATGAAGGCTGGACAATTGTGCTAAAT | |
| | | GAATCATCACAAAAATTAGGTGACCATGGTTATGATAATT | |
| | | CTTTGCCTAGTATGCATCCATTTCTAGCTGCCCACGGACC | |
| | | TGCATTTCACAAAGGCTACAAGCATAGCACAATTAACATT | |
| | | GTGGATATTTATCCAATGATGTGCCACATCCTGGGATTAA | |
| | | AACCACATCCCAATAATGGGACCTTTGGTCATACTAAGTG | |
| | | CTTGTTAGTTGACCAGTGGTGCATTAATCTCCCAGAAGCC | |
| | | ATCGCGATTGTTATCGGTTCACTCTTGGTGTTAACCATGC | |
| | | TAACATGCCTCATAATAATCATGCAGAATAGACTTTCTGT | |
| | | ACCTCGTCCATTTCTCGACTTCAGCTACAAGAAGATGAT | |
| | | GATGATCCTTTAATTGGGTGACATGTGCTAGGGCTTATAC | |
| | | AAAGTGTCTTTGATTAATCACAAAACTAAGAATACATCCA | |
| | | AAGAATAGTGTTGTAACTATGAAAAGAATACTTTGAAAG | |
| | | ACAAAGAACTTAGACTAAGCATGTTAAAATTATTACTTTG | |
| | | TTTTCCTTGTGTTTTGTTTCGGTGCATTTGCTAATAAGAT | |
| | | AACGCTGACCATAGTAAAATTGTTAGTAAATCATTAGGTA | |
| | | ACATCTTGTGGTAGGAAATCATTAGGTAACATCAATCCTA | |
| | | ACTAGAAATACTAAAAATGGCTTTTGAGAAAAATACTTCC | |
| | | TCTGCTTGTATTTTGCGATGAAGATGTGATACATCTTTAA | |
| | | ATGAAAATATACCAAATTTAGTAGGCATGTTTTTCTAAT | |
| | | AAATTTATATATTTGTAAAGAAAACAACAGAAATCTTTAT | |
| | | GCAATTTGTGAATTTTGTATATTAGGGAGGAAAAGCTTCC | |
| | | TATATTTTTATATTTACCTTTAATTAGTTTGTATCTCAAG | |
| | | TACCCTCTTGAGGTAGGAAATGCTCTGTGATGGTAAATAA | |
| | | AATTGGAGCAGACAGAAAAGATATAGCAAATGAAGAAATA | |
| | | TTTTAAGGAAACCTATTTGAAAAAAAAAGCAAAGACCATT | |
| | | TGATAAAAGCCTGAGTTGTCACCATTATGTCTTAAGCTGT | |
| | | TAGTCTTAAAGATTATTGTTAAAAAATTCAGAAGAAAAGA | |
| | | GAGACAAGTGCTCTTCTCTCTATCTATGCTTAATGCCTTT | |
| | | ATGTAAGTTACTTAGTTGTTTGCGTGTGCCTGTGCAAGTG | |
| | | TGTTTGTGTGTGGTTGTGTGGACATTATGTGATTTACTAT | |
| | | ATAAGGAGGTCAGAGATGGACTGTGGCCAGGCTTCCACAT | |
| | | TCCTGAAGCACACAGATCTCAGGAAAGGTTATTTTTGCAC | |
| | | TTCATATTTGTTTACTTTCTCCTAACTCACAAGTTAAAAT | |
| | | CATAACTTAATTTCATTAACTTTTATCATTTAACTCTCTC | |
| | | ATGTTTGTTGTAACCTGAGGTATCCAAATGCTACAGAAAA | |
| | | ATTTATGACCCAAATACAAATCTCAATTTGACTGGGACAG | |
| | | AATGAGGAATGGAGATTTTTGTATTTATCTTTGGGACTTT | |
| | | ATGCCTTACTTTTTAGGCTATAGAATAGTTAAGAAATTTT | |
| | | AAACAAAATTTAGTATCTTTTGGTCTTTCACACCATTCAT | |
| | | ATGTTAAGTGGCAGAATAGCCTTAGTGCTACCTCCACTTT | |
| | | TTTCTCCAGTATTTGCATCACAGAAATAATCCCTCTGTTT | |
| | | AACATGTTTGTTCAGAGCCAAGGGTTTATTGTGAAGAACT | |
| | | GTCATCCTGCCTTTGCTAGCTGGTACCTTCTAGTAATCAA | |
| | | AATTAATATGAAGAAACTAGGTTGTGACAGACTAGATTAT | |
| | | ATTTAGTAGGGAAAAATTGGGCTCAAGAACCATTCATCA | |
| | | GTACGTGAGACAAGCAGTTAATAGTATGATCTTTAAAGTT | |
| | | TTGACAATATAAAATAAACTTGGTAACTGTTTTACAAATA | |
| | | TAAAAGTATAATAAATATGCAGCCCAGTTAAATATTGATT | |
| | | ATCTGTGATGGTAAAGAACAACAGTGGTGCCAGTCATCAA | |
| | | ACATACAGTGCGTCCTATTGAGTCACTGCTAATTTCTTGA | |
| | | GCCTGGTATTTGCTGCCTATTGTATTTGTGGTTGTTGAGA | |
| | | GGCATTTTCAAACCCTGTATAAATAATCCATGCTGTTGGT | |
| | | CATAAGTTAACTGTATTAAGAACAGTAAAATAAATAAAAA | |
| | | CCAATAGTACTAATTTTGCTTTAAAAAAATTTCTAATTTT | |
| | | TTTCACATAAAACAATTATCCTAAAGGTAATAGTTGATC | |
| | | GAAACAGAATAATAGAAAAATTCTACTTTAATTTCCATTA | |
| | | AAAAGCAAATAGCATTGACACATTTAAAGCTTTTCATTTA | |
| | | AAGTAGTGGATGTTTTTGAAGTATCTAAAATAGTAGCAGA | |
| | | ATATTTTATACTTGGTCCTTGCAATGGTGTGAGTTTTAAT | |
| | | GATTGCATTATCGTGATTGGTGGTTATGAGTTTCAGAAAT | |
| | | CTATACTTGGCATCCAACTCATGAGTGGATTTTATATAGG | |
| | | ATGGAACAGGAAGGTATGTCCTGTCAGTATCTTAACCCTT | |
| | | TCAACAAGACATTTACCTATTTGTCTTTCCTTACGTTCTC | |
| | | AAAATATTAACTCGAATTGTAAATTAAGCAAAAATTTAAA | |
| | | AAGTATATGTTGATGGGACAAGAAGAATAGTATTTATTTA | |
| | | ATAAAACATATATTATATTGAACTATGTGTTAATTCATTT | |
| | | GTATCTTTTAAAAAATTATCACTGTTAAAGCCATTGACTC | |
| | | CTTTAGTACACTGAGAAAAATCTTATAGTAAAACTAGCCT | |
| | | TTCACATTAAGGTTTTGGTGTGTATTTTGTTAAATAACTA | |
| | | ACATGCTGCTCTATTTTCTGGGTGTAGAAAGTATTTGGCT | |
| | | CTAGGGAAACATTTACTTGTTTGTGAAAACAATACCCCAAG | |
| | | GTAATAGGAAAAGTTTGAGTTAAGTGTTTTTAATTCAGTC | |
| | | AGTGAATTCAGAATAAGTACATTCATGTATAACATAGGGA | |
| | | CAGTTCTGCTGCTGTTATTTATATGCAATTCTTCTGGTAA | |

TABLE 1-continued

GEP-NEN Biomarker/Houskeeper Sequence Information

| Gene Name | RefSeq Accession | Sequence | SEQ ID NO: |
|---|---|---|---|
| | | ATAGCAATAGAATAAAACATATTTCAATGTTTGTGTATAG<br>GTTTTATATTATTATTCCACTAGGAATGGCATAAGAATTT<br>ATAGATAAATTCTTGTAACATTAAAGGATTAAAATGTTTT<br>TACATTGTTTTTGGGTGTCTCCTTCTTGTGCCCATATCTG<br>ATAAGCTTTATGGATTATTGCATTTAATTCCTTTTATTTG<br>GAGGGTTTTACTTCCTTGTTAACATATAAAGTTATAAATG<br>AAGGACAAGGAGGAGATGGAAAATGTGTATTTATTGTTAA<br>TTCTTAAAATAGTGTGTAAATAAAATAACATCAGTGTGCT<br>TTAAAGAAATGTGTATGTAGTGCCTTAATTTAAATTAAAA<br>TATTTTTGACTGTTACTTGAGTTCAGAATTAATGACTTTG<br>TTCATGATTTTTAAAATGTGTGTGAATAAAATCTACCAAA<br>AAATTCTTACTGTAATTATTAAATATAAAGTTCAGTGTCA<br>AAAAAAAAAAAAAAAAA | |
| FAM131A | NM_001171093.1 | ACCGGCCCGGTTCCCTCTCCGGGGAGCGGCGGCGGACGCG<br>CGGCTCCCACCCCTCCCCTCTCACGGGCTCTCCCCTCCCC<br>AGTGTGGCCGCGACCCTACCCTCTGCAAGGCGATGGCCCG<br>CGCCCCGAGCGCAGGCTAGCGTGCCTGGGTGCCCGGCCAT<br>GGGCTGTATCGGCTCTCGGAGCCCGGCGGGTCAGGCATTT<br>CTGGGGACCAACAGCTGGCCGAGGCTCAGGGATAGAGACG<br>GCTGCTCCAGCTAAAGGTGAATGTTGGAGACACAGTCGCG<br>ATGCTGCCCAAGTCCCGGCGAGCCCTAACTATCCAGGAGA<br>TCGCTGCGCTGGCCAGGTCCTCCCTGCATGGTATTTCCCA<br>GGTGGTGAAGGACCACGTGACCAAGCCTACCGCCATGGCC<br>CAGGGCCGAGTGGCTCACCTCATTGAGTGGAAGGGCTGGA<br>GCAAGCCGAGTGACTCACCTGCTGCCCTGGAATCAGCCTT<br>TTCCTCCTATTCAGACCTCAGCGAGGGCGAACAAGAGGCT<br>CGCTTTGCAGCAGGAGTGGCTGAGCAGTTTGCCATCGCGG<br>AAGCCAAGCTCCGAGCATGGTCTTCGGTGGATGGCGAGGA<br>CTCCACTGATGACTCCTATGATGAGGACTTTGCTGGGGGA<br>ATGGACACAGACATGGCTGGGCAGCTGCCCCTGGGGCCGC<br>ACCTCCAGGACCTGTTCACCGGCCACCGGTTCTCCCGGCC<br>TGTGCGCCAGGGCTCCGTGGAGCCTGAGAGCGACTGCTCA<br>CAGACCGTGTCCCCAGACACCCTGTGCTCTAGTCTGTGCA<br>GCCTGGAGGATGGGTTGTTGGGCTCCCCGGCCCGGCTGGC<br>CTCCCAGCTGCTGGGCGATGAGCTGCTTCTCGCCAAACTG<br>CCCCCCAGCCGGGAAAGTGCCTTCCGCAGCCTGGGCCCAC<br>TGGAGGCCCAGGACTCACTCTACAACTCGCCCCTCACAGA<br>GTCCTGCCTTTCCCCCGCGGAGGAGGAGCCAGCCCCTGC<br>AAGGACTGCCAGCCACTCTGCCCACCACTAACGGGCAGCT<br>GGGAACGGCAGCGGCAAGCCTCTGACCTGGCCTCTTCTGG<br>GGTGGTGTCCTTAGATGAGGATGAGGCAGAGCCAGAGGAA<br>CAGTGACCCACATCATGCCTGGCAGTGGCATGCATCCCCC<br>GGCTGCTGCCAGGGGCAGAGCCTCTGTGCCCAAGTGTGGG<br>CTCAAGGCTCCCAGCAGAGCTCCACAGCCTAGAGGGCTCC<br>TGGGAGCGCTCGCTTCTCCGTTGTGTGTTTTGCATGAAAG<br>TGTTTGGAGAGGAGGCAGGGGCTGGGCTGGGGGCGCATGT<br>CCTGCCCCACTCCCGGGGCTTGCCGGGGGTTGCCCGGGG<br>CCTCTGGGGCATGGCTACAGCTGTGGCAGACAGTGATGTT<br>CATGTTCTTAAAATGCCACACACACATTTCCTCCTCGGAT<br>AATGTGAACCACTAAGGGGGTTGTGACTGGGCTGTGTGAG<br>GGTGGGGTGGGAGGGGGCCCAGCAACCCCCCCACCCTCCCC<br>ATGCCTCTCTCTTCTCTGCTTTTCTTCTCACTTCCGAGTC<br>CATGTGCAGTGCTTGATAGAATCACCCCCACCTGGAGGGG<br>CTGGCTCCTGCCCTCCCGGAGCCTATGGGTTGAGCCGTCC<br>CTCAAGGGCCCCTGCCCAGCTGGGCTCGTGCTGTGCTTCA<br>TTCACCTCTCCATCGTCTCTAAATCTTCCTCTTTTTTCCT<br>AAAGACAGAAGGTTTTTGGTCTGTTTTTTCAGTCGGATCT<br>TCTCTTCTCTGGGAGGCTTTGGAATGATGAAAGCATGTAC<br>CCTCCACCCTTTTCCTGGCCCCTAATGGGCCTGGGCCC<br>TTTCCCAACCCCTCCTAGGATGTGCGGGCAGTGTGCTGGC<br>GCCTCACAGCCAGCCGGGCTGCCCATTCACGCAGAGCTCT<br>CTGAGCGGGAGGTGGAAGAAAGGATGGCTCTGGTTGCCAC<br>AGAGCTGGGACTTCATGTTCTTCTAGAGAGGGCCACAAGA<br>GGGCCACAGGGGTGGCCGGGAGTTGTCAGCTGATGCCTGC<br>TGAGAGGCAGGAATTGTGCCAGTGAGTGACAGTCATGAGG<br>GAGTGTCTCTTCTTGGGGAGGAAAGAAGGTAGAGCCTTTC<br>TGTCTGAATGAAAGGCCAAGGCTACAGTACAGGGCCCCAC<br>CCCAGCCAGGGTGTTAATGCCCACGTAGTGGAGGCCTCTG<br>GCAGATCCTGCATTCCAAGGTCACTGGACTGTACGTTTTT<br>ATGGTTGTGGGAAGGGTGGGTGGCTTTAGAATTAAGGGCC<br>TTGTAGGCTTTGGCAGGTAAGAGGGCCCAAGGTAAGAACG | 13 |

TABLE 1-continued

GEP-NEN Biomarker/Houskeeper Sequence Information

| Gene Name | RefSeq Accession | Sequence | SEQ ID NO: |
|---|---|---|---|
| | | AGAGCCAACGGGCACAAGCATTCTATATATAAGTGGCTCA TTAGGTGTTTATTTTGTTCTATTTAAGAATTTGTTTTATT AAATTAATATAAAAATCTTTGTAAATCTCTAAAAAAAAAA AAAAAAAA | |
| FLJ10357 | NM_018071.4 | GGAGCGGGCCGAGCCGCCACCGCGGCCGGAGCTGTCCCTT AGCCAGACCCGGCGAGACACGAGCGGCGGGAGGGAGGCGG TGGCGCCCGGCCCCGCCCGCCGACCAAGCGTCGGACG CGGCCCGGCGCCGAGCCATGGAGCCTGAGCCAGTGGAGGA CTGTGTGCAGAGCACTCTCGCCGCCCTGTATCCACCCTTT GAGGCAACAGCCCCCACCCTGTTGGGCCAGGTGTTCCAGG TGGTGGAGAGGACTTATCGGGAGGACGCACTGAGGTACAC GCTGGACTTCCTGGTACCAGCCAAGCACCTGCTTGCCAAG GTCCAGCAGGAAGCCTGTGCCCAATACAGTGGATTCCTCT TCTTCCATGAGGGGTGGCCGCTCTGCCTGCATGAACAGGT GGTGGTGCAGCTAGCAGCCCTACCCTGGCAACTGCTGCGC CCAGGAGACTTCTATCTGCAGGTGGTGCCCTCAGCTGCCC AAGCACCCCGACTAGCACTCAAGTGTCTGGCCCCTGGGGG TGGGCGGGTGCAGGAGGTTCCTGTGCCCAATGAGGCTTGT GCCTACCTATTCACACCTGAGTGGCTACAAGGCATCAACA AGGACCGGCCAACAGGTCGCCTCAGTACCTGCCTACTGTC TGCGCCCTCTGGGATTCAGCGGCTGCCCTGGGCTGAGCTC ATCTGTCCACGATTTGTGCACAAAGAGGGCCTCATGGTTG GACATCAGCCAAGTACACTGCCCCCAGAACTGCCCTCTGG ACCTCCAGGGCTTCCCAGCCCTCCACTTCCTGAGGAGGCG CTGGGTACCCGGAGTCCTGGGGATGGGCACAATGCCCCTG TGGAAGGACCTGAGGGCGAGTATGTGGAGCTGTTAGAGGT GACGCTGCCCGTGAGGGGGAGCCCAACAGATGCTGAAGGC TCCCCAGGCCTCTCCAGAGTCCGGACGGTACCCACCCGCA AGGGCGCTGGAGGGAAGGGCCGCCACCGGAGACACCGGGC GTGGATGCACCAGAAGGGCCTGGGGCCTCGGGGCCAGGAT GGAGCACGCCCACCCGGCGAGGGGAGCAGCACCGGAGCCT CCCCTGAGTCTCCCCCAGGAGCTGAGGCTGTCCCAGAGGC AGCAGTCTTGGAGGTGTCTGAGCCCCCAGCAGAGGCTGTG GGAGAAGCCTCCGGATCTTGCCCCCTGAGGCCAGGGGAGC TTAGAGGAGGAGGAGGAGGAGGCCAGGGGGCTGAAGGACC ACCTGGTACCCCTCGGAGAACAGGCAAAGGAAACAGAAGA AAGAAGCGAGCTGCAGGTCGAGGGGCTCTTAGCCGAGGAG GGGACAGTGCCCCACTGAGCCCTGGGGACAAGGAAGATGC CAGCCACCAAGAAGCCCTTGGCAATCTGCCCTCACCAAGT GAGCACAAGCTTCCAGAATGCCACCTGGTTAAGGAGGAAT ATGAAGGCTCAGGGAAGCCAGAATCTGAGCCAAAAGAGCT CAAAACAGCAGGCGAGAAAGAGCCTCAGCTCTCTGAAGCC TGTGGGCCTACAGAAGAGGGGGCCGGAGAGAGAGAGCTGG AGGGGCCAGGCCTGCTGTGTATGGCAGGACACACAGGCCC AGAAGGCCCCCTGTCTGACACTCCAACACCTCCGCTGGAG ACTGTGCAGGAAGGAAAAGGGGACAACATTCCAGAAGAGG CCCTTGCAGTCTCCGTCTCTGATCACCCTGATGTAGCTTG GGACTTGATGGCATCTGGATTCCTCATCCTGACGGGAGGG GTGGACCAGAGTGGGCGAGCTCTGCTGACCATTACCCCAC CGTGCCCTCCTGAGGAGCCCCACCCTCCCGAGACACGCT GAACACAACTCTTCATTACCTCCACTCACTGCTCAGGCCT GATCTACAGACACTGGGGCTGTCCGTCCTGCTGGACCTTC GTCAGGCACCTCCACTGCCTCCAGCACTCATTCCTGCCTT GAGCCAACTTCAGGACTCAGGAGATCCTCCCCTTGTTCAG CGGCTGCTGATTCTCATTCATGATGACCTTCCAACTGAAC TCTGTGGATTTCAGGGTGCTGAGGTGCTGTCAGAGAATGA TCTGAAAAGAGTGGCCAAGCCAGAGGAGCTGCAGTGGGAG TTAGGAGGTCACAGGGACCCCTCTCCCAGTCACTGGGTAG AGATACACCAGGAAGTGGTAAGGCTATGTCGCCTGTGCCA AGGTGTGCTGGGCTCGGTACGGCAGGCCATTGAGGAGCTG GAGGGAGCAGCAGAGCCAGAGGAAGAGGAGGCAGTGGGAA TGCCCAAGCCACTGCAGAAGGTGCTGGCAGATCCCCGGCT GACGGCACTGCAGAGGGATGGGGGGGCCATCCTGATGAGG CTGCGCTCCACTCCCAGCAGCAAGCTGGAGGGCAAGGCC CAGCTACACTGTATCAGGAAGTGGACGAGGCCATTCACCA GCTTGTGCGCCTCTCCAACCTGCACGTGCAGCAGCAAGAG CAGCGGCAGTGCCTGCGGCGACTCCAGCAGGTGTTGCAGT GGCTCTCGGGCCCAGGGGAGGAGCAGCTGGCAAGCTTTGC TATGCCTGGGGACACCTTGTTGCCCTGCAGGAGACAGAG CTGCGATTCCGTGCTTTCAGCGCTGAGGTCCAGGAGCGCC TGGCCCAGGCACGGGAGGCCCTGGCTCTGGAGGAGAATGC CACCTCCCAGAAGGTGCTGGATATCTTTGAACAGCGGCTG GAGCAGGTTGAGAGTGGCCTCCATCGGGCCCTGCGGCTAC AGCGCTTCTTCCAGCAGGCACATGAATGGGTGGATGAGGG | 14 |

TABLE 1-continued

GEP-NEN Biomarker/Houskeeper Sequence Information

| Gene Name | RefSeq Accession | Sequence | SEQ ID NO: |
|---|---|---|---|
| | | CTTTGCTCGGCTGGCAGGAGCTGGGCCGGGTCGGGAGGCT | |
| | | GTGCTGGCTGCACTGGCCCTGCGGCGGGCCCCAGAGCCCA | |
| | | GTGCCGGCACCTTCCAGGAGATGCGGGCCCTGGCCCTGGA | |
| | | CCTGGGCAGCCCAGCAGCCCTGCGAGAATGGGGCCGCTGC | |
| | | CAGGCCCGCTGCCAAGAGCTAGAGAGGAGGATCCAGCAAC | |
| | | ACGTGGGAGAGGAGGCGAGCCCACGGGGCTACCGACGACG | |
| | | GCGGGCAGACGGTGCCAGCAGTGGAGGGGCCCAGTGGGGG | |
| | | CCCCGCAGCCCCTCGCCCAGCCTCAGCTCCTTGCTGCTCC | |
| | | CCAGCAGCCCTGGGCCACGGCCAGCCCCATCCCATTGCTC | |
| | | CCTGGCCCCATGTGGAGAGGACTATGAGGAAGAGGGCCCT | |
| | | GAGCTGGCTCCAGAAGCAGAGGGCAGGCCCCCAAGAGCTG | |
| | | TGCTGATCCGAGGCCTGGAGGTCACCAGCACTGAGGTGGT | |
| | | AGACAGGACGTGCTCACCACGGGAACACGTGCTGCTGGGC | |
| | | CGGGCTAGGGGGCCAGACGGACCCTGGGGAGTAGGCACCC | |
| | | CCCGGATGGAGCGCAAGCGAAGCATCAGTGCCCAGCAGCG | |
| | | GCTGGTGTCTGAGCTGATTGCCTGTGAACAAGATTACGTG | |
| | | GCCACCTTGAGTGAGCCAGTGCCACCCCCTGGGCCTGAGC | |
| | | TGACGCCTGAACTTCGGGGCACCTGGGCTGCTGCCCTGAG | |
| | | TGCCCGGGAAAGGCTTCGCAGCTTCCACCGGACACA<u>CTTT | |
| | | CTGCGGGAGCTTCAGGGCTGCGCCACCCACCCCCTACGCA | |
| | | TTGGGGCCTGCTTCCTTCGCCACGGGGACCAGTTCAGCCT | |
| | | TTATGCACAGTACGTGAAGCACCGACACAAACTGGAGAAT</u> | |
| | | GGTCTGGCTGCGCTCAGTCCCTTAAGCAAGGGCTCCATGG | |
| | | AGGCTGGCCCTTACCTGCCCCGAGCCCTGCAGCAGCCTCT | |
| | | GGAACAGCTGACTCGGTATGGGCGGCTCCTGGAGGAGCTC | |
| | | CTGAGGGAAGCTGGGCCTGAGCTCAGTTCTGAGTGCCGGG | |
| | | CCCTTGGGGCTGCTGTACAGCTGCTCCGGGAACAAGAGGC | |
| | | CCGTGGCAGAGACCTGCTGGCCGTGGAGGCGGTGCGTGGC | |
| | | TGTGAGATAGATCTGAAGGAGCAGGGACAGCTCTTGCATC | |
| | | GAGACCCCTTCACTGTCATCTGTGGCCGAAAGAAGTGCCT | |
| | | TCGCCATGTCTTTCTCTTCGAGCATCTCCTCCTGTTCAGC | |
| | | AAGCTCAAGGGCCCTGAAGGGGGGTCAGAGATGTTTGTTT | |
| | | ACAAGCAGGCCTTTAAGACTGCTGATATGGGGCTGACAGA | |
| | | AAACATCGGGGACAGCGGACTCTGCTTTGAGTTGTGGTTT | |
| | | CGGCGGCGGCGTGCACGAGAGGCATACACTCTGCAGGCAA | |
| | | CCTCACCAGAGATCAAACTCAAGTGGACAAGTTCTATTGC | |
| | | CCAGCTGCTGTGGAGACAGGCAGCCCACAACAAGGAGCTC | |
| | | CGAGTGCAGCAGATGGTGTCCATGGGCATTGGGAATAAAC | |
| | | CCTTCCTGGACATCAAAGCCCTTGGGGAGCGGACGCTGAG | |
| | | TGCCCTGCTCACTGGAAGAGCCGCCCGCACCCGGGCCTCC | |
| | | GTGGCCGTGTCATCCTTTGAGCATGCCGGCCCCTCCCTTC | |
| | | CCGGCCTTTCGCGGGAGCCTGCTCCCTGCCTGCCCGCGT | |
| | | CGAGGAGGAGGCCTGGGATCTGGACGTCAAGCAAATTTCC | |
| | | CTGGCCCCAGAAACACTTGACTCTTCTGGAGATGTGTCCC | |
| | | CAGGACCAAGAAACAGCCCCAGCCTGCAACCCCCCCACCC | |
| | | TGGGAGCAGCACTCCCACCCTGGCCAGTCGAGGGATCTTA | |
| | | GGGCTATCCCGACAGAGTCATGCTCGAGCCCTGAGTGACC | |
| | | CCACCACGCCTCTGTGACCTGGAGAAGATCCAGAACTTGC | |
| | | GTGCAGCTTCTCCTCTCAGCACACTTTGGGCTGGGATGGC | |
| | | AGTGGGGCATAATGGAGCCCTGGGCGATCGCTGAATTTCT | |
| | | TCCCTCTGCTTCCTGGACACAGAGGAGGTCTAACGACCAG | |
| | | AGTATTGCCCTGCCACCACTATCTCTAGTCTCCCTAGCTT | |
| | | GGTGCCTTCTCCTGCAGGAGTCAGAGCAGCCACATTGCTT | |
| | | GCCTTCATACCCTGGAGGTGGGGAAGTTATCCCTCTTCCG | |
| | | GTGCTTTCCCATCCTGGGCCACTGTATCCAGGACATCACT | |
| | | CCCATGCCAGCCCTCCCTGGCAGCCCATGTTCTCCTCTTT | |
| | | TCTCACCCCCTGACTTTCCCTGAGAAGAATCATCTCTGCC | |
| | | AGGTCAACTGGAGTCCCTGGTGACTCCATTCTGAGGTGTC | |
| | | ACAAGCAATGAAGCTATGCAAACAATAGGAGGGTGTGACA | |
| | | GGGGAACCGTAGACTTTATATATGTAATTACTGTTATTAT | |
| | | AATACTATTGTTATATTAAATGTATTTACTCACACTTTGC | |
| | | CTCTAAGGAGCTAGAGTAGTCCTCTGGATTAAGGTGATAA | |
| | | ATAACTTGAGCACTTTCCCTCAACCAGCCCTTAACTAGAA | |
| | | CACAGAAAATAAAACCAAGACTGGAAGGTCCCCTCTACCC | |
| | | CTCCCAGGCCCAGAGCTAGCTGACTGTGTATGAGCCTGGG | |
| | | AGAATGTGTCTCCTCCACAGTGGCTCCCAGAGGTTCCACA | |
| | | CACTCTCTGAAGCTCCTTCTCCCACACTGCACCTACTCCT | |
| | | TGAGGCTGAACTGGTCACAGACAAACTGGGATCCAGCACA | |
| | | GTCCAGCAGTTCTCAAAATGAGGTCCTCAGGCCACAGTGC | |
| | | GTGAGAACTTGCTTGGCTGTTTGTTAAATGCTAATTCTTG | |
| | | GGCCCCATCAGAGCTACTGCATCGAAACCTGGGGGTAAAA | |
| | | CCCAATATTCTGCATTTCTTATCAAACTCTTTGGGTGATA | |
| | | ACTAAGTGTCTGAAGAGGTGACTATTTCCTGACAGAAGGA | |
| | | CCCAAAGAGGGAAGCAGGACATAGGTAGGCAGACAGACAC | |
| | | AGGGCCCTGTGCCTCAAGACACCTGTTTATTGGGGACACG | |

TABLE 1-continued

GEP-NEN Biomarker/Houskeeper Sequence Information

| Gene Name | RefSeq Accession | Sequence | SEQ ID NO: |
|---|---|---|---|
| | | ACTCTGCAATAGGGATGACAGGAATCGTACCAAAAATAGC GACGTCTACAGGGCCCCTGATGGGGCTAGAAGGGTACAGT GCCCCCCACCCTCACCCCTTGTACAAAAATAAACTCTCAC GCCTATGGACCAGCAAAAAAAAAAAAAAA | |
| FZD7 | NM_003507.1 | <u>CTCTCCCAACCGCCTCGTCGCACTCCTCAGGCTGAGAGCA</u><br><u>CCGCTGCACTCGCGGCCGGCGATGCGGGACCCCGGCGCGG</u><br>CCGCTCCGCTTTCGTCCCTGGGCCTCTGTGCCCTGGTGCT<br>GGCGCTGCTGGGCGCACTGTCCGCGGGCGCCGGGGCGCAG<br>CCGTACCACGGAGAGAAGGGCATCTCCGTGCCGGACCACG<br>GCTTCTGCCAGCCCATCTCCATCCCGCTGTGCACGGACAT<br>CGCCTACAACCAGACCATCCTGCCCAACCTGCTGGGCCAC<br>ACGAACCAAGAGGACGCGGGCCTCGAGGTGCACCAGTTCT<br>ACCCGCTGGTGAAGGTGCAGTGTTCTCCCGAACTCCGCTT<br>TTTCTTATGCTCCATGTATGCGCCCGTGTGCACCGTGCTC<br>GATCAGGCCATCCCGCCGTGTCGTTCTCTGTGCGAGCGCG<br>CCCGCCAGGGCTGCGAGGCGCTCATGAACAAGTTCGGCTT<br>CCAGTGGCCCGAGCGGCTGCGCTGCGAGAACTTCCCGGTG<br>CACGGTGCGGGCGAGATCTGCGTGGGCCAGAACACGTCGG<br>ACGGCTCCGGGGGCCCAGGCGGCGGCCCCACTGCCTACCC<br>TACCGCGCCCTACCTGCCGGACCTGCCCTTCACCGCGCTG<br>CCCCCGGGGGCCTCAGATGGCAGGGGGCGTCCCGCCTTCC<br>CCTTCTCATGCCCCCGTCAGCTCAAGGTGCCCCCGTACCT<br>GGGCTACCGCTTCCTGGGTGAGCGCGATTGTGGCGCCCCG<br>TGCGAACCGGGCCGTGCCAACGGCCTGATGTACTTTAAGG<br>AGGAGGAGAGGCGCTTCGCCCGCCTCTGGGTGGGCGTGTG<br>GTCCGTGCTGTGCTGCGCCTCGACGCTCTTTACCGTTCTC<br>ACCTACCTGGTGGACATGCGGCGCTTCAGCTACCCAGAGC<br>GGCCCATCATCTTCCTGTCGGGCTGCTACTTCATGGTGGC<br>CGTGGCGCACGTGGCCGGCTTCCTTCTAGAGGACCGCGCC<br>GTGTGCGTGGAGCGCTTCTCGGACGATGGCTACCGCACGG<br>TGGCGCAGGGCACCAAGAAGGAGGGCTGCACCATCCTCTT<br>CATGGTGCTCTACTTCTTCGGCATGGCCAGCTCCATCTGG<br>TGGGTCATTCTGTCTCTCACTTGGTTCCTGGCGGCCGGCA<br>TGAAGTGGGGCCACGAGGCCATCGAGGCCAACTCGCAGTA<br>CTTCCACCTGGCCGCGTGGGCCGTGCCCGCCGTCAAGACC<br>ATCACTATCCTGGCCATGGGCCAGGTAGACGGGGACCTGC<br>TGAGCGGGGTGTGCTACGTTGGCCTCTCCAGTGTGGACGC<br>GCTGCGGGGCTTCGTGCTGGCGCCTCTGTTCGTCTACCTC<br>TTCATAGGCACGTCCTTCTTGCTGGCCGGCTTCGTGTCCC<br>TCTTCCGTATCCGCACCATCATGAAACACGACGGCACCAA<br>GACCGAGAAGCTGGAGAAGCTCATGGTGCGCATCGGCGTC<br>TTCAGCGTGCTCTACACAGTGCCCGCCACCATCGTCCTGG<br>CCTGCTACTTCTACGAGCAGGCCTTCCGCGAGCACTGGGA<br>GCGCACCTGGCTCCTGCAGACGTGCAAGAGCTATGCCGTG<br>CCCTGCCCGCCCGGCCACTTCCCGCCCATGAGCCCCGACT<br>TCACCGTCTTCATGATCAAGTACCTGATGACCATGATCGT<br>CGGCATCACCACTGGCTTCTGGATCTGGTCGGGCAAGACC<br>CTGCAGTCGTGGCGCCGCTTCTACCACAGACTTAGCCACA<br>GCAGCAAGGGGGAGACTGCGGTATGAGCCCCGGCCCCTCC<br>CCACCTTTCCCACCCCAGCCCTCTTGCAAGAGGAGAGGCA<br>CGGTAGGGAAAAGAACTGCTGGGTGGGGCCTGTTTCTGT<br>AACTTTCTCCCCCTCTACTGAGAAGTGACCTGGAAGTGAG<br>AAGTTCTTTTGCAGATTTGGGGCGAGGGGTGATTTGGAAAA<br>GAAGACCTGGGTGGAAAGCGGTTTGGATGAAAAGATTTCA<br>GGCAAAGACTTGCAGGAAGATGATGATAACGGCGATGTGA<br>ATCGTCAAAGGTACGGGCCAGCTTGTGCCTAATAGAAGGT<br>TGAGACCAGCAGAGACTGCTGTGAGTTTCTCCCGGCTCCG<br>AGGCTGAACGGGGACTGTGAGCGATCCCCCTGCTGCAGGG<br>CGAGTGGCCTGTCCAGACCCCTGTGAGGCCCCGGGAAAGG<br>TACAGCCCTGTCTGCGGTGGCTGCTTTGTTGGAAAGAGGG<br>AGGGCCTCCTGCGGTGTGCTTGTCAAGCAGTGGTCAAACC<br>ATAATCTCTTTTCACTGGGGCCAAACTGGAGCCCAGATGG<br>GTTAATTTCCAGGGTCAGACATTACGGTCTCTCCTCCCCT<br>GCCCCCTCCCGCCTGTTTTCCTCCCGTACTGCTTTCAGG<br>TCTTGTAAAATAAGCATTTGGAAGTCTTGGGAGGCCTGCC<br>TGCTAGAATCCTAATGTGAGGATGCAAAAGAAATGATGAT<br>AACATTTTGAGATAAGGCCAAGGAGACGTGGAGTAGGTAT<br>TTTTGCTACTTTTTCATTTTCTGGGGAAGGCAGGAGGCAG<br>AAAGACGGGTGTTTATTTGGTCTAATACCCTGAAAAGAA<br>GTGATGACTTGTTGCTTTTCAAAACAGGAATGCATTTTC<br>CCCTTGTCTTTGTTGTAAGAGACAAAAGAGGAAACAAAAG<br>TGTCTCCCTGTGGAAAGGCATAACTGTGACGAAAGCAACT<br>TTTATAGGCAAAGCAGCGCAAATCTGAGGTTTCCCGTTGG<br>TTGTTAATTTGGTTGAGATAAACATTCCTTTTTAAGGAAA | 15 |

TABLE 1-continued

GEP-NEN Biomarker/Houskeeper Sequence Information

| Gene Name | RefSeq Accession | Sequence | SEQ ID NO: |
|---|---|---|---|
| | | AGTGAAGAGCAGTGTGCTGTCACACACCGTTAAGCCAGAG GTTCTGACTTCGCTAAAGGAAATGTAAGAGGTTTTGTTGT CTGTTTTAAATAAATTTAATTCGGAACACATGATCCAACA GACTATGTTAAAATATTCAGGGAAATCTCTCCCTTCATTT ACTTTTTCTTGCTATAAGCCTATATTTAGGTTTCTTTTCT ATTTTTTTCTCCCATTTGGATCCTTTGAGGTAAAAAAACA TAATGTCTTCAGCCTCATAATAAAGGAAAGTTAATTAAAA AAAAAAAGCAAAGAGCCATTTTGTCCTGTTTTCTTGGTTC CATCAATCTGTTTATTAAACATCATCCATATGCTGACCCT GTCTCTGTGTGGTTGGGTTGGGAGGCGATCAGCAGATACC ATAGTGAACGAAGAGGAAGGTTTGAACCATGGGCCCCATC TTTAAAGAAAGTCATTAAAAGAAGGTAAACTTCAAAGTGA TTCTGGAGTTCTTTGAAATGTGCTGGAAGACTTAAATTTA TTAATCTTAAATCATGTACTTTTTTTCTGTAATAGAACTC GGATTCTTTTGCATGATGGGGTAAAGCTTAGCAGAGAATC ATGGGAGCTAACCTTTATCCCACCTTTGACACTACCCTCC AATCTTGCAACACTATCCTGTTTCTCAGAACAGTTTTTAA ATGCCAATCATAGAGGGTACTGTAAAGTGTACAAGTTACT TTATATATGTAATGTTCACTTGAGTGGAACTGCTTTTTAC ATTAAAGTTAAAATCGATCTTGTGTTTCTTCAACCTTCAA AACTATCTCATCTGTCAGATTTTTAAAACTCCAACACAGG TTTTGGCATCTTTTGTGCTGTATCTTTTAAGTGCATGTGA AATTTGTAAAATAGAGATAAGTACAGTATGTATATTTTGT AAATCTCCCATTTTTGTAAGAAAATATATATTGTATTTAT ACATTTTTACTTTGGATTTTTGTTTTGTTGGCTTTAAAGG TCTACCCCACTTTATCACATGTACAGATCACAAATAAATT TTTTTAAATAC | |
| GLT8D1 | NM_001010983.2 | GACGGGCCGGTACAGCCCGTGTCCCCGCCCCGCGCCATCG CTAGGCGACGTGCGCTTTTGCCGCGCCGTGCTGCCCGCGA GGGCAGCTGAGGTGGTGGTGGCGGCCGCCTTGTCGAGGCA TCGCGCGCCCGTGAAGTGTTCGCCGTCAGTGCTGTTGGGT GCCTGGAGCCGCGTCCCCCGTCCCGAAAACTGTCCTTGAC AGTACTTGCGCGGCCCAACGGCCGCCGGCGCCCCCGCGTC TCCATGGCGACGGCCTTTTTCCCTGCGAGGACCCCGGCGG CAGGGCTGCCCCGCGGCGCCTGCTTGGCGCGACGCTCTAG CGGTTACCGCTGCGGGCTGGCTGGGCGTAGTGGGGCTGCG CGGCTGCCACGGAGCTAGAGGGCAAGTGTGCTCGGCCCAG CGTGCAGGGAACGCGGGCGGCCAGACAACGGGCTGGGCTC CGGGGCCTGCGGCGCGGGCGCTGAGCTGGCAGGGCGGGTC GGGGCGCGGGCTGCATCCGCATCTCCTCCATCGCCTGCAG TAAGGGCGGCCGCGGCGAGCCTTTGAGGGGAACGACTTGT CGGAGCCCTAACCAGGGGTATCTCTGAGCCTGGTGGGATC CCCGGAGCGTCACATCACTTTCCGATCACTTCAAAGTACA GCAGACCGAGGACACGGTTGTTACCAAGACCAGGCTGTTG CCTTGGAAGAGCCCAGAGCGTGTCAAGGGAGACAGCCACA TCACGCCAGAAATACATGACAGCTGGATTAGCCCTGGGAG AGGGAGGCCCAGATGTGGGAGCTCAGGGGAGGTGCAGCTC AACGTGGAGTTTGGAGGAGGCTACCTTGACCTTTGAATGC CAAGTGGGAGCCAGCCAGATGAAAGGGGTTAAAAACTAAT ATTTATATGACAGAAGAAAAAGATGTCATTCCGTAAAGTA AACATCATCATCTTGGTCCTGGCTGTTGCTCTCTTCTTAC TGGTTTTGCACCATAACTTCCTCAGCTTGAGCAGTTTGTT AAGGAATGAGGTTACAGATTCAGGAATTGTAGGGCCTCAA CCTATAGACTTTGTCCCAAATGCTCTCCGACATGCAGTAG ATGGGAGACAAGAGGAGATTCCTGTGGTCATCGCTGCATC TGAAGACAGGCTTGGGGGGGCCATTGCAGCTATAAACAGC ATTCAGCACAACACTCGCTCCAATGTGATTTTCTACATTG TTACTCTCAACAATACAGCAGACCATCTCCGGTCCTGGCT CAACAGTGATTCCCTGAAAAGCATCAGATACAAAATTGTC AATTTTGACCCTAAACTTTTGGAAGGAAAAGTAAAGGAGG ATCCTGACCAGGGGAATCCATGAAACCTTTAACCTTTGC AAGGTTCTACTTGCCAATTCTGGTTCCCAGCGCAAAGAAG GCCATATACATGGATGATGATGTAATTGTGCAAGGTGATA TTCTTGCCCTTTACAATACAGCACTGAAGCCAGGACATGC AGCTGCATTTTCAGAAGATTGTGATTCAGCCTCTACTAAA GTTGTCATCCGTGGGAGCAGGAAACCAGTACAATTACATTG GCTATCTTGACTATAAAAAGGAAAGAATTCGTAAGCTTTC CATGAAAGCCAGCACTTGCTCATTTAATCCTGGAGTTTTT GTTGCAAACCTGACGGAATGGAAACGACAGAATATAACTA ACCAACTGGAAAAATGGATGAAACTCAATGTAGAAGAGGG ACTGTATAGCAGAACCCTGGCTGGTAGCATCACAACACCT CCTCTGCTTATCGTATTTATCAACAGCACTCTACCATCG ATCCTATGTGGAATGTCCGCCACCTTGGTTCCAGTGCTGG AAAACGATATTCACCTCAGTTTGTAAAGGCTGCCAAGTTA | 16 |

TABLE 1-continued

GEP-NEN Biomarker/Housekeeper Sequence Information

| Gene Name | RefSeq Accession | Sequence | SEQ ID NO: |
|---|---|---|---|
| | | CTCCATTGGAATGGACATTTGAAGCCATGGGGAAGGACTG<br>CTTCATATACTGATGTTTGGGAAAAATGGTATATTCCAGA<br>CCCAACAGGCAAATTCAACCTAATCCGAAGATATACCGAG<br>ATCTCAAACATAAAGTGAAACAGAATTTGAACTGTAAGCA<br>AGCATTTCTCAGGAAGTCCTGGAAGATAGCATGCGTGGGA<br>AGTAACAGTTGCTAGGCTTCAATGCCTATCGGTAGCAAGC<br>CATGGAAAAGATGTGTCAGCTAGGTAAAGATGACAAACT<br>GCCCTGTCTGGCAGTCAGCTTCCCAGACAGACTATAGACT<br>ATAAATATGTCTCCATCTGCCTTACCAAGTGTTTTCTTAC<br>TACAATGCTGAATGACTGGAAAGAAGAACTGATATGGCTA<br>GTTCAGCTAGCTGGTACAGATAATTCAAAACTGCTGTTGG<br>TTTTAATTTTGTAACCTGTGGCCTGATCTGTAAATAAAAC<br>TTACATTTTTCAATAGGTAAAAAAAAAAAAAAAA | |
| HDAC9 | NM_001204144.1 | GCAGCGCGCACCGAGCCGGCCGCGCCGCGCCCGCCGCTCT<br>CGCCGCTTTCGCCGCGGTCTCCTCCTCTAGCGCCCGCCGC<br>GGCCGGTAAATCTCGGCTGGAGGAGCAGCGGCGGCCCCCG<br>AGTCAACTTTCATTCCCTTTTTGCTTCTGCCTCACCATTC<br>TCTTCTCCTCCTCGAAAGATGGCTGTTTGGAGAAGGGGGA<br>GAAGTTAAGAGGTCGCCAGCGCGGAGCGAAGGAGGGCGCG<br>ATAGCCTCAGCAGGAGCGGGCGGAGGTTTCTCCTCTGCCA<br>ACCCCTCCTGGACCATTGTCAGCAGTTGAACGACAAAGGC<br>TGTGAATCTGCATCCTAGTCTTAGCAGTCCCTCTGATTCT<br>CATGATGAGCTCACCTGCACAGCCTGACCTCATGTGGAAC<br>CTTGTACCATGGGTGCTATTCTGTGGCTGCTGTAGGATCT<br>TCCCAGATGGGGTGCTGGACGAGAGCAGCTCTTGGCTCA<br>GCAAAGAATGCACAGTATGATCAGCTCAGTGGATGTGAAG<br>TCAGAAGTTCCTGTGGGCCTGGAGCCCATCTCACCTTTAG<br>ACCTAAGGACAGACCTCAGGATGATGATGCCCGTGGTGGA<br>CCCTGTTGTCCGTGAGAAGCAATTGCAGCAGGAATTACTT<br>CTTATCCAGCAGCAGCAACAAATCCAGAAGCAGCTTCTGA<br>TAGCAGAGTTTCAGAAACAGCATGAGAACTTGACACGGCA<br>GCACCAGGCTCAGCTTCAGGAGCATATCAAGGAACTTCTA<br>GCCATAAAACAGCAACAAGAACTCCTAGAAAAGGAGCAGA<br>AACTGGAGCAGCAGAGGCAAGAACAGGAAGTAGAGAGGCA<br>TCGCAGAGAACAGCAGCTTCCTCCTCTCAGAGGCAAAGAT<br>AGAGGACGAGAAAGGGCAGTGGCAAGTACAGAAGTAAAGC<br>AGAAGCTTCAAGAGTTCCTACTGAGTAAATCAGCAACGAA<br>AGACACTCCAACTAATGGAAAAAATCATTCCGTGAGCCGC<br>CATCCCAAGCTCTGGTACACGGCTGCCCACCACACATCAT<br>TGGATCAAAGCTCTCCACCCCTTAGTGGAACATCTCCATC<br>CTACAAGTACACATTACCAGGAGCACAAGATGCAAAGGAT<br>GATTTCCCCCTTCGAAAAACTGAATCCTCAGTCAGTAGCA<br>GTTCTCCAGGCTCTGGTCCCAGTTCACCAAACAATGGGCC<br>AACTGGAAGTGTTACTGAAAATGAGACTTCGGTTTTGCCC<br>CCTACCCCTCATGCCGAGCAAATGGTTTCACAGCAACGCA<br>TTCTAATTCATGAAGATTCCATGAACCTGCTAAGTCTTTA<br>TACCTCTCCTTCTTTGCCCAACATTACCTTGGGGCTTCCC<br>GCAGTGCCATCCCAGCTCAATGCTTCGAATTCACTCAAAG<br>AAAAGCAGAAGTGTGAGACGCAGACGCTTAGGCAAGGTGT<br>TCCTCTGCCTGGGCAGTATGGAGGCAGCATCCCGGCATCT<br>TCCAGCCACCCTCATGTTACTTTAGAGGGAAAGCCACCCA<br>ACAGCAGCCACCAGGCTCTCCTGCAGCATTTATTATTGAA<br>AGAACAAATGCGACAGCAAAAGCTTCTTGTAGCTGGTGGA<br>GTTCCCTTACATCCTCAGTCTCCCTTGGCAACAAAAGAGA<br>GAATTTCACCTGGCATTAGAGGTACCCACAAATTGCCCCG<br>TCACAGACCCCTGAACCGAACCCAGTCTGCACCTTTGCCT<br>CAGAGCACGTTGGCTCAGCTGGTCATTCAACAGCAACACC<br>AGCAATTCTTGGAGAAGCAGAAGCAATACCAGCAGCAGAT<br>CCACATGAACAAACTGCTTTCGAAATCTATTGAACAACTG<br>AAGCAACCAGGCAGTCACCTTGAGGAAGCAGAGGAAGAGC<br>TTCAGGGGGACCAGGCGATGCAGGAAGACAGAGCGCCCTC<br>TAGTGGCAACAGCACTAGGAGCGACAGCAGTGCTTGTGTG<br>GATGACACACTGGGACAAGTTGGGCTGTGAAGGTCAAGG<br>AGGAACCAGTGGACAGTGATGAAGATGCTCAGATCCAGGA<br>AATGGAATCTGGGGAGCAGGCTGCTTTTATGCAACAGGTA<br>ATAGGCAAAGATTTAGCTCCAGGATTTGTAATTAAAGTCA<br>TTATCTGAACATGAAATGCATTGCAGGTTTGGTAAATGGA<br>TATGATTTCCTATCAGTTTATATTTCTCTATGATTTGAGT<br>TCAGTGTTTAAGGATTCTACCTAATGCAGATATATGTATA<br>TATCTATATAGAGGTCTTTCTATATACTGATCTCTATATA<br>GATATCAATGTTTCATTGAAAATCCACTGGTAAGGAAATA<br>CCTGTTATACTAAAATTATGATACATAATATCTGAGCAGT<br>TAATAGGCTTTAAATTTATCCCAAGCCTGCTACACCAAT<br>TACTTCTAAAGAAAACAAATTCACTGTTATTTTGAGTTTA | 17 |

TABLE 1-continued

GEP-NEN Biomarker/Houskeeper Sequence Information

| Gene Name | RefSeq Accession | Sequence | SEQ ID NO: |
|---|---|---|---|
| | | TGTGTTGAGATCAGTGACTGCTGGATAGTCTCCCAGTCTG<br>ATCAATGAAGCATTCGATTAGTTTTTGATTTTTTGCAACA<br>TCTAGAATTTAATTTTCACATCACTGTACATAATGTATCA<br>TACTATAGTCTTGAACACTGTTAAAGGTAGTCTGCCCCTT<br>CCTTCCTCTCTCTTTTTTTAGTTAAGTAGAAATGTTCTGG<br>TCACCATGCCAGTAGTCCTAGGTTATTGTGTAGGTTGCAA<br>TTGAACATATTAGGAATACAGGTGGTTTTAAATATATGA<br>TGCAAATTGCAGCACTACTTTAAATATTAGATTATGTCTC<br>ACATAGCACTGCTCATTTTACTTTTATTTTGTGTAATTTG<br>ATGACACTGTCTATCAAAAAGAGCAAATGAAGCAGATGC<br>AAATGTTAGTGAGAAGTAATGTGCAGCATTATGGTCCAAT<br>CAGATACAATATTGTGTCTACAATTGCAAAAAACACAGTA<br>ACAGGATGAATATTATCTGATATCAAGTCAAAATCAGTTT<br>GAAAAGAAGGTGTATCATATTTTATATTGTCACTAGAATC<br>TCTTAAGTATAATTCCATAATGACATGGGCATATACCGTA<br>ACATTCTGGCAAATAACAATTAGAAAAGATAGGTTTAACA<br>AAAAAATTTACTTGTATATAATGCACCTTCAGGAGGACTA<br>TGTCCTTTGATGCTATAAAATACAAACAACTTTGAAGGCA<br>ACAGAAGACACTGTTTATTCAAGTCAGTTCTTTGTCAGGT<br>TCCTGCTGTTCTCCTACAGAAAAGTGATTCTGTGAGGGTG<br>AACAGGAAATGCCTTGTGGAAACAGGAAGTCCAAGTGATT<br>CATGTACTGAGGAATGTAGGAAAAAAAATCTGAGGATAGT<br>GCTTTACTCTTTCTGTTTTTAAAGGGCACTCTATGAATTG<br>ATTTATTGTCTAAGAAAATAACACCACAAGTAGGGAAATT<br>GTTACGGAAGCTTTTCACTGGAACATTTCCTTCATATTCC<br>CTTTTGATATGTTTACCTTGTTTTATAGGTTTACTTTTGT<br>TAAGCTAGTTAAAGGTTCGTTGTATTAAGACCCCTTTAAT<br>ATGGATAATCCAAATTGACCTAGAATCTTTGTGAGGTTTT<br>TTCTATTAAAATATTTATATTTCTAAATCCGAGGTATTTC<br>AAGGTGTAGTATCCTATTTCAAAGGAGATATAGCAGTTTT<br>GCCAAATGTAGACATTGTTCAACTGTATGTTATTGGCACG<br>TGTTGTTTACATTTTGCTGTGACATTTAAAAATATTTCTT<br>TAAAAATGTTACTGCTAAAGATACATTATCCTTTTTTAAA<br>AAGTCTCCATTCAAATTAAATTAACATAACTAGAAGTTAG<br>AAAGTTTAAAAGTTTTCCACATAATGAAAGTCCTTCTGAT<br>AATTTGACAAATAGCTATAATAGGAACACTCCCTATCACC<br>AACATATTTTGGTTAGTATATTCCTTCATATTAAAATGAC<br>TTTTTGTCAGTTGTTTTGCATTAAAAATATGGCATGCCTA<br>AGATAAAATTGTATATTTTTCCATCTCATAAATATTCAT<br>TTTCTTCAAAGTCTTTTTTCAATCTCATAAAAAAGGGATA<br>GTGCATCTTTTAAAATACATTTTATTTGGGGAGGAACATG<br>TGGCTGAGCAGACTTTTGTATAATATTACTTCAAAGATAT<br>GTAATCACAAACAAAAAAAACTATTTTTTATAATGTCATT<br>TGAGAGAGTTTCATCAGTACAGTTGGTGGACGTTAATTGT<br>TTGAATTTGATAGTCTTTGAATTTAATCAAGAAACTACCT<br>GGAACCAGTGAAAAGGAAAGCTGGACTTAAATAATCTTAG<br>AATTAATTGATAAATGTCTCTTTTAAAATCTACTGTATTT<br>ATTATAATTTACACCCTTGAAGGTGATCTCTTGTTTTGTG<br>TTGTAAATATATTGTTTGTATGTTTCCCTTCTTGCCTTCT<br>GTTATAAGTCTCTTCCTTTCTCAAATAAAGTTTTTTTAA<br>AAGAAAAAAAAAAAAAAAAAA | |
| HSF2 | NM_004506.3 | ACTTGTCCGTCACGTGCGGCCGCCCGGCCTCTCGGCCTTG<br>CCGCGCGCCTGGCGGGGTTGGGGGGGCGGGGACCAAGATC<br>TGCTGCGCCTGCGTTGTGGGCGTTCTCGGGGAGCTGCTGC<br>CGTAGCTGCCGCCGCCGCTACCACCGCGTTCGGGTGTAGA<br>ATTTGGAATCCCTGCGCCGCGTTAACAATGAAGCAGAGTT<br>CGAACGTGCCGGCTTTCCTCAGCAAGCTGTGGACGCTTGT<br>GGAGGAAACCCACACTAACGAGTTCATCACCTGGAGCCAG<br>AATGGCCAAAGTTTTCTGGTCTTGGATGAGCAACGATTTG<br>CAAAAGAAATTCTTCCCAAATATTTCAAGCACAATAATAT<br>GGCAAGCTTTGTGAGGCAACTGAATATGTATGGTTTCCGT<br>AAAGTAGTACATATCGACTCTGGAATTGTAAAGCAAGAAA<br>GAGATGGTCCTGTAGAATTTCAGCATCCTTACTTCAAACA<br>AGGACAGGATGACTTGTTGGAGAACATTAAAAGGAAGGTT<br>TCATCTTCAAAACCAGAAGAAAATAAAATTCGTCAGGAAG<br>ATTTAACAAAAATTATAAGTAGTGCTCAGAAGGTTCAGAT<br>AAAACAGGAAACTATTGAGTCCAGGCTTTCTGAATTAAAA<br>AGTGAGAATGAGTCCCTTTGGAAGGAGGTGTCAGAATTAC<br>GAGCAAAGCATGCACAACAGCAACAAGTTATTCGAAAGAT<br>TGTCCAGTTTATTGTTACATTGGTTCAAAATAACCAACTT<br>GTGAGTTTAAAACGTAAAAGGCCTCTACTTCTAAACACTA<br>ATGGAGCCCAAAAGAAGAACCTGTTTCAGCACATAGTCAA<br>AGAACCAACTGATAATCATCATCATAAAGTTCCACACAGT<br>AGGACTGAAGGTTAAAGCCAAGGGAGAGGATTTCAGATG | 18 |

TABLE 1-continued

GEP-NEN Biomarker/Houskeeper Sequence Information

| Gene Name | RefSeq Accession | Sequence | SEQ ID NO: |
|---|---|---|---|
| | | ACATCATTATTTATGATGTTACTGATGATAATGCAGATGA<br>AGAAAATATCCCAGTTATTCCAGAAACTAATGAGGATGTT<br>ATATCTGATCCCTCCAACTGTAGCCAGTACCCTGATATTG<br>TCATCGTTGAAGATGACAATGAAGATGAGTATGCACCTGT<br>CATTCAGAGTGGAGAGCAGAATGAACCAGCCAGAGAATCC<br>CTAAGTTCAGGCAGTGATGGCAGCAGCCCTCTCATGTCTA<br>GTGCTGTCCAGCTAAATGGCTCATCCAGTCTGACCTCAGA<br>AGATCCAGTGACCATGATGGATTCCATTTTGAATGATAAC<br>ATCAATCTTTTGGGAAAGGTTGAGCTGTTGGATTATCTTG<br>ACAGTATTGACTGCAGTTTAGAGGACTTCCAGGCCATGCT<br>ATCAGGAAGACAATTTAGCATAGACCCAGATCTCCTGGTT<br>GATCTTTTCACTAGTTCTGTGCAGATGAATCCCACAGATT<br>ACATCAATAATACAAAATCTGAGAATAAAGGATTAGAAAC<br>TACCAAGAACAATGTAGTTCAGCCAGTTTCGGAAGAGGGA<br>AGAAAATCTAAATCCAAACCAGATAAGCAGCTTATCCAGT<br>ATACCGCCTTTCCACTTCTTGCATTCCTCGATGGGAACCC<br>TGCTTCTTCTGTTGAACAGGCGAGTACAACAGCATCATCA<br>GAAGTTTTGTCCTCTGTAGATAAACCCATAGAAGTTGATG<br>AGCTTCTGGATAGCAGCCTAGACCCAGAACCAACCCAAAG<br>TAAGCTTGTTCGCCTGGAGCCATTGACTGAAGCTGAAGCT<br>AGTGAAGCTACACTGTTTTATTTATGTGAACTTGCTCCTG<br>CACCTCTGGATAGTGATATGCCACTTTTAGATAGCTAAAT<br>CCCCAGGAAGTGGACTTTACATGTATATATTCATCAAAAT<br>GATGAACTATTTATTTTAAAGTATCATTTGGTACTTTTTT<br>TGTAAATTGCTTTGTTTTGTTTAATCAGATACTGTGGAAT<br>AAAAGCACCTTTTGCTTTTCTCACTAACCACACACTCTTG<br>CAGAGCTTTCAGGTGTTACTCAGCTGCATAGTTACGCAGA<br>TGTAATGCACATTATTGGCGTATCTTTAAGTTGGATTCAA<br>ATGGCCATTTTCTCCAATTTTGGTAAATTGGATATCTTT<br>TTTTTACAAATACGACCATTAACCTCAGTTAAATTTTTGT<br>TTGTTTTCCTGTTTGATGCTGTCTATTTGCATTGAGTGTA<br>AGTCATTTGAACTAATGGTATAACTCCTAAAGCTTTCTCT<br>GCTCCAGTTATTTTTATTAAATATTTTTCACTTGGCTTAT<br>TTTTAAAACTGGGAACATAAAGTGCCTGTATCTTGTAAAA<br>CTTCATTTGTTTCTTTTGGTTCAGAGAAGTTCATTTATGT<br>TCAAAGACGTTTATTCATGTTCAACAGGAAAGACAAAGTG<br>TACGTGAATGCTCGCTGTCTGATAGGGTTCCAGCTCCATA<br>TATATAGAAAGATCGGGGTGGGATGGGATGGAGTGAGCC<br>CCATCCAGTTAGTTGGACTAGTTTTAAATAAAGGTTTTCC<br>GGTTTGTGTTTTTTGAACCATACTGTTTAGTAAAATAAA<br>TACAATGAATGTTGAGTACTAGTGTCTGTTATGTGTCTTC<br>TTTAGAGGTGACACTCACATGAAACAATTTTTTCTTCTCA<br>TAGGAAGCAGTAGCTTTAAACTGTCTGTGGTTCATTATTC<br>TCAATATGAATCATACCAAGATATTTGTGCCTCATCTCGA<br>AAATATATTGTATATTG | |
| Ki-67 | NM_001145966.1 | TACCGGGCGGAGGTGAGCGCGGCGCCGGCTCCTCCTGCGG<br>CGGACTTTGGGTGCGACTTGACGAGCGGTGGTTCGACAAG<br>TGGCCTTGCGGGCCGGATCGTCCCAGTGGAAGAGTTGTAA<br>ATTTGCTTCTGGCCTTCCCCTACGGATTATACCTGGCCTT<br>CCCCTACGGATTATACTCAACTTACTGTTTAGAAAATGTG<br>GCCCACGAGACGCCTGGTTACTATCAAAAGGAGCGGGGTC<br>GACGGTCCCCACTTTCCCCTGAGCCTCAGCACCTGCTTGT<br>TTGGAAGGGGTATTGAATGTGACATCCGTATCCAGCTTCC<br>TGTTGTGTCAAAACAACATTGCAAAATTGAAATCCATGAG<br>CAGGAGGCAATATTACATAATTTCAGTTCCACAAATCCAA<br>CACAAGTAAATGGGTCTGTTATTGATGAGCCTGTACGGCT<br>AAAACATGGAGATGTAATAACTATTATTGATCGTTCCTTC<br>AGGTATGAAAATGAAAGTCTTCAGAATGGAAGGAAGTCAA<br>CTGAATTTCCAAGAAAATACGTGAACAGGAGCCAGCACG<br>TCGTGTCTCAAGATCTAGCTTCTCTTCTGACCCTGATGAG<br>AGTGAGGGAATACCTTTGAAAAGAAGGCGTGTGTCCTTTG<br>GTGGGCACCTAAGACCTGAACTATTTGATGAAAACTTGCC<br>TCCTAATACGCCTCTCAAAAGGGGAGAAGCCCCAACCAAA<br>AGAAAGTCTCTGGTAATGCACACTCCACCTGTCCTGAAGA<br>AAATCATCAAGGAACAGCCTCAACCATCAGGAAAACAAGA<br>GTCAGGTTCAGAAATCCATGTGGAAGTGAAGGCACAAAGC<br>TTGGTTATAAGCCCTCCAGCTCCTAGTCCTAGGAAAACTC<br>CAGTTGCCAGTGATCAACGCCGTAGGTCCTGCAAAACAGC<br>CCCTGCTTCCAGCAGCAAATCTCAGACAGAGGTTCCTAAG<br>AGAGGAGGGAGAAAGAGTGGCAACCTGCCTTCAAAGAGAG<br>TGTCTATCAGCCGAAGTCAACATGATATTTTACAGATGAT<br>ATGTTCCAAAAGAAGAAGTGGTGCTTCGGAAGCAAATCTG<br>ATTGTTGCAAAATCATGGGCAGATGTAGTAAAACTTGGTG<br>CAAAACAAACACAAACTAAAGTCATAAAACATGGTCCTCA | 19 |

TABLE 1-continued

GEP-NEN Biomarker/Houskeeper Sequence Information

| Gene Name | RefSeq Accession | Sequence | SEQ ID NO: |
|---|---|---|---|
| | | AAGGTCAATGAACAAAAGGCAAAGAAGACCTGCTACTCCA | |
| | | AAGAAGCCTGTGGGCGAAGTTCACAGTCAATTTAGTACAG | |
| | | GCCCACGCAAACTCTCCTTGTACCATAATAATAGGGAAAGC | |
| | | TCATACTGAAAAAGTACATGTGCCTGCTCGACCCTACAGA | |
| | | GTGCTCAACAACTTCATTTCCAACCAAAAAATGGACTTTA | |
| | | AGGAAGATCTTTCAGGAATAGCTGAAATGTTCAAGACCCC | |
| | | AGTGAAGGAGCAACCGCAGTTGACAAGCACATGTCACATC | |
| | | GCTATTTCAAATTCAGAGAATTTGCTTGGAAAACAGTTTC | |
| | | AAGGAACTGATTCAGGAGAAGAACCTCTGCTCCCCACCTC | |
| | | AGAGAGTTTTGGAGGAAATGTGTTCTTCAGTGCACAGAAT | |
| | | GCAGCAAAACAGCCATCTGATAAATGCTCTGCAAGCCCTC | |
| | | CCTTAAGACGGCAGTGTATTAGAGAAAATGGAAACGTAGC | |
| | | AAAAACGCCCAGGAACACCTACAAAATGACTTCTCTGGAG | |
| | | ACAAAAACTTCAGATACTGAGACAGAGCCTTCAAAAACAG | |
| | | TATCCACTGCAAACAGGTCAGGAAGGTCTACAGAGTTCAG | |
| | | GAATATACAGAAGCTACCTGTGGAAAGTAAGAGTGAAGAA | |
| | | ACAAATACAGAAATTGTTGAGTGCATCCTAAAAAGAGGTC | |
| | | AGAAGGCAACACTACTACAACAAAGGAGAGAAGGAGAGAT | |
| | | GAAGGAAATAGAAAGACCTTTTGAGACATATAAGGAAAAT | |
| | | ATTGAATTAAAAGAAAACGATGAAAAGATGAAAGCAATGA | |
| | | AGAGATCAAGAACTTGGGGGCAGAAATGTGCACCAATGTC | |
| | | TGACCTGACAGACCTCAAGAGCTTGCCTGATACAGAACTC | |
| | | ATGAAAGACACGGCACGTGGCCAGAATCTCCTCCAAACCC | |
| | | AAGATCATGCCAAGGCACCAAAGAGTGAGAAAGGCAAAAT | |
| | | CACTAAAATGCCCTGCCAGTCATTACAACCAGAACCAATA | |
| | | AACACCCCAACACACACAAAACAACAGTTGAAGGCATCCC | |
| | | TGGGGAAAGTAGGTGTGAAAGAAGAGCTCCTAGCAGTCGG | |
| | | CAAGTTCACACGGACGTCAGGGGAGACCACGCACACGCAC | |
| | | AGAGAGCCAGCAGGAGATGGCAAGAGCATCAGAACGTTTA | |
| | | AGGAGTCTCCAAAGCAGATCCTGGACCCAGCAGCCCGTGT | |
| | | AACTGGAATGAAGAAGTGGCCAAGAACGCCTAAGGAAGAG | |
| | | GCCCAGTCACTAGAAGACCTGGCTGGCTTCAAAGAGCTCT | |
| | | TCCAGACACCAGGTCCCTCTGAGGAATCAATGACTGATGA | |
| | | GAAAACTACCAAAATAGCCTGCAAATCTCCACCACCAGAA | |
| | | TCAGTGGACACTCCAACAAGCACAAAGCAATGGCCTAAGA | |
| | | GAAGTCTCAGGAAAGCAGATGTAGAGGAAGAATTCTTAGC | |
| | | ACTCAGGAAACTAACACCATCAGCAGGGAAAGCCATGCTT | |
| | | ACGCCCAAACCAGCAGGAGGTGATGAGAAAGACATTAAAG | |
| | | CATTTATGGGAACTCCAGTGCAGAAACTGGACCTGGCAGG | |
| | | AACTTTACCTGGCAGCAAAAGACAGCTACAGACTCCTAAG | |
| | | GAAAAGGCCCAGGCTCTAGAAGACCTGGCTGGCTTTAAAG | |
| | | AGCTCTTCCAGACTCCTGGTCACACCGAGGAATTAGTGGC | |
| | | TGCTGGTAAAACCACTAAAATACCCTGCGACTCTCCACAG | |
| | | TCAGACCCAGTGGACACCCCAACAAGCACAAAGCAACGAC | |
| | | CCAAGAGAAGTATCAGGAAAGCAGATGTAGAGGGAGAACT | |
| | | CTTAGCGTGCAGGAATCTAATGCCATCAGCAGGCAAAGCC | |
| | | ATGCACACGCCTAAACCATCAGTAGGTGAAGAGAAAGACA | |
| | | TCATCATATTTGTGGGAACTCCAGTGCAGAAACTGGACCT | |
| | | GACAGAGAACTTAACCGGCAGCAAGAGACGGCCACAAACT | |
| | | CCTAAGGAAGAGGCCCAGGCTCTGGAAGACCTGACTGGCT | |
| | | TTAAAGAGCTCTTCCAGACCCCTGGTCATACTGAAGAAGC | |
| | | AGTGGCTGCTGGCAAAACTACTAAAATGCCCTGCGAATCT | |
| | | TCTCCACCAGAATCAGCAGACACCCCAACAAGCACAAGAA | |
| | | GGCAGCCCAAGACACCTTTGGAGAAAAGGGACGTACAGAA | |
| | | GGAGCTCTCAGCCCTGAAGAAGCTCACACAGACATCAGGG | |
| | | GAAACCACACACACAGATAAAGTACCAGGAGGTGAGGATA | |
| | | AAAGCATCAACGCGTTTAGGGAAACTGCAAAACAGAAACT | |
| | | GGACCCAGCAGCAAGTGTAACTGGTAGCAAGAGGCACCCA | |
| | | AAAACTAAGGAAAAGGCCCAACCCCTAGAAGACCTGGCTG | |
| | | GCTTGAAAGAGCTCTTCCAGACACCAGTATGCACTGACAA | |
| | | GCCCACGACTCACGAGAAAACTACCAAAATAGCCTGCAGA | |
| | | TCACAACCAGACCCAGTGGACACACCCAACAAGCTCCAAGC | |
| | | CACAGTCCAAGAGAAGTCTCAGGAAAGTGGACGTAGAAGA | |
| | | AGAATTCTTCGCACTCAGGAAACGAACACCATCAGCAGGC | |
| | | AAAGCCATGCACACACCCAAACCAGCAGTAAGTGGTGAGA | |
| | | AAAACATCTACGCATTTATGGGAACTCCAGTGCAGAAACT | |
| | | GGACCTGACAGAGAACTTAACTGGCAGCAAGAGACGGCTA | |
| | | CAAACTCCTAAGGAAAAGGCCCAGGCTCTAGAAGACCTGG | |
| | | CTGGCTTTAAAGAGCTCTTCCAGACACGAGGTCACACTGA | |
| | | GGAATCAATGACTAACGATAAAACTGCCAAAGTAGCCTGC | |
| | | AAATCTTCACAACCAGACCCAGACAAAAACCCAGCAAGCT | |
| | | CCAAGCGACGGCTCAAGACATCCCTGGGAAAGTGGGCGT | |
| | | GAAAGAAGAGCTCCTAGCAGTTGGCAAGCTCACACAGACA | |
| | | TCAGGAGAGACTACACACACACACAGAGCCAACAGGAG | |
| | | ATGGTAAGAGCATGAAAGCATTTATGGAGTCTCCAAAGCA | |

TABLE 1-continued

GEP-NEN Biomarker/Houskeeper Sequence Information

| Gene Name | RefSeq Accession | Sequence | SEQ ID NO: |
|---|---|---|---|
| | | GATCTTAGACTCAGCAGCAAGTCTAACTGGCAGCAAGAGG<br>CAGCTGAGAACTCCTAAGGGAAAGTCTGAAGTCCCTGAAG<br>ACCTGGCCGGCTTCATCGAGCTCTTCCAGACACCAAGTCA<br>CACTAAGGAATCAATGACTAACGAAAAAACTACCAAAGTA<br>TCCTACAGAGCTTCACAGCCAGACCAGTGGACACCCCAA<br>CAAGCTCCAAGCCACAGCCCAAGAGAAGTCTCAGGAAAGC<br>AGACACTGAAGAAGAATTTTTAGCATTTAGGAAACAAACG<br>CCATCAGCAGGCAAAGCCATGCACACACCCAAACCAGCAG<br>TAGGTGAAGAGAAAGACATCAACACGTTTTTGGGAACTCC<br>AGTGCAGAAACTGGACCAGCCAGGAAATTTACCTGGCAGC<br>AATAGACGGCTACAAACTCGTAAGGAAAAGGCCCAGGCTC<br>TAGAAGAACTGACTGGCTTCAGAGAGCTTTTCCAGACACC<br>ATGCACTGATAACCCCACGACTGATGAGAAAACTACCAAA<br>AAAATACTCTGCAAATCTCCGCAATCAGACCCAGCGGACA<br>CCCCAACAAACACAAAGCAACGGCCCAAGAGAAGCCTCAA<br>GAAAGCAGACGTAGAGGAAGAATTTTTAGCATTCAGGAAA<br>CTAACACCATCAGCAGGCAAAGCCATGCACACGCCTAAAG<br>CAGCAGTAGGTGAAGAGAAAGACATCAACACATTTGTGGG<br>GACTCCAGTGGAGAAACTGGACCTGCTAGGAAATTTACCT<br>GGCAGCAAGAGACGGCCACAAACTCCTAAAGAAAAGGCCA<br>AGGCTCTAGAAGATCTGGCTGGCTTCAAAGAGCTCTTCCA<br>GACACCAGGTCACACTGAGGAATCAATGACCGATGACAAA<br>ATCACAGAAGTATCCTGCAAATCTCCACAACCAGACCCAG<br>TCAAAACCCCAACAAGCTCCAAGCAACGACTCAAGATATC<br>CTTGGGGAAAGTAGGTGTGAAAGAAGAGGTCCTACCAGTC<br>GGCAAGCTCACACAGACGTCAGGGAAGACCACACAGACAC<br>ACAGAGAGACAGCAGGAGATGGAAAGAGCATCAAAGCGTT<br>TAAGGAATCTGCAAAGCAGATGCTGGACCCAGCAAACTAT<br>GGAACTGGGATGGAGAGGTGGCCAAGAACACCTAAGGAAG<br>AGGCCCAATCACTAGAAGACCTGGCCGGCTTCAAAGAGCT<br>CTTCCAGACACCAGACCACACTGAGGAATCAACAACTGAT<br>GACAAAACTACCAAAATAGCCTGCAAATCTCCACCACCAG<br>AATCAATGGACACTCCAACAAGCACAAGGAGGCGGCCCAA<br>AACACCTTTGGGGAAAAGGGATATAGTGGAAGAGCTCTCA<br>GCCCTGAAGCAGCTCACACAGACCACACACACAGACAAAG<br>TACCAGGAGATGAGGATAAAGGCATCAACGTGTTCAGGGA<br>AACTGCAAAACAGAAACTGGACCCAGCAGCAAGTGTAACT<br>GGTAGCAAGAGGCAGCCAAGAACTCCTAAGGGAAAAGCCC<br>AACCCCTAGAAGACTTGGCTGGCTTGAAAGAGCTCTTCCA<br>GACACCAATATGCACTGACAAGCCCACGACTCATGAGAAA<br>ACTACCAAAATAGCCTGCAGATCTCCACAACCAGACCCAG<br>TGGGTACCCCAACAATCTTCAAGCCACAGTCCAAGAGAAG<br>TCTCAGGAAAGCAGACGTAGAGGAAGAATCCTTAGCACTC<br>AGGAAACGAACACCATCAGTAGGGAAAGCTATGGACACAC<br>CCAAACCAGCAGGAGGTGATGAGAAAGACATGAAAGCATT<br>TATGGGAACTCCAGTGCAGAAATTGGACCTGCCAGGAAAT<br>TTACCTGGCAGCAAAAGATGGCCACAAACTCCTAAGGAAA<br>AGGCCCAGGCTCTAGAAGACCTGGCTGGCTTCAAAGAGCT<br>CTTCCAGACACCAGGCACTGACAAGCCCACGACTGATGAG<br>AAAACTACCAAAATAGCCTGCAAATCTCCACAACCAGACC<br>CAGTGGACACCCCAGCAAGCACAAAGCAACGGCCCAAGAG<br>AAACCTCAGGAAAGCAGACGTAGAGGAAGAATTTTTAGCA<br>CTCAGGAAACGAACACCATCAGCAGGCAAAGCCATGGACA<br>CACCAAAACCAGCAGTAAGTGATGAGAAAAATATCAACAC<br>ATTTGTGGAAACTCCAGTGCAGAAACTGGACCTGCTAGGA<br>AATTTACCTGGCAGCAAGAGACAGCCACAGACTCCTAAGG<br>AAAAGGCTGAGGCTCTAGAGGACCTGGTTGGCTTCAAAGA<br>ACTCTTCCAGACACCAGGTCACACTGAGGAATCAATGACT<br>GATGACAAAATCACAGAAGTATCCTGTAAATCTCCACAGC<br>CAGAGTCATTCAAAACCTCAAGAGCTCCAAGCAAAGGCT<br>CAAGATACCCCTGGTGAAAGTGGACATGAAAGAAGAGCCC<br>CTAGCAGTCAGCAAGCTCACACGGACATCAGGGGAGACTA<br>CGCAAACACACACAGAGCCAACAGGAGATAGTAAGAGCAT<br>CAAAGCGTTTAAGGAGTCTCCAAAGCAGATCCTGGACCCA<br>GCAGCAAGTGTAACTGGTAGCAGGAGGCAGCTGAGAACTC<br>GTAAGGAAAAGGCCCGTGCTCTAGAAGACCTGGTTGACTT<br>CAAAGAGCTCTTCTCAGCACCAGGTCACACTGAAGAGTCA<br>ATGACTATTGACAAAAACACAAAAATTCCCTGCAAATCTC<br>CCCCACCAGAACTAACAGACACTGCCACGAGCACAAAGAG<br>ATGCCCAAGACACGTCCCAGGAAGAAGTAAAAGAGGAG<br>CTCTCAGCAGTTGAGAGGCTCACGCAAACATCAGGGCAAA<br>GCACACACACACAAAGAACCAGCAAGCGGTGATGAGGG<br>CATCAAAGTATTGAAGCAACGTGCAAAGAAGAAACCAAAC<br>CCAGTAGAAGAGGAACCCAGCAGGAGAAGGCCAAGAGCAC<br>CTAAGGAAAAGGCCCAACCCCTGGAAGACCTGGCCGGCTT | |

TABLE 1-continued

GEP-NEN Biomarker/Houskeeper Sequence Information

| Gene Name | RefSeq Accession | Sequence | SEQ ID NO: |
|---|---|---|---|
| | | CACAGAGCTCTCTGAAACATCAGGTCACACTCAGGAATCA | |
| | | CTGACTGCTGGCAAAGCCACTAAAATACCCTGCGAATCTC | |
| | | CCCCACTAGAAGTGGTAGACACCACAGCAAGCACAAAGAG | |
| | | GCATCTCAGGACACGTGTGCAGAAGGTACAAGTAAAAGAA | |
| | | GAGCCTTCAGCAGTCAAGTTCACACAAACATCAGGGGAAA | |
| | | CCACGGATGCAGACAAAGAACCAGCAGGTGAAGATAAAGG | |
| | | CATCAAAGCATTGAAGGAATCTGCAAAACAGACACCGGCT | |
| | | CCAGCAGCAAGTGTAACTGGCAGCAGGAGACGGCCAAGAG | |
| | | CACCCAGGGAAAGTGCCCAAGCCATAGAAGACCTAGCTGG | |
| | | CTTCAAAGACCCAGCAGCAGGTCACACTGAAGAATCAATG | |
| | | ACTGATGACAAAACCACTAAAATACCCTGCAAATCATCAC | |
| | | CAGAACTAGAAGACACCGCAACAAGCTCAAAGAGACGGCC | |
| | | CAGGACACGTGCCCAGAAAGTAGAAGTGAAGGAGGAGCTG | |
| | | TTAGCAGTTGGCAAGCTCACACAAACCTCAGGGGAGACCA | |
| | | CGCACACCGACAAAGAGCCGGTAGGTGAGGGCAAAGGCAC | |
| | | GAAAGCATTTAAGCAACCTGCAAAGCGGAAGCTGGACGCA | |
| | | GAAGATGTAATTGGCAGCAGGAGACAGCCAAGAGCACCTA | |
| | | AGGAAAAGGCCCAACCCCTGGAAGATCTGGCCAGCTTCCA | |
| | | AGAGCTCTCTCAAACACCAGGCCACACTGAGGAACTGGCA | |
| | | AATGGTGCTGCTGATAGCTTTACAAGCGCTCCAAAGCAAA | |
| | | CACCTGACAGTGGAAAACCTCTAAAAATATCCAGAAGAGT | |
| | | TCTTCGGGCCCCTAAAGTAGAACCCGTGGGAGACGTGGTA | |
| | | AGCACCAGAGACCCTGTAAAATCACAAAGCAAAAGCAACA | |
| | | CTTCCCTGCCCCCACTGCCCTTCAAGAGGGGAGGTGGCAA | |
| | | AGATGGAAGCGTCACGGGAACCAAGAGGCTGCGCTGCATG | |
| | | CCAGCACCAGAGGAAATTGTGGAGGAGCTGCCAGCCAGCA | |
| | | AGAAGCAGAGGGTTGCTCCCAGGGCAAGAGGCAAATCATC | |
| | | CGAACCCGTGGTCATCATGAAGAGAAGTTTGAGGACTTCT | |
| | | GCAAAAAGAATTGAACCTGCGGAAGAGCTGAACAGCAACG | |
| | | ACATGAAAACCAACAAAGAGGAACACAAATTACAAGACTC | |
| | | GGTCCCTGAAAATAAGGGAATATCCCTGCGCTCCAGACGC | |
| | | CAAAATAAGACTGAGGCAGAACAGCAAATAACTGAGGTCT | |
| | | TTGTATTAGCAGAAAGAATAGAAATAAACAGAAATGAAAA | |
| | | GAAGCCCATGAAGACCTCCCCAGAGATGGACATTCAGAAT | |
| | | CCAGATGATGGAGCCCGGAAACCCATACCTAGAGACAAAG | |
| | | TCACTGAGAACAAAAGGTGCTTGAGGTCTGCTAGACAGAA | |
| | | TGAGAGCTCCCAGCCTAAGGTGGCAGAGGAGAGCGGAGGG | |
| | | CAGAAGAGTGCGAAGGTTCTCATGCAGAATCAGAAAGGGA | |
| | | AAGGAGAAGCAGGAAATTCAGACTCCATGTGCCTGAGATC | |
| | | AAGAAAGACAAAAAGCCAGCCTGCAGCAAGCACTTTGGAG | |
| | | AGCAAATCTGTGCAGAGAGTAACGCGGAGTGTCAAGAGGT | |
| | | GTGCAGAAAATCCAAAGAAGGCTGAGGACAATGTGTGTGT | |
| | | CAAGAAAATAAGAACCAGAAGTCATAGGGACAGTGAAGAT | |
| | | ATTTGACAGAAAAATCGAACTGGGAAAAATATAATAAAGT | |
| | | TAGTTTTGTGATAAGTTCTAGTGCAGTTTTTGTCATAAAT | |
| | | TACAAGTGAATTCTGTAAGTAAGGCTGTCAGTCTGCTTAA | |
| | | GGGAAGAAAACTTTGGATTTGCTGGGTCTGAATCGGCTTC | |
| | | ATAAACTCCACTGGGAGCACTGCTGGGCTCCTGGACTGAG | |
| | | AATAGTTGAACACCGGGGGCTTTGTGAAGGAGTCTGGGCC | |
| | | AAGGTTTGCCCTCAGCTTTGCAGAATGAAGCCTTGAGGTC | |
| | | TGTCACCACCCACAGCCACCCTACAGCAGCCTTAACTGTG | |
| | | ACACTTGCCACACTGTGTCGTCGTTTGTTTGCCTATGTCC | |
| | | TCCAGGGCACGGTGGCAGGAACAACTATCCTCGTCTGTCC | |
| | | CAACACTGAGCAGGCACTCGGTAAACACGAATGAATGGAT | |
| | | GAGCGCACGGATGAATGGAGCTTACAAGATCTGTCTTTCC | |
| | | AATGGCCGGGGCATTTGGTCCCCAAATTAAGGCTATTGG | |
| | | ACATCTGCACAGGACAGTCCTATTTTTGATGTCCTTTCCT | |
| | | TTCTGAAAATAAAGTTTTGTGCTTTGGAGAATGACTCGTG | |
| | | AGCACATCTTTAGGGACCAAGAGTGACTTTCTGTAAGGAG | |
| | | TGACTCGTGGCTTGCCTTGGTCTCTTGGGAATACTTTTCT | |
| | | AACTAGGGTTGCTCTCACCTGAGACATTCTCCACCCGCGG | |
| | | AATCTCAGGGTCCCAGGCTGTGGGCCATCACGACCTCAAA | |
| | | CTGGCTCCTAATCTCCAGCTTTCCTGTCATTGAAAGCTTC | |
| | | GGAAGTTTACTGGCTCTGCTCCCGCCTGTTTTCTTTCTGA | |
| | | CTCTATCTGGCAGCCCGATGCCACCCAGTACAGGAAGTGA | |
| | | CACCAGTACTCTGTAAAGCATCATCATCCTTGGAGAGACT | |
| | | GAGCACTCAGCACCTTCAGCCACGATTTCAGGATCGCTTC | |
| | | CTTGTGAGCCGCTGCCTCCGAAATCTCCTTTGAAGCCCAG | |
| | | ACATCTTTCTCCAGCTTCAGACTTGTAGATATAACTCGTT | |
| | | CATCTTCATTTACTTTCCACTTTGCCCCCTGTCTCTCTG | |
| | | TGTTCCCCAAATCAGAGAATAGCCCGCCATCCCCCAGGTC | |
| | | ACCTGTCTGGATTCCTCCCCATTCACCCACCTTGCCAGGT | |
| | | GCAGGTGAGGATGGTGCACCAGACAGGGTAGCTGTCCCCC | |
| | | AAAATGTGCCCTGTGCGGGCAGTGCCCTGTCTCCACGTTT | |
| | | GTTTCCCCAGTGTCTGGCGGGGAGCCAGGTGACATCATAA | |

TABLE 1-continued

GEP-NEN Biomarker/Houskeeper Sequence Information

| Gene Name | RefSeq Accession | Sequence | SEQ ID NO: |
|---|---|---|---|
| | | ATACTTGCTGAATGAATGCAGAAATCAGCGGTACTGACTT<br>GTACTATATTGGCTGCCATGATAGGGTTCTCACAGCGTCA<br>TCCATGATCGTAAGGGAGAATGACATTCTGCTTGAGGGAG<br>GGAATAGAAAGGGGCAGGGAGGGGACATCTGAGGGCTTCA<br>CAGGGCTGCAAAGGGTACAGGGATTGCACCAGGGCAGAAC<br>AGGGGAGGGTGTTCAAGGAAGAGTGGCTCTTAGCAGAGGC<br>ACTTTGGAAGGTGTGAGGCATAAATGCTTCCTTCTACGTA<br>GGCCAACCTCAAAACTTTCAGTAGGAATGTTGCTATGATC<br>AAGTTGTTCTAACACTTTAGACTTAGTAGTAATTATGAAC<br>CTCACATAGAAAAATTTCATCCAGCCATATGCCTGTGGAG<br>TGGAATATTCTGTTTAGTAGAAAAATCCTTTAGAGTTCAG<br>CTCTAACCAGAAATCTTGCTGAAGTATGTCAGCACCTTTT<br>CTCACCCTGGTAAGTACAGTATTTCAAGAGCACGCTAAGG<br>GTGGTTTTCATTTTACAGGGCTGTTGATGATGGGTTAAAA<br>ATGTTCATTTAAGGGCTACCCCCGTGTTTAATAGATGAAC<br>ACCACTTCTACACAACCCTCCTTGGTACTGGGGGAGGGAG<br>AGATCTGACAAATACTGCCCATTCCCCTAGGCTGACTGGA<br>TTTGAGAACAAATACCCACCCATTTCCACCATGGTATGGT<br>AACTTCTCTGAGCTTCAGTTTCCAAGTGAATTTCCATGTA<br>ATAGGACATTCCCATTAAATACAAGCTGTTTTTACTTTTT<br>CGCCTCCCAGGGCCTGTGGGATCTGGTCCCCAGCCTCTC<br>TTGGGCTTTCTTACACTAACTCTGTACCTACCATCTCCTG<br>CCTCCCTTAGGCAGGCACCTCCAACCACCACACACTCCCT<br>GCTGTTTTCCCTGCCTGGAACTTTCCCTCCTGCCCCACCA<br>AGATCATTTCATCCAGTCCTGAGCTCAGCTTAAGGGAGGC<br>TTCTTGCCTGTGGGTTCCCTCACCCCCATGCCTGTCCTCC<br>AGGCTGGGCAGGTTCTTAGTTTGCCTGGAATTGTTCTGT<br>ACCTCTTTGTAGCACGTAGTGTTGTGGAAACTAAGCCACT<br>AATTGAGTTTCTGGCTCCCCTCCTGGGGTTGTAAGTTTTG<br>TTCATTCATGAGGGCCGACTGCATTTCCTGGTTACTCTAT<br>CCCAGTGACCAGCCACAGGAGATGTCCAATAAAGTATGTG<br>ATGAAATGGTCTTAAAAAAAAAAAAA | |
| KRAS | NM_004985.4 | TCCTAGGCGGCGGCCGCGGCGGCGGAGGCAGCAGCGGCGG<br>CGGCAGTGGCGGCGGCGAAGGTGGCGGCGGCTCGGCCAGT<br>ACTCCCGGCCCCCGCCATTTCGGACTGGGAGCGAGCGCGG<br>CGCAGGCACTGAAGGCGGCGGCGGGGCCAGAGGCTCAGCG<br>GCTCCCAGGTGCGGGAGAGAGGCCTGCTGAAAATGACTGA<br>ATATAAACTTGTGGTAGTTGGAGCTGGTGGCGTAGGCAAG<br>AGTGCCTTGACGATACAGCTAATTCAGAATCATTTTGTGG<br>ACGAATATGATCCAACAATAGAGGATTCCTACAGGAAGCA<br>AGTAGTAATTGATGGAGAAACCTGTCTCTTGGATATTCTC<br>GACACAGCAGGTCAAGAGGAGTACAGTGCAATGAGGGACC<br>AGTACATGAGGACTGGGGAGGGCTTTCTTTGTGTATTTGC<br>CATAAATAATACTAAATCATTTGAAGATATTCACCATTAT<br>AGAGAACAAATTAAAAGAGTTAAGGACTCTGAAGATGTAC<br>CTATGGTCCTAGTAGGAAATAAATGTGATTTGCCTTCTAG<br>AACAGTAGAC<u>ACAAAACAGGCTCAGGACTTAGCAAGAAGT</u><br><u>TATGGAATTCCTTTTATTGAAACATCAGCAAAGACAAGAC</u><br><u>AGGGTGTTGATGATGCCTTCTATACATTAGTTCGAGAAAT</u><br><u>TCGAAAACATAAAGAAAAGATGAGCAAAGATGGTAAAAAG</u><br>AAGAAAAAGAAGTCAAAGACAAAGTGTGTAATTATGTAAA<br>TACAATTTGTACTTTTTCTTAAGGCATACTAGTACAAGT<br>GGTAATTTTTGTACATTACACTAAATTATTAGCATTTGTT<br>TTAGCATTACCTAATTTTTTTCCTGCTCCATGCAGACTGT<br>TAGCTTTTACCTTAAATGCTTATTTTAAAATGACAGTGGA<br>AGTTTTTTTTTCCTCTAAGTGCCAGTATTCCCAGAGTTTT<br>GGTTTTTGAACTAGCAATGCCTGTGAAAAAGAAACTGAAT<br>ACCTAAGATTTCTGTCTTGGGGTTTTGGTGCATGCAGTT<br>GATTACTTCTTATTTTCTTACCAATTGTGAATGTTGGTG<br>TGAAACAAATTAATGAAGCTTTTGAATCATCCCTATTCTG<br>TGTTTTATCTAGTCACATAAATGGATTAATTACTAATTTC<br>AGTTGAGACCTTCTAATTGGTTTTTACTGAAACATTGAGG<br>GAACACAAATTTATGGGCTTCCTGATGATGATTCTTCTAG<br>GCATCATGTCCTATAGTTTGTCATCCCTGATGAATGTAAA<br>GTTACACTGTTCACAAAGGTTTTGTCTCCTTTCCACTGCT<br>ATTAGTCATGGTCACTCTCCCCAAAATATTATATTTTTTC<br>TATAAAAGAAAAAATGAAAAAAATTACAAGGCAATGG<br>AAACTATTATAAGGCCATTTCCTTTTCACATTAGATAAAT<br>TACTATAAAGACTCCTAATAGCTTTTCCTGTTAAGGCAGA<br>CCCAGTATGAAATGGGGATTATTATAGCAACCATTTTGGG<br>GCTATATTTACATGCTACTAAATTTTATAATAATTGAAA<br>AGATTTTAACAAGTATAAAAAATTCTCATAGGAATTAAAT<br>GTAGTCTCCCTGTGTCAGACTGCTCTTTCATAGTATAACT<br>TTAAATCTTTTCTTCAACTTGAGTCTTTGAAGATAGTTTT | 20 |

TABLE 1-continued

GEP-NEN Biomarker/Houskeeper Sequence Information

| Gene Name | RefSeq Accession | Sequence | SEQ ID NO: |
|---|---|---|---|
| | | AATTCTGCTTGTGACATTAAAAGATTATTTGGGCCAGTTA TAGCTTATTAGGTGTTGAAGAGACCAAGGTTGCAAGGCCA GGCCCTGTGTGAACCTTTGAGCTTTCATAGAGAGTTTCAC AGCATGGACTGTGTCCCCACGGTCATCCAGTGTTGTCATG CATTGGTTAGTCAAAATGGGGAGGGACTAGGGCAGTTTGG ATAGCTCAACAAGATACAATCTCACTCTGTGGTGGTCCTG CTGACAAATCAAGAGCATTGCTTTTGTTTCTTAAGAAAAC AAACTCTTTTTAAAAATTACTTTTAAATATTAACTCAAA AGTTGAGATTTTGGGGTGGTGGTGTGCCAAGACATTAATT TTTTTTTAAACAATGAAGTGAAAAAGTTTTACAATCTCT AGGTTTGGCTAGTTCTCTTAACACTGGTTAAATTAACATT GCATAAACACTTTTCAAGTCTGATCCATATTTAATAATGC TTTAAAATAAAAATAAAAACAATCCTTTTGATAAATTTAA AATGTTACTTATTTTAAAATAAATGAAGTGAGATGGCATG GTGAGGTGAAAGTATCACTGGACTAGGAAGAAGGTGACTT AGGTTCTAGATAGGTGTCTTTTAGGACTCTGATTTTGAGG ACATCACTTACTATCCATTTCTTCATGTTAAAAGAAGTCA TCTCAAACTCTTAGTTTTTTTTTTTACAACTATGTAATT TATATTCCATTTACATAAGGATACACTTATTTGTCAAGCT CAGCACAATCTGTAAATTTTTAACCTATGTTACACCATCT TCAGTGCCAGTCTTGGGCAAAATTGTGCAAGAGGTGAAGT TTATATTTGAATATCCATTCTCGTTTTAGGACTCTTCTTC CATATTAGTGTCATCTTGCCTCCCTACCTTCCACATGCCC CATGACTTGATGCAGTTTTAATACTTGTAATTCCCCTAAC CATAAGATTTACTGCTGCTGTGGATATCTCCATGAAGTTT TCCCACTGAGTCACATCAGAAATGCCCTACATCTTATTTC CTCAGGGCTCAAGAGAATCTGACAGATACCATAAAGGGAT TTGACCTAATCACTAATTTTTCAGGTGGTGGCTGATGCTTT GAACATCTCTTTGCTGCCCAATCCATTAGCGACAGTAGGA TTTTTCAAACCTGGTATGAATAGACAGAACCCTATCCAGT GGAAGGAGAATTTAATAAAGATAGTGCTGAAAGAATTCCT TAGGTAATCTATAACTAGGACTACTCCTGGTAACAGTAAT ACATTCCATTGTTTTAGTAACCAGAAATCTTCATGCAATG AAAAATACTTTAATTCATGAAGCTTACTTTTTTTTTTGG TGTCAGAGTCTCGCTCTTGTCACCCAGGCTGGAATGCAGT GGCGCCATCTCAGCTCACTGCAACCTCCATCTCCCAGGTT CAAGCGATTCTCGTGCCTCGGCCTCCTGAGTAGCTGGGAT TACAGGCGTGTGCCACTACACTCAACTAATTTTTGTATTT TTAGGAGAGACGGGGTTTCACCCTGTTGGCCAGGCTGGTC TCGAACTCCTGACCTCAAGTGATTCACCCACCTTGGCCTC ATAAACCTGTTTTGCAGAACTCATTTATTCAGCAAATATT TATTGAGTGCCTACCAGATGCCAGTCACCGCACAAGGCAC TGGGTATATGGTATCCCCAAACAAGAGACATAATCCCGGT CCTTAGGTAGTGCTAGTGTGGTCTGTAATATCTTACTAAG GCCTTTGGTATACGACCCAGAGATAACACGATGCGTATTT TAGTTTTGCAAAGAAGGGGTTTGGTCTCTGTGCCAGCTCT ATAATTGTTTTGCTACGATTCCACTGAAACTCTTCGATCA AGCTACTTTATGTAAATCACTTCATTGTTTTAAAGGAATA AACTTGATTATATTGTTTTTTTATTTGGCATAACTGTGAT TCTTTTAGGACAATTACTGTACACATTAAGGTGTATGTCA GATATTCATATTGACCCAAATGTGTAATATTCCAGTTTTC TCTGCATAAGTAATTAAAATACTTAAAAATTAATAGTT TTATCTGGGTACAAATAAACAGGTGCCTGAACTAGTTCAC AGACAAGGAAACTTCTATGTAAAAATCACTATGATTTCTG AATTGCTATGTGAAACTACAGATCTTTGGAACACTGTTTA GGTAGGGTGTTAAGACTTACACAGTACCTCGTTTCTACAC AGAGAAAGAAATGGCCATACTTCAGGAACTGCAGTGCTTA TGAGGGGATATTTAGGCCTCTTGAATTTTTGATGTAGATG GGCATTTTTTAAGGTAGTGGTTAATTACCTTTATGTGAA CTTTGAATGGTTTAACAAAAGATTTGTTTTTGTAGAGATT TTAAAGGGGAGAATTCTAGAAATAAATGTTACCTAATTA TTACAGCCTTAAAGACAAAAATCCTTGTTGAAGTTTTTTT AAAAAAAGCTAAATTACATAGACTTAGGCATTAACATGTT TGTGGAAGAATATAGCAGACGTATATTGTATCATTTGAGT GAATGTTCCCAAGTAGGCATTCTAGGCTCTATTTAACTGA GTCACACTGCATAGGAATTTAGAACCTAACTTTTATAGGT TATCAAAACTGTTGTCACCATTGCACAATTTTGTCCTAAT ATATACATAGAAACTTTGTGGGGCATGTTAAGTTACAGTT TGCACAAGTTCATCTCATTTGTATTCCATTGATTTTTTT TTCTTCTAAACATTTTTTCTTCAAACAGTATATAACTTTT TTTAGGGGATTTTTTTTAGACAGCAAAAACTATCTGAAG ATTTCCATTTGTCAAAAGTAATGATTTCTTGATAATTGT GTAGTAATGTTTTTTAGAACCCAGCAGTTACCTTAAAGCT GAATTTATATTTAGTAACTTCTGTGTTAATACTGGATAGC ATGAATTCTGCATTGAGAAACTGAATAGCTGTCATAAAAT | |

TABLE 1-continued

GEP-NEN Biomarker/Houskeeper Sequence Information

| Gene Name | RefSeq Accession | Sequence | SEQ ID NO: |
|---|---|---|---|
| | | GAAACTTTCTTTCTAAAGAAAGATACTCACATGAGTTCTT<br>GAAGAATAGTCATAACTAGATTAAGATCTGTGTTTTAGTT<br>TAATAGTTTGAAGTGCCTGTTTGGGATAATGATAGGTAAT<br>TTAGATGAATTTAGGGGAAAAAAAAGTTATCTGCAGATAT<br>GTTGAGGGCCCATCTCTCCCCCCACACCCCCACAGAGCTA<br>ACTGGGTTACAGTGTTTTATCCGAAAGTTTCCAATTCCAC<br>TGTCTTGTGTTTTCATGTTGAAAATACTTTTGCATTTTTC<br>CTTTGAGTGCCAATTTCTTACTAGTACTATTTCTTAATGT<br>AACATGTTTACCTGGAATGTATTTTAACTATTTTTGTATA<br>GTGTAAACTGAAACATGCACATTTTGTACATTGTGCTTTC<br>TTTTGTGGGACATATGCAGTGTGATCCAGTTGTTTTCCAT<br>CATTTGGTTGCGCTGACCTAGGAATGTTGGTCATATCAAA<br>CATTAAAAATGACCACTCTTTTAATTGAAATTAACTTTTA<br>AATGTTTATAGGAGTATGTGCTGTGAAGTGATCTAAAATT<br>TGTAATATTTTTGTCATGAACTGTACTACTCCTAATTATT<br>GTAATGTAATAAAAATAGTTACAGTGACTATGAGTGTGTA<br>TTTATTCATGAAATTTGAACTGTTTGCCCCGAAATGGATA<br>TGGAATACTTTATAAGCCATAGACACTATAGTATACCAGT<br>GAATCTTTTATGCAGCTTGTTAGAAGTATCCTTTATTTCT<br>AAAAGGTGCTGTGGATATTATGTAAAGGCGTGTTTGCTTA<br>AACTTAAAACCATATTTAGAAGTAGATGCAAAACAAATCT<br>GCCTTTATGACAAAAAAATAGGATAACATTATTTATTTAT<br>TTCCTTTTATCAAAGAAGGTAATTGATACACAACAGGTGA<br>CTTGGTTTTAGGCCCAAAGGTAGCAGCAGCAACATTAATA<br>ATGGAAATAATTGAATAGTTAGTTATGTATGTTAATGCCA<br>GTCACCAGCAGGCTATTTCAAGGTCAGAAGTAATGACTCC<br>ATACATATTATTTATTTCTATAACTACATTTAAATCATTA<br>CCAGG | |
| LEO1 | NM_138792.3 | CGTAAAGAGAGGCCGGGAGCTGCCCCTAACCGAGGCAGCA<br>GCGGACGTGAGCGATAATGGCGGATATGGAGGATCTCTTC<br>GGGAGCGACGCCGACAGCGAAGCTGAGCGTAAAGATTCTG<br>ATTCTGGATCTGACTCAGATTCTGATCAAGAGAATGCTGC<br>CTCTGGCAGTAATGCCTCTGGAAGTGAAAGTGATCAGGAT<br>GAAAGAGGTGATTCAGGACAACCAAGTAATAAGGAACTGT<br>TTGGAGATGACAGTGAGGACGAGGGAGCTTCACATCATAG<br>TGGTAGTGATAATCACTCTGAAAGATCAGACAATAGATCA<br>GAAGCTTCTGAGCGTTCTGACCATGAGGACAATGACCCCT<br>CAGATGTAGATCAGCACAGTGGATCAGAAGCCCCTAATGA<br>TGATGAAGACGAAGGTCATAGATCGGATGGAGGGAGCCAT<br>CATTCAGAAGCAGAAGGTTCTGAAAAAGCACATTCAGATG<br>ATGAAAAATGGGGCAGAGAAGATAAAAGTGACCAGTCAGA<br>TGATGAAAAGATACAAAATTCTGATGATGAGGAGAGGGCA<br>CAAGGATCTGATGAAGATAAGCTGCAGAATTCTGACGATG<br>ATGAGAAAATGCAGAACACAGATGATGAGGAGAGGCCTCA<br>GCTTTCCGATGATGAGAGACAACAGCTATCTGAGGAGGAA<br>AAGGCTAATTCTGATGATGAACGGCCGGTAGCTTCTGATA<br>ATGATGATGAGAAACAGAATTCTGATGATGAAGAACAACC<br>ACAGCTGTCTGATGAAGAGAAAATGCAAAATTCTGATGAT<br>GAAAGGCCACAGGCCTCAGATGAAGAACACAGGCATTCAG<br>ATGATGAAGAGGAACAGGATCATAAATCAGAATCTGCAAG<br>AGGCAGTGATAGTGAAGATGAAGTTTTACGAATGAAACGC<br>AAGAATGCGATTGCATCTGATTCAGAAGCGGATAGTGACA<br>CTGAGGTGCCAAAAGATAATAGTGGAACCATGGATTTATT<br>TGGAGGTGCAGATGATATCTCTTCAGGGAGTGATGGAGAA<br>GACAAACCACCTACTCCAGGACAGCCTGTTGATGAAAATG<br>GATTGCCTCAGGATCAACAGGAAGAGGAGCCAATTCCTGA<br>GACCAGAATAGAAGTAGAAATACCCAAAGTAAACACTGAT<br>TTAGGAAACGACTTATATTTTGTTAAACTGCCCAACTTTC<br>TCAGTGTAGAGCCCAGACCTTTTGATCCTCAGTATTATGA<br>AGATGAATTTGAAGATGAAGAATGCTGGATGAAGAAGGT<br>AGAACCAGGTTAAAATTAAAGGTAGAAAATACTATAAGAT<br>GGAGGATACGCCGAGATGAAGAAGGAAATGAAATTAAAGA<br>AAGCAATGCTCGGATAGTCAAGTGGTCAGATGGAAGCATG<br>TCCCTGCATTTAGGCAATGAAGTGTTTGATGTGTACAAAG<br>CCCCACTGCAGGGCGACCACAATCATCTTTTTATAAGACA<br>AGGTACTGGTCTACAGGGACAAGCAGTCTTTAAAACGAAA<br>CTCACCTTCAGACCTCACTCTACGGACAGTGCCACACATA<br>GAAAGATGACTCTGTCACTTGCAGATAGGTGTTCAAAGAC<br>ACAGAAGATTAGAATCTTGCCAATGGCTGGTCGTGATCCT<br>GAATGCCAACGCACAGAAATGATTAAGAAAGAAGAAGAAC<br>GTTTGAGGGCTTCCATACGTAGGGAATCTCAGCAGCGCCG<br>AATGAGAGAGAAACAGCACCAGCGGGGGCTGA<u>GCGCCAGT</u><br><u>TACCTGGAACCTGATCGATACGATGAGGAGGAGGAAGGCG</u><br><u>AGGAGTCCATCAGCTTGGCTGCCATTAAAAACCGATATAA</u> | 21 |

TABLE 1-continued

GEP-NEN Biomarker/Housekeeper Sequence Information

| Gene Name | RefSeq Accession | Sequence | SEQ ID NO: |
|---|---|---|---|
| | | AGGGGGCATTCGAGAGGAACGAGCCAGAATCTATTCATCA<br>GACAGTGATGAGGGATCAGAAGAAGATAAAGCTCAAAGAT<br>TACTCAAAGCAAAGAAACTTACCAGTGATGAGGAAGGTGA<br>ACCTTCCGGAAAGAGAAAAGCAGAAGATGATGATAAAGCA<br>AATAAAAAGCATAAGAAGTATGTGATCAGCGATGAAGAGG<br>AAGAAGATGATGATTGAAGTATGAAATATGAAAACATTTT<br>ATATATTTTATTGTACAGTTATAAATATGTAAACATGAGT<br>TATTTTGATTGAAATGAATCGATTTGCTTTTGTGTAATTT<br>TAATTGTAATAAAACAATTTAAAAGCAAAAAAAAAAAAAA<br>AA | |
| MORF4L2 | NM_001142418.1 | TTGATTATGGAACATTCTAAAACTTAGACAAGACGATTGT<br>GATTGGCTGAAGGGCATACGCCCTCCTCCAGGGTGACGTG<br>TCTGCCTATGGATATCAGTTGCCAGAGAAACCTGGCTTTA<br>CTATGGCGGTTGGAGGAACGGCAGTGATCACACGTCGGCT<br>GCTGGGAAGATCTGGATTCTCGTTTCAGGTCACCATCAGA<br>AAAGCTAAGTTTGCTGTATAGTGAGGATCAGGAGATCTGA<br>TCCTGATTGCAGAACCTTCCCTGATTACAGAATCTTGGGA<br>TTGTTGAGAGGATTACATGTAAAGTACCAGGACAGTGCAT<br>GGCACATATGATTTCACAAAAGTTCATCTTCATTGCAGAT<br>ACCTGCCTTTCTTTCTAGGTTGTATCTCCCACTTCACCCT<br>TCTAGACCATCCCAGAAGATCTATAAGATTTCATCTGGGA<br>AATCACTAGGAGTTCTTGGAAGGGAAAGAAGGAAGATTGT<br>TGGTTGGAATAAAAACAGGGTTGAATGAGTTCCAGAAAGC<br>AGGGTTCTCAACCTCGTGGACAGCAATCTGCAGAAGAAGA<br>GAACTTCAAAAAACCAACTAGAAGCAACATGCAGAGAAGT<br>AAAATGAGAGGGGCCTCCTCAGGAAAGAAGACAGCTGGTC<br>CACAGCAGAAAAATCTTGAACCAGCTCTCCCAGGAAGATG<br>GGGTGGTCGCTCTGCAGAGAACCCCCCTTCAGGATCCGTG<br>AGGAAGACCAGAAAGAACAAGCAGAAGACTCCTGGAAACG<br>GAGATGGTGGCAGTACCAGCGAAGCACCTCAGCCCCCTCG<br>GAAGAAAAGGGCCCGGGCAGACCCCACTGTTGAAAGTGAG<br>GAGGCGTTTAAGAATAGAATGGAGGTTAAAGTGAAGATTC<br>CTGAAGAATTAAAACCATGGCTTGTTGAGGACTGGGACTT<br>AGTTACCAGGCAGAAGCAGCTGTTTCAACTCCCTGCCAAG<br>AAAAATGTAGATGCAATTCTGGAGGAGTATGCAAATTGCA<br>AGAAATCGCAGGGAAATGTTGATAATAAGGAATATGCGGT<br>TAATGAAGTTGTGGCAGGAATAAAAGAATATTTCAATGTG<br>ATGTTGGGCACTCAGCTGCTCTACAAATTTGAGAGGCCCC<br>AGTATGCTGAAATCCTCTTGGCTCACCCTGATGCTCCAAT<br>GTCCCAGGTTTATGGAGCACCACACCTACTGAGATTATTT<br>GTAAGAATTGGAGCAATGTTGGCCTATACGCCCCTTGATG<br>AGAAAAGCCTTGCATTATTGTTGGGCTATTTGCATGATTT<br>CCTAAAATATCTGGCAAAGAATTCTGCATCTCTCTTTACT<br>GCCAGTGATTACAAAGTGGCTTCTGCTGAGTACCACCGCA<br>AAGCCCTGTGAGCGTCTACAGACAGCTCACCATTTTTGTC<br>CTGTATCTGTAAACACTTTTTGTTCTTAGTCTTTTTCTTG<br>TAAAATTGATGTTCTTTAAAATCGTTAATGTATAACAGGG<br>CTTATGTTTCAGTTTGTTTTCCGTTCTGTTTTAAACAGAA<br>AATAAAAGGAGTGTAAGCTCCTTTTCTCATTTCAAAGTTG<br>CTACCAGTGTATGCAGTAATTAGAACAAAGAAGAAACATT<br>CAGTAGAACATTTTATTGCCTAGTTGACAACATTGCTTGA<br>ATGCTGGTGGTTCCTATCCCTTTGACACTACACAATTTTC<br>TAATATGTGTTAATGCTATGTGACAAAACGCCCTGATTCC<br>TAGTGCCAAAGGTTCAACTTAATGTATATACCTGAAAACC<br>CATGCATTTGTGCTCTTTTTTTTTTTTATGGTGCTTGAA<br>GTAAAACAGCCCATCCTCTGCAAGTCCATCTATGTTGTTC<br>TTAGGCATTCTATCTTTGCTCAAATTGTTGAAGGATGGTG<br>ATTTGTTTCATGGTTTTTGTATTTGAGTCTAATGCACGTT<br>CTAACATGATAGAGGCAATGCATTATTGTGTAGCCACGGT<br>TTTCTGGAAAAGTTGATATTTTAGGAATTGTATTTCAGAT<br>CTTAAATAAAATTTGTTTCTAAATTTCAAAGCAAAAAAA<br>AAAAAA | 22 |
| NAP1L1 | NM_139207.2 | AAAAGATATGGTGGGGTGCTTAACAGAGGAGGTTAGACAC<br>CGGCGGGAACCAGAGGAGCCCAAGCGCGGCGCCTGGGCCT<br>CGGGGCTGCAGGAGTCCTCGGTGGGGGTATGGAGGTCGCC<br>GGGGAAGGAGGACGGTTCAGTTGCTAGGCAACCCGGCCTG<br>GACCCGCCTCTCGCTCGCGTTGCTGGGAGACTACAAGGCC<br>GGGAGGAGGGCGGCGAAAGGGCCCTACGTGCTGACGCTAA<br>TTGTATATGAGCGCGAGCGGCGGGCTCTTGGGTCTTTTTT<br>AGCGCCATCTGCTCGCGGCGCCGCCTCCTGCTCCTCCCGC<br>TGCTGCTGCCGCTGCCGCCCTGAGTCACTGCCTGCGCAGC<br>TCCGGCCGCCTGGCTCCCCATACTAGTCGCCGATATTTGG<br>AGTTCTTACAACATGGCAGACATTGACAACAAAGAACAGT | 23 |

TABLE 1-continued

GEP-NEN Biomarker/Houskeeper Sequence Information

| Gene Name | RefSeq Accession | Sequence | SEQ ID NO: |
|---|---|---|---|
| | | CTGAACTTGATCAAGATTTGGATGATGTTGAAGAAGTAGA | |
| | | AGAAGAGGAAACTGGTGAAGAAACAAAACTCAAAGCACGT | |
| | | CAGCTAACTGTTCAGATGATGCAAAATCCTCAGATTCTTG | |
| | | CAGCCCTTCAAGAAAGACTTGATGGTCTGGTAGAAACACC | |
| | | AACAGGATACATTGAAAGCCTGCCTAGGGTAGTTAAAAGA | |
| | | CGAGTGAATGCTCTCAAAAACCTGCAAGTTAAATGTGCAC | |
| | | AGATAGAAGCCAAATTCTATGAGGAAGTTCACGATCTTGA | |
| | | AAGGAAGTATGCTGTTCTCTATCAGCCTCTATTTGATAAG | |
| | | CGATTTGAAATTATTAATGCAATTTATGAACCTACGGAAG | |
| | | AAGAATGTGAATGGAAACCAGATGAAGAAGATGAGATTTC | |
| | | GGAGGAATTGAAAGAAAAGGCCAAGATTGAAGATGAGAAA | |
| | | AAAGATGAAGAAAAGAAGACCCCAAAGGAATTCCTGAAT | |
| | | TTTGGTTAACTGTTTTTAAGAATGTTGACTTGCTCAGTGA | |
| | | TATGGTTCAGGAACACGATGAACCTATTCTGAAGCACTTG | |
| | | AAAGATATTAAAGTGAAGTTCTCAGATGCTGGCCAGCCTA | |
| | | TGAGTTTTGTCTTAGAATTTCACTTTGAACCCAATGAATA | |
| | | TTTTACAAATGAAGTGCTGACAAAGACATACAGGATGAGG | |
| | | TCAGAACCAGATGATTCTGATCCCTTTTCTTTTGATGGAC | |
| | | CAGAAATTATGGGTTGTACAGGGTGCCAGATAGATTGGAA | |
| | | AAAAGGAAAGAATGTCACTTTGAAAACTATTAAGAAGAAG | |
| | | CAGAAACACAAGGGACGTGGGACAGTTCGTACTGTGACTA | |
| | | AAACAGTTTCCAATGACTCTTTCTTTAACTTTTTTGCCCC | |
| | | TCCTGAAGTTCCTGAGAGTGGAGATCTGGATGATGATGCT | |
| | | GAAGCTATCCTTGCTGCAGACTTCGAAATTGGTCACTTTT | |
| | | TACGTGAGCGTATAATCCCAAGATCAGTGTTATATTTTAC | |
| | | TGGAGAAGCTATTGAAGATGATGATGATGATTATGATGAA | |
| | | GAAGGTGAAGAAGCGGATGAGGAAGGGGAAGAAGAAGGAG | |
| | | ATGAGGAAAATGATCCAGACTATGACCCAAAGAAGGATCA | |
| | | AAACCCAGCAGAGTGCAAGCAGCAGTGAAGCAGGATGTAT | |
| | | GTGGCCTTGAGGATAACCTGCACTGGTCTACCTTCTGCTT | |
| | | CCCTGGAAAGGATGAATTTACATCATTTGACAAGCCTATT | |
| | | TTCAAGTTATTTGTTGTTTGTTTGCTTGTTTTTGTTTTTG | |
| | | CAGCTAAAATAAAAATTTCAAATACAATTTTAGTTCTTAC | |
| | | AAGATAATGTCTTAATTTTGTACCAATTCAGGTAGAAGTA | |
| | | GAGGCCTACCTTGAATTAAGGGTTATACTCAGTTTTTAAC | |
| | | ACATTGTTGAAGAAAAGGTACCAGCTTTGGAACGAGATGC | |
| | | TATACTAATAAGCAAGTGTAAAAAAAAAAAAAAAAGAGGA | |
| | | AGAAAATCTTAAGTGATTGATGCTGTTTTCTTTTAAAAAA | |
| | | AAAAAAAAAAATTCATTTTCTTTGGGTTAGAGCTAGAGAG | |
| | | AAGGCCCCAAGCTTCTATGGTTTCTTCTAATTCTTATTGC | |
| | | TTAAAGTATGAGTATGTCACTTACCCGTGCTTCTGTTTAC | |
| | | TGTGTAATTAAAATGGGTAGTACTGTTTACCTAACTACCT | |
| | | CATGGATGTGTTAAGGCATATTGAGTTAAATCTCATATAA | |
| | | TGTTTCTCAATCTTGTTAAAAGCTCAAAATTTTGGGCCTA | |
| | | TTTGTAATGCCAGTGTGACACTAAGCATTTTGTTCACACC | |
| | | ACGCTTTGATAACTAAACTGGAAAACAAAGGTGTTAAGTA | |
| | | CCTCTGTTCTGGATCTGGGCAGTCAGCACTCTTTTTAGAT | |
| | | CTTTGTGTGGCTCCTATTTTTATAGAAGTGGAGGGATGCA | |
| | | CTATTTCACAAGGTCCAAGATTTGTTTTCAGATATTTTG | |
| | | ATGACTGTATTGTAAATACTACAGGGATAGCACTATAGTA | |
| | | TTGTAGTCATGAGACTTAAAGTGGAAATAAGACTATTTTT | |
| | | GACAAAAGATGCCATTAAATTTCAGACTGTAGAGCCACAT | |
| | | TTACAATACCTCAGGCTAATTACTGTTAATTTTGGGGTTG | |
| | | AACTTTTTTTTGACAGTGAGGGTGGATTATTGGATTGTCA | |
| | | TTAGAGGAAGGTCTAGATTTCCTGCTCTTAATAAAATTAC | |
| | | ATTGAATTGATTTTTAGAGGTAATGAAAACTTCCTTTCTG | |
| | | AGAAGTTAGTGTTAAGGTCTTGGAATGTGAACACATTGTT | |
| | | TGTAGTGCTATCCATTCCTCTCCTGAGATTTTAACTTACT | |
| | | ACTGGAAATCCTTAACCAATTATAATAGCTTTTTTTCTTT | |
| | | ATTTTCAAAATGATTTCCTTTGCTTTGATTAGACACTATG | |
| | | TGCTTTTTTTTTTAACCATAGTTCATCGAAATGCAGCTT | |
| | | TTTCTGAACTTCAAAGATAGAATCCCATTTTTAATGAACT | |
| | | GAAGTAGCAAAATCATCTTTTTCATTCTTTAGGAAATAGC | |
| | | TATTGCCAAAGTGAAGGTGTAGATAATACCTAGTCTTGTT | |
| | | ACATAAAGGGGATGTGGTTGCAGAAGAATTTTCTTTATA | |
| | | AAATTGAAGTTTTAAGGGACGTCAGTGTTTATGCCATTTT | |
| | | TCCAGTTCCAAAATGATTCCATTCCATTCTAGAAATTTGA | |
| | | AGTATGTAACCTGAAATCCTTAATAAAATTTGGATTTAAT | |
| | | TTTATAAAATGTACTGGTGATATTTTGGGTGTTTTTTTTT | |
| | | AAATGAATGTATATACTTTTTTTTTGAAGAGTGGGAGAGTA | |
| | | GTGATGTCTAGAGGGAGCTATTTTGTGCTGAGGCCACTAT | |
| | | GTTCTGTAAATATATAATTTTAAGAGCAACCTCACAATCC | |
| | | CTGCTAAGTGGAGTTTATTATTTGAAGACTAAAATGGAAT | |
| | | TCCATAGTTCCTGATAGGTTATATTCTGGGTTATTATTCT | |
| | | GAGTTATCTACAAACATTTTTGAGATTTGTCTTTACACTC | |

TABLE 1-continued

GEP-NEN Biomarker/Houskeeper Sequence Information

| Gene Name | RefSeq Accession | Sequence | SEQ ID NO: |
|---|---|---|---|
| | | TGATTGTAGTTTCCAGCAGCCCATGCACACTGCCAAGTAA GTCTCATTTTTTCCTGTTAGAAATGGTGAAATATCATATA ATCACTTATAAAGAAAACTGATATGAAAAAATTTTAGAGT TGTTTGCTTTATGGTCACTCAAGTAGGGTAAGTGTTCCAC AAATTCCACAAGTTGATAGTTTAACATGGATGTCTGAAAG CCACATATATAATTTCTTAGGATTCTTAAATTAGTAAATC TAGCTTACTGAAGCAGTATTAGCATCACTATTTTAGATTG CAAAAATACCTTAATTGTGTGGAACTGGCTTGTAGAGTGG TACTTAAGAAAAATGGGATTCTACCTCTATTTCTGTTTTA GCACACTTAATCAGGAAAGGATATATTAACTTTCATAAAA ATATTTTTGTTGTGTGAATAGGTTAATGATATGGTAAGGC CCCTAAAATAACTGAATTAATTGTTTATTGTAATTGTAGG CCATTCCCATTATTAAAAATAAAGACAAAACTTGAAGTAA CTGAAAATCTTATCGTGCTATGTAGAAATATTGAACTAAT ATTCAAATATTTGAATGCTTTGGTTTCAGGGATTGGTTTA AAATTGGAGTCCTTTTTTATGGGTTAGTCTTACAAAAATT TAAGCCTTTATATTTTTGACTTTAAATCAAAACAAATGTT ATTTTAAATGTACAGAATAGATTGGTAGTGCAGAAGAGTG TAAGTTCTTCATAGGAGCTTTAGAAAAGAGAAATATGTGC TAATTCAGTTTTTTTTTAATCTGCACTGTACATATATACT TGGTAATTATGAGCTTGATTTTGTTTTTGGAAATATGTGT TCATAATTTAGGTAATTTGCTACTTAAAGCACTAAGTCTC TGATACCTGAAAAGTACATGTAAATGGTGATGGTGAAATA ATACTGCAGTTAACTTAATAGATGTATACTGGTGATTTTT GTATGCTGGATTAAAACTCCAGATATTAAAATATAACCTG GATAAAAAGCC | |
| NOL3 | NM_001185057.2 | GGCATTCAGAGAGTAGATGCCAGTCCTGGGAAAGGCAGGG GAGGAGAGGAGAGCCACGGCTGACGCTTGGGGACAGAAGG AGGAGCCTGAGGAGGAGACAGGACAGAGCGTCTGGAGAGG CAGGAGGACA<u>CCGAGTTCCCCGTGTTGGCCTCCAGGTCCT GTGCTTGCGGAGCCGTCCGGCGGCTGGGATCGAGCCCCGA CAATGGGCAACGCGCAGGAGCGGCCGTCAGAGACTATCGA CCGCGAGC</u>GGAAACGCCTGGTCGAGACGCTGCAGGCGGAC TCGGGACTGCTGTTGGACGCGCTGCTGGCGCGGGGCGTGC TCACCGGGCCAGAGTACGAGGCATTGGATGCACTGCCTGA TGCCGAGCGCAGGGTGCGCCGCCTACTGCTGCTGGTGCAG GGCAAGGGCGAGGCCGCCTGCCAGGAGCTGCTACGCTGTG CCCAGCGTACCGCGGGCGCGCCGGACCCCGCTTGGGACTG GCAGCACGCTACCGGGACCGCAGCTATGACCCTCCATGCC CAGGCCACTGGACGCCGGAGGCACCCGGCTCGGGGACCAC ATGCCCCGGGTTGCCCAGAGCTTCAGACCCTGACGAGGCC GGGGGCCCTGAGGGCTCCGAGGCGGTGCAATCCGGGACCC CGGAGGAGCCAGAGCCAGAGCTGGAAGCTGAGGCCTCTAA AGAGGCTGAACCGGAGCCGGAGCCAGAGCCAGAGCTGGAA CCCGAGGCTGAAGCAGAACCAGAGCCGGAACTGGAGCCAG AACCGGACCCAGAGCCCGAGCCCGACTTCGAGGAAAGGGA CGAGTCCGAAGATTCCTGAAGGCCAGAGCTCTGACAGGCG GTGCCCCGCCCATGCTGGATAGGACCTGGGATGCTGCTGG AGCTGAATCGGATGCCACCAAGGCTCGGTCCAGCCCAGTA CCGCTGGAAGTGAATAAACTCCGGAGGGTCGGACGGGACC TGGGCTCTCTCCACGATTCTGGCTGTTTGCCCAGGAACTT AGGGTGGGTACCTCTGAGTCCCAGGGACCTGGGCAGGCCC AAGCCCACCACGAGCATCATCCAGTCCTCAGCCCTAATCT GCCCTTAGGAGTCCAGGCTGCACCCTGGAGATCCCAAACC TAGCCCCCTAGTGGGACAAGGACCTGACCCTCCTGCCCGC ATACACAACCCATTTCCCCTGGTGAGCCACTTGGCAGCAT ATGTAGGTACCAGCTCAACCCCACGCAAGTTCCTGAGCTG AACATGGAGCAAGGGGAGGGTGACTTCTCTCCACATAGGG AGGGCTTAGAGCTCACAGCCTGGGAAGTGAGACTAGAAG AGGGGAGCAGAAAGGGACCTTGAGTAGACAAAGGCCACAC ACATCATTGTCATTACTGTTTTAATTGTCTGGCTTCTCTC TGGACTGGGAGCTCAGTGAGGATTCTGACCAGTGACTTAC ACAAAAGGCGCTCTATACATATTATAATATATTCGCTTAC TAAATGAATAAGGACTTTCCAAAAAAAAAAAAAAAAAAA AAAAAAAAA | 24 |
| NUDT3 | NM_006703.3 | GGTGCAGCCTTACGCCGCTGACGCATCGCGCCCAAGATGG CGGCGCGGTCGTCGTCGGGGGTGGCGGCGGCAGAGGGGGC GGCGGCCCTGGCGGCAGCGGAGACGGCCAGCCGTGACGGTG GCAGCGGCGGCGCGGGACCTGGGCCTGGGGGAATGAGGCG GCCGCGGCGGGCCAGCGGCGGAGCCGTGTAGCGGAGAAGC TCCCCCCTCCCTGCTTCCCTTGGCCGAGCCGGGGCGCGCG CGCACGCGGCCGTCCAGAGCGGGCTCCCCACCCCCTCGACT CCTGCGACCCGCACCGCACCCCCACCCGGGCCCGGAGGAT | 25 |

TABLE 1-continued

GEP-NEN Biomarker/Houskeeper Sequence Information

| Gene Name | RefSeq Accession | Sequence | SEQ ID NO: |
|---|---|---|---|
| | | GATGAAGCTCAAGTCGAACCAGACCCGCACCTACGACGGC<br>GACGGCTACAAGAAGCGGGCCGCATGCCTGTGTTTCCGCA<br>GCGAGAGCGAGGAGGAGGTGCTACTCGTGAGCAGTAGTCG<br>CCATCCAGACAGATGGATTGTCCCTGGAGGAGGCATGGAG<br>CCCGAGGAGGAGCCAAGTGTGGCAGCAGTTCGTGAAGTCT<br>GTGAGGAGGCTGGAGTAAAAGGGACATTGGGAAGATTAGT<br>TGGAATTTTTGAGAACCAGGAGAGGAAGCACAGGACGTAT<br>GTCTATGTGCTCATTGTCACTGAAGTGCTGGAAGACTGGG<br>AAGATTCAGTTAACATTGGAAGGAAGAGGGAATGGTTTAA<br>AATAGAAGACGCCATAAAAGTGCTGCAGTATCACAAACCC<br>GTGCAGGCATCATATTTTGAAACATTGAGGCAAGGCTACT<br>CAGCCAACAATGGCACCCCAGTCGTGGCCACCACATACTC<br>GGTTTCTGCTCAGAGCTCGATGTCAGGCATCAGATGACTG<br>AAGACTTCCTGTAAGAGAAATGGAAATTGGAAACTAGACT<br>GAAGTGCAAATCTTCCCTCTCACCCTGGCTCTTTCCACTT<br>CTCACAGGCCTCCTCTTTCAAATAAGGCATGGTGGGCAGC<br>AAAGAAAGGGTGTATTGATAATGTTGCTGTTTGGTGTTAA<br>GTGATGGGCTTTTTCTTCTGTTTTTATTGAGGGTGGGGG<br>TTGGGTGTGTAATTTGTAAGTACTTTTGTGCATGATCTGT<br>CCCTCCCTCTTCCCACCCCTGCAGTCCTCTGAAGAGAGGC<br>CAACAGCCTTCCCCTGCCTTGGATTCTGAAGTGTTCCTGT<br>TTGTCTTATCCTGGCCCTGGCCAGACGTTTTCTTTGATTT<br>TTAATTTTTTTTTTTATTAAAAGATACCAGTATGAGATG<br>AAAACTTCCAATAATTTGTCCTATAATGTGCTGTACAGTT<br>CAGTAGAGTGGTCACTTTCACTGCAGTATACATTTATCTA<br>CACATTATATATCGGACATATAATATGTAAATAAATGACT<br>TCTAGAAAGAGAAATTTGTTTAATTTTTCAAGGTTTTTTT<br>CTCTTTTAATTTGGGCATTTCTAGAATTGAGAGCCTCACA<br>ATTAACATACCTTTTTGTTTTCGATGCTAGTGGCTGGGCA<br>GGTTGCCCTGTCCTTTCTCTATTTCCCAGTCATTGACTGT<br>AGATATGGGAAGAGTTTAGCTACCTTCATAGTGCTCCCAG<br>GACTCATGGCCTTTCCTTCTTTAAGCTGTATTTCCCTGCC<br>CAGAAAGAAACAGGAAGAAACCTTTTTTATTTTTTATT<br>TTTTTTAACCAAGCAAGGAGCAAATGGCCTCAGCCCAGA<br>TCTGTAAAAACAATGATAGAAATTGAATTCTGCCCCACAT<br>GTTGACAGTAGAGTTGGAACTGGATTCTTGGGATTACTTA<br>TCTAAAAAACTGGAGCATCAGGTCCATTTCTGTTCTGCTG<br>GTTTGGAATCTTTTCCGTAATGCTATTTATTGCCAACAAT<br>GGCCTCTCTTTGTGTCCATATATGCCTTACACCGTGCTGA<br>CCTGGGTATCATCCATGTGCTCTGAAGCATCCAACTTTAC<br>TTTGCAGGTGCATCAATGTAGTCCTGTCCCTGAACTGAGT<br>AACCGTGTTCCTGAAAAGTACACTAGGGAAATTCACCTGC<br>TTGCTTGTCTTTGTATTGGCATGGCACTTGTGATTGCACC<br>ATGGAGCATGCTCAGAGCTATTAAATTGGTCTCCCATCTC<br>CCACCAGGATATGAAAGGTCCATATGGGAGGCCACGTAAT<br>CACTTATTACAGTGGTTACATAATACACTGGCTCACTGCA<br>GACTCTCTTGTTTTTTGATACAGTTTCGTGCTGGCTTCAT<br>TTGCCAATTGTGTTGTTTAGTTCGGAAGTAAGAGGGTCTT<br>GAGATTGAGGGGTAGGGAGGGCTACACTGACTGATCCGTG<br>GCTTAAGACAGGAGATTATCTCTGTACTCCAGTGGCATCT<br>CCTTAGCCAAGATGTGAAATTAAAATCATAGTTCGCCTCA<br>TTTAAAAATTCTAATAAAGCACTCAAACTTTGAAAAAAAA<br>AAAAAAAAA | |
| OAZ2 | NM_002537.3 | ATGCAGATGAGGCACTCGGGGGCGGGGCGGCGGCGGCGGC<br>GGCGGCGGTGGCGGCCGGGGAGGGTCAGTTGGAGGCAGGC<br>GCTCGCTGAGGCAAAAGGAGGCGCTCGGCCCGCGGCCTGA<br>CAGGGACTTAGCCCGCAGAGATCGACCCCGCGCGCGTGAC<br>CCCACACCCACCCACTCATCCATCTATCCACTCCCTGCGC<br>CGCCTCCTCCCACCCTGAGCAGAGCCGCCGAGGATGATAA<br>ACACCCAGGACAGTAGTATTTTGCCTTTGAGTAACTGTCC<br>CCAGCTCCAGTGCTGCAGGCACATTGTTCCAGGGCCTCTG<br>TGGTGCTCCTGATGCCCCTCACCCACTGTCGAAGATCCCC<br>GGTGGGCGAGGGGCGGCAGGGATCCTTCTCTCTCAGCTC<br>TAATATATAAGGACGAGAAGCTCACTGTGACCCAGGACCT<br>CCCTGTGAATGATGGAAAACCTCACATCGTCCACTTCCAG<br>TATGAGGTCACCGAGGTGAAGGTCTCTTCTTGGGATGCAG<br>TCCTGTCCAGCCAGAGCCTGTTTGTAGAAATCCCAGATGG<br>ATTATTAGCTGATGGGAGCAAAGAAGGATTGTTAGCACTG<br>CTAGAGTTTGCTGAAGAGAAGATGAAAGTGAACTATGTCT<br>TCATCTGCTTCAGGAAGGGCCGAGAAGACAGAGCTCCACT<br>CCTGAAGACCTTCAGCTTCTTGGGCTTTGAGATTGTACGT<br>CCAGGCCATCCCTGTGTCCCCTCTCGGCCAGATGTGATGT<br>TCATGGTTTATCCCCTGGACCAGAACTTGTCCGATGAGGA<br>CTAATAGTCATAGAGGATGCTTTACCCAAGAGCCACAGTG | 26 |

TABLE 1-continued

GEP-NEN Biomarker/Houskeeper Sequence Information

| Gene Name | RefSeq Accession | Sequence | SEQ ID NO: |
|---|---|---|---|
| | | GGGGAAGAGGGGAAGTTAGGCAGCCCTGGGACAGACGAGA<br>GGGCTCCTCGCTGTCTAGGGAAGGACACTGAGGGGCTCAG<br>GGTGAGGGTTGCCTATTGTGTTCTCGGAGTTGACTCGTTG<br>AAATTGTTTTCCATAAAGAACAGTATAAACATATTATTCA<br>CATGTAATCACCAATAGTAAATGAAGATGTTTATGAACTG<br>GCATTAGAAGCTTTCTAAACTGCGCTGTGTGATGTGTTCT<br>ATCTAGCCTAGGGGAGGACATTGCCTAGAGGGGAGGGAC<br>TGTCTGGGTTCAGGGGCATGGCCTGGAGGGCTGGTGGGCA<br>GCACTGTCAGGCTCAGGTTTCCCTGCTGTTGGCTTTCTGT<br>TTTGGTTATTAAGACTTGTGTATTTTCTTTCTTTGCTTCC<br>TGTCACCCCAGGGGCTCCTGAGTATAGGCTTTTCAGTCCC<br>TGGGCAGTGTCCTTGAGTTGTTTTTTGACACTCTTACCTG<br>GGCTTCTCTGTGTGCATTTGCGTCTGGCCTGGAGTAAGCA<br>GGTCCGACCCCTCCTTCTTTACAGCTTAGTGTTATTCTGG<br>CATTTGGTTAAGCTGGCTTAATCTGTTTAATGTTATCAGT<br>ACATTTTAAATAGGGGCATTGAAATTTACTCCCACCACCA<br>GGGCTTTTTTGGGGGATGCCTGGGCCTTTAAAACACTAGC<br>CAAACTCTAATTAATTCTCAAATCACTGCCAGGAGTTCTT<br>GCTCCTGGCTGCAGGCCCAGGCCCCAAGGTCTCCTTCTTG<br>GGGTCACAAACAGCAGTAAGGAAGAGGAATATATAGCAAC<br>TCAGGGCCTGGGAATTGTGGGGCAATCCGTTCTTAGGGAC<br>TGGATACTTCTGGCTGGCTGAGTATAGTACTAGCTGCCTC<br>CCCACCAGGTTCCGAGTAGTGTCTGAGACTCTGCTCTGCA<br>GGGCCTAGGGTAGCGCTGGGAGTGTAGAAGTGGCCTGCCC<br>TTAACTGTTTTCACTAAACAGCTTTTTCTAAGGGGAGAGC<br>AAGGGGGAGAGATCTAGATTGGGTGAGGGGGACGGGGATG<br>TCAGGGAGGCAAGTGTGTTGTGTTACTGTGTCAATAAACT<br>GATTTAAAGTTGTGAAAAAAAAAAAA | |
| PANK2 | NM_024960.4 | ATGCTGGGGAGGGGCTGGCGGCCTCGACGGCAGCTGCGG<br>AACTAGGCCGAGGGACAAAGGCTAAGTTTTTCCATGGTTT<br>GGACTGGATATCGGTGGAACTCTGGTCAAGCTGGTATATT<br>TTGAACCCAAAGACATCACTGCTGAAGAAGAAGAGGAAGA<br>AGTGGAAAGTCTTAAAAGCATTCGGAAGTACCTGACCTCC<br>AATGTGGCTTATGGGTCTACAGGCATTCGGGACGTGCACC<br>TCGAGCTGAAGGACCTGACTCTGTGTGGACGCAAAGGCAA<br>TCTGCACTTTATACGCTTTCCCACTCATGACATGCCTGCT<br>TTTATTCAAATGGGCAGAGATAAAAACTTCTCGAGTCTCC<br>ACACTGTCTTTTGTGCCACTGGAGGTGGAGCGTACAAATT<br>TGAGCAGGATTTTCTCACAATAGGTGATCTTCAGCTTTGC<br>AAACTGGATGAACTAGATTGCTTGATCAAAGGAATTTTAT<br>ACATTGACTCAGTCGGATTCAATGGACGGTCACAGTGCTA<br>TTACTTTGAAAACCCTGCTGATTCTGAAAAGTGTCAGAAG<br>TTACCATTTGATTTGAAAAATCCGTATCCTCTGCTTCTGG<br>TGAACATTGGCTCAGGGGTTAGCATCTTAGCAGTATATTC<br>CAAAGATAATTACAAACGGGTCACAGGTACTAGTCTTGGA<br>GGAGGAACTTTTTTTGGTCTCTGCTGTCTTCTTACTGGCT<br>GTACCACTTTTGAAGAAGCTCTTGAAATGGCATCTCGTGG<br>AGATAGCACCAAAGTGGATAAACTAGTACGAGATATTTAT<br>GGAGGGGACTATGAGAGGTTTGGACTGCCAGGCTGGGCTG<br>TGGCTTCAAGCTTTGGAAACATGATGAGCAAGGAGAAGCG<br>AGAGGCTGTCAGTAAAGAGGACCTGGCCAGAGCGACTTTG<br>ATCACCATCACCAACAACATTGGCTCAATAGCAAGAATGT<br>GTGCCCTTAATGAAAACATTAACCAGGTGGTATTTGTTGG<br>AAATTTCTTGAGAATTAATACGATCGCCATGCGGCTTTTG<br>GCATATGCTTTGGATTATTGGTCCAAGGGGCAGTTGAAAG<br>CACTTTTTTCGGAACACGAGGGTTATTTTGGAGCTGTTGG<br>AGCACTCCTTGAGCTGTTGAAGATCCCGTGATCATTACCT<br>GGGGAGGGGTTCCTGAAACCTTCCACAATGGGATCTGTGG<br>ACTTTCATTTTTTTAAGAGACTTACTCAATTTCATGACTG<br>TACTACCTGAAACAAAGTGAGAAAGGACAGGTGTATTTTT<br>CTAAGTCATCAAGATAAATCCTTAAGAATTCAGTCTAAAT<br>TAGCAACCAGGAAGGAAAAATATATTAAAAACAACAAAAA<br>AGTGGCACATGTCCAGGCAGTGTGAGGATTTGCTGTATAT<br>AAGTTGCCTGCTTTGTATTTTTGAAATCTCTGCATCACTC<br>ATTGGAAGTGCTTCTGAAGAGAGCTGCTCTGTGTTCAGTT<br>GACTGGTTTTGTGTCCTGTTTGAACTTGCTGAATGTAAGG<br>CAGGCTACTATGCGTTATAATCTAATCACAATTTGTCAAT<br>ATGGTCTTGGCAATCATCTGTGCATTACTCTGGTTTGCAT<br>TAAGCCTGTGTGTGAACTTACTGTAAAACATGTTTTATTT<br>CAAGGTTCTGCAAAATTAATTGGGCAGGTTAATTGTGTAC<br>CTGAAACTTAACAAGCAGTTTTTGGAAGGGCA | 27 |
| PHF21A | NM_001101802.1 | GGTGAATGGGCTGGTGGTGCTCGCTGCTGCTGCTGAGAGG<br>AGGAGGAGGATGAAGAGTTGGGCTTGTTTGTCTCCTACAG | 28 |

TABLE 1-continued

GEP-NEN Biomarker/Houskeeper Sequence Information

| Gene Name | RefSeq Accession | Sequence | SEQ ID NO: |
|---|---|---|---|
| | | TTTCTCTCCTGCTGCTCTGATTCCCCCCTCCCGATTCCGG | |
| | | CCCGGGGCCTGTGTGTGTCCCTCCTGGAGGAGGAGGAGGA | |
| | | TCCAGTTCCTCCCCCCAACCCCCTCCTCCCCACCCCCCCT | |
| | | TGCCTGGGGAAGAGGAGGAAAGAAACAGCCCAGAGAGAGA | |
| | | GAGAGAGAGAGAGTGAGTGAGAGAGAGAGGAGAGGAGAGG | |
| | | AGGAGGAGGAGGAGGGAGAAGGGAACAACCTACCATCTTA | |
| | | ACACACTAATATCTAAAAAGTGCGAGAGGCCCAGAGCAGC | |
| | | AGCAGAAGCAGCAGCAGCAGCTCCAGCTTCTTCCCTCCCT | |
| | | CCCCATGAAGAAGAGTTCCCTCCTCCTCCTCCTCCTGCTT | |
| | | CTCCTGCTCAGAGTTCCTGCCTCCAGCTGCCAGGGGGGAC | |
| | | AGCCAGCCAGCAGCAGGAGGGGGGCTAGAGAGCTGAAGGA | |
| | | GAGCCAGTTTCCCCAAAATTGCTGCAGTGAGAAGAGGAGT | |
| | | TTGTTACTTTAAACAGAGGCTGAAGAAACTATAGAATTAG | |
| | | CAGAGAAAGTGGAGAAGGTAGAGGATGGAGTTGCAGACTC | |
| | | TACAGGAGGCTCTTAAAGTGGAAATTCAGGTTCACCAGAA | |
| | | ACTGGTTGCTCAAATGAAGCAGGATCCACAGAATGCTGAC | |
| | | TTAAAGAAACAGCTTCATGAACTCCAAGCCAAAATCACAG | |
| | | CTTTGAGTGAGAAACAGAAAAGAGTAGTTGAACAGCTACG | |
| | | GAAGAACCTGATAGTAAAGCAAGAACAACCGGACAAGTTC | |
| | | CAAATACAGCCATTGCCACAATCTGAAAACAAACTACAAA | |
| | | CAGCACAGCAGCAACCACTACAGCAACTACAACAACAGCA | |
| | | GCAGTACCACCACCACCACGCCCAGCAGTCAGCTGCAGCC | |
| | | TCTCCCAACCTGACTGCTTCACAGAAGACTGTAACTACAG | |
| | | CTTCTATGATTACCACAAAGACACTACCTCTCGTCTTGAA | |
| | | AGCAGCAACTGCGACCATGCCTGCCTCTGTGGTGGGCCAG | |
| | | AGACCTACCATTGCTATGGTGACCGCCATCAACAGTCAGA | |
| | | AGGCTGTGCTCAGCACTGATGTGCAGAACACACCAGTCAA | |
| | | CCTCCAGACGTCTAGTAAGGTCACTGGGCCTGGGGCAGAG | |
| | | GCTGTCCAAATTGTGGCAAAAAACACAGTCACTCTGGTTC | |
| | | AGGCAACACCTCCTCAGCCCATCAAAGTACCACAGTTTAT | |
| | | CCCCCCTCCTAGACTCACTCCACGTCCAAACTTTCTTCCA | |
| | | CAGGTTCGACCCAAGCCTGTGGCCCAGAATAACATTCCTA | |
| | | TTGCCCCAGCACCACCTCCCATGCTCGCAGCTCCTCAGCT | |
| | | TATCCAGAGGCCCGTCATGCTGACCAAGTTCACCCCCACA | |
| | | ACCCTTCCCACATCCCAGAATTCCATCCACCCCGTCCGTG | |
| | | TCGTCAATGGGCAGACTGCAACCATAGCCAAAACGTTCCC | |
| | | CATGGCCCAGCTCACCAGCATTGTGATAGCTACTCCAGGG | |
| | | ACCAGACTCGCTGGACCTCAAACTGTACAGCTTAGCAAGC | |
| | | CAAGTCTTGAAAAACAGACAGTTAAATCTCACACAGAAAC | |
| | | AGATGAGAAACAAACAGAGAGCCGCACCATCACCCCACCT | |
| | | GCTGCACCCAAACCAAAACGGGAGGAGAACCCTCAGAAAC | |
| | | TTGCCTTCATGGTGTCTCTAGGGTTGGTAACACATGACCA | |
| | | TCTAGAAGAAATCCAAAGCAAGAGGCAAGAGCGAAAAAGA | |
| | | AGAACAACAGCAAATCCGGTCTACAGTGGAGCAGTCTTTG | |
| | | AGCCAGAGCGTAAGAAGAGTGCAGTGACATACCTAAACAG | |
| | | CACAATGCACCCTGGGACCCGGAAGAGAGGTCGTCCTCCA | |
| | | AAATACAATGCAGTGCTGGGGTTTGGAGCCCTTACCCCAA | |
| | | CATCCCCCCAATCCAGTCATCCTGACTCCCCTGAAAATGA | |
| | | AAAGACAGAGACCACATTCACTTTCCCTGCACCTGTTCAG | |
| | | CCTGTGTCCCTGCCCAGCCCCACCTCCACAGACGGTGATA | |
| | | TTCATGAGGATTTTTGCAGCGTTTGCAGAAAAAGTGGCCA | |
| | | GTTACTGATGTGCGACACATGTTCCCGTGTATATCATTTG | |
| | | GACTGCTTAGACCCCCCTCTGAAAACAATTCCCAAGGGCA | |
| | | TGTGGATCTGTCCCAGATGTCAGGACCAGATGCTGAAGAA | |
| | | <u>GGAAGAAGCAATTCCATGGCCTGGAACTTTAGCAATTGTT</u> | |
| | | <u>CATTCCTATATTGCCTACAAAGCAGCAAAAGAAGAAGAGA</u> | |
| | | <u>AACAGAAGTTACTTAAATGGAGTTCAGATTTAAAACAAGA</u> | |
| | | <u>ACGAGAA</u>CAACTAGAGCAAAAGGTGAAACAGCTCAGCAAT | |
| | | TCCATAAGTAAATGCATGGAAATGAAGAACACCATCCTGG | |
| | | CCCGGCAGAAGGAGATGCACAGCTCCCTGGAGAAGGTAAA | |
| | | ACAGCTGATTCGCCTCATCCACGGCATCGACCTCTCCAAA | |
| | | CCTGTAGACTCTGAGGCCACTGTGGGGCCATCTCCAATG | |
| | | GCCCGGACTGCACCCCCCCTGCCAATGCCGCCACCTCCAC | |
| | | GCCGGCCCCTTCCCCCTCCTCCCAGAGCTGCACAGCGAAC | |
| | | TGTAACCAGGGGAAGAGACTAAATAACAGAGCCCCTCTA | |
| | | GGAGAAGCCACGGGATCCCGGCGGCAAGGAGAACAGAACA | |
| | | CTGAAGACTCTAGAAAAGCAAAGCCGGATTTCTGGAAAGT | |
| | | GCAGAATTCTTTTGGTTCTTTGGTTCCAGAGAGAGAGAAG | |
| | | ATGCTTGTGCCAGGTGGCACCAGAGTTTGCCAATTGATCC | |
| | | TTCTTATTCTGTGTGTACATGCAAAGATTGGACCATGTTA | |
| | | CATGAAATAGTGCCAGCTGGAGGTTCTTTGCCAGCACCAT | |
| | | GCCAAGTGAAATAATATATTTACTCTCTATTATACACC | |
| | | AGTGTGTGCCTGCAGCAGCCTCCACAGCCACGATGGGTTT | |
| | | GTTTCTGTTTTCTTGGGTGGGAGCAGGGACGGGCGGAGG | |
| | | GAGGAGAGCAGGTTTCAGATCCTTACTTGCCGAGCCGTTT | |

TABLE 1-continued

GEP-NEN Biomarker/Houskeeper Sequence Information

| Gene Name | RefSeq Accession | Sequence | SEQ ID NO: |
|---|---|---|---|
| | | GTTTAGGTAGAGAAGACAAGTCCAAAGAGTGTGTGGGCTT | |
| | | TCCTGTTTCTAAACTTTCGCTACTATAAAACCAAAAAAAG | |
| | | GAATTGAGATTTCACCAACCCCAGTGCCCAGAAGAGGGAA | |
| | | GGGGAGTGGCTGGAGGGAGCAGGGGGTGGGACAGTGTATC | |
| | | AAATAAGCAGTATTTAATCACCTCTGGCGGGGGCCTCGTG | |
| | | CAAGGGGAGACTGACACCAAGAACAGCCAGTAGGTTCTTC | |
| | | TCCCCTGCACTCTGCTCCCTGCGCGGTAACCCCACCACTC | |
| | | CTGAAGCCTGCCCAGTCTCCTTCCTTCCCTGCTTGGTGAG | |
| | | TCGCGCATCTCCGTGGTTATCCCGCTGTCTCCTCTCCAAG | |
| | | AACAAGCAGAGCCCGGGCCACTGGCCCTTGCCCAAGGCAG | |
| | | GGAAGAAGGATGTGTGTGTCCAGGAAGGAAAAAAAGGTGG | |
| | | ATCAGTGATTTTACTTGAAAACAAGCTCCATCCCTTTTCT | |
| | | ATATTTATAAGAAGAGAAGATCTTGAGTGAAGCAGCACGC | |
| | | GACCCAGGTGTGTGTGAATTGAATGGAGACGTTTCTTTTC | |
| | | TCTTTCTTTAATTTTGTTTTTGTTCTTTTTTTCTTTAAG | |
| | | GAAAGTTTTATTTTACTGTTCATTTTACTTTCTTGGTAAC | |
| | | AAAAACTAAAATAAGGAATAGAAAAGCTGTTTTTCAGGCT | |
| | | GACAGTCCAATTAAGGGTAGCCAAGACCTTGCATGGTAGA | |
| | | GTAGGAATCATAGTGTCAGTGAGGTCCCGTGAGTCTTTGT | |
| | | GAGTCCTTGTGTCATCGTTCGGGCACTGTTTTTTATGCA | |
| | | AGGGCAAAAATCTTTGTATCTGGGGAAAAAAAACTTTTTT | |
| | | TTAAATTAAAAAGGAAAATAAAAGATATTGAGGTCTTCCT | |
| | | AGTGTTACTTAAATTAAGATCAAGGTAAGAAACATTGTAA | |
| | | AAAAAAATTACAAAAGTGCTATTTGTTTCCTAAAAACAGT | |
| | | GATTTCTATTAAAAAGGTGTCAGAACTGGAGAAAATGCCG | |
| | | TGTAGTTATAATTTTTTAGCACAGACCCTGCTGATCACGA | |
| | | TGACATTTTGCCGTGTGTGTCTCTAGACTGGTGGGCCA | |
| | | GTCTCCTTGAAGGACAGAGGCGGAGCTCCCCACCCTTCTC | |
| | | TCTCCTCAGAAAAGACCGTGCTCTCTTCTTGGTGCAGGGA | |
| | | TCTTGTCTCCTGTTGTGAAGCCCAAATGGAAGCGTGGATG | |
| | | GTATCAGGGCCCTACCCGTGGTCTTCTCAGATTCTGCTAG | |
| | | AGCAAAAGGCTGGTGCCTAAATAAGATCCCTTCCTTTGGT | |
| | | GCTGCTTTTGGTCTTTCAGCCACCAGCATTATGAGTGCCT | |
| | | GGGGGACACCTCCGAGGGAACTGGCCAGCGGAGCTCTGTG | |
| | | GTGCGCACGCACCCTGGCCGTGACAGGAGGGTGCGGGAGT | |
| | | ACAGGCTGGCTGCATCAGCCCTTGGTGCTTAGAACAGAGG | |
| | | AGGAGTGACATGTTTTGAGGGTACGTCTCTGAGACAGAGC | |
| | | CCCAGCGTGGCCTTCGCTCTGTCTTGCCTTTGGGGAGAGG | |
| | | TCTGAAGCTCCCACTCCTTTCTCTGCCTGTTGGCTCCAGG | |
| | | CACCAGAAATTTACTCCACTCCACCCACCCACAAGCCTCC | |
| | | TGGGTGACCCTGGGCTAGAATTGCTGCGCTTGCCTCGGCT | |
| | | TGGCCGGTTGTGGCCTCTCCTTGAGAAAACCAGGGTTGTG | |
| | | AAAGACTCAGACCATTCTCTCATCTTGCCTTGTCAGAAGT | |
| | | AAATTGTGTCAGATTTGTGCTCTCGCTGGAGACCTTTGCC | |
| | | CCTTGCGTGCCCCTGGCCGATGGGAGGGCGGTGGAGGCTC | |
| | | TGTACCCTGGCCCTGCTGGAGCATCTCCCCCAAGCCCACT | |
| | | CCAGGCCCTGGGAATGGCCAGAGTCTAGGAGAGGTAGAAA | |
| | | CGATCCTATCAGCTTCTCTCCCACCCAATTAGGCCCAGAG | |
| | | AGACAAAGACAGATCTGAAAGCAAATGCAACAGAGAAGAG | |
| | | ACACTTCTTAGAGTAAAATGTGTCTCATCTCTATCAGCCA | |
| | | TCGCCTTTCATCTTCCCAGGGGCCTCAGAAGAAGGAATTA | |
| | | AGTTAGGCTGAACAGGCCTCAGAGTTAGGCCCTGGCTGCT | |
| | | TGATTGGCTGAGGGGGAAAGAGTTCCCTTTTCTCATTCAG | |
| | | AAACCAAGGTGCTGTGTCTAGTCAGGGAGCCTTGGAGATG | |
| | | CCTGGACTAGTTGGAGGAATCGTTGGCAGAGGATCAGAGA | |
| | | CCAGCAGCAGGCTGTCTGCCCTGTCTAGAGCTCTTCCCCT | |
| | | CAACTTGTCTGGGCCCATCTGGGGGTTGCCACACAACACC | |
| | | TAACTTACCTTTTCCTGAAAGAAGTTGGGAAACCATCATC | |
| | | ACTAGAGGCCTTTGCTCAGAGAGGAGCTGCCTTAGGAGTC | |
| | | TTGGGTCGGAGGACGGGGCTAGGAATTGACCAGGGCTTTG | |
| | | CCTGCCGCCCTCAGCAGTGTCGGGTACATTCTGACCTCGC | |
| | | CTGCAGCTGGGCTGTGGATTCTTCCTGACATTCAGATGTG | |
| | | AGCTGTTTTGGGAGTCAGCTAGTATGGAGTACGAGATGCA | |
| | | ACCCAGCCCCCAAACCTACATTCTGCACTCAAATTCCAAA | |
| | | ACACTGCTTTACTGTAAAGAAGAGGCCCCTGGCACCCAAT | |
| | | CTCCCTGTCCTTCACTGTCCCCTCAGACCTGGGCGGGAG | |
| | | GGGGGGGGGCCTGTGACCACCTGAGACATACGCTCGTGAC | |
| | | ACTGCCCACCCCAGCCACCTCCACTTGCTTCCTCCTCCT | |
| | | TCCCTCCGCTGCTCTTTCCCCACGGCCCAGAATTTAGCTG | |
| | | CTCTGACAGCCACTTTTGAGACCAGCTGGCTTTGTAGTCA | |
| | | CTTCAGAGAGCTGGAGCGGCTGCCCACTGGGCCCTGACTG | |
| | | GGAGTCCCTGCCAGCTCCTGATCAGGCGCTGCGCCCTGG | |
| | | TGGCAGTGATGACTGGGAGTCCCTGCCAGCTCCTGTCCA | |
| | | GGCGCTGCATCCTGGTAACAGTGAGGCCATGTTGCTGTCA | |
| | | TCTCCACCTCTGCATTCTTGCTGCCTGTGGGTCCTTTTTC | |

TABLE 1-continued

GEP-NEN Biomarker/Houskeeper Sequence Information

| Gene Name | RefSeq Accession | Sequence | SEQ ID NO: |
|---|---|---|---|
| | | TTTCATGGAGCCTGCTGGGTCTTGTCTCACCTGTGCTGAG<br>CTCCTCTGGGGTTTTGATTTCTTCCTTCCTTATCAGGCCC<br>TTTGGGGTAAGCCTGCTGGTTGTACCTGACATAGGGAGGC<br>AGTTAGGGGCAGTCCCTGGTGGGGCCGCCCTGGCAGCCTC<br>CAGCTGGCACCATCGTGTGCCTGGTTTCCCTGCAACACCT<br>GCCTCTCTGTCCCTGCTGCTGCTTGGCTCAGGCCCAACAG<br>GCAGCGTGCATGGAGGTGGTTACACACAGCTGTTTCCGTG<br>AGGGTGACCGTGTCTGCAGCACGCTTCCGTCTCCGCATGC<br>ACGGCTGCCTCTCCAGCCACCTCTGATACTTCTCTCTTGG<br>GGCCATCAGAGCCTCCCTTGGGCTGTCACCTCCCAGCTCA<br>CACACACTCTTCAGTGGTTTCCTCTCTTCATTCTCTTATA<br>GGGCGTGGTCCTTCTTATTTATCTAAAGGGCTGAATTTAG<br>GAGACTTTTTACCCAGGGGCAAAAGGCTCTTAGGGTAATG<br>AGATGGATGGTGGCCCAGGTGCATTTTCCAGGGCCTGGGT<br>TCTCCAGATCCCGTGGCTTCTGTTGAGTGGAGGCAACTTT<br>GCTCTGTGTGAACCTCGCCCTGTCCCTCTGCCGGGCACC<br>CCTGGCAGGAAGCAGGACTCCCATCCTCACCCTGACTTAG<br>ACTGTCCTCTGAGTCAGCTCCTCTCCAAGACAGGAGTGGG<br>CAGCCCTGGGCAGTCTTCTGGCCCCTTGCTAAAGTGAGGG<br>GCAGGAAGCTGGGGCTGCCCTCCAGAAAGCCGGGGTAGGA<br>ACTCTGAAAAATACCTCCTCTAAACGGAAGCAGGGCTCTC<br>CAGTTCCACTTGGCGCCCCTCCCACAAGGCCCTTCCTCC<br>CTGAGGACCCCACCCCCCTACCCCTTCCCCAGCAGCCTTT<br>GGACCCTCACCTCTCTCCGGTGTCCGTGGGTCCTCAGCCC<br>AGGGTGAGCTGCAGTCAGGCGGGATGGGACGGGCAGGCCA<br>GAGGTCAGCCAGCTCCTAGCAGAGAAGAGCCAGCCAGACC<br>CCAACCCTGTCTCTTGTCCATGCCCTTTGTGATTTCAGTC<br>TTGGTAGACTTGTATTTGGAGTTTTGTGCTTCAAAGTTTT<br>TGTTTTTGTTTGTTTGGTTTTTGTTTTGAGGGGGTGGGGG<br>GGGATACAGAGCAGCTGATCAATTTGTATTTATTTATTTT<br>AACATTTTACTAAATAAAGCCAAATAAAGCCTCTCAAAAA<br>AAAAAAAAAAA | |
| PKD1 | NM_000296.3 | GCACTGCAGCGCCAGCGTCCGAGCGGGCGGCCGAGCTCCC<br>GGAGCGGCCTGGCCCCGAGCCCCGAGCGGGCGTCGCTCAG<br>CAGCAGGTCGCGGCCGCAGCCCCATCCAGCCCCGCGCCCG<br>CCATGCCGTCCGCGGGCCCCGCCTGAGCTGCGGCCTCCGC<br>GCGCGGGCGGGCCTGGGGACGGCGGGGCCATGCGCGCGCT<br>GCCCTAACGATGCCGCCCGCCGCGCCCGCCCGCCTGGCGC<br>TGGCCCTGGGCCTGGGCCTGTGGCTCGGGGCGCTGGCGGG<br>GGGCCCCGGGCGCGGCTGCGGGCCCTGCGAGCCCCCCTGC<br>CTCTGCGCGCCCAGCGCCCGGCGCCGCCTGCCGCGTCAACT<br>GCTCGGGCCGCGGGCTGCGGACGCTCGGTCCCGCGCTGCG<br>CATCCCCGCGGACGCCACAGCGCTAGACGTCTCCCACAAC<br>CTGCTCCGGGCGCTGGACGTTGGGCTCCTGGCGAACCTCT<br>CGGCGCTGGCAGAGCTGGATATAAGCAACAACAAGATTTC<br>TACGTTAGAAGAAGGAATATTTGCTAATTTATTTAATTTA<br>AGTGAAATAAACCTGAGTGGGAACCCGTTTGAGTGTGACT<br>GTGGCCTGGCGTGGCTGCCGCGATGGGCGGAGGAGCAGCA<br>GGTGCGGGTGGTGCAGCCCGAGGCAGCCACGTGTGCTGGG<br>CCTGGCTCCCTGGCTGGCCAGCCTCTGCTTGGCATCCCCT<br>TGCTGGACAGTGGCTGTGGTGAGGAGTATGTCGCCTGCCT<br>CCCTGACAACAGCTCAGGCACCGTGGCAGCAGTGTCCTTT<br>TCAGCTGCCCACGAAGGCCTGCTTCAGCCAGAGGCCTGCA<br>GCGCCTTCTGCTTCTCCACCGGCCAGGGCCTCGCAGCCCT<br>CTCGGAGCAGGGCTGGTGCCTGTGTGGGGCGGCCCAGCCC<br>TCCAGTGCCTCCTTTGCCTGCCTGTCCCTCTGCTCCGGCC<br>CCCCGCCACCTCCTGCCCCCACCTGTAGGGGCCCCACCCT<br>CCTCCAGCACGTCTTCCCTGCCTCCCCAGGGGCCACCCTG<br>GTGGGGCCCCACGGACCTCTGGCCTCTGGCCAGCTAGCAG<br>CCTTCCACATCGCTGCCCCGCTCCCTGTCACTGCCACACG<br>CTGGGACTTCGGAGACGGCTCCGCCGAGGTGGATGCCGCT<br>GGGCCGGCTGCCTCGCATCGCTATGTGCTGCCTGGGCGCT<br>ATCACGTGACGGCCGTGCTGGCCCTGGGGGCCGGCTCAGC<br>CCTGCTGGGACAGACGTGCAGGTGGAAGCGGCACCTGCC<br>GCCCTGGAGCTCGTGTGCCCGTCCTCGGTGCAGAGTGACG<br>AGAGCCTTGACCTCAGCATCCAGAACCGCGGTGGTTCAGG<br>CCTGGAGGCCGCCTACAGCATCGTGGCCCTGGGCGAGGAG<br>CCGGCCCGAGCGGTGCACCCGCTCTGCCCCTCGGACACGG<br>AGATCTTCCCTGGCAACGGGCACTACTACCGCCTGGTGGT<br>GGAGAAGGCGGCCTGGCTGCAGGCGCAGGAGCAGTGTCAG<br>GCCTGGGCCGGGGCCGCCCTGGCAATGGTGGACAGTCCCG<br>CCGTGCAGCGCTTCCTGGTCTCCCGGGTCACCAGGAGCCT<br>AGACGTGTGGATCGGCTTCTCGACTGTGCAGGGGGTGGAG<br>GTGGGCCCAGCGCCGCAGGGCGAGGCCTTCAGCCTGGAGA | 29 |

TABLE 1-continued

GEP-NEN Biomarker/Houskeeper Sequence Information

| Gene Name | RefSeq Accession | Sequence | SEQ ID NO: |
|---|---|---|---|
| | | GCTGCCAGAACTGGCTGCCCGGGGAGCCACACCCAGCCAC<br>AGCCGAGCACTGCGTCCGGCTCGGGCCCACCGGGTGGTGT<br>AACACCGACCTGTGCTCAGCGCCGCACAGCTACGTCTGCG<br>AGCTGCAGCCCGGAGGCCCAGTGCAGGATGCCGAGAACCT<br>CCTCGTGGGAGCGCCCAGTGGGGACCTGCAGGGACCCCTG<br>ACGCCTCTGGCACAGCAGGACGGCCTCTCAGCCCCGCACG<br>AGCCCGTGGAGGTCATGGTATTCCCGGGCCTGCGTCTGAG<br>CCGTGAAGCCTTCCTCACCACGGCCGAATTTGGGACCCAG<br>GAGCTCCGGCGGCCCGCCCAGCTGCGGCTGCAGGTGTACC<br>GGCTCCTCAGCACAGCAGGGACCCCGGAGAACGGCAGCGA<br>GCCTGAGAGCAGGTCCCCGGACAACAGGACCCAGCTGGCC<br>CCCGCGTGCATGCCAGGGGGACGCTGGTGCCCTGGAGCCA<br>ACATCTGCTTGCCGCTGGACGCCTCCTGCCACCCCCAGGC<br>CTGCGCCAATGGCTGCACGTCAGGGCCAGGGCTACCCGGG<br>GCCCCCTATGCGCTATGGAGAGAGTTCCTCTTCTCCGTTC<br>CCGCGGGGCCCCCCGCGCAGTACTCGGTCACCCTCCACGG<br>CCAGGATGTCCTCATGCTCCCTGGTGACCTCGTTGGCTTG<br>CAGCACGACGCTGGCCCTGGCGCCCTCCTGCACTGCTCGC<br>CGGCTCCCGGCCACCCTGGTCCCCAGGCCCCGTACCTCTC<br>CGCCAACGCCTCGTCATGGCTGCCCCACTTGCCAGCCCAG<br>CTGGAGGGCACTTGGGCCTGCCCTGCCTGTGCCCTGCGGC<br>TGCTTGCAGCCACGGAACAGCTCACCGTGCTGCTGGGCTT<br>GAGGCCCAACCCTGGACTGCGGCTGCCTGGGCGCTATGAG<br>GTCCGGGCAGAGGTGGGCAATGGCGTGTCCAGGCACAACC<br>TCTCCTGCAGCTTTGACGTGGTCTCCCCAGTGGCTGGGCT<br>GCGGGTCATCTACCCTGCCCCCCGCGACGGCCGCCTCTAC<br>GTGCCCACCAACGGCTCAGCCTTGGTGCTCCAGGTGGACT<br>CTGGTGCCAACGCCACGGCCACGGCTCGCTGGCCTGGGGG<br>CAGTGTCAGCGCCCGCTTTGAGAATGTCTGCCCTGCCCTG<br>GTGGCCACCTTCGTGCCCGGCTGCCCCTGGGAGACCAACG<br>ATACCCTGTTCTCAGTGGTAGCACTGCCGTGGCTCAGTGA<br>GGGGGAGCACGTGGTGGACGTGGTGGTGGAAAACAGCGCC<br>AGCCGGGCCAACCTCAGCCTGCGGGTGACGGCGGAGGAGC<br>CCATCTGTGGCCTCCGCGCCACGCCCAGCCCCGAGGCCCG<br>TGTACTGCAGGGAGTCCTAGTGAGGTACAGCCCCGTGGTG<br>GAGGCCGGCTCGGACATGGTCTTCCGGTGGACCATCAACG<br>ACAAGCAGTCCCTGACCTTCCAGAACGTGGTCTTCAATGT<br>CATTTATCAGAGCGCGGCGGTCTTCAAGCTCTCACTGACG<br>GCCTCCAACCACGTGAGCAACGTCACCGTGAACTACAACG<br>TAACCGTGGAGCGGATGAACAGGATGCAGGGTCTGCAGGT<br>CTCCACAGTGCCGGCCGTGCTGTCCCCCAATGCCACGCTA<br>GCACTGACGGCGGGCGTGCTGGTGGACTCGGCCGTGGAGG<br>TGGCCTTCCTGTGGACCTTTGGGGATGGGGAGCAGGCCCT<br>CCACCAGTTCCAGCCTCCGTACAACGAGTCCTTCCCGGTT<br>CCAGACCCCTCGGTGGCCCAGGTGCTGGTGGAGCACAATG<br>TCATGCACACCTACGCTGCCCCAGGTGAGTACCTCCTGAC<br>CGTGCTGGCATCTAATGCCTTCGAGAACCTGACGCAGCAG<br>GTGCCTGTGAGCGTGCGCGCCTCCCTGCCCTCCGTGGCTG<br>TGGGTGTGAGTGACGGCGTCCTGGTGGCCGGCCGGCCCGT<br>CACCTTCTACCCGCACCCGCTGCCCTCGCCTGGGGGTGTT<br>CTTTACACGTGGGACTTCGGGGACGGCTCCCCTGTCCTGA<br>CCCAGAGCCAGCCGGCTGCCAACCACACCTATGCCTCGAG<br>GGGCACCTACCACGTGCGCCTGGAGGTCAACAACACGGTG<br>AGCGGTGCGGCGGCCCAGGCGGATGTGCGCGTCTTTGAGG<br>AGCTCCGCGGACTCAGCGTGGACATGAGCCTGGCCGTGGA<br>GCAGGGCGCCCCCGTGGTGGTCAGCGCCGCGGTGCAGACG<br>GGCGACAACATCACGTGGACCTTCGACATGGGGGACGGCA<br>CCGTGCTGTCGGGCCCGGAGGCAACAGTGGAGCATGTGTA<br>CCTGCGGGCACAGAACTGCACAGTGACCGTGGGTGCGGCC<br>AGCCCCGCCGGCCACCTGGCCCGGAGCCTGCACGTGCTGG<br>TCTTCGTCCTGGAGGTGCTGCGCGTTGAACCCGCCGCCTG<br>CATCCCCACGCAGCCTGACGCGCGGCTCACGGCCTACGTC<br>ACCGGGAACCCGGCCCACTACCTCTTCGACTGGACCTTCG<br>GGGATGGCTCCTCCAACACGACCGTGCGGGGGTGCCCGAC<br>GGTGACACACAACTTCACGCGGAGCGGCACGTTCCCCCTG<br>GCGCTGGTGCTGTCCAGCCGCGTGAACAGGCGCATTACT<br>TCACCAGCATCTGCGTGGAGCCAGAGGTGGGCAACGTCAC<br>CCTGCAGCCAGAGAGGCAGTTTGTGCAGCTCGGGGACGAG<br>GCCTGGCTGGTGGCATGTGCCTGGCCCCGTTCCCCTACC<br>GCTACACCTGGGACTTTGGCACCGAGGAAGCCGCCCCCAC<br>CCGTGCCAGGGGCCCTGAGGTGACGTTCATCTACCGAGAC<br>CCAGGCTCCTATCTTGTGACAGTCACCGCGTCCAACAACA<br>TCTCTGCTGCCAATGACTCAGCCCTGGTGGAGGTGCAGGA<br>GCCCGTGCTGGTCACCAGCATCAAGGTCAATGGCTCCCTT<br>GGGCTGGAGCTGCAGCAGCCGTACCTGTTCTCTGCTGTGG | |

TABLE 1-continued

GEP-NEN Biomarker/Houskeeper Sequence Information

| Gene Name | RefSeq Accession | Sequence | SEQ ID NO: |
|---|---|---|---|
| | | GCCGTGGGCGCCCCGCCAGCTACCTGTGGGATCTGGGGGA | |
| | | CGGTGGGTGGCTCGAGGGTCCGGAGGTCACCCACGCTTAC | |
| | | AACAGCACAGGTGACTTCACCGTTAGGGTGGCCGGCTGGA | |
| | | ATGAGGTGAGCCGCAGCGAGGCCTGGCTCAATGTGACGGT | |
| | | GAAGCGGCGCGTGCGGGGGCTCGTCGTCAATGCAAGCCGC | |
| | | ACGGTGGTGCCCCTGAATGGGAGCGTGAGCTTCAGCACGT | |
| | | CGCTGGAGGCCGGCAGTGATGTGCGCTATTCCTGGGTGCT | |
| | | CTGTGACCGCTGCACGCCCATCCCTGGGGGTCCTACCATC | |
| | | TCTTACACCTTCCGCTCCGTGGGCACCTTCAATATCATCG | |
| | | TCACGGCTGAGAACGAGGTGGGCTCCGCCCAGGACAGCAT | |
| | | CTTCGTCTATGTCCTGCAGCTCATAGAGGGGCTGCAGGTG | |
| | | GTGGGCGGTGGCCGCTACTTCCCCACCAACCACACGGTAC | |
| | | AGCTGCAGGCCGTGGTTAGGGATGGCACCAACGTCTCCTA | |
| | | CAGCTGGACTGCCTGGAGGGACAGGGGCCCGGCCCTGGCC | |
| | | GGCAGCGGCAAAGGCTTCTCGCTCACCGTGCTCGAGGCCG | |
| | | GCACCTACCATGTGCAGCTGCGGGCCACCAACATGCTGGG | |
| | | CAGCGCCTGGGCCGACTGCACCATGGACTTCGTGGAGCCT | |
| | | GTGGGGTGGCTGATGGTGGCCGCCTCCCCGAACCCAGCTG | |
| | | CCGTCAACACAAGCGTCACCCTCAGTGCCGAGCTGGCTGG | |
| | | TGGCAGTGGTGTCGTATACACTTGGTCCTTGGAGGAGGGG | |
| | | CTGAGCTGGGAGACCTCCGAGCCATTTACCACCCATAGCT | |
| | | TCCCCACACCCGGCCTGCACTTGGTCACCATGACGGCAGG | |
| | | GAACCCGCTGGGCTCAGCCAACGCCACCGTGGAAGTGGAT | |
| | | GTGCAGGTGCCTGTGAGTGGCCTCAGCATCAGGGCCAGCG | |
| | | AGCCCGGAGGCAGCTTCGTGGCGGCCGGGTCCTCTGTGCC | |
| | | CTTTTGGGGGCAGCTGGCCACGGGCACCAATGTGAGCTGG | |
| | | TGCTGGGCTGTGCCCGGCGGCAGCAGCAAGCGTGGCCCTC | |
| | | ATGTCACCATGGTCTTCCCGGATGCTGGCACCTTCTCCAT | |
| | | CCGGCTCAATGCCTCCAACGCAGTCAGCTGGGTCTCAGCC | |
| | | ACGTACAACCTCACGGCGGAGGAGCCCATCGTGGGCCTGG | |
| | | TGCTGTGGGCCAGCAGCAAGGTGGTGGCGCCCGGGCAGCT | |
| | | GGTCCATTTTCAGATCCTGCTGGCTGCCGGCTCAGCTGTC | |
| | | ACCTTCCGCCTGCAGGTCGGCGGGGCCAACCCCGAGGTGC | |
| | | TCCCCGGGCCCCGTTTCTCCCACAGCTTCCCCCGCGTCGG | |
| | | AGACCACGTGGTGAGCGTGCGGGGCAAAAACCACGTGAGC | |
| | | TGGGCCCAGGCGCAGGTGCGCATCGTGGTGCTGGAGGCCG | |
| | | TGAGTGGGCTGCAGGTGCCCAACTGCTGCGAGCCTGGCAT | |
| | | CGCCACGGGCACTGAGAGGAACTTCACAGCCCGCGTGCAG | |
| | | CGCGGCTCTCGGGTCGCCTACGCCTGGTACTTCTCGCTGC | |
| | | AGAAGGTCCAGGGCGACTCGCTGGTCATCCTGTCGGGCCG | |
| | | CGACGTCACCTACACGCCCGTGGCCGCGGGGCTGTTGGAG | |
| | | ATCCAGGTGCGCGCCTTCAACGCCCTGGGCAGTGAGAACC | |
| | | GCACGCTGGTGCTGGAGGTTCAGGACGCCGTCCAGTATGT | |
| | | GGCCCTGCAGAGCGGCCCCTGCTTCACCAACCGCTCGGCG | |
| | | CAGTTTGAGGCCGCCACCAGCCCCAGCCCCCGGCGTGTGG | |
| | | CCTACCACTGGGACTTTGGGGATGGGTCGCCAGGGCAGGA | |
| | | CACAGATGAGCCCAGGGCCGAGCACTCCTACCTGAGGCCT | |
| | | GGGGACTACCGCGTGCAGGTGAACGCCTCCAACCTGGTGA | |
| | | GCTTCTTCGTGGCGCAGGCCACGGTGACCGTCCAGGTGCT | |
| | | GGCCTGCCGGGAGCCGGAGGTGGACGTGGTCCTGCCCCTG | |
| | | CAGGTGCTGATGCGGCGATCACAGCGCAACTACTTGGAGG | |
| | | CCCACGTTGACCTGCGCGACTGCGTCACCTACCAGACTGA | |
| | | GTACCGCTGGGAGGTGTATCGCACCGCCAGCTGCCAGCGG | |
| | | CCGGGGCGCCCAGCGCGTGTGGCCCTGCCCGGCGTGGACG | |
| | | TGAGCCGGCCTCGGCTGGTGCTGCCGCGGCTGGCGCTGCC | |
| | | TGTGGGGCACTACTGCTTTGTGTTTGTCGTGTCATTTGGG | |
| | | GACACGCCACTGACACAGAGCATCCAGGCCAATGTGACGG | |
| | | TGGCCCCCGAGCGCCTGGTGCCCATCATTGAGGGTGGCTC | |
| | | ATACCGCGTGTGGTCAGACACACGGGACCTGGTGCTGGAT | |
| | | GGGAGCGAGTCCTACGACCCCAACCTGGAGGACGGCGACC | |
| | | AGACGCCGCTCAGTTTCCACTGGGCCTGTGTGGCTTCGAC | |
| | | ACAGAGGGAGGCTGGCGGGTGTGCGCTGAACTTTGGGCCC | |
| | | CGCGGGAGCAGCACGGTCACCATTCCACGGGAGCGGCTGG | |
| | | CGGCTGGCGTGGAGTACACCTTCAGCCTGACCGTGTGGAA | |
| | | GGCCGGCCGCAAGGAGGAGGCCACCAACCAGACGGTGCTG | |
| | | ATCCGGAGTGGCCGGGTGCCCATTGTGTCCTTGGAGTGTG | |
| | | TGTCCTGCAAGGCACAGGCCGTGTACGAAGTGAGCCGCAG | |
| | | CTCCTACGTGTACTTGGAGGGCCGCTGCCTCAATTGCAGC | |
| | | AGCGGCTCCAAGCGAGGGCGGTGGGCTGCACGTACGTTCA | |
| | | GCAACAAGACGCTGGTGCTGGATGAGACCACCACATCCAC | |
| | | GGGCAGTGCAGGCATGCGACTGGTGCTGCGGCGGGGCGTG | |
| | | CTGCGGGACGGCGAGGGATACACCTTCACGCTCACGGTGC | |
| | | TGGGCCGCTCTGGCGAGGAGGAGGGCTGCGCCTCCATCCG | |
| | | CCTGTCCCCAACCGCCCGCCGCTGGGGGGCTCTTGCCGC | |
| | | CTCCTTCCCACTGGGCGCTGTGCACGCCCTCACCACCAAGG | |

TABLE 1-continued

GEP-NEN Biomarker/Houskeeper Sequence Information

| Gene Name | RefSeq Accession | Sequence | SEQ ID NO: |
|---|---|---|---|
| | | TGCACTTCGAATGCACGGGCTGGCATGACGCGGAGGATGC | |
| | | TGGCGCCCCGCTGGTGTACGCCCTGCTGCTGCGGCGCTGT | |
| | | CGCCAGGGCCACTGCGAGGAGTTCTGTGTCTACAAGGGCA | |
| | | GCCTCTCCAGCTACGGAGCCGTGCTGCCCCCGGGTTTCAG | |
| | | GCCACACTTCGAGGTGGGCCTGGCCGTGGTGGTGCAGGAC | |
| | | CAGCTGGGAGCCGCTGTGGTCGCCCTCAACAGGTCTTTGG | |
| | | CCATCACCCTCCCAGAGCCCAACGGCAGCGCAACGGGGCT | |
| | | CACAGTCTGGCTGCACGGGCTCACCGCTAGTGTGCTCCCA | |
| | | GGGCTGCTGCGGCAGGCCGATCCCCAGCACGTCATCGAGT | |
| | | ACTCGTTGGCCCTGGTCACCGTGCTGAACGAGTACGAGCG | |
| | | GGCCCTGGACGTGGCGGCAGAGCCCAAGCACGAGCGGCAG | |
| | | CACCGAGCCCAGATACGCAAGAACATCACGGAGACTCTGG | |
| | | TGTCCCTGAGGGTCCACACTGTGGATGACATCCAGCAGAT | |
| | | CGCTGCTGCGCTGGCCCAGTGCATGGGGCCCAGCAGGGAG | |
| | | CTCGTATGCCGCTCGTGCCTGAAGCAGACGCTGCACAAGC | |
| | | TGGAGGCCATGATGCTCATCCTGCAGGCAGAGACCACCGC | |
| | | GGGCACCGTGACGCCCACCGCCATCGGAGACAGCATCCTC | |
| | | AACATCACAGGAGACCTCATCCACCTGGCCAGCTCGGACG | |
| | | TGCGGGCACCACAGCCCTCAGAGCTGGGAGCCGAGTCACC | |
| | | ATCTCGGATGGTGGCGTCCCAGGCCTACAACCTGACCTCT | |
| | | GCCCTCATGCGCATCCTCATGCGCTCCCGCGTGCTCAACG | |
| | | AGGAGCCCCTGACGCTGGCGGGCGAGGAGATCGTGGCCCA | |
| | | GGGCAAGCGCTCGGACCCGCGGAGCCTGCTGTGCTATGGC | |
| | | GGCGCCCCAGGGCCTGGCTGCCACTTCTCCATCCCCGAGG | |
| | | CTTTCAGCGGGGCCCTGGCCAACCTCAGTGACGTGGTGCA | |
| | | GCTCATCTTTCTGGTGGACTCCAATCCCTTTCCCTTTGGC | |
| | | TATATCAGCAACTACACCGTCTCCACCAAGGTGGCCTCGA | |
| | | TGGCATTCCAGACACAGGCCGGCGCCCAGATCCCCATCGA | |
| | | GCGGCTGGCCTCAGAGCGCGCCATCACCGTGAAGGTGCCC | |
| | | AACAACTCGGACTGGGCTGCCCGGGGCCACCGCAGCTCCG | |
| | | CCAACTCCGCCAACTCCGTTGTGGTCCAGCCCCAGGCCTC | |
| | | CGTCGGTGCTGTGGTCACCCTGGACAGCAGCAACCCTGCG | |
| | | GCCGGGCTGCATCTGCAGCTCAACTATACGCTGCTGGACG | |
| | | GCCACTACCTGTCTGAGGAACCTGAGCCCTACCTGGCAGT | |
| | | CTACCTACACTCGGAGCCCCGGCCCAATGAGCACAACTGC | |
| | | TCGGCTAGCAGGAGGATCCGCCCAGAGTCACTCCAGGGTG | |
| | | CTGACCACCGGCCCTACACCTTCTTCATTTCCCGGGGAG | |
| | | CAGAGACCCAGCGGGGAGTTACCATCTGAACCTCTCCAGC | |
| | | CACTTCCGCTGGTCGGCGCTGCAGGTGTCCGTGGGCCTGT | |
| | | ACACGTCCCTGTGCCAGTACTTCAGCGAGGAGGACATGGT | |
| | | GTGGCGGACAGAGGGGCTGCTGCCCCTGGAGGAGACCTCG | |
| | | CCCCGCCAGGCCGTCTGCCTCACCCGCCACCTCACCGCCT | |
| | | TCGGCGCCAGCCTCTTCGTGCCCCCAAGCCATGTCCGCTT | |
| | | TGTGTTTCCTGAGCCGACAGCGGATGTAAACTACATCGTC | |
| | | ATGCTGACATGTGCTGTGTGCCTGGTGACCTACATGGTCA | |
| | | TGGCCGCCATCCTGCACAAGCTGGACCAGTTGGATGCCAG | |
| | | CCGGGGCCGCGCCATCCCTTTCTGTGGGCAGCGGGGCCGC | |
| | | TTCAAGTACGAGATCCTCGTCAAGACAGGCTGGGGCCGGG | |
| | | GCTCAGGTACCACGGCCCACGTGGGCATCATGCTGTATGG | |
| | | GGTGGACAGCCGGAGCGGCCACCGGCACCTGGACGGCGAC | |
| | | AGAGCCTTCCACCGCAACAGCCTGGACATCTTCCGGATCG | |
| | | CCACCCCGCACAGCCTGGGTAGCGTGTGGAAGATCCGAGT | |
| | | GTGGCACGACAACAAAGGGCTCAGCCCTGCCTGGTTCCTG | |
| | | CAGCACGTCATCGTCAGGGACCTGCAGACGGCACGCAGCG | |
| | | CCTTCTTCCTGGTCAATGACTGGCTTTCGGTGGAGACGGA | |
| | | GGCCAACGGGGGCCTGGTGGAGAAGGAGGTGCTGGCCGCG | |
| | | AGCGACGCAGCCCTTTTGCGCTTCCGGCGCCTGCTGGTGG | |
| | | CTGAGCTGCAGCGTGGCTTCTTTGACAAGCACATCTGGCT | |
| | | CTCCATATGGGACCGGCCGCCTCGTAGCCGTTTCACTCGC | |
| | | ATCCAGAGGGCCACCTGCTGCGTTCTCCTCATCTGCCTCT | |
| | | TCCTGGGCGCCAACGCCGTGTGGTACGGGGCTGTTGGCGA | |
| | | CTCTGCCTACAGCACGGGGCATGTGTCCAGGCTGAGCCCG | |
| | | CTGAGCGTCGACACAGTCGCTGTTGGCCTGGTGTCCAGCG | |
| | | TGGTTGTCTATCCCGTCTACCTGGCCATCCTTTTTCTCTT | |
| | | CCGGATGTCCCGGAGCAAGGTGGCTGGGAGCCCGAGCCCC | |
| | | ACACCTGCCGGGCAGCAGGTGCTGGACATCGACAGCTGCC | |
| | | TGGACTCGTCCGTGCTGGACAGCTCCTTCCTCACGTTCTC | |
| | | AGGCCTCCACGCTGAGGCCTTTGTTGGACAGATGAAGAGT | |
| | | GACTTGTTTCTGGATGATTCTAAGAGTCTGGTGTGCTGGC | |
| | | CCTCCGGCGAGGGAACGCTCAGTTGGCCGGACCTGCTCAG | |
| | | TGACCCGTCCATTGTGGGTAGCAATCTGCGGCAGCTGGCA | |
| | | CGGGGCCAGGCGGGCCATGGGCTGGGCCCAGAGGAGGACG | |
| | | GCTTCTCCCTGGCCAGCCCCTACTCGCCTGCCAAATCCTT | |
| | | CTCAGCATCAGATGAAGACCTGATCCAGCAGGTCCTTGCC | |
| | | GAGGGGGTCAGCAGCCCAGCCCCTACCCAAGACACCCACA | |

TABLE 1-continued

GEP-NEN Biomarker/Houskeeper Sequence Information

| Gene Name | RefSeq Accession | Sequence | SEQ ID NO: |
|---|---|---|---|
| | | TGGAAACGGACCTGCTCAGCAGCCTGTCCAGCACTCCTGG | |
| | | GGAGAAGACAGAGACGCTGGCGCTGCAGAGGCTGGGGGAG | |
| | | CTGGGGCCACCCAGCCCAGGCCTGAACTGGGAACAGCCCC | |
| | | AGGCAGCGAGGCTGTCCAGGACAGGACTGGTGGAGGGTCT | |
| | | GCGGAAGCGCCTGCTGCCGGCCTGGTGTGCCTCCCTGGCC | |
| | | CACGGGCTCAGCCTGCTCCTGGTGGCTGTGGCTGTGGCTG | |
| | | TCTCAGGGTGGGTGGGTGCGAGCTTCCCCCCGGGCGTGAG | |
| | | TGTTGCGTGGCTCCTGTCCAGCAGCGCCAGCTTCCTGGCC | |
| | | TCATTCCTCGGCTGGGAGCCACTGAAGGTCTTGCTGGAAG | |
| | | CCCTGTACTTCTCACTGGTGGCCAAGCGGCTGCACCCGGA | |
| | | TGAAGATGACACCCTGGTAGAGAGCCCGGCTGTGACGCCT | |
| | | GTGAGCGCACGTGTGCCCCGCGTACGGCCACCCCACGGCT | |
| | | TTGCACTCTTCCTGGCCAAGGAAGAAGCCCGCAAGGTCAA | |
| | | GAGGCTACATGGCATGCTGCGGAGCCTCCTGGTGTACATG | |
| | | CTTTTTCTGCTGGTGACCCTGCTGGCCAGCTATGGGGATG | |
| | | CCTCATGCCATGGGCACGCCTACCGTCTGCAAAGCGCCAT | |
| | | CAAGCAGGAGCTGCACAGCCGGGCCTTCCTGGCCATCACG | |
| | | CGGTCTGAGGAGCTCTGGCCATGGATGGCCCACGTGCTGC | |
| | | TGCCCTACGTCCACGGGAACCAGTCCAGCCCAGAGCTGGG | |
| | | GCCCCCACGGCTGCGGCAGGTGCGGCTGCAGGAAGCACTC | |
| | | TACCCAGACCCTCCCGGCCCCAGGGTCCACACGTGCTCGG | |
| | | CCGCAGGAGGCTTCAGCACCAGCGATTACGACGTTGGCTG | |
| | | GGAGAGTCCTCACAATGGCTCGGGACGTGGGCCTATTCA | |
| | | GCGCCGGATCTGCTGGGGGCATGGTCCTGGGGCTCCTGTG | |
| | | CCGTGTATGACAGCGGGGGCTACGTGCAGGAGCTGGGCCT | |
| | | GAGCCTGGAGGAGAGCCGCGACCGGCTGCGCTTCCTGCAG | |
| | | CTGCACAACTGGCTGGACAACAGGAGCCGCGCTGTGTTCC | |
| | | TGGAGCTCACGCGCTACAGCCCGGCCGTGGGGCTGCACGC | |
| | | CGCCGTCACGCTGCGCCTCGAGTTCCCGGCGGCCGGCCGC | |
| | | GCCCTGGCCGCCCTCAGCGTCCGCCCCTTTGCGCTGCGCC | |
| | | GCCTCAGCGCGGGCCTCTCGCTGCCTCTGCTCACCTCGGT | |
| | | GTGCCTGCTGCTGTTCGCCGTGCACTTCGCCGTGGCCGAG | |
| | | GCCCGTACTTGGCACAGGGAAGGGCGCTGGCGCGTGCTGC | |
| | | GGCTCGGAGCCTGGGCGCGGTGGCTGCTGGTGGCGCTGAC | |
| | | GGCGGCCACGGCACTGGTACGCCTCGCCCAGCTGGGTGCC | |
| | | GCTGACCGCCAGTGGACCCGTTTCGTGCGCGGCCGCCCGC | |
| | | GCCGCTTCACTAGCTTCGACCAGGTGGCGCAGCTGAGCTC | |
| | | CGCAGCCCGTGGCCTGGCGGCCTCGCTGCTCTTCCTGCTT | |
| | | TTGGTCAAGGCTGCCCAGCAGCTACGCTTCGTGCGCCAGT | |
| | | GGTCCGTCTTTGGCAAGACATTATGCCGAGCTCTGCCAGA | |
| | | GCTCCTGGGGGTCACCTTGGGCCTGGTGGTGCTCGGGGTA | |
| | | GCCTACGCCCAGCTGGCCATCCTGCTCGTGTCTTCCTGTG | |
| | | TGGACTCCCTCTGGAGCGTGGCCCAGGCCCTGTTGGTGCT | |
| | | GTGCCCTGGGACTGGGCTCTCTACCCTGTGTCCTGCCGAG | |
| | | TCCTGGCACCTGTCACCCCTGCTGTGTGTGGGGCTCTGGG | |
| | | CACTGCGGCTGTGGGGCGCCCTACGGCTGGGGGCTGTTAT | |
| | | TCTCCGCTGGCGCTACCACGCCTTGCGTGGAGAGCTGTAC | |
| | | CGGCCGGCCTGGGAGCCCCAGGACTACGAGATGGTGGAGT | |
| | | TGTTCCTGCGCAGGCTGCGCCTCTGGATGGGCCTCAGCAA | |
| | | GGTCAAGGAGTTCCGCCACAAAGTCCGCTTTGAAGGGATG | |
| | | GAGCCGCTGCCCTCTCGCTCCTCCAGGGGCTCCAAGGTAT | |
| | | CCCCGGATGTGCCCCCACCCAGCGCTGGCTCCGATGCCTC | |
| | | GCACCCCTCCACCTCCTCCAGCCAGCTGGATGGGCTGAGC | |
| | | GTGAGCCTGGCCGGCTGGGGACAAGGTGTGAGCCTGAGC | |
| | | CCTCCCGCCTCCAAGCCGTGTTCGAGGCCCTGCTCACCCA | |
| | | GTTTGACCGACTCAACCAGGCCACAGAGGACGTCTACCAG | |
| | | CTGGAGCAGCAGCTGCACAGCCTGCAAGGCCGCAGGAGCA | |
| | | GCCGGGCGCCCGCCGGATCTTCCCGTGGCCCATCCCCGGG | |
| | | CCTGCGGCCAGCACTGCCCAGCCGCCTTGCCCGGGCCAGT | |
| | | CGGGGTGTGGACCTGGCCACTGGCCCCAGCAGGACACCCC | |
| | | TTCGGGCCAAGAACAAGGTCCACCCCAGCAGCACTTAGTC | |
| | | CTCCTTCCTGGCGGGGTGGGCCGTGGAGTCGGAGTGGAC | |
| | | ACCGCTCAGTATTACTTTCTGCCGCTGTCAAGGCCGAGGG | |
| | | CCAGGCAGAATGGCTGCACGTAGGTTCCCAGAGAGCAGG | |
| | | CAGGGGCATCTGTCTGTCTGTGGGCTTCAGCACTTTAAAG | |
| | | AGGCTGTGTGGCCAACCAGGACCCAGGGTCCCCTCCCCAG | |
| | | CTCCCTTGGGAAGGACACAGCAGTATTGGACGGTTTCTAG | |
| | | CCTCTGAGATGCTAATTTATTTCCCCGAGTCCTCAGGTAC | |
| | | AGCGGGCTGTGCCCGGCCCCACCCCCTGGGCAGATGTCCC | |
| | | CCACTGCTAAGGCTGCTGGCTTCAGGGAGGGTTAGCCTGC | |
| | | ACCGCCGCCACCCCTGCCCCTAAGTTATTACCTCTCCAGTT | |
| | | CCTACCGTACTCCCTGCACCGTCTCACTGTGTGTCTCGTG | |
| | | TCAGTAATTTATATGGTGTTAAAATGTGTATATTTTTGTA | |
| | | TGTCACTATTTTCACTAGGGCTGAGGGGCCTGCGCCCAGA | |
| | | GCTGGCCTCCCCCAACACCTGCTGCGCTTGGTAGGTGTGG | |

TABLE 1-continued

GEP-NEN Biomarker/Houskeeper Sequence Information

| Gene Name | RefSeq Accession | Sequence | SEQ ID NO: |
|---|---|---|---|
| | | TGGCGTTATGGCAGCCCGGCTGCTGCTTGGATGCGAGCTT<br>GGCCTTGGGCCGGTGCTGGGGGCACAGCTGTCTGCCAGGC<br>ACTCTCATCACCCCAGAGGCCTTGTCATCCTCCCTTGCCC<br>CAGGCCAGGTAGCAAGAGAGCAGCGCCCAGGCCTGCTGGC<br>ATCAGGTCTGGGCAAGTAGCAGGACTAGGCATGTCAGAGG<br>ACCCCAGGGTGGTTAGAGGAAAAGACTCCTCCTGGGGGCT<br>GGCTCCCAGGGTGGAGGAAGGTGACTGTGTGTGTGTGT<br>GTGCGCGCGCACGCGCGAGTGTGCTGTATGGCCCAGGC<br>AGCCTCAAGGCCCTCGGAGCTGGCTGTGCCTGCTTCTGTG<br>TACCACTTCTGTGGGCATGGCCGCTTCTAGAGCCTCGACA<br>CCCCCCCAACCCCCGCACCAAGCAGACAAAGTCAATAAAA<br>GAGCTGTCTGACTGC | |
| PLD3 | NM_001031696.3 | GCATCCTCTCACCGCCGGAAGCTGAACTGACTCGTCCGCG<br>GCCGCTCTACCCCAACAGGCCGCCACCAGCGAGAGTGCGG<br>CCATAACCATCACGTGACCGCCCACCGACACCAGCGAGAG<br>TGCAGTCGTAACCGTCACGTGACCGCCCACCGTCGGCCCG<br>GCGCTCCCCTCCGCCCGAAGCTAGCAAGCGGCGCGGCCAA<br>TGAGAAAGGCGCATGCCTGGCCCCCGCCGGCCTGCAGTCT<br>AGCCGTAGTGCGCCTGCGCGCGGCTAGGAGGGGCCGTCAG<br>GCGGGGATACAGCCTGGAAGGTAATGCATGTCCATGGTAC<br>ACAAATTCACAAGTTTGGAGACCCTGACACACCCACCTTC<br>TCACCTGGGCTCTGCGTATCCCCCAGCCTTGAGGGAAGAT<br>GAAGCCTAAACTGATGTACCAGGAGCTGAAGGTGCCTGCA<br>GAGGAGCCCGCCAATGAGCTGCCCATGAATGAGATTGAGG<br>CGTGGAAGGCTGCGGAAAAGAAAGCCCGCTGGGTCCTGCT<br>GGTCCTCATTCTGGCGGTTGTGGGCTTCGGAGCCCTGATG<br>ACTCAGCTGTTTCTATGGGAATACGGCGACTTGCATCTCT<br>TTGGGCCCAACCAGCGCCCAGCCCCTGCTATGACCCTTG<br>CGAAGCAGTGCTGGTGGAAAGCATTCCTGAGGGCCTGGAC<br>TTCCCCAATGCCTCCACGGGGAACCCTTCCACCAGCCAGG<br>CCTGGCTGGGCCTGCTCGCCGGTGCGCACAGCAGCCTGGA<br>CATCGCCTCCTTCTACTGG<u>ACCCTCACCAACAATGACACC<br>CACACGCAGGAGCCCTCTGCCCAGCAGGGTGAGGAGGTCC<br>TCCGGCAGCTGCAGACCCTGGCACCAAAGGGCGTGAACGT<br>CCG</u>CATCGCTGTGAGCAAGCCCAGCGGGCCCCAGCCACAG<br>GCGGACCTGCAGGCTCTGCTGCAGAGCGGTGCCCAGGTCC<br>GCATGGTGGACATGCAGAAGCTGACCCATGGCGTCCTGCA<br>TACCAAGTTCTGGGTGGTGGACCAGACCCACTTCTACCTG<br>GGCAGTGCCAACATGGACTGGCGTTCACTGACCCAGGTCA<br>AGGAGCTGGGCGTGGTCATGTACAACTGCAGCTGCCTGGC<br>TCGAGACCTGACCAAGATCTTTGAGGCCTACTGGTTCCTG<br>GGCCAGGCAGGCAGCTCCATCCCATCAACTTGGCCCCGGT<br>TCTATGACACCCGCTACAACCAAGAGACACCAATGGAGAT<br>CTGCCTCAATGGAACCCCTGCTCTGGCCTACCTGGCGAGT<br>GCGCCCCCACCCCTGTGTCCAAGTGGCCGCACTCCAGACC<br>TGAAGGCTCTACTCAACGTGGTGGACAATGCCCGGAGTTT<br>CATCTACGTCGCTGTCATGAACTACCTGCCCACTCTGGAG<br>TTCTCCCACCCTCACAGGTTCTGGCCTGCCATTGACGATG<br>GGCTGCGGCGGGCCACCTACGAGCGTGGCGTCAAGGTGCG<br>CCTGCTCATCAGCTGCTGGGGACACTCGGAGCCATCCATG<br>CGGGGCCTTCCTGCTCTCTCTGGCTGCCCTGCGTGACAACC<br>ATACCCACTCTGACATCCAGGTGAAACTCTTTGTGGTCCC<br>CGCGGATGAGGCCCAGGCTCGAATCCCATATGCCCGTGTC<br>AACCACAACAAGTACATGGTGACTGAACGCGCCACCTACA<br>TCGGAACCTCCAACTGGTCTGGCAACTACTTCACGGAGAC<br>GGCGGGCACCTCGCTGCTGGTGACGCAGAATGGGAGGGGC<br>GGCCTGCGGAGCCAGCTGGAGGCCATTTTCCTGAGGGACT<br>GGGACTCCCCTTACAGCCATGACCTTGACACCTCAGCTGA<br>CAGCGTGGGCAACGCCTGCCGCCTGCTCTGAGGCCCGATC<br>CAGTGGGCAGGCCAAGGCCTGCTGGGCCCCCGCGGACCCA<br>GGTGCTCTGGGTCACGGTCCCTGTCCCCGCGCCCCCGCTT<br>CTGTCTGCCCCATTGTGGCTCCTCAGGCTCTCTCCCCTGC<br>TCTCCCACCCTCTACCTCCACCCCCACCGGCCTGACGCTGT<br>GGCCCCGGGACCCAGCAGAGCTGGGGAGGGATCAGCCCC<br>CAAAGAAATGGGGGTGCATGCTGGGCCTGGCCCCCTGGCC<br>CACCCCACTTTCCAGGGCAAAAAGGGCCCAGGGTTATAA<br>TAAGTAAATAACTTGTCTGTACAGCCTGGAAAAAAAAAA<br>AAAAAAA | 30 |
| PNMA2 | NM_007257.5 | GAGCGGTGCTCAGGGGAGGGCTGGAGGGGAGGGAAGGAGA<br>GAGAGAGGGGAGGGCGGCACCGCCCCTAGCCCCGCGCTCC<br>GGAAGTGAAGCGGCCAGACCACCAGCTAATGGATGCGGAG<br>CGGAGGGCCCGCTGACCGCTCTCCGCGCCTGGAGCAGCTT<br>GGCTTGGCTGGAGCTAAGAGCCAGACACACCACTGTGTGG | 31 |

TABLE 1-continued

GEP-NEN Biomarker/Houskeeper Sequence Information

| Gene Name | RefSeq Accession | Sequence | SEQ ID NO: |
|---|---|---|---|
| | | AGGTGGGTGATGTCTTCCTGTGCTAAAAGGTGAATAAATA<br>AGCTCCTCACCTCTCGCGGAACACTCGGGAACACATCAAC<br>AGGGGTCCAAGCCGCCCTGCTGGGAGGCTTCTCTTCAAGA<br>GTTCTGGGTCCCAGAGTGGAAGGCATTTTCCCATCAACTG<br>GAGAGAGACGAAACATCAGAGACCAGGAGGCTGTGGAGAA<br>AGCAGCTGTCCCAGGTGCCTCAACTATCAGAGAAGGGTCA<br>GCGTCACGTGGCTGCCAGCATCTTTGAGAAAATCACTGGC<br>AATCGGACTTCAGAGCTGCGGGCACAGGTGTGGTTAGAAC<br>TGAGATACGACCTGCCCACCTGGGTCAGGCCTAAAGACAA<br>GAAGTCCTGAGTTCTTGCCACTGAGTAGGCCAGGGTCATT<br>TGTCCAGAAAACTTTGTGACTGTCTTTGAGTGACCTAGTC<br>TGGGACCCATTCATTGGTGGGTTCTAAGGTTAGAAGCTCA<br>TCCAGGATATTTTCAATATTAAGTCAGTGCATAGCTGCAC<br>CACTAACAAATTGGTGCCTGTAGAGTCAGAGTGGGTCAAT<br>TCTTAGGACAATGGCGCTGGCACTGTTAGAGGACTGGTGC<br>AGGATAATGAGTGTGGATGAGCAGAAGTCACTGATGGTTA<br>CGGGGATACCGGCGGACTTTGAGGAGGCTGAGATTCAGGA<br>GGTCCTTCAGGAGACTTTAAAGTCTCTGGGCAGGTATAGA<br>CTGCTTGGCAAGATATTCCGGAAGCAGGAGAATGCCAATG<br>CTGTCTTACTAGAGCTTCTGGAAGATACTGATGTCTCGGC<br>CATTCCCAGTGAGGTCCAGGGAAAGGGGGGTGTCTGGAAG<br>GTGATCTTTAAGACCCCTAATCAGGACACTGAGTTTCTTG<br>AAAGATTGAACCTGTTTCTAGAAAAAGAGGGGCAGACGGT<br>CTCGGGTATGTTTCGAGCCCTGGGGCAGGAGGGCGTGTCT<br>CCAGCCACAGTGCCCTGCATCTCACCAGAATTACTGGCCC<br>ATTTGTTGGGACAGGCAATGGCACATGCGCCTCAGCCCCT<br>GCTACCCATGAGATACCGGAAACTGCGAGTATTCTCAGGG<br>AGTGCTGTCCCAGCCCCAGAGGAAGAGTCCTTTGAGGTCT<br>GGTTGGAACAGGCCACGGAGATAGTCAAAGAGTGGCCAGT<br>AACAGAGGCAGAAAAGAAAAGGTGGCTGGCGGAAAGCCTG<br>CGGGGCCCTGCCCTGGACCTCATGCACATAGTGCAGGCAG<br>ACAACCCGTCCATCAGTGTAGAAGAGTGTTTGGAGGCCTT<br>TAAGCAAGTGTTTGGGAGCCTAGAGAGCCGCAGGACAGCC<br>CAGGTGAGGTATCTGAAGACCTATCAGGAGGAAGGAGAGA<br>AGGTCTCAGCCTATGTGTTACGGCTAGAAACCCTGCTCCG<br>GAGAGCGGTGGAGAAACGCGCCATCCCTCGGCGTATTGCG<br>GACCAGGTCCGCCTGGAGCAGGTCATGGCTGGGGCCACTC<br>TTAACCAGATGCTGTGGTGCCGGCTTAGGGAGCTGAAGGA<br>TCAGGGCCCGCCCCCCAGCTTCCTTGAGCTAATGAAGGTA<br>ATACGGGAAGAAGAGGAGGAAGAGGCCTCCTTTGAGAATG<br>AGAGTATCGAAGAGCCAGAGGAACGAGATGGCTATGGCCG<br>CTGGAATCATGAGGGAGACGACTGAAAACCACCTGGGGGC<br>AGGACCCACAGCCAGTGGGCTAAGACCTTTAAAAAATTTT<br>TTTCTTTAATGTATGGGACTGAAATCAAACCATGAAAGCC<br>AATTATTGACCTTCCTTCCTTCCTTCCTTCCCTCCCTTCC<br>TCCTTCTCTCCTTCTCTCCTCCTCTCTCCTCTCCTCTCCT<br>CTCTTTCCTTCCTTCCTTCCTTTTTTCTTTTTCTCTTTCT<br>TCTTTATTTCTTGGGTCTCACTCTCATCACCCAGGCTAGA<br>GTGCAGTGGCACAAAAATCTCGGCTCACTGCAGCCTTGAC<br>TTCCCAGGCTCAGGCTCAGGTGATCCTCACACCTTAGCCT<br>CCCAAGTACCTGGGACTACAGGCACGCACCACCATGCCTA<br>GCTATTCTTTTGTATTTTTGGTAGAGACAGGGTTTTGCTG<br>TGTTGCTCAGGCTGGTCTGGAACCCCTAGGCTCAAATGAT<br>GTGCCCAACTCGGCCTCCCAAAGTGCTGGGATTACAGGCA<br>TGAACCGCCATGCCTGGCCCTTGATTTTTCTTTTTAAGAA<br>AAAAATATCTAGGAGTTTCTTAGACCCTATGTAGATTATT<br>AATGAACAAAAGATTAAACTCCAAATATTAAATAGTAAGC<br>CTGAAGGAATCTGAAACACTTGTACTTCCAATTTTCTTTA<br>AATAATCCCAATAGACCAGAATTGGCCCATACCATAGAA<br>GAAAGAATTGGCAGTCAAAAAAAAAAATACCTTTTGTAAT<br>GTTTGAAAAATAAAGCTGTTTGACTTGTCAGGTGTTTTCC<br>TTTCTCAAATCAGCAAATTCTCTCTGAGTGCCTGGCTTTG<br>TGAGACACTGTACAAGGAGTTACAAGACTACAGCTATAAC<br>CTGCAGTTGAGCAGTTATAAACCTACAAAATGGGCCCTGC<br>CCTCAGAGAGGTTCCAGTCTAGATGAGGAGCTGATCTAGA<br>CAGGTAAAGGCTAACTAACCCTTTGTGTAAATAAGTTCA<br>TCACCCCAGTAAAGTGTCATCACCCAGTGAATAGGACCA<br>CCTCTGCCTGCAGATTTTGTTGTTGTTGTTGTCATTGTT<br>GTTGTTGTTTAACCTGGGAAGTGTTCTTCCTGCCTTTCT<br>GCTAGGTGTCAGATAGATGGTCCCAGAGCTAGGTGCTGTG<br>TCAGGCCCTGAAGACACAGATGACTCAACCTAAGCTTTAC<br>TTTCCAGAGGTCCACAGCCTGAGAGGTGTCCCCAAAGAAA<br>GGGGACATGAGGGGACTGCATGCTTGAGAGCAGGGTTGT<br>TTAGGGCAGGTTTGGATTTAGTGAGCAGGCTGGTTTGCTT<br>AGAGAAGGCTTTTAGTGGCAACAAAGGATGAAGAGGAGAG | |

TABLE 1-continued

GEP-NEN Biomarker/Houskeeper Sequence Information

| Gene Name | RefSeq Accession | Sequence | SEQ ID NO: |
|---|---|---|---|
| | | AAAAGGAACTCACATTTATTGAGGGCCTACTGTGTGCAAA GTGTTTCATGTATATCTCATTGAATGTATACAGCCACCCT GTTGTGGTATAATTTTGCTCTTTATAAAGAGAAAGACCGA AGCTCAGATGAGTTAAGTGGTCTCCTCAACACCAAAATGC CAAGAAGTGATGGAGCCTAGACAGAAGCCCAGAACTTTCT GACTCACACTAGTCCATCCTCTACCATCACGATGACTTTC AAATTGTGCTCTGCAGTTCTGCAGATTTTCTAGCAGTGCC ATCTCCAAAATGTGTTTTAAACTCTTTATTTTTTTAATTA TTATTAGTATTATTTTGAGACTGAGTCTTGCTCTATCACC CAGGCTGGAGTGCAGTGGTGCAATCTCAGCTCACTGCAAC CTCCGCCTCCCAGGTTCAAGCGATTTCGTGCCTCAGCCTC CCGAGTAGCTGGGATTACAGGCACCCACCACCACGCCCAG CTAATTTTTGTATTTTTAGTAGAAATGGGGTTTCACCATG TTGGCCAGGCTGGTCTCGAACTCCTGACCTCAAGTGATCC ACTCACCTCGGCCTCCCAAAGTGCTGGGATTACAGGTGTG AGCCACCATGCCTGGGCTAAACTCTTTAAGTCTCTAGTAA ATGCAGCTAGATTCAAATGGGCTGATAACCAAATTTTAAC ACATCAGCATTCACCACCAGGTTTACTTTTATTTTCAGAT TGGCTCATTTTGTGCAGACCTTAGAGCAAAGTTTCCTTTA TGGTATCTGTGTACGTATCCAAACTTCTTTTAATTGTTCA CAGATTTTAAAAGCGGTAGCACCACATGGTTGTGTAGATC AGACCTGTGTATTTAGATCAGACCTGTGTATCACGTAAGT GTGTGAGTGCAGTGCAGATGAGCACCATTTAGTTATATGT GCTAGGCAAATCTCCAACACAGTTGATGTGTAGTCTTGTG GTAGATTTGTGCATACTGTAAGCAAATTGCTTAGCTTCTC TAGACATCAGTTTCCACATCTGAAAAATAAGAAGATGAGA GTACACGGTTGTTATGAACAAATGACTTAATGCTTTTTAA GCACGTTGCATGACATCTGGAACACAGAAAGCCCTCAATA CATTGAAGCTCTTAGGATTTTCACGATGTTCCTGTCTGCT CAATGCATGCTTTCTTTATTGTTCTGACAGTTGTGTGGTA ACAAGCTAATATGCTTCCAGTTGACTTCCAGTCTACCCTG GTGTTAGAAACCGTTTCATCTCTTATTGTAAATTTGAGTG CTTGTTGTTTTTTATATTTGTGATGACTCTTCCAGCAGTT GTTGACAATTGTTAGAGGTTTGACTTTTAAATAATTACTT ATTTTTTCTGATTGTGGTTCAGTTTAACTGAAGAATATCC TGAGATTGTAAGAAAAGCATTTTTTAAAAGGTATCACTTG TGATCATTTATCTTTCTAAATTCTATTTTTAATACTGTTC CACCAAAGTGATGCAGTGGTTACCATGACACCCTAATTTC ATGTGTTTTTGTATTTATGAAAATAGTTTCATTGTCATTT ATTGGCGGTATACAAAGTAAAATGTTATAAATGTGAAGTT ATAAAATAAATATGCTAATAAAATCCTGAGTTTTTCTG TTTCCT | |
| PQBP1 | NM_001032381.1 | TGCCTCCTGAGCGTAGTCCAGTTACTTTCAGGCTCGGGGA GTGAAGGCCTCGTTGAGAGAAGGTCTCATTCGGTGTTTTG GGAAGAGAGTCGTGTGGGCCCAGGTCTGTCTGCTATCAGC TATGCCGCTGCCCGTTGCGCTGCAGACCCGCTTGGC<u>CAAG AGAGGCATCCTCAAACATCTGGAGCCTGAACCAGAGGAAG AGATCATTGCCGAGGACTATGACGATGATCCTGTGGACTA</u> CGAGGCCACCAGGTTGGAGGGCCTACCACCAAGCTGGTAC AAGGTGTTCGACCCTTCCTGCGGGCTCCCTTACTACTGGA ATGCAGACACAGACCTTGTATCCTGGCTCTCCCCACATGA CCCCAACTCCGTGGTTACCAAATCGGCCAAGAAGCTCAGA AGCAGTAATGCAGATGCTGAAGAAAAGTTGGACCGGAGCC ATGACAAGTCGGACAGGGGCCATGACAAGTCGGACCGCAG CCATGAGAAACTAGACAGGGGCCACGACAAGTCAGACCGG GGCCACGACAAGTCTGACAGGGATCGAGAGCGTGGCTATG ACAAGGTAGACAGAGAGAGAGAGCGAGACAGGGAACGGGA TCGGGACCGCGGGTATGACAAGGCAGACCGGGAAGAGGGC AAAGAACGGCGCCACCATCGCCGGGAGGAGCTGGCTCCCT ATCCCAAGAGCAAGAAGGCAGTAAGCCGAAAGGATGAAGA GTTAGACCCCATGGACCCTAGCTCATACTCAGACGCCCCC CGGGGCACGTGGTCAACAGGACTCCCCAAGCGGAATGAGG CCAAGACTGGCGCTGACACCACAGCAGCTGGGCCCCTCTT CCAGCAGCGGCCGTATCCATCCCCAGGGGCTGTGCTCCGG GCCAATGCAGAGGCCTCCCGAACCAAGCAGCAGGATTGAA GCTTCGGCCTCCCTGGCCCTGGGTTAAAATAAAAGCTTTC TGGTGATCCTGCCCACCAAAAAAAAAAAAAAAAAAAAAAA AAAAAAAAAAAAA | 32 |
| RAF1 | NM_002880.3 | AGAATCGGAGAGCCGGTGGCGTCGCAGGTCGGGAGGACGA GCACCGAGTCGAGGGCTCGCTCGTCTGGGCCGCCCGAGAG TCTTAATCGCGGGCGCTTGGGCCGCCATCTTAGATGGCGG GAGTAAGAGGAAAACGATTGTGAGGCGGGAACGGCTTTCT GCTGCCTTTTTTGGGCCCCGAAAAGGGTCAGCTGGCCGGG | 33 |

TABLE 1-continued

GEP-NEN Biomarker/Houskeeper Sequence Information

| Gene Name | RefSeq Accession | Sequence | SEQ ID NO: |
|---|---|---|---|
| | | CTTTGGGGCGCGTGCCCTGAGGCGCGGAGCGCGTTTGCTA<br>CGATGCGGGGCTGCTCGGGGCTCCGTCCCTGGGCTGGG<br>GACGCGCCGAATGTGACCGCCTCCCGCTCCCTCACCCGCC<br>GCGGGGAGGAGGAGCGGGCGAGAAGCTGCCGCCGAACGAC<br>AGGACGTTGGGGCGGCCTGGCTCCCTCAGGTTTAAGAATT<br>GTTTAAGCTGCATCAATGGAGCACATACAGGGAGCTTGGA<br>AGACGATCAGCAATGGTTTTGGATTCAAAGATGCCGTGTT<br>TGATGGCTCCAGCTGCATCTCTCCTACAATAGTTCAGCAG<br>TTTGGCTATCAGCGCCGGGCATCAGATGATGGCAAACTCA<br>CAGATCCTTCTAAGACAAGCAACACTATCCGTGTTTTCTT<br>GCCGAACAAGCAAAGAACAGTGGTCAATGTGCGAAATGGA<br>ATGAGCTTGCATGACTGCCTTATGAAAGCACTCAAGGTGA<br>GGGGCCTGCAACCAGAGTGCTGTGCAGTGTTCAGACTTCT<br>CCACGAACACAAAGGTAAAAAAGCACGCTTAGATTGGAAT<br>ACTGATGCTGCGTCTTTGATTGGAGAAGAACTTCAAGTAG<br>ATTTCCTGGATCATGTTCCCCTCACAACACACAACTTTGC<br>TCGGAAGACGTTCCTGAAGCTTGCCTTCTGTGACATCTGT<br>CAGAAATTCCTGCTCAATGGATTTCGATGTCAGACTTGTG<br>GCTACAAATTTCATGAGCACTGTAGCACCAAAGTACCTAC<br>TATGTGTGGACTGGAGTAACATCAGACAACTCTTATTG<br>TTTCCAAATTCCACTATTGGTGATAGTGGAGTCCCAGCAC<br>TACCTTCTTTGACTATGCGTCGTATGCGAGAGTCTGTTTC<br>CAGGATGCCTGTTAGTTCTCAGCACAGATATTCTACACCT<br>CACGCCTTCACCTTTAACACCTCCAGTCCCTCATCTGAAG<br>GTTCCCTCTCCCAGAGGCAGAGGT<u>CGACATCCACACCTAA</u><br><u>TGTCCACATGGTCAGCACCACCCTGCCTGTGGACAGCAGG</u><br><u>ATGATTGAGGATGCAATTCGAAGTCACAGCGAATCAGCCT</u><br>CACCTTCAGCCCTGTCCAGTAGCCCCAACAATCTGAGCCC<br>AACAGGCTGGTCACAGCCGAAAACCCCCGTGCCAGCACAA<br>AGAGAGCGGGCACCAGTATCTGGGACCCAGGAGAAAAACA<br>AAATTAGGCCTCGTGGACAGAGAGATTCAAGCTATTATTG<br>GGAAATAGAAGCCAGTGAAGTGATGCTGTCCACTCGGATT<br>GGGTCAGGCTCTTTTGGAACTGTTTATAAGGGTAAATGGC<br>ACGGAGATGTTGCAGTAAAGATCCTAAAGGTTGTCGACCC<br>AACCCCAGAGCAATTCCAGGCCTTCAGGAATGAGGTGGCT<br>GTTCTGCGCAAAACACGGCATGTGAACATTCTGCTTTTCA<br>TGGGGTACATGACAAAGGACAACCTGGCAATTGTGACCCA<br>GTGGTGCGAGGGCAGCAGCCTCTACAAACACCTGCATGTC<br>CAGGAGACCAAGTTTCAGATGTTCCAGCTAATTGACATTG<br>CCCGGCAGACGGCTCAGGGAATGGACTATTTGCATGCAAA<br>GAACATCATCCATAGAGACATGAAATCCAACAATATATTT<br>CTCCATGAAGGCTTAACAGTGAAAATTGGAGATTTTGGTT<br>TGGCAACAGTAAAGTCACGCTGGAGTGGTTCTCAGCAGGT<br>TGAACAACCTACTGGCTCTGTCCTCTGGATGGCCCCAGAG<br>GTGATCCGAATGCAGGATAACAACCCATTCAGTTTCCAGT<br>CGGATGTCTACTCCTATGGCATCGTATTGTATGAACTGAT<br>GACGGGGGAGCTTCCTTATTCTCACATCAACAACCGAGAT<br>CAGATCATCTTCATGGTGGGCCGAGGATATGCCTCCCCAG<br>ATCTTAGTAAGCTATATAAGAACTGCCCCAAAGCAATGAA<br>GAGGCTGGTAGCTGACTGTGTGAAGAAAGTAAAGGAAGAG<br>AGGCCTCTTTTTCCCCAGATCCTGTCTTCCATTGAGCTGC<br>TCCAACACTCTCTACCGAAGATCAACCGGAGCGCTTCCGA<br>GCCATCCTTGCATCGGGCAGCCCACACTGAGGATATCAAT<br>GCTTGCACGCTGACCACGTCCCCGAGGCTGCCTGTCTTCT<br>AGTTGACTTTGCACCTGTCTTCAGGCTGCCAGGGGAGGAG<br>GAGAAGCCAGCAGGCACCACTTTTCTGCTCCCTTTCTCCA<br>GAGGCAGAACACATGTTTTCAGAGAAGCTGCTGCTAAGGA<br>CCTTCTAGACTGCTCACAGGGCCTTAACTTCATGTTGCCT<br>TCTTTTCTATCCCTTTGGGCCCTGGGAGAAGGAAGCCATT<br>TGCAGTGCTGGTGTGTCCTGCTCCCTCCCCACATTCCCCA<br>TGCTCAAGGCCCAGCCTTCTGTAGATGCGCAAGTGGATGT<br>TGATGGTAGTACAAAAAGCAGGGGCCCAGCCCCAGCTGTT<br>GGCTACATGAGTATTTAGAGGAAGTAAGGTAGCAGGCAGT<br>CCAGCCCTGATGTGGAGACACATGGGATTTTGGAAATCAG<br>CTTCTGGAGGAATGCATGTCACAGGCGGGACTTTCTTCAG<br>AGAGTGGTGCAGCGCCAGACATTTTGCACATAAGGCACCA<br>AACAGCCCAGGACTGCCGAGACTCTGGCCGCCCGAAGGAG<br>CCTGCTTTGGTACTATGGAACTTTTCTTAGGGGACACGTC<br>CTCCTTTCACAGCTTCTAAGGTGTCCAGTGCATTGGGATG<br>GTTTTCCAGGCAAGGCACTCGGCCAATCCGCATCTCAGCC<br>CTCTCAGGGAGCAGTCTTCCATCATGCTGAATTTTGTCTT<br>CCAGGAGCTGCCCCTATGGGGCGGGGCCGCAGGGCCAGCC<br>TTGTTTCTCTAACAAACAAACAAACAAACAGCCTTGTTTC<br>TCTAGTCACATCATGTGTATACAAGGAAGCCAGGAATACA<br>GGTTTTCTTGATGATTTGGGTTTTAATTTTGTTTTTATTG | |

TABLE 1-continued

GEP-NEN Biomarker/Houskeeper Sequence Information

| Gene Name | RefSeq Accession | Sequence | SEQ ID NO: |
|---|---|---|---|
| | | CACCTGACAAAATACAGTTATCTGATGGTCCCTCAATTAT GTTATTTTAATAAAATAAATTAAATTTAGGTGTAAAAAAA AAAAAAAAAA | |
| RNF41 | NM_001242826.1 | GATGTCCCAGGGGTATTGGGCGGGGGGTTGAAATAACTG GGGTTCAGGAGGAGGGATGGTGGTAGAGATAAAAATGTGA GAAGGGAGCAGCACTGGCGAGGAGTCGGGAGAGTACTCCT GATTGTGACATCACATTCATCCCCTGGGCGATGGAGCTTG TCACTGGGAAGGAATACTCAGTCGGAGAATAGCCAACAAG ATGGGTTACTGGGAGAATCTCTTCAGTGGCACTGAGTGGA GGCATCAGGGGGTTGGAGCCTTGT<u>GAACAGGGAACCTGCC CCCCAACACTTGGAAGGACCTGGGTTTCAGTGATGAGACA TGGGGTATGATGTAAC</u>CCGTTTCCAGGGGGATGTTGACGA AGATCTTATCTGCCCTATTTGCAGTGGAGTCTTGGAGGAG CCAGTACAGGCACCTCATTGTGAACATGCTTTCTGCAACG CCTGCATCACCCAGTGGTTCTCTCAGCAACAGACATGTCC AGTGGACCGTAGTGTTGTGACGGTCGCCCATCTGCGCCCA GTACCTCGGATCATGCGGAACATGTTGTCAAAGCTGCAGA TTGCCTGTGACAACGCTGTGTTCGGCTGTAGTGCCGTTGT CCGGCTTGACAACCTCATGTCTCACCTCAGCGACTGTGAG CACAACCCGAAGCGGCCTGTGACCTGTGAACAGGGCTGTG GCCTGGAGATGCCCAAAGATGAGCTGCCCAACCATAACTG CATTAAGCACCTGCGCTCAGTGGTACAGCAGCAGCAGACA CGCATCGCAGAGCTGGAGAAGACGTCAGCTGAACACAAAC ACCAGCTGGCGGAGCAGAAGCGAGACATCCAGCTGCTAAA GGCATACATGCGTGCAATCCGCAGTGTCAACCCCAACCTT CAGAACCTGGAGGAGACAATTGAATACAACGAGATCCTAG AGTGGGTGAACTCCCTTCAGCCAGCAAGAGTGACCCGCTG GGGAGGGATGATCTCGACTCCTGATGCTGTGCTCCAGGCT GTAATCAAGCGCTCCCTGGTGGAGAGTGGCTGTCCTGCTT CTATTGTCAACGAGCTGATTGAAAATGCCCACGAGCGTAG CTGGCCCCAGGGTCTGGCCACACTAGAGACTAGACAGATG AACCGACGCTACTATGAGAACTACGTGGCCAAGCGCATCC CTGGCAAGCAGGCTGTTGTCGTGATGGCCTGTGAGAACCA GCACATGGGGGATGACATGGTGCAAGAGCCAGGCCTTGTC ATGATATTTGCGCATGGCGTGGAAGAGATATAAGAGAACT CGACTGGCTATCAGGAAGAGATGGAAATCAGAAAATCCCA TCACTCCAGCAGCTGGGACCTGAGTCCTACCCACCATTCT TAATACTGTGGCTTATACCTGAGCCACACATCTCCCTGCC CTTCTGGCACTGAAGGGCCTTGGGGTAGTTTGCTCAGCCT TTCAGGTGGGAAACCCAGATTTCCTCCCTTTGCCATATTC CCCTAAAATGTCTATAAATTATCAGTCTGGGTGGGAAAGC CCCCACCTCCATCCATTTTCCTGCTTAGGGTCCCTGGTTC CAGTTATTTTCAGAAAGCACAAAGAGATTCAATTTCCCTG GAGGATCAGGACAGAGGAAGGAATCTCTAATCGTCCCTCT CCTCCAAAACCAGGGAATCAGAGCAGTCAGGCCTGTTGAC TCTAAGCAGCAGACATCCTGAAGAAATGGTAAGGGTGGAG CCAAATCTCTAGAAATAAGTAGTGAGGCCGTTAATTGGCC ATCACTGATGGCCCTTAGGGAAAGACTGGACCTCTGTGCC AAGCAGTATCCCTGTTCAGCCCACCTTAAAGGTGTAGGCA CCCACTGGGTCTACCAGTATGCAGGTTGGGATACTGAAAA TTTCCAGATGAGCTCTTCTTTCCTACAAGTTTTCATAATT AGGGAATGCCAGGGTTTAGGGTAGGGGTTAATCTGTTGGG GGTTGATGTGTTTAGCAAGAAGCTACTCCTAGCTTTTGCT AAAAATATGGTTGGCACTGCCTCTTGTGGCACAGGCCATAA TTGTTCCATAGACCCCTCTCTAGCCCTGTGACTGTAGTTA GTTACTTTGATAATTTTCTTTGGCCATTGTTTGTTTATAT TCACAAACTCCACCTACTGCCCCCCCCCCTCTTTTTTTT AAGAATGGCCTGATCATGGCTATCTCAGCCACATTGTTGG CAATTTAATTTATTTACTTCCTTTTTTTTTTTTTAAGAAA GGAAAAAAGAAAAAAAAATCAAACTTGAAACTTTTCTTTT GATGTTCCTATTGTGGGGGTTCTGGATAGGGTGGGACAGG GATGGGGGTGTGTTTATATTTTTTCCTTTTCAGCACAAC CTTTGGCTTTAATATAGGAAGAGCCAAGGGAGTCCTCGGC TGAACTTACGATATCTGCCCCAAACCTCTGTAACCCCAAC TGAAATGAGGAGCTTCCTCTCTTCCTGTGAAGGATATGAC AGTCCAGCATCGATGCCTGTGCCCTCTGGAAAAATTTCCT CCTAGCCCTTCCAGGGCCTTATCATAAAACTCTGGATTTA GAGTATTCATTTTGAAGGCAACTCCCCCTTCCCCAAGTTT CCTTGGAGCTGTATAGCTGGGTTCTAAGCTTCACCATGCA AATCAGAAATTTTATCTCTAAGTACAGGCTGTGCCGTGTC TCACCCACACCCCCTGGGGACTTCAGTTCCATTTCAGGT TACCTGGGGTATACCTTGATCCCTAGAGTGACTGGCAGAG TAAGAGAAGGGGAGAGATAATAGGTGTGATTATTTTAATA TGGAGGTGGGAGTGTGGTTGGAGATAGAAAGGCTCCTCCC | 34 |

TABLE 1-continued

GEP-NEN Biomarker/Houskeeper Sequence Information

| Gene Name | RefSeq Accession | Sequence | SEQ ID NO: |
|---|---|---|---|
| | | CACCATGTAATGGCTTCCTCTCAGAATTTTATTCCAGGCT<br>AGCTTGCTGCAGGTCTGGGTAGTTGGATCATGGCTCCACT<br>GGGATTGGGGTGGAAAGCTTGAGGGGAGTAGGGTTCCAGC<br>TCTGGGACATTGTGCTCAGGAATTTGAAAACGCTGCTATA<br>CTTACTCTGGTTACTACATTTCTTCCACTCCCCTTTCCCC<br>TACCTGCCTTAACCAAGGCTCATACTGTCCTGTCCTTACC<br>CTCAGATGGAGCCAGGAAGCTCAGTGAAAGGCTTCCCTAC<br>CCTTTGCACTAGTGTCTCTGCAGGTTGCTGGTTGTGTTGT<br>ATGTGCTGTTCCATGGTGTTGACTGCACTAATAATAAACC<br>TTTTACTCAACTCTCTAAATTCTTCAGCATTACTCCCTTT<br>CTTGAGAAGGTTTCCCCTCTGCTTTTGCCTTTCTCTCACC<br>TTAATTCCCTTTCTTCCTTACTTTGTTACCTACCCTTATC<br>TTAGTGCTAACTTCTCTTTCAGGAGGATGTCTGGGAGTAG<br>TGTGCACTTCACAGCTGCTTTCCCATGTACCCTCCTGCAT<br>TCTTCCCTCCTATCTCCTGTTCTGTAGCAGCCAAAGCTCT<br>CTAGTGATCTGAACTGTGTGCTTCCCAGGGTCTGCCTTTA<br>TCCTAAATTCCATGTCTTCCCTGAGTGGTCCTGAGTTTTT<br>GGGATAATTTCTACAGAAGATATGTATATATCTTTTTCCT<br>TTGTCCCACAAGCAACTTTGCTTTAGAATCTAGAATTCCT<br>TTGCAGGCAGAGAAGTCTCTACCTCCCAGTGTTTCCTAGC<br>TAAGAACGTAAATGTGAGGAGGGAAATGTACTTGCAGAGG<br>TTTCATAATTATTTACTTATAAAAATAGTCTTCATAGCCG<br>GGCGCGGTGGCTCACGCCTGTAATCCCAGCACTTTGGGAG<br>GCCGAGGTGGGTGGATCACAAGGTCAGGAGTTCGAGACCA<br>TCCTGGCTAACACAGTGAAACCCCGTCTCTACTAAAAATA<br>CAAAAAATTAGCCGGGCGTGGTGGCAGGCACCTGTAGTCC<br>CAGCTACTTAGGAGGCTGAGGCAGGAGAATGGCGTGAACC<br>CGGGAGGCAGAGCTTGCAGTGAGCAGAGATTGGGCCACTG<br>CATTCCAGCCTGGGCGACAGAGCAAGGCTCCGTCTAAAAA<br>AAAAAAAAAAAAAAAAGTCTTCATAGGCCGGGCACGGTG<br>GCTCACGTCTGTAATCCCAGCACTTTGGGAGGCCAAGGTG<br>GGTGGATCACAACGTCAGGAGATCGAGACCATCCTGGCTA<br>ACATGGTGAAACCCTGTCTCTACTAAAAATATAAATAAAT<br>TAGCCGGACAGGCGCCTGTCCTCCCAGCTACTCAGGAGGC<br>TGAGGCAGGAGAATGGTGTGAACCTGGGAGGCGGAGCTTG<br>CAGTGAGCTGAGATCACGCCACTGCACTCCAGCCTGGGCA<br>ACAGAGCAAGACTCCGTCTCAAAAAAAAAAAAAAAAAAAC<br>CAGTCTTCATAAGTATTTGCTGCTACCTTTCCCTGTCATA<br>AGAAAAAGGATAGCCAGACATGGTGGGACGCCACTATGAT<br>CCCAGCTCCTTGGAAGGCTAAGGCACAAGAATCGCTTGAA<br>CCTGGGAGGTGGAGGTTGCAGTGAGCTGAGATCATGCCAC<br>TGCACTCCAGCCTGGTGACAGAGCAAGAGCCTGTCTCAAA<br>AAAAAAAAAGAAAAGAAAAGAAAAAGGGATATCTTTTCCT<br>CCTCCCAGAAGTTTGTTTTAAATTTGAGCATTTATCATGC<br>ACCTGATGTAAACCTAATAGTACTCTTGATACTCTAGTGG<br>CTTGAAAAAAAAAAAAAAGGCATTTCTGTGCTGAGTCTGC<br>GCTTCTATGCACACAAGGTATGTTTATAAAATACTGATAA<br>GCATGTCACAGTATAGAGCATAAGAGGCAATGTATGTATC<br>CTAGTGACATTAGCAGTGCTTTTCCCCCCTTAAACTCCTT<br>TAAAATTACTTTTAGAACTTGCTGCTCATTCTTGTGAATG<br>TTATGAATGGTGTCATATTGTCCTTTTACAGAAGATACGA<br>TTTTTAGAAACAAATATTCATTGAATGTCTGCCCTGTGAG<br>ATACTCACTAGAGTGAACATGAGGAGGCTTATGTAGCAAA<br>ATGGCACCTACCTGCAAAGAACTTAGTCCCTAATGGAGAT<br>GAATATATAATAAGGGATCATAAATGTGCTAAGTGGATTT<br>ACTAGTAATATGTGAGCCAAGGACGATAAAGCTCCTGATT<br>CTGATGGGTATCAGGAAAGGCTTTTCAGGAAGTGTTACTT<br>GTTATAGGTCAGAGGTCAGCAAACTACAGGTTACAACCCC<br>ACTGCCTGCTTTTGTAAAAAACTTTATTGGAATACAGTTA<br>TGCCCACTTGTTTATA | |
| RSF1 | NM_016578.3 | GATCCGCAGAGGAGCCCACTTGAGAGCGCCTCCTGTCGTC<br>TGTAAGGTTGCCTTGCCATCCCTCGGCACCCCAACTTCCC<br>CCGCCCCCCATCGCCTCCTCCTCCATCCTCCAGTTCAAA<br>ATGGCGACGGCGGCGGCAGCGGCGGCGGTGATGGCTCCTC<br>CGGGCTGCCCGGGTTCGTGCCCCAACTTCGCCGTAGTCTG<br>CTCCTTCTTGGAGCGCTACGGGCCGCTGCTAGACCTGCCT<br>GAGTTGCCGTTCCCTGAGCTGGAGCGGGTGCTGCAGGCGC<br>CGCCGCGGACGTCGGCAACGGAGAAGTACCAAAAGAATT<br>GGTGGAGCTCCATTTGAAGCTGATGAGGAAAATTGGCAAA<br>TCTGTTACTGCAGACAGATGGGAAAAATATTTGATCAAGA<br>TATGCCAAGAGTTTAACAGTACCTGGGCATGGGAGATGGA<br>GAAGAAGGGCTATCTTGAAATGAGTGTTGAATGCAAACTA<br>GCACTCTTAAAGTACCTCTGTGAGTGTCAGTTTGATGACA<br>ATCTCAAATTCAAGAATATTATTAATGAGGAGGATGCCGA | 35 |

TABLE 1-continued

GEP-NEN Biomarker/Houskeeper Sequence Information

| Gene Name | RefSeq Accession | Sequence | SEQ ID NO: |
|---|---|---|---|
| | | TACTATGCGTCTCCAGCCAATTGGTCGAGACAAAGATGGC<br>CTCATGTACTGGTACCAATTGGATCAAGATCACAATGTCA<br>GAATGTACATAGAAGAACAAGATGATCAAGATGGCTCTTC<br>ATGGAAATGCATTGTCAGAAATCGAAACGAGTTGGCTGAG<br>ACTCTTGCACTCCTGAAAGCACAAATTGATCCTGTACTAT<br>TGAAAAACTCTAGCCAACAAGACAACTCTTCTCGGGAAAG<br>TCCCAGCTTAGAGGATGAGGAGACTAAAAAAGAGGAAGAA<br>ACACCTAAACAAGAGGAACAGAAAGAAAGTGAAAAGATGA<br>AAAGTGAGGAGCAGCCTATGGATTTAGAAAACCGTTCTAC<br>AGCCAATGTTCTAGAAGAGACTACTGTGAAAAAAGAAAAA<br>GAAGATGAAAAGGAACTTGTGAAACTGCCAGTCATAGTGA<br>AGCTAGAAAAACCTTTGCCAGAAAATGAAGAAAAAAAGAT<br>TATCAAAGAAGAAAGTGATTCCTTCAAGGAAAATGTCAAA<br>CCCATTAAAGTTGAGGTGAAGGAATGTAGAGCAGATCCTA<br>AAGATACCAAAAGTAGCATGGAGAAGCCAGTGGCACAGGA<br>GCCTGAAAGGATCGAATTTGGTGGCAATATTAAATCTTCT<br>CACGAAATTACTGAGAAATCTACTGAAGAAACTGAGAAAC<br>TTAAAAATGACCAGCAGGCCAAGATACCACTAAAAAAACG<br>AGAAATTAAACTGAGTGATGATTTTGACAGTCCAGTCAAG<br>GGACCTTTGTGTAAATCAGTTACTCCAACAAAAGAGTTTT<br>TGAAAGATGAAATAAAACAAGAGGAAGAGACTTGTAAAAG<br>GATCTCTACAATCACTGCTTTGGGTCATGAAGGGAAACAG<br>CTGGTAAATGGAGAAGTTAGTGATGAAAGGGTAGCTCCAA<br>ATTTTAAGACAGAACCAATAGAGACAAAGTTTTATGAGAC<br>AAAGGAAGAGAGCTATAGCCCCTCTAAGGACAGAAATATC<br>ATCACGGAGGGAAATGGAACAGAGTCCTTAAATTCTGTCA<br>TAACAAGTATGAAAACAGGTGAGCTTGAGAAAGAAACAGC<br>CCCTTTGAGGAAAGATGCAGATAGTTCAATATCAGTCTTA<br>GAGATCCATAGTCAAAAAGCACAAATAGAGGAACCCGATC<br>CTCCAGAAATGGAAACTTCTCTTGATTCTTCTGAGATGGC<br>AAAAGATCTCTCTTCAAAAACTGCTTTATCTTCCACCGAG<br>TCGTGTACCATGAAAGGTGAAGAGAAGTCTCCCAAAACTA<br>AGAAGGATAAGCGCCCACCAATCCTAGAATGTCTTGAAAA<br>GTTAGAGAAGTCCAAAAAGACTTTTCTTGATAAGGACGCA<br>CAAAGATTGAGTCCAATACCAGAAGAAGTTCCAAAGAGTA<br>CTCTAGAGTCAGAAAAGCCTGGCTCTCCTGAGGCAGCTGA<br>AACTTCTCCACCATCTAATATCATTGACCACTGTGAGAAA<br>CTAGCCTCAGAAAAAGAAGTGGTAGAATGCCAGAGTACAA<br>GTACTGTTGGTGGCCAGTCTGTGAAAAAAGTAGACCTAGA<br>AACCCTAAAAGAGGATTCTGAGTTCACAAAGGTAGAAATG<br>GATAATCTGGACAATGCCCAGACCTCTGGCATAGAGGAGC<br>CTTCTGAGACAAAGGGTTCTATGCAAAAAAGCAAATTCAA<br>ATATAAGTTGGTTCCTGAAGAAGAAACCACTGCCTCAGAA<br>AATACAGAGATAACCTCTGAAAGGCAGAAAGAGGGCATCA<br>AATTAACAATCAGGATATCAAGTCGGAAAAAGAAGCCCGA<br>TTCTCCCCCCAAAGTTCTAGAACCAGAAAACAAGCAAGAG<br>AAGACAGAAAAGGAAGAGGAGAAAACAAATGTGGGTCGTA<br>CTTTAAGAAGATCTCCAAGAATATCTAGACCCACTGCAAA<br>AGTGGCTGAGATCAGAGATCAGAAAGCTGATAAAAAAAGA<br>GGGGAAGGAGAAGATGAGGTGGAAGAAGAGTCAACAGCTT<br>TGCAAAAAACTGACAAAAAGGAAATTTTGAAAAAATCAGA<br>GAAAGATACAAATTCTAAAGTAAGCAAGGTAAAACCCAAA<br>GGCAAAGTTCGATGGACTGGTTCTCGGACACGTGGCAGAT<br>GGAAATATTCCAGCAATGATGAAAGTGAAGGGTCTGGCAG<br>TGAAAAATCATCTGCAGCTTCAGAAGAGGAGGAAGAAAAG<br>GAAAGTGAAGAAGCCATCCTAGCAGATGATGATGAACCAT<br>GCA<u>AAAAAATGTGGCCTTCCAAACCATCCTGAGCTAATTCT</u><br><u>TCTGTGTGACTCTTGCGATAGTGGATACCATACTGCCTGC</u><br>CTTCGCCCTCCTCTGATGATCATCCCAGATGGAGAATGGT<br>TCTGCCCACCTTGCCAACATAAACTGCTCTGTGAAAAATT<br>AGAGGAACAGTTGCAGGATTTGGATGTTGCCTTAAAGAAG<br>AAAGAGCGTGCCGAACGAAGAAAAGAACGCTTGGTGTATG<br>TTGGTATCAGTATTGAAAACATCATTCCTCCACAAGAGCC<br>AGACTTTTCTGAAGATCAAGAAGAAAGAAAAAAGATTCA<br>AAAAAATCCAAAGCAAACTTGCTTGAAAGGAGGTCAACAA<br>GAACAAGGAAATGTATAAGCTACAGATTTGATGAGTTTGA<br>TGAAGCAATTGATGAAGCTATTGAAGATGACATCAAAGAA<br>GCCGATGGAGGAGGAGTTGGCCGAGGAAAAGATATCTCCA<br>CCATCACAGGTCATCGTGGGAAAGACATCTCTACTATTTT<br>GGATGAAGAAAGAAAAGAAAATAAACGACCCCAGAGGGCA<br>GCTGCTGCTCGAAGGAAGAAACGCCGGCGATTAAATGATC<br>TGGACAGTGATAGCAACCTGGATGAAGAAGAGAGCGAGGA<br>TGAATTCAAGATCAGTGATGGATCTCAAGATGAGTTTGTT<br>GTGTCTGATGAAAACCCAGATGAAAGTGAAGAAGATCCGC<br>CATCTAATGATGACAGTGACACTGACTTTTGTAGCCGTAG | |

TABLE 1-continued

GEP-NEN Biomarker/Houskeeper Sequence Information

| Gene Name | RefSeq Accession | Sequence | SEQ ID NO: |
|---|---|---|---|
| | | ACTGAGGCGACACCCCTCTCGGCCAATGAGGCAGAGCAGG<br>CGTTTGCGAAGAAAGACCCCAAAGAAAAAATATTCCGATG<br>ATGATGAAGAGGAGGAATCTGAGGAGAATAGTAGAGACTC<br>TGAAAGTGACTTCAGTGATGATTTTAGTGATGATTTTGTA<br>GAAACTCGGCGAAGGCGGTCAAGGAGAAATCAGAAAAGAC<br>AAATTAACTACAAAGAAGACTCAGAAAGTGACGGTTCCCA<br>GAAGAGTTTGCGACGTGGTAAAGAAATAAGGCGAGTACAC<br>AAGCGAAGACTTTCCAGCTCAGAGAGTGAAGAGAGCTATT<br>TGTCCAAGAACTCTGAAGATGATGAGCTAGCTAAAGAATC<br>AAAGCGGTCAGTTCGAAAGCGGGGCCGAAGCACAGACGAG<br>TATTCAGAAGCAGATGAGGAGGAGGAGGAAGAGGAAGGCA<br>AACCATCCCGCAAACGGCTACACCGGATTGAGACGGATGA<br>GGAGGAGAGTTGTGACAATGCTCATGGAGATGCAAATCAG<br>CCTGCCCGTGACAGCCAGCCTAGGGTCCTGCCCTCAGAAC<br>AAGAGAGCACCAAGAAGCCCTACCGGATAGAAAGTGATGA<br>GGAAGAGGACTTTGAAAATGTAGGCAAAGTGGGGAGCCCA<br>TTGGACTATAGCTTAGTGGACTTACCTTCAACCAATGGAC<br>AGAGCCCTGGCAAAGCCATTGAGAACTTGATTGGCAAGCC<br>TACTGAGAAGTCTCAGACCCCCAAGGACAACAGCACAGCC<br>AGTGCAAGCCTAGCCTCCAATGGGACAAGTGGTGGGCAGG<br>AGGCAGGAGCACCAGAAGAGGAGGAAGATGAGCTTTTGAG<br>AGTGACTGACCTTGTTGATTATGTCTGTAACAGTGAACAG<br>TTATAAGACTTTTTTTCCATTTTTGTGCTAATTTATTCCA<br>CGGTAGCTCTCACACCAGCGGGCCAGTTATTAAAAGCTGT<br>TTAATTTTTCCTAGAAAACTCCACTACAGAATGACTTTTA<br>GAAGAAAAATTTCAACAAATCCTGAAGTCTTTCTGTGAAG<br>TGACCAGTTCTGAACTTTGAAGATAAATAATTGCTGTAAA<br>TTCCTTTTGATTTTCTTTTTCCAGGTTCATGGTCCTTGGT<br>AATTTCATTCATGGAAAAAAATCTTATTATAATAACAACA<br>AAGATTTGTATATTTTTGACTTTATATTTCCTGAGCTCTC<br>CTGACTTTGTGAAAAAGGGTGGATGAAAATGCATTCCGAA<br>TCTGTGAGGGCCCAAAACAGAATTTAGGGGTGGGTGAAAG<br>CACTTGTGCTTTAGCTTTTTCATATTAAATATATATTATA<br>TTTAAACATTCATGGCATAGATGATGATTTACAGACAATT<br>TAAAAGTTCAAGTCTGTACTGTTACAGTTTGAGAATTGTA<br>GATAACATCATACATAAGTCATTTAGTAACAGCCTTTGTG<br>AAATGAACTTGTTTACTATTGGAGATAACCACACTTAATA<br>AGAAGAGACAGTGAAAGTACCATCATAATTAACCTAAAT<br>TTTTGTTATAGCAGAGTTTCTTGTTTAAAAAAAAATAAAA<br>TCATCTGAAAAGCAAAAA | |
| RTN2 | NM_005619.4 | CGCGCGCTGCAGTGCCTTCCCCACCTCGGCCCCGCCCGCC<br>CCCGCCGAGCCGAGCACCAGGGCGGCGGCGGCGGCGGCGG<br>CGGCGGCGGCGGCTGGAGCAGCCCGGGAGGAGGAGGCGGC<br>GAGAATGGCAGCGGCGTCGTGGGCGCGGCGGAGATGAGCG<br>CCCGCGACCCCGGGCCCAGGGCGGCACAGCCGGAGTGGGC<br>GGGGGTCCCGATGCAGGCCCGAGGGGGGCCATGGGGCAGG<br>TCCTGCCGGTCTTCGCCCACTGCAAAGAAGCTCCGTCTAC<br>AGCCTCCTCAACTCCTGATTCCACAGAAGGAGGGAACGAC<br>GACTCTGATTTTCGAGAGCTGCACACAGCCCGGGAATTCT<br>CAGAGGAGGACGAGGAGGAGACCACGTCGCAGGACTGGGG<br>CACCCCCCGGGAGCTGACCTTCTCCTACATCGCCTTTGAT<br>GGTGTAGTGGGCTCCGGGGGCCGCAGGGATTCAACTGCCC<br>GCCGCCCCGCCCCCAGGGCCGCTCAGTCTCGGAACCACG<br>AGACCAGCACCCTCAGCCCAGCCTGGGCGACAGCTTGGAG<br>AGCATCCCCAGCCTGAGCCAATCCCCGGAGCCTGGACGAC<br>GGGGTGATCCTGACACCGCGCCTCCATCCGAGCGCCCTCT<br>GGAAGACCTGAGGCTTCGGTTGGACCATCTGGGCTGGGTG<br>GCCCGGGGAACGGGATCCGGGGAGGACTCTTCCACCAGCA<br>GCTCCACCCCGCTGGAAGACGAAGAACCCCAAGAACCCAA<br>CAGATTGGAGACAGGAGAAGCTGGGGAAGAACTGGACCTA<br>CGACTCCGACTTGCTCAGCCCTCATCGCCCGAGGTCTTGA<br>CTCCCCAGCTCAGTCGGGCTCTGGGACACCCCAGGCCGG<br>TACTCCGTCCCCATCCCGATCGCGAGATTCGAACTCTGGG<br>CCCGAAGAGCCATTGCTGGAAGAGGAAGAAAAGCAGTGGG<br>GGCCACTGGAGCGAGAGCCAGTAAGGGGACAGTGCCTCGA<br>TAGCACGGACCAATTAGAATTCACGGTGGAGCCACGCCTT<br>CTAGGAACAGCTATGGAATGGTTAAAGACATCATTGCTTT<br>TGGCTGTTTACAAGACGGTTCCAATTTTGGAATTGTCCCC<br>ACCTCTGTGACAGCCATTGGCTGGGTCCAAAGGGGCCCC<br>ACCCCCCCTACTCCTGTCCTCCGGGTTCTACTGAAGTGGG<br>CAAAATCCCCGAGAAGCAGCGGTGTCCCCAGCCTCTCACT<br>CGGAGCCGATATGGGGAGTAAAGTGGCGGACCTGCTGTAC<br>TGGAAGGACACGAGGACGTCAGGAGTGGTCTTCACAGGCC<br>TGATGGTCTCCCTCCTCTGCCTCCTGCACTTTAGCATCGT | 36 |

TABLE 1-continued

GEP-NEN Biomarker/Houskeeper Sequence Information

| Gene Name | RefSeq Accession | Sequence | SEQ ID NO: |
|---|---|---|---|
| | | GTCCGTGGCCGCGCACTTGGCTCTGTTGCTGCTCTGCGGC<br>ACCATCTCTCTCAGGGTTTACCGCAAAGTGCTGCAGGCCG<br>TGCACCGGGGGATGGAGCCAACCCTTTCCAGGCCTACCT<br>GGATGTGGACCTCACCCTGACTCGGGAGCAGACGGAACGT<br>TTGTCCCACCAGATCACCTCCCGCGTGGTCTCGGCGGCCA<br>CGCAGCTGCGGCACTTCTTCCTGGTAGAAGACCTCGTGGA<br>TTCCCTCAAGCTGGCCCTCCTCTTCTACATCTTGACCTTC<br>GTGGGTGCCATCTTCAATGGTTTGACTCTTCTCATTCTGG<br><u>GAGTGATTGGTCTATTCACCATCCCCCTGCTGTACCGGCA</u><br><u>GCACCAGGCTCAGATCGACCAATATGTGGGGTTGGTGACC</u><br><u>AATCAG</u>TTGAGCCACATCAAAGCTAAGATCCGAGCTAAAA<br>TCCCAGGGACCGGAGCCCTGGCCTCTGCAGCAGCCGCAGT<br>CTCCGGATCCAAAGCCAAAGCCGAATGAGAACGGTGTCTC<br>TGCCCGCAGGACGCCTGCCCCCAGCCCCGCAGCCCTCTG<br>GCCCCCTCCATCTCTTGTCCGTTCCCACCCACCCCCCTCC<br>TCGGCCCGAGCCTTTTCCCGGTGGGTGTCAGGATCACTCC<br>CACTAGGGACTCTGCGCTAATTACCTGAGCGACCAGGACT<br>ACATTTCCCAAGAGGCTCTGCTCCAGGAGTCCAGGAAAGA<br>CGAGGCACCTTGGCCGCGGGGCCTGCTGGGACTTGTAGTT<br>GCCTAGACAGGGCACCACCCTGCACTTCCGGACCCGCCGC<br>TGGAGGCGCCGTGAGGCGTTGGTGTCTCCTGGATGCTACT<br>AGCCCCAACGCCGGGGCTTTGCATGGGGCCCAGGGGAGGC<br>CTGAGCTTGGATTTACACTGTAATAAAGACTCCTGTGGAA<br>AACCCGAG | |
| SMARCD3 | NM_001003801.1 | AGCAGGACTCAGAGGGGAGAGTTGGAGGAAAAAAAAAGGC<br>AGAAAAGGGAAAGAAAGAGGAAGAGAGAGAGAGAGTGAGA<br>GGAGCCGCTGAGCCCACCCCGATGGCCGCGGACGAAGTTG<br>CCGGAGGGGCGCGCAAAGCCACGAAAAGCAAACTTTTTGA<br>GTTTCTGGTCCATGGGGTGCGCCCCGGGATGCCGTCTGGA<br>GCCCGGATGCCCCACCAGGGGCGCCCATGGGCCCCCCGG<br>GCTCCCCGTACATGGGCAGCCCCGCCGTGCGACCCGGCCT<br>GGCCCCCGCGGGCATGGAGCCCGCCCGCAAGCGAGCAGCG<br>CCCCCGCCCGGGCAGAGCCAGGCACAGAGCCAGGGCCAGC<br>CGGTGCCCACCGCCCCCGCGCGGAGCCGCAGTGCCAAGAG<br>GAGGAAGATGGCTGACAAAATCCTCCCTCAAAGGATTCGG<br>GAGCTGGTCCCCGAGTCCCAGGCTTACATGGACCTCTTGG<br>CATTTGAGAGGAAACTGGATCAAACCATCATGCGGAAGCG<br>GGTGGACATCCAGGAGGCTCTGAAGAGGCCCATGAAGCAA<br>AAGCGGAAGCTGCGACTCTATATCTCCAACACTTTTAACC<br>CTGCGAAGCCTGATGCTGAGGATTCCGACGGCAGCATTGC<br>CTCCTGGGAGCTACGGGTGGAGGGGAAGCTCCTGGATGAT<br>CCCAGCAAACAGAAGCGGAAGTTCTCTTCTTTCTTCAAGA<br>GTTTGGTCATCGAGCTGGACAAAGATCTTTATGCCCTGA<br>CAACCACCTCGTTGAGTGGCATCGGACACCCACGACCCAG<br>GAGACGGACGGCTTCCAGGTGAAACGGCCTGGGGACCTGA<br>GTGTGCGCTGCACGCTGCTCCTCATGCTGGACTACCAGCC<br>TCCCCAGTTCAAACTGGATCCCCGCCTAGCCCGGCTGCTG<br>GGGCTGCACACACAGAGCCGCTCAGCCATTGTCCAGGCCC<br>TGTGGCAGTATGTGAAGACCAACAGG<u>CTGCAGGACTCCCA</u><br><u>TGACAAGGAATACATCAATGGGGACAAGTATTTCCAGCAG</u><br><u>ATTTTTGATTGTCCCCGGCTGAAGTTTTCTGAGATTCCCC</u><br><u>AGCGCCTCACAGCCCTGCTATTGCCCCCTGACCCAATTGT</u><br>CATCAACCATGTCATCAGCGTGGACCCTTCAGACCAGAAG<br>AAGACGGCGTGCTATGACATTGACGTGGAGGTGGAGGAGC<br>CATTAAAGGGGCAGATGAGCAGCTTCCTCCTATCCACGGC<br>CAACCAGCAGGAGATCAGTGCTCTGGACAGTAAGATCCAT<br>GAGACGATTGAGTCCATAAACCAGCTCAAGATCCAGAGGG<br>ACTTCATGCTAAGCTTCTCCAGAGACCCCAAAGGCTATGT<br>CCAAGACCTGCTCCGCTCCCAGAGCCGGGACCTCAAGGTG<br>ATGACAGATGTAGCCGGCAACCCTGAAGAGGAGCGCCGGG<br>CTGAGTTCTACCACCAGCCCTGGTCCCAGGAGGCCGTCAG<br>TCGCTACTTCTACTGCAAGATCCAGCAGCGCAGGCAGGAG<br>CTGGAGCAGTCGCTGGTTGTGCGCAACACCTAGGAGCCCA<br>AAAATAAGCAGCACGACGGAACTTTCAGCCGTGTCCCGGG<br>CCCCAGCATTTTGCCCCGGGCTCCAGCATCACTCCTCTGC<br>CACCTTGGGGTGTGGGGCTGGATTAAAAGTCATTCATCTG<br>ACAAAAAAAAAAAAAAAAA | 37 |
| SPATA7 | NM_001040428.3 | ACAATAGCGACTCACTGGACCCAGCCCTTAGCAACGGCCT<br>GGCGACGGTTTCCCTGCTGCTGCAGCCCCCGTCGGCTCCT<br>CTTTTCCAGTCCTCCACTGCCGGGGCTGGGCCCGGCCGCG<br>GGAAGGACCGAAGGGGATACAGCGTGTCCTGCGGCGGC<u>T</u><br><u>GCAAGAGGACTAAGCATGGATGGCAGCCGGAGAGTCAGAG</u><br><u>CAACCTCTGTCCTTCCCAGATATGGTCCACCGTGCCTATT</u> | 38 |

TABLE 1-continued

GEP-NEN Biomarker/Houskeeper Sequence Information

| Gene Name | RefSeq Accession | Sequence | SEQ ID NO: |
|---|---|---|---|
| | | TAAAGGACACTTGAGCACCAAAAGTAATGCTGCAGTAGAC<br>TGCTCGGTTCCAGTAAGCGTGAGTACCAGCATAAAGTATG<br>CAGACCAACAACGAAGAGAGAAACTCAAAAAGGAATTAGC<br>ACAATGTGAAAAAGAGTTCAAATTAACTAAAACTGCAATG<br>CGAGCCAATTATAAAAATAATTCCAAGTCACTTTTTAATA<br>CCTTACAAAAGCCCTCAGGCGAACCGCAAATTGAGGATGA<br>CATGTTAAAAGAAGAAATGAATGGATTTTCATCCTTTGCA<br>AGGTCACTAGTACCCTCTTCAGAGAGACTACACCTAAGTC<br>TACATAAATCCAGTAAAGTCATCACAAATGGTCCTGAGAA<br>GAACTCCAGTTCCTCCCCGTCCAGTGTGGATTATGCAGCC<br>TCCGGGCCCCGGAAACTGAGCTCTGGAGCCCTGTATGGCA<br>GAAGGCCCAGAAGCACATTCCCAAATTCCCACCGGTTTCA<br>GTTAGTCATTTCGAAAGCACCCAGTGGGGATCTTTTGGAT<br>AAACATTCTGAACTCTTTTCTAACAAACAATTGCCATTCA<br>CTCCTCGCACTTTAAAAACAGAAGCAAAATCTTTCCTGTC<br>ACAGTATCGCTATTATACACCTGCCAAAAGAAAAAAGGAT<br>TTTACAGATCAACGGATAGAAGCTGAAACCCAGACTGAAT<br>TAAGCTTTAAATCTGAGTTGGGGACAGCTGAGACTAAAAA<br>CATGACAGATTCAGAAATGAACATAAAGCAGGCATCTAAT<br>TGTGTGACATATGATGCCAAAGAAAAAATAGCTCCTTTAC<br>CTTTAGAAGGGCATGACTCAACATGGGATGAGATTAAGGA<br>TGATGCTCTTCAGCATTCCTCACCAAGGGCAATGTGTCAG<br>TATTCCCTGAAGCCCCCTTCAACTCGTAAAATCTACTCTG<br>ATGAAGAAGAACTGTTGTATCTGAGTTTCATTGAAGATGT<br>AACAGATGAAATTTTGAAACTTGGTTTATTTTCAAACAGG<br>TTTTTAGAACGACTGTTCGAGCGACATATAAAACAAAATA<br>AACATTTGGAGGAGGAAAAAATGCGCCACCTGCTGCATGT<br>CCTGAAAGTAGACTTAGGCTGCACATCGGAGGAAAACTCG<br>GTAAAGCAAAATGATGTTGATATGTTGAATGTATTTGATT<br>TTGAAAAGGCTGGGAATTCAGAACCAAATGAATTAAAAAA<br>TGAAAGTGAAGTAACAATTCAGCAGGAACGTCAACAATAC<br>CAAAAGGCTTTGGATATGTTATTGTCGGCACCAAAGGATG<br>AGAACGAGATATTCCCTTCACCAACTGAATTTTTCATGCC<br>TATTTATAAATCAAAGCATTCAGAAGGGGTTATAATTCAA<br>CAGGTGAATGATGAAACAAATCTTGAAACTTCAACTTTGG<br>ATGAAAATCATCCAAGTATTTCAGACAGTTTAACAGATCG<br>GGAAACTTCTGTGAATGTCATTGAAGGTGATAGTGACCCT<br>GAAAAGGTTGAGATTTCAAATGGATTATGTGGTCTTAACA<br>CATCACCCTCCCAATCTGTTCAGTTCTCCAGTGTCAAAGG<br>CGACAATAATCATGACATGGAGTTATCAACTCTTAAAATC<br>ATGGAAATGAGCATTGAGGACTGCCCTTTGGATGTTTAAT<br>CTTCATTAATAAATACCTCAAATGGCCAGTAACTCAAAAA<br>AAAAAAAAAAAAAAA | |
| SST1 | NM_001049.2 | TGGTCATCGCACGGCGGCAGCTCCTCACCTGGATTTAGAA<br>GAGCTGGCGTCCCGCCCGCCCAAGCCTTTAAACTCTCGT<br>CTGCCAGAACCCGCCAACTCTCCAGGCTTAGGGCCAGTTT<br>CCGCGATTCTAAGAGTAATTGCGTGGGCACCTGTGCTGGG<br>GCCAGGCGCAAAGAAGGGAGTTGGTCTGCGCGAAGATCGT<br>CAACCTGCTAACAGACCGCACATGCACTTTGCACCGACCA<br>TCTACGTCTCAGTCTGGAGGTTGCGCACTTTGGCTGCTGA<br>CGCGCTGGTGGTGCCTATTAATCATTTACCAGTCCAGAGC<br>CGCGCCAGTTAATGGCTGTGCCGTGCGGTGCTCCCACATC<br>CTGGCCTCTCCTCTCCACGGTCGCCTGTGCCCGGGCACCC<br>CGGAGCTGCAAACTGCAGAGCCCAGGCAACCGCTGGGCTG<br>TGCGCCCCGCCGGCGCCGGTAGGAGCCGCGCTCCCCGCAG<br>CGGTTGCGCTCTACCCGGAGGCGCTGGGCGGCTGTGGGCT<br>GCAGGCAAGCGGTCGGGTGGGAGGGAGGGCGCAGGCGGC<br>GGGTGCGCGAGGAGAAAGCCCCAGCCCTGGCAGCCCCACT<br>GGCCCCCCTCAGCTGGGATGTTCCCCAATGGCACCGCCTC<br>CTCTCCTTCCTCCTCTCCTAGCCCCAGCCCGGGCAGCTGC<br>GGCGAAGGCGGCGGCAGCAGGGGCCCCGGGGCCGGCGCTG<br>CGGACGGCATGGAGGAGCCAGGGCGAAATGCGTCCCAGAA<br>CGGGACCTTGAGCGAGGGCCAGGGCAGCGCCATCCTGATC<br>TCTTTCATCTACTCCGTGGTGTGCCTGGTGGGCTGTGTG<br>GGAACTCTATGGTCATCTACGTGATCCTGCGCTATGCCAA<br>GATGAAGACGGCCACCAACATCTACATCCTAAATCTGGCC<br>ATTGCTGATGAGCTGCTCATGCTCAGCGTGCCCTTCCTAG<br>TCACCTCCACGTTGTTGCGCCACTGGCCCTTCGGTGCGCT<br>GCTCTGCCGCCTCGTGCTCAGCGTGGACGCGGTCAACATG<br>TTCACCAGCATCTACTGTCTGACTGTGCTCAGCGTGGACC<br>GCTACGTGGCCGTGGTGCATCCCATCAAGGCGGCCCGCTA<br>CCGCCGGCCCACCGTGGCCAAGGTAGTAAACCTGGGCGTG<br>TGGGTGCTATCGCTGCTCGTCATCCTGCCCATCGTGGTCT<br>TCTCTCGCACCGCGGCCAACAGCGACGGCACGGTGGCTTG | 39 |

TABLE 1-continued

GEP-NEN Biomarker/Houskeeper Sequence Information

| Gene Name | RefSeq Accession | Sequence | SEQ ID NO: |
|---|---|---|---|
| | | CAACATGCTCATGCCAGAGCCCGCTCAACGCTGGCTGGTG GGCTTCGTGTTGTACACATTTCTCATGGGCTTCCTGCTGC CCGTGGGGGCTATCTGCCTGTGCTACGTGCTCATCATTGC TAAGATGCGCATGGTGGCCCTCAAGGCCGGCTGGCAGCAG CGCAAGCGCTCGGAGCGCAAGATCACCTTAATGGTGATGA TGGTGGTGATGGTGTTTGTCATCTGCTGGATGCCTTTCTA CGTGGTGCAGCTGGTCAACGTGTTTGCTGAGCAGGACGAC GCCACGGTGAGTCAGCTGTCGGTCATCCTCGGCTATGCCA ACAGCTGCGCCAACCCCATCCTCTATGGCTTTCTCTCAGA CAACTTCAAGCGCTCTTTCCAACGCATCCTATGCCTCAGC TGGATGGACAACGCCGCGGAGGAGCCGGTTGACTATTACG CCACCGCGCTCAAGAGCCGTGCCTACAGTGTGGAAGACTT CCAACCTGAGAACCTGGAGTCCGGCGGCGTCTTCCGTAAT GGCACCTGCACGTCCCGGATCACGACGCTCTGAGCCCGGG CCACGCAGGGGCTCTGAGCCCGGGCCACGCAGGGGCCCTG AGCCAAAAGAGGGGGAGAATGAGAAGGGAAGGCCGGGTGC GAAAGGGACGGTATCCAGGGCGCCAGGGTGCTGTCGGGAT AACGTGGGCTAGGACACTGACAGCCTTTGATGGAGGAAC CCAAGAAAGGCGCGCGACAATGGTAGAAGTGAGAGCTTTG CTTATAAACTGGGAAGGCTTTCAGGCTACCTTTTTCTGGG TCTCCCACTTTCTGTTCCTTCCTCCACTGCGCTTACTCCT CTGACCCTCCTTCTATTTTCCCTACCCTGCAACTTCTATC CTTTCTTCCGCACCGTCCCGCCAGTGCAGATCACGAACTC ATTAACAACTCATTCTGATCCTCAGCCCCTCCAGTCGTTA TTTCTGTTTGTTTAAGCTGAGCCACGGATACCGCCACGGG TTTCCCTCGGCGTTAGTCCCTAGCCGCGCGGGGCCGCTGT CCAGGTTCTGTCTGGTGCCCCTACTGGAGTCCCGGGAATG ACCGCTCTCCCTTTGCGCAGCCCTACCTTAAGGAAAGTTG GACTTGAGAAAGATCTAAGCAGCTGGTCTTTTCTCCTACT CTTGGGTGAAGGTGCATCTTTCCCTGCCCTCCCCTGTCCC CCTCTCGCCGCCCGCCCGCCACCACCACTCTCACTCCACC CAGAGTAGAGCCAGGTGCTTAGTAAAATAGGTCCCGCGCT TCGAACTCCAGGCTTTCTGGAGTTCCCACCCAAGCCCTCC TTTGGAGCAAAGAAGGAGCTGAGAACAAGCCGAATGAGGA GTTTTTATAAGATTGCGGGGTCGGAGTGTGGGCGCGTAAT AGGAATCACCCTCCTACTGCGCGTTTTCAAAGACCAAGCG CTGGGCGCTCCCGGGCCGCGTCTGCGTTAGGCAGGGCA GGGTAGTGCAGGGCACACCTTCCCCGGGGTTCGGGGTTCG GGGTTCGGTTGCAGGGCTGCAGCCCGCCTTGGCTTTCTCC CTCACCCAAGTTTCCGGAGGAGCCGACCTAAAAGTAACAA TAGATAAGGTTTCCTGCTCCAGTGTATCTCAAAAGACCGG GCGCCAGGGGCGGGGACCTAGGGCGACGTCTTCAGAGTC CGCCAGTGTTGGCGGTGTCGCCGCAACCTGCAGGCTCCCG AGTGGGGCCTGCCTGGTCTCTAGAGGGTTGCTGCCTTTCA AGCGGTGCCTAAGAAGTTATTTTCTTGTTTAACATATATA TTTATTAATTTATTTGTCGTGTTGGAAAATGTGTCTCTGC TTTCCTTTTCTCTGCTTGCCTAGCCCCAGGTCTTTTCTTT GGGACCCTGGGGGCGGGCATGGAAGTGGAAGTAGGGGCAA GCTCTTGCCCCACTCCCTGGCCATCTCAACGCCTCTCCTC AATGCTGGGCCCTCTTATCTCATCCTTTCCTCTAGCTTTT CTATTTTTGATTGTGTTGAGTGAAGTTTGGAGATTTTTCA TACTTTTCTTACTATAGTCTCTTGTTTGTCTTATTAGGAT AATACATAAATGATAATGTGGGTTATCCTCCTCTCCATGC ACAGTGGAAAGTCCTGAACTCCTGGCTTTCCAGGAGACAT ATATAGGGGAACATCACCCTATATATAATTTGAGTGTATA TATATTTATATATATGATGTGGACATATGTATACTTATCT TGCTCCATTGTCATGAGTCCATGAGTCTAAGTATAGCCAC TGATGGTGACAGGTGTGAGTCTGGCTGGAACACTTTCAGT TTCAGGAGTGCAAGCAGCACTCAAACCTGGAGCTGAGGAA TCTAATTCAGACAGAGACTTTAATCACTGCTGAAGATGCC CCTGCTCCCTCTGGGTTCCAGCAGAGGTGATTCTTACATA TGATCCAGTTAACATCATCACTTTTTTTGAGGACATTGAA AGTGAAATAATTTGTGTCTGTGTTTAATATTACCAACTAC ATTGGAAGCCTGAGCAGGGCGAGGACCAATAATTTTAATT ATTTATATTTCCTGTATTGCTTTAGTATGCTGGCTTGTAC ATAGTAGGCACTAAATACATGTTTGTTGGTTGATTGTTTA AGCCAGAGTGTATTACAACAATCTGGAGATACTAAATCTG GGGTTCTCAGGTTCACTCATTGACATGATATACAATGGTT AAAATCACTATTGAAAATACGTTTTGTGTATATTTGCTT CAACAACTTTGTGCTTTCCTGAAAGCAGTAACCAAGAGTT AAGATATCCCTAATGTTTTGCTTAAACTAATGAACAAATA TGCTTTGGGTCATAAATCAGAAAGTTTAGATCTGTCCCTT AATAAAAATATATATTACTACTCCTTTGGAAAATAGATTT TTAATGGTTAAGAACTGTGAAATTTACAAATCAAATCTT AATCATTATCCTTCTAAGAGGATACAAATTTAGTGCTCTT | |

TABLE 1-continued

GEP-NEN Biomarker/Housekeeper Sequence Information

| Gene Name | RefSeq Accession | Sequence | SEQ ID NO: |
|---|---|---|---|
| | | AACTTGTTACCATTGTAATATTAACTAAATAAACAGATGT ATTATGCTGTTAAAAAAAAAAAAAAAAAAAAAAAAAAAAA AAAAAAAAAAAAAAAAAAAAAA | |
| SST3 | NM_001051.4 | CTGCATCTCTCCCTCTCACCCGTGTCTCCTCTCCTCTCTT TCCTTCTCGTCTTCTCCCTGTCACGCATCTCTCATCACTC CCCCTCATTCTGCCTTTCCTCCTACTCACGGTCTCCTCTC CCTCTCCCTCTCTCTCTCTCCCCCTCCCTCTTTCTCTCTC TCTCTCTTTCTCCACCTCCTCCCGACCCCCTTTCCCCTCT ATTTCTATTGGCTTCTGTGTCCCTTGCTCCCCTCTTCTCT TCCTCACCCTGGGAAGCTTCTCCCCCCTATCCTTGCCCCT GCCCCCCCAGGATGTGTCCTGGAGATGGGGGGTGACGTAC CAGGCTCTGGTTGGGAAGTCAGGGCCGGAGACCAGATGGG AGAGGCTCTGTGGACAGCCGTGGCCGAGGGCCTGGGAGGG AACCTGAGCCCGCAAGCGGTCTAGAAGTGGGTGCCTTGTG GGGACCCTAGTTAGGAGTGCCCTGGGGGCACCTGGGGACT GGGCAGGGAGAGGGGACAGCAGAATGATAACCAGCCTGGC GGCAAGGAGGGAAGCCCTCACCCCATGGGCAGGCAAATAG CTGACTGCTGACCACCCTCCCCTCAGCCATGGACATGCTT CATCCATCATCGGTGTCCACGACCTCAGAACCTGAG<u>AATG</u> <u>CCTCCTCGGCCTGGCCCCCAGATGCCACCCTGGGCAACGT</u> <u>GTCGGCGGGCCCAAGCCCGGCAGGGCTGGCCGTCAGTGGC</u> GTTCTGATCCCCCTGGTCTACCTGGTGGTGTGCGTGGTGG GCCTGCTGGGTAACTCGCTGGTCATCTATGTGGTCCTGCG GCACACGGCCAGCCCTTCAGTCACCAACGTCTACATCCTC AACCTGGCGCTGGCCGACGAGCTCTTCATGCTGGGGCTGC CCTTCCTGGCCGCCCAGAACGCCCTGTCCTACTGGCCCTT CGGCTCCCTCATGTGCCGCCTGGTCATGGCGGTGGATGGC ATCAACCAGTTCACCAGCATATTCTGCCTGACTGTCATGA GCGTGGACCGCTACCTGGCCGTGGTACATCCCACCCGCTC GGCCCGCTGGCGCACAGCTCCGGTGGCCCGCACGGTCAGC GCGGCTGTGTGGGTGGCCTCAGCCGTGGTGGTGCTGCCCG TGGTGGTCTTCTCGGGAGTGCCCCGCGGCATGAGCACCTG CCACATGCAGTGGCCCGAGCCGGCGGCGGCCTGGCGAGCC GGCTTCATCATCTACACGGCCGCACTGGGCTTCTTCGGGC CGCTGCTGGTCATCTGCCTCTGCTACCTGCTCATCGTGGT GAAGGTGCGCTCAGCTGGGCGCCGGGTGTGGGCACCCTCG TGCCAGCGGCGGCGGCGCTCCGAACGCAGGGTCACGCGCA TGGTGGTGGCCGTGGTGGCGCTCTTCGTGCTCTGCTGGAT GCCCTTCTACGTGCTCAACATCGTCAACGTGGTGTGCCCA CTGCCCGAGGAGCCTGCCTTCTTTGGGCTCTACTTCCTGG TGGTGGCGCTGCCCTATGCCAACAGCTGTGCCAACCCCAT CCTTTATGGCTTCCTCTCCTACCGCTTCAAGCAGGGCTTC CGCAGGGTCCTGCTGCGGCCCTCCCGCCGTGTGCGCAGCC AGGAGCCCACTGTGGGGCCCCGGAGAAGACTGAGGAGGA GGATGAGGAGGAGGAGGATGGGGAGGAGAGCAGGGAGGGG GGCAAGGGGAAGGAGATGAACGGCCGGGTCAGCCAGATCA CGCAGCCTGGCACCAGCGGGCAGGAGCGGCCGCCCAGCAG AGTGGCCAGCAAGGAGCAGCAGCTCCTACCCCAAGAGGCT TCCACTGGGGAGAAGTCCAGCACGATGCGCATCAGCTACC TGTAGGGGCCTGGGGAAAGCCAGGATGGCCCGAGGAAGAG GCAGAAGCCGTGGGTGTGCCTAGGGCCTACTTCCCAAGGT GCCACAGGCCCATGATGGGATGTTGAGGGGCCTGGACTTT GATGCTATTGCTGCCAGGTCTTGCTGTGTGACCTTGGGTA GGTTGCTTCTACTCTCTGGGCCTTGTTTTCTCCTCTGTGA CTCAGGGATAGGAGTCATCAGCCTGGATGAGCTATGTCAG ATGAGAGGTTTGGAGGGCACTGTTGCTGGGCTGACCTGGC TGAGCAGGCAAAAGGTGGGTGCAGACTGGCCTCCCCCCAG GGATGGAGTGTCTTGGGGCATCAACTAGAATCTTGGCCCT CAGAGGGATAAACCAAGGCCAGGATTTCTTGGGCTCAGAG TCAGGAACACAGGAGCTGCTGGGGGCTGGGCTGGAAACCT AAACAGAAGAAAGCCTAACCCGGTGGGAGGAGTGGGGCAG AAATGGTCAGGCCCCAGATCAGCTCCCTCCCCTCGACTGT GAGGCCTTGGACCAGCTCTGCTCCTCTCTAGGCCTCAGGC TTCACCTGGGTAAAACCCAACAACCTCTACACCCTTTTGG CCCAGGCAGTCAATGCTGGAGGTCCTGTGCTCCTGGACGG GAAGAGCAGGTGAATTTCCTGCTCATGGAAGCGAATGAAG TCCAGCTTCAGGGTCTCTCACTGCCTGGGCTTTTGCAAGG CCCTGCATCTACTTTTGTACTTGTCATTTTGTATTCGTTT TCTTAAAGAGGGACCTCGAACTGCATAAGCTTAGGCCACC CAAAGCCTGGCTCTGCCCCTGCTGAGGTCAGCCACCCAAT CCCCAAGGAAGCTCATGTTGGGTCTTATGGCTGGAGTAGG GGCCCCGGGGGTTCCAGGTCTTTTGAGGGCTTCCAGGC ACCTCCTTGTAGGAAGGGCCATCCCTGTTCCTCTCCTTGT GACCCATATTCTCCCTTCCTGGAGACCGAGACAGGGACCC | 40 |

TABLE 1-continued

GEP-NEN Biomarker/Houskeeper Sequence Information

| Gene Name | RefSeq Accession | Sequence | SEQ ID NO: |
|---|---|---|---|
| | | AGCCCATGAGGACTGGCATGGAAAGGCAGAGTGTCTGAAG<br>AGCGCTGTGAGGAGAAGGAAGAGGAAGGGAGAAGAGGAAG<br>AGGAAGGAGAAGGAAGAGGAAGACAAGGGGGAAAGGGGAG<br>GATGAGGAGGGGAAGGAGAAGTACAGATCTGTTTCCTGG<br>AGCCGTCTTTGGCCCCCCTGGGCTGAGCTCAGTGGTAGCA<br>TCTGTGAACCTGAGTTGCCGACAACAGCCCCACCCAACCA<br>GTACTGAGGGAAGGACACGATCAGGGTGGAACAGCCAGGG<br>TGCAATGGCAAATGCACAGAGTACAGACAGGCACAGGGCC<br>TGCGTCCCTGAGGGGCCTCAGAGTGCTGCCAAGAGGGCTC<br>AGGCCTTAATAAAGCCCTAGGGTGGAGCTGGCTACCAGGG<br>ACATTGGGAGGACTGGGGAGCTCCCTCCCCATGCTCTATC<br>ATCCTGGAGACTACAGGTCGGGAGGCCCAGGGAAGACAAG<br>AAGAGGCTGAAGTGGGACTGTGGAGGGGGACCATGGGGAG<br>CAGCCACCATCCAAGGCTGGGCCTAGACTCCCTCCCAGAG<br>ATGGTCCCTCAGAGCTGTGGTGAGGCTGGCCCTGGGAGGG<br>TGAGACCCCCGGTGAAATCCTTCCGCTTCCCCACCCCTTG<br>CAGAGGGCAGGGTCCTCAGGGAAAGCACAGGAACCAGAC<br>TTTTGGAGACTTGGATCTTCAGCACACCTCAGGGTCCTGG<br>GCTGGCATTGGCCTTCCGGGCCTCAATTTCCCCATCAACA<br>AATGGAGATGAATCCCAGCTTGGCTGCCTCCTGGGATCTA<br>ACGAGAAAATGAGTCATGTGAGGTAACTTCCAGGCTCACT<br>GCAATGGGTACGGTGGGGTGTATCAGATTATAAAGTGGGG<br>GTGCCCTCCTCACCCCCAGGCTTGGCCTATACCCCCCTCT<br>CCATCAAGTGGCCTCTCTGTGTCTGTCCTTTGGGGTGAGG<br>ACACTGTAGGCCATGAGAAATGGGCAGTTGGGGGGTCAGA<br>GGCCAAGGGTTAGGGAGGCAGGGCTTGGGGAGAGTGTGGG<br>ACCATCAGAAGAGAAGGAAGTTTACAAAACCACATTTTGT<br>GTGGAGATGGAGGCTGGAGGCCCGGCCCTGGGACTTGGTC<br>TGGGGTTTCTTGAGGAAGATCTGAGGGTCCAAGGGAGGAA<br>GGATGCCCTGGCCTTCTGGCCTTCTCTGGCTGATCCTGCC<br>TTCTTGCTGCCTAGGACAGGAGAGTAATGTCCTAGAATGG<br>TCCCTGGGAGGCCAGTTAGGAAACCCTTTGCTGCTTCTGT<br>CTCTAGCTCTTGTCAATAAAGACGGTGACACCTGAAAAAA<br>AAAAAAAAAA | |
| SST4 | NM_001052.2 | CCGAGCTCTCTGGCGCAGCGCTAGCTCCGCCGCGCTCAGC<br>TGCCCTGCGCCGGCACCCCTGGTCATGAGCGCCCCCTCGA<br>CGCTGCCCCCC<u>CGGGGGCGAGGAAGGGCTGGGGACGGCCTG</u><br><u>GCCCTCTGCAGCCAATGCCAGTAGCGCTCCGGCGGAGGCG</u><br><u>GAGGAGGCGGTGGCGGGGCCCGGGGACGCGCGGGCGGCGG</u><br>GCATGGTCGCTATCCAGTGCATCTACGCGCTGGTGTGCCT<br>GGTGGGGCTGGTGGGCAACGCCCTGGTCATCTTCGTGATC<br>CTTCGCTACGCCAAGATGAAGACGGCTACCAACATCTACC<br>TGCTCAACCTGGCCGTAGCCGACGAGCTCTTCATGCTGAG<br>CGTGCCCTTCGTGGCCTCGTCGGCCGCCCTGCGCCACTGG<br>CCCTTCGGCTCCGTGCTGTGCCGCGCGGTGCTCAGCGTCG<br>ACGGCCTCAACATGTTCACCAGCGTCTTCTGTCTCACCGT<br>GCTCAGCGTGGACCGCTACGTGGCCGTGGTGCACCCTCTG<br>CGCGCGGCGACCTACCGGCGGCCCAGCGTGGCCAAGCTCA<br>TCAACCTGGGCGTGTGGCTGGCATCCCTGTTGGTCACTCT<br>CCCCATCGCCATCTTCGCAGACACCAGACCGGCTCGCGGC<br>GGCCAGGCCGTGGCCTGCAACCTGCAGTGGCCACACCCGG<br>CCTGGTCGGCAGTCTTCGTGGTCTACACTTTCCTGCTGGG<br>CTTCCTGCTGCCCGTGCTGGCCATTGGCCTGTGCTACCTG<br>CTCATCGTGGGCAAGATGCGCGCCGTGGCCCTGCGCGCTG<br>GCTGGCAGCAGCGCAGGCGCTCGGAGAAGAAAATCACCAG<br>GCTGGTGCTGATGGTCGTGGTCGTCTTTGTGCTCTGCTGG<br>ATGCCTTTCTACGTGGTGCAGCTGCTGAACCTCTTCGTGA<br>CCAGCCTTGATGCCACCGTCAACCACGTGTCCCTTATCCT<br>TAGCTATGCCAACAGCTGCGCCAACCCCATTCTCTATGGC<br>TTCCTCTCCGACAACTTCCGCCGATTCTTCCAGCGGGTTC<br>TCTGCCTGCGCTGCTGCCTCCTGGAAGGTGCTGGAGGTGC<br>TGAGGAGGAGCCCCTGGACTACTATGCCACTGCTCTCAAG<br>AGCAAAGGTGGGGCAGGGTGCATGTGCCCCCCACTCCCCT<br>GCCAGCAGGAAGCCCTGCAACCAGAACCCGGCCGCAAGCG<br>CATCCCCCTCACCAGGACCACCACCTTCTGAGGAGCCCTT<br>CCCCTACCCACCCTGCGT | 41 |
| SST5 | NM_001053.3 | ATGCCTGCATGTGCTGGTTCAGGGACTCACCACCCTGGCG<br>TCCTCCCTTCTTCTCTTGCAGAGCCTGACGCACCCCAGGG<br>CTGCCGCCATGGAGCCCCTGTTCCCAGCCTCCACGCCCAG<br>CTGAACGCCTCCTCCCCGGGGCTGCCTCTGGAGGCGGT<br>GACAACAGGACGCTGGTGGGGCCGGCGCCCTCGGCAGGGG<br>CCCGGGCGGTGCTGGTGCCCGTGCTGTACCTGCTGGTGTG<br>TGCGGCCGGGCTGGGCGGGAACACGCTGGTCATCTACGTG | 42 |

TABLE 1-continued

GEP-NEN Biomarker/Houskeeper Sequence Information

| Gene Name | RefSeq Accession | Sequence | SEQ ID NO: |
|---|---|---|---|
| | | GTGCTGCGCTTCGCCAAGATGAAGACCGTCACCAACATCT<br>ACATTCTCAACCTGGCAGTGGCCGACGTCCTGTACATGCT<br>GGGGCTGCCTTTCCTGGCCACGCAGAACGCCGCGTCCTTC<br>TGGCCCTTCGGCCCCGTCCTGTGCCGCCTGGTCATGACGC<br>TGGACGGCGTCAACCAGTTCACCAGTGTCTTCTGCCTGAC<br>AGTCATGAGCGTGGACCGCTACCTGGCAGTGGTGCACCCG<br>CTGAGCTCGGCCCGCTGGCGCCGCCCGCGTGTGGCCAAGC<br>TGGCGAGCGCCGCGGCCTGGGTCCTGTCTCTGTGCATGTC<br>GCTGCCGCTCCTGGTGTTCGCGGACGTGCAGGAGGGCGGT<br>ACCTGCAACGCCAGCTGGCCGGAGCCCGTGGGGCTGTGGG<br>GCGCCGTCTTCATCATCTACACGGCCGTGCTGGGCTTCTT<br>CGCGCCGCTGCTGGTCATCTGCCTGTGCTACCTGCTCATC<br>GTGGTGAAGGTGAGGGCGGCGGGCGTGCGCGTGGGCTGCG<br>TGCCGGCGGCGCTCGGAGCGGAAGGTGACGCGCATGGTGTT<br>GGTGGTGGTGCTGGTGTTTGCGGGATGTTGGCTGCCCTTC<br>TTCACCGTCAACATCGTCAACCTGGCCGTGGCGCTGCCCC<br>AGGAGCCCGCCTCCGCCGGCCTCTACTTCTTCGTGGTCAT<br>CCTCTCCTACGCCAACAGCTGTGCCAACCCCGTCCTCTAC<br>GGCTTCCTCTCTGACAACTTCCGCCAGAGCTTCCAGAAGG<br>TTCTGTGCCTCCGCAAGGGCTCTGGTGCCAAGGACGCTGA<br>CGCCACGGAGCCGCGTCCAGACAGGATCCGGCAGCAGCAG<br>GAGGCCACGCCACCCGCGCACCGCGCCGCAGCCAACGGGC<br>TTATGCAGACCAGCAAGCTGTGAGAGTGCAGGCGGGGGGT<br>GGGCGGCCCCGTGTCACCCCCAGGAGCGGAGGTTGCACTG<br>CGGTGACCCCCACCCATGACCTGCCAGTCAGGATGCTCCC<br>CGGCGGTGGTGTGAGGACAGAGCTGGCTGAAGCCAGGCTG<br>GGGTAGACACAGGGCAGTAGGTTCCCCACCGTGACCGACC<br>ATCCCTCTAACCGTCTGCCACACAGCGGGGGCTCCCGGG<br>AGGTAGGGGAGGTGGCCAGACCGGTGGGGGGCTCCGCCAT<br>GCCGTGCAAGTGCTCAGGGCCGCCTCACCCTCCATCTGGC<br>CCCAGCCCATGCCGGCCTTC<u>CCTCTGGGGAGCGACTTTTC</u><br><u>CAGAAGGCCGGCCAGGCGAGAGGGTCTTCCTGACGGCGGA</u><br><u>GCTGACCTGCCCGGCCCACCAGCTGCATGTCAGCTCCGAG</u><br><u>CCACCGGGTCCCCGTCCAAGGCTGCTCTGCTAAGTTAAAG</u><br><u>ACACCCGAAAGCGCTTG</u>ACTCAGGTCCCCGGAGTCCCTGG<br>CCAGGGCCCCAGCCCCTCGCTTGCCCTGCACTGTGTGGAC<br>TCTGGGGATGCAGGTGTAAGGGGAGTGTGGCTGGGCAGCC<br>CCTGGTCAGCCAGGGTCACGCCTGTCCTGGGGGCCCCACC<br>CTGCTGCCCGACACCCCCCATGGGAGGCTGCGGGCGGCAG<br>TTGCTGTCTCAGAGAGGGGAGTGTGGGGCTTGGGCGCTG<br>GCCTAGCCAGGGGCGAGGTGGGGAGGCGGCTGGTGCAGAG<br>GAGAGCTGGGGGCTGAGGTTGGGGTGAAGGCTGCAGCCCT<br>CCAGGCTGCTGGGGGTGCAGATGGCTGTGCCGTGCTGAGA<br>TTGGCTCTGTCTGGAGGGGTCCAGTGTGGGGTGCCTGAGG<br>GCACTAGGGAGAGGTGCTCCTGCTGCAGGAGGACCTGAGG<br>GTCAGGGCTTGGAGAGGACAGGGAACCTGCCGGCCGTCTCT<br>TCTGCTTTGGGGCAGGGGCTCTGGCCCGGGAGAGGGAACG<br>GGGACAGGAGCAGAGGACGGTCATCCAGGCGCAGCGGGGA<br>GCTGCTCCCCAGGCCACAGCAGAGACAGCACTGCTGAGAGGC<br>AGCGGCCGCGCGGGTGACGCAAATGGCAGGCCCTGGGAAT<br>CCCGCCGCCTCCCACCTAGAATTGTCCTACCTCCCCCACC<br>CCAAACACCAGCTTTTCCTGGCGCCCCAGGCCCAGAACGT<br>GGGCCCAGAGAGCCTTGCTGGGGTCTCTGGGGCACCTTGG<br>CCTTGCTCTGAGGCTGGAAGGAGAAGGACCAGGGTGCGGC<br>ATCACTCGGCCTCAGGGACCCCTCTGCCCTGCCCAGCACT<br>GGCCCCGACCCGTGCTCCCGCCGTCTGCCCAGAGCAGGAC<br>CTCAACCTCCTGGAGGGCACAGGGAGCGGCTGAGTGGGCA<br>CAAATCCTGGCAGGAGAAAGGCCCAGGCTGAGGCCAGGCC<br>TGGGAAACATCCAAGCAGTGAGGACACGCGTGTTTGACAA<br>CTGCTCCCCTGAATAAATGCGAGGATAAATGTTT | |
| TECPR2 | NM_001172631.1 | CCCCCGGCGGAGCCAGCTGCTGCTCTTCGGTGCTGGCCCC<br>GGTGCCGGCCCCGTTGCCCAGGGAACAGGCTCCCGGCAGC<br>CCCCGCGGCCCGGAGTCCATCCCGCCTCCTCCGGCCCGGC<br>GGGGCCGACGAGTCCGGAGGGGCTGCCGCGGGAGCCCCCA<br>GGTTTCCCTAGATGACAAATAAACATTCCTTTTCCTGCGT<br>GAAGATAGTCTGTGGAAACCTTGGCCATGGCATCGATATC<br>AGAGCCTGTTACATTCAGAGAGTTCTGCCCGTTGTACTAT<br>CTCCTCAATGCCATTCCGACAAAGATCCAGAAGGGTTTCC<br>GCTCTATCGTGGTCTATCTCACGGCCCTCGACACCAACGG<br>GGACTACATCGCGGTGGGCAGCAGCATCGGCATGCTCTAT<br>CTGTACTGCCGGCACCTCAACCAGATGAGGAAGTACAACT<br>TTGAGGGGAAGACGGAATCTATCACTGTGGTGAAGCTGCT<br>GAGCTGCTTTGATGACCTGGTGGCAGCAGGCACAGCCTCT<br>GGCAGGGTTGCAGTTTTTCAACTTGTATCTTCATTGCCAG | 43 |

TABLE 1-continued

GEP-NEN Biomarker/Houskeeper Sequence Information

| Gene Name | RefSeq Accession | Sequence | SEQ ID NO: |
|---|---|---|---|
| | | GGAGAAATAAACAGCTTCGGAGATTTGATGTCACTGGTAT<br>TCACAAAAATAGCATTACAGCTCTGGCTTGGAGCCCCAAT<br>GGAATGAAATTGTTCTCTGGAGATGACAAAGGCAAAATTG<br>TTTATTCTTCTCTGGATCTAGACCAGGGGCTCTGTAACTC<br>CCAGCTGGTGTTGGAGGAGCCATCTTCCATTGTGCAGCTG<br>GATTATAGCCAGAAAGTGCTGCTGGTCTCTACTCTGCAAA<br>GAAGTCTGCTCTTTTACACTGAAGAAAGTCTGTAAGGCA<br>AATTGGAACACAACCAAGGAAAAGTACTGGGAAATTTGGT<br>GCTTGTTTTATACCAGGACTCTGTAAGCAAAGTGATCTAA<br>CCTTGTATGCGTCACGGCCCGGGCTCCGGCTATGGAAGGC<br>TGATGTCCACGGGACTGTTCAAGCACGTTTATCTTAAAA<br>GATGCTTTTGCCGGGGAGTCAAGCCTTTTGAACTGCACC<br>CGCGTCTGGAATCCCCCAACAGTGGAAGTTGCAGCTTACC<br>TGAGAGGCACCTGGGGCTTGTTTCATGTTTCTTTCAAGAA<br>GGCTGGGTGCTGAGTTGGAATGAATATAGTATCTATCTCC<br>TAGACACAGTCAACCAGGCCACAGTTGCTGGTTTGGAAGG<br>ATCCGGTGATATTGTGTCTGTTTCGTGCACAGAAAATGAA<br>ATATTTTTCTTGAAAGGAGATAGGAACATTATAAGAATTT<br>CAAGCAGGCCTGAAGGATTAACATCAACAGTGAGAGATGG<br>TCTGGAGATGTCTGGATGCTCAGAGCGTGTCCACGTGCAG<br>CAAGCGGAGAAGCTGCCAGGGGCCACAGTTTCTGAGACGA<br>GGCTCAGAGGCTCTTCCATGGCCAGCTCCGTGGCCAGCGA<br>GCCAAGGAGCAGGAGCAGCTCGCTCAACTCCACCGACAGC<br>GGCTCCGGGCTCCTGCCCCCTGGGCTCCAGGCCACCCCTG<br>AGCTGGGCAAGGGCAGCCAGCCCTGTCACAGAGATTCAA<br>CGCCATCAGCTCAGAGGACTTTGACCAGGAGCTTGTCGTG<br>AAGCCTATCAAAGTGAAAAGGAAGAAGAAGAAGAAGAAGA<br>CAGAAGGTGGAAGCAGGAGCACCTGTCACAGCTCCCTGGA<br>ATCGACACCCTGCTCCGAATTTCCTGGGGACAGTCCCCAG<br>TCCTTGAACACAGACTTGCTGTCGATGACCTCAAGTGTCC<br>TGGGCAGTAGCGTGGATCAGTTAAGTGCAGAGTCTCCAGA<br>CCAGGAAAGCAGCTTCAATGGTGAAGTGAACGGTGTCCCA<br>CAGGAAAATACTGACCCCGAAACGTTTAATGTCCTGGAGG<br>TGTCAGGATCAATGCCTGATTCTCTGGCTGAGGAAGATGA<br>CATTAGAACTGAAATGCCACACTGTCACCATGCACATGGG<br>CGGGAGCTGCTCAATGGAGCGAGGGAAGATGTGGGAGGCA<br>GTGATGTCACGGGACTCGGAGATGAGCCGTGTCCTGCAGA<br>TGATGGACCAAATAGCACACAGTTACCCTTCCAAGAACAG<br>GACAGCTCTCCTGGGGCGCATGATGGGGAAGACATCCAAC<br>CCATTGGCCCCCAAAGCACTTTTTGTGAAGTCCCCCTCCT<br>GAACTCACTCACTGTGCCTTCCAGCCTCAGCTGGGCCCCA<br>AGTGCTGAACAGTGGCTGCCTGGGACCAGAGCTGATGAAG<br>GCAGCCCCGTGGAGCCCAGCCAAGAGCAGGACATCCTAAC<br>CAGCATGGAGGCCTCTGGCCACCTCAGCACAAATCTCTGG<br>CATGCTGTCACTGATGATGACACAGGTCAGAAAGAAATAC<br>CCATTTCTGAACGTGTCTTGGGGAGTGTGGGAGGACAGCT<br>GACTCCGGTCTCTGCCTTGGCAGCCAGCACTCACAAGCCC<br>TGGCTTGAGCAGCCTCCACGGGATCAGACATTGACGTCCA<br>GCGATGAGGAGGACATCTATGCCCACGGGCTTCCTTCTTC<br>ATCCTCAGAGACGAGTGTGACAGAGCTCGGACCTAGTTGC<br>TCCCAGCAGGACCTGAGCCGGCTGGGTGCAGAGGACGCCG<br>GGCTGCTCAAGCCAGATCAGTTTGCAGAAAGCTGGATGGG<br>CTACTCGGGTCCCGGCTATGGCATCCTCAGCTTGGTGGTC<br>TCCGAGAAGTATATCTGGTGCCTGGACTACAAAGGCGGCC<br>TGTTCTGCAGCGCGTTGCCGGGCGCCGGGCTGCGCTGGCA<br>GAAGTTTGAAGATGCTGTCCAGCAGGTGGCAGTCTCGCCC<br>TCAGGAGCCCTTCTCTGGAAGATTGAACAGAAATCTAACC<br>GGGCTTTTGCTTGTGGGAAAGTCACCATCAAGGGGAAGCG<br>GCACTGGTACGAAGCCCTGCCCCAGGCAGTGTTTGTGGCC<br>CTGAGCGATGACACGGCCTGGATCATCAGGACCAGTGGGG<br>ACCTATACTTGCAGACAGGTCTGAGCGTGGATCGCCCTTG<br>TGCCAGAGCCGTAAAGGTGGACTGTCCCTACCCGCTGTCC<br>CAGATCACAGCCCGGAACAATGTGGTGTGGGCGCTGACAG<br>AGCAGAGGGCCCTCCTGTACCGGGAGGGCGTGAGCAGCTT<br>CTGTCCGGA<u>AGGCGAGCAGTGGAAGTGTGACATTGTCAGC<br>GAAAGGCAAGCTTTAGAACCCGTCTGCATAACGCTCGGGG</u><br>ATCAGCAGACTCTCTGGGCCCTGGACATCCATGGGAACCT<br>GTGGTTCAGAACTGGCATTATTTCCAAGAAGCCCCAAGGA<br>GATGACGACCATTGGTGGCAAGTGAGCATCACGGACTATG<br>TGGTGTTTGACCAGTGCAGCTTATTTCAGACGATAATCCA<br>TGCCACTCACTCGGTGGCCACAGCAGCCCAAGCCCCCGTA<br>GAAAAGGTGGCAGATAAGCTGCGCATGGCGTTTTGGTCCC<br>AGCAGCTTCAGTGCCAGCCAAGCCTTCTCGGGGTCAATAA<br>CAGCGGTGTCTGGATCTCCTGGGCAAGAATGAATTCCAC<br>GTCGCTAAGGGAAGTCTCATAGGCACCTACTGGAATCATG | |

TABLE 1-continued

GEP-NEN Biomarker/Houskeeper Sequence Information

| Gene Name | RefSeq Accession | Sequence | SEQ ID NO: |
|---|---|---|---|
| | | TGGTTCCCCGTGGGACAGCTTCTGCTACAAAATGGGCCTT<br>TGTGTTGGCTTCTGCAGCTCCCACGAAGGAAGGAAGCTTC<br>CTGTGGCTGTGCCAGAGCAGCAAGGACCTGTGCAGCGTCA<br>GCGCCCAGAGCGCACAGTCGCGGCCCTCCACGGTGCAGCT<br>GCCTCCCGAAGCCGAGATGCGCGCCTATGCCGCCTGCCAG<br>GATGCGCTGTGGGCGCTGGACAGCCTCGGCCAGGTGTTCA<br>TCAGGACGCTCTCCAAGAGCTGCCCCACGGGCATGCACTG<br>GACCAGGCTGGACCTCTCCCAGCTAGGAGCTGTAAAATTG<br>ACAAGCTTGGCATGTGGAAATCAGCACATCTGGGCCTGTG<br>ATTCCAGGGGTGGAGTTTACTTCCGTGTAGGGACTCAGCC<br>TCTCAATCCCAGTCTCATGCTTCCAGCCTGGATAATGATT<br>GAGCCACCTGTCCAGGTAAGCAGAAGTTAGCTGGTGGAAC<br>TCACTCTTCAGTAAGACAGAAACTGTGAGGATGCTGGTAC<br>TGGGAAAAAGGATCTGCACAGCCTCTAGAGGCCTCCCAGC<br>AAATGCGGGGAGCCATGCCCCCAGGGTCTACACACTCTCG<br>TTCATCAACATCACAACTGGAATTCGGGATTTGTGAAGTT<br>TAGAGCTGAACAGACTGTTACAGATTATGAGTCAACACGT<br>ATATTTTCTCTTTCAAAATAATAATATTTCGTTTTTGACT<br>TTTTACTAAGTGAATATTATTTTTAAATCTGCCTATATA<br>TTGGAACCTCTATTTTATAATAATAATGATAATAAATCAG<br>TACCCAGAAGTATAAAGAAGGTAAAAGTTACTTTGAAAAA<br>AAAAAAAAAAAAAAAAAAAAAAAAA | |
| TPH1 | NM_004179.2 | TTTTAGAGAATTACTCCAAATTCATCATGATTGAAGACAA<br>TAAGGAGAACAAAGACCATTCCTTAGAAAGGGG<u>GAAGAGCA</u><br><u>AGTCTCATTTTTTCCTTAAAGAATGAAGTTGGAGGACTTA</u><br><u>TAAAAGCCCTGAAAATCTTTCAGGAGAAGCATGTGAATCT</u><br><u>GTTACATATCGAGTCCCGAAATCAAAAAGAAGAAACTCA</u><br><u>GAATTTGAGATTTTTGTTGACTGTGCACATCAACAGAGAAC</u><br>AATTGAATGATATTTTCATCTGCTGAAGTCTCATACCAA<br>TGTTCTCTCTGTGAATCTACCAGATAATTTTACTTTGAAG<br>GAAGATGGTATGGAAACTGTTCCTTGGTTTCCAAAGAAGA<br>TTTCTGACCTGGACCATTGTGCCAACAGAGTTCTGATGTA<br>TGGATCTGAACTAGATGCAGACCATCCTGGCTTCAAAGAC<br>AATGTCTACCGTAAACGTCGAAAGTATTTTGCGGACTTGG<br>CTATGAACTATAAACATGGAGACCCCATTCCAAAGGTTGA<br>ATTCACTGAAGAGGAGATTAAGACCTGGGGAACCGTATTC<br>CAAGAGCTCAACAAACTCTACCCAACCCATGCTTGCAGAG<br>AGTATCTCAAAAACTTACCTTTGCTTTCTAAATATTGTGG<br>ATATCGGGAGGATAATATCCCACAATTGGAAGATGTCTCC<br>AACTTTTTAAAAGAGCGTACAGGTTTTTCCATCCGTCCTG<br>TGGCTGGTTACTTATCACCAAGAGATTTCTTATCAGGTTT<br>AGCCTTTCGAGTTTTTCACTGCACTCAATATGTGAGACAC<br>AGTTCAGATCCCTTCTATACCCCAGAGCCAGATACCTGCC<br>ATGAACTCTTAGGTCATGTCCCGCTTTTGGCTGAACCTAG<br>TTTTGCCCAATTCTCCCAAGAAATTGGCTTGGCTTCTCTT<br>GGCGCTTCAGAGGAGGCTGTTCAAAAACTGGCAACGTGCT<br>ACTTTTTCACTGTGGAGTTTGGTCTATGTAAACAAGATGG<br>ACAGCTAAGAGTCTTTGGTGCTGGCTTACTTTCTTCTATC<br>AGTGAACTCAAACATGCACTTTCTGGACATGCCAAAGTAA<br>AGCCCTTTGATCCAAGATTACCTGCAAACAGGAATGTCT<br>TATCACAACTTTTCAAGATGTCTACTTTGTATCTGAAAGT<br>TTTGAAGATGCAAAGGAGAAGATGAGAGAATTTACCAAAA<br>CAATTAAGCGTCCATTTGGAGTGAAGTATAATCCATATAC<br>ACGGAGTATTCAGATCCTGAAAGACACCAAGAGCATAACC<br>AGTGCCATGAATGAGCTGCAGCATGATCTCGATGTTGTCA<br>GTGATGCCCTTGCTAAGGTCAGCAGGAAGCCGAGTATCTA<br>ACAGTAGCCAGTCATCCAGGAACATTTGAGCATCAATTCG<br>GAGGTCTGGGCCATCTCTTGCTTTCCTTGAACACCTGATC<br>CTGGAGGGACAGCATCTTCTGGCCAAACAATATTATCGAA<br>TTCCACTACTTAAGGAATCACTAGTCTTTGAAAATTTGTA<br>CCTGGATATTCTATTTACCACTTATTTTTTGTTTAGTTT<br>TATTTCTTTTTTTTTGGTAGCAGCTTTAATGAGACAAT<br>TTATATACCATACAAGCCACTGACCACCCATTTTTAATAG<br>AGAAGTTGTTTGACCCAATAGATAGATCTAATCTCAGCCT<br>AACTCTATTTTCCCCAATCCTCCTTGAGTAAAATGACCCT<br>TTAGGATCGCTTAGAATAACTTGAGGAGTATTATGGCGCT<br>GACTCATATTGTTACCTAAGATCCCCTTATTTCTAAAGTA<br>TCTGTTACTTATTGC | 44 |
| TRMT112 | NM_016404.2 | GGCCACCCGCAGAACAGAGCTTCCGGGACCCACGCCTCGT<br>TTGC<u>ACTGGGTGCTGGACAGCCGACGCAACTACAAATGGG</u><br><u>GCGGAGCTTTCGGCACTGGAGCAGCTAATTTGCATATAGG</u><br><u>AATGAGGTGCGGCTCGGCTTCCATGGGCCTAATTTACAGA</u><br>TAGGGCGGTATTTCTGCCCCTTAACCGAAAGTGGGATACA | 45 |

TABLE 1-continued

GEP-NEN Biomarker/Houskeeper Sequence Information

| Gene Name | RefSeq Accession | Sequence | SEQ ID NO: |
|---|---|---|---|
| | | GAGGACGACGGTGTTAGGCGCCTGTGTAGGAGTAAAATGT GTTTATTTTGCATTCAACGAGAGCTCCTGCATTGCAGCTA TTTTGCATATGATTTGCATCTTACGAAGAATTTGTGGCAA AAAAAAGCTGGGCGTGCGCCGTAGGAACCTCCTGCTGAGA CGCTTCCGGTAGCGGCGCGTGACCCGACAGGTCTTTCACC TACCTACCTCAGCTCCCACAAACACGAGAAGTTCCAGCAA GTTCGCCACTTCCGGTTCTCCTGGCTATCCAATAGCATCG AGAGGAGCATCCCCGGAAGTGAGGCAGCGGAGGACGACCT TTTTCCGGTTCCGGCCTGGCGAGAGTTTGTGCGGCGACAT GAAACTGCTTACCCACAATCTGCTGAGCTCGCATGTGCGG GGGGTGGGGTCCCGTGGCTTCCCCCTGCGCCTCCAGGCCA CCGAGGTCCGTATCTGCCCTGTGGAATTCAACCCCAACTT CGTGGCGCGTATGATACCTAAAGTGGAGTGGTCGGCGTTC CTGGAGGCGGCCGATAACTTGCGTCTGATCCAGGTGCCGA AAGGGCCGGTTGAGGGATATGAGGAGAATGAGGAGTTTCT GAGGACCATGCACCACCTGCTGCTGGAGGTGGAAGTGATA GAGGGCACCCTGCAGTGCCCGGAATCTGGACGTATGTTCC CCATCAGCCGCGGGATCCCCAACATGCTGCTGAGTGAAGA GGAAACTGAGAGTTGATTGTGCCAGGCGCCAGTTTTTCTT GTTATGACTGTGTATTTTTGTTGATCTATACCCTGTTTCC GAATTCTGCCGTGTGTATCCCCAACCCTTGACCCAATGAC ACCAAACACAGTGTTTTTGAGCTCGGTATTATATATTTTT TTCTCATTAAAGGTTTAAAACCAAAAGCGGTTTCTCTTTG CAGCAAATATACATTAAAATAGAGTCTCTGTACAGCCAAG GGCTCTGGGCCCTGGCTTGCCCCATGTCCCTGCGCCTCCC TGGCCAAACCCAAAAATAAATATAGTGTTATTGCTCTGCA GGGCATAGAGGCAGTGCTCTCCTACCCCCTGAGGAGGCTC GTTGGGAGCTGATGGGGAAGCCCTG | |
| VMAT1 | NM_003053.3 | CACACACACACATACACAGAATCCTCAGATAACAGGAGGC AATAAATCCAACAGCACATCCACGTTCAGAGAACAGTGTC CCTGCTGTCTTGCTAACAGCTGCCAATACCTCACTGAGTG CCTCACACCAACATGGGCTCCAAGTGAGTTTCCTTCGTCT GGGCAGACTCCCTCCCCTCTTCCATAAAGGCTGCAGGAGA CCTGTAGCTGTCACAGGACCTTCCCTAAGAGCCCGCAGGG GAAGACTGCCCCAGTCCGGCCATCACCATGCTCCGGACCA TTCTGGATGCTCCCCAGCGGTTGCTGAAGGAGGGGAGAGC GTCCCGGCAGCTGGTGCTGGTGGTGGTATTCGTCGCTTTG CTCCTGGACAACATGCTGTTTACTGTGGTGGTGCCAATTG TGCCCACCTTCCTATATGACATGGAGTTCAAAGAAGTCAA CTCTTCTCTGCACCTCGGCCATGCCGGAAGTTCCCCACAT GCCCTCGCCTCTCCTGCCTTTTCCACCATCTTCTCCTTCT TCAACAACAACACCGTGGCTGTTGAAGAAAGCGTACCTAG TGGAATAGCATGGATGAATGACACTGCCAGCACCATCCCA CCTCCAGCCACTGAAGCCATCTCAGCTCATAAAAACAACT GCTTGCAAGGCACAGGTTTCTTGGAGGAAGAGATTACCCG GGTCGGGGTTCTGTTTGCTTCAAAGGCTGTGATGCAACTT CTGGTCAACCCATTCGTGGGCCCTCTCACCAACAGGATTG GATATCATATCCCCATGTTTGCTGGCTTTGTTATCATGTT TCTCTCCACAGTTATGTTTGCTTTTTCTGGGACCTATACT CTACTCTTTGTGGCCCGAACCCTTCAAGGCATTGGATCTT CATTTTCATCTGTTGCAGGTCTTGGAATGCTGGCCAGTGT CTACACTGATGACCATGAGAGAGGACGAGCCATGGGAACT GCTCTGGGGGCCTGGCCTTGGGGTTGCTGGTGGGAGCTC CCTTTGGAAGTGTAATGTACGAGTTTGTTGGGAAGTCTGC ACCCTTCCTCATCCTGGCCTTCCTGGCACTACTGGATGGA GCACTCCAGCTTTGCATCCTACAGCCTTCCAAAGTCTCTC CTGAGAGTGCCAAGGGGACTCCCCTCTTTATGCTTCTCAA AGACCCTTACATCCTGGTGGCTGCAGGGTCCATCTGCTTT GCCAACATGGGGTGGCCATCCTGGAGCCCACACTGCCCA TCTGGATGATGCAGACCATGTGCTCCCCCAAGTGGCAGCT GGGTCTAGCTTTCTTGCCTGCCAGTGTGTCCTACCTCATT GGCACCAACCTCTTTGGTGTGTTGGCAACAAGATGGGTC GGTGGCTGTGTTCCCTAATCGGGATGCTGGTAGTAGGTAC CAGCTTGCTCTGTGTTCCTCTGGCTCACAATATTTTGGT CTCATTGGCCCCAATGCAGGGCTTGGCCTTGCCATAGGCA TGGTGGATTCTTCTATGATGCCCATCATGGGGCACCTGGT GGATCTACGCCACACCTCGGTGTATGGGAGTGTCTACGCC ATCGCTGATGTGGCTTTTTGCATGGGCTTTGCTATAGGTC CATCCACCGGTGGTGCCATTGTAAAGGCCATCGGTTTTCC CTGGCTCATGGTCATCACTGGGGTCATCAACATCGTCTAT GCTCCACTCTGCTACTACCTGCGGAGCCCCCCGGCAAAGG AAGAGAAGCTTGCTATTCTGAGTCAGGACTGCCCCATGGA GACCCGGATGTATGCAACCCAGAAGCCCACGAAGGAATTT CCTCTGGGGGAGGACAGTGATGAGGAGCCTGACCATGAGG | 46 |

TABLE 1-continued

GEP-NEN Biomarker/Houskeeper Sequence Information

| Gene Name | RefSeq Accession | Sequence | SEQ ID NO: |
|---|---|---|---|
| | | AGTAGCAGCAGAAGGTGCTCCTTGAATTCATGATGCCTCA<br>GTGACCACCTCTTTCCCTGGGACCAGATCACCATGGCTGA<br>GCCCACGGCTCAGTGGGCTTCACATACCTCTGCCTGGGAA<br>TCTTCTTTCCTCCCCTCCCATGGACACTGTCCCTGATACT<br>CTTCTCACCTGTGTAACTTGTAGCTCTTCCTCTATGCCTT<br>GGTGCCGCAGTGGCCCATCTTTTATGGGAAGACAGAGTGA<br>TGCACCTTCCCGCTGCTGTGAGGTTGATTAAACTTGAGCT<br>GTGACGGGTTCTGCAAGGGGTGACTCATTGCATAGAGGTG<br>GTAGTGAGTAATGTGCCCCTGAAACCAGTGGGGTGACTGA<br>CAAGCCTCTTTAATCTGTTGCCTGATTTTCTCTGGCATAG<br>TCCCAACAGATCGGAAGAGTGTTACCCTCTTTTCCTCAAC<br>GTGTTCTTTCCCGGGTTTTCCCAGCCGAGTTGAGAAAATG<br>TTCTCAGCATTGTCTTGCTGCCAAATGCCAGCTTGAAGAG<br>TTTTGTTTTGTTTTTTTTCATTTATTTTTTTTTTAATAA<br>AGTGAGTGATTTTCTGTGGCTAAATCTAGAGCTGCTAAA<br>AGGGCTTTACCCTCAGTGAAAAGTGTCTTCTATTTTCATT<br>ATCTTTCAGAAACAGGAGCCCATTTCTCTTCTGCTGGAGT<br>TATTGACATTCTCCTGACCTCCCCTGTGTGTTCCTACCTT<br>TTCTGAACCTCTTAGACTCTTAGAAATAAAAGTAGAAGAA<br>AGACAGAAAAAATAACTGATTAGACCCAAGATTTCATGGG<br>AAGAAGTTAAAAGAAACTGCCTTGAAATCCCTCCTGATTG<br>TAGATTTCCTAACAGGAGGGGTGTAATGTGACATTGTTCA<br>TACTTGCTAATAAATACATTATTGCCTAATTCAAAAAAAA<br>AAAAAAAAA | |
| VMAT2 | NM_003054.4 | AGAGCCGGACGGGGTAAACTGAGCGGCGGCGGCGGGGCGC<br>TGGGGCGGAGACTGCGACCCGGAGCCGCCCGGACTGACGG<br>AGCCCACTGCGGTGCGGGCGTTGGCGCGGGCACGGAGGAC<br>CCGGGCAGGCATCGCAAGCGACCCCGAGCGGAGCCCCGGA<br>GCCATGGCCCTGAGCGAGCTGGCGCTGGTCCGCTGGCTGC<br>AGGAGAGCCGCCGCTCGCGGAAGCTCATCCTGTTCATCGT<br>GTTCCTGGCGCTGCTGCTGGACAACATGCTGCTCACTGTC<br>GTGGTCCCCATCATCCCAAGTTATCTGTACAGCATTAAGC<br>ATGAGAAGAATGCTACAGAAATCCAGACGGCCAGGCCAGT<br>GCACACTGCCTCCATCTCAGACAGCTTCCAGAGCATCTTC<br>TCCTATTATGATAACTCGACTATGGTCACCGGGAATGCTA<br>CCAGAGACCTGACACTTCATCAGACCGCCACACAGCACAT<br>GGTGACCAACGCGTCCGCTGTTCCTTCCGACTGTCCCAGT<br>GAAGACAAAGACCTCCTGAATGAAAACGTGCAAGTTGGTC<br>TGTTGTTTGCCTCGAAAGCCACCGTCCAGCTCATCACCAA<br>CCCTTTCATAGGACTACTGACCAACAGAATTGGCTATCCA<br>ATTCCCATATTTGCGGGATTCTGCATCATGTTTGTCTCAA<br>CAATTATGTTTGCCTTCTCCAGCAGCTATGCCTTCCTGCT<br>GATTGCCAGGTCGCTGCAGGGCATCGGCTCGTCCTGCTCC<br>TCTGTGGCTGGGATGGGCATGCTTGCCAGTGTCTACACAG<br>ATGATGAAGAGAGGCAACGTCATGGGAATCGCCTTGGG<br>AGGCCTGGCCATGGGGGTCTTAGTGGGCCCCCCCTTCGGG<br>AGTGTGCTCTATGAG<u>TTTGTGGGGAAGACGGCTCCGTTCC</u><br>TGGTGCTGGCCGCCCTGGTACTCTTGGATGGAGCTATTCA<br>GCTCTTTGTGCTCCAGCCGTCCCGGGTGCAGCCAGAGAGT<br>CAGAAGGGGACACCCCTAACCACGCTGCTGAAGGACCCGT<br>ACATCCTCATTGCTGCAGGCTCCATCTGCTTTGCAAACAT<br>GGGCATCGCCATGCTGGAGCCAGCCCTGCCCATCTGGATG<br>ATGGAGACCATGTGTTCCCGAAAGTGGCAGCTGGGCGTTG<br>CCTTCTTGCCAGCTAGTATCTCTTATCTCATTGGAACCAA<br>TATTTTTGGGATACTTGCACACAAAATGGGGAGGTGGCTT<br>TGTGCTCTTCTGGGAATGATAATTGTTGGAGTCAGCATTT<br>TATGTATTCCATTTGCAAAAAACATTTATGGACTCATAGC<br>TCCGAACTTTGGAGTTGGTTTTGCAATTGGAATGGTGGAT<br>TCGTCAATGATGCCTATCATGGGCTACCTCGTAGACCTGC<br>GGCACGTGTCCGTCTATGGGAGTGTGTACGCCATTGCGGA<br>TGTGGCATTTTGTATGGGTATGCTATAGGTCCTTCTGCT<br>GGTGGTGCTATTGCAAAGGCAATTGGATTTCCATGGCTCA<br>TGACAATTATTGGGATAATTGATATTCTTTTTGCCCCTCT<br>CTGCTTTTTCTTCGAAGTCCACCTGCCAAAGAAGAAAA<br>ATGGCTATTCTCATGGATCACAACTGCCCTATTAAAACAA<br>AAATGTACACTCAGAATAATATCCAGTCATATCCGATAGG<br>TGAAGATGAAGAATCTGAAAGTGACTGAGATGAGATCCTC<br>AAAAATCATCAAAGTGTTTAATTGTATAAAACAGTGTTTC<br>CAGTGACACAACTCATCCAGAACTGTCTTAGTCATACCAT<br>CCATCCCTGGTGAAAGAGTAAAACCAAAGGTTATTATTTC<br>CTTTCCATGGTTATGGTCGATTGCCAACAGCCTTATAAAG<br>AAAAAGAAGCTTTTCTAGGGGTTTGTATAAATAGTGTTGA<br>AACTTTATTTTATGTATTTAATTTTATTAAATATCATACA<br>ATATATTTTGATGAAATAGGTATTGTGTAAATCTATAAAT | 47 |

TABLE 1-continued

GEP-NEN Biomarker/Houskeeper Sequence Information

| Gene Name | RefSeq Accession | Sequence | SEQ ID NO: |
|---|---|---|---|
| | | ATTTGAATCCAAACCAAATATAATTTTTTAACTTACATTA<br>ACAAACATTTGGGCAAAAATCATATTGGTAATGAGTGTTT<br>AAAATTAAAGCACACATTATCTCTGAGACTCTTCCAACAA<br>AGAGAAACTAGAATGAAGTCTGAAAAACAGAATCAAGTAA<br>GACAGCATGTTATATAGTGACACTGAATGTTATTTAACTT<br>GTAGTTACTATCAATATATTTATGCGTTAAACAGCTAGTT<br>CTCTCAAGTGTAGAGGACAAGAACTTGTGTCAGTTATCTT<br>TTGAATCCATAAATCTTAGCTGGCATTAGTTTTCTATGTA<br>ATCACCTACCTAGAGAGAGTTGTAAATTATATGTTAACAT<br>GTTATCTGGTTGGCAGCAAACACTAAAGCCAATAAAGGAA<br>AAACAGTAAATGTTCCGAAAGCAGAGAAAAGCAACCAAAC<br>ATATTGTTATGAACTAAAAGCTTTCCCTTTAAGATGCATA<br>CTTGTCTTACTGGATGAAGAAAATTGAGGGTACATGTACC<br>TTATACTGTCAAGGTTGTTTAAACATGATAAGGTTAATCG<br>CCATCTACTTCAAGTTTTAGAAAAGGAAACAAGAAGCTGA<br>AAACAGCTGCTCTGACTTTAATATCTGACTATATCTTTGA<br>TCTGTTTGCAGGTCATCCAAGTGTTTTCTAGGAATATATT<br>TATTTTAGGTTGTCTGAAACTACTATTTTTTAGACTCCTG<br>AAAGTTGTTCACATCAATGTGAAGACAAATTTTAAATGAA<br>AATGAAGAATGAAATTATGTCTTGAATCATATATTAAGAA<br>GTAAAAATAATAGTGATCAGGCAGAAAAGAAAAATGGAAC<br>ATCTAAAAATGTATGTGCTAACTATATCATCCAGTGTGCA<br>GTGTTGTGTATTTTTCTAAGCATGACAACATTGATGTGCC<br>TTTTCAGTGTAACAGCAAATACTGTTAGTGAACATTGTCA<br>ATTTATGTCATTTTGTTAAGAGATATGACTGGAGTGTGCA<br>GTGTGGAATGTCTCTAATACTACTTGTGAATCCTGCAGTT<br>CTATAATCATAAACAAAAATTACTTAGTTTCGTTAAGCTA<br>AGATTGTGTTTGTGTTAACTTCGACATCAAGGAGCAAAGA<br>ACTTTAGAACAGACTCCTCAATCTTGTGACTTTCTTATTC<br>TCTAGGAAAGTAACACTTCGTTTCATGAAGCTTTTCTGTG<br>GGGCTTCGATTATTTCAAGTCTGGTTTCTAAGTGCAGTGT<br>GTTTGAAGCAAACGAACTTCCAACTCACTTATTTGGCATT<br>GGGCAACTTGGCCAAGTCTGCCACTTTGGAAGATGGCTCT<br>GGAGGAAACTCTCATATGGCTAAAAAGGCAGGCTAGTTTC<br>TTACTTCTACAGGGGTAGAGCCTTAAAAAAGAACGTGCTA<br>CAAATTGGTTCTCTTTGAGGGTTTCTGGTTCTCCCTGCCC<br>CCAATACCATATACTTTATTGCAATTTTATTTTTGCCTTT<br>ACGGCTCTGTGTCTTTCTGCAAGAAGGCCTGGCAAAGGTA<br>TGCCTGCTGTTGGTCCCTCGGGATAAGATAAAATATAAAT<br>AAAACCTTCAGAACTGTTTTGGAGCAAAAGATAGCTTGTA<br>CTTGGGGAAAAAAATTCTAAGTTCTTTTATATGACTAATA<br>TTCTTGGTTAGCAAGACTGGAAAGAGGTGTTTTTTTAAAA<br>TGTACATACCAGAACAAAGAACATACAGCTCTCTGAACAT<br>TTATTTTTTGAACAGAGGTGGTTTTATGTTTGGACCTGG<br>TAATACAGATACAAAAACTTTAATGAGGTAGCAATGAATA<br>TTCAACTGTTTGACTGCTAAGTGTATCTGTCCATATTTTA<br>GCAAGTTTACTTAATAAATCTTCTGAACCATGAAAAAAAA<br>AAAAA | |
| VPS13C | NM_001018088.2 | CCGGAGGGGCTGTCATTTGCAGCGCTGGTCGCAGCCCTCA<br>GCTGCGCCGGGCGGTTCCGGCTCCTCCCTCTCCTTGTGCC<br>TCAGCGCCACCATGGTGCTGGAGTCGGTGGTCGCGGACTT<br>GCTGAACCGCTTCCTGGGGGACTATGTGGAGAACCTGAAC<br>AAGTCCCAGCTGAAGCTGGGCATCTGGGGCGGAAATGTGG<br>CTTTAGATAATCTACAGATAAAAGAAAATGCCCTGAGTGA<br>ATTGGATGTTCCTTTTAAAGTCAAGGCTGGCCAAATTGAT<br>AAATTAACTTTGAAGATTCCTTGGAAGAACCTTTATGGAG<br>AAGCAGTTGTTGCGACCCTGGAAGGATTATACCTGCTTGT<br>TGTCCCTGGAGCAAGTATTAAGTATGATGCTGTAAAAGAA<br>GAAAAATCCTTGCAGGATGTTAAACAGAAAGAGCTATCCC<br>GAATTGAAGAAGCCCTTCAAAAAGCAGCAGAAAAGGCAC<br>ACATTCAGGGGAGTTCATATATGGCTTGGAGAACTTTGTT<br>TACAAGGACATCAAGCCTGGACGTAAACGTAAAAAGCACA<br>AAAAACATTTTAAGAAACCTTTTAAAGGTCTTGATCGTTC<br>AAAAGATAAGCCAAAAGAAGCCAAAAAGGATACATTTGTG<br>GAAAAATTGGCAACTCAAGTAATAAAAAATGTACAAGTAA<br>AAATCACAGATATTCACATTAAATATGAAGATGATGTCAC<br>TGATCCAAAGCGGCCTCTTTCATTTGGTGTCACACTGGGA<br>GAGCTTAGTCTACTGACTGCAAATGAACACTGGACTCCAT<br>GCATATTAAATGAAGCAGACAAAATTATATACAAGCTTAT<br>ACGACTTGATAGTCTTAGCGCCTACTGGAATGTAAATTGC<br>AGCATGTCTTACCAGAGATCAAGGGAACAGATTTTGGATC<br>AGCTGAAAATGAAATTCTTACAAGTGGAAATATACCCCC<br>AAATTATCAATACATTTTCCAGCCAATATCAGCCTCTGCA<br>AAACTCTACATGAATCCTTATGCAGAATCAGAGCTCAAAA | 48 |

TABLE 1-continued

GEP-NEN Biomarker/Houskeeper Sequence Information

| Gene Name | RefSeq Accession | Sequence | SEQ ID NO: |
|---|---|---|---|
| | | CGCCCAAACTGGATTGCAACATAGAAATACAAAATATTGC | |
| | | CATTGAACTGACCAAACCTCAGTACTTAAGTATGATTGAC | |
| | | CTTTTGGAGTCAGTGGATTATATGGTTAGGAATGCGCCTT | |
| | | ATAGGAAATACAAGCCTTATTTACCACTTCATACCAATGG | |
| | | TCGACGATGGTGGAAATATGCAATTGATTCTGTTCTTGAA | |
| | | GTTCATATAAGAAGGTATACACAGATGTGGTCATGGAGTA | |
| | | ACATAAAAAAGCACAGGCAGTTACTCAAGAGTTATAAAAT | |
| | | TGCCTACAAAAACAAGTTAACACAGTCTAAAGTCTCAGAA | |
| | | GAAATACAGAAAGAAATTCAGGACTTGGAGAAGACTCTAG | |
| | | ATGTTTTTAACATAATTTTAGCAAGGCAACAAGCACAAGT | |
| | | TGAGGTGATTCGGTCTGGGCAAAAATTAAGGAAAAAGTCT | |
| | | GCTGACACAGGCGAGAAACGTGGAGGCTGGTTTAGTGGGT | |
| | | TGTGGGGTAAGAAAGAGTCTAAGAAAAAGGACGAAGAATC | |
| | | ATTGATTCCTGAAACTATTGATGACCTTATGACTCCAGAG | |
| | | GAAAAAGATAAACTCTTCACTGCCATTGGTTATAGTGAGA | |
| | | GTACCCACAACCTAACTTTACCTAAGCAGTATGTTGCCCA | |
| | | TATTATGACCCTGAAGTTAGTAAGCACCTCTGTTACGATA | |
| | | AGAGAAAACAAGAATATTCCAGAAATACTAAAAATTCAGA | |
| | | TAATTGGCCTGGGCACTCAAGTATCTCAGCGACCAGGAGC | |
| | | ACAAGCACTTAAGGTAGAAGCGAAATTAGAACACTGGTAT | |
| | | ATAACAGGTTTGAGACAGCAGGATATTGTGCCATCACTTG | |
| | | TGGCTTCAATTGGTGACACTACATCATCCTTGCTTAAAAT | |
| | | TAAATTTGAAACCAATCCGGAGGATAGTCCTGCTGACCAG | |
| | | ACTCTGATTGTTCAGTCCCAGCCTGTGGAGGTCATCTATG | |
| | | ATGCTAAAACTGTCAATGCAGTGGTTGAATTCTTTCAATC | |
| | | AAATAAGGGATTGGATCTTGAGCAAATAACATCAGCAACA | |
| | | TTGATGAAGCTGGAAGAAATTAAGGAGAGAACAGCTACAG | |
| | | GACTTACACATATTATTGAAACTCGAAAAGTCCTTGATTT | |
| | | AAGGATAAATCTGAAGCCTTCTTATCTAGTAGTTCCACAG | |
| | | ACGGGTTTCCACCATGAAAAGTCAGATCTTCTGATTTTAG | |
| | | ATTTTGGTACATTTCAGCTCAACAGTAAAGATCAAGGTTT | |
| | | ACAGAAGACTACTAATTCATCTCTGGAAGAAATAATGGAT | |
| | | AAGGCATATGACAAGTTTGATGTTGAAATAAAAAATGTAC | |
| | | AACTACTTTTTGCAAGAGCAGAGGAAACCTGGAAAAAGTG | |
| | | TCGATTTCAGCATCCATCAACTATGCATATATTGCAACCC | |
| | | ATGGATATTCATGTTGAGTTGGCTAAGGCCATGGTAGAAA | |
| | | AAGACATTAGAATGGCCAGATTTAAAGTGTCAGGAGGACT | |
| | | TCCTTTGATGCATGTGAGAATTTCTGACCAGAAGATGAAA | |
| | | GATGTGCTATATTTGATGAACAGTATACCTTTGCCACAGA | |
| | | AATCATCAGCCCAGTCTCCAGAGAGACAGGTATCCTCAAT | |
| | | TCCTATTATTTCAGGTGGTACAAAAGGTCTACTTGGTACT | |
| | | TCACTATTGCTAGACACTGTGGAATCAGAGTCTGATGATG | |
| | | AGTATTTTGATGCTGAAGATGGAGAACCACAGACTTGTAA | |
| | | AAGTATGAAAGGATCAGAACTTAAAAAAGCTGCAGAGGTC | |
| | | CCAAATGAGGAGCTCATCAATCTTCTACTCAAGTTTGAAA | |
| | | TTAAAGAAGTGATTTTGGAATTTACTAAACAGCAGAAAGA | |
| | | AGAAGATACAATTCTAGTATTTAATGTTACTCAGTTAGGA | |
| | | ACAGAGGCCACAATGAGAACATTTGACTTAACTGTGGTAT | |
| | | CTTATTTAAAGAAAATCAGCTTGGATTATCATGAAATTGA | |
| | | AGGATCCAAAAGGAAGCCCCTTCACTTGATTAGCTCTTCT | |
| | | GACAAACCTGGATTAGATCTTTTGAAAGTGGAGTATATTA | |
| | | AGGCTGATAAGAATGGACCTAGTTTTCAAACTGCTTTTGG | |
| | | AAAAACTGAACAAACAGTTAAGGTGGCCTTTTCATCTTTA | |
| | | AATCTGTTGCTGCAAACACAAGCTCTTGTCGCTTCTATTA | |
| | | ATTACCTCACAACCATTATTCCATCTGATGATCAAAGCAT | |
| | | AAGTGTTGCTAAGGAGGTACAAATTTCAACTGAAAAACAA | |
| | | CAAAAAAATTCAACTCTGCCAAAAGCGATTGTATCCTCCA | |
| | | GAGATAGTGACATTATTGATTTCAGGCTATTTGCCAAGTT | |
| | | GAATGCTTTCTGTGTCATTGTTTGCAACGAAAAGAACAAT | |
| | | ATCGCCGAAATCAAGATTCAAGGACTGGATTCCTCCCTTT | |
| | | CTCTCCAGTCAAGAAAGCAGTCACTTTTTGCCCGACTAGA | |
| | | AAATATTATTGTCACAGATGTTGATCCAAAGACAGTTCAT | |
| | | AAGAAAGCTGTGTCAATAATGGGAAATGAAGTTTTCCGTT | |
| | | TTAATTTGGATTTGTATCCAGATGCTACTGAGGGGGATTT | |
| | | GTATACTGACATGTCCAAAGTGGATGGTGTGCTGTCTCTG | |
| | | AATGTTGGCTGTATTCAGATTGTCTATCTTCATAAATTCC | |
| | | TTATGTCACTTCTGAACTTCCTGAATAATTTCCAGACAGC | |
| | | CAAAGAGTCTCTGAGTGCTGCCACTGCCCAGGCTGCAGAA | |
| | | AGGGCTGCCACAAGTGTGAAAGATCTTGCCCAGAGGAGTT | |
| | | TTCGTGTTTCCATCAATATTGATTTGAAAGCACCGGTTAT | |
| | | AGTCATCCCACAGTCTTCTATTTCCACCAATGCAGTAGTG | |
| | | GTAGATCTTGGGTTAATCAGAGTTCATAATCAGTTCAGTC | |
| | | TGGTGTCTGATGAAGACTACTTAAATCCTCCAGTAATTGA | |
| | | TAGAATGGATGTGCAGCTAACAAAGCTTACACTTTATAGG | |
| | | ACAGTGATCCAGCCAGGCATCTACCATCCTGATATTCAGC | |

TABLE 1-continued

GEP-NEN Biomarker/Houskeeper Sequence Information

| Gene Name | RefSeq Accession | Sequence | SEQ ID NO: |
|---|---|---|---|
| | | TGTTGCACCCAATTAACTTGGAATTTCTTGTAAATCGGAA | |
| | | TCTAGCTGCATCTTGGTACCACAAGGTGCCTGTTGTGGAA | |
| | | ATTAAAGGACATCTTGATTCAATGAATGTTAGTCTAAATC | |
| | | AAGAAGATCTTAATCTTTTATTTAGGATACTAACAGAAAA | |
| | | TCTCTGTGAGGGTACTGAAGACTTGGATAAAGTGAAACCA | |
| | | AGAGTACAAGAGACAGGTGAAATTAAAGAGCCCCTTGAAA | |
| | | TCTCTATATCACAAGATGTACATGATTCAAAAAATACTTT | |
| | | AACAACTGGAGTGGAAGAAATTAGGTCTGTATAGACATCATT | |
| | | AATATGCTGCTGAATTTTGAAATTAAAGAGGTTGTGGTTA | |
| | | CTTTGATGAAAAAATCAGAAAAGAAAGGAAGGCCTTTACA | |
| | | TGAGCTAAATGTCCTGCAACTTGGAATGGAAGCTAAAGTT | |
| | | AAAACCTATGACATGACTGCTAAAGCTTATCTAAAAAAAA | |
| | | TTAGTATGCAGTGCTTTGATTTCACTGACTCTAAAGGGGA | |
| | | ACCTCTTCACATTATTAACTCTTCTAATGTGACTGACGAA | |
| | | CCCCTTCTGAAAATGTTACTGACAAAGGCAGACAGTGATG | |
| | | GACCAGAATTTAAAACTATTCATGACAGTACCAAACAGAG | |
| | | ACTGAAGGTTTCATTTGCATCCTTAGACTTAGTACTTCAT | |
| | | TTGGAAGCTTTACTTTCCTTCATGGATTTTTTATCATCTG | |
| | | CTGCTCCATTCTCTGAGCCTTCCTCTTCTGAGAAGGAATC | |
| | | CGAGCTGAAACCACTTGTGGGGAGTCCAGAAGTATCGCT | |
| | | GTCAAAGCTGTATCCAGCAACATTTCCCAAAAGGATGTGT | |
| | | TTGATTTAAAGATCACAGCTGAATTAAATGCATTTAATGT | |
| | | CTTTGTCTGTGATCAGAAGTGTAACATTGCAGATATTAAA | |
| | | ATACATGGAATGGATGCCTCTATTTCTGTGAAGCCTAAGC | |
| | | AGACTGATGTGTTTGCCAGACTTAAAGATATTATAGTTAT | |
| | | GAATGTAGATTTGCAGTCCATTCACAAAAAGGCTGTCTCT | |
| | | ATTTTGGGAGATGAAGTCTTTAGGTTCCAACTGACTCTTT | |
| | | ATCCAGATGCCACAGAAGGAGAGGCCTATGCTGATATGTC | |
| | | CAAAGTAGACGGCAAACTTAGTTTTAAAGTGGGTTGTATT | |
| | | CAGATTGTTTATGTTCATAAATTCTTCATGTCTCTTTTGA | |
| | | ACTTCCTCAACAATTTCCAAACTGCTAAAGAAGCTTTGAG | |
| | | TACAGCCACAGTCCAGGCTGCAGAAAGAGCTGCTTCCAGC | |
| | | ATGAAAGACTTGGCTCAAAAGAGTTTCCGCCTTTTGATGG | |
| | | ATATTAATTTGAAAGCACCAGTTATTATTATTCCTCAGTC | |
| | | TTCAGTATCACCTAATGCTGTTATAGCAGATCTGGGTTTA | |
| | | ATCAGAGTTGAAAACAAGTTTAGCTTGGTTCCTATGGAAC | |
| | | ATTATTCTCTTCCTCCAGTCATTGATAAAATGAACATCGA | |
| | | ACTCACTCAGTTGAAGCTGTCAAGAACTATTTTGCAGGCT | |
| | | AGCTTGCCACAAAATGACATTGAATTTTAAAACCAGTCA | |
| | | ACATGCTTTTGTCCATACAGCGAAACTTAGCAGCAGCATG | |
| | | GTATGTGCAAATTCCAGGGATGGAGATAAAAGGAAAACTA | |
| | | AAACCTATGCAGGTTGCTCTCAGTGAAGATGACTTGACAG | |
| | | TTTTAATGAAAATTTTGCTAGAAAATCTTGGAGAAGCTTC | |
| | | CTCACAACCAAGCCCTACACAGTCTGTGCAGGAGACTGTA | |
| | | AGAGTGAGAAAAGTTGATGTTTCAAGTGTACCTGACCATC | |
| | | TCAAAGAACAAGAAGATTGGACAGACTCAAAGCTCTCTAT | |
| | | GAACCAGATTGTCAGTCTCCAATTTGACTTTCACTTTGAA | |
| | | TCTCTTTCCATTATCCTTTATAACAATGATATCAACCAGG | |
| | | AATCTGGAGTTGCATTTCATAATGACAGTTTCCAACTTGG | |
| | | TGAACTCAGACTACATCTTATGGCCTCCTCAGGGAAGATG | |
| | | TTTAAGGATGGCTCAATGAATGTCAGCGTTAAACTTAAGA | |
| | | CATGCACCCTTGATGATCTCAGAGAAGGAATTGAGAGAGC | |
| | | AACATCGAGAATGATTGACAGAAAGAATGACCAAGATAAC | |
| | | AACAGTTCTATGATTGATATAAGTTACAAACAAGACAAAA | |
| | | ATGGAAGTCAAATTGATGCTGTTCTTGACAAGCTGTATGT | |
| | | ATGTGCCAGTGTGGAATTTCTGATGACTGTGGCAGATTTC | |
| | | TTTATCAAAGCTGTGCCTCAGAGTCCAGAAAATGTGGCAA | |
| | | AAGAAACACAGATTTTACCAAGACAGACTGCCACAGGGAA | |
| | | GGTCAAGATAGAGAAAGATGACTCTGTTAGACCAAATATG | |
| | | ACTTTAAAGGCCATGATCACAGATCCAGAAGTGGTATTTG | |
| | | TTGCCAGCCTGACAAAGGCTGATGCTCCTGCTCTGACAGC | |
| | | CTCGTTTCAGTGCAACCTTTCTCTGTCAACATCCAAACTC | |
| | | GAACAGATGATGGAAGCTTCTGTGAGAGATCTGAAAGTGC | |
| | | TCGCTTGCCCTTTTCTCAGAGAAAGAGAGGGAAAAACAT | |
| | | TACCACAGTCTTGCAGCCCTGTTCTTTATTTATGGAAAAA | |
| | | TGTACGTGGGCTTCAGGAAAGCAAATATAAATATTATGG | |
| | | TTAAAGAATTTATAATTAAGATTTCACCCATAATTCTTAA | |
| | | TACTGTGTTGACAATCATGGCTGCATTGTCTCCAAAAACA | |
| | | AAAGAAGATGGATCCAAAGATACGTCTAAGGAAATGGAAA | |
| | | ATCTTTGGGGTATCAAATCGATTAATGATTATAACACTTG | |
| | | GTTTCTTGGTGTTGACACGGCAACAGAAATAACGGAAAGC | |
| | | TTCAAAGGCATTGAACATTCACTGATAGAGGAAATTGTG | |
| | | GTGTTGTTGTAGAATCCATTCAAGTTACCTTAGAATGTGG | |
| | | CCTTGGACATCGAACTGTACCTTTATTATTGGCAGAGTCT | |
| | | AAGTTTTCAGGAAATATTAAAAATTGGACTTCTCTAATGG | |

TABLE 1-continued

GEP-NEN Biomarker/Housekeeper Sequence Information

| Gene Name | RefSeq Accession | Sequence | SEQ ID NO: |
|---|---|---|---|
| | | CTGCTGTTGCTGACGTGACACTACAGGTGCACTATTACAA<br>TGAGATCCATGCTGTCTGGGAGCCACTGATTGAGAGAGTG<br>GAGGGGAAGAGACAATGGAATTTAAGGCTTGATGTAAAGA<br>AGAACCCAGTTCAGGATAAAAGTTTGCTGCCAGGAGATGA<br>TTTTATTCCTGAGCCACAAATGGCAATTCATATTCTTCA<br>GGAAATACAATGAATATAACAATATCCAAAAGTTGTCTTA<br>ATGTTTTCAACAATTTAGCAAAAGGTTTTTCAGAGGGCAC<br>TGCTTCTACTTTTGACTACTCTTTAAAGGACAGAGCTCCT<br>TTTACGGTAAAAAATGCTGTAGGTGTTCCCATTAAGGTGA<br>AGCCCAATTGTAATCTCAGAGTAATGGGCTTCCCTGAGAA<br>AAGTGATATTTTTGATGTTGATGCTGGCCAGAATTTGGAA<br>CTGGAGTATGCCAGCATGGTACCTTCAAGTCAAGGGAACC<br>TATCTATATTGAGCCGTCAAGAAAGCTCCTTCTTCACTCT<br>GACCATTGTACCTCATGGATATACAGAAGTTGCAAATATC<br>CCTGTGGCCAGACCTGGACGGCGATTGTATAATGTACGGA<br>ATCCCAATGCCAGTCATTCTGACTCTGTCTTGGTACAAAT<br>TGATGCAACTGAAGGGAATAAAGTAATTACCCTTCGCTCT<br>CCTCTACAGATCAAAAACCATTTCTCCATTGCATTTATCA<br>TCTATAAATTTGTTAAGAATGTTAAGCTATTGGAGCGCAT<br>TGGGATAGCCAGACCTGAAGAGGAGTTCCATGTTCCTTTA<br>GATTCATATAGATGTCAATTGTTTATCCAGCCAGCTGGAA<br>TCTTAGAGCATCAGTACAAAGAATCTACCACTTATATTTC<br>CTGGAAGGAAGAACTTCATAGGAGCAGGGAAGTCAGATGC<br>ATGTTGCAGTGTCCATCAGTAGAAGTCAGCTTCTTACCTC<br>TCATAGTGAATACAGTTGCTCTGCCTGATGAATTGAGCTA<br>CATATGTACACATGGGGAAGACTGGGATGTAGCTTACATT<br>ATTCATCTTTATCCTTCTCTCACTTTGCGGAATCTTCTCC<br>CATATTCCCTAAGATATTTACTTGAGGGAACAGCAGAAAC<br>TCATGAGCTGGCAGAAGGCAGTACTGCTGATGTTCTGCAT<br>TCGAGAATCAGTGGTGAAATAATGGAATTAGTCCTGGTGA<br>AATACCAGGGCAAAAACTGGAATGGACATTTCCGCATACG<br>TGATACACTACCAGAATTCTTTCCTGTGTGTTTTTCTTCT<br>GACTCCACAGAAGTGACGACAGTCGACCTGTCAGTCCACG<br>TCAGGAGAATTGGCAGCCGGATGGTGCTGTCTGTCTTTAG<br>TCCCTATTGGTTAATCAACAAGACTACCCGGGTTCTCCAG<br>TATCGTTCAGAAGATATTCATGTGAAACATCCAGCTGATT<br>TCAGGGATATTATTTTATTTTCTTTCAAGAAGAAGAACAT<br>TTTTACTAAAAATAAGGTACAATTAAAAATTTCAACCAGT<br>GCCTGGTCCAGTAGTTTCTCATTGGATACAGTGGGAAGTT<br>ATGGGTGTGTGAAGTGTCCTGCCAACAATATGGAGTACCT<br>GGTTGGTGTTAGCATCAAAATGAGCAGTTTCAACCTTTCA<br>CGAATAGTTACCCTGACTCCCTTTTGTACCATTGCAAACA<br>AGTCATCATTAGAACTAGAAGTTGGCGAGATTGCATCTGA<br>TGGCTCAATGCCAACTAATAAATGGAACTATATTGCTTCT<br>TCAGAGTGCCTTCCATTTTGGCCAGAAAGTTTGTCAGGCA<br>AACTTTGTGTGAGAGTGGTGGGCTGTGAAGGATCTTCCAA<br>ACCATTCTTTTATAACCGACAGGATAATGGCACTTTATTG<br>AGCTTAGAAGATCTGAATGGGGGTATCTTGGTGGATGTAA<br>ACACTGCCGAACATTCAACTGTCATAACTTTTTCTGATTA<br>CCATGAGGGATCTGCACCTGCCTTGATAATGAACCATACA<br>CCATGGGACATCCTCACATACAAACAGAGTGGGTCACCAG<br>AAGAAATGGTCTTGCTGCCAAGACAGGCTCGACTTTTTGC<br>CTGGGCAGATCCTACTGGTACCAGAAAACTTACATGGACA<br>TATGCAGCAAATGTTGGGGAACATGATCTGTTAAAGGATG<br>GATGTGGACAGTTTCCATATGATGCAAACATCCAGATACA<br>CTGGGTATCATTTCTGGATGGGCGCCAGAGAGTTTTGCTT<br>TTCACCGATGATGTTGCCTTGGTTTCCAAAGCACTGCAGG<br>CAGAAGAAATGGAACAGGCTGATTATGAAATAACCTTGTC<br>TCTCCACAGTCTTGGGCTTTCACTGGTTAACAATGAAAGC<br>AAGCAGGAAGTTTCCTATATTGGGATAACCAGTTCTGGTG<br>TTGTTTGGGAGGTGAAACCAAAGCAGAAATGGAAGCCATT<br>TAGTCAAAAGCAGATAATCTTATTGGAACAATCCTATCAG<br>AAACATCAAATATCAAGAGACCATGGCTGGATTAAGCTAG<br>ATAATAATTTTGAGGTCAATTTTGATAAAGATCCAATGGA<br>AATGCGCCTCCCTATTCGTAGCCCTATTAAACGAGACTTT<br>TTATCAGGAATTCAGATTGAATTTAAGCAGTCTTCTCACC<br>AGAGAAGTTTAAGGGCCAGGTTGTACTGGCTTCAGGTTGA<br>TAATCAGTTACCAGGTGCAATGTTCCCTGTTGTATTTCAT<br>CCTGTTGCCCCTCCAAAATCTATTGCTTTAGATTCAGAGC<br>CCAAGCCTTTCATTGATGTGAGTGTCATCACAAGATTTAA<br>TGAGTACAGTAAAGTCTTACAGTTCAAGTATTTTATGGTC<br>CTCATTCAGGAAATGGCCTTAAAAATTGATCAAGGGTTTC<br>TAGGAGCTATTATTGCACTGTTTACCCCAACAACAGACCC<br>TGAAGCTGAAAGAAGACGGACAAAGTTAATCCAACAAGAT<br>ATTGATGCTCTAAATGCAGAATTAATGGAGACTTCAATGA | |

TABLE 1-continued

GEP-NEN Biomarker/Houskeeper Sequence Information

| Gene Name | RefSeq Accession | Sequence | SEQ ID NO: |
|---|---|---|---|
| | | CTGATATGTCAATTCTTAGTTTCTTTGAACATTTCCATAT<br>TTCTCCTGTGAAGTTGCATTTGAGTTTGTCTTTGGGTTCC<br>GGAGGTGAAGAATCAGACAAAGAAAAACAGGAAATGTTTG<br>CAGTTCATTCTGTCAACTTGCTGTTGAAAAGCATAGGTGC<br>TACTCTGACTGATGTGGATGACCTTATATTCAAACTTGCT<br>TATTATGAAATTCGATATCAGTTCTACAAGAGAGATCAGC<br>TTATATGGAGTGTTGTTAGGCATTACAGTGAACAGTTCTT<br>GAAACAGATGTATGTCCTTGTATTGGGGTTAGATGTACTT<br>GGAAACCCATTTGGATTAATTAGAGGTCTGTCTGAAGGAG<br>TTGAAGCTTTATTCTATGAACCCTTCCAGGGTGCTGTTCA<br>AGGCCCTGAAGAATTTGCAGAGGGGTTAGTGATTGGAGTG<br>AGAAGCCTCTTTGGACACACAGTAGGTGGTGCAGCAGGAG<br>TTGTATCTCGAATCACCGGTTCTGTTGGGAAAGGTTTGGC<br>AGCAATTACAATGGACAAGGAATATCAGCAAAAAGAAGA<br>GAAGAGTTGAGTCGACAGCCCAGAGATTTTGGAGACAGCC<br>TGGCCAGAGGAGGAAAGGGCTTTCTGCGAGGAGTTGTTGG<br>TGGAGTGACTGGAATAATAACAAAACCTGTGGAAGGTGCC<br>AAAAAGGAAGGAGCTGCTGGATTCTTTAAAGGAATTGGAA<br>AAGGGCTTGTGGGTGCTGTGGCCCGTCCAACTGGTGGAAT<br>CGTAGATATGGCCAGTAGTACCTTCCAAGGCATTCAGAGG<br>GCAGCAGAATCAACTGAGGAAGTATCTAGCCTCCGTCCCC<br>CTCGCCTGATCCATGAAGATGGCATCATTCGTCCTTATGA<br>CAGACAGGAATCTGAGGGCTCTGACTTACTTGAGCAAGAA<br>CTGGAAATACAGGAATAAATGTTTCCTAAACTACTACTTG<br>ATTTCATCCTTAAAAATCAAAACAAACTGTGGTGTTAATT<br>GACTGTGTGTGAATTCCATTGTCAATTTTAATGAAATTTT<br>CTTTAAAACTCTCACCTCCATCTGAACTTTTCATAGTAGT<br>GGGATTGACTACAAATAAAAACTTGTGGTATTCCTGGTAA<br>TACTGTCCAGAAATAAGAGATTAGTATAAAATATTAAGG<br>ATGCAGAGAATCAGCTCTCTTCTGCGTTTAATAGATGAAA<br>GCCTTTATTGAGCTCAGAAGCAGATACTGTTACTATCATT<br>TCGAAAATTTTATCTTATGGTGTTCATGTGCATTTCAGGT<br>AAAATTGAAAAACAGGACAATTATTATGTCCAATTAATAT<br>GTTTATGTTTGTGAGTCTTGATGATGGAATTACATAGCTT<br>TCTGTTTCACAAATGGCTCTAAATTTGCTTAAGTTACGGG<br>ACTATTACCTGGAGCATCTGCTTTAATAATTGAATTGTCA<br>GTTGCTCTGAGCCTGCCCTTAGACCTCAAGTAATAAATAG<br>TTGGCACATGAATTTTGAGGATATGTTTCCTCTTCCCTCT<br>TTTTCCTATTTAACCCCTTGGTACTGTTGCTAAATAAATG<br>ATAGCCATTTTATAATTATGTTATATACATTTTCAGCCTT<br>TAGCATTTCTGCTTTTCAAAAATTGAATCTCCTTGTTGGT<br>TATGCTTATTTCATAATTATTAGTTTTAATTAATGTAGAT<br>AGAAGTTAACATGTAATTAGGCAAATTGCTGTGTGGCAC<br>TTGAATACATAGATTTCTTTATTTTCAAAAACCAACCTTT<br>TGCTTTTAAATCCTTAGAGAGGGTTTATTATCTTAGAGAA<br>AAAATAATTATAATCATTATTTTTGAAATTAGTATCCTCT<br>TAATTCTCAACATAAGTTATGTTTCAATTTCTTTTTTTTG<br>TAATAAATGATGGAAATGTTTAACAATGTCTTATCTAGCA<br>ACTTTCATGCTTCTCCTCAGAAATGAAGCCAAAGTATAAA<br>CTTAGATTTAATGTGTTGTATATTTGAAGAGAATGAAACT<br>ATTAACATATAATTGTTCAGTTGGATTATGTATTTTAAGG<br>ATTGCAGTTATCAAAATAATAAATTGAATGTTTTATGTTT<br>AACCACTTTAAAGAAGAAAGACTGACATCCAAAAACCAGC<br>GTGTGCTAGATATACAAAGGAAATTACTTCTGTCCTTAAG<br>GGACCAAGTATAACAAAACATGTAACTGTTAAAAGTAGCT<br>GACAAACCTTTCTTGTGCCTAGATAATTTAGCATTGGCAA<br>AAATGTCACCACATGCAGTTTTCTAGGAGAGTCAAGCACA<br>AATAACTAATTCAAGATGCTGACTTAAATCATCTCCAATA<br>GTTACCCTTCCTGAGATTCTAAAGTAACAATTTTTAATTT<br>TACTGGTTATATTGCTGTTTTACTGAGACTTACTTTTAAG<br>AACCCCTGTAACTTAAGATTTTTTCTTAATTGTTTTGTTT<br>AGCTCTGTTATTAATTTTTTCCTTGTGATATCTTTTTATA<br>ACTCTCTGTCAAAAAGCACAAAACTTCAAGAAACTTTTAA<br>TTATTTTGTCTGAACATATAATCTTGTCTGATTTCTTAGT<br>TTTTATTAAGATATCAGACAACTTTTAAAACTTTAGTGCA<br>TTATTATAATTACTGGAAGAAAAAGAATGATTATACACTA<br>ATGAGAGGACTTGGTAGTTTTTGTCGTGGATGTCAAGTGT<br>GGGCATGGATAATTGAAATATTTAGGCTATTTCATTCTTT<br>GCCCATCTTGCTGTGATCAGTTAGTTGGGTAAAAATATTT<br>ATTGATTATTTAGACTGTACTGGATATACAAAAGAAGCCT<br>TCTGTCCTTAAGGGACCGAGTAAAACAAAACATGGAAATA<br>TTAAAGAGTATTAGAGTATAAAAGTATATCTTTTTAGCCC<br>TTTGTAATATGGCCAAATTCTAAATAATTTATTTGGGGAT<br>CTTTTGATCCTCATGTTCCTTTTTCTCCTAAGTACTACTT<br>TGTATTCTTTAATATGCAGCTTTGAGAGTTACTGAATCAT | |

TABLE 1-continued

GEP-NEN Biomarker/Houskeeper Sequence Information

| Gene Name | RefSeq Accession | Sequence | SEQ ID NO: |
|---|---|---|---|
| | | ATATTATATTTCCATGAGATGTACTATTCTACTTATCCTC<br>TAATCTTCATATATATACACACACACATATATATACAC<br>ATACATATATACACACGTACATATATGTACACATACAGAT<br>ATACATACACACAAACACATATATACACACATACATATAC<br>ACACATATATATACACATACAAATATACACATATATACAC<br>ATACATATATATACACACATACAAATATACCCATATGTAC<br>ACATATATATATACACATACATATATACACACACATATAC<br>ACACATATATACGCAAACATACACATATTTACACATACAT<br>ATATACATACATTATATGTATGTATATATAGTCATTTAAT<br>ACTCATTTTGGTTCACATACTTATGATCATGCAACGTTTA<br>AAACAGCATTTCTTGCTTTTTAGTTTTAGTTATATTTTC<br>CATGTTCTTAGAAATGCCTCATTAACATTTTTAATTCTTG<br>TATTGCCATCTATTGAGGTGACATTACATTGTGTTTTTAT<br>CTCGTCTTAATTCATGACATTAAATTATTCTACTAACAGT<br>AATAATGCTGTAATAAACATCATTATAGATTTTGCTTTTT<br>TATATCTTGTTTGCTTTTTCATATTTCCTTAGAATTTACT<br>TGAAAAAATTGAATTACTGGGTAAAGGGCTTTTGCAAAGT<br>ATTGTTAAATTCCTCGAGTTGCATTTTTGGAAAGGGGACG<br>TGAATATTTTATCAACTAATTTGGTCTCCCTGCTGCCATT<br>AGTGACTGAATATCTTAATCTGAATCTCAGAGTGTAGTGG<br>GTTTTTAGTAGTGCTGAAGACAAGTTTTCTAAAGTGTATT<br>ATGGTGATAAATTATATTTTAAAAACTGTCAATGGCTTGA<br>AGCACAATAGCCTAATAACTAACGAAAATACATACAAGAT<br>AGAAAGTGGGTAGTATTTCTTGTACTTGCATTTCAGATCT<br>AAATATTTTAACATATTTAAATTTCAAGCTGCAGATAAAT<br>GCATTACATTATTAAATTCATTTCCCATTTTCTCTTTGAA<br>GAAATTAAGGCAAAAGTGTTAAAAGATTTTAACTAATTCG<br>CACAAGTGAATTGTGAAACAAGTAGCTATTGCTGTGAAAT<br>CTGCACTCCTCTCTGAGACTCATTCTGAAGATGAGATCCC<br>AGTTCTTTGTGGATTCCTCTTCCTTATTCATGGCTTTTTG<br>CAATTGTCAAGGAATGACTAGGTACCAAGCAACTTTAAAA<br>AATGTATATTTAAGCATTGAAATAATATCAAATGTGATTT<br>CTCTGCTTGTGGTTATATTGATTATATTATCCTTTTAATA<br>ATATTGGCATTATATTCTTGGTCGTAAAATGTCAAGGTCT<br>TATTTATTCAGTATATTTATGTTCTGTATTTTCATATATA<br>TTATCTATTTTCAGCCATGCATTATATATAATGTCAGTAA<br>TAGTATTTCATTAGCATTCATTATAAAAAAACTCGTTTTT<br>AATATTTGACTAATTCAAGTCACAGTACTTTTGAGATAGC<br>TGAAAAGGAAAATAAATGTGTTTTAATGTGCTACTAAAAA<br>AAAAAAA | |
| WDFY3 | NM_014991.4 | GCGGCCGCAGAATCGAGCTCGGGCCCCGGCCCCCGGCCCG<br>CGGCGCGGGGCTCCCGGGCCCCGCCGCGGACGTCGCGCCG<br>GTCGCCCCTTCCCCGTAGCCCGTGCGCCCTCGGCGCGGAG<br>CCCCGGCCCGCCGCGGGTCCCGTCTCCTGGGCCTGTCCCGC<br>CCGCGCCCTCCGCCGGCCCTCAGGTATAATACTTCTCCAC<br>GTCTGCTTCAGGAAGAAAGTGCCTGCCATTCTTATCATTT<br>CTAAGCAGGTTCATGCCAGCCCAGAACAGAGAATCAGCTG<br>GAGCCCAGATTTCAAGTTTTGAGTAAAATACCTTCAAGCG<br>AATGGGCCCTATTGTGCTCACACATTCAGAACCTGTTACC<br>CAAGGAATTCCCTAAAGAATTAGAAGTGCGTCTCACCAAC<br>CAGCCAAGATGAACATGGTGAAGAGGATCATGGGCGGCC<br>GAGGCAGGAGGAGTGCAGCCCACAAGACAACGCCTTAGGA<br>CTGATGCACCTCCGCCGGCTCTTCACGGAGTTGTGCCATC<br>CTCCCCGGCACATGACTCAGAAGGAACAAGAAGAGAAACT<br>GTATATGATGCTGCCAGTGTTTAACAGGGTTTTTGGAAAT<br>GCTCCGCCGAATACAATGACAGAAAAATTTTCTGATCTTC<br>TGCAGTTCACAACACAAGTCTCACGACTAATGGTGACAGA<br>AATTCGAAGGAGAGCATCAAACAAATCCACAGAGGCTGCA<br>AGTCGGGCCATAGTTCAGTTCCTAGAGATTAATCAGAGTG<br>AAGAAGCCAGTAGAGGCTGGATGCTTCTAACGACAATTAA<br>TTTGTTAGCTTCCTCTGGTCAGAAAACCGTGGACTGCATG<br>ACAACAATGTCAGTGCCTTCCACCCTGGTTAAATGTTTAT<br>ATCTGTTTTTTGACCTTCCACATGTGCCTGAGGCAGTTGG<br>AGGTGCACAGAATGAGCTACCTCTAGCAGAACGTCGAGGA<br>CTACTCCAGAAAGTTTTTGTACAGATCTTAGTGAAACTGT<br>GCAGTTTTGTTTCCCCTGCGGAGGAGCTGGCTCAGAAAGA<br>TGATCTCCAGCTTCTATTCAGTGCAATAACCTCTTGGTGC<br>CCTCCCTATAACCTGCCTTGGAGAAAGAGTGCTGGAGAAG<br>TCCTCATGACCATATCTCGTCATGGTCTTAGTGTCAATGT<br>AGTGAAGTATATTCATGAGAAAGAGTGTTTATCTACATGT<br>GTTCAGAATATGCAGCAATCAGATGACCTGTCTCCCCTAG<br>AAATTGTCGAAATGTTTGCTGGGCTTTCTTGTTTCCTCAA<br>AGATTCCAGCGATGTTTCCCAAACACTTCTGGATGATTTT<br>CGGATATGGCAAGGATATAATTTTCTTTGTGATCTCTTGC | 49 |

TABLE 1-continued

GEP-NEN Biomarker/Houskeeper Sequence Information

| Gene Name | RefSeq Accession | Sequence | SEQ ID NO: |
|---|---|---|---|
| | | TTAGATTGGAACAAGCAAAAGAGGCAGAATCCAAAGATGC<br>CTTGAAAGATCTGGTTAATCTGATAACTTCCCTAACAACA<br>TATGGTGTCAGTGAACTAAAACCAGCTGGTATTACCACAG<br>GGGCACCCTTTTTATTGCCTGGATTTGCAGTACCTCAGCC<br>TGCAGGCAAAGGTCACAGTGTGAGAAACGTCCAGGCCTTT<br>GCAGTTCTTCAGAATGCATTTTTAAAAGCAAAAACCAGCT<br>TCCTTGCCCAAATCATCCTTGATGCTATCACAAATATTTA<br>CATGGCTGACAATGCCAATTACTTCATCCTAGAGTCACAG<br>CACACATTGTCACAGTTTGCAGAGAAGATTTCTAAACTCC<br>CAGAAGTACAAAACAAATACTTTGAGATGCTGGAGTTTGT<br>TGTTTTTAGCTTAAATTATATACCTTGTAAAGAACTTATT<br>AGTGTCAGTATCCTCTTAAAATCTAGCTCTTCTTATCACT<br>GTAGCATTATTGCAATGAAAACACTTCTTAAGTTTACAAG<br>ACATGACTACATATTTAAAGACGTGTTCAGGGAGGTTGGC<br>CTTTTGGAGGTCATGGTAAACCTTTTGCATAAATATGCTG<br>CCCTGTTGAAGGATCCAACTCAGGCACTAAATGAACAAGG<br>GGACTCAAGAAATAATAGTTCAGTTGAAGACCAAAAACAC<br>CTGGCTTTATTGGTTATGGAGACCTTGACAGTGCTTCTTC<br>AAGGATCAAACACAAATGCAGGAATTTTTCGAGAATTTGG<br>AGGTGCAAGATGTGCACATAATATAGTAAAGTACCCTCAA<br>TGCCGGCAGCATGCCTTGATGACTATCCAACAGCTGGTGC<br>TCTCCCCAAATGGGGACGATGACATGGGCACTCTCCTGGG<br>GCTAATGCATTCAGCCCCACCGACGGAATTGCAGTTGAAG<br>ACTGATATTTTAAGGGCCCTCCTGTCGGTCCTTCGAGAAA<br>GCCATCGTTCAAGAACAGTTTTTAGGAAAGTTGGAGGATT<br>TGTGTACATTACATCCTTGCTCGTTGCTATGGAAAGATCT<br>TTGAGCTGTCCACCCAAGAATGGCTGGGAGAAAGTGAACC<br>AGAATCAAGTGTTTGAACTTCTTCACACTGTGTTCTGCAC<br>GTTGACTGCAGCAATGCGCTATGAGCCAGCCAACTCTCAT<br>TTCTTCAAAACAGAGATTCAGTATGAGAAGTTGGCAGATG<br>CTGTTCGATTTCTTGGCTGCTTCTCAGACCTAAGAAAAAT<br>AAGCGCCATGAATGTCTTCCCCTCAAATACACAGCCATTT<br>CAAAGACTTTTAGAGGAAGATGTAATCTCAATAGAATCAG<br>TGTCACCCACGTTACGGCACTGCAGTAAACTTTTTATTTA<br>TCTTTACAAAGTAGCCACAGATTCTTTTGACAGTCGTGCA<br>GAACAGATCCCTCCTTGCCTGACAAGTGAGTCTTCTCTCC<br>CCTCTCCTTGGGGTACACCAGCTTTGTCCAGGAAAAGGCA<br>TGCATATCATTCTGTTTCAACTCCCCCTGTTTACCCTCCT<br>AAAAATGTTGCCGACCTGAAACTACATGTGACAACTTCAT<br>CTCTGCAGAGTTCTGATGCAGTCATCATTCATCCTGGAGC<br>CATGCTTGCCATGCTGGACCTACTGGCCTCTGTTGGGTCA<br>GTGACACAGCCAGAACATGCTTTGGATCTTCAACTTGCCG<br>TGGCAAATATTTTACAATCCCTGGTGCACACAGAAAGGAA<br>CCAGCAAGTCATGTGTGAAGCTGGTCTTCATGCACGACTG<br>CTGCAGAGGTGCAGTGCTGCATTGGCTGATGAGGACCACT<br>CACTGCACCCGCCCCTGCAGCGGATGTTTGAACGATTAGC<br>CTCTCAGGCTCTGGAACCCATGGTGTTGAGGGAGTTTTTA<br>CGTTTGGCAAGTCCTTTAAATTGTGGTGCCTGGGACAAAA<br>AACTGCTAAAACAATATAGGGTCCACAAACCAAGTTCACT<br>GAGTTATGAACCAGAAATGAGAAGTAGTATGATCACATCT<br>CTGGAAGGTCTGGGTACTGATAATGTTTTTAGCTTACATG<br>AAGATAACCATTACCGGATAAGCAAGAGCCTGGTAAAATC<br>TGCCGGAAGGAAGTACTGTACCCCTGACCAGGGTGAAGTGT<br>CTGGTCTCCATGACAACCCCACATGACATCAGACTTCATG<br>GGTCATCAGTTACTCCAGCTTTTGTTGAATTTGACACATC<br>ACTTGAAGGGTTTGGATGTCTTTTTTTGCCCAGTTTGGCC<br>CCTCATAATGCTCCTACAAATAATACCGTCACAACAGGTC<br>TTATTGATGGGCTGTGGTCAGTGGCATTGGTTCTGGTGA<br>AAGATTCTTCCCTCCTCCCTCCGGCTTAAGTTACTCTAGC<br>TGGTTTTGTATTGAACATTTTAGTTCTCCTCCAAATAACC<br>ACCCTGTCAGACTTCTTACTGTTGTGCGCCGAGCAAATTC<br>TTCTGAGCAACATTACGTGTGCCTTGCAATAGTTCTATCA<br>GCAAAAGACCGATCTCTGATTGTTTCCACCAAAGAGGAAC<br>TCCTCCAAAATTATGTTGATGATTTTAGTGAAGAGTCCTC<br>ATTTTATGAAATTCTCCCATGCTGTGCTCGCTTTCGATGT<br>GGAGAGCTTATCATTGAGGGACAGTGGCATCATTTGGTCC<br>TGGTAATGAGCAAAGGCATGTTGAAAAACAGTACTGCAGC<br>CCTTTATATTGATGGACAGCTTGTTAACACTGTAAAGCTT<br>CATTATGTCCACAGTACTCCAGGGGGTTCAGGTTCGGCAA<br>ATCCACCAGTGGTGAGCACGGTCTATGCCTACATTGGTAC<br>TCCACCTGCCCAACGCCAAATTGCCTCATTGGTTTGGCGC<br>CTGGGACCCACACATTTTCTAGAAGAAGTTTTACCTTCTT<br>CAAATGTTACTACCATTTATGAACTTGGACCAAATTATGT<br>TGGAAGCTTTCAGGCTGTATGTATGCCATGTAAAGATGCA<br>AAATCCGAAGGGGTGGTGCCATCCCCTGTGTCATTAGTAC | |

TABLE 1-continued

GEP-NEN Biomarker/Houskeeper Sequence Information

| Gene Name | RefSeq Accession | Sequence | SEQ ID NO: |
|---|---|---|---|
| | | CAGAGGAGAAAGTGTCATTTGGCCTCTATGCACTCTCTGT<br>GTCGTCTCTAACAGTGGCAAGAATCCGGAAAGTGTATAAC<br>AAATTGGATAGCAAAGCCATTGCTAAGCAGTTAGGCATTT<br>CCTCACATGAGAATGCCACTCCTGTGAAGTTGATACACAA<br>TTCAGCAGGACATCTTAATGGATCTGCACGGACAATTGGG<br>GCCGCTCTGATTGGATACTTGGGAGTAAGAACATTTGTCC<br>CTAAGCCTGTTGCCACTACTTTGCAGTACGTTGGTGGAGC<br>TGCAGCCATCCTGGGCCTGGTGGCCATGGCCTCTGATGTG<br>GAAGGGTTATATGCAGCAGTCAAGGCCCTGGTTTGTGTGG<br>TCAAGAGTAACCCACTAGCCAGCAAAGAAATGGAAAGAAT<br>CAAGGGCTACCAGTTGCTGGCAATGTTGCTTAAGAAGAAA<br>CGTTCCCTTCTTAACAGCCACATCCTCCATCTAACTTTTT<br>CTTTGGTGGGAACTGTTGATAGTGGACATGAGACCTCCAT<br>TATTCCAAATTCAACTGCTTTCCAGGACCTCCTCTGTGAT<br>TTTGAAGTCTGGCTCCATGCACCATATGAACTTCATCTTT<br>CCTTATTTGAACACTTTATTGAACTGCTCACAGAGTCCAG<br>TGAAGCCTCAAAGAATGCCAAATTAATGAGAGAATTCCAG<br>TTAATCCCAAAGCTGCTCCTGACTCTTCGAGATATGTCTT<br>TATCCCAGCCTACTATTGCTGCTATTAGTAATGTCCTGAG<br>CTTCTTACTGCAAGGTTTTCCTAGCAGCAATGATCTGCTC<br>AGATTTGGGCAGTTTATTTCTTCTACTTTGCCAACCTTTG<br>CGGTTTGTGAGAAATTTGTAGTAATGGAAATAAATAATGA<br>AGAGAAGCTTGACACTGGAACTGAAGAGGAGTTTGGAGGT<br>CTTGTATCAGCTAATCTTATACTTTTGAGGAACAGACTTC<br>TGGATATCTTGCTAAAACTAATTTATACATCTAAAGAAAA<br>GACAAGCATTAATTTGCAAGCTTGTGAAGAACTGGTGAAG<br>ACACTGGGTTTTGACTGGATCATGATGTTTATGGAGGAAC<br>ACTTACATTCCACCACAGTTACAGCAGCCATGAGGATTCT<br>TGTTGTCCTACTAAGTAATCAGTCTATTCTCATCAAGTTT<br>AAAGAAGGACTCAGTGGTGGAGGATGGCTTGAACAGACAG<br>ATTCTGTCTTAACTAATAAGATTGGAACTGTATTAGGATT<br>CAACGTGGGCAGAAGTGCTGGTGGGAGATCGACGGTCAGG<br>GAGATTAACCGAGATGCTTGTCATTTTCCTGGTTTTCCAG<br>TCCTTCAGTCATTCCTTCCTAAACACACTAATGTCCCTGC<br>CCTCTATTTTCTCCTCATGGCCTTGTTTCTGCAGCAGCCA<br>GTTAGTGAGCTGCCTGAGAACCTGCAGGTCAGTGTGCCTG<br>TCATCAGCTGCCGGAGTAAGCAGGGTTGCCAGTTTGATTT<br>GGATTCCATTTGGACATTCATCTTTGGAGTTCCTGCCTCC<br>AGCGGAACTGTGGTCTCTTCTATCCATAACGTATGCACAG<br>AAGCTGTTTTTTATTATTGGGAATGCTCCGCAGCATGCT<br>GACTTCACCTTGGCAATCAGAAGAAGAGGGATCTTGGCTC<br>CGAGAATATCCTGTGACCCTGATGCAGTTCTTCAGATATT<br>TGTATCACAACGTGCCAGACCTTGCCTCCATGTGGATGAG<br>CCCTGACTTCCTGTGTGCATTAGCAGCCACCGTCTTCCCC<br>TTCAATATTCGCCCTTACTCAGAGATGGTGACTGACCTTG<br>ATGATGAAGTTGGATCTCCAGCAGAAGAGTTTAAAGCGTT<br>TGCAGCAGACACAGGGATGAACAGGAGCCAATCAGAGTAC<br>TGCAATGTGGGCACCAAGACATATCTGACCAATCACCCGG<br>CTAAAAAGTTCGTTTTTGACTTCATGCGGGTCTTAATCAT<br>AGACAACCTCTGTCTCACTCCTGCCAGCAAGCAAACTCCA<br>CTAATTGATCTTTTGTTGGAGGCTTCCCCTGAAAGGTCTA<br>CAAGAACTCAGCAAAAAGAATTTCAAACTTACATTTTGGA<br>TAGCGTGATGGACCATTTGCTTGCAGCTGATGTGTTATTA<br>GGGGAAGATGCATCTCTGCCTATTACCAGTGGAGGAAGCT<br>ACCAGGTATTGGTGAACAATGTGTTTTATTTCACACAGCG<br>TGTGGTGGACAAGCTTTGGCAAGGCATGTTCAACAAAGAA<br>TCTAAACTTCTTATAGATTTTATAATTCAACTAATTGCAC<br>AGTCAAAGAGAAGATCACAGGGATTGTCACTGGATGCAGT<br>GTATCATTGCCTCAATAGGACCATCTTGTACCAGTTCTCA<br>CGGGCACACAAAACCGTTCCTCAGCAAGTAGCTCTGCTTG<br>ATTCACTCAGGGTCCTCACTGTAAACAGAAACTTGATCCT<br>GGGACCTGGGAACCATGACCAAGAATTCATTAGCTGTCTG<br>GCCCACTGCTTGATAAATCTACATGTTGGAAGCAACGTGG<br>ATGGATTTGGACTGGAAGCAGAAGCCCGCATGACCACATG<br>GCACATTATGATCCCCTCGGACATTGAACCAGATGGTAGT<br>TACAGCCAAGATATTAGTGAAGGGCGTCAGCTTCTCATAA<br>AAGCTGTCAACAGAGTTTGGACTGAACTGATACATAGTAA<br>GAAACAAGTCTTAGAGGAACTTTTCAAAGTAACTCTACCT<br>GTGAATGAAGGGGCCACGTGGACATAGCTACAGCAAGGC<br>CACTCATTGAAGAAGCTGCCCTGAAGTGCTGGCAGAATCA<br>TTTGGCCCATGAAAAGAAATGCATAAGTCGAGGAGAAGCT<br>TTAGCGCCCACCACACAGTCCAAATTATCCCGTGTCAGCA<br>GTGGCTTTGGTCTTTCCAAGTTAACAGGATCAAGAAGGAA<br>TCGAAAAGAAAGTGGTCTTAATAAACACAGTCTTTCCACC<br>CAGGAGATTTCGCAGTGGATGTTACTCACATTGCTGTTG | |

TABLE 1-continued

GEP-NEN Biomarker/Houskeeper Sequence Information

| Gene Name | RefSeq Accession | Sequence | SEQ ID NO: |
|---|---|---|---|
| | | TTCGTGACTTAGTAGATACACAATATAAAGAATATCAGGA | |
| | | GCGTCAGCAGAATGCCCTGAAGTACGTGACAGAAGAGTGG | |
| | | TGTCAGATCGAGTGCGAGCTGTTGAGGGAGCGGGGGCTGT | |
| | | GGGGCCCTCCCATCGGCTCCCACCTCGACAAGTGGATGCT | |
| | | GGAGATGACAGAAGGGCCCTGCAGGATGAGGAAAAAGATG | |
| | | GTGCGAAATGATATGTTTTATAACCATTACCCTTACGTGC | |
| | | CAGAAACTGAGCAAGAGACAAATGTGGCGTCTGAGATCCC | |
| | | AAGTAAACAGCCTGAGACACCCGATGATATTCCTCAAAAG | |
| | | AAACCTGCTCGATATAGAAGAGCCGTAAGTTATGACAGTA | |
| | | AAGAGTACTACATGCGACTGGCCTCTGGCAATCCCGCCAT | |
| | | TGTCCAAGACGCCATTGTGGAGAGTTCAGAAGGTGAAGCT | |
| | | GCTCAGCAAGAACCAGAGCATGGGGAAGACACTATTGCTA | |
| | | AAGTCAAAGGTTTGGTCAAGCCTCCTCTAAAACGCTCCCG | |
| | | ATCTGCACCTGATGGAGGAGATGAGGAGAACCAGGAGCAG | |
| | | CTACAAGACCAGATTGCTGAGGGCAGCTCCATAGAAGAGG | |
| | | AGGAGAAAACAGATAATGCTACCTTACTGCGCCTGTTAGA | |
| | | GGAAGGAGAAAAGATCCAACACATGTACCGCTGTGCTCGA | |
| | | GTCCAGGGCCTAGATACCAGTGAGGGGCTCCTTCTTTTTG | |
| | | GTAAAGAGCATTTTTATGTGATTGATGGATTTACCATGAC | |
| | | AGCAACCAGGGAAATAAGAGATATTGAAACCTTACCTCCA | |
| | | AATATGCATGAGCCTATTATTCCTAGAGGAGCCAGGCAAG | |
| | | GCCCTAGTCAACTCAAGAGAACATGCAGCATTTTTGCATA | |
| | | TGAAGATATCAAGGAAGTTCATAAAAGGAGATATCTCCTG | |
| | | CAGCCTATTGCTGTGGAAGTTTTCTCTGGAGATGGACGGA | |
| | | ATTACCTCCTTGCTTTTCAGAAAGGAATCAGAAACAAAGT | |
| | | CTATCAAAGGTTTTTGGCTGTAGTGCCATCTCTAACGGAC | |
| | | AGTTCAGAATCTGTATCTGGGCAACGACCAAACACGAGTG | |
| | | TGGAGCAGGGATCTGGGTTACTTAGCACTTTGGTTGGAGA | |
| | | GAAGTCTGTGACTCAGAGATGGGAGAGAGGTGAAATCAGC | |
| | | AACTTCCAATATTTGATGCATTTGAACACTTTGGCTGGCA | |
| | | GATCATATAATGATCTCATGCAGTATCCTGTCTTCCCCTG | |
| | | GATCCTTGCAGATTATGACTCAGAGGAGGTGGATCTTACT | |
| | | AATCCCAAGACGTTTAGAAACCTGGCTAAGCCAATGGGAG | |
| | | CACAAACAGATGAACGATTAGCTCAGTATAAGAAGCGGTA | |
| | | TAAAGACTGGGAGGATCCTAATGGAGAAACTCCTGCATAC | |
| | | CACTATGGGACCCACTATTCATCTGCAATGATTGTGGCCT | |
| | | CATACCTTGTAAGGATGGAGCCTTTCACACAGATATTCTT | |
| | | AAGGCTACAGGGTGGCCACTTTGACCTGGCTGACCGGATG | |
| | | TTTCACAGTGTGCGCGAGGCCTGGTATTCAGCGTCAAAGC | |
| | | ACAATATGGCAGATGTAAAAGAACTTATCCCAGAGTTCTT | |
| | | TTATTTACCAGAATTCCTGTTCAATTCCAACAACTTTGAT | |
| | | CTAGGCTGTAAACAAAATGGCACCAAGCTTGGAGATGTTA | |
| | | TCCTTCCACCCTGGGCAAAAGGGGACCCACGAGAATTCAT | |
| | | CAGAGTCCATCGTGAGGCTTTGGAGTGTGATTACGTGAGT | |
| | | GCCCATCTACATGAGTGGATTGACTTAATCTTCGGTTATA | |
| | | AACAGCAAGGCCCTGCTGCAGTAGAAGCTGTAAATGTCTT | |
| | | CCATCATCTTTTTTATGAGGGTCAAGTGGATATCTACAAC | |
| | | ATCAATGACCCACTAAAGGAGACAGCCACAATTGGGTTCA | |
| | | TTAATAACTTCGGTCAGATCCCTAAACAGTTATTTAAAAA | |
| | | ACCTCATCCACCAAAGCGAGTGAGAAGTCGACTCAATGGA | |
| | | GACAATGCAGGAATCTCTGTCCTACCAGGATCTACAAGTG | |
| | | ACAAGATCTTTTTTCATCATCTAGACAACTTGAGGCCTTC | |
| | | TCTAACACCTGTAAAAGAACTCAAAGAACCTGTAGGACAA | |
| | | ATCGTATGTACAGATAAAGGTATTCTTGCGGTGGAACAGA | |
| | | ATAAGGTTCTTATCCCACCAACCTGGAATAAAACTTTTGC | |
| | | TTGGGGCTATGCAGACCTCAGTTGCAGACTGGGAACCTAT | |
| | | GAGTCAGACAAGGCCATGACTGTTTATGAATGCTTGTCTG | |
| | | AGTGGGGCCAGATTCTCTGTGCAATCTGCCCCAACCCCAA | |
| | | GCTGGTCATCACGGGTGGAACAAGCACGGTTGTGTGTGTG | |
| | | TGGGAGATGGGCACCTCCAAAGAAAAGGCCAAGACCGTCA | |
| | | CCCTCAAACAGGCCTTACTGGGCCACACTGATACCGTCAC | |
| | | CTGCGCCACAGCATCATTAGCCTATCACATAATTGTCAGT | |
| | | GGGTCCCGTGATCGAACCTGTATCATTTGGGATTTGAACA | |
| | | AACTGTCATTTCTAACCCAGCTTCGAGGGCATCGAGCTCC | |
| | | AGTTTCTGCTCTTTGTATCAATGAATTAACAGGGGACATT | |
| | | GTGTCCTGCGCTGGCACATATATCCATGTGTGGAGCATCA | |
| | | ATGGGAACCCTATCGTGAGTGTCAACACGTTCACAGGTAG | |
| | | GAGCCAGCAGATCATCTGCTGCTGCATGTCGGAGATGAAC | |
| | | GAATGGGACACGCAGAACGTCATAGTGACAGGACACTCAG | |
| | | ATGGAGTGGTTCGGTTTTGGAGAATGGAATTTTTGCAAGT | |
| | | TCCTGAAACACCAGCTCCTGAGCCTGCT<u>AAGTCCTAGAA</u> | |
| | | <u>ATGCAGGAAGACTGTCCAGAAGCACAAATAGGGCAGGAAG</u> | |
| | | <u>CCCAAGACGAGGACAGCAGTGATTCAGAAGCAGATGAGCA</u> | |
| | | GAGCATCAGCCAGGACCCTAAGGACACTCCAAGCCAACCC | |
| | | AGCAGCACCAGCCACAGGCCCCGGGCAGCCTCCTGCCGCG | |

TABLE 1-continued

GEP-NEN Biomarker/Houskeeper Sequence Information

| Gene Name | RefSeq Accession | Sequence | SEQ ID NO: |
|---|---|---|---|
| | | CAACAGCCGCCTGGTGTACTGACAGTGGCTCTGACGACTC | |
| | | CAGACGCTGGTCCGACCAGCTCAGTCTAGATGAGAAAGAC | |
| | | GGCTTCATATTTGTGAACTATTCAGAGGGCCAGACCAGAG | |
| | | CCCATCTGCAGGGCCCCCTTAGCCACCCCCACCCCAATCC | |
| | | CATTGAGGTGCGGAATTACAGCAGATTGAAACCTGGGTAC | |
| | | CGATGGGAACGGCAGCTGGTGTTCAGGAGTAAGCTGACTA | |
| | | TGCACACAGCCTTTGATCGAAAGGACAATGCACACCCAGC | |
| | | TGAGGTCACTGCCTTGGGCATCTCCAAGGATCACAGTAGG | |
| | | ATCCTCGTTGGTGACAGTCGAGGCCGAGTTTTCAGCTGGT | |
| | | CTGTGAGTGACCAGCCAGGCCGTTCTGCTGCTGATCACTG | |
| | | GGTGAAGGATGAAGGTGGTGACAGCTGCTCAGGCTGCTCG | |
| | | GTGAGGTTTTCACTCACAGAAAGACGACACCATTGCAGGA | |
| | | ACTGTGGTCAGCTCTTCTGCCAGAAGTGCAGTCGCTTTCA | |
| | | ATCTGAAATCAAACGCTTGAAAATCTCATCCCCGGTGCGT | |
| | | GTTTGTCAGAACTGTTATTATAACTTACAGCATGAGAGAG | |
| | | GTTCAGAAGATGGGCCTCGAAATTGTTGAAGATTCAACAA | |
| | | GCTGAGTGGAGACCATGGTCTGTAGACCCCTTCCCGATTC | |
| | | TCCTGTCCCAGCTTGGAAGGCATTGAAAACAGTCTCCGTT | |
| | | TACACATCTCTTCATACCACGTGTTTGAAGTGTTAAAATT | |
| | | CAAAGGGATCATTGAATAAAACGGGTGTAGAGTACAGGAA | |
| | | TGGGGCAGACGCGATTCAGGTGAACAGCACAAGAAGAATA | |
| | | TGAGGTGGTTCCTAGGAGCAACACTTTCGACCTCCAGTTC | |
| | | TCCCTGATGACAGTAGCTGTCTCCAAGAGAAAAATCCTCA | |
| | | CTTATTAACTCTCTTTTCTTGCATCTCATTTTTATAGAGC | |
| | | TACTCATCCTTATTTGGAAAAACCAACAACAAAAAAGGCT | |
| | | TTTAGAAAATGGTTGTAAATCTGACTTCTTTGCAAGTAAC | |
| | | TATGTATATTGTAAATAGATATAAAAGGCCTTTTTTCTAA | |
| | | ATAAGGACTTAACTGCCTGTAACATGAAACTTCAAACTAA | |
| | | ACCACTAACTCAATGAACTACTTATGGTTTGTCTGACATC | |
| | | CCTCACTTACCAATTAATTATAAATATGTTTTTTTAAATC | |
| | | CCCAAAGACATTATCTGTGGTCTTTTTTTCCTTTCAAGCT | |
| | | CAGCCTGTGTGCCTGATGTCATTTCTTTCAAGTTGCCCAC | |
| | | AGTATCTCCACTTAAACTAGGCTAGTAACCAAAATAATGT | |
| | | GGACCTTCTTTAGGAAACAGTGTGGGAGAATAGGAGTCCA | |
| | | GCCGTAAGATAAACTGGAAATATTTGGGCGTCTTGTACCT | |
| | | GGCTACGCACCACCTCAGTGTTGTTCCTACATAAACAGGG | |
| | | CCCCTTTTAAACTTGTATGTGGACTGCTGTTTGGTCAAAG | |
| | | AATACCTTCTTAGCATTGCAGAAAGGTGGTCAGATGACCA | |
| | | GTGTAGTCAGGAAACAGCCCTGTCTCAACTAATGGAAAT | |
| | | ATATTTGCATGTAACCCAAAATTAGCTTATCTTGCATAGA | |
| | | ACATAATAAGTATGTGTCTTTGGTGACACTAATGTTCTAC | |
| | | TATAGCTTATTTTCAAACAAGGGGTAAAAAAAGGAAAGAA | |
| | | AGAAGTGTACAGAATTAACATATAAACTTTGTTGTAAAAC | |
| | | TGAATCATGTCAGAACTGCTTAAAATTAACCTTTACCATT | |
| | | TAATGTCATCTACCTGAAAACAGTGAGATTTATACTGTAT | |
| | | CAATGTCTATTTTTTGTTTTTGCTATGAATATAATTACA | |
| | | GTATTTTAATATTTAGTTATTTAATTTGTTCTACTAGTTG | |
| | | GATACAGAACACACAAATCCAGGGGATTAAAGCTGGAAG | |
| | | GGGCTAAGAGATTAGTTTACAGAGAAAAGGCTTGGTGGTG | |
| | | GGATTTTTTAAATGTGTGTTATGTACATATATATATATA | |
| | | TATAATATATATTAAAAATGAAACAATTAATCTAGATTTT | |
| | | AACATTTTCAGAAACTTAGTGATAACATTATGAACAATTC | |
| | | TAAAAGCCCTGTGATTTGAAAAATATAGAATCATTAATGG | |
| | | CCCAAGATAGGCCTTCACACCTTCACAGGTGCGAAAGGAA | |
| | | AGGCCTTCACACCCTCACAGAGGCATCATGCAAAGGACAG | |
| | | CGGCTTTGGCTTTTCCAATTTTCCATCTTTAGGCCCTGGT | |
| | | GAGAGGCACACTTATGCACTAAAATGCACATATATGCACA | |
| | | TGCATTCAAAAATAGGCATTTGGTACAATGGTGATCTTGT | |
| | | ACCTGATGGGCTGAAACCAGCTTAAGAACAAATTTGTTCT | |
| | | TCCTGATATGATAACTAGGTCTCCAAGAGAAAATAGAAAG | |
| | | GCTGCTTTAGTGCCTTACGCTTACTAAATTTAAATCTTTA | |
| | | TTTACCTGGGTTTGAGCCTACAGTCTATTTATGATTACAT | |
| | | ATCAAAATTGATTAAAACACTTCCATTTCTAAAAGTTCAA | |
| | | ATATACTTGTTAATAAAAGGATTATCGGCATTAATACTTT | |
| | | AATTTAAAGAAAAGTTGTGTTCTGTTTTCCTTTCTGTGTC | |
| | | TTACTCCCCCACACTCTCCCTCCCCCATCACCATCTTCA | |
| | | ATTCTAATAAATAATGCTGATGTTCAACAGTTGCAGAAAT | |
| | | TGTGCTATTATGTAACTGTGGGCCTTGCCCCTGTCTGGCC | |
| | | CTCTAGATGATTTGTAGCAGTGTTATTCTACACTTTTTAA | |
| | | AAGAAGCGTCCTCCTTTTGTCCATGAATCATGTTTACCCC | |
| | | ATACCCAGTGGCAGAGGTGTTCTTTAAAGACTTGAATATA | |
| | | TGAATGTGTGTGTAGTTACTTAAAGGTTATTCCTCTTT | |
| | | GTAATAGGAAACTATATGGGATGAACACTTTTAAACTTTC | |
| | | CGACACAACTTCCATTACTAACTTTCTAACAGAACTTCCA | |
| | | TAACTAGAAGGTGGAAACCAAAACCCTCATGGTAGTATTT | |

TABLE 1-continued

GEP-NEN Biomarker/Houskeeper Sequence Information

| Gene Name | RefSeq Accession | Sequence | SEQ ID NO: |
|---|---|---|---|
| | | CCTCTGGCAGCTGGTGCTGTGGGCAACTGTTTTGTTCAAT<br>CGGGTTTCTTTTCTTTTTGCCTCTAATGCAGAAATCAACA<br>GAATCACTCACACATACAAGTACACTCACATACATAAACT<br>AATTATTTCTCTGGATATCTTTCTGTGTTCCATGTAAATT<br>TATTTACCAACATCTATTGTCAACATGTACATCTACCTTA<br>GTATGGTCTGCATTCTTTTTCTGAGAGTACCTCATAGGGC<br>TCCTGCCTGATCTTTGTAGTTTGTTCATTCATCCATCCAC<br>CTGTTCATTTGTTCATCCATGTATTCTAACATTTCTATGT<br>AGTGTGCAACTCTAATGTCATGCTTTTGAAGAAGAGAATA<br>GCTGCCCATAGCAGCCATCCGTCTGGATAATAGCAAAACA<br>CTCTAGATAAGTTATTTTGCACTTTCTTATGTATAAAGTT<br>GGTAGAAACTTATTTTTGCTTTGTATCATTTAAATACATT<br>TTGTTTTGGTAAATGAACTGTGTATAAAATATTTATGCCG<br>TTAAAACTGTTTTAGAAAGTATTTTTAATTTCAGCAAGT<br>TTGGTTACTTGTTGCATGACTCTTAACACAGCTGACTTTT<br>TGTGTCAGTGCAATGTATATTTTTTGTCCTGTTATTAACT<br>TGTAAGCCCTAGTAATGGCCAATTATTTGTACAGCAACAG<br>AAGTAAATTGAAGATACTGGCTAAGACTGGATTGATTGTG<br>GACTTTTATACTATATTGCAGAAACCAATATCTGTTTCTT<br>GGTGGTTATGTAAAAGACCTGAAGAATTACTATCTAGTGT<br>GCAGTCTGTGATATCTGAATGTTCATTGTATATTTGTCTC<br>TGATGCAAAAAGGTAGAGTAACACAATTACAATACATGAT<br>TAAATGCAATAGTCCAGGTACTTAAGTAATTTTTTTTTCA<br>TTTCAAATAAATACCTATTTACCACCAAAAGAAAGAAAAA<br>AAAAAAAAA | |
| ZFHX3 | NM_001164766.1 | CGCGGCCCGAGCGCCTCTTTTCGGGATTAAAAGCGCCGCC<br>AGCTCCCGCCGCCGCCGCCGTCGCCAGCAGCGCCGCTGCA<br>GCCGCCGCCGCCGGAGAAGCAACCGCTGGGCGGTGAGATC<br>CCCCTAGACATGCGGCTCGGGGGCGGGCAGCTGGTGTCAG<br>AGGAGCTGATGAACCTGGGCGAGAGCTTCATCCAGACCAA<br>CGACCCGTCGCTGAAGCTCTTCCAGTGCGCCGTCTGCAAC<br>AAGTTCACGACGGACAACCTGGACATGCTGGGCCTGCACA<br>TGAACGTGGAGCGCAGCCTGTCGGAGGACGAGTGGAAGGC<br>GGTGATGGGGGACTCATACCAGTGCAAGCTCTGCCGCTAC<br>AACACCCAGCTCAAGGCCAACTTCCAGCTGCACTGCAAGA<br>CAGACAAGCACGTGCAGAAGTACCAGCTGGTGGCCCACAT<br>CAAGGAGGGCGGCAAGGCCAACGAGTGGAGGCTCAAGTGT<br>GTGGCCATCGGCAACCCCGTGCACCTCAAGTGCAACGCCT<br>GTGACTACTACACCAACAGCCTGGAGAAGCTGCGGCTGCA<br>CACGGTCAACTCCAGGCACGAGGCCAGCCTGAAGTTGTAC<br>AAGCACCTGCAGCAGCATGAGAGTGGTGTAGAAGGTGAGA<br>GCTGCTACTACCACTGCGTTCTGTGCAACTACTCCACCAA<br>GGCCAAGCTCAACCTCATCCAGCATGTGCGCTCCATGAAG<br>CACCAGCGAAGCGAGAGCCTGCGAAAGCTGCAGCGGCTGC<br>AGAAGGGCCTTCCAGAGGAGGACGAGGACCTGGGGCAGAT<br>CTTCACCATCCGCAGGTGCCCCTCCACGGACCCAGAAGAA<br>GCCATTGAAGATGTTGAAGGACCCAGTGAAACAGCTGCTG<br>ATCCAGAGGAGCTTGCTAAGGACCAAGAGGGCGGAGCATC<br><u>GTCCAGCCAAGCAGAGAAGGAGCTGACAGATTCTCCTGCA</u><br>ACCTCCAAACGCATCTCCTTCCCAGGTAGCTCAGAGTCTC<br>CCCTCTCTTCGAAGCGACCAAAAACAGCTGAGGAGATCAA<br>ACCGGAGCAGATGTACCAGTGTCCCTACTGCAAGTACAGT<br>AATGCCGATGTCAACCGGCTCCGGGTGCATGCCATGACGC<br>AGCACTCGGTGCAACCCATGCTTCGCTGCCCCCTGTGCCA<br>GGACATGCTCAACAACAAGATCCACCTCCAGCTGCACCTC<br>ACCCACCTCCACAGCGTGGCACCTGACTGCGTGGAGAAGC<br>TCATTATGACGGTGACCACCCCTGAGATGGTGATGCCAAG<br>CAGCATGTTCCTCCCAGCAGCTGTTCCAGATCGAGATGGG<br>AATTCCAATTTGGAAGAGGCAGGAAAGCAGCCTGAAACCT<br>CAGAGGATCTGGGAAAGAACATCTTGCCATCCGCAAGCAC<br>AGAGCAAAGCGGAGATTTGAAACCATCCCTGCTGACCCA<br>GGCTCTGTGAGAGAAGACTCAGGCTTCATCTGCTGGAAGA<br>AGGGGTGCAACCAGGTTTTCAAAACTTCTGCTGCCCTTCA<br>GACGCATTTTAATGAAGTGCATGCCAAGAGGCCTCAGCTG<br>CCGGTGTCAGATCGCCATGTGTACAAGTACCGCTGTAATC<br>AGTGTAGCCTGGCCTTCAAGACCATTGAAAAGTTGCAGCT<br>CCATTCTCAGTACCATGTGATCAGAGCTGCCACCATGTGC<br>TGTCTTTGTCAGCGCAGTTTCCGAACTTTCCAGGCTCTGA<br>AGAAGCACCTTGAGACAAGCCACCTGGAGCTGAGTGAGGC<br>TGACATCCAACAGCTTTATGGTGGCCTGCTGGCCAATGGG<br>GACCTCCTGGCAATGGGAGACCCCACTCTGGAGAGGACC<br>ATACCATAATTGTGAGGAAGACAAGGAGGAAGAGAGTGA<br>CTTGGAAGATAAACAGAGCCCAACGGGCAGTGACTCTGGG<br>TCAGTACAAGAAGACTCGGGCTCAGAGCCAAAGAGAGCTC | 50 |

TABLE 1-continued

GEP-NEN Biomarker/Houskeeper Sequence Information

| Gene Name | RefSeq Accession | Sequence | SEQ ID NO: |
|---|---|---|---|
| | | TGCCTTTCAGAAAAGGTCCCAATTTTACTATGGAAAAGTT<br>CCTAGACCCTTCTCGCCCTTACAAGTGTACCGTCTGCAAG<br>GAATCTTTCACTCAAAAGAATATCCTGCTAGTACACTACA<br>ATTCTGTCTCCCACCTGCATAAGTTAAAGAGAGCCCTTCA<br>AGAATCAGCAACCGGTCAGCCAGAACCCACCAGCAGCCCA<br>GACAACAAACCTTTTAAGTGTAACACTTGTAATGTGGCCT<br>ACAGCCAGAGTTCCACTCTGGAGATCCATATGAGGTCTGT<br>GTTACATCAAACCAAGGCCCGGGCAGCCAAGCTGGAGGCT<br>GCAAGTGGCAGCAGCAATGGGACTGGGAACAGCAGCAGTA<br>TTTCCTTGAGCTCCTCCACGCCAAGTCCTGTGAGCACCAG<br>TGGCAGTAACACCTTTACCACCTCCAATCCAAGCAGTGCT<br>GGCATTGCTCCAAGCTCTAACTTACTAAGCCAAGTGCCCA<br>CTGAGAGTGTAGGGATGCCACCCCTGGGGAATCCTATTGG<br>TGCCAACATTGCTTCCCCTTCAGAGCCCAAAGAGGCCAAT<br>CGGAAGAAACTGGCAGATATGATTGCATCCAGGCAGCAGC<br>AACAACAGCAGCAGCAACAGCAACAACAACAACAACAACA<br>ACAACAACAAGCACAAACGCTGGCCCAGGCCCAGGCTCAA<br>GTTCAAGCTCACCTGCAGCAGGAGCTGCAGCAACAGGCTG<br>CCCTGATCCAGTCTCAGCTGTTTAACCCCACCCTCCTTCC<br>TCACTTCCCCATGACAACTGAGACCCTGCTGCAACTACAG<br>CAGCAGCAGCACCTCCTCTTCCCTTTCTACATCCCCAGTG<br>CTGAGTTCCAGCTTAACCCCGAGGTGAGCTTGCCAGTGAC<br>CAGTGGGGCACTGACACTGACTGGGACAGGCCCAGGCCTG<br>CTGGAAGATCTGAAGGCTCAGGTTCAGGTCCCACAGCAGA<br>GCCATCAGCAGATCTTGCCGCAGCAGCAGCAGAACCAACT<br>CTCTATAGCCCAGAGTCACTCTGCCCTCCTTCAGCCAAGC<br>CAGCACCCCGAAAAGAAGAACAAATTGGTCATCAAAGAAA<br>AGGAAAAAGAAAGCCAGAGAGAGAGGGACAGCGCCGAGGG<br>GGGAGAGGGCAACACCGGTCCGAAGGAAACACTGCCAGAT<br>GCCTTGAAGGCCAAAGAGAAGAAAGAGTTGGCACCAGGGG<br>GTGGTTCTGAGCCTTCCATGCTCCCTCCACGCATTGCTTC<br>AGATGCCAGAGGGAACGCCACCAAGGCCCTGCTGGAGAAC<br>TTTGGCTTTGAGTTGGTCATCCAGTATAATGAGAACAAGC<br>AGAAGGTGCAGAAAAAGAATGGGAAGACTGACCAGGGAGA<br>GAACCTGGAAAAGCTCGAGTGTGACTCCTGCGGCAAGTTG<br>TTTTCCAACATCTTGATTTTAAAGAGTCATCAAGAGCACG<br>TTCATCAGAATTACTTTCCTTTCAAACAGCTCGAGAGGTT<br>TGCCAAACAGTACAGAGACCACTACGATAAACTGTACCCA<br>CTGAGGCCCCAGACCCCAGAGCCACCACCACCTCCCCCTC<br>CACCCCCTCCACCCCCACTTCCGGCAGCGCCGCCTCAGCC<br>GGCGTCCACACCAGCCATCCCCGCATCAGCCCCACCCATC<br>ACCTCACCTACAATTGCACCGGCCCAGCCATCAGTGCCGC<br>TCACCCAGCTCTCCATGCCGATGGAGCTGCCCATCTTCTC<br>GCCGCTGATGATGCAGACGATGCCGCTGCAGACCTTGCCG<br>GCTCAGCTACCCCCGCAGCTGGGACCTGTGGAGCCTCTGC<br>CTGCGGACCTGGCCCAACTCTACCAGCATCAGCTCAATCC<br>AACCCTGCTCCAGCAGCAGAACAAGAGGCCTCGCACCAGG<br>ATCACAGATGATCAGCTCCGAGTCTTGCGGCAATATTTTG<br>ACATTAACAACTCCCCAGTGAAGAGCAAATAAAAGAGAT<br>GGCAGACAAGTCCGGGTTGCCCCAGAAAGTGATCAAGCAC<br>TGGTTCAGGAACACTCTCTTCAAAGAGAGGCAGCGTAACA<br>AGGACTCCCCTTACAACTTCAGTAATCCTCCTATCACCAG<br>CCTGGAGGAGCTCAAGATTGACTCCCGGCCCCCTTCGCCG<br>GAACCTCCAAAGCAGGAGTACTGGGGAAGCAAGAGGTCTT<br>CAAGAACAAGGTTTACGGACTACCAGCTGAGGGTCTTACA<br>GGACTTCTTCGATGCCAATGCTTACCCAAAGGATGATGAA<br>TTTGAGCAACTCTCTAATTTACTGAACCTTCCAACCCGAG<br>TGATAGTGGTGTGGTTTCAGAATGCCCGACAGAAGGCCAG<br>GAAGAATTATGAGAATCAGGGAGAGGGCAAAGATGGAGAG<br>CGGCGTGAGCTTACAAATGATAGATACATTCGAACAAGCA<br>ACTTGAACTACCAGTGCAAAAAATGTAGCCTGGTGTTTCA<br>GCGCATCTTTGATCTCATCAAGCACCAGAAGAAGCTGTGT<br>TACAAGGATGAGGATGAGGAGGGCAGGACGACAGCCAAA<br>ATGAGGATTCCATGGATGCCATGGAAATCCTGACGCCTAC<br>CAGCTCATCCTGCAGTACCCCGATGCCCTCACAGGCTTAC<br>AGCGCCCCAGCACCATCAGCCAATAATACAGCTTCCTCCG<br>CTTTCTTGCAGCTTACAGCGGAGGCTGAGGAACTGGCCAC<br>CTTCAATTCAAAAACAGAGGCAGGCGATGAGAAACCAAAG<br>CTGGCGGAAGCTCCCAGTGCACAGCCAAACCAAACCCAAG<br>AAAAGCAAGGACAACCAAAGCCAGAGCTGCAGCAGCAAGA<br>GCAGCCCGAGCAGAAGACCAACACTCCCCAGCAGAAGCTC<br>CCCCAGCTGGTGTCCCTGCCTTCGTTGCCACAGCCTCCTC<br>CACAAGCGCCCCTCCACAGTGCCCCTTACCCCAGTCGAG<br>CCCCAGTCCTTCCCAGCTCTCCCACCTGCCCCTCAAGCCC<br>CTCCACACATCAACTCCTCAACAGCTCGCAAACCTACCTC | |

TABLE 1-continued

GEP-NEN Biomarker/Houskeeper Sequence Information

| Gene Name | RefSeq Accession | Sequence | SEQ ID NO: |
|---|---|---|---|
| | | CTCAGCTAATCCCCTACCAGTGTGACCAGTGTAAGTTGGC ATTTCCGTCATTTGAGCACTGGCAGGAGCATCAGCAGCTC CACTTCCTGAGCGCGCAGAACCAGTTCATCCACCCCCAGT TTTTGGACAGGTCCCTGGATATGCCTTTCATGCTCTTTGA TCCCAGTAACCCACTCCTGGCCAGCCAGCTGCTCTCTGGG GCCATACCTCAGATTCCAGCAAGCTCAGCCACTTCTCCTT CAACTCCAACCTCCACAATGAACACTCTCAAGAGGAAGCT GGAGGAAAAGGCCAGTGCAAGCCCTGGCGAAAACGACAGT GGGACAGGAGGAGAAGAGCCTCAGAGAGACAAGCGTTTGA GAACAACCATCACACCGGAACAACTAGAAATTCTCTACCA GAAGTATCTACTGGATTCCAATCCGACTCGAAAGATGTTG GATCACATTGCACACGAGGTGGGCTTGAAGAAACGTGTGG TACAAGTCTGGTTTCAGAACACCCGAGCTCGGGAAAGGAA AGGACAGTTCCGGGCTGTAGGCCCAGCGCAGGCCCACAGG AGATGCCCTTTTTGCAGAGCGCTCTTCAAAGCCAAGACTG CTCTTGAGGCTCATATCCGGTCCCGTCACTGGCATGAAGC CAAGAGAGCTGGCTACAACCTAACTCTGTCTGCGATGCTC TTAGACTGTGATGGGGGACTCCAGATGAAAGGAGATATTT TTGACGGAACTAGCTTTTCCCACCTACCCCCAAGCAGTAG TGATGGTCAGGGTGTCCCCCTCTCACCTGTGAGTAAAACC ATGGAATTGTCACCCAGAACTCTTCTAAGCCCTTCCTCCA TTAAGGTGGAAGGGATTGAAGACTTTGAAAGCCCCTCCAT GTCCTCAGTTAATCTAAACTTTGACCAAACTAAGCTGGAC AACGATGACTGTTCCTCTGTCAACACAGCAATCACAGATA CCACAACTGGAGACGAGGGCAACGCAGATAACGACAGTGC AACGGGAATAGCAACTGAAACCAAATCCTCTTCTGCACCC AACGAAGGGTTGACCAAAGCGGCCATGATGGCAATGTCTG AGTATGAAGATCGGTTGTCATCTGGTCTGGTCAGCCCGGC CCCGAGCTTTTATAGCAAGGAATATGACAATGAAGGTACA GTGGACTACAGTGAAACCTCAAGCCTTGCAGATCCCTGCT CCCCGAGTCCTGGTGCGAGTGGATCTGCAGGCAAATCTGG TGACAGCGGAGATCGGCCTGGGCAGAAACGTTTTCGCACT CAAATGACCAATCTGCAGCTGAAGGTCCTCAAGTCATGCT TTAATGACTACAGGACACCCACTATGCTAGAATGTGAGGT CCTGGGCAATGACATTGGACTGCCAAAGAGAGTCGTTCAG GTCTGGTTCCAGAATGCCCGGGCAAAAGAAAAGAAGTCCA AGTTAAGCATGGCCAAGCATTTTGGTATAAACCAAACGAG TTATGAGGGACCCAAAACAGAGTGCACTTTGTGTGGCATC AAGTACAGCGCTCGGCTGTCTGTACGTGACCATATCTTTT CCCAACAGCATATCTCCAAAGTTAAAGACACCATTGGAAG CCAGCTGGACAAGGAGAAAGAATACTTTGACCCAGCCACC GTACGTCAGTTGATGGCTCAACAAGAGTTGGACCGGATTA AAAAGGCCAACGAGGTCCTTGGACTGGCAGCTCAGCAGCA AGGGATGTTTGACAACACCCCTCTTCAGGCCCTTAACCTT CCTACAGCATATCCAGCGCTCCAGGGCATTCCTCCTGTGT TGCTCCCGGGCCTCAACAGCCCCTCCTTGCCAGGCTTTAC TCCATCCAACACAGCTTTAACGTCTCCTAAGCCGAACTTG ATGGGTCTGCCCAGCACAACTGTTCCTTCCCTGGCCTCC CCACTTCTGGATTACCAAATAAACCGTCCTCAGCGTCGCT GAGCTCCCCAACCCCAGCACAAGCCACGATGGCGATGGGC CCTCAGCAACCCCCCAGCAGCAGCAGCAGCAGCAGCAAC CACAGGTGCAGCAGCCTCCCCCGCCGCCAGCAGCCCAGCC GCCACCCACACCACAGCTCCCACTGCAACAGCAGCAGCAA CGCAAGGACAAAGACAGTGAGAAAGTAAAGGAGAAGGAAA AGGCACACAAAGGGAAGGGGAACCCCTGCCTGTCCCCAA GAAGGAGAAAGGAGAGGCCCCCACGGCAACTGCAGCCACG ATCTCAGCCCCGCTGCCCACCATGGAGTATGCGGTAGACC CTGCACAGCTGCAGGCCCTGCAGGCCGCGTTGACTTCGGA CCCCACAGCATTGCTCACAAGCCAGTTCCTTCCTTACTTT GTACCAGGCTTTTCTCCTTATTATGCTCCCCAGATCCCTG GCGCCCTGCAGAGCGGGTACCTGCAGCCTATGTATGGCAT GGAAGGCCTGTTCCCCTACAGCCCTGCACTGTCGCAGGCC CTGATGGGGCTGTCCCCAGGCTCCCTACTGCAGCAGTACC AGCAATACCAGCAGAGTCTGCAGGAGGCAATTCAGCAGCA GCAGCAGCGGCAACTACAGCAGCAGCAGCAGCAAAAAGTG CAGCAGCAGCAGCCCAAAGCAAGCCAAACCCCAGTCCCCC CCGGGGCTCCTTCCCCAGACAAAGACCCTGCCAAAGAATC CCCCAAACCAGAAGAACAGAAAAACACCCCCGTGAGGTG TCCCCCCTCCTGCCGAAACTCCCTGAAGAGCCAGAAGCAG AAAGCAAAAGTGCGGACTCCCTCTACGACCCCTTCATTGT TCCAAAGGTGCAGTACAAGTTGGTCTGCCGCAAGTGCCAG GCGGGCTTCAGCGACGAGGAGGCAGCGAGGAGCCACCTGA AGTCCCTCTGCTTCTTCGGCCAGTCTGTGGTGAACCTGCA AGAGATGGTGCTTCACGTCCCCACCGGCGGCGGCGGCGGT GGCAGTGGCGGCGGCGGCGGCGGTGGCGGCGGCGGCGGCG | |

TABLE 1-continued

GEP-NEN Biomarker/Houskeeper Sequence Information

| Gene Name | RefSeq Accession | Sequence | SEQ ID NO: |
|---|---|---|---|
| | | GCGGCGGCTCGTACCACTGCCTGGCGTGCGAGAGCGCGCT<br>CTGTGGGGAGGAAGCTCTGAGTCAACATCTCGAGTCGGCC<br>TTGCACAAACACAGAACAATCACGAGAGCAGCAAGAAACG<br>CCAAAGAGCACCCTAGTTTATTACCTCACTCTGCCTGCTT<br>CCCCGATCCTAGCACCGCATCTACCTCGCAGTCTGCCGCT<br>CACTCAAACGACAGCCCCCCTCCCCCGTCGGCCGCCGCCC<br>CCTCCTCCGCTTCCCCCCACGCCTCCAGGAAGTCTTGGCC<br>GCAAGTGGTCTCCCGGGCTTCGGCAGCGAAGCCCCCTTCT<br>TTTCCTCCTCTCTCCTCATCTTCAACGGTTACCTCAAGTT<br>CATGCAGCACCTCAGGGGTTCAGCCCTCGATGCCAACAGA<br>CGACTATTCGGAGGAGTCTGACACGGATCTCAGCCAAAAG<br>TCCGACGGACCGGCGAGCCCGGTGGAGGGTCCCAAAGACC<br>CCAGCTGCCCCAAGGACAGTGGTCTGACCAGTGTAGGAAC<br>GGACACCTTCAGATTGTAAGCTTTGAAGATGAACAATACA<br>AACAAATGAATTTAAATACAAAAATTAATAACAAACCAAT<br>TTCAAAAATAGACTAACTGCAATTCCAAAGCTTCTAACCA<br>AAAAACAAAAAAAAAAAAAAAAGAAAAAAAGAAAAAGC<br>GTGGGTTGTTTCCCATATACCTATCTATGCCGGTGATTT<br>TACATTCTTGTCTTTTCTTTTCTTTTAATATTAAAAAAA<br>AAAAAAAGCCCTAACCCTGTTACATTGTGTCCTTTTGAA<br>GGTACTATTGGTCTGGGAAACAGAAGTCCGCAGGGCCTCC<br>CTAATGTCTTTGGAGCTTAAACCCCTTGTATATTTGCCCC<br>TTTTCAATAAACGCCCCACGCTGATAGCACAGAGGAGCCC<br>GGCATGCACTGTATGGGAAAGCAGTCCACCTTGTTACAGT<br>TTTAAATTTCTTGCTATCTTAGCATTCAGATACCAATGGC<br>TTGCTAAAAGAAAAAAGAAATGTAATGTCTTTTTATTCT<br>CAGGTCAATCGCTCACACTTTGTTTTCAGAATCATTGTTT<br>TATATATTATTGTTTTTCAGTTTTTTTTTTTTTTTTGT<br>TCCAGAAAAGATTTTTTGTTTTGTTAACTTAAAAATGGGC<br>AGAAAGTATTCAAGAAAAACAATGTGAACTGCTTTAGCTT<br>TCTGGGGATTTTTAAGGATAGCTTTTCTGCTGAAGCCAAT<br>TTCAAGGGGAAAAGTTAAGCACTCCCACTTTCAAAAAAAA<br>AAAAAAATAATAACCCACACACACAAAGAGTGTTGAGGAC<br>TTGTAGCTTAAAAAAAATAAGTTTTAAAAACTGACTTTCT<br>GTATTTATGATAGATATGACCATTTTTGGTGTTGAGTAGA<br>TTGTTGCATTGGAAATGAACTGAAGCAGTATGGTAGATTT<br>AAAAGGAAAAAAAAAAAAAAACCTTTTGTGTACATTTAGC<br>TTTTTGTATGGTCCAGCTGACAGCTCCTCATTTGATGTTG<br>TCTTGTTCATTCCTAGCAGATGATAGATTGCAATCCGTTG<br>ATTCGCCTAAGCTTTTCTCCCCTTGTCCCTTAATTCCACT<br>TTCTCTTTCTTGTCCCTTAATTCCACTTTCTCTTTCCTTC<br>TCCCACCTCCCGTCCTATAATCTCCCACTTAAGGTAGCTG<br>CCTTCATTTCTTAGAGGGAGCTGCAGAATTATTTTATAAA<br>ACTAAAGAAAGAATTTCAAGGGATTCTAGGGGTCATTAGG<br>ATCCTCACAGATTATTTTTGGTTGGGGAGTTGAAACTTTT<br>TAAAGGCATATAATTCTAGTTACCTGTGTCTGTTAGCTTT<br>GTGCATTTATTTTTATTTATCCTTCTTTTGGCTTTTTTT<br>TCTTTGTACCCCTTCTTTTCCTCCTTGTTTGGTAGGAGCT<br>TCAAATATTCTTTTTTTTCTATACTAAAGGATTTGTTTC<br>CATTTGTGTAATTGGCTGTGTACTTTTCTTTTCTAAAAAA<br>AGTTTTTGGTTAGGGATTTGGTTTTTGGTTTTGTGTTTGT<br>TTTTTCTTTCCTCTCTCAGAAAAAAAAATTTCATGCTTTA<br>AATAAAATCCAAAGACACACCCTTTCACTGCTGATGCAGA<br>AAAAAGGGAAAGGGTTCTTGTTACTTGAGAATTTGTTTCT<br>GATTTAAACAAACAAGACTTAGTTTAATAAAAGAAAGAGA<br>AAAACAAAAGATTCCCAGGTTGTTATGTGCTTCTTCTGCA<br>AGCAGAGAGGCAAATGTTAATGACAATTCCATATACCAAA<br>AGACACATTTTTACTTCAAAGTTTTGTCCTTGTGTTAGG<br>CAGTCTGAGCAGCGAGTGATCCAGAGCGCAGCCAACAAAG<br>CAGCAGATAGCAGTGTACAGAAAGCAAAAAGGAACTGTA<br>TGTGAGGCACTTGTTTCTGTTAATATCCATATTCCTGTTA<br>ACACACACCCTTTCTCATGTAAAAAGAAAAATAAATAAAT<br>GGTCTGAACTTTGAAAACTTTGTGCTGCTAAAACATAGAT<br>TTTGGAGACAAATAAATAGATGCTTTGCTGTTTCACTTTC<br>ATAGCTAAACATCAACAGAAACCATCTCCCCTTGCCCCCA<br>AAGTGTGAAATCCTTCTTCCCTTCGTTTTCTTCCTTATGT<br>TTCAAAAGGGAACTTTGAAGACTGTGAATACAGGTTCCAT<br>TGGTCACCTTTCGGGCTTCTTTCCCCAGTGCTGAAGCCAC<br>TCATCGACTTTGCAAAAGACTGGAGCATTCCAAGATCTGA<br>AAATGGATTTTTTTCTTTTTTCTTTTTTAGCCGGGACT<br>ATTTTATTTTTATGAATTTGTTTTTAGTTTAATGAAATAG<br>TAGATCCTGAAATGTTGTACATATTTCTAACTAGGCTGAT<br>GCACAGTGCAAATTCCTTTTTAATTGTTTTTTTTAAGTA<br>GAAATACTAAAGAAAGAATACCATCTAACTATTCATACCA<br>GTATCCAGTTGTAGCATAAGGTGTCAAAAGCAAGTACGCA | |

TABLE 1-continued

GEP-NEN Biomarker/Houskeeper Sequence Information

| Gene Name | RefSeq Accession | Sequence | SEQ ID NO: |
|---|---|---|---|
| | | AAACATTTACTGTTTTAACAAGCTATTTCCTTTTAACAAG<br>AAATCTTGTATTTCTTCCTGTGTTTGAGATGAACATTTTT<br>AAATTTTAAAGTTGTACAGTTTTTTGTTTTCCATTATTTT<br>ATCTTGTTTGTAACTCTATGAAATATATATATATATATTT<br>TTTGCCATTTAACTGTTGTATGTTACTCTGTGTCTGTACC<br>ATATAGAAAAAAAATTGTTTTTGTTTTTGGTTCTCTATGT<br>GATATCAGTTAACAATGTAACACTAGCTTTACCTGTCAAA<br>TTCTGCTAGGTCTTCTCTGAAAACGTTGTTTTTAAAAATG<br>ATATTGCTTGGTAATAGTGCAATTTCTATCCTTTTCCCTC<br>CCCCCTCAACTTTTAAGTTCTTTTCTTTATAATTTTGCTG<br>CCCCCTCCCTGATGGTTTGGGTTTTTGTTTTTGTTTTTGT<br>TTTTTTTTTTCATGGAGCTACTATGCCATCCTCCCTCTGT<br>GAGGCAGAGTGACTGTCAGTGTTTTGTTATGCCATGCCTT<br>GAGCTGTGGGTGTTTGGCGACAATAAGGTGGTTGAATAGA<br>TTGGCTGAGCACACTTCCACCCACCTAGTGTTCTCAGAGG<br>GGTTATGTGATTGTTTCAACCTGGAGTGGGTTGCACCCTT<br>AATGCTTTCCTCTGCAACTAAACCGCCCACATATATGTTC<br>ATTGAAAAAAGTAAGAATAATTCTCAGCACTAACCCAGAA<br>GTAGCAAAGCAGTCAGTGATGGTGAACATTAGAGGTCAAA<br>CATGAGTTAGATGTTTGTGGGCTGACAGCCATCGTGGCTA<br>TGACCAGTACTATTTACAAAGCATGAATTCACTACAATGC<br>TCAACTGTTTGTTTAGCTTTATCTCACTTGGGGAATTTAT<br>TCCTGTCTGCTGCATTGTAGGTAGCTGGGTAGGATATATT<br>TCCACTTGCTTTTTAAATTAGTTCTTCACCTCCATTGACA<br>CTCGTTTTTTGGTTTTCTCCCTATAGTGTGGGTTGGTGCT<br>AGACACCAGTCTGACCCACAGAATGGGAGTTATTTCATCC<br>ATCTTTCCTCCATCCTTCCAAAAACCACATATCTACACAA<br>GGAAAAATTTAATACATCTAGGAATTTTTTTTTAATTAC<br>AAGCTATTTAAAGAGATGAATGTGGCCAAAGTTTTACACA<br>ATTGAAAATAAAGTAAAACAGACGGCATGTGTTTAAACCT<br>GAGTTTATCAGGCATGGCAGGAAGTTGCAGGAGAGAGAGG<br>CAGTGACCCAAGCCAGTGCACTTGATGTTCATGGACATAT<br>ATTTTTTTTAAATAATAAATTAAAACATTTTAAATAGAAG<br>CATAAATTGAGTTGTTTGTTGGCGCTGAGATACTGCCCAC<br>TGTGAAACAAAGCTTTGACTAGTTTTTTGTTTGTTTACTT<br>TCTTCAGGGGGGAGGGGGGCAAGTTTGGGTAGGAAAGAAA<br>GCATAAATGAACGTGACCCTGAGGTGAAGAGGTATATGAA<br>CAGCCTTTGCAATGTACAAAAAGAAAAAAAAACAAAAAAC<br>AACAAAAAAATAGAGCAAGTGAAACCAAAAATGATGTTC<br>TTGGTGTTTTTCTATAATGTAGTCTTGTTAGCTTTTTTGT<br>TACTGTAACAATGCTGATCTCGAACTGTACCAAAATACAT<br>GGAGACTAACAAACAGAACCACATGGAACTTTCAAACTGA<br>AAAAAAAATTTGTCACAAAAACTTTGTTGTCATAGTTAAG<br>TTGATTGTAGATGGTAATTGAATATACTCCTTTGAAAATA<br>TTTCATCAAGTATGTTTCCTGCTCATTGTGATACATTAAA<br>AAAAAAATATGAGCAAAA | |
| ZXDC | NM_001040653.3 | GGGCGCGGGCAGCTCTGCGTCCGAAGCTGCTCCGACGCCG<br>TCGCTGGGACCAAGATGGACCTCCCGGCGCTGCTCCCCGC<br>CCCGACTGCGCGCGGAGGGCAACATGGCGGCGGCCCCGGC<br>CCGCTCCGCCGAGCCCCAGCGCCGCTCGGCGCGAGCCCCG<br>CGCGCCGCCGCCTGCTACTGGTGCGGGGCCCTGAAGATGG<br>CGGGCCCGGGGCGCGGCCCCGGGGAGGCCTCCGGGCCAAGC<br>CCGCCGCCCGCCGAGGACGACAGCGACGGCGACTCTTTCT<br>TGGTGCTGCTGGAAGTGCCGCACGGCGGCGCTGCCGCCGA<br>GGCTGCCGGATCACAGGAGGCCGAGCCTGGCTCCCGTGTC<br>AACCTGGCGAGCCGCCCCGAGCAGGGCCCCAGCGGCCCGG<br>CCGCCCCCCCGGCCCTGGCGTAGCCCCGGCGGGCGCCGT<br>CACCATCAGCAGCCAGGACCTGCTGGTGCGTCTCGACCGC<br>GGCGTCCTCGCGCTGTCTGCGCCGCCCGGCCCCGCAACCG<br>CGGGCGCCGCCGCTCCCCGCCGCGCGCCCCAGGCCTCCGG<br>CCCCAGCACGCCCGGCTACCGCTGCCCCGAGCCGCAGTGC<br>GCGCTGGCCTTCGCCAAGAAGCACCAGCTCAAGGTGCACC<br>TGCTCACGCACGGCGGCGGTCAGGGCCGGCGGCCCTTCAA<br>GTGCCCACTGGAGGGCTGTGGTTGGGCCTTCACAACGTCC<br>TACAAGCTCAAGCGGCACCTGCAGTCGCACGACAAGCTGC<br>GGCCCTTCGGCTGTCTGTCCAGTGGGCGGCTGTGGCAAGAAGTT<br>CACTACGGTCTATAACCTCAAGGCGCACATGAAGGGCCAC<br>GAGCAGGAGAGCCTGTTCAAGTGCGAGGTGTGCGCCGAGC<br>GCTTCCCCACGCACGCCAAGCTCAGCTCCCACCAGCGCAG<br>CCACTTCGAGCCCGAGCGCCCTTACAAGTGTGACTTTCCC<br>GGCTGTGAGAAGACATTTATCACAGTGAGTGCCCTGTTTT<br>CCCATAACCGAGCCCACTTCAGGGAACAAGAGCTCTTTTC<br>CTGCTCCTTTCCTGGGTGCAGCAAGCAGTATGATAAAGCC<br>TGTCGGCTGAAAATTCACCTGCGGAGCCATACAGGTGAAA | 51 |

TABLE 1-continued

GEP-NEN Biomarker/Houskeeper Sequence Information

| Gene Name | RefSeq Accession | Sequence | SEQ ID NO: |
|---|---|---|---|
| | | GACCATTTATTTGTGACTCTGACAGCTGTGGCTGGACCTT | |
| | | CACCAGCATGTCCAAACTTCTAAGGCACAGAAGGAAACAT | |
| | | GACGATGACCGGAGGTTTACCTGCCCTGTCGAGGGCTGTG | |
| | | GGAAATCATTCACCAGAGCAGAGCATCTGAAAGGCCACAG | |
| | | CATAACCCACCTAGGCACAAAGCCGTTCGAGTGTCCTGTG | |
| | | GAAGGATGTTGCGCGAGGTTCTCCGCTCGTAGCAGTCTGT | |
| | | ACATTCACTCTAAGAAACACGTGCAGGATGTGGGTGCTCC | |
| | | GAAAAGCCGTTGCCCAGTTTCTACCTGCAACAGACTCTTC | |
| | | ACCTCCAAGCACAGCATGAAGGCGCACATGGTCAGACAGC | |
| | | ACAGCCGGCGCCAAGATCTCTTACCTCAGCTAGAAGCTCC | |
| | | GAGTTCTCTTACTCCCAGCAGTGAACTCAGCAGCCCAGGC | |
| | | CAAAGTGAGCTCACTAACATGGATCTTGCTGCACTCTTCT | |
| | | CTGACACACCTGCCAATGCTAGTGGTTCTGCAGGTGGGTC | |
| | | GGATGAGGCTCTGAACTCCGGAATCCTGACTATTGACGTC | |
| | | ACTTCTGTGAGCTCCTCTCTGGGAGGGAACCTCCCTGCTA | |
| | | ATAATAGCTCCCTAGGGCCGATGGAACCCCTGGTCCTGGT | |
| | | GGCCCACAGTGATATTCCCCCAAGCCTGGACAGCCCTCTG | |
| | | GTTCTCGGGACAGCAGCCACGGTTCTGCAGCAGGGCAGCT | |
| | | TCAGTGTGGATGACGTGCAGACTGTGAGTGCAGGAGCATT | |
| | | AGGCTGTCTGGTGGCTCTGCCCATGAAGAACTTGAGTGAC | |
| | | GACCCACTGGCTTTGACCTCCAATAGTAACTTAGCAGCAC | |
| | | ATATCACCACACCGACCTCTTCGAGCACCCCCCGAGAAAA | |
| | | TGCCAGTGTCCCGGAACTGCTGGCTCCAATCAAGGTGGAG | |
| | | CCGGACTCGCCTTCTCGCCCAGGAGCAGTTGGGCAGCAGG | |
| | | AAGGAAGCCATGGGCTGCCCCAGTCCACGTTGCCCAGTCC | |
| | | AGCAGAGCAGCACGGTGCCCAGGACACAGAGCTCAGTGCA | |
| | | GGCACTGGCAACTTCTATTTGGTATGAAGCACTCTATTCA | |
| | | GTCACCACCATATAGGTCACTTCTCTCATACTCGGTCTTG | |
| | | AGGATATTCTGGATTAATCCTTTCTATGCAGACGTTTCTG | |
| | | GTTTACAAAAGGACGCAGCCCTGGACTACAAGTCTGGAAC | |
| | | TGACAAGTTCTTATGACCTTGACAAATCACCTTAACCCAT | |
| | | CTGAGCCTTAAATTCTCATTTATTTCCTGCATAAGGAGAT | |
| | | TTGGCTAAATGCTTTCTGAGGTCCTTTGGAGTCCTGTGGC | |
| | | TCCATGGTAATGTGCTCCTTTCCTTGAAGATTGGGGGTTT | |
| | | TGTAATGTTGAGATACTTTGCCTCTATGCTTGTCAGCTCA | |
| | | TGACCAGTCCTAGAAGAGGAGTCGAGACATAAGCCACCTT | |
| | | CAGAGGTTCAATGGAAACTTTAAAACCATACCAAACTCTT | |
| | | TTTTAAAATTAGAATTAACAAGAAAAAAAAAAAGGGTGGG | |
| | | GTTTATGAGCCTTAGTTCTTGGAGGATTATAAGAGTACTT | |
| | | CCCCAGTTTTGAGGCTGGACAGTTAATATACTTTATATCA | |
| | | ATTATACATTTAATATAATTTAATTTAAAATAATTTAAAG | |
| | | ATTCTTAGGAGATAGTCTGACTTTCCTGACCTAGATGGGA | |
| | | ATGATCAGATAGGGATTTTTTTTGTGGCACAGGCTAAATT | |
| | | TGATGGTGACATTTATATTGTTGAGAATGTTACATCTTAT | |
| | | TTTACCACAACTTTTAAAAAATGTTACATCTTTTGCAGTA | |
| | | GGATCAGTTGTGAGGCACATAGTAGCTGAGGCTCCATGGA | |
| | | GCCACCTTTCATTTCTTTCAGTCAGAGAGGAGGACAGTCT | |
| | | CTGTCTCTGCATTTCTGGTGTCTTGCTTGTCGGTGGCAGA | |
| | | GCCATGCTTGCCGGCATTTGCTTAGGCGGCCATAGTAGTT | |
| | | GCTAAGTGTACAGGTGACTGGGCAGGGATGGGAGGTGGCC | |
| | | ACAGGTCAGAGACAAGTGCTCAGTCAGTCCCTGGTGCCAG | |
| | | GACTGTGTGCCTCGGTGCCTTGGGAAATGGAAGCTCCCTG | |
| | | GTGCAGCTGCAGCTGTGGGTGGAGGTAGAGAAGCCAGCAA | |
| | | GACCTTGGTCTTAACCCCGTGTTCATTTTCTTGCTAGCTG | |
| | | TGTGACGTTGGGCTACCTCGCTTCTCTGAGTACAAATGGT | |
| | | GTGTGGTGAATGGGTCCCAGGTATGCTACGAGCTTTGAGG | |
| | | GCTGCTCTTTTTCTCTTCATAGCGATAAGTGTTAAACTGT | |
| | | CTTTCTTAGGAAACGTTCACAGACTTGCAACAGCTGATGT | |
| | | CCTCTGAGTACTGTCTGACTCCCTCAGGCAAGTTCCTGAA | |
| | | TTCAGTACCATCATTATTATTTTGTGTAAGACTTTGACA | |
| | | AAGTATAGCCCCTGCCACCAGAGCAGCCTGTACAGTGGGT | |
| | | CTCTAAGGTGGGACCTGCCCCGGGCCTGCCATGCACGTGT | |
| | | GTGAAACAGCGTGAAAAGTGTCGCGGTAAGGTGACCCTGG | |
| | | GTTACCCAGGCAAGGCTCGGTGTTTGTTTCAGAAAGCAGA | |
| | | GAAGTATGTAATTGATTTTAAAAGTTTCTGTTTAAAATAT | |
| | | TTGGCTATGTTTTAGACTATGAAGGAATGAACTTTGCTTC | |
| | | TCTGGATAAGAAAGTCACATACATTGTTCCAGCTCCAAGT | |
| | | TTGTTCGGCCCTCGCCACAAGTGGATGTAGCGTTTGGCCC | |
| | | TTTGTGTGCCTTGCTGGTGACTCTGGTTTTGGGAGCTCGG | |
| | | ATATGTCCCAGAAGCAGGCTTATGGCACTTCTGTAGCTCC | |
| | | CTTGCTACCCTTCCTTTGTGTCTAGATAAGTGACTGACAT | |
| | | GCTTTTCTTTGGTCTCAGGAAAGTGGGGCTCAGCAAGAA | |
| | | CTGATTACCGAGCCATTCAACTAGCCAAGGAAAAAAAGCA | |
| | | GAGAGGAGCGGGGAGCAATGCAGGTGAGGCCGTGTGTGCT | |
| | | GCAGCCGGACGAGCAAGGGCCTGAGGGTTCTCTGTCACTG | |

TABLE 1-continued

GEP-NEN Biomarker/Houskeeper Sequence Information

| Gene Name | RefSeq Accession | Sequence | SEQ ID NO: |
|---|---|---|---|
| | | TTACTGGCAGAAGAAACACAGCAGGTGTTTCTGTGCTCTT<br>GGTTTTACTTTTCTGTTCAGAATACCCTTTTATCAACTCC<br>TTAGTTTTATTTGAACTTAAGGGAAAAAATTAGTAACAAA<br>ATTCCCAGCATCAGTATGAACATATTTTATTTGCCTAAAC<br>AAGCTTTGTGAAAGTTAAGCGTTCAAACACCAGTGTCAGT<br>TACCTGGAAGGCTACTAAGGTAAATAAGCAAAGCAGGCCA<br>GTTGTCAGGAAAGCAGAGATTGTGCCTGGTGCTGAATGGC<br>CTTGGGGCCTGATCTTGGCATGGCAGAGACCTGGGGACTG<br>CCACTGTCCCCAGGTACGTGTACATGGAGCCAAACTGTGT<br>GTCCTGTGGCATTGTCAGAGTTATGTTGAAATCTTATTTG<br>AAAATGTTAGCAACTTACTTGCATTTTTAAAGACCAAACA<br>AGAGCTGGTAACCTATGGCCTCAAGCATCTGTCCTTCCTA<br>AAAATGGAATAGTGGGATGTAGTGCTTAATGGAAACTGCT<br>AAATCTTTTTCTAAAAACTAACAGTGGATTTTTAAAATAT<br>ATTGTTTTTTGTGTATTTCATTTGTCCTTTGTATTTATCT<br>AAAAGGGTTGATATGATTTTATATCTTGCTCTCTATTCCT<br>AATAGTATTATGACTTCTTATTTAAAATAAATAACAATTG<br>CCGGTTTTCTGTTAAAAAAAAAAAA | |
| ZZZ3 | NM_015534.4 | GTTGGCAGAGCAGTTGTCCTGGATGGCGGAGCCTTGGGTT<br>CCGGGGGCCTGGGACCTGCAACTCTTTCTACAAGATATCA<br>AGTTATTCTAGTACAACCATATAAATAAATAATACCTGAA<br>GTCTCAGTGTAACATGGACAATTAACAGTGATGACAGATA<br>AATACAGACGCATGGGGATCAAATACTAGGCAAAACGCTT<br>TTTAAAAGTGTATCAGGCTTTTAAGAAACACTGCAGGATC<br>CTGTCTATCTTAATGCTGATAGAGCTCAGCTAAAAATTTA<br>GGAGGTTCTAGTATTCTTCATGGCTGAAGCTGAGAGAGTC<br>TGAAACCCTGATGCTTAAGCTCCATTCTAGATCATAGCTC<br>CAACTCCTTCAGGATATAAGGAAAAGAGATTATATTTCCA<br>CAATGATAGATCTTTGGTTGTACAGGTTTCCCAATGAGTG<br>GATCATGATGACCGTATTGTAGGGACTTGCCATAGTATGG<br>CTGCTTCCCGATCTACTCGTGTTACAAGATCAACAGTGGG<br>GTTAAACGGCTTGGATGAATCTTTTTGTGGTAGAACTTTA<br>AGGAATCGTAGCATTGCGCATCCTGAAGAAATCTCTTCTA<br>ATTCTCAAGTACGATCAAGATCACCAAAGAAGAGACCAGA<br>GCCTGTGCCAATTCAGAAAGGAAATAATAATGGGAGAACC<br>ACTGATTTAAAACAGCAGAGTACCCGAGAATCATGGGTAA<br>GCCCTAGGAAAAGAGGACTTTCTTCTTCAGAAAAGGATAA<br>CATAGAAAGGCAGGCTATAGAAAATTGTGAGAGAAGGCAA<br>ACAGAACCTGTTTCACCAGTTTTAAAAAGAATTAAGCGTT<br>GTCTTAGATCTGAAGCACCAAACAGTTCAGAAGAAGATTC<br>TCCTATAAAATCAGACAAGGAGTCAGTAGAACAGAGGAGT<br>ACAGTAGTGGACAATGATGCAGATTTTCAAGGGACTAAAC<br>GAGCTTGTCGATGTCTTATACTGGATGATTGTGAGAAAAG<br>GGAAATTAAAAAGGTGAATGTCAGTGAGGAAGGGCCACTT<br>AATTCTGCAGTAGTTGAAGAAATCACAGGCTATTTGGCTG<br>TCAATGGTGTTGATGACAGTGATTCAGCTGTTATAAACTG<br>TGATGACTGTCAGCCTGATGGGAACACTAAACAAAATAGC<br>ATTGGTTCCTATGTGTTACAGGAAAAATCAGTAGCTGAAA<br>ATGGGGATACGGATACCCAAACTTCAATGTTCCTTGATAG<br>TAGGAAGGAGGACAGTTATATAGACCATAAGGTGCCTTGC<br>ACAGATTCACAAGTGCAGGTCAAGTTGGAGGACCACAAAA<br>TAGTAACTGCCTGCTTGCCTGTGGAACATGTTAATCAGCT<br>GACTACTGAGCCAGCTACAGGGCCCTTTTCTGAAACTCAG<br>TCATCTTTAAGGGATTCTGAGGAGGAAGTAGATGTGGTGG<br>GAGATAGCAGTGCCTCAAAAGAGCAGTGTAAAGAAAACAC<br>CAATAACGAACTGGACACAAGTCTTGAGAGTATGCCAGCC<br>TCCGGAGAACCTGAACCATCTCCTGTTCTAGACTGTGTTT<br>CAGCTCAAATGATGTCTTTATCAGAACCTCAAGAACATCG<br>TTATACTCTGAGAACCTCACCACGAAGGCAGCCCCTACC<br>AGAGGTAGTCCCACTAAAAACAGTTCTCCTTACAGAGAAA<br>ATGGACAATTTGAGGAGAATAATCTTAGTCCTAATGAAAC<br>AAATGCAACTGTTAGTGATAATGTAAGTCAATCTCCTACA<br>AATCCTGGTGAAATTTCTCAAATGAAAAAGGGATATGTT<br>GTGACTCTCAAAATAATGGAAGTGAAGGAGTAAGTAAACC<br>ACCCTCAGAGGCAAGACTCAATATTGGACATTTGCCATCT<br>GCCAAAGAGAGTGCCAGTCAGCACATTACAGAAGAGGAAG<br>ATGATGATCCTGATGTTTATTACTTTGAATCAGATCATGT<br>GGCACTGAAACACAACAAAGATTATCAGAGACTATTACAG<br>ACGATTGCTGTACTCGAGGCTCAGCGTTCTCAAGCAGTCC<br>AAGACCTTGAAAGTTTAGGCAGGCACCAGAGAGAAGCACT<br>GAAAAATCCCATTGGATTTGTGGAAAAACTCCAGAAGAAG<br>GCTGATATTGGGCTTCCATATCCACAGAGAGTTGTTCAAT<br>TGCCTGAGATCGTATGGGACCAATATACCCATAGCCTTGG<br>GAATTTTGAAAGAGAATTTAAAAATCGTAAAAGACATACT | 52 |

TABLE 1-continued

GEP-NEN Biomarker/Houskeeper Sequence Information

| Gene Name | RefSeq Accession | Sequence | SEQ ID NO: |
|---|---|---|---|
| | | AGAAGAGTTAAGCTAGTTTTTGATAAAGTAGGTTTACCTG<br>CTAGACCAAAAAGTCCTTTAGATCCTAAGAAGGATGGAGA<br>GTCCCTTTCATATTCTATGTTGCCTTTGAGTGATGGTCCA<br>GAAGGCTCAAGCAGTCGTCCTCAGATGATAAGAGGACGCT<br>TGTGTGATGATACCAAACCTGAAACATTTAACCAGTTGTG<br>GACTGTTGAAGAACAGAAAAAGCTGGAACAGCTACTCATC<br>AAATACCCTCCTGAAGAAGTAGAATCTCGACGCTGGCAGA<br>AGATAGCAGATGAATTGGGCAACAGGACAGCAAAACAGGT<br>TGCCAGCCGAGTACAGAAGTATTTCATAAAGCTAACTAAA<br>GCTGGCATTCCAGTACCAGGCAGAACACCAAACTTATATA<br>TATACTCCAAAAAGTCTTCAACAAGCAGACGACAGCACCC<br>TCTTAATAAGCATCTCTTTAAGCCTTCCACTTTCATGACT<br>TCACATGAACCGCCAGTGTATATGGATGAAGATGATGACC<br>GATCTTGTTTTCATAGCCACATGAACACTGCTGTTGAAGA<br>TGCATCAGATGACGAAAGTATTCCTATCATGTATAGGAAT<br>TTACCTGAATATAAAGAACTATTACAGTTTAAAAAGTTAA<br>AGAAGCAGAAACTTCAGCAAATGCAAGC<u>TGAAAGTGGATT<br>TGTGCAACATGTGGGCTTTAAGTGTGATAACTGTGGCATA<br>GAACCCATCCAGGGTGTTCGGTGGCATTGCCAGGATTGTC</u><br>CTCCAGAAATGTCTTTGGATTTCTGTGATTCTTGTTCAGA<br>CTGTCTACATGAAACAGATATTCACAAGGAAGATCACCAA<br>TTAGAACCTATTTATAGGTCAGAGACATTCTTAGACAGAG<br>ACTACTGTGTGTCTCAGGGCACCAGTTACAATTACCTTGA<br>CCCAAACTACTTTCCAGCAAACAGATGACATGGAAGAGAA<br>CATCATTTACTAGTCCTCTTCAACACATAGCAATGGTATC<br>ATTGTTAATTATGTGCACAGTTTGGAAAGATTCTCTGCTT<br>TCCCAGAAATGACACTCACAGCATGAGAGCTTCCTGAGTG<br>TTCTCGTCAAGTACAGCTCTGCACCGTTGTGGCTCTAGAT<br>CACTGTTCAGCAGCTGAACATTCCTGGTGAGCAAAGGTTT<br>CCCTGGTGAATTTTTCACCACTGCGTTTTAGGTGGTGATC<br>TTAAATGGGTGAGATGGAACGAGAGCACACATTAAAGAGA<br>GAGTAAATTCCAAAGGTTTCAAAGAACTTGGTCATAAATA<br>TGATAATGAGAAGACAAAGTATTTATATTAAAACAGTTTA<br>GTAGCCTTCAGTTTTGTGAAAATAGTTTTCAGCACAGAAA<br>CTGACTTCTTTAGACAAAGTTTTAACCAATGATGGTGTTT<br>GCTTCTAGGATATACACTTTAAAAGAACTCACTGTCCCAG<br>TGGTGGTCATTGATGGCCTTTAGTAAATTGGAGCTGCTTA<br>ATCATATTGATATCTAATTTCTTTTAACCACAATGAATTG<br>TCCTTAATTACCAACAGTGAAGCACTACAGGAGGCAACTG<br>TGGCATTGCTTCCTTAACCAGCTCATGGTGTGTGAATGTT<br>ATAAAATTGTCACTCAGATATATTTTTTAAATGTAATGTT<br>ATATAAGATGATCATGTGATGTGTACAAACTATGGTGAAA<br>AGTGCCAGTGGTAGTAACTGTGTAAAGTTTCTAATTCACA<br>ACATTAATTCCTTTAAAATACACAGCCTTCTGCCTCTGTA<br>TTTGGAGTTGTCAGTACAACTCATCAAAGAAAACTGCCTA<br>ATATAAAAATCATATATATGGTAATAATTTCCCTCTTTTG<br>TAGTCTGCACAAGATCCATAAAAGATTGTATTTTTATTAC<br>TATTTAAACAAGTGATTAAATTTAGTCTGCACAGTGAGCA<br>AGGGTTCACATGCATTCTTTTATACTGCTGGATTTTGTTG<br>TGCATCATTTAAAACATTTTGTATGTTTCTTCTTATCTGT<br>GTATACAGTATGTTCTTGAATGATGTTCATTTGTCAGGAG<br>AACTGTGAGAAATAAACTATGTGGATACTGTCTGTTTATA<br>TTAAAGAAAAAAAAAAAAAAAAAA | |

The 51 GEP-NEN biomarkers include: AKAP8L (A kinase (PRKA) anchor protein 8-like), APLP2 (amyloid beta (A4) precursor-like protein 2), ARAF 1 (v-raf murine sarcoma 3611 viral oncogene homolog), ATP6V1H (ATPase, H+ transporting, lysosomal 50/57 kDa, VI subunit H), BNIP3L (BCL2/adenovirus E1B 19 kDa interacting protein 3-like), BRAF (v-raf murine sarcoma viral oncogene homolog BI), C21ORF7 (chromosome 21 open reading frame 7), CD59 (CD59 molecule, complement regulatory protein), COMMD9 (COMM domain containing 9), CTGF (connective tissue growth factor), ENPP4 (ectonucleotide pyrophosphatase/phosphodiesterase 4), FAM131A (family with sequence similarity 131, member A, transcript variant 2), FLJ 10357 (Rho guanine nucleotide exchange factor (GEF) 40 (ARHGEF40), FZD7 (frizzled homolog 7 (Drosophila)), GLT8D1 (glycosyltransferase 8 domain containing 1, transcript variant 3), HDAC9 (histone deacetylase 9, transcript variant 6), HSF2 (heat shock transcription factor 2, transcript variant 1), Ki-67 (antigen identified by monoclonal antibody Ki-67), KRAS (v-Ki-ras2 Kirsten rat sarcoma viral oncogene homolog), LEO1 (Pafl/RNA polymerase II complex component homolog (S. cerevisiae)), MORF4L2 (mortality factor 4 like 2, transcript variant 1), NAP1L1 (nucleosome assembly protein 1-like 1), NOL3 (nucleolar protein 3 (apoptosis repressor with CARD domain), transcript variant 3), NUDT3 (nudix (nucleoside diphosphate linked moiety X)-type motif 3), OAZ2 (ornithine decarboxylase antizyme 2), PANK2 (pantothenate kinase 2), PHF21A (PHD finger protein 21A, transcript variant 1), PKD1 (polycystic kidney disease 1 (autosomal dominant), transcript variant 2), PLD3 (phospholipase D family, member 3, transcript variant 1), PNMA2 (paraneoplastic antigen MA2), PQBP1 (polyglutamine binding protein 1, transcript variant 2), RAF1 (v-raf-1 murine leukemia viral oncogene homolog 1), RNF41 (ring finger protein 41, transcript variant 4), RSF1 (remodeling and spacing factor 1), RTN2 (reticulon 2, transcript variant 1), SMARCD3 (SWI/SNF related, matrix associated, actin dependent regulator of chromatin, subfamily d, member 3, transcript variant 3), SPATA7 (spermatogenesis associated 7, transcript variant 2), SST1 (somatostatin receptor 1), SST3 (somatostatin receptor 3), SST4 (somatostatin receptor 4), SST5 (somatostatin receptor 5, transcript variant 1), TECPR2 (tectonin beta-propeller repeat containing 2, transcript variant 2), TPH1 (tryptophan hydroxylase 1), TRMT112 (tRNA methyltransferase 11-2 homolog (S. cerevisiae)), VMAT1 (solute carrier family 18 (vesicular monoamine), member 1), VMAT 2 (solute carrier family 18 (vesicular monoamine), member 2), VPS13C (vacuolar protein sorting 13 homolog C (S. cerevisiae), transcript variant 2B), WDFY3 (WD repeat and FYVE domain containing 3), ZFHX3 (zinc finger homeobox 3, transcript variant B), ZXDC (zinc finger C, transcript variant 2), and ZZZ3 (zinc finger, ZZ-type containing 3), including gene products typically human gene products, including transcripts, mRNA, cDNA, coding sequences, proteins and polypeptides, as well as polynucleotides (nucleic acids) encoding the proteins and polypeptides, including naturally occurring variants, e.g., allelic variants, splice variants, transcript variants, and single nucleotide polymorphism (SNP) variants. For example, the biomarkers include polynucleotides, proteins, and polypeptides having the sequences disclosed herein, and naturally occurring variants thereof.

The housekeeping gene used to normalize expression of the 51 marker genes is the human ALG9 (asparagine-linked glycosylation 9, alpha-1,2-mannosyltransferase homolog).

Of these 51 differentially expressed biomarker genes, 38 biomarker genes are useful for the generation of mathematically-derived expression level scores for diagnosing, monitoring, and/or prognosticating the presence of GEP-NEN and/or different states of GEP-NENs. These 38 GEP-NEN biomarkers include: PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MK167/KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and GLT8DI.

Of the 38 biomarker genes useful for the generation of a mathematically-derived expression level score for diagnosing, monitoring, and/or prognosticating the presence of GEP-NENs, at least 22 biomarker genes may be needed to generate an adequate classifier. These at least 22 biomarker genes include PNMA2, NAP1L1, FZD7, SLC 18A2, NOL3, SSTR5, TPH1, RAF1, RSF1, SSTR3, SSTR1, CD59, ARAF, APLP2, KRAS, MORF4L2, TRMT112, MK167, SSTR4, CTGF, SPATA7, and ZFHX3.

The ALG9 biomarkers/housekeeping genes include human ALG9 gene products, including natural variants, e.g., allelic variants, and homologs and analogs thereof. In one example, the ALG9 biomarker/housekeeping gene is a polynucleotide having the nucleotide sequence set forth in SEQ ID NO: 1 (referenced at NM_024740.2), or containing a protein-coding portion thereof, a natural variant thereof, or a protein encoded by such a polynucleotide.

The AKAP8L biomarkers include human AKAP8L gene products, including natural variants, e.g., allelic variants, and homologs and analogs thereof. In one example, the AKAP8L biomarker is a polynucleotide having the nucleotide sequence set forth in SEQ ID NO: 2 (referenced at NM_014371.3), or containing a protein-coding portion thereof, a natural variant thereof, or a protein encoded by such a polynucleotide.

The APLP2 biomarkers include human APLP2 gene products, including natural variants, e.g., allelic variants, and homologs and analogs thereof. In one example, the APLP2 biomarker is a polynucleotide having the nucleotide sequence set forth in SEQ ID NO: 3 (referenced at NM_001142276.1) or containing a protein-coding portion thereof, a natural variant thereof, or a protein encoded by such a polynucleotide.

The ARAF1 biomarkers include human ARAF1 gene products, including natural variants, e.g., allelic variants, and homologs and analogs thereof. In one example, the ARAF1 biomarker is a polynucleotide having the nucleotide sequence set forth in SEQ ID NO: 4 (referenced at NM_001654.4), or containing a protein-coding portion thereof, a natural variant thereof, or a protein encoded by such a polynucleotide.

The ATP6V1H biomarkers include human ATP6V1H gene products, including natural variants, e.g., allelic variants, and homologs and analogs thereof. In one example, the ATP6V1H biomarker is a polynucleotide having the nucleotide sequence set forth in SEQ ID NO: 5 (referenced at NM_015941.3), or containing a protein-coding portion thereof, a natural variant thereof, or a protein encoded by such a polynucleotide.

The BNIP3L biomarkers include human BNIP3L gene products, including natural variants, e.g., allelic variants, and homologs and analogs thereof. In one example, the BNIP3L biomarker is a polynucleotide having the nucleotide sequence set forth in SEQ ID NO: 6 (referenced at NM_004331.2), or containing a protein-coding portion thereof, a natural variant thereof, or a protein encoded by such a polynucleotide.

The BRAF biomarkers include BRAF gene products, including natural variants, e.g., allelic variants, and homologs and analogs thereof. In one example, the BRAF biomarker is a polynucleotide having the nucleotide sequence set forth in SEQ ID NO: 7 (referenced at NM_004333.4), or containing a protein-coding portion thereof, a natural variant thereof, or a protein encoded by such a polynucleotide.

The C21ORF7 biomarkers include C21ORF7 gene products, including natural variants, e.g., allelic variants, and homologs and analogs thereof. In one example, the C21ORF7 biomarker is a polynucleotide having the nucleotide sequence set forth in SEQ ID NO: 8 (referenced at NM_020152.3), or containing a protein-coding portion thereof, a natural variant thereof, or a protein encoded by such a polynucleotide.

The CD59 biomarkers include CD59 gene products, including natural variants, e.g., allelic variants, and homologs and analogs thereof. In one example, the CD59 biomarker is a polynucleotide having the nucleotide sequence set forth in SEQ ID NO: 9 (referenced at NM_203331.2), or containing a protein-coding portion thereof, a natural variant thereof, or a protein encoded by such a polynucleotide.

The COMMD9 biomarkers include COMMD9 gene products, including natural variants, e.g., allelic variants, and homologs and analogs thereof. In one example, the COMMD9 biomarker is a polynucleotide having the nucleotide sequence set forth in SEQ ID NO: 10 (referenced at NM_001101653.1), or containing a protein-coding portion thereof, a natural variant thereof, or a protein encoded by such a polynucleotide.

The CTGF biomarkers include CTGF gene products, including natural variants, e.g., allelic variants, and homologs and analogs thereof. In one example, the CTGF biomarker is a polynucleotide having the nucleotide sequence set forth in SEQ ID NO: 11 (referenced at NM_001901.2), or containing a protein-coding portion thereof, a natural variant thereof, or a protein encoded by such a polynucleotide.

The ENPP4 biomarkers include ENPP4 gene products, including natural variants, e.g., allelic variants, and homologs and analogs thereof. In one example, the ENPP4 biomarker is a polynucleotide having the nucleotide sequence set forth in SEQ ID NO: 12 (referenced at NM_014936.4), or containing a protein-coding portion thereof, a natural variant thereof, or a protein encoded by such a polynucleotide.

The FAM131A biomarkers include FAM131A gene products, including natural variants, e.g., allelic variants, and homologs and analogs thereof. In one example, the FAM131A biomarker is a polynucleotide having the nucleotide sequence set forth in SEQ ID NO: 13 (referenced at NM_001171093.1), or containing a protein-coding portion thereof, a natural variant thereof, or a protein encoded by such a polynucleotide.

The FLJ1035 biomarkers include FLJ 1035 gene products, including natural variants, e.g., allelic variants, and homologs and analogs thereof. In one example, the FLJ 1035 biomarker is a polynucleotide having the nucleotide sequence set forth in SEQ ID NO: 14 (referenced at NM_018071.4), or containing a protein-coding portion thereof, a natural variant thereof, or a protein encoded by such a polynucleotide.

The FZD7 biomarkers include FZD7 gene products, including natural variants, e.g., allelic variants, and homologs and analogs thereof. In one example, the FZD7 biomarker is a polynucleotide having the nucleotide sequence set forth in SEQ ID NO: 15 (referenced at NM_003507.1), or containing a protein-coding portion thereof, a natural variant thereof, or a protein encoded by such a polynucleotide.

The GLT8D1 biomarkers include GLT8D1 gene products, including natural variants, e.g., allelic variants, and homologs and analogs thereof. In one example, the GLT8D1 biomarker is a polynucleotide having the nucleotide sequence set forth in SEQ ID NO: 16 (referenced at NM_001010983.2), or containing a protein-coding portion thereof, a natural variant thereof, or a protein encoded by such a polynucleotide.

The HDAC9 biomarkers include HDAC9 gene products, including natural variants, e.g., allelic variants, and homologs and analogs thereof. In one example, the HDAC9 biomarker is a polynucleotide having the nucleotide sequence set forth in SEQ ID NO: 17 (referenced at NM_001204144.1), or containing a protein-coding portion thereof, a natural variant thereof, or a protein encoded by such a polynucleotide.

The HSF2 biomarkers include HSF2 gene products, including natural variants, e.g., allelic variants, and homologs and analogs thereof. In one example, the HSF2 biomarker is a polynucleotide having the nucleotide sequence set forth in SEQ ID NO: 18 (referenced at NM_004506.3), or containing a protein-coding portion thereof, a natural variant thereof, or a protein encoded by such a polynucleotide.

The Ki-67 biomarkers include Ki-67 gene products, including natural variants, e.g., allelic variants, and homologs and analogs thereof. In one example, the Ki-67 biomarker is a polynucleotide having the nucleotide sequence set forth in SEQ ID NO: 19 (referenced at NM_001145966.1), or containing a protein-coding portion thereof, a natural variant thereof, or a protein encoded by such a polynucleotide.

The KRAS biomarkers include KRAS gene products, including natural variants, e.g., allelic variants, and homologs and analogs thereof. In one example, the KRAS biomarker is a polynucleotide having the nucleotide sequence set forth in SEQ ID NO: 20 (referenced at NM_004985.4), or containing a protein-coding portion thereof, a natural variant thereof, or a protein encoded by such a polynucleotide.

The LEO1 biomarkers include LEO1 gene products, including natural variants, e.g., allelic variants, and homologs and analogs thereof. In one example, the LEO1 biomarker is a polynucleotide having the nucleotide sequence set forth in SEQ ID NO: 21 (referenced at NM_138792.3), or containing a protein-coding portion thereof, a natural variant thereof, or a protein encoded by such a polynucleotide.

The MORF4L2 biomarkers include MORF4L2 gene products, including natural variants, e.g., allelic variants, and homologs and analogs thereof. In one example, the MORF4L2 biomarker is a polynucleotide having the nucleotide sequence set forth in SEQ ID NO: 22 (referenced at NM_001142418.1), or containing a protein-coding portion thereof, a natural variant thereof, or a protein encoded by such a polynucleotide.

The NAP1L1 biomarkers include NAP1L1 gene products, including natural variants, e.g., allelic variants, and homologs and analogs thereof. In one example, the NAP1L1 biomarker is a polynucleotide having the nucleotide sequence set forth in SEQ ID NO: 23 (referenced at NM_139207.2), or containing a protein-coding portion thereof, a natural variant thereof, or a protein encoded by such a polynucleotide.

The NOL3 biomarkers include NOL3 gene products, including natural variants, e.g., allelic variants, and homologs and analogs thereof. In one example, the NOL3 biomarker is a polynucleotide having the nucleotide sequence set forth in SEQ ID NO: 24 (referenced at NM_001185057.2), or containing a protein-coding portion thereof, a natural variant thereof, or a protein encoded by such a polynucleotide.

The NUDT3 biomarkers include NUDT3 gene products, including natural variants, e.g., allelic variants, and homologs and analogs thereof. In one example, the NUDT3 biomarker is a polynucleotide having the nucleotide sequence set forth in SEQ ID NO: 25 (referenced at NM_006703.3), or containing a protein-coding portion thereof, a natural variant thereof, or a protein encoded by such a polynucleotide.

The OAZ2 biomarkers include OAZ2 gene products, including natural variants, e.g., allelic variants, and homologs and analogs thereof. In one example, the OAZ2 biomarker is a polynucleotide having the nucleotide sequence set forth in SEQ ID NO: 26 (referenced at NM_002537.3), or containing a protein-coding portion thereof, a natural variant thereof, or a protein encoded by such a polynucleotide.

The PANK2 biomarkers include PANK2 gene products, including natural variants, e.g., allelic variants, and homologs and analogs thereof. In one example, the PANK2 biomarker is a polynucleotide having the nucleotide sequence set forth in SEQ ID NO: 27 (referenced at NM_024960.4), or containing a protein-coding portion thereof, a natural variant thereof, or a protein encoded by such a polynucleotide.

The PHF21A biomarkers include PHF21A gene products, including natural variants, e.g., allelic variants, and homologs and analogs thereof. In one example, the PHF21A biomarker is a polynucleotide having the nucleotide sequence set forth in SEQ ID NO: 28 (referenced at NM_001101802.1), or containing a protein-coding portion thereof, a natural variant thereof, or a protein encoded by such a polynucleotide.

The PKD1 biomarkers include PKD1 gene products, including natural variants, e.g., allelic variants, and homologs and analogs thereof. In one example, the PKD1 biomarker is a polynucleotide having the nucleotide sequence set forth in SEQ ID NO: 29 (referenced at NM_000296.3), or containing a protein-coding portion thereof, a natural variant thereof, or a protein encoded by such a polynucleotide.

The PLD3 biomarkers include PLD3 gene products, including natural variants, e.g., allelic variants, and homologs and analogs thereof. In one example, the PLD3 biomarker is a polynucleotide having the nucleotide sequence set forth in SEQ ID NO: 30 (referenced at NM_001031696.3), or containing a protein-coding portion thereof, a natural variant thereof, or a protein encoded by such a polynucleotide.

The PNMA2 biomarkers include PNMA2 gene products, including natural variants, e.g., allelic variants, and homologs and analogs thereof. In one example, the PNMA2 biomarker is a polynucleotide having the nucleotide sequence set forth in SEQ ID NO: 31 (referenced at NM_007257.5), or containing a protein-coding portion thereof, a natural variant thereof, or a protein encoded by such a polynucleotide.

The PQBP1 biomarkers include PQBP1 gene products, including natural variants, e.g., allelic variants, and homologs and analogs thereof. In one example, the PQBP1 biomarker is a polynucleotide having the nucleotide sequence set forth in SEQ ID NO: 32 (referenced at NM_001032381.1), or containing a protein-coding portion thereof, a natural variant thereof, or a protein encoded by such a polynucleotide.

The RAF1 biomarkers include RAF1 gene products, including natural variants, e.g., allelic variants, and homologs and analogs thereof. In one example, the RAF1 biomarker is a polynucleotide having the nucleotide sequence set forth in SEQ ID NO: 33 (referenced at NM_002880.3), or containing a protein-coding portion thereof, a natural variant thereof, or a protein encoded by such a polynucleotide.

The RNF41 biomarkers include RNF41 gene products, including natural variants, e.g., allelic variants, and homologs and analogs thereof. In one example, the RNF41 biomarker is a polynucleotide having the nucleotide sequence set forth in SEQ ID NO: 34 (referenced at NM_001242826.1), or containing a protein-coding portion thereof, a natural variant thereof, or a protein encoded by such a polynucleotide.

The RSF1 biomarkers include RSF1 gene products, including natural variants, e.g., allelic variants, and homologs and analogs thereof. In one example, the RSF1 biomarker is a polynucleotide having the nucleotide sequence set forth in SEQ ID NO: 35 (referenced at NM_016578.3), or containing a protein-coding portion thereof, a natural variant thereof, or a protein encoded by such a polynucleotide.

The RTN2 biomarkers include RTN2 gene products, including natural variants, e.g., allelic variants, and homologs and analogs thereof. In one example, the RTN2 biomarker is a polynucleotide having the nucleotide sequence set forth in SEQ ID NO: 36 (referenced at NM_005619.4), or containing a protein-coding portion thereof, a natural variant thereof, or a protein encoded by such a polynucleotide.

The SMARCD3 biomarkers include SMARCD3 gene products, including natural variants, e.g., allelic variants, and homologs and analogs thereof. In one example, the SMARCD3 biomarker is a polynucleotide having the nucleotide sequence set forth in SEQ ID NO: 37 (referenced at NM_001003801.1), or containing a protein-coding portion thereof, a natural variant thereof, or a protein encoded by such a polynucleotide.

The SPATA7 biomarkers include SPATA7 gene products, including natural variants, e.g., allelic variants, and homologs and analogs thereof. In one example, the SPATA7 biomarker is a polynucleotide having the nucleotide sequence set forth in SEQ ID NO: 38 (referenced at NM_001040428.3), or containing a protein-coding portion thereof, a natural variant thereof, or a protein encoded by such a polynucleotide.

The SSTR1 biomarkers include SSTR1 gene products, including natural variants, e.g., allelic variants, and homologs and analogs thereof. In one example, the SSTR1 biomarker is a polynucleotide having the nucleotide sequence set forth in SEQ ID NO: 39 (referenced at NM_001049.2), or containing a protein-coding portion thereof, a natural variant thereof, or a protein encoded by such a polynucleotide.

The SSTR3 biomarkers include SSTR3 gene products, including natural variants, e.g., allelic variants, and homologs and analogs thereof. In one example, the SSTR3 biomarker is a polynucleotide having the nucleotide sequence set forth in SEQ ID NO: 40 (referenced at NM_001051.4), or containing a protein-coding portion thereof, a natural variant thereof, or a protein encoded by such a polynucleotide.

The SST4 biomarkers include SST4 gene products, including natural variants, e.g., allelic variants, and homologs and analogs thereof. In one example, the SST4 biomarker is a polynucleotide having the nucleotide sequence set forth in SEQ ID NO: 41 (referenced at NM_001052.2), or containing a protein-coding portion thereof, a natural variant thereof, or a protein encoded by such a polynucleotide.

The SST5 biomarkers include SST5 gene products, including natural variants, e.g., allelic variants, and homologs and analogs thereof. In one example, the SST5 biomarker is a polynucleotide having the nucleotide sequence set forth in SEQ ID NO: 42 (referenced at NM_001053.3), or containing a protein-coding portion thereof, a natural variant thereof, or a protein encoded by such a polynucleotide.

The TECPR2 biomarkers include TECPR2 gene products, including natural variants, e.g., allelic variants, and homologs and analogs thereof. In one example, the TECPR2 biomarker is a polynucleotide having the nucleotide sequence set forth in SEQ ID NO: 43 (referenced at NM_001172631.1), or containing a protein-coding portion thereof, a natural variant thereof, or a protein encoded by such a polynucleotide.

The TPH1 biomarkers include TPH1 gene products, including natural variants, e.g., allelic variants, and homologs and analogs thereof. In one example, the TPH1 biomarker is a polynucleotide having the nucleotide sequence set forth in SEQ ID NO: 44 (referenced at NM_004179.2), or containing a protein-coding portion thereof, a natural variant thereof, or a protein encoded by such a polynucleotide.

The TRMT112 biomarkers include TRMT112 gene products, including natural variants, e.g., allelic variants, and homologs and analogs thereof. In one example, the TRMT112 biomarker is a polynucleotide having the nucleotide sequence set forth in SEQ ID NO: 45 (referenced at NM_016404.2), or containing a protein-coding portion thereof, a natural variant thereof, or a protein encoded by such a polynucleotide.

The VMAT1 biomarkers include VMAT1 gene products, including natural variants, e.g., allelic variants, and homologs and analogs thereof. In one example, the VMAT1 biomarker is a polynucleotide having the nucleotide sequence set forth in SEQ ID NO: 46 (referenced at NM_003053.3), or containing a protein-coding portion thereof, a natural variant thereof, or a protein encoded by such a polynucleotide.

The VMAT2 biomarkers include VMAT2 gene products, including natural variants, e.g., allelic variants, and homologs and analogs thereof. In one example, the VMAT2 biomarker is a polynucleotide having the nucleotide sequence set forth in SEQ ID NO: 47 (referenced at NM_003054.4), or containing a protein-coding portion thereof, a natural variant thereof, or a protein encoded by such a polynucleotide.

The VPS13C biomarkers include VPS13C gene products, including natural variants, e.g., allelic variants, and homologs and analogs thereof. In one example, the VPS13C biomarker is a polynucleotide having the nucleotide sequence set forth in SEQ ID NO: 48 (referenced at NM_001018088.2), or containing a protein-coding portion thereof, a natural variant thereof, or a protein encoded by such a polynucleotide.

The WDFY3 biomarkers include WDFY3 gene products, including natural variants, e.g., allelic variants, and homologs and analogs thereof. In one example, the WDFY3 biomarker is a polynucleotide having the nucleotide sequence set forth in SEQ ID NO: 49 (referenced at NM_014991.4), or containing a protein-coding portion thereof, a natural variant thereof, or a protein encoded by such a polynucleotide.

The ZFHX3 biomarkers include ZFHX3 gene products, including natural variants, e.g., allelic variants, and homologs and analogs thereof. In one example, the ZFHX3 biomarker is a polynucleotide having the nucleotide sequence set forth in SEQ ID NO: 50 (referenced at NM_001164766.1), or containing a protein-coding portion thereof, a natural variant thereof, or a protein encoded by such a polynucleotide.

The ZXDC biomarkers include ZXDC gene products, including natural variants, e.g., allelic variants, and homologs and analogs thereof. In one example, the ZXDC biomarker is a polynucleotide having the nucleotide sequence set forth in SEQ ID NO: 51 (referenced at NM_001040653.3), or containing a protein-coding portion thereof, a natural variant thereof, or a protein encoded by such a polynucleotide.

The ZZZ3 biomarkers include ZZZ3 gene products, including natural variants, e.g., allelic variants, and homologs and analogs thereof. In one example, the ZZZ3 biomarker is a polynucleotide having the nucleotide sequence set forth in SEQ ID NO: 52 (referenced at NM_015534.4), or containing a protein-coding portion thereof, a natural variant thereof, or a protein encoded by such a polynucleotide.

In some embodiments, the panel of polynucleotides further includes one or more polynucleotide able to specifically hybridize to "housekeeping," or reference genes, for example, genes for which differences in expression is known or not expected to correlate with differences in the variables analyzed, for example, with the presence or absence of GEP-NEN or other neoplastic disease, differentiation of various GEP-NEN sub-types, metastasis, mucosal or other tissue types, prognostic indications, and/or other phenotype, prediction, or outcome. In some aspects, expression levels of such housekeeping genes are detected and used as an overall expression level standards, such as to normalize expression data obtained for GEP-NEN biomarkers across various samples.

Housekeeping genes are well known in the art. Typically, the housekeeping genes include one or more genes characterized as particularly appropriate for analyzing GEP-NEN samples, such as ALG9. See Kidd M, et al., "GeneChip, geNorm and Gastrointestinal tumors: novel reference genes for real-time PCR." *Physiol Genomics* 2007; 30:363-70. In the current application, ALG9 is the housekeeping gene of choice.

The present invention provides methods, compositions, and systems, for the detection of the GEP-NEN biomarkers and for identifying, isolating, and enriching tumors and cells that express the GEP-NEN biomarkers. For example, provided are agents, sets of agents, and systems for detecting the GEP-NEN biomarkers and methods for use of the same, including for diagnostic and prognostic uses.

In one embodiment, the agents are proteins, polynucleotides or other molecules which specifically bind to or specifically hybridize to the GEP-NEN biomarkers. The agents include polynucleotides, such as probes and primers, e.g. sense and antisense PCR primers, having identity or complementarity to the polynucleotide biomarkers, such as mRNA, or proteins, such as antibodies, which specifically bind to such biomarkers. Sets and kits containing the agents, such as agents specifically hybridizing to or binding the panel of biomarkers, also are provided.

Thus, the systems, e.g., microarrays, sets of polynucleotides, and kits, provided herein include those with nucleic acid molecules, typically DNA oligonucleotides, such as primers and probes, the length of which typically varies between 15 bases and several kilo bases, such as between 20 bases and 1 kilobase, between 40 and 100 bases, and between 50 and 80 nucleotides or between 20 and 80 nucleotides. In one aspect, most (i.e. at least 60% of) nucleic acid molecules of a nucleotide microarray, kit, or other system, are capable of hybridizing to GEP-NEN biomarkers.

In one example, systems containing polynucleotides that specifically hybridize to the biomarkers, e.g., nucleic acid microarrays, are provided to detect and measure changes in expression levels and determine expression profiles of the biomarkers according to the provided methods. Among such systems, e.g., microarrays, are those comprising polynucleotides able to hybridize to at least as at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following sets of biomarkers:

PNMA2, NAP1L1, FZD7, SLC18A2/VMAT2, NOL3, SSTR5, TPH1, RAF1, RSF1, SSTR3, SSTR1, CD59, ARAF, APLP2, KRAS, MORF4L2, TRMT112, MKI67/ KI67, SSTR4, CTGF, SPATA7, ZFHX3, PHF21A, SLC18A1/VMAT1, ZZZ3, TECPR2, ATP6V1H, OAZ2, PANK2, PLD3, PQBP1, RNF41, SMARCD3, BNIP3L, WDFY3, COMMD9, BRAF, and GLT8DI gene products;

In some aspects, at least 60%, or at least 70%, at least 80%, or more, of the nucleic acid molecules of the system, e.g., microarray, are able to hybridize to biomarkers in the panel of biomarkers. In one example, probes immobilized on such nucleotide microarrays comprise at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more nucleic acid molecules able to hybridize to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more of the biomarkers, where each of the nucleic acid molecules is capable of specifically hybridizing to a different one of the biomarkers, such that at least that many different biomarkers can be bound.

In one example, the remaining nucleic acid molecules, such as 40% or at most 40% of the nucleic acid molecules on the microarray or in the set of polynucleotides are able to hybridize to a set of reference genes or a set of normalization genes (such as housekeeping genes), for example, for normalization in order to reduce systemic bias. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment. To reduce systemic bias, the determined RNA levels are preferably corrected for background non-specific hybridization and normalized.

The use of such reference probes is advantageous but not mandatory. In one embodiment a set of polynucleotides or system, e.g., microarray, is provided wherein at least 90% of the nucleic acid sequences are able to hybridize to the GEP-NEN biomarkers; further embodiments include such systems and sets in which at least 95% or even 100% of the polynucleotides hybridize to the biomarkers.

Disclosed herein are exemplary suitable polynucleotides, such as PCR primers. Other nucleic acid probes and primers, able to hybridize to different regions of the biomarkers are of course also suitable for use in connection with the provided systems, kits and methods.

The present invention provides methods for detecting and quantifying the biomarkers, including detecting the presence, absence, amount or relative amount, such as expression levels or expression profile of the biomarkers. Typically, the methods are nucleic acid based methods, for example, measuring the presence, amount or expression levels of biomarker mRNA expression. Such methods typically are carried out by contacting polynucleotide agents to biological samples, such as test samples and normal and reference samples, for example, to quantify expression levels of nucleic acid biomarkers (e.g., mRNA) in the samples.

Detection and analysis of biomarkers according to the provided embodiments can be performed with any suitable method known in the art. For example, where the biomarkers are RNA biomarkers, RNA detection and quantification methods are used.

Exemplary methods for quantifying or detecting nucleic acid expression levels, e.g., mRNA expression, are well known, and include northern blotting and in situ hybridization (Parker and Barnes, Methods in Molecular Biology 106:247-283, 1999); RNAse protection assays (Hod, Biotechniques 13:852-854, 1992); and quantitative or semi-quantitative reverse transcription polymerase chain reaction (RT-PCR) (Weis et al., *Trends in Genetics* 8:263-264, 1992), representative methods for sequencing-based gene expression analysis include Serial Analysis of Gene Expression (SAGE), and gene expression analysis by massively parallel signature sequencing (MPSS).

Therefore, in one embodiment, expression of the biomarker or biomarker panel includes RNA expression; the methods include determining levels of RNA of the biomarkers, such as RNA obtained from and/or present in a sample of a patient, and performing analysis, diagnosis, or predictive determinations based upon the RNA expression levels determined for the biomarkers or panel of biomarkers.

RNA samples can be processed in numerous ways, as is known to those in the art. Several methods are well known for isolation of RNA from samples, including guanidinium thiocyanate-phenol-chloroform extraction, which may be carried out using the TRIZOL® reagent, a proprietary formulation (see Chomczynski P, Sacchi N (2006). "The single-step method of RNA isolation by acid guanidinium thiocyanate-phenol-chloroform extraction: twenty-something years on". Nat Protoc 1 (2): 581-5). In this method, TRIZOL® is used to extract RNA and DNA; chloroform and centrifugation are used to separate RNA from other nucleic acids, followed by a series of washes with ethanol for cleanup of the RNA sample.

The RNA samples can be freshly prepared from samples e.g., cells or tissues at the moment of harvesting; alternatively, they can be prepared from samples that stored at $-70°$ C. until processed for sample preparation. Alternatively, tissues or cell samples can be stored under and/or subjected to other conditions known in the art to preserve the quality of the RNA, including fixation for example with formalin or similar agent; and incubation with RNase inhibitors such as RNASIN® (ribonuclease inhibitors) or RNASECURE™ (RNase inactivation reagents); aqueous solutions such as RNALATER® (RNA stabilization solutions), Hepes-Glutamic acid buffer mediated Organic solvent Protection Effect (HOPE®), and RCL2® (formalin-free tissue fixatives); and non-aqueous solutions such as Universal Molecular Fixative (Sakura Finetek USA Inc.). A chaotropic nucleic acid isolation lysis buffer (Boom method, Boom et al. J Clin Microbiol. 1990; 28:495-503) may also be used for RNA isolation.

In one embodiment, RNA is isolated from buffy coat by incubating samples with TRIZOL®, followed by RNA clean-up. RNA is dissolved in diethyl pyrocarbonate water and measured spectrophotometrically, and an aliquot analyzed on a Bioanalyzer (Agilent Technologies, Palo Alto, Calif.) to assess the quality of the RNA (Kidd M, et al. "The role of genetic markers—NAP 1L1, MAGE-D2, and MTA1—in defining small-intestinal carcinoid neoplasia," Ann Surg Oncol 2006; 13(2):253-62). In another embodiment, RNA is isolated from plasma using the QIAamp® RNA Blood Mini Kit (a kit for the preparation of cellular RNA from human whole blood); in some cases, this method allows better detection by real-time PCR of significantly more housekeeping genes from plasma compared to the TRIZOL® approach. In another embodiment, RNA is isolated directly from whole blood, for example, using the QIAamp® RNA Blood Mini Kit in a similar manner.

Methods for isolating RNA from fixed, paraffin-embedded tissues as the RNA source are well-known and generally include mRNA isolation, purification, primer extension and amplification (for example: T. E. Godfrey et al, Molec. Diagnostics 2: 84-91 [2000]; K. Specht et al., Am. J. Pathol. 158: 419-29 [2001]). In one example, RNA is extracted from a sample such as a blood sample using the QIAamp® RNA Blood Mini Kit RNA. Typically, RNA is extracted from tissue, followed by removal of protein and DNA and analysis of RNA concentration. An RNA repair and/or amplification step may be included, such as a step for reverse transcription of RNA for RT-PCR.

Expression levels or amounts of the RNA biomarkers may be determined or quantified by any method known in the art, for example, by quantifying RNA expression relative to housekeeping gene or with relation to RNA levels of other genes measured at the same time. Methods to determine RNA levels of genes are known to a skilled person and include, but are not limited to, Northern blotting, (quantitative) PCR, and microarray analysis.

RNA biomarkers can be reverse transcribed to produce cDNA and the methods of the present invention can include detecting and quantifying that produced cDNA. In some embodiments, the cDNA is detected by forming a complex with a labeled probe. In some embodiments, the RNA biomarkers are directed detected by forming a complex with a labeled probe or primer.

Northern blotting may be performed for quantification of RNA of a specific biomarker gene or gene product, by hybridizing a labeled probe that specifically interacts with the RNA, following separation of RNA by gel electrophoresis. Probes are for example labeled with radioactive isotopes or chemiluminescent substrates. Quantification of the labeled probe that has interacted with said nucleic acid expression product serves as a measure for determining the level of expression. The determined level of expression can be normalized for differences in the total amounts of nucleic acid expression products between two separate samples with for instance an internal or external calibrator by comparing the level of expression of a gene that is known not to differ in expression level between samples or by adding a known quantity of RNA before determining the expression levels.

For RT-PCR, biomarker RNA is reverse transcribed into cDNA. Reverse transcriptase polymerase chain reaction (RT-PCR) is, for example, performed using specific primers that hybridize to an RNA sequence of interest and a reverse transcriptase enzyme. Furthermore, RT-PCR can be performed with random primers, such as for instance random hexamers or decamers which hybridize randomly along the RNA, or oligo d(T) which hybridizes to the poly(A) tail of mRNA, and reverse transcriptase enzyme.

In some embodiments, RNA expression levels of the biomarkers in a sample, such as one from a patient suffering from or suspected of suffering from GEP-NEN or associated symptom or syndrome, are determined using quantitative methods such as by real-time rt-PCR (qPCR) or microarray analysis. In some embodiments, quantitative Polymerase Chain Reaction (QPCR) is used to quantify the level of expression of nucleic acids. In one aspect, detection and determining expression levels of the biomarkers is carried out using RT-PCR, GeneChip analysis, quantitative real-time PCR (Q RT-PCR), or carcinoid tissue microarray (TMA) immunostaining/quantitation, for example, to compare biomarker RNA, e.g., mRNA, or other expression product, levels in different sample populations, characterize patterns of gene expression, to discriminate between closely related mRNAs, and to analyze RNA structure.

In one example, QPCR is performed using real-time PCR (RTPCR), where the amount of product is monitored during the amplification reaction, or by end-point measurements, in which the amount of a final product is determined. As is known to a skilled person, rtPCR is for instance performed by the use of a nucleic acid intercalator, such as for example ethidium bromide or SYBR® Green I dye, which interacts which all generated double stranded products resulting in an increase in fluorescence during amplification, or for instance by the use of labeled probes that react specifically with the generated double stranded product of the gene of interest. Alternative detection methods that can be used are provided by amongst other things dendrimer signal amplification, hybridization signal amplification, and molecular beacons.

In one embodiment, reverse transcription on total RNA is carried out using the High Capacity cDNA Archive Kit (Applied Biosystems (ABI), Foster City, Calif.) following the manufacturer's suggested protocol (briefly, using 2 micrograms of total RNA in 50 microliters water, mixing with 50 uL of 2×RT mix containing Reverse Transcription Buffer, deoxynucleotide triphosphate solution, random primers, and Multiscribe Reverse Transcriptase). RT reaction conditions are well known. In one example, the RT reaction is performed using the following thermal cycler conditions: 10 mins, 25° C.; 120 min., 37° C. {see Kidd M, et al., "The role of genetic markers—NAP1L1, MAGE-D2, and MTA1—in defining small-intestinal carcinoid neoplasia," Ann Surg Oncol 2006; 13(2):253-62).

For measurement of individual transcript levels, in one embodiment, Assays-on-Demand™ products (pre-designed gene expression assays) are used with the ABI 7900 Sequence Detection System according to the manufacturer's suggestions (see Kidd M, Eick G, Shapiro M D, et al. Microsatellite instability and gene mutations in transforming growth factor-beta type II receptor are absent in small bowel carcinoid tumors. Cancer 2005; 103(2):229-36). In one example, cycling is performed under standard conditions, using the TagMan® Universal PCR Master Mix Protocol, by mixing cDNA in 7.2 uL water, 0.8 uL 20Assays-on-Demand™ primer and probe mix and 8 uL of 2 X TagMan Universal Master mix, in a 384-well optical reaction plate, under the following conditions: 50° C., 2 min.; 95° C.; 10 min.; 50 cycles at 95° C. for 15 min., 60° for 1 min (see Kidd M, et al, "The role of genetic markers NAP 1 L1, MAGE-D2, and MTA1—in defining small-intestinal carcinoid neoplasia," Ann Burg Oncol 2006; 13(2):253-62).

Typically, results from real-time PCR are normalized, using internal standards and/or by comparison to expression levels for housekeeping genes. For example, in one embodiment, Raw $AC_T$ (delta $C_T$=change in cycle time as a function of amplification) data from QPCR as described above is normalized using well-known methods, such as geNorm (see Vandesompele J, De Preter K, Pattyn F, et al. Accurate normalization of real-time quantitative RT-PCR data by geometric averaging of multiple internal control genes. Genome Biol 2002; 3(7):RESEARCH0034). Normalization by house-keeping gene expression levels is also well-known. See Kidd M, et al., "GeneChip, geNorm, and gastrointestinal tumors: novel reference genes for real-time PCR," Physiol Genomics 2007; 30(3):363-70.

Microarray analysis involves the use of selected nucleic acid molecules that are immobilized on a surface. These nucleic acid molecules, termed probes, are able to hybridize to nucleic acid expression products. In a preferred embodiment the probes are exposed to labeled sample nucleic acid, hybridized, washed and the (relative) amount of nucleic acid expression products in the sample that are complementary to a probe is determined. Microarray analysis allows simultaneous determination of nucleic acid expression levels of a large number of genes. In a method according to the invention it is preferred that at least 5 genes according to the invention are measured simultaneously.

Background correction can be performed for instance according to the "offset" method that avoids negative intensity values after background subtraction. Furthermore, normalization can be performed in order to make the two channels on each single array comparable for instance using global loess normalization, and scale normalization which ensures that the log-ratios are scaled to have the same median-absolute-deviation (MAD) across arrays.

Protein levels may, for example, be measured using antibody-based binding assays. Enzyme labeled, radioactively labeled or fluorescently labeled antibodies may be used for detection of protein. Exemplary assays include enzyme-linked immunosorbent assays (ELISA), radio-immuno assays (RIA), Western Blot assays and immunohistochemical staining assays. Alternatively, in order to determine the expression level of multiple proteins simultaneously protein arrays such as antibody-arrays are used.

Typically, the biomarkers and housekeeping markers are detected in a biological sample, such as a tissue or fluid sample, such as a blood, such as whole blood, plasma, serum, stool, urine, saliva, tears, serum or semen sample, or a sample prepared from such a tissue or fluid, such as a cell preparation, including of cells from blood, saliva, or tissue, such as intestinal mucosa, tumor tissue, and tissues containing and/or suspected of containing GEP-NEN metastases or shed tumor cells, such as liver, bone, and blood. In one embodiment, a specific cell preparation is obtained by fluorescence-activated cell sorting (FACS) of cell suspensions or fluid from tissue or fluid, such as mucosa, e.g., intestinal mucosa, blood or buffy coat samples.

In some embodiments, the sample is taken from a GEP-NEN patient, a patient suspected of having GEP-NEN, a patient having and/or suspected of having cancer generally, a patient exhibiting one or more GEP-NEN symptoms or syndromes or determined to be at-risk for GEP-NEN, or a GEP-NEN patient undergoing treatment or having completed treatment, including patients whose disease is and/or is thought to be in remission.

In other embodiments, the sample is taken from a human without GEP-NEN disease, such as a healthy individual or an individual with a different type of cancer, such as an adenocarcinoma, for example, a gastrointestinal adenocarcinoma or one of the breast, prostate, or pancreas, or a gastric or hepatic cancer, such as esophageal, pancreatic, gallbladder, colon, or rectal cancer.

In some embodiments, the sample is taken from the GEP-NEN tumor or metastasis. In other embodiments, the sample is taken from the GEP-NEN patient, but from a tissue or fluid not expected to contain GEP-NEN or GEP-NEN cells; such samples may be used as reference or normal samples. Alternatively, the normal or reference sample may be a tissue or fluid or other biological sample from a patient without GEP-NEN disease, such as a corresponding tissue, fluid or other sample, such as a normal blood sample, a normal small intestinal (SI) mucosa sample, a normal enterochromaffin (EC) cell preparation.

In some embodiments, the sample is a whole blood sample. As neuroendocrine tumors metastasize, they typically shed cells into the blood. Accordingly, detection of the panels of GEP-NEN biomarkers provided herein in plasma and blood samples may be used for identification of GEP-NENs at an early time point and for predicting the presence of tumor metastases, e.g., even if anatomic localization studies are negative. Accordingly, the provided agents and methods are useful for early diagnosis.

Thus, in some embodiments, the methods can identify a GEP-NEN molecular signature or expression profile in 1 mL or about 1 mL of whole blood. In some aspects, the molecular signature or expression profile is stable for up to four hours (for example, when samples are refrigerated 4-8° C. following phlebotomy) prior to freezing. In one aspect, the approach able to diagnose, prognosticate or predict a given GEP-NEN-associated outcome using a sample obtained from tumor tissue is also able to make the same diagnosis, prognosis, or prediction using a blood sample.

A number of existing detection and diagnostic methodologies require 7 to 10 days to produce a possible positive result, and can be costly. Thus, in one aspect, the provided methods and compositions are useful in improving simplicity and reducing costs associated with GEP-NEN diagnosis, and make early-stage diagnosis feasible.

Thus in one example, the biomarkers are detected in circulation, for example by detection in a blood sample, such as a serum, plasma, cells, e.g., peripheral blood mononuclear cells (PBMCs), obtained from buffy coat, or whole blood sample.

Tumor-specific transcripts have been detected in whole blood in some cancers. See Sieuwerts A M, et al., "Molecular characterization of circulating tumor cells in large quantities of contaminating leukocytes by a multiplex real-time PCR," Breast Cancer Res Treat 2009; 118(3):455-68 and Mimori K, et al, "A large-scale study of MT1-MMP as a marker for isolated tumor cells in peripheral blood and bone marrow in gastric cancer cases," Ann Surg Oncol 2008; 15(10):2934-42.

The CELLSEARCH® CTC Test (circulating tumor cell kits) (described by Kahan L., "Medical devices; immunology and microbiology devices; classification of the immunomagnetic circulating cancer cell selection and enumeration system. Final rule," Fed Regist 2004; 69:26036-8) uses magnetic beads coated with EpCAM-specific antibodies that detects epithelial cells (CK-8/18/19) and leukocytes (CD45), as described by Sieuwerts A M, Kraan J, Bolt-de Vries J, et al., "Molecular characterization of circulating tumor cells in large quantities of contaminating leukocytes by a multiplex real-time PCR," Breast Cancer Res Treat 2009; 118(3):455-68. This method has been used to detect circulating tumor cells (CTCs), and monitoring disease progression and therapy efficacy in metastatic prostate (Danila D C, Heller G, Gignac G A, et al. Circulating tumor cell number and prognosis in progressive castration-resistant prostate cancer. Clin Cancer Res 2007; 13(23):7053-8), colorectal (Cohen S J, Alpaugh R K, Gross S, et al.).

Isolation and characterization of circulating tumor cells in patients with metastatic colorectal cancer. Clin Colorectal Cancer 2006; 6(2): 125-32. and breast (Cristofanilli M, Budd G T, Ellis M J, et al., Circulating tumor cells, disease progression, and survival in metastatic breast cancer. N Engl J Med 2004, 351(8):781-91).

This and other existing approaches have not been entirely satisfactory for detection of GEP-NEN cells, which can exhibit variable expression and/or not express cytokeratin (See Van Eeden S, et al, Classification of low-grade neuroendocrine tumors of midgut and unknown origin," Hum Pathol 2002; 33(11): 1126-32; Cai Y C, et al., "Cytokeratin 7 and 20 and thyroid transcription factor 1 can help distinguish pulmonary from gastrointestinal carcinoid and pancreatic endocrine tumors," Hum Pathol 2001; 32(10): 1087-93, and studies described herein, detecting EpCAM transcript expression in two of twenty-nine GEP-NEN samples).

Factors to consider in the available detection methods for circulating tumor cells are relatively low numbers of the cells in peripheral blood, typically about 1 per $10^6$ peripheral blood mononuclear cells (PBMCs) (see Ross A A, et al. "Detection and viability of tumor cells in peripheral blood stem cell collections from breast cancer patients using immunocytochemical and clonogenic assay techniques," Blood 1993; 82(9):2605-10), and the potential for leukocyte contamination. See Sieuwerts A M, et al. "Molecular characterization of circulating tumor cells in large quantities of contaminating leukocytes by a multiplex real-time PCR," Breast Cancer Res Treat 2009; 118(3):455-68; Mimori K, et al) and technical complexity of available approaches. These factors can render available methods not entirely satisfactory for use in the clinical laboratory.

In some embodiments, Neuroendocrine cells are FACS-sorted to heterogeneity, using known methods, following acridine orange (AO) staining and uptake, as described Kidd M, et al., "Isolation, Purification and Functional Characterization of the Mastomys E C cell," Am J Physiol 2006; 291:G778-91; Modlin E V I, et al., "The functional characterization of normal and neoplastic human enterochromaffin cells," Clin Endocrinol Metab 2006; 91(6):2340-8.

In some embodiments, the provided detection methods are used to detect, isolate, or enrich for the GEP-NEN cells and/or biomarkers in two to three mL of blood or less. The methods are performed using standard laboratory apparatuses and thus are easily performed in the clinical laboratory setting. In one example, a readout is obtained within 12 hours, at an average cost of approximately 20-30 per sample.

The present invention provides diagnostic, prognostic, and predictive uses for the agents and detection methods provided herein, such as for the diagnosis, prognosis, and prediction of GEP-NEN, associated outcomes, and treatment responsiveness. For example, available GEP-NEN classification methods are limited, in part due to incorrect classifications and that individual lesions or tumors can evolve into different GEP-NEN sub-types or patterns, and/or contain more than one GEP-NEN sub-type. Known classification frameworks are limited, for example, in the ability to predict response to treatment or discriminate accurately between tumors with similar histopathologic features that may vary substantially in clinical course and treatment response, and to predict treatment responsiveness.

There is therefore a need for molecular or gene-based classification schemes. The provided methods and systems, including GEP-NEN-specific predictive gene-based models, address these issues, and may be used in identifying and analyzing molecular parameters that are predictive of biologic behavior and prediction based on such parameters.

Among the provided diagnostic, prognostic, and predictive methods are those which employ statistical analysis and biomathematical algorithms and predictive models to analyze the detected information about expression of GEP-NEN biomarkers and other markers such as housekeeping genes. In some embodiments, expression levels, detected binding or other information is normalized and assessed against reference value(s), such as expression levels in normal samples or standards. Provided embodiments include methods and systems for classification and prediction of GEP-NENs using the detected and measured information about the expression of the GEP-NEN biomarkers, for example, in classification, staging, prognosis, treatment design, evaluation of treatment options, and prediction of GEP-NEN disease outcomes, e.g., predicting development of metastases.

In some embodiments, the methods are used to establish GEP-NEN diagnosis, such as diagnosis or detection of early-stage disease or metastasis, define or predict the extent of disease, identify early spread or metastasis, predict outcome or prognosis, predict progression, classify disease activity, monitor treatment responsiveness, detect or monitor for recurrence, and to facilitate early therapeutic intervention. For example, among the provided methods and algorithms are those for use in classification, staging, prognosis, treatment design, evaluation of treatment options, and prediction of GEP-NEN disease outcomes, e.g., predicting development of metastases.

In one embodiment, the methods, algorithms and models are useful for diagnostic surveillance, such as routine surveillance and patient follow-up. In some embodiments, the methods, algorithms and models provide for early diagnosis; in one aspect, the methods are capable of detection of low-volume tumors, and detection of circulating tumor cells, including at early stages of disease, such as detection of as few as at or about 3 circulating GEP-NEN cells per milliliter of blood. In some embodiments, early evidence of disease allows early therapeutic intervention, at a time when therapies are more effective, which can improve survival rates and disease outcomes.

For example, in one embodiment, the methods useful for early detection of the recurrence and/or metastasis of GEP-NEN, such as after treatment for example following surgical or chemical intervention. In some aspect, the methods are performed weekly or monthly following therapeutic intervention, for example, on human blood samples. In some aspects, the methods are capable of detecting micrometastases that are too small to be detected by conventional means, such as by imaging methods. For example, in one aspect the methods are capable of detecting metastases less than one centimeter (cm), such as at or about 1 cm, 0.9 cm, 0.8 cm, 0.7 cm, 0.6 cm, 0.5 cm, 0.4 cm, 0.3 cm, 0.2 cm, or 0.1 cm metastases, such as in the liver.

For example, among the provided methods and systems are those that determine the presence or absence (or both) of a GEP-NEN in a subject or sample with a correct call rate of between 56 and 92%, such as at least or at least about a 65%, 700, 75%, 80%, 81%, 82%, 83%, 84%, 85%, 86%, 87%, 88%, 89%, 90%, 91%, 92%, 93%, 94%, 95%, 96%, 97%, 98%, 99%, or 100% correct call rate. In some cases, the methods are useful for diagnosis with a specificity or sensitivity of at least or at least about 70%, 7%5, 80%, 81%, 82%, 83%, 84%, 85%, 86%, 87%, 88%, 89%, 90%, 91%, 92%, 93%, 94%, 95%, 96%, 97%, 98%, 990/%, or 100%.

In other aspects, the methods are capable of detecting the recurrence, metastasis, or spread of GEP-NEN following treatment or during initial disease progression at an earlier stage as compared with other diagnostic methods, such as imaging and detection of available biomarkers. In some aspects, the detected expression levels and/or expression signature of the biomarkers correlate significantly with the progression of disease, disease severity or aggressiveness, lack of responsiveness of treatment, reduction in treatment efficacy, GEP-NEN-associated events, risk, prognosis, type or class of GEP-NEN or disease stage.

Among the provided embodiments are methods that use the provided biomarkers and detection thereof in treatment development, strategy, and monitoring, including evaluation of response to treatment and patient-specific or individualized treatment strategies that take into consideration the likely natural history of the tumor and general health of the patient.

GEP-NEN management strategies include surgery—for cure (rarely achieved) or cytoreduction—radiological intervention—for example, by chemoembolization or radiofrequency ablation—chemotherapy, cryoablation, and treatment with somatostatin and somatostatin analogues (such as SANDOSTATIN® LAR (Octreotide acetate injection)) to control symptoms caused by released peptides and neuroamines. Biological agents, including interferon, and hormone therapy, and somatostatin-tagged radionucleotides are under investigation.

In one example, Cryoablation liberates GEP-NEN tissue for entry into the blood, which in turn induces symptoms, as described by Mazzaglia P J, et al, "Laparoscopic radiofrequency ablation of neuroendocrine liver metastases: a 10-year experience evaluating predictors of survival," Surgery 2007; 142(I): 10-9. Chemo therapeutic agents, e.g., systemic cytotoxic chemo therapeutic agents, include etoposide, cisplatin, 5-fluorouracil, streptozotocin, doxorubicin; vascular endothelial growth factor inhibitors, receptor tyrosine kinase inhibitors (e.g., Sunitinib, Sorafenib, and Vatalanib), and mammalian target of rapamycin (mTOR) inhibitors (e.g., Temsirolimus and Everolimus), and combinations thereof, for example to treat disseminated and/or poorly differentiated/aggressive disease. Other treatment approaches are well known.

In some embodiments, the detection and diagnostic methods are used in conjunction with treatment, for example, by performing the methods weekly or monthly before and/or after treatment. In some aspects, the expression levels and profiles correlate with the progression of disease, ineffectiveness or effectiveness of treatment, and/or the recurrence or lack thereof of disease. In some aspects, the expression information indicates that a different treatment strategy is preferable. Thus, provided herein are therapeutic methods, in which the GEP-NEN biomarker detection methods are performed prior to treatment, and then used to monitor therapeutic effects.

At various points in time after initiating or resuming treatment, significant changes in expression levels or expression profiles of the biomarkers (e.g., as compared to expression or expression profiles before treatment, or at some other point after treatment, and/or in a normal or reference sample) indicates that a therapeutic strategy is or is not successful, that disease is recurring, or that a different therapeutic approach should be used. In some embodiments, the therapeutic strategy is changed following performing of the detection methods, such as by adding a different therapeutic intervention, either in addition to or in place of the current approach, by increasing or decreasing the aggressiveness or frequency of the current approach, or stopping or reinstituting the treatment regimen.

In another aspect, the detected expression levels or expression profile of the biomarkers identifies the GEP-NEN disease for the first time or provides the first definitive diagnosis or classification of GEP-NEN disease. In some aspects of this embodiment, a treatment approach is designed based upon the expression levels or expression profiles, and/or the determined classification. The methods include iterative approaches, whereby the biomarker detection methods are followed by initiation or shift in therapeutic intervention, followed by continued periodic monitoring, reevaluation, and change, cessation, or addition of a new therapeutic approach, optionally with continued monitoring.

In some aspects, the methods and systems determine whether or not the assayed subject is responsive to treatment, such as a subject who is clinically categorized as in complete remission or exhibiting stable disease. In some aspects, the methods and systems determine whether or not the subject is untreated (or treatment-I, i.e., has not received treatment) or is non-responsive (i.e., clinically categorized as "progressive." For example, methods are provided for distinguishing treatment-responsive and non-responsive patients, and for distinguishing patients with stable disease or those in complete remission, and those with progressive disease. In various aspects, the methods and systems make such calls with at least at or about 65%, 70%, 75%, 80%, 81%, 82%, 83%, 84%, 85%, 86%, 87%, 88%, 89%, 90%, 91%, 92%, 93%, 940%, 95%, 96%, 97%, 98%, 99%, or 100% correct call rate (i.e., accuracy), specificity, or sensitivity.

In some aspects, the sensitivity or correct call rate for the diagnostic or predictive or prognostic outcome is greater than, e.g., significantly greater than, that obtained using a known diagnosis or prognosis method, such as detection and measurement of circulating CgA or other single protein.

Typically, the diagnostic, prognostic, and predictive methods, often in an initial step, select a subset of biomarkers based on their ability to build a classifier that may accurately predict and classify GEP-NEN and/or different stages of GEP-NEN.

Any of a number of well-known methods for evaluating differences in gene expression may be used to select the subset of biomarkers. For example, an accurate classifier may be based on topographic, pattern-recognition based protocols e.g., support vector machines (SVM) (Noble W S. What is a support vector machine? Nat Biotechnol. 2006; 24(12): 1565-7). Machine-learning based techniques are typically desirable for developing sophisticated, automatic, and/or objective algorithms for analyzing high-dimensional and multimodal biomedical data. In some examples, SVM—a variant of the supervised learning algorithm—is used in connection with the provided methods and systems. SVMs have been used to predict the grading of astrocytomas with a >90 accuracy, and prostatic carcinomas with an accuracy of 74-80% (Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11; Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11).

Other algorithms for building an accurate classifier include linear discriminant analysis (LDA), naïve Bayes (NB), and K-nearest neighbor (KNN) protocols. Such approaches are useful for identifying individual or multivariable alterations in neoplastic conditions (Drozdov I, Tsoka S, Ouzounis C A, Shah A M. Genome-wide expression patterns in physiological cardiac hypertrophy. BMC Genomics. 2010; 11:55; Freeman T C, Goldovsky L, Brosch M, et al. Construction, visualization, and clustering of transcription networks from microarray expression data. PLoS Comput Biol 2007; 3(10): 2032-42; Zampetaki A, Kiechl S, Drozdov I, et al. Plasma microRNA profiling reveals loss of endothelial miR-126 and other microRNAs in type 2 diabetes. Circ Res. 2010; 107(6); 810-7. Epub 2010 Jul. 22; Dhawan M, Selvaraja S, Duan Z H. Application of committee kNN classifiers for gene expression profile classification. Int J Bioinform Res Appl. 2010; 6(4): 344-52; Kawarazaki S, Taniguchi K, Shirahata M, et al. Conversion of a molecular classifier obtained by gene expression profiling into a classifier based on real-time PCR: a prognosis predictor for gliomas. BMC Med Genomics. 2010, 3: 52; Vandebriel R J, Van Loveren H, Meredith C. Altered cytokine (receptor) mRNA expression as a tool in immunotoxicology. Toxicology. 1998; 130(1): 43-67; Urgard E, Vooder T, Vosa U, et al. Metagenes associated with survival in non-small cell lung cancer. Cancer Inform. 2011; 10: 175-83. Epub 2011 Jun. 2; Pimentel M, Amichai M, Chua K, Braham L. Validating a New Genomic Test for Irritable Bowel Syndrome Gastroenterology 2011; 140 (Suppl 1): S-798; Lawlor G, Rosenberg L, Ahmed A, et al. Increased Peripheral Blood GATA-3 Expression in Asymptomatic Patients With Active Ulcerative Colitis at Colonoscopy. *Gastroenterology* 2011, 140 (Suppl 1)).

In some embodiments, an accurate classifier for GEP-NEN and/or different stages of GEP-NEN is based on a combination of the SVM, LDA, NB, and KNN protocols. This is termed the Multi-Analyte-Algorithm Risk Classifier for NETs (MAARC-NET).

Methods using the predictive algorithms and models use statistical analysis and data compression methods, such as those well known in the art. For example, expression data may be transformed, e.g., ln-transformed, and imported into a statistical analysis program, such as PARTEK® GENOMICS SUITE® (genomic data analysis software) or similar program, for example. Data are compressed and analyzed for comparison.

Whether differences in expression level score or values are deemed significant may be determined by well-known statistical approaches, and typically is done by designating a threshold for a particular statistical parameter, such as a threshold p-value (e.g., p<0.05), threshold S-value (e.g., +0.4, with S<−0.4 or S>0.4), or other value, at which differences are deemed significant, for example, where expression of a biomarker is considered significantly down- or up-regulated, respectively, among two different samples, for example, representing two different GEP-NEN subtypes, tumors, stages, localizations, aggressiveness, or other aspect of GEP-NEN or normal or reference sample.

In one aspect, the algorithms, predictive models, and methods are based on biomarkers expressed from genes associated with regulatory gene clusters (i.e., SSTRome, Proliferome. Signalome. Metabolome, Secretome, Secretome, Plurome, EpiGenome, and Apoptome) underlying various GEP-NEN subtypes.

In one aspect, the methods apply the mathematical formulations, algorithms or models identify specific cutoff points, for example, pre-determined expression level scores, which distinguish between normal and GEP-NEN samples, between GEP-NEN and other cancers, and between various sub-types, stages, and other aspects of disease or disease outcome. In another aspect, the methods are used for prediction, classification, prognosis, and treatment monitoring and design. In one aspect, the predictive embodiments are useful for identifying molecular parameters predictive of biologic behavior, and prediction of various GEP-NEN-associated outcomes using the parameters. In one aspect of these embodiments, machine learning approaches are used, e.g., to develop sophisticated, automatic and objective algorithms for the analysis of high-dimensional and multimodal biomedical data.

A "ROC curve" as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a subset or panel of GEP-NEN biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a subset or panel of GEP-NEN has an AUC in the range of about 0.75 to 1.0. In certain of these embodiments, the AUC is in the range of about 0.50 to 0.85, 0.85 to 0.9, 0.9 to 0.95, or 0.95 to 1.0.

For the comparison of expression level scores or other values, and to identify expression profiles (expression signatures) or regulatory signatures based on GEP-NEN biomarker expression, data are compressed. Compression typically is by Principal Component Analysis (PCA) or similar technique for describing and visualizing the structure of high-dimensional data. PCA allows the visualization and comparison of GEP-NEN biomarker expression and determining and comparing expression profiles (expression signatures, expression patterns) among different samples, such as between normal or reference and test samples and among different tumor types.

In some embodiments, expression level data are acquired, e.g., by real-time PCR, and reduced or compressed, for example, to principal components.

PCA is used to reduce dimensionality of the data (e.g., measured expression values) into uncorrelated principal components (PCs) that explain or represent a majority of the variance in the data, such as about 50%, 60%, 70%, 75%, 80%, 85%, 90%, 95%, or 99% of the variance.

In one example, the PCA is 3-component PCA, in which three PCs are used that collectively represent most of the variance, for example, about 75%, 80%, 85%, 90%, or more variance in the data (Jolliffe I T, "Principle Component Analysis," Springer, 1986).

PCA mapping, e.g., 3-component PCA mapping is used to map data to a three dimensional space for visualization, such as by assigning first ($1^{st}$), second ($2^{nd}$) and third ($3^{rd}$) PCs to the X-, Y-, and Z-axes, respectively.

PCA may be used to determine expression profiles for the biomarkers in various samples. For example, reduced expression data for individual sample types (e.g., each tumor type, sub-type or grade, or normal sample type) are localized in a PCA coordinate system and localized data used to determine individual transcript expression profiles or signatures.

In one aspect, the expression profile is determined for each sample by plotting or defining a centroid (center of mass, average expression), corresponding to or representing the sample's individual transcript expression profile (regulatory signature), as given by the principal component vector, as determined by PCA for the panel of biomarkers.

Generally, two centroids or points of localization separated by a relatively large distance in this coordinate system represent two relatively distinct transcript expression profiles. Likewise, relatively close centroids represent relatively similar profiles. In this representation, the distance between centroids is inversely equivalent to the similarity measure (greater distance=less similarity) for the different samples, such that large distances or separation between centroids indicates samples having distinct transcript expression signatures. Proximity of centroids indicates similarity between samples. For example, the relative distance between centroids for different GEP-NEN tumor samples represents the relative similarity of their regulatory signatures or transcript expression profiles.

In one aspect, the statistical and comparative analysis includes determining the inverse correlation between expression levels or values for two biomarkers. In one example, this correlation and the cosine of the angle between individual expression vectors (greater angle=less similarity), is used to identify related gene expression clusters (Gabriel K R, "The biplot graphic display of matrices with application to principal component analysis," Biometrika 1971; 58(3):453).

In some embodiments, there is a linear correlation between expression levels of two or more biomarkers, and/or the presence or absence of GEP-NEN, sub-type, stage, or other outcome. In one aspect, there is an expression-dependent correlation between the provided GEP-NEN biomarkers and characteristics of the biological samples, such as between biomarkers (and expression levels thereof) and various GEP-NEN sub-types (e.g., benign versus active disease).

Pearson's Correlation (PC) coefficients ($R^2$) may be used to assess linear relationships (correlations) between pairs of values, such as between expression levels of a biomarker for different biological samples (e.g., tumor sub-types) and between pairs of biomarkers. This analysis may be used to linearly separate distribution in expression patterns, by calculating PC coefficients for individual pairs of the biomarkers (plotted on x- and y-axes of individual Similarity Matrices). Thresholds may be set for varying degrees of linear correlation, such as a threshold for highly linear correlation of (R>0.50, or 0.40). Linear classifiers can be applied to the datasets. In one example, the correlation coefficient is 1.0.

In one embodiment, regulatory clusters are determined by constructing networks of correlations using statistical analyses, for example, to identify regulatory clusters composed of subsets of the panel of biomarkers. In one example, PC correlation coefficients are determined and used to construct such networks of correlations. In one example, the networks are identified by drawing edges between transcript pairs having R above the pre-defined threshold. Degree of correlation can provide information on reproducibility and robustness.

Also provided herein are objective algorithms, predictive models, and topographic analytical methods, and methods using the same, to analyze high-dimensional and multimodal biomedical data, such as the data obtained using the provided methods for detecting expression of the GEP-NEN biomarker panels. As discussed above, the objective algorithms, models, and analytical methods include mathematical analyses based on topographic, pattern-recognition based protocols e.g., support vector machines (SVM) (Noble W S. What is a support vector machine? Nat Biotechnol. 2006; 24(12): 1565-7), linear discriminant analysis (LDA), naïve Bayes (NB), and K-nearest neighbor (KNN) protocols, as well as other supervised learning algorithms and models, such as Decision Tree, Perceptron, and regularized discriminant analysis (RDA), and similar models and algorithms well-known in the art (Gallant S I, "Perceptron-based learning algorithms," Perceptron-based learning algorithms 1990; 1(2): 179-91).

In some embodiments, Feature Selection (FS) is applied to remove the most redundant features from a dataset, such as a GEP-NEN biomarker expression dataset, and generate a relevant subset of GEP-NEN biomarkers. FS enhances the generalization capability, accelerates the learning process, and improves model interpretability. In one aspect, FS is employed using a "greedy forward" selection approach, selecting the most relevant subset of features for the robust learning models. (Peng H, Long F, Ding C, "Feature selection based on mutual information: criteria of max-dependency, max-relevance, and min-redundancy," IEEE Transactions on Pattern Analysis and Machine Intelligence, 2005; 27(8): 1226-38).

In some embodiments, Support Vector Machines (SVM) algorithms are used for classification of data by increasing the margin between the n data sets (Cristianini N, Shawe-Taylor J. An Introduction to Support Vector Machines and other kernel-based learning methods. Cambridge: Cambridge University Press, 2000).

In some embodiments, the predictive models include Decision Tree, which maps observations about an item to a conclusion about its target value (Zhang H, Singer B. "Recursive Partitioning in the Health Sciences," (Statistics for Biology and Health): Springer, 1999.). The leaves of the tree represent classifications and branches represent conjunctions of features that devolve into the individual classifications. It has been used effectively (70-90° %) to predict prognosis of metastatic breast cancer (Yu L et al "TGF-beta receptor-activated p38 MAP kinase mediates Smad-independent TGF-beta responses," Embo J 2002; 21(14):3749-59), as well as colon cancer (Zhang H et al "Recursive partitioning for tumor classification with gene expression microarray data.," Proc Natl Acad Sci USA 2001; 98(12): 6730-5), to predict the grading of astrocytomas (Glotsos D et al "Automated diagnosis of brain tumours astrocytomas using probabilistic neural network clustering and support vector machines," Int J Neural Syst 2005; 15(1-2): 1-11) with a >90% accuracy, and prostatic carcinomas with an accuracy of 74-80% (Mattfeldt T et al. "Classification of prostatic carcinoma with artificial neural networks using comparative genomic hybridization and quantitative stereological data," Pathol Res Pract 2003; 199(12):773-84). The efficiency of this technique has been measured by 10-fold cross-validation (Pirooznia M et al "A comparative study of different machine learning methods on microarray gene expression data," BMC Genomics 2008; 9 Suppl 1:S13).

The predictive models and algorithms further include Perceptron, a linear classifier that forms a feed forward neural network and maps an input variable to a binary classifier (Gallant S I. "Perceptron-based learning algorithms," Perceptron-based learning algorithms 1990; 1(2): 179-91). It has been used to predict malignancy of breast cancer (Markey M K et al. "Perceptron error surface analysis; a case study in breast cancer diagnosis," Comput Biol Med 2002; 32(2):99-109). In this model, the learning rate is a constant that regulates the speed of learning. A lower learning rate improves the classification model, while increasing the time to process the variable (Markey M K et al. "Perceptron error surface analysis: a case study in breast cancer diagnosis," Comput Biol Med 2002; 32(2):99-109). In one example, a learning rate of 0.05 is used. In one aspect, a Perceptron algorithm is used to distinguish between localized or primary tumors and corresponding metastatic tumors. In one aspect, three data scans are used to generate decision boundaries that explicitly separate data into classes.

The predictive models and algorithms further include Regularized Discriminant Analysis (RDA), which can be used as a flexible alternative to other data mining techniques, including Linear and Quadratic Discriminant Analysis (LDA, QDA) (Lilien R H, Farid H, Donald B R. "Probabilistic disease classification of expression-dependent proteomic data from mass spectrometry of human serum.," J Comput Biol 2003; 10(6):925-46; Cappellen D, Luong-Nguyen N H, Bongiovanni S, et al. "Transcriptional program of mouse osteoclast differentiation governed by the macrophage colony-stimulating factor and the ligand for the receptor activator of NFkappa B." J Biol Chem 2002; 277(24):21971-82.). RDA's regularization parameters, $\gamma$ and $\lambda$, are used to design an intermediate classifier between LDA and QDA. QDA is performed when $\gamma=0$ and $\lambda\hat{\ }0$ while LDA is performed when $\gamma=0$ and $\lambda=1$ (Picon A, Gold L I, Wang J, Cohen A, Friedman E. A subset of metastatic human colon cancers expresses elevated levels of transforming growth factor beta 1. Cancer Epidemiol. Biomarkers Prev. 1998; 7(6):497-504).

To reduce over-fitting, RDA parameters are selected to minimize cross-validation error while not being equal 0.0001, thus forcing RDA to produce a classifier between LDA, QDA, and L2 (Pima I, Aladjem M., "Regularized discriminant analysis for face recognition," Pattern Recognition 2003; 37(9): 1945-48). Finally, regularization itself has been used widely to overcome over-fitting in machine learning (Evgeniou T, Pontil M, Poggio T. "Regularization Networks and Support Vector Machines.," Advances in Computational Math 2000; 13(1): 1-50; Ji S, Ye J. Kernel "Uncorrelated and Regularized Discriminant Analysis: A Theoretical and Computational Study.," IEEE Transactions on Knowledge and Data Engineering 2000; 20(10): 1311-21.).

In one example, regularization parameters are defined as $\gamma=0.002$ and $\lambda 4=0$. In one example, for each class pair, S-values are assigned to all transcripts which are then arranged by a decreasing S-value. RDA is performed, e.g., 21 times, such that the $N^{th}$ iteration consists of top N scoring transcripts. Error estimation can be carried out by a 10-fold cross-validation of the RDA classifier. This can be done by partitioning the tissue data set into complementary subsets, performing the analysis on one subset (called the training set), and validating the analysis on the other subset (called the validation set or testing set).

In one example, misclassification error is averaged to reduce variability in the overall predictive assessment, which can provide a more accurate approach to error estimation compared to other approaches, including bootstrapping and leave-one-out cross-validation (Kohavi R. "A study of cross-validation and bootstrap for accuracy estimation and model selection.," Proceedings of the Fourteenth International Joint Conference on Artificial Intelligence, 1995; 2(12): 1137-43.).

In one example, selection for tissue classification is performed, for example, by computing the rank score (S) for each gene and for each class pair as:

$$S = \frac{|\mu_{c2} - \mu_{c1}|}{\sigma_{c1} + \sigma_{c2}}$$

where $\mu_{C1}$ and $\mu_{C2}$ represent means of first and second class respectively and $\sigma_{C1}$ and $\sigma_{C2}$ are inter-class standard deviations. A large S value is indicative of a substantial differential expression ("Fold Change") and a low standard deviation ("transcript stability") within each class. Genes may be sorted by a decreasing S-value and used as inputs for the regularized discriminant analysis algorithm (RDA).

The algorithms and models may be evaluated, validated and cross-validated, for example, to validate the predictive and classification abilities of the models, and to evaluate specificity and sensitivity. In one example, radial basis function is used as a kernel, and a 10-fold cross-validation used to measure the sensitivity of classification (Cristianini N, Shawe-Taylor J. "An Introduction to Support Vector Machines and other kernel-based learning methods.," Cambridge: Cambridge University Press, 2000.). Various classification models and algorithms may be compared by the provided methods, for example, using training and cross-validation, as provided herein, to compare performance of the predictive models for predicting particular outcomes.

Embodiments of the provided methods, systems, and predictive models are reproducible, with high dynamic range, can detect small changes in data, and are performed using simple methods, at low cost, e.g., for implementation in a clinical laboratory.

Kits and other articles of manufacture are provided for use in the diagnostic, prognostic, predictive, and therapeutic applications described herein. In some embodiments, the kits include a carrier, package, or packaging, compartmentalized to receive one or more containers such as vials, tubes, plates, and wells, in which each of the containers includes one of the separate elements for use in the methods provided herein, and in some aspects further include a label or insert with instructions for use, such as the uses described herein. In one example, the individual containers include individual agents for detection of the GEP-NEN biomarkers as provided herein; in some examples, individual containers include agents for detection of housekeeping genes and/or normalization.

For example, the container(s) can comprise an agent, such as a probe or primer, which is or can be detectably labeled. Where the method utilizes nucleic acid hybridization for detection, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody.

The kits will typically comprise the container(s) described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapeutic or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself, a label can be associated with a container when it is present within a receptacle or carrier that also holds the container, e.g., as a package insert. The label can indicate that the composition is used for diagnosing, treating, prophylaxing or prognosing a condition, such as GEP-NEN.

In another embodiment, an article(s) of manufacture containing compositions, such as amino acid sequence(s), small molecule(s), nucleic acid sequence(s), and/or antibody(s), e.g., materials useful for the diagnosis, prognosis, or therapy of GEP-NEN is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of GEP-NEN biomarkers in biological samples, e.g., blood or cells and tissues, or for relevant laboratory, prognostic, diagnostic, prophylactic and therapeutic purposes; indications and/or directions for such uses can be included on or with such container, as can reagents and other compositions or tools used for these purposes.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Differential Expression of NET Marker GENESIN Primary NETs—An exon-level screen of localized small intestinal NETs using Affymetrix Human Exon 1.0 ST arrays was performed to define alternative splicing events in neuroendocrine tumor tissue in comparison to a control (normal intestinal mucosa). Exon expression analysis identified 1287 differentially expressed genes between normal intestinal mucosa and NET tumor tissues. Five hundred and twenty nine genes were upregulated and 758 were downregulated. As an example, a subset of NET marker genes was focused on, in particular CgA, Tph1, VMAT2, SCG5, and PTPRN2. The RMA-normalized exon expression of the NET marker genes in this subset is shown in FIGS. 1A-1E in normal (green) and tumor (red) samples. Of these genes, Tph1 was the only gene where all exons were differentially expressed in tumor (FC>1.5, p<0.05), while CgA was the only gene where all exon expressions remained constant between tumor and normal samples.

Two of 17 differentially expressed exons were identified in VMAT2 and eight of 9 in SCG5. In PTPRN2 six of 30 exons were differentially expressed. These results demonstrate that specific primer/probe sets are required to maximize differences between neoplasia and normal gene expression.

Validating Alternative Splicing in NET Marker Genes by RT-PCR—With reference to FIGS. 2A-2E, the findings of differential exon transcript levels was validated using reverse transcriptase polymerase chain reaction (RT-PCR). All marker gene exons, including $Tph1_{1-2}$, $VMAT2_{9-10}$, $SCG5_{2-3}$, and $PTPRN2_{12-13}$, were confirmed to be differentially expressed in tumor samples versus normal mucosa, with the exception of $CgA_{4-5}$.

Genomic and RT-PCR data from FIGS. 1A-1E and 2A-2E, respectively, identify that differential splicing occurs in NETs and that candidate biomarkers, e.g., VMAT2, require the use of specific primer/probe sets to effectively capture differences in expression of target transcripts.

To evaluate the relevance in blood, a microarray analysis of peripheral NET blood samples was performed. Up-regulated genes (n=1,397) included GO-Fat terms such as "RNA splicing", "Vesicle-mediated transport", and "Chromatin modification" which is consistent with known roles for these processes in NET pathobiology. Comparisons of the blood transcriptome with GEP-NET transcriptomes identified 236 up-regulated genes, 72 of which were examined for utility as biomarkers. A preliminary screen identified 51 genes as upregulated in tumor blood samples compared to controls. Forty-two genes (83%) were transcribed from multiple exons. A minimum of two primer/probe sets were tested for these genes in blood to define the most relevant combinations for target amplification. The housekeeping gene and 51 validated targets and exons of interest for primer/probe sets are described in TABLE 2. The amplicon positions identified for each GEN-NEN biomarker in Table 2 are the identified as underlined sequences in Table 1.

TABLE 2

Primer Details

| | GEP-NEN Biomarker | | NCBI Chromosome | UniGene | | Amplicon Size | Exon | |
|---|---|---|---|---|---|---|---|---|
| Symbol | Name | | location | ID | RefSeq | Length | Boundary | Position |
| ALG9 | asparagine-linked glycosylation 9, alpha-1,2-mannosyl transferase homolog | | Chr. 11-111652919-111742305 | Hs.503850 | NM_024740.2 | 68 | 4-5 | 541-600 |
| AKAP8L | A kinase (PRKA) anchor protein 8-like | | Chr.19: 15490859-15529833 | Hs.399800 | NM_014371.3 | 75 | 12-13 | 1596-1670 |

TABLE 2-continued

Primer Details

| Symbol | GEP-NEN Biomarker Name | NCBI Chromosome location | UniGene ID | RefSeq | Amplicon Size Length | Exon Boundary | Position |
|---|---|---|---|---|---|---|---|
| APLP2 | amyloid beta (A4) precursor-like protein 2 | Chr. 11-129939716-130014706 | Hs.370247 | NM_001142276.1 | 102 | 14-15 | 2029-2132 |
| ARAF1 | v-raf murine sarcoma 3611 viral oncogene homolog | Chr. X-47420578-47431320 | Hs.446641 | NM_001654.4 | 74 | 10-11 | 1410-1475 |
| ATP6V1H | ATPase, H+ transporting, lysosomal 50/57 kDa, V1, Subunit H | Chr.8: 54628115-54755850 | Hs.491737 | NM_015941.3 | 102 | 13-14 | 1631-1732 |
| BNIP3L | BCL2/adenovirus E1B 19 kDa interacting protein 3-like | Chr.8: 26240523-26270644 | Hs.131226 | NM_004331.2 | 69 | 2-3 | 374-342 |
| BRAF | v-raf murine sarcoma viral oncogene homolog B1 | Chr. 7-140433812-140624564 | Hs.550061 | NM_004333.4 | 77 | 1-2 | 165-233 |
| C21ORF7 | chromosome 21 open reading frame 7 | Chr.21: 30452873-30548204 | Hs.222802 | NM_020152.3 | 76 | — | 611-686 |
| CD59 | CD59 molecule, complement regulatory protein | Chr. 11-33724556-33758025 | Hs.278573 | NM_203331.2 | 70 | 3-4 | 193-264 |
| COMMD9 | COMM domain containing 9 | Chr.11: 36293842-36310999 | Hs.279836 | NM_001101653.1 | 85 | 2-3 | 191-275 |
| CTGF | connective tissue growth factor | Chr. 6-132269316-132272518 | Hs.410037 | NM_001901.2 | 60 | 4-5 | 929-990 |
| ENPP4 | ectonucleotide pyrophosphatase/phosphodiesterase 4 | Chr.6: 46097701-46114436 | Hs.643497 | NM_014936.4 | 82 | 3-4 | 1221-1303 |
| FAM131A | family with sequence similarity 131, member A, transcript variant 2 | Chr.3: 184053717-184064063 | Hs.591307 | NM_001171093.1 | 64 | 4-5 | 498-561 |
| FLJ10357 | Rho guanine nucleotide exchange factor (GEF) 40 (ARHGEF40) | Chr.14: 21538527-21558036 | Hs.35125 | NM_018071.4 | 102 | 16-17 | 3557-3658 |
| FZD7 | frizzled homolog 7 (Drosophila) | Chr. 2-202899310-202903160 | Hs. 173859 | NM_003507.1 | 70 | 1-1 | 1-70 |
| GLT8D1 | glycosyltransferase 8 domain containing | Chr.3: 52728504-52740048 | Hs.297304 | NM_001010983.2 | 87 | 4-5 | 924-1010 |

TABLE 2-continued

| | Primer Details | | | | | | |
|---|---|---|---|---|---|---|---|
| GEP-NEN Biomarker | | NCBI Chromosome | UniGene | | Amplicon Size | Exon | |
| Symbol | Name | location | ID | RefSeq | Length | Boundary | Position |
| HDAC9 | 1, transcript variant 3 histone deacetylase 9, transcript variant 6 | Chr.7: 18535369-19036993 | Hs.196054 | NM_001204144.1 | 69 | 11-12 | 1777-1845 |
| HSF2 | heat shock transcription factor 2, transcript variant 1 | Chr.6: 122720696-122754264 | Hs.158195 | NM_004506.3 | 82 | 10-11 | 1324-1405 |
| Ki-67 | antigen identified by monoclonal antibody Ki-67 | Chr. 10-129894923-129924655 | Hs.689823 | NM_001145966.1 | 78 | 6-7 | 556-635 |
| KRAS | v-Ki-ras2 Kirsten rat sarcoma viral oncogene homolog | Chr. 12-25358180-25403854 | Hs.505033 | NM_004985.4 | 130 | 4-5 | 571-692 |
| LEO1 | Leo1, Paf1/RNA polymerase II complex component homolog (S. cerevisiae) | Chr.15: 52230222-52263958 | Hs.567662 | NM_138792.3 | 122 | 10-11 | 1753-1874 |
| MORF4L2 | mortality factor 4 like 2, transcript variant 1 | Chr.X: 102930426-102943086 | Hs.326387 | NM_001142418.1 | 153 | 5-5 | 1294-1447 |
| NAP1L1 | nucleosome assembly protein 1-like 1 | Chr. 12-76438672-76478738 | Hs.524599 | NM_139207.2 | 139 | 16-16 | 1625-1764 |
| NOL3 | nucleolar protein 3 (apoptosis repressor with CARD domain), transcript variant 3 | Chr.16: 67204405-67209643 | Hs.513667 | NM_001185057.2 | 118 | 1-2 | 131-248 |
| NUDT3 | nudix (nucleoside diphosphate linked moiety X)-type motif 3 | Chr.6: 34255997-34360441 | Hs.188882 | NM_006703.3 | 62 | 2-3 | 500-561 |
| OAZ2 | ornithine decarboxylase antizyme 2 | Chr.15: 64979773-64995462 | Hs.713816 | NM_002537.3 | 96 | 1-2 | 189-284 |
| PANK2 | pantothenate kinase 2 | Chr.20: 3869486-3904502 | Hs.516859 | NM_024960.4 | 126 | 4-5 | 785-910 |
| PHF21A | PHD finger protein 21A, transcript variant 1 | Chr.11: 45950870-46142985 | Hs.502458 | NM_001101802.1 | 127 | 16-17 | 2241-2367 |

TABLE 2-continued

Primer Details

| Symbol | GEP-NEN Biomarker Name | NCBI Chromosome location | UniGene ID | RefSeq | Amplicon Size Length | Exon Boundary | Position |
|---|---|---|---|---|---|---|---|
| PKD1 | polycystic kidney disease 1 (autosomal dominant), transcript variant 2 | Chr.16: 2138711-2185899 | Hs.75813 | NM_000296.3 | 110 | 16-17 | 7224-7333 |
| PLD3 | phospholipase D family, member 3, transcript variant 1 | Chr.19: 40854332-40884390 | Hs.257008 | NM_001031696.3 | 104 | 6-7 | 780-883 |
| PNMA2 | paraneoplastic antigen MA2 | Chr. 8-26362196-26371483 | Hs.591838 | NM_007257.5 | 60 | 3-3 | 283-343 |
| PQBP1 | polyglutamine binding protein 1, transcript variant 2 | Chr.X: 48755195-48760422 | Hs.534384 | NM_001032381.1 | 68 | 2-3 | 157-224 |
| RAF1 | v-raf-1 murine leukemia viral oncogene homolog 1 | Chr. 3-12625100-12705700 | Hs.159130 | NM_002880.3 | 90 | 7-8 | 1186-1277 |
| RNF41 | ring finger protein 41, transcript variant 4 | Chr.12: 56598285-56615735 | Hs.524502 | NM_001242826 | 72 | 2-3 | 265-336 |
| RSF1 | remodeling and spacing factor 1 | Chr.11: 77377274-77531880 | Hs.420229 | NM_016578.3 | 60 | 7-8 | 2804-2863 |
| RTN2 | reticulon 2, transcript variant 1 | Chr.19: 45988550-46000313 | Hs.47517 | NM_005619.4 | 87 | 9-10 | 1681-1766 |
| SMARCD3 | SWI/SNF related, matrix associated, actin dependent regulator of chromatin, subfamily d, member 3, transcript variant 3 | Chr.7: 150936059-150974231 | Hs.647067 | NM_001003801.1 | 109 | 8-9 | 986-1094 |
| SPATA7 | spermatogenesis associated 7, transcript variant 2 | Chr.14: 88851988-88904804 | Hs.525518 | NM_001040428.3 | 81 | 1-2 | 160-241 |
| SST1 | somatostatin receptor 1 | Chr.14: 38677204-38682268 | Hs.248160 | NM_001049.2 | 85 | 3-3 | 724-808 |
| SST3 | somatostatin receptor 3 | Chr.22: 37602245-37608353 | Hs.225995 | NM_001051.4 | 84 | 2-2 | 637-720 |
| SST4 | somatostatin receptor 4 | Chr.20: 23016057-23017314 | Hs.673846 | NM_001052.2 | 104 | 1-1 | 91-194 |
| SST5 | somatostatin receptor 5, transcript variant 1 | Chr.16: 1122756-1131454 | Hs.449840 | NM_001053.3 | 157 | 1-1 | 1501-1657 |

TABLE 2-continued

Primer Details

| GEP-NEN Biomarker Symbol | Name | NCBI Chromosome location | UniGene ID | RefSeq | Amplicon Size Length | Exon Boundary | Position |
|---|---|---|---|---|---|---|---|
| TECPR2 | tectonin beta-propeller repeat containing 2, transcript variant 2 | Chr.14: 102829300-102968818 | Hs.195667 | NM_001172631.1 | 61 | 12-13 | 3130-3191 |
| TPH1 | tryptophan hydroxylase 1 | Chr. 11-18042538-18062309 | Hs.591999 | NM_004179.2 | 145 | 1-2 | 73-219 |
| TRMT112 | tRNA methyltransferase 11-2 homolog (S. cerevisiae) | Chr.11: 64084163-64085033 | Hs.333579 | NM_016404.2 | 91 | 1-2 | 45-135 |
| VMAT1 | solute carrier family 18 (vesicular monoamine), member 1 | Chr. 8-20002366-20040717 | Hs.158322 | NM_003053.3 | 102 | 1-2 | 93-196 |
| VMAT2 | solute carrier family 18 (vesicular monoamine), member 2 | Chr. 10-119000716-119037095 | Hs.596992 | NM_003054.4 | 60 | 9-10 | 896-957 |
| VPS13C | vacuolar protein sorting 13 homolog C (S. cerevisiae), transcript variant 2B | Chr.15: 62144588-62352647 | Hs.511668 | NM_001018088.2 | 65 | 69-70 | 9685-9749 |
| WDFY3 | WD repeat and FYVE domain containing 3 | Chr.4: 85590690-85887544 | Hs.480116 | NM_014991.4 | 81 | 64-65 | 10190-10270 |
| ZFHX3 | zinc finger homeobox 3, transcript variant B | Chr.16: 72816784-73092534 | Hs.598297 | NM_001164766.1 | 68 | 5-6 | 886-953 |
| ZXDC | zinc finger C, transcript variant 2 | Chr.3: 126156444-126194762 | Hs.440049 | NM_001040653.3 | 61 | 1-2 | 936-1001 |
| ZZZ3 | zinc finger, ZZ-type containing 3 | Chr.1: 78030190-78148343 | Hs.480506 | NM_015534.4 | 62 | 13-14 | 2909-2971 |

Delineation of Minimum Gene Set for Mathematically-Derived (MAARC-NET) Scoring System—Four classification algorithms (SVM, LDA, KNN, and Bayes) and a 10-fold cross-validation design were used to build a classifier for the identification of GEP-NETs in blood. See Modlin I, Drozdov I, Kidd M: The Identification of gut neuroendocrine tumor disease by multiple synchronous transcript analysis in blood. *Plos One* 2013, e63364. These classifiers were built on a training set and significantly up-regulated features between control and tumor cases were calculated by t-test. With reference to FIG. 3, an examination of the 51 genes featured in TABLE 2 identified that inclusion of at least 22 genes was sufficient to build an accurate (>0.85) classifier. FIG. 3 shows the prediction accuracy of each classifier algorithm using sequential addition of up to 27 significantly up-regulated genes (p<0.05) in the GEP-NET samples obtained using results of the 10-fold cross validation. The average accuracy of the SVM, LDA, KNN, and Bayes algorithms to distinguish GEP-NET from control blood samples using the sequentially added 27 genes was comparable—0.89 (0.85-1.0), 0.89 (0.86-0.93), 0.88 (0.85-0.93), and 0.86 (0.85-0.93) respectively. The "majority voting" combination of the four classifiers achieved an accuracy of 0.88. The at least 22 genes sufficient to build an accurate classifier were used to develop the MAARC-NET scoring system, and are featured in TABLE 3.

TABLE 3

Twenty Two Genes Included in the Mathematically-Derived MAARC-NET Scoring System

| | Fold Change | p-value | Adjusted p-value |
|---|---|---|---|
| PNMA2 | 0.819515 | 6.74E−21 | 3.43E−19 |
| NAP1L1 | 0.662434 | 4.9E−18 | 1.25E−16 |
| FZD7 | 0.799858 | 3.82E−15 | 6.5E−14 |
| SLC18A2 | 0.524046 | 1.08E−12 | 1.37E−11 |
| NOL3 | 0.809571 | 7.22E−10 | 7.36E−09 |
| SSTR5 | 0.877322 | 1.64E−09 | 1.4E−08 |
| TPH1 | 0.459185 | 1.75E−07 | 1.27E−06 |
| RAF1 | 0.316509 | 1.54E−06 | 7.86E−06 |
| RSF1 | 0.530054 | 1.74E−06 | 8.07E−06 |
| SSTR3 | 0.555269 | 3.82E−06 | 1.62E−05 |
| SSTR1 | 0.493052 | 1.73E−05 | 6.81E−05 |
| CD59 | 0.26257 | 2.7E−05 | 9.82E−05 |
| ARAF | 0.228332 | 4.07E−05 | 0.000138 |
| APLP2 | 0.228153 | 4.42E−05 | 0.000141 |
| KRAS | 0.205822 | 9.92E−05 | 0.000298 |
| MORF4L2 | 0.319826 | 0.000169 | 0.000453 |
| TRMT112 | 0.269618 | 0.001125 | 0.002524 |
| MKI67 | 0.191245 | 0.003468 | 0.007074 |
| SSTR4 | 0.313807 | 0.003734 | 0.007324 |
| CTGF | 0.196845 | 0.007665 | 0.01303 |
| SPATA7 | 0.288625 | 0.01467 | 0.02338 |
| ZFHX3 | 0.13248 | 0.031354 | 0.045687 |

Figure 4A:
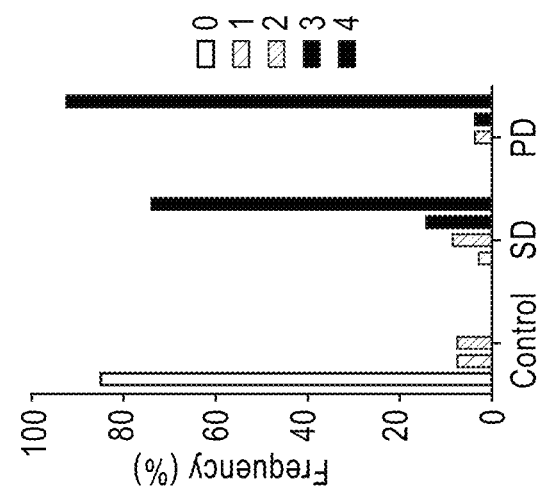
FIGS. 4A-4C are graphs showing mathematically-derived MAARC-NET scores in the test set.

Refinement of Mathematically-Derived MAARC-NET Scoring System—Individual PCR-based gene expressions are included in a score. See Modlin I, Drozdov I, Kidd M, *Plos One* 2013. The score is based on a "majority vote" strategy and was developed from a binary classification system whereby a sample will be called "normal" and given a score of 0 or "tumor" and will be scored "1". The score can range from 0 (four calls all "normal") to 4 (four calls all "tumor"). Each "call" is the binary result (either "0" for normal or "1" for tumor) of one of four different learning algorithms: Support Vector Machine (SVM), Linear Discrimination Analysis (LDA), K-Nearest Neighbor (KNN), and Naïve Bayes (Bayes). Each of these four learning algorithms were trained on an internal training set including 67 controls and 63 GEP-NEN. In this training set, differentially expressed genes (control versus GEP-NEN) were identified as significant using a t-test. Based upon the training set, each of the learning algorithms were trained to differentiate between normal and tumor gene expression to within a level of significance of at least $p<0.05$. According to the majority voting strategy, those samples with less than 2 "normal" calls are classified as GEP-NEN. With reference to FIG. 4A, an audit of samples identified that 85% of controls exhibited a score of "0." No tumors scored "0." ROC analyses identified that a score of 2 was the cut-off for normal samples (controls) versus tumors (score≥2). This approach exhibited correct call rates of 91-97% with sensitivities and specificities of 85-98% and 93-97% for the identification of GEP-NETs in two independent sets. See Modlin I, Drozdov I, Kidd M, *Plos One* 2013.

These data were initially derived from a test data set of 130 samples (n−67 controls, n=−63 NETs). Inherent in the test set are two classes of NETs—clinically defined as treated, stable disease (SD: n=35) and untreated, progressive disease (PD: n=28). The classification algorithm also segregated the tumor call into two units "treated" and "untreated." The 0-4 binary classification was therefore amended to represent 3 possible calls for each particular sample: "normal", "tumor (treated)" and "tumor (untreated)".

A number of rules were implemented to generate an amended majority vote strategy. A call of "normal" was assigned a value of 0; a call of tumor "treated" was assigned a value of 1; a call of tumor "untreated" was assigned a value of 2. By way of example, if a sample results in four calls of "normal," a value of 0 was assigned for each call, thereby totaling a score of 0. If a sample results in four calls of tumor "treated," a value of 1 was assigned for call, thereby totaling a score of 4. If a sample results in four calls of tumor "untreated," a "2" is assigned for each, thereby totaling a score of 8. Scores in the amended majority vote strategy can therefore range between 0 and 8.

Figure 4B:
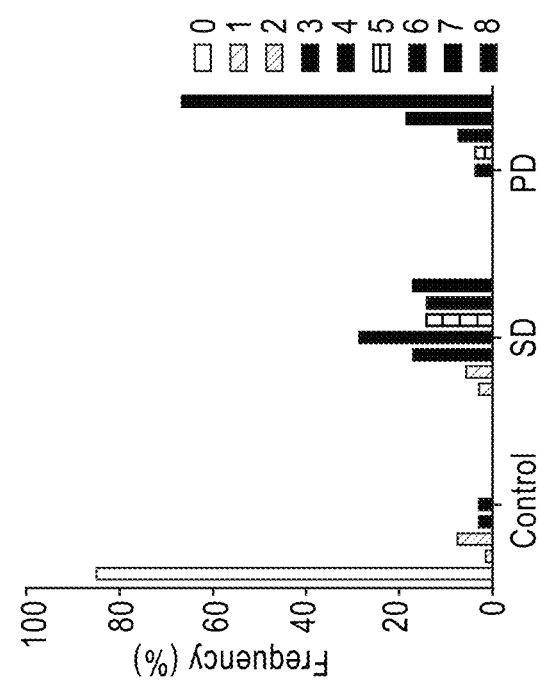
Figure 4C:
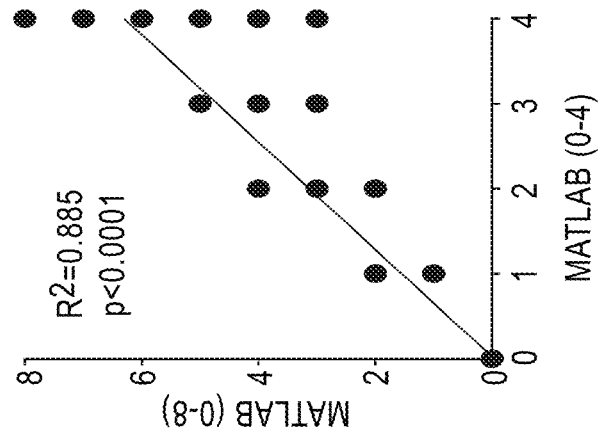

Examination of the test dataset (n=130) was used to establish whether the amended majority vote-derived score could serve as a measure of "treatment" responses. Similarly to the published 0-4 score shown in FIG. 4A, the majority of NET patients exhibited an amended majority vote score≥2 as shown in FIG. 4B. With reference to FIG. 4C, majority vote and amended majority vote scores were significantly related ($R^2=0.89$, $p<0.0001$).

Figure 5A:
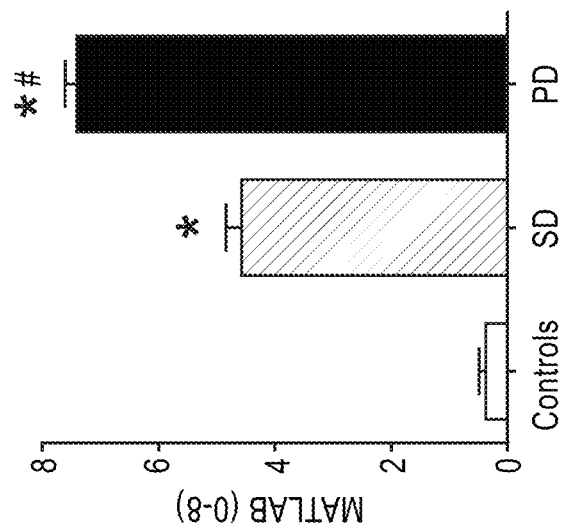
FIGS. 5A-5B are graphs showing MAARC-NET scores in the test set and a Receiver Operating Characteristics (ROC) analysis.

With reference to FIG. 5A, analysis of the data in the test set identified that an amended mathematically-derived score (0-8) was significantly elevated in tumors compared to controls and was highest in PD relative to SD.

Figure 5B:
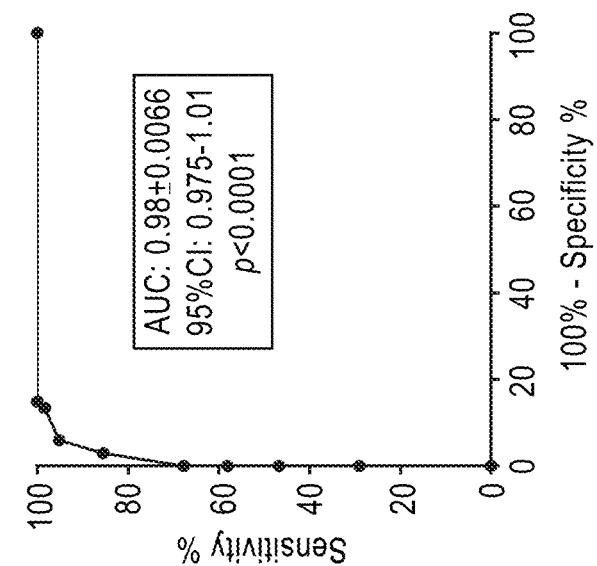

With reference to FIG. 5B, a receiver operating characteristic (ROC) curve was generated of controls versus GEP-NETs (SD and PD combined). A ROC curve is a generalization of the set of potential combinations of sensitivity and specificity possible for predictors. A ROC curve is a plot of the true positive rate (sensitivity) against the false positive rate (1-specificity) for the different possible cut-points of a diagnostic test. FIG. 5B is a graphical representation of the functional relationship between the distribution of the sensitivity and specificity values in the test set and in a cohort of control samples. The area under the curve (AUC) is an overall indication of the diagnostic accuracy of (1) the amended mathematically-derived scores and (2) a receiver operating characteristic (ROC) curve. AUC may be determined by the "trapezoidal rule." For a given ROC curve, the data points are connected by straight line segments, perpendiculars are erected from the abscissa to each data point, and the sum of the areas of the triangles and trapezoids so constructed is computed.

The ROC curve in FIG. 5B identifies that the amended mathematically-derived score may be utilized to differentiate between controls and GEP-NETs—exhibiting an AUC of >0.98, and a $p<0.0001$; *$p<0.05$ vs. controls; #$p<0.05$ vs. SD (2-tailed Mann-Whitney U-test).

Figure 6B:
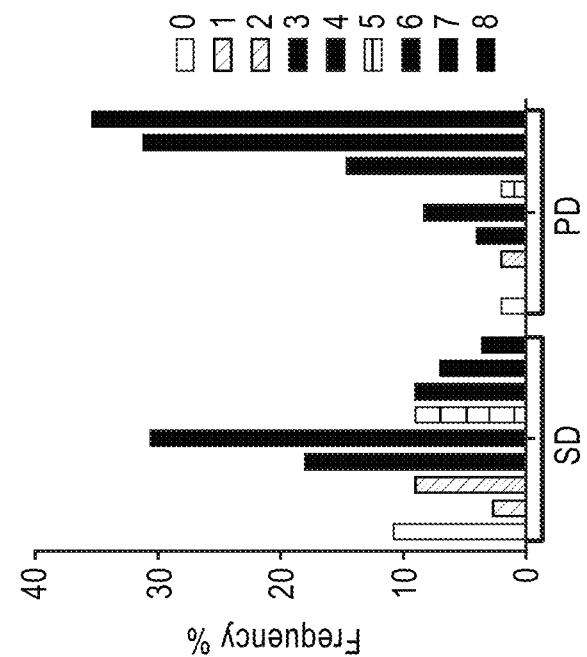
FIG. 6A-6B are (FIG. 6A) a graph of MAARC-NET scores in the independent set, wherein Progressive Disease (PD) NETs had a significantly higher elevated score compared to Stable Disease (SD)
Figure 6A:
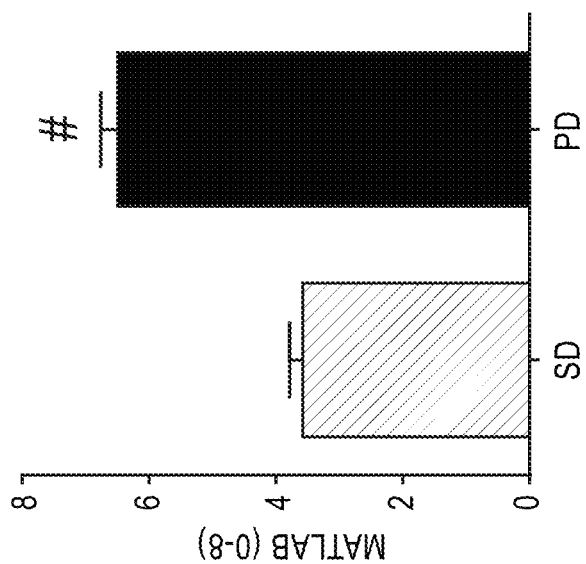

Amended mathematically-derived scores were subsequently examined in an independent set (SD: n=111, PD: n=48). With reference to FIG. 6A, the scores were significantly elevated in the independent set, exhibiting a $p<0.0001$. With reference to FIG. 6B, a frequency distribution plot of amended mathematically-derived scores in SD and PD patients confirmed that PD samples exhibited higher scores, with #$p<0.0001$ vs. SD (2-tailed Mann-Whitney U-test).

With reference to FIG. 7A, a second ROC curve was generated to determine whether the amended mathematically-derived score could be utilized to differentiate SD from PD. In the test set (SD: n=35, PD: n=28), the ROC analysis identified that the score could be used to differentiate PD from SD tumors with an AUC of 0.93. A score cutoff of >6.5 (i.e. a score of ≥7) had a sensitivity of 85% and 83% specificity for detecting PDs (Likelihood ratio: 4.97).

With reference to FIG. 7B, the utility of the amended mathematically-derived scoring system to differentiate between SD and PD in the independent set (n=111 SD, n=48 PD) was assessed. The percentage correctly called ranged between 70-90% using a cut-off of ≥7. For SD, 89% of NETs were correctly predicted using the cut-off of ≥7 while 67% of PD were correctly predicted. The performance metrics were: sensitivity=67%, specificity=89%, PPV=73% and NPV=86%. Accordingly, the data indicate that a mathematically-derived MAARC-NET score ranging from 0-8 has utility for discriminating between controls and GEP-NETs.

Application of Scoring System and Developing a Nomogram for "NETEST 1"—To differentiate between controls and NETs, a cut-off of ≥3 has a sensitivity of 95% and 94% specificity. The sensitivity can be improved to 98% using a cut-off of ≥2. To differentiate between SD and PD, a cut-off of ≥7 can be used (sensitivity of 85% and 83% specificity). The sensitivity can be improved to 96% using a cut-off of ≥5.

The mathematically-derived MAARC-NET scores therefore range from 0-2 (control); 2-5 (SD); and 5-8 (PD). These scores can be converted to a percentage as displayed in TABLE 4.

TABLE 4

| Mathematically-Derived Scores Percentage | | | | |
|---|---|---|---|---|
| Mathematically-derived Score | 0-2 | 2-5 | 5-7 | 7-8 |
| Disease Nomogram Score | 0 | 0-55% | 55-75% | 75-100% |
| | | Low | Moderate | High |

Figure 8:
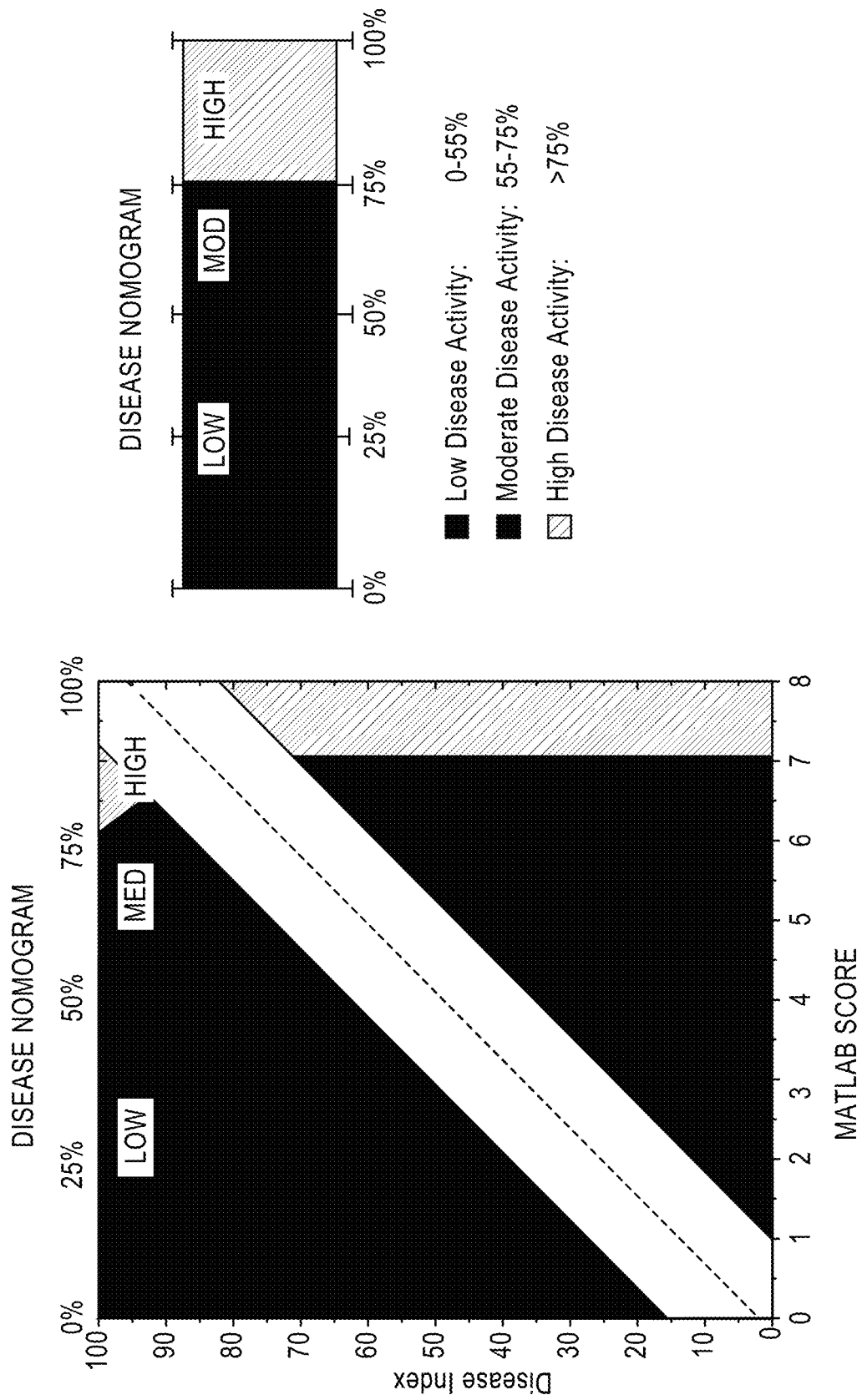
FIG. 8 is a nomogram for NETest 1 demonstrating how the score is achieved and categorizing patients into different disease classes.

With reference to FIG. 8, the score percentages from TABLE 4 can be displayed within a nomogram representing "NETest 1." The NETest 1 nomogram demonstrates how the amended mathematically-derived score is achieved and how it categorizes patients into different classes of GEP-NEN (no disease, stable disease, or progressive disease).

Figure 9:
FIG. 9 is a graph of the utility of the nomogram of FIG. 8. The percentages of correctly predicted SD and PD NETs, including the level of disease activity, using the nomogram of FIG. 8 are shown.

With reference to FIG. 9, the utility of the NETest 1 nomogram was assessed. Values for the correct predictions of SD and PD using the NETest 1 nomogram of FIG. 8 are shown. Overall, the NETest 1 nomogram identified 80% of SD patients as exhibiting low or moderate disease activity and 84% of PD patients as exhibiting high disease activity.

Figure 10B:
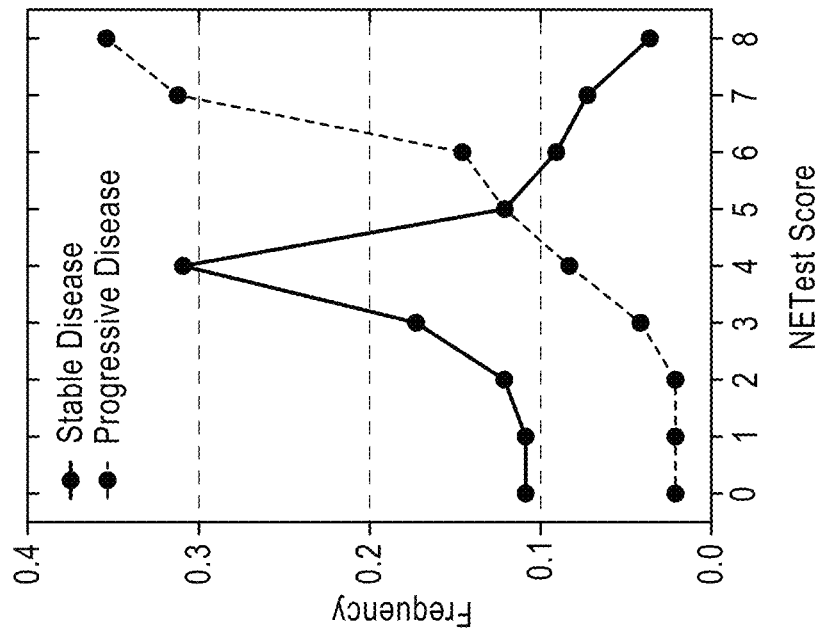
FIGS. 10A-10B are graphs each showing the frequency distribution for the 0-8 score in SD and PD NET tumors in (FIG. 10A) the test set and (FIG. 10B) the independent set.
Figure 10A:
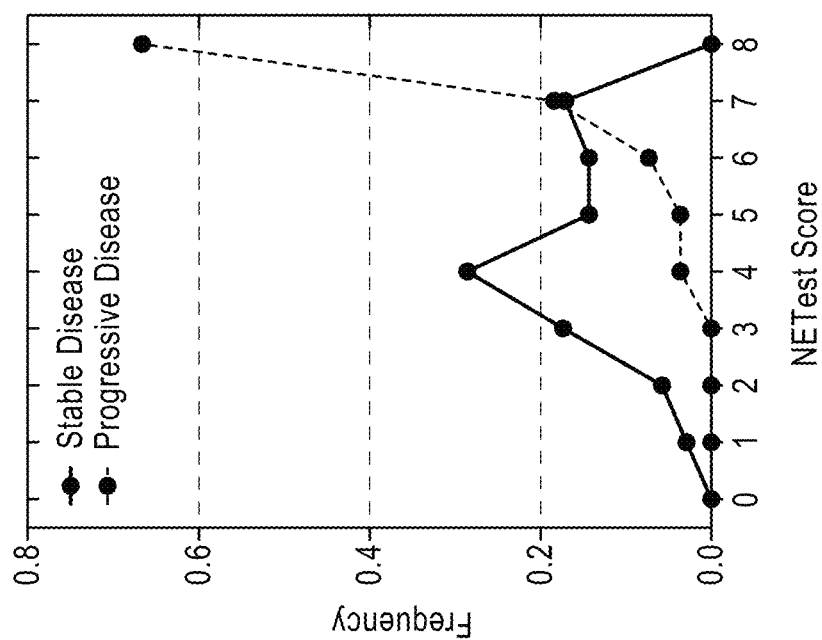

Application of Scoring System and Developing a Nomogram for "NETEST 2"-MAARC-NET-derivedNETest Scores (0-8) in patients clinically defined as either stable or progressive disease (best clinical judgment and/or imaging data) were examined. The frequency distribution of scores for each subtype in both the test set (FIG. 10A) or the independent set (FIG. 10B) demonstrate that SD patients have a median NETest value of 4 and PD patients range from 7-8. However, SD patients can exhibit MAARC-NET-derived scores >4 while PD can exhibit scores <7.

Figure 11B:
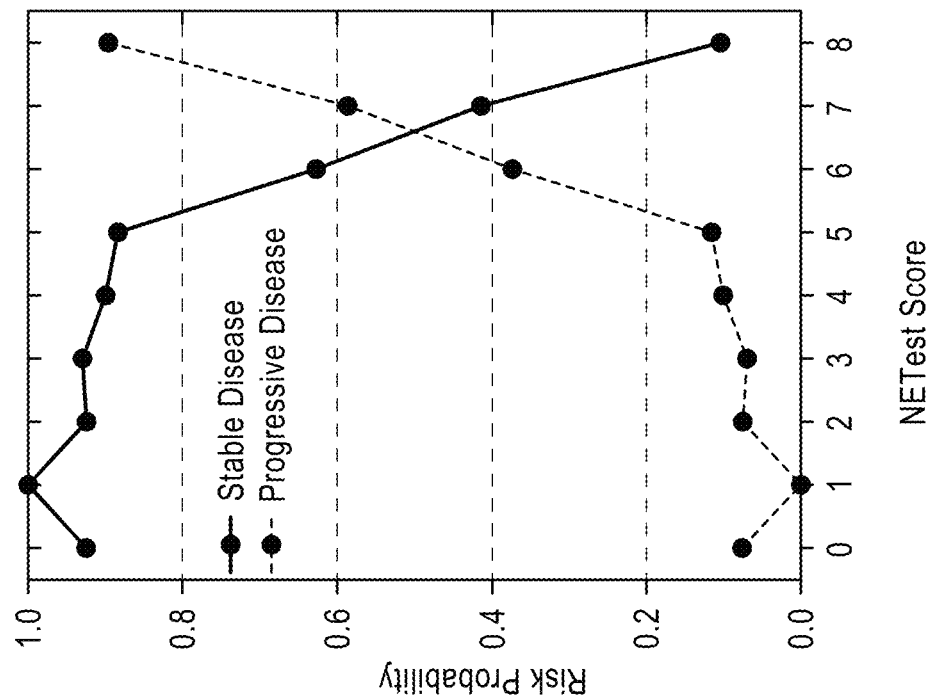
FIGS. 11A-11B are graphs of (FIG. 11A) the frequency distribution for the 0-8 score in SD and PD in the combined sets and (FIG. 11B) the risk probability for a score being either SD or PD vs. NETest Score.
Figure 11A:
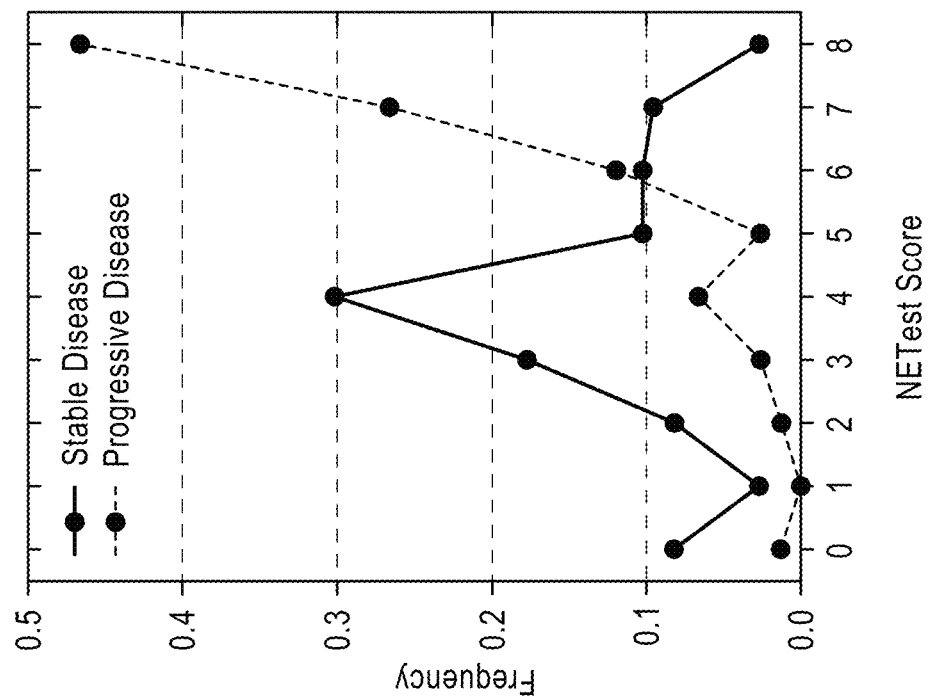

An assessment of the complete patient group (test set+ independent set) demonstrated that the highest frequency SD score was 4 (30%—FIG. 11A), while 46% of PD had a score of 8 (FIG. 11A). A risk probability assessment identified that NETest scores ranging between 0-5 were associated with SD with a ≥90% certainty (FIG. 11B). A score of 8 was most likely PD (>90%). However, scores of 6 and 7 could not accurately differentiate SD versus PD.

Based on these results from FIGS. 11A and 11B, the NETest 1 nomogram from FIG. 8 can be updated to include risk values. The NETest 2a nomogram of FIG. 12 includes the NETest with the inclusion of score and risk categorizations.

To upgrade the risk assessment NETest 2a nomogram, individual gene expression in SD and PD samples may be evaluated. The genes that were most differentially expressed in SD and PD samples were identified and used in decision trees to generate the rules for defining whether a NETest score was SD or PD. This approach provides the basis for NETest 2.

Figure 12:
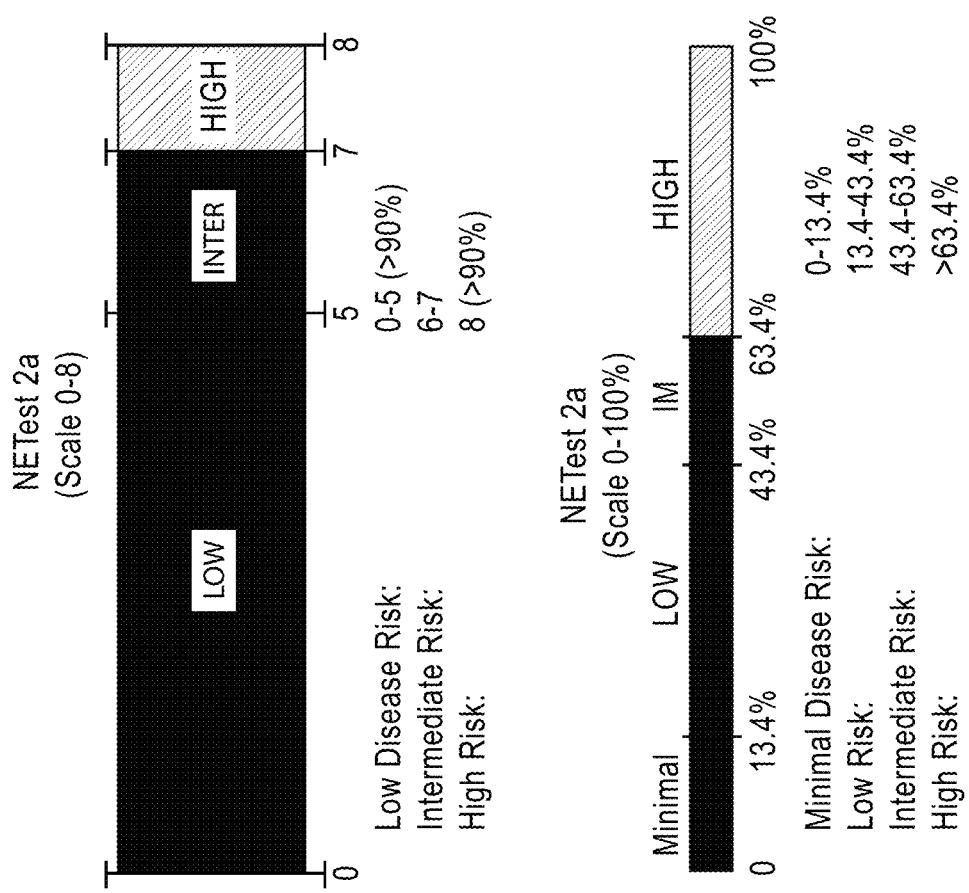
FIG. 12 is a nomogram of NETest 2a with the inclusion of score and risk categorizations. Top figure includes MAARC-NET as 0-8 scores; bottom figure is the 0-100% scaled version.

A NETest score of 5 has a >90% chance of identifying an SD sample (as shown in FIGS. 11A-11B and 12). Comparisons of the individual 51 gene expression profiles between patients scored as 5 (SD versus PD) identified expression of SMARCD3 and TPH1 as candidate differentiation markers. Using the rule: If SMARCD3<0.13 and TPH1<4 then call PD.

This allowed for 100% accuracy in defining progressive disease.

A NETest score of 6 has a ~50% chance of differentiating SD from PD samples. Gene expression profile analysis identified VMAT1 and PHF21A as candidates. A ROC analysis defined the AUCs for each to differentiate PD from SD to be:
VMAT1: ROC=0.835
PHF21A: ROC=0.733
Using the Rule:
If VMAT1≥0 and PHF21A<1.2 then SD
If VMAT1≥0 and PHF21A≥1.2 then PD This allowed for 100% accuracy in defining progressive disease and 90% accuracy in defining SD. The overall accuracy was 93%.

A NETest score of 7 has a ~50% chance of differentiating SD from PD samples. As for NETest scores of 6, gene expression profile analysis identified both VMAT1 and PHF21A as candidates. A ROC analysis defined the AUCs for each to differentiate PD from SD to be:
VMAT1: ROC=0.835
PHF21A: ROC=0.733
Using the Rule:
If VMAT1≥0 and PHF21A>1 then SD
If VMAT1≥0 and PHF21A≤then PD This allowed for a 100% accuracy for defining progressive disease and 95% accuracy for SD. The overall accuracy was 97.5%.

A NETest score of 8 has a ≥90% chance of identifying a sample as PD. Expression of ZZZ3 was identified as a candidate. A ROC analysis defined the AUC for this gene to be 1.0.
Using the Rule:
If ZZZ3≤14 then PD This allowed for a 100% accuracy for defining progressive disease and differentiating from SD.

Figure 13:
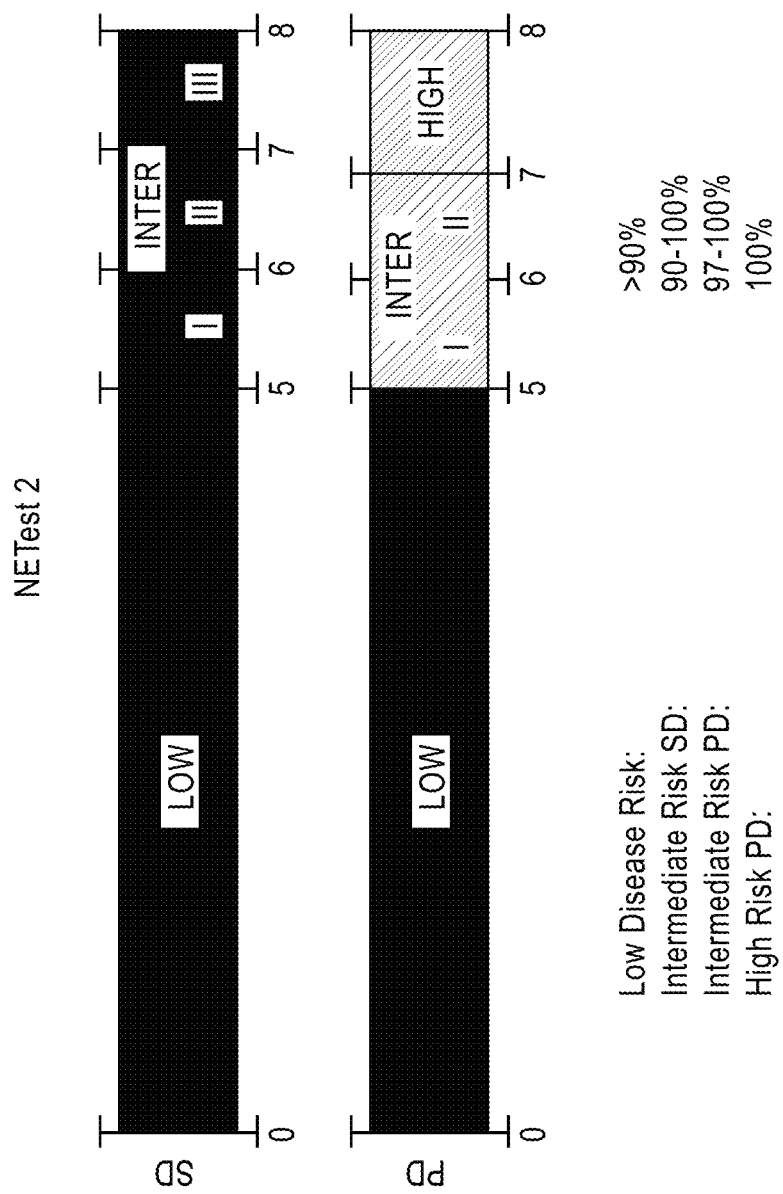
FIG. 13 is a nomogram of NETest 2 with the inclusion of risk category delineation.

With reference to FIG. 13, this individual gene expression information was used to finalize the "NETest 2" nomogram, which provides an accurate disease categorization profile for the patient. The combination of NETest scores and individual gene expression information used in the NETest 2 nomogram of FIG. 13 is further detailed in TABLE 5.

TABLE 5

| NETEST 2 Nomogram Information | | |
|---|---|---|
| | | Accuracy |
| Low risk stable disease | NETest score 0-5 | 90-100% |
| Intermediate risk stable disease (I) | NETest score 6 (low PHF21A) | 90-100% |
| Intermediate risk stable disease (II) | NETest score 7 (high PHF21A) | 95-100% |

TABLE 5-continued

NETEST 2 Nomogram Information

| | | Accuracy |
|---|---|---|
| Intermediate risk stable disease (III) | NETest score 8 (high ZZZ3) | 100% |
| Intermediate risk progressive disease (I) | NETest score 6 (high PHF21A) | 100% |
| Intermediate risk progressive disease (II) | NETest score 7 (low PHF21A) | 97.5-100% |
| High risk progressive disease | NETest score 8 (low ZZZ3) | 100% |

Defining Clinically Relevant Genes—To further refine the scoring system, gene cluster expression was examined and algorithms were developed to capture the information. Individual gene clusters incorporate biological information that may augment the mathematically-derived MAARC-NET scoring systems. One focus may be given to literature-curated gene clusters which are included in TABLE 6.

TABLE 6

Genes included in each Cluster

| Cluster Name | Genes |
|---|---|
| Proliferome | Ki67, NAP1L1, NOL3, TECPR2 |
| Growth Factor Signalome | ARAF1, BRAF, KRAS, RAF1 |
| Metabolome | ATP6V1H, OAZ2, PANK2, PLD3 |
| Secretome I (General) | PNMA2, VMAT2 |
| Secretome II (Progressive) | PQBP1, TPH1 |
| Epigenome | MORF4L2, NAP1L1, PQBP1, RNF41, RSF1, SMARCD3, ZFHX3 |
| Apoptome | BNIP3L, WDFY3 |
| Plurome | COMMD9 |
| SSTRome | SSTR1, SSTR3, SSTR4, SSTR5 |

Figures 14A, 14B:
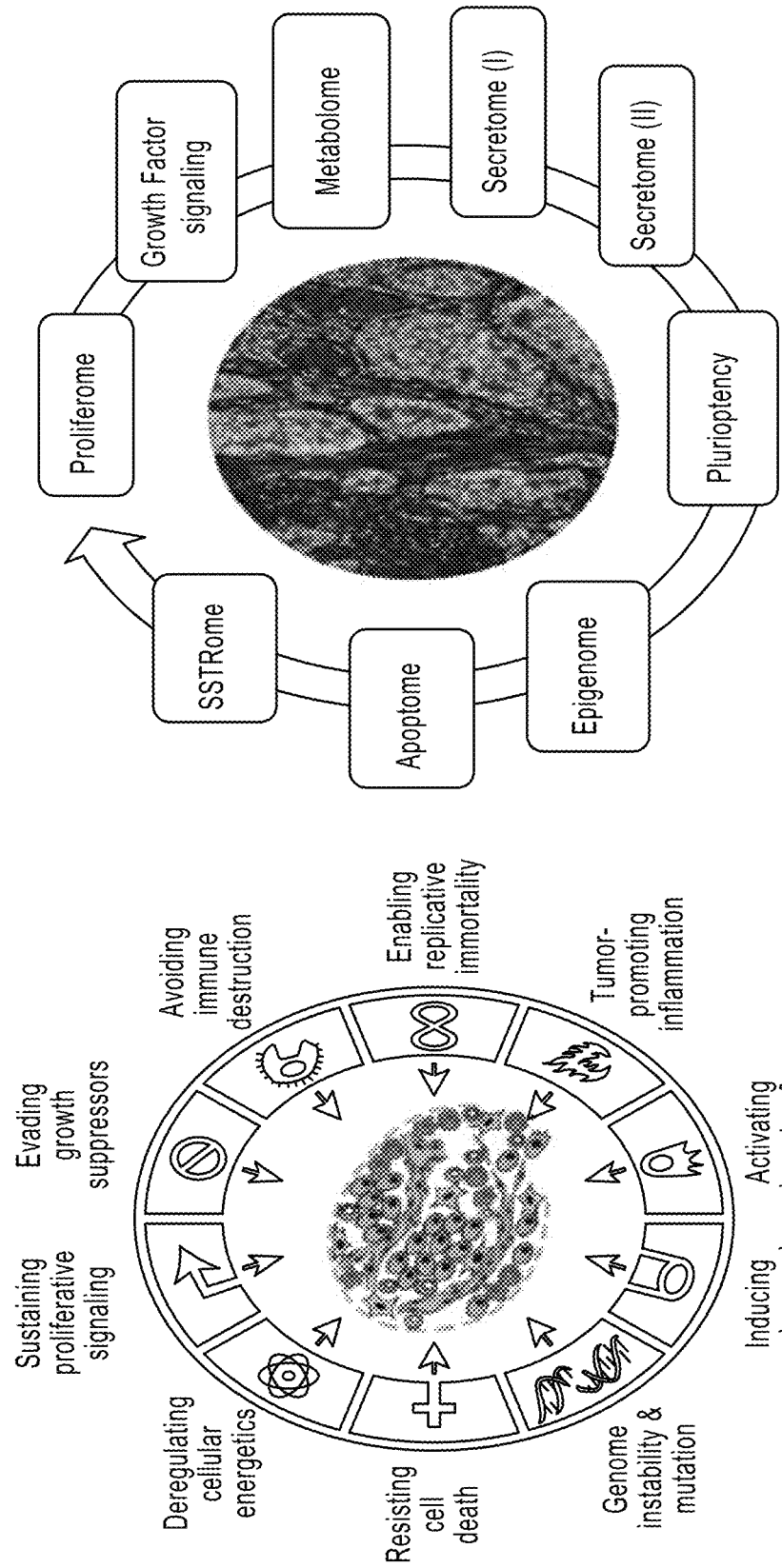
FIGS. 14A-14B are illustrations representing the Hallmarks of Neoplasia refocused on NETs.

With reference to FIG. 14A, the Hallmarks of Neoplasia are illustrated, including the delineation of tumor (adenocarcinoma)-derived hallmarks. With reference to FIG. 14B, the NET hallmarks based on the Hanahan and Weinberg classifications are illustrated.

Values for the nine clusters represented in FIGS. 14A-14B were derived from gene addition. In addition to the gene clusters, two algorithms were also assessed:

1) the "PDA" algorithm, which included a summation of the proliferome, signalome, secretome II, plurome and epigenome (the PDA algorithm is also referred to as Progressive Diagnostic I);

2) the "NDA" algorithm, which included expression of 15 genes associated with disease: these included ARAF1, BRAF, KRAS, RAF1, Ki67, NAP1L1, NOL3, GLT8D1, PLD3, PNMA2, VMAT2, TPH1, FZD7, MORF4L2 and ZFHX3 (the NDA algorithm is also referred to as Progressive Diagnostic II). Genes were summated and an averaged value was derived.

Figure 15B:
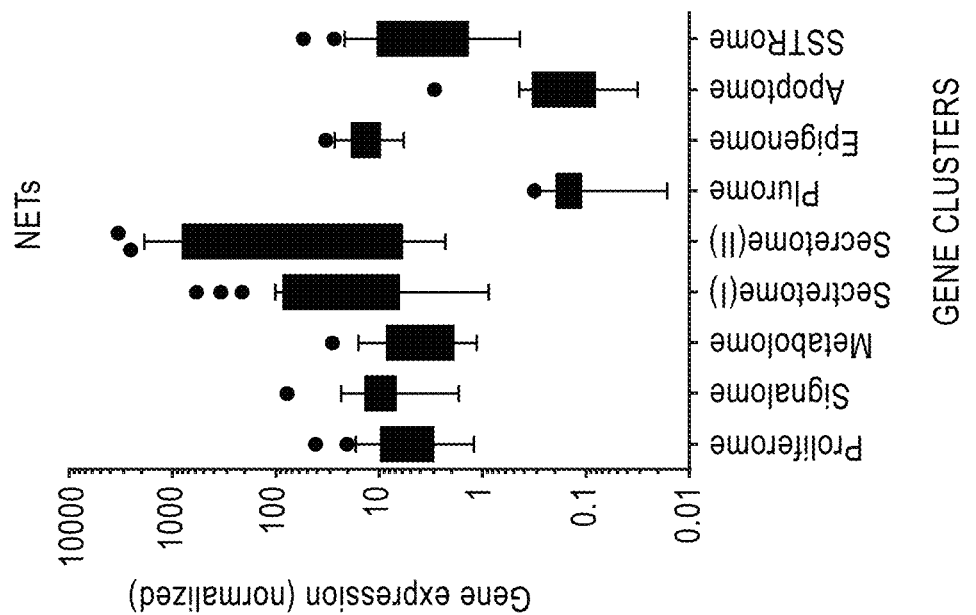
FIGS. 15A-15B are graphs showing normalized gene expression of gene clusters in (FIG. 15A) normal mucosa and (FIG. 15B) NETs.
Figure 15A:
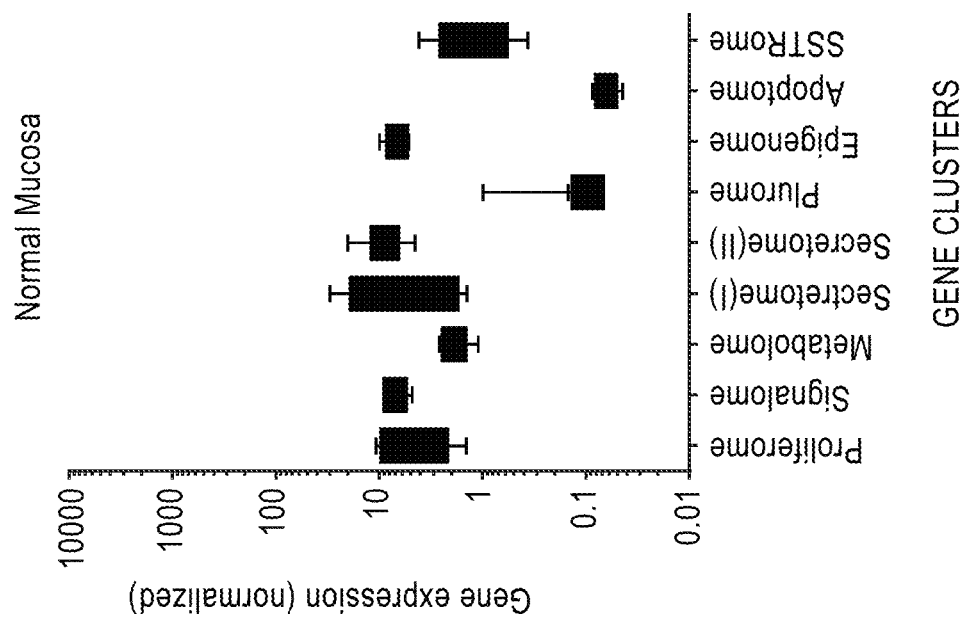
Figure 16:
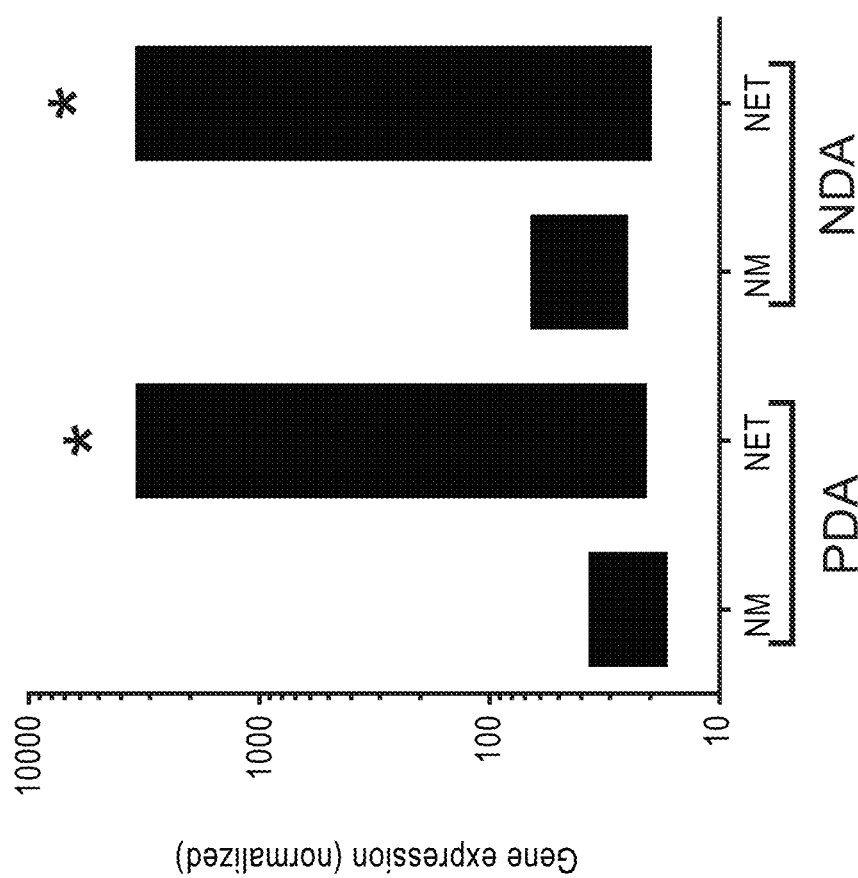
FIG. 16 is a graph of normalized gene expression as evaluated by the PDA and NDA algorithms in normal mucosa (NM) and NET.

Prior to assessing the value of the nine gene clusters and two algorithms in blood samples, their expression in NET tumor tissue was assessed to confirm that these were NET-relevant. With reference to FIGS. 15B and 15A, respectively, expression in 22 NETs may be compared to expression in normal mucosa (n=10). Assessment identified that seven of the nine clusters were specific to NETs (in comparison to normal mucosa). In particular, expression of the signalome, metabolome, secretome (I) and (II), epigenome, apoptome and SSTRome were elevated in NETs (p<0.05). Genes in the apoptome were decreased in NETs, while the proliferome was not different between NETs and normal mucosa. With respect to the algorithms, FIG. 16 shows that each of the PDA and NDA were significantly increased (p<0.05) in NET tumor tissue compared to normal mucosa.

Figures 17A, 17B, 17C:
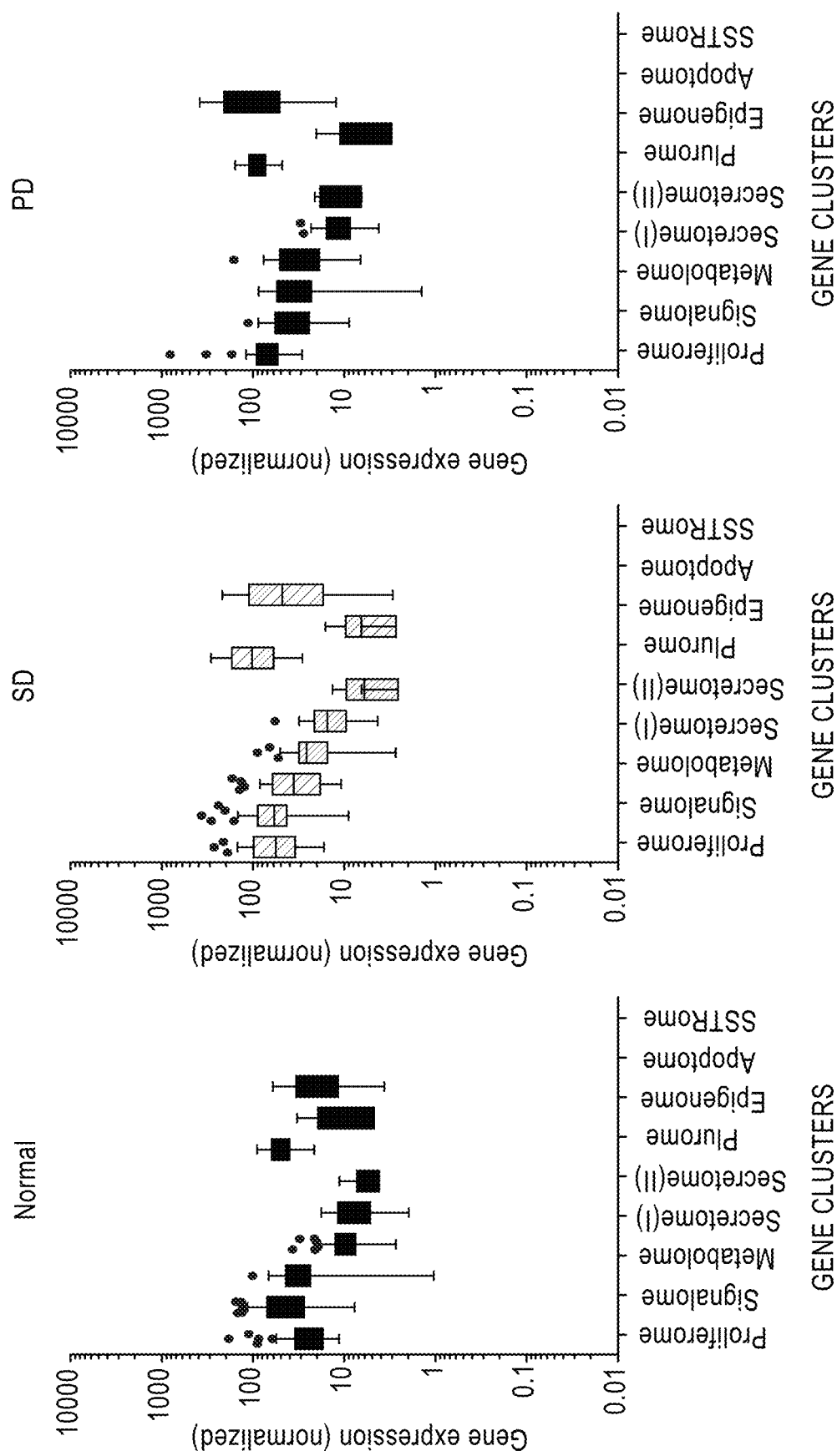
FIGS. 17A-17C are graphs of normalized gene expression in (FIG. 17A) normal mucosa, (FIG. 17B) a SD related gene cluster, and (FIG. 17C) a PD related gene cluster.

Thereafter, the expression of each of the clusters was assessed in blood samples. We examined the test (n=130) set and evaluated whether expression they were related to SD or PD. Significant differences were noted in gene expression between controls and SD/PD, as shown in FIGS. 17A-17C and TABLE 7.

TABLE 7

Gene Clusters and Clinical Outcome

| Cluster Name | Con vs SD | Con vs PD | SD vs PD |
|---|---|---|---|
| Proliferome | p < 0.05 | p < 0.05 | ns |
| Growth Factor Signalome | p < 0.05 | ns | p < 0.05 |
| Metabolome | ns | p < 0.05 | ns |
| Secretome I (General) | p < 0.05 | p < 0.05 | p < 0.05 |
| Secretome II (Progressive) | p < 0.05 | p < 0.05 | p < 0.05 |
| Epigenome | ns | p < 0.05 | p < 0.05 |
| Apoptome | p < 0.05 | p < 0.05 | ns |
| Plurome | p < 0.05 | p < 0.05 | ns |
| SSTRome | p < 0.05 | p < 0.05 | p < 0.05 | ns = not significant
Two-tailed Mann-Whitney U-test

These data demonstrate that gene clusters can be used to differentiate SD and PD from controls as well as identify differences between SD and PD.

Figure 18:
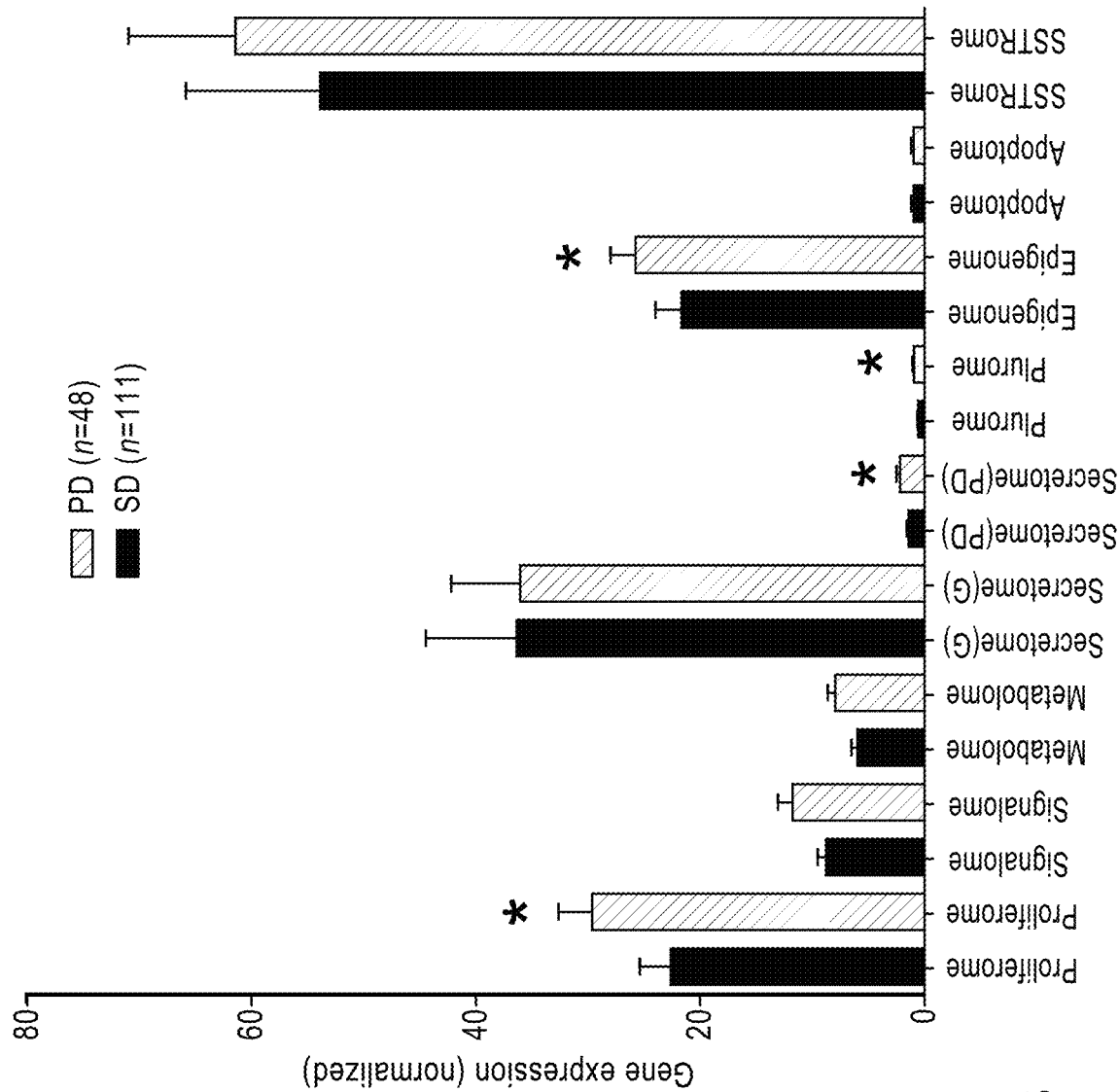
FIG. 18 is a graph of normalized gene expression in an independent test set, where the genes in PD and SD tumors were evaluated.

With reference to FIG. 18, gene cluster results were examined in the independent set (n=159), evaluating each of the clusters in SD vs PD. In the independent set, the proliferome, secretome (II), plurome and epigenome were significantly increased.

Figure 19B:
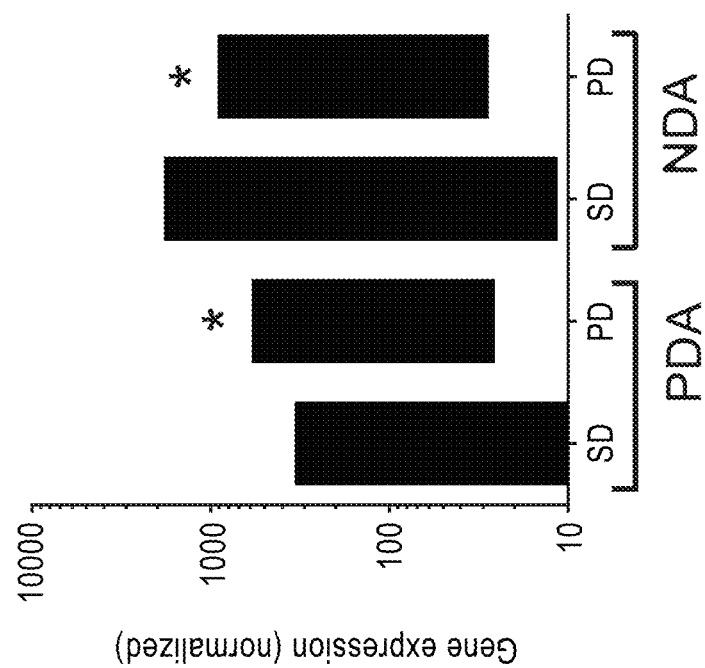
FIGS. 19A-19B are graphs showing normalized gene expression of PDA and NDA gene cluster algorithms in (FIG. 19A) the test set and (FIG. 19B) the independent set.
Figure 19A:
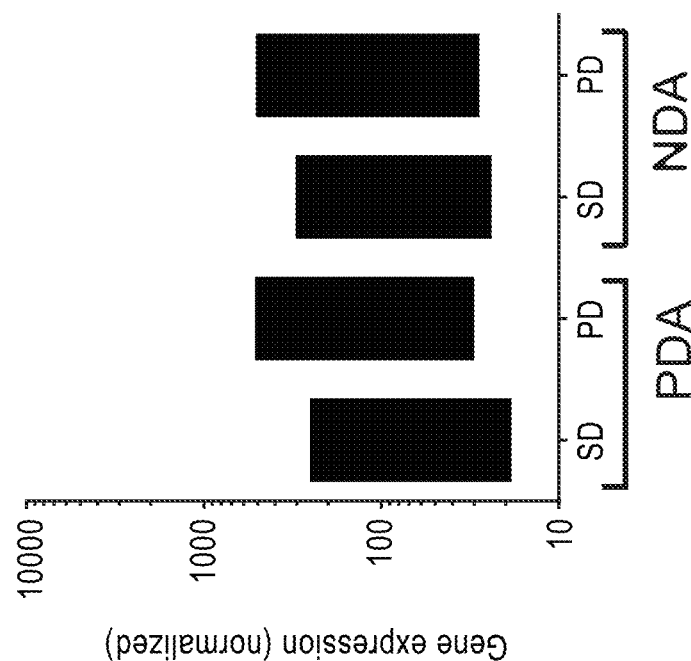

Next the PDA and NDA were evaluated in each of the two datasets (independent and test sets). With reference to FIG. 19A, no significant differences were identified between SD and PD for either of the two algorithms in the test set. With reference to FIG. 19B, each of the PDA and NDA were elevated in the independent set.

Next each of the algorithms were included in a combined set (test+independent: n=222) and their utility to predict SD versus PD was evaluated. With reference to FIG. 20A, both PDA and NDA were elevated in PD compared to SD in the combined sets. With reference to FIG. 20B, a ROC analysis identified the following parameters for PDA and NDA listed in TABLE 8.

TABLE 8

ROC Analysis Parameters, PDA and NDA in Combined Set

| | PDA | NDA |
|---|---|---|
| AUC | 0.72 ± 0.034 | 0.6 ± 0.038 |
| 95% CI | 0.652-0.785 | 0.525-0.675 |
| p-value | <0.0001 | 0.014 |
| ROC cut-off | 58 | 74 |

Two additional algorithms based on gene cluster expression differences in the test (TDA) and independent (IDA) set were evaluated. TDA included a summation of gene clusters significantly different between SD and PD in the test set.

These included TDA: Secretome (I), Plurome and SSTRome (the TDA algorithm is also referred to as Progressive Diagnostic III); and IDA: Proliferome, secretome (II), plurome and epigenome (the IDA algorithm is also referred to as Progressive Diagnostic IV).

Figure 21A:
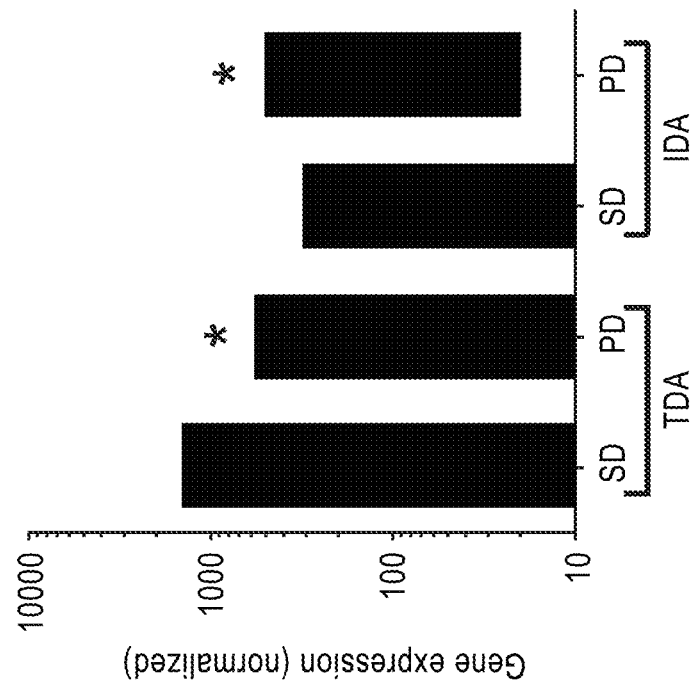
FIGS. 21A-21B are graphs showing normalized gene expression as evaluated by TDA and IDA gene cluster algorithms in (FIG. 21A) the test set, and (FIG. 21B) the independent set.
Figure 21B:
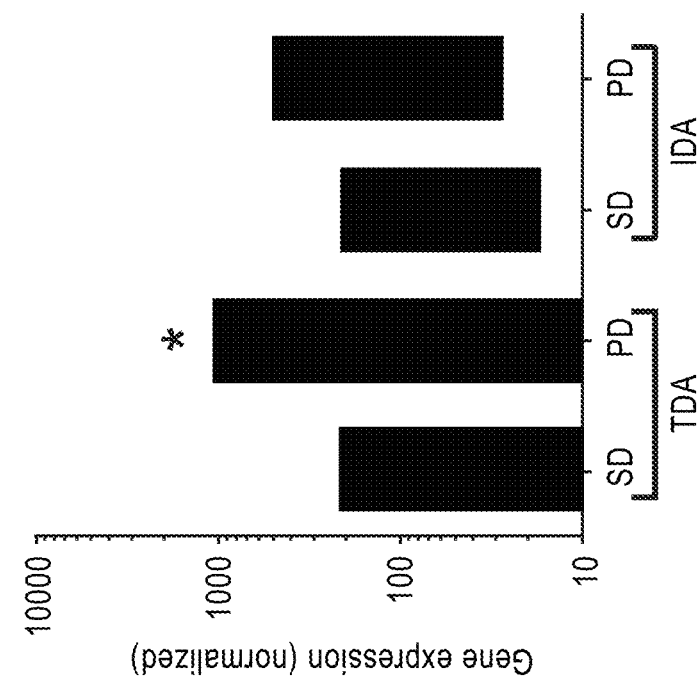

Each of the algorithms in the test set and independent set were evaluated. With reference to FIG. 21A, TDA was significantly elevated in PD compared to SD in the test set. With reference to FIG. 21B, both TDA and IDA algorithms were significantly elevated in the independent set.

Next, a ROC analyses with both algorithms in the combined dataset was performed. The ROC analysis identified the following parameters for TDA and IDA listed in TABLE 9.

TABLE 9

ROC Analysis Parameters, TDA and IDA in Combined Set

|  | TDA | IDA |
|---|---|---|
| AUC | 0.62 ± 0.04 | 0.70 ± 0.034 |
| 95% CI | 0.542-0.698 | 0.637-0.770 |
| p-value | 0.003 | <0.001 |
| ROC-cut-off | >43 | >46 |

Figure 22A:
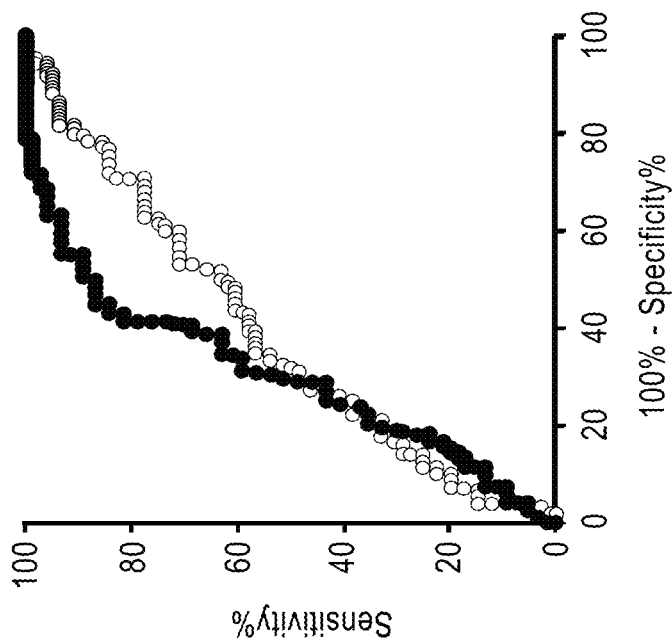
FIGS. 22A-22B are graphs showing a ROC analysis of (FIG. 22A) TDA and IDA for differentiating SD from PD, and (FIG. 22B) for each of the individual gene clusters.
Figure 22B:
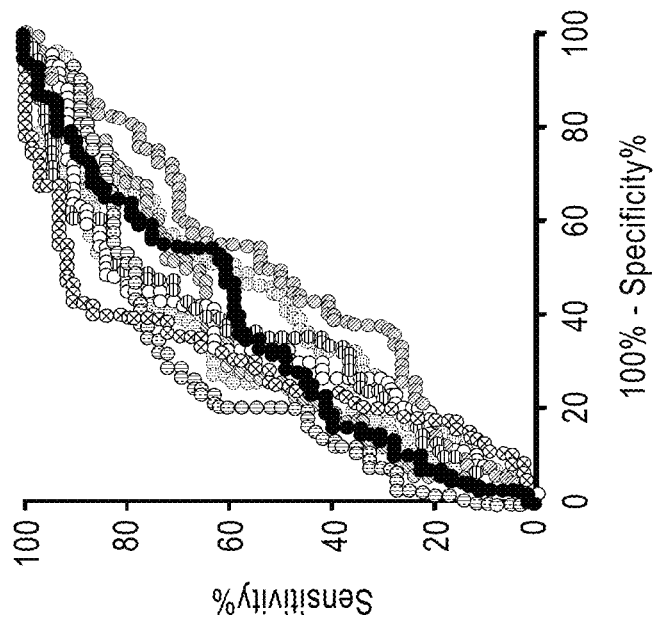

Algorithm-generated ROC curves of TDA and IDA for differentiating between SD and PD are shown in FIG. 22A. Algorithm-generated ROC curves for each of the clusters for differentiating between SD and PD are shown in FIG. 22B. The ROC curves in FIGS. 22A and 22B demonstrate that AUCs range from 0.51 (GF signalome) to 0.72 (plurome) for the differentiation of SD and PD.

Accordingly, individual gene cluster expression and algorithms that capture this information contain biologically relevant information that correlates with clinical observations. These provide the basis for defining clinically relevant MAARC-NET scoring systems.

Demonstration of Clinical Utility of NETEST Genes—The clinical utility of NETest scores, as well as the scores from pertinent gene clusters and algorithms, will now be defined. An examination of how surgical removal of a NET altered the circulating gene signature was performed to demonstrate how the test will have utility as a measure of the completeness of surgical therapy.

Figure 23B:
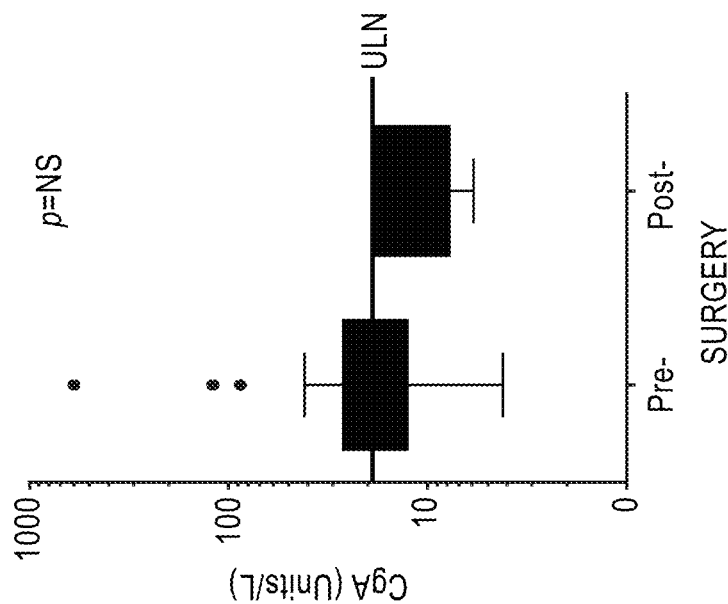
FIGS. 23A-23B are graphs showing the alternation in (FIG. 23A) NETest Score in Pre- and Post-Surgery conditions and (FIG. 23B) circulating Chromogranin A (CgA) levels in Pre- and Post-Surgery conditions.
Figure 23A:
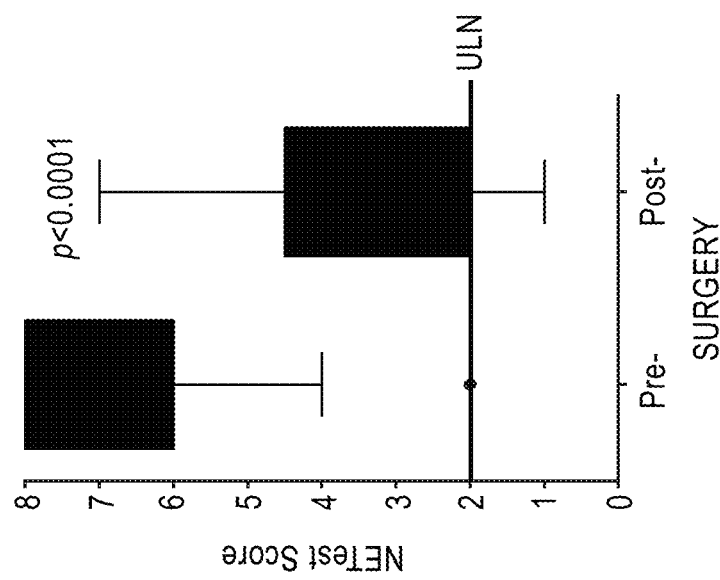

Parameters in 29 surgically treated patients prior to surgery and >1 month post-surgery was examined. As a group, MAARC-NET scores were significantly decreased (p<0.0001) from a mean of 6.58±1.48 to 3.65±1.6, as shown in in FIG. 23A. Chromogranin A (CgA), a gene used in a prior known single biomarker assay for NETs, was not significantly decreased (58.5±137.9 ng/ml vs. 55.25±154.8), as shown in FIG. 23B.

An examination of how NETest 1 performed, i.e. changes in NETest score pre- and post-surgical therapy, is included in FIGS. 24A-24B. Prior to surgery, 62% of patients were included in the high disease category; after surgery this was 0% ($\chi^2=24$, $p=5 \times 10^{-8}$).

Figures 25A, 25B:
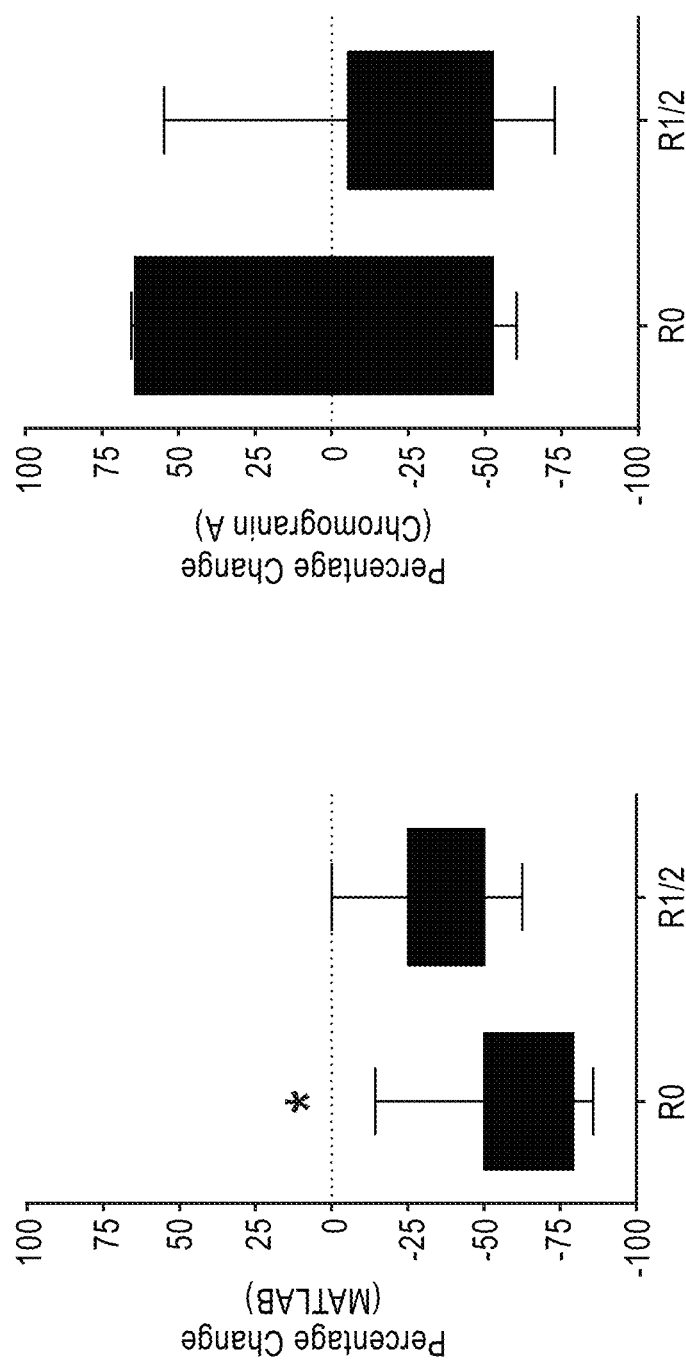
FIGS. 25A-25B are graphs showing the percentage change in (FIG. 25A) mathematically-derived score and (FIG. 25B) Chromogranin A in both R0 (complete resections) and R½ (incomplete sections) conditions.

An alternative assessment of how surgery affected disease status is provided by the percentage changes in surgical approaches—no evidence of residual disease (R0) versus evidence of residual disease including metastases. With reference to FIG. 25A, levels for the MAARC-NET score were significantly decreased (p<0.003) in the R0 group (complete resection) compared to the R1/R2 group (incomplete resection).

Figure 26B:
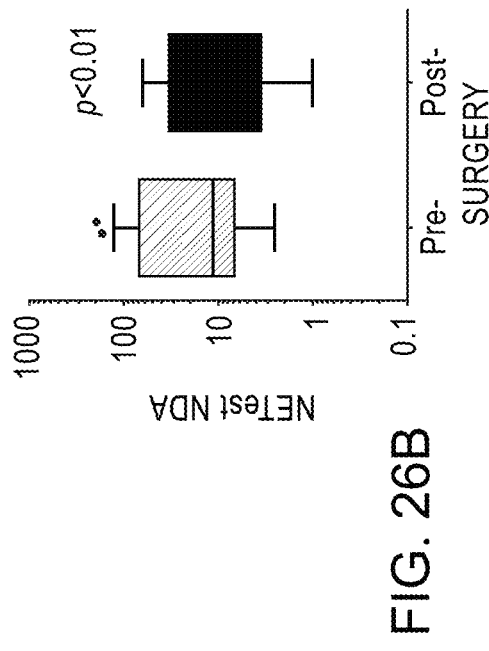
FIGS. 26A-26D are graphs showing the difference in NETest score for gene-derived algorithms, (FIG. 26A) PDA, (FIG. 26B) NDA, (FIG. 26C) TDA, and (FIG. 26D) IDA, in pre- and post-surgery conditions.
Figure 26D:
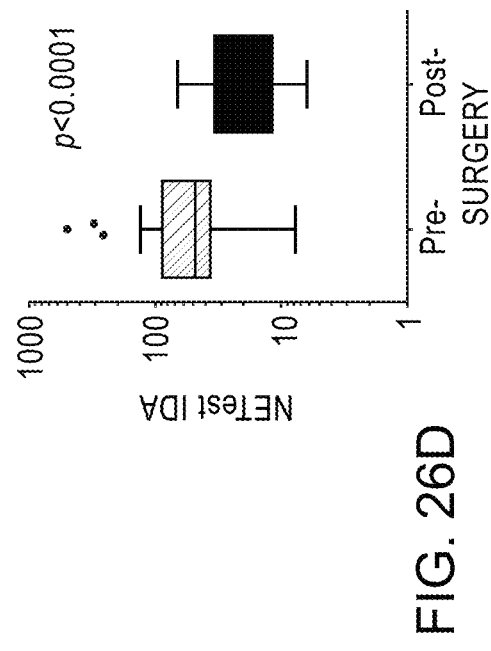
Figure 26A:
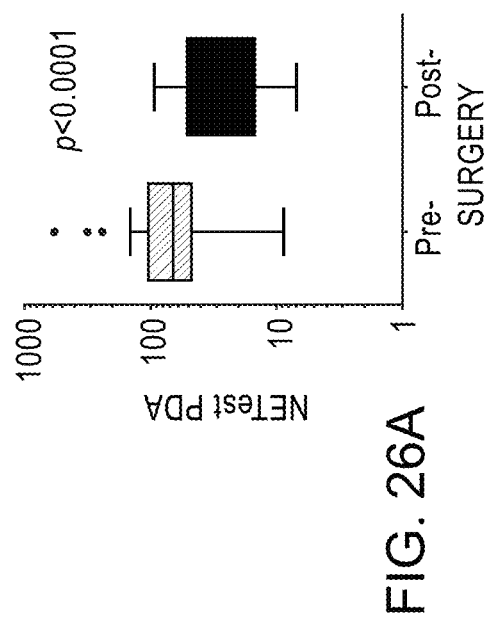
Figure 26C:
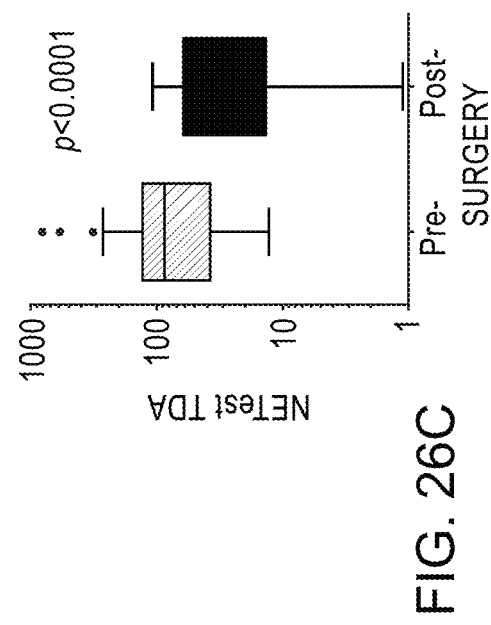

To better define the role of surgery each of the four algorithms were examined. Significant decreases were identified (post-surgery) in PDA (99.3±21 vs. 41.1±7.5, p<0.0001; FIG. 26A), NDA (45.8±10.3 vs. 29.6±7.8, p<0.01; FIG. 26B), TDA (133.3±32.3 vs. 43.8±9.3, p<0.0001; FIG. 26C) and IDA (86.1±19.3 vs. 34.1±7.2, p<0.0001; FIG. 26D).

With reference to FIGS. 27A-27I, an examination of individual clusters identified significant decreases in the SSTRome, proliferome, GF signalome, metabolome, secretome I/II and the epigenome pre- and post-surgery.

With reference to TABLE 10, surgical removal of the tumor tissue was associated with decreases in circulating gene expression to levels not different to or below ROC cut-off values for SD for each of the four algorithms and for 6 of the 9 gene clusters.

TABLE 10

Relationship Between Surgical Excision, Gene Clusters and Each of the Algorithms

| Algorithm/ Cluster | p-value | Change | Pre-surgery | Post-surgery | ROC for SD |
|---|---|---|---|---|---|
| NDA | 0.009 | ↓ | 45 | 30 | <74 |
| PDA | <0.0001 | ↓ | 99 | 41 | <58 |
| TDA | <0.0001 | ↓ | 133 | 44 | <74 |
| IDA | <0.0001 | ↓ | 86 | 34 | <46 |
| SSTRome | <0.0001 | ↓ | 93 | 23 | <25.5 |
| Proliferome | <0.0001 | ↓ | 34 | 15 | <20 |
| GF Signalome | 0.009 | ↓ | 14.8 | 8 | <9 |
| Metabolome | 0.004 | ↓ | 8.2 | 6.8 | <6.5 |
| Secretome (I) | 0.004 | ↓ | 39.2 | 19.5 | <11 |
| Secretome (II) | 0.04 | ↓ | 2.4 | 0.85 | <1.6 |
| Plurome | NS | ↔ | 0.8 | 0.8 | <0.9 |
| Epigenome | 0.005 | ↓ | 48.7 | 17.7 | <2.3 |
| Apoptome | NS | ↔ | 0.72 | 0.84 | >0.5 |

All patients who had surgery can be considered as exhibiting progressive/active disease. Following surgery, the scores or algorithms were indicative of progressive disease in 3-7 of the twenty-nine patients (10-24%) depending on the algorithm used.

Surgery significantly reduced the circulating tumor signature and can provide evidence for the degree both of tumor removal as well as for evidence of residual active disease.

The clinical utility of the test therefore is defined by the examination of scores, algorithms and clusters and evaluation in comparison to pre-surgical bloods. Evidence of elevated expression of e.g., PDA or proliferome in post-surgical samples is indicative of residual progressive (highly active disease).

Figure 28:
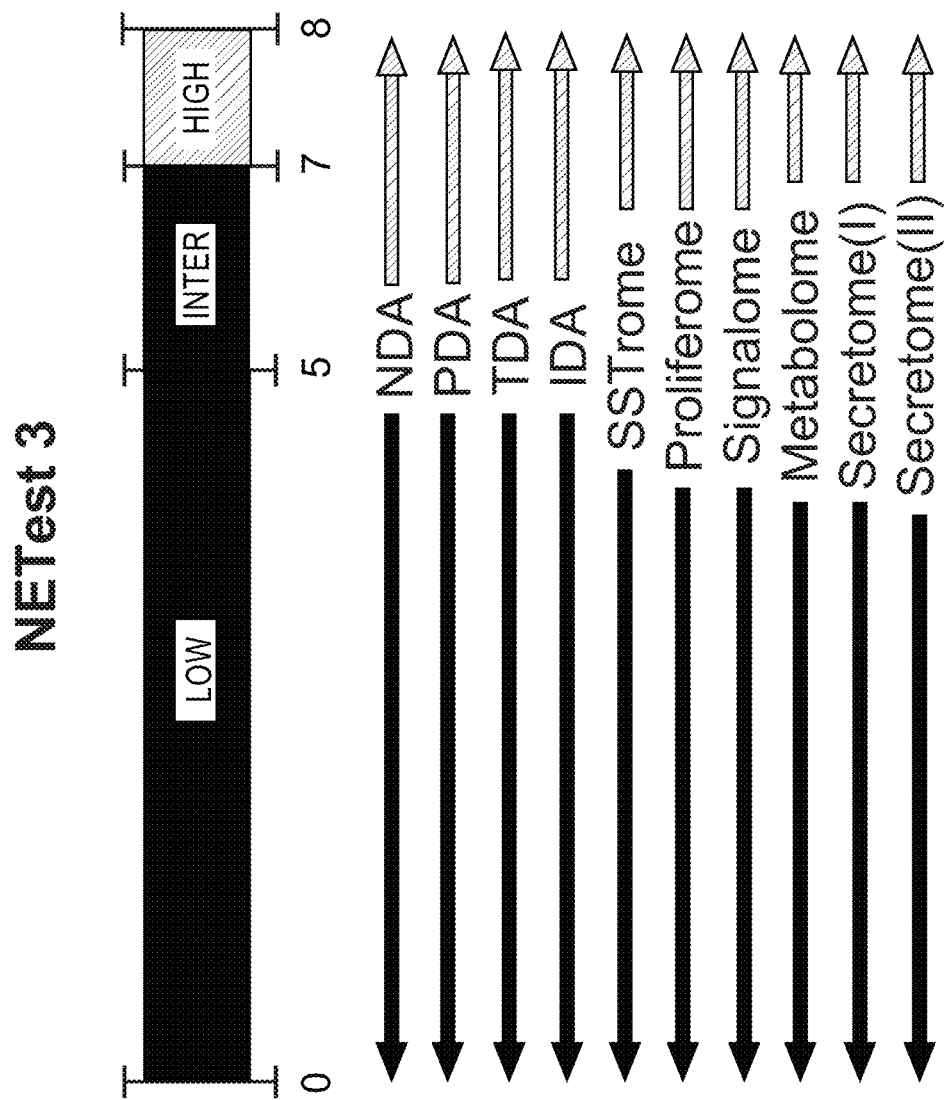
FIG. 28 is a nomogram of NETest 3 with the inclusion of surgically-relevant algorithms and gene clusters.

With reference to FIG. 28, a NETest 3 nomogram is illustrated with the inclusion of surgically-relevant algorithms and gene clusters. A combination score, as well as alterations in gene clusters e.g., a significant increase in the proliferome, will be indicative of disease regrowth following surgery. Of note, is that while post-operative imaging identified disease in n=1 (10%) of the R0 patients, elevated gene scores were evident in 6 (60%) at 1 month. Subsequently, two R0 individuals developed positive imaging at 6 months.

Effect of Standard Drug Therapies on Circulating NET Signature—The efficacy of a standard pharmacological therapy for NETs, somatostatin (used to treat >80% of patients), was evaluated on the circulating NET signature. Signatures were evaluated in patients treated with a somatostatin analog who were considered as either SD (n=63) or PD (n=26) by imaging and best clinical judgment. Those patients who were SD on somatostatin analogs were considered to be stable-treated patients, while those patients who were PD on somatostatin analogs were considered to be failing therapy.

Figure 29B:
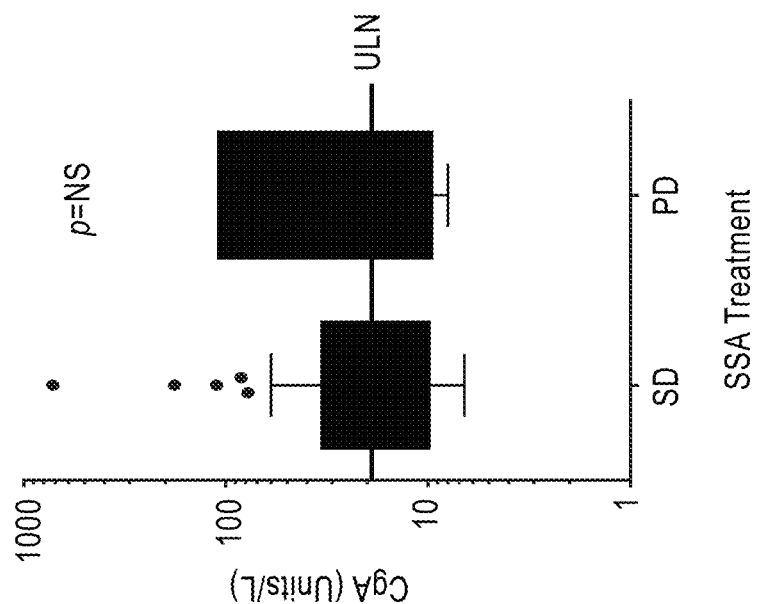
FIGS. 29A-29B are graphs showing the differences in (FIG. 29A) NETest score and (FIG. 29B) circulating CgA levels, each in in stable disease (SD) conditions and somatostatin analog (SSA) treatment failure (equivalent of PD conditions).
Figure 29A:
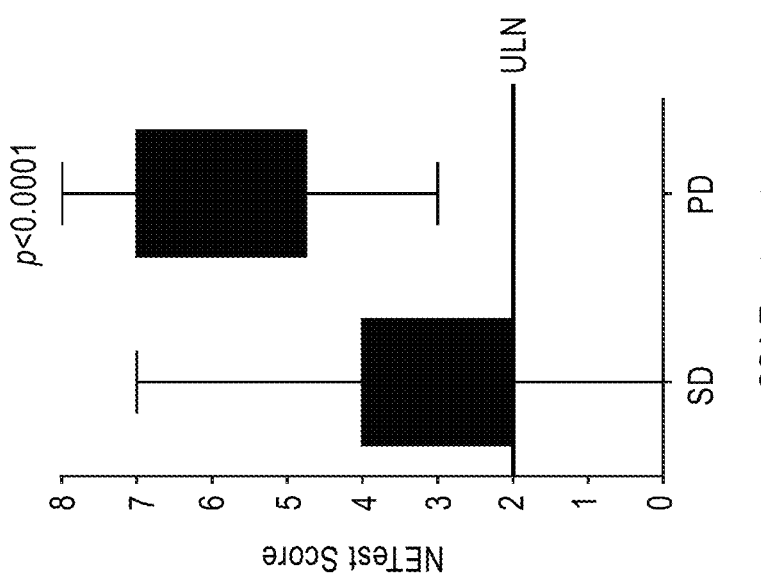

With reference to FIG. 29A, MAARC-NET scores were significantly lower in the SD group than those failing therapy: 3.33±0.21 vs 5.77±0.3 (p<0.001). With reference to FIG. 29B, Chromogranin A was not significantly different in the two groups (44.7±17.2 ng/ml vs. 102.4±58.7).

Figure 30A:
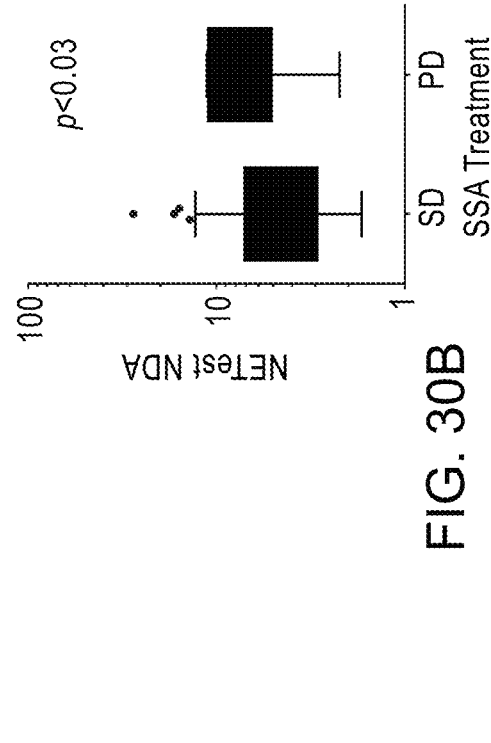
FIGS. 30A-30D are graphs showing the differences in gene-derived algorithms, (FIG. 30A) PDA, (FIG. 30B) NDA, (FIG. 30C) TDA, and (FIG. 30D) IDA, in stably treated patients (SD) and treatment failure (PD).
Figure 30B:
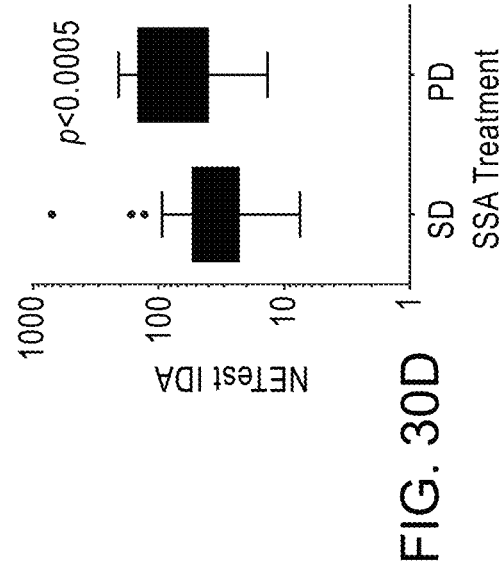
Figure 30C:
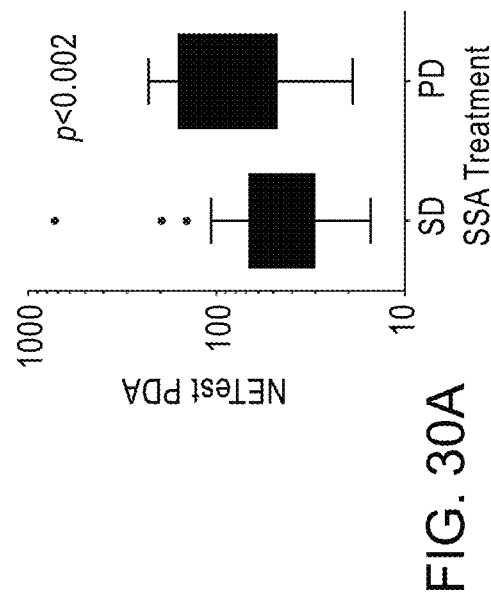
Figure 30D:
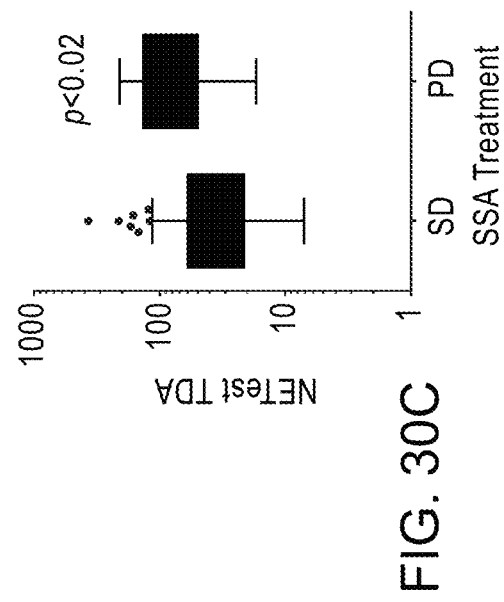

An assessment of the algorithms demonstrated significant differences in each of them in SD compared to PD. Specifically, PDA (62.8±11.4 vs. 153.9±36.2, p<0.002; FIG. 30A), NDA (6±0.6 vs. 13.5±3, p<0.03; FIG. 30B), TDA (56.8±7.4 vs. 154±37.2, p<0.02; FIG. 30C) and IDA (51.7±11.1 vs. 140.5±36, p<0.0005; FIG. 30D).

With reference to FIGS. 31A-31I examination of individual clusters identified that the SSTRome, proliferome, secretome II, plurome and the epigenome were significantly lower in the SD group relative to the PD group.

These data demonstrate that patients who exhibit progressive disease despite somatostatin analog (SSA) therapy exhibit increases in the MAARC-NET score, as well as each of the four algorithms and specific gene clusters including an increase in proliferation, as well as the epigenome. One mechanism to evaluate whether the SSA treatment is effective therefore is to evaluate whether scores for these parameters alter. However, given the overlap in each of these parameters between the SD and PD groups, it would be helpful to better define the PD group. To do this, the expression may be compared of the circulating signature in those failing therapy to that in controls. The hypothesis behind this approach was that an effective therapy (i.e. SD) would normalize the signatures. The corollary is that PD will be significantly different to normal. To establish this, ROC analyses were used to examine normal circulating transcripts and compared to PD. All four algorithms were examined as well as the gene clusters.

Figures 32A, 32B:
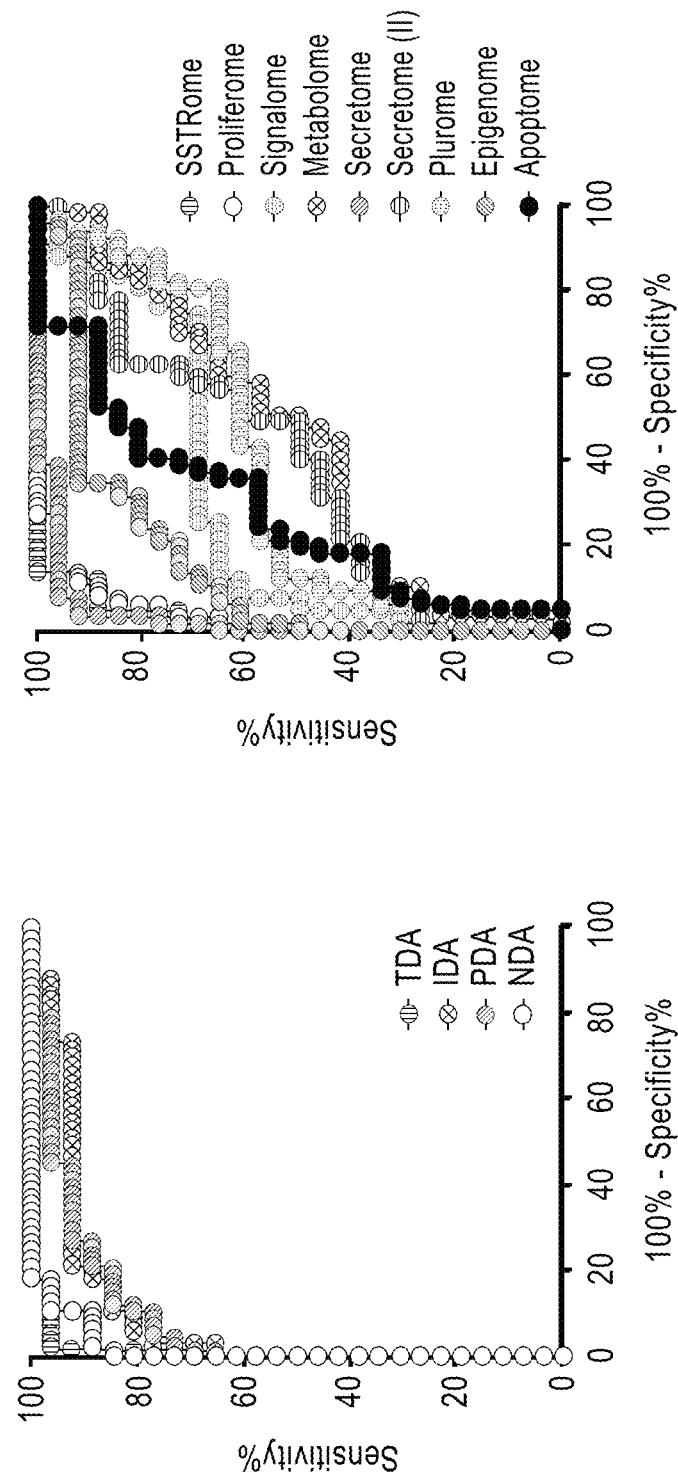
FIGS. 32A-32B are graphs showing a ROC analysis according to (FIG. 32A) gene-derived cluster algorithms and (FIG. 32B) gene clusters for differentiating treatment failure (equivalent of PD conditions) from controls.

With reference to FIGS. 32A-32B, analysis of the data identified that algorithms (FIG. 32A) and selected clusters (FIG. 32B) differentiated controls from PD treated with SSAs. Data for the individual clusters are included in TABLE 11.

TABLE 11

Relationship between Gene Clusters and each of the Algorithms for those Failing SSA Therapy and Controls

| Algorithm/Cluster | AUC | 95% CI | p-value | ROC for PD |
|---|---|---|---|---|
| NDA | 0.98 ± 0.01 | 0.965-1.00 | <0.0001 | >3 |
| PDA | 0.92 ± 0.04 | 0.851-0.994 | <0.0001 | >40 |
| TDA | 0.99 ± 0.01 | 0.975-1.01 | <0.0001 | >29 |
| IDA | 0.91 ± 0.04 | 0.828-0.998 | <0.0001 | >31 |
| SSTRome | 0.98 ± 0.01 | 0.95-1 | <0.0001 | >22 |
| Proliferome | 0.97 ± 0.02 | 0.94-1 | <0.0001 | >14 |
| GF Signalome | 0.71 ± 0.07 | 0.564-0.855 | <0.002 | >5 |
| Metabolome | 0.56 ± 0.07 | 0.41-0.7 | NS | <8 |
| Secretome (I) | 0.98 ± 0.02 | 0.944-1 | <0.0001 | >4 |
| Secretome (II) | 0.62 ± 0.07 | 0.486-0.759 | NS | >1.6 |
| Plurome | 0.61 ± 0.08 | 0.454-0.763 | NS | <0.7 |
| Epigenome | 0.86 ± 0.05 | 0.756-0.962 | <0.0001 | >16 |
| Apoptome | 0.73 ± 0.06 | 0.618-0.834 | <0.001 | <0.95 |

Based on the data in TABLE 11, NDA and TDA were examined as well as the SSTRome, Proliferome, and Secretome (I) in the SD cases to evaluate whether these parameters correlated with clinical assessments of therapeutic efficacy.

Figure 33B:
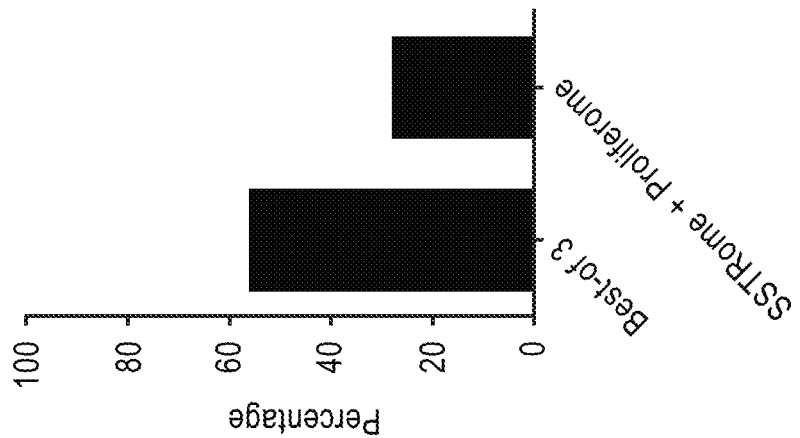
FIGS. 33A-33B are graphs showing the percentage of correct calls for each of (FIG. 33A) the gene-derived cluster algorithms and clusters for defining treatment failure in patients categorized as SD and (FIG. 33B) a Best-of-3 outperformed by a combination of SSTRome and Proliferome.
Figure 33A:
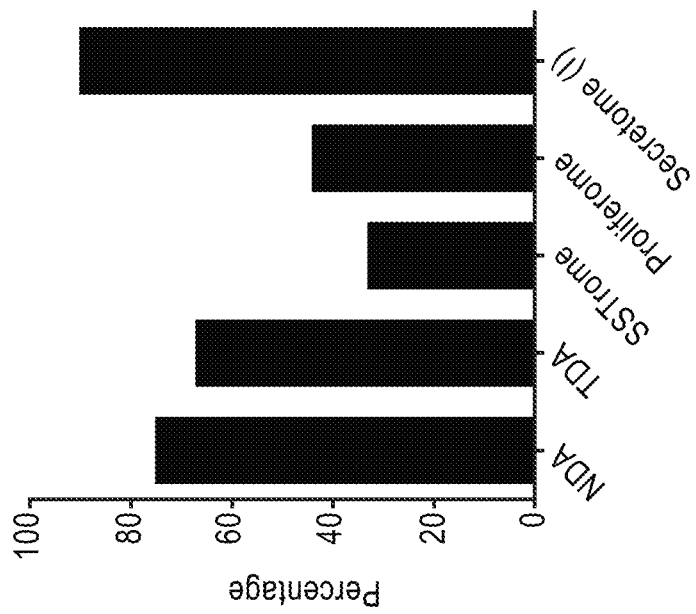
Figure 34:
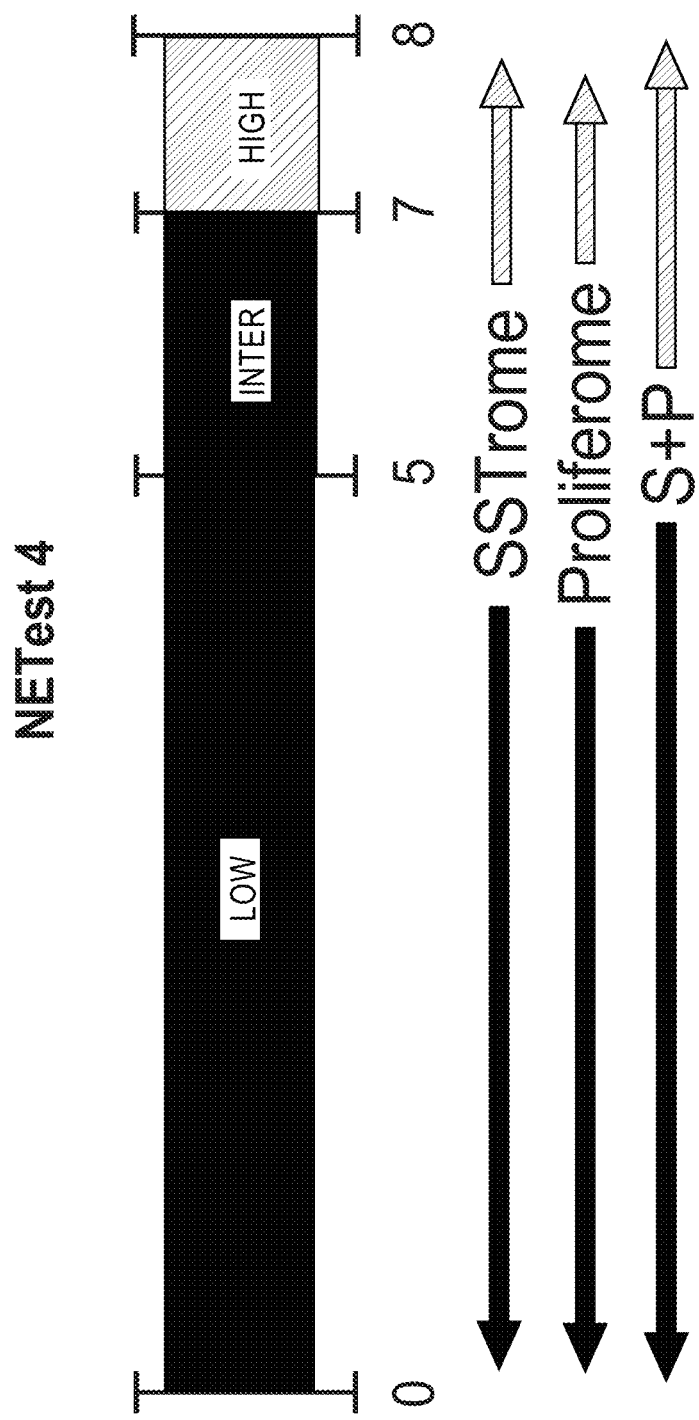
FIG. 34 is a nomogram for somatostatin analog treated patients including the mathematically-derived score as well as the SSTRome, Proliferome, and their combination.

An assessment of individual algorithms or gene clusters identified that samples would be categorized as exhibiting disease in 33-75% of cases (FIG. 33A). In comparison to a best of 3 score (56%) a combination of elevations in the SSTRome and Proliferome resulted in the lowest number of cases (28%) predicted as exhibiting progressive disease (FIG. 33B). With reference to FIG. 34, the nomogram for somatostatin analog treated patients, named "NETest 4," therefore includes the MAARC-NET score as well as the SSTRome, proliferome and their combination.

Utility of NETEST and Gene Expression for the Prediction of Somatostatin Analog Efficacy—To evaluate the utility of the NETest in therapy, the relationship between SSAs and clinically defined outcomes (per RECIST criteria) were evaluated. Samples were collected both pre-therapy as well as monthly in twenty-eight patients. Imaging was available to stage and categorize disease patterns pre- and during therapy (up to 12 months follow-up). In this prospective sample set, SSA resulted in a significant reduction in the number of patients with progressive disease (FIG. 35A).

Scores were also determined in blood samples collected prior to as well as monthly during SSA treatment to evaluate whether early alterations were predictive of outcome, i.e., response to therapy.

Figure 35B:
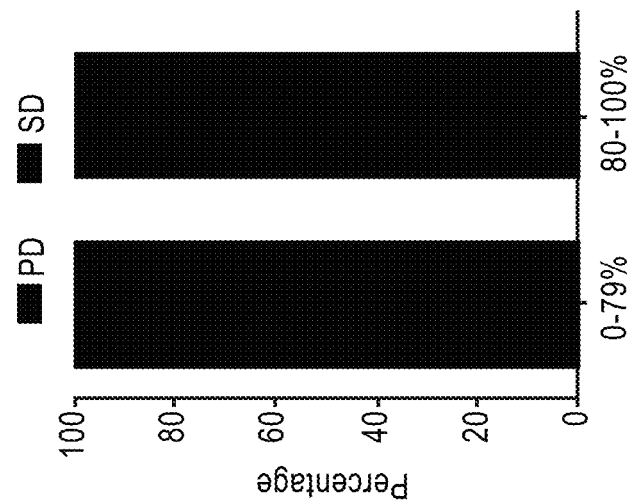
FIGS. 35A-35B are graphs that demonstrate therapeutic efficacy of SSAs and the proportion of patients with low/high NETest scores that developed disease recurrence.
Figure 35A:
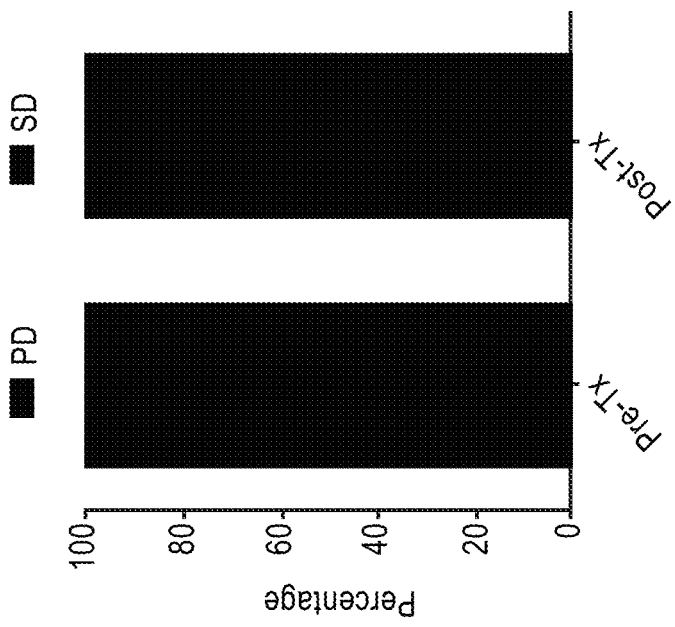

With reference to FIG. 35B, the results identify that elevated NETest scores (80-100% activity) measured at any time point during therapy were predictive of therapeutic responsiveness. With reference to FIG. 36A, a significant rise in the NETest (80-100%) occurred from 48-252 days (mean=105 days) prior to the detection of clinically significant disease (PD). The mean time for CgA was 70 days (range: 0-196 days). The NETest was more informative, occurring at an earlier time ($p=0.0^4$), and in more patients (high activity was noted in 100%) than CgA (57% exhibited >25% elevation, p=0.016).

Figure 36B:
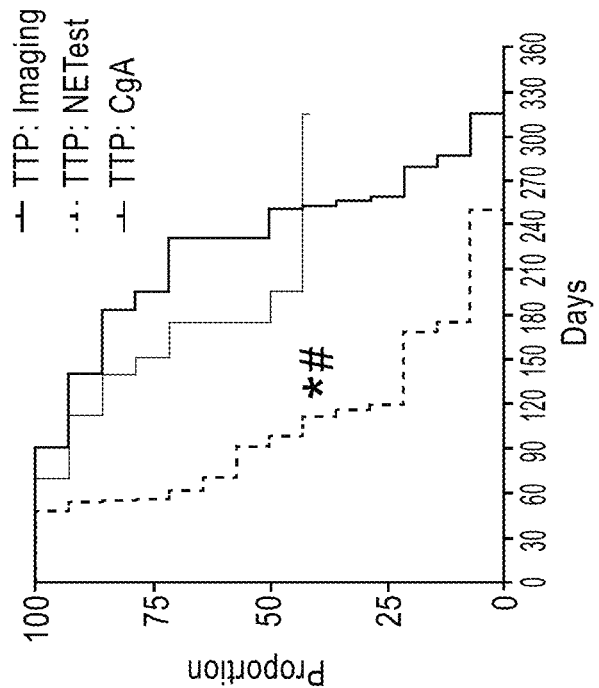
FIGS. 36A-36B are graphs that demonstrate the time point when either the NETest was elevated (>80%) or CgA was abnormal prior to the development of image positive disease recurrence as well as the times that these events occurred prior to image-positive disease recurrence.
Figure 36A:
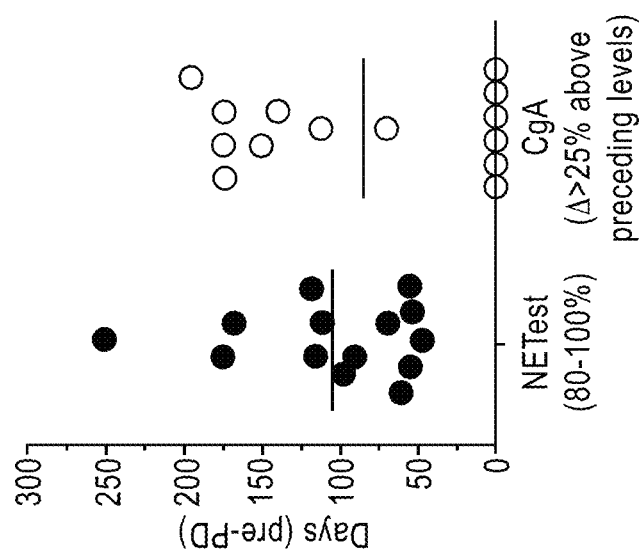

With reference to FIG. 36B, the elevation in NETest (80-100% score) occurred at a significantly earlier time (94.5 days) than image-identifiable disease progression (241 days) in the 14 patients (*p<0.0001, $Chi^2=19$). A similar analysis for CgA identified that this was not different to image-based assessment (FIG. 36B, 185.5 days vs. 241 days). CgA alterations occurred significantly later than the NETest (p=0.002, $Chi^2=13.6$).

Utility of NETEST and Gene Expression for the Prediction of Disease Recurrence—Utility of NETEST To evaluate the utility of the NETest disease recurrence, the relationship between the NETest and clinically defined outcomes (per RECIST criteria) was evaluated in a long-term prospective study. Samples were collected both pre-therapy as well as at intervals up to five years in thirty four patients. Imaging was available to stage and categorize disease patterns pre- and during therapy (up to 65 months follow-up).

Figure 37A:
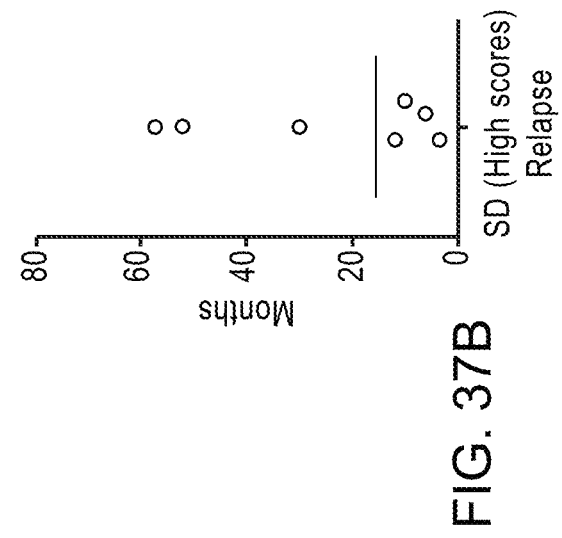
FIGS. 37A-37D are graphs that demonstrate the NETest scores prior to long-term follow up (FIG. 37A), and the times to relapse in patients with elevated scores (FIGS. 37B, 37D) or disease-free time (FIG. 37C).
Figure 37B:
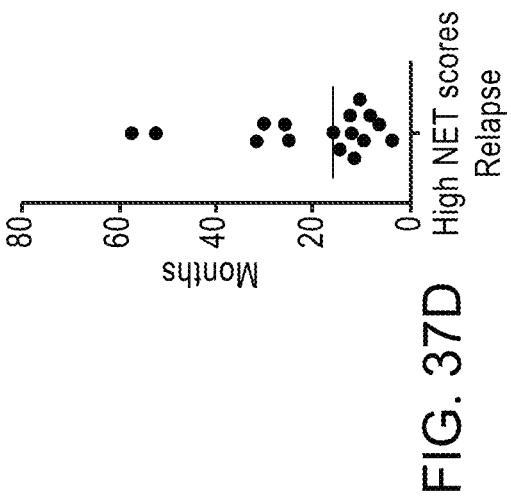
Figure 37C:
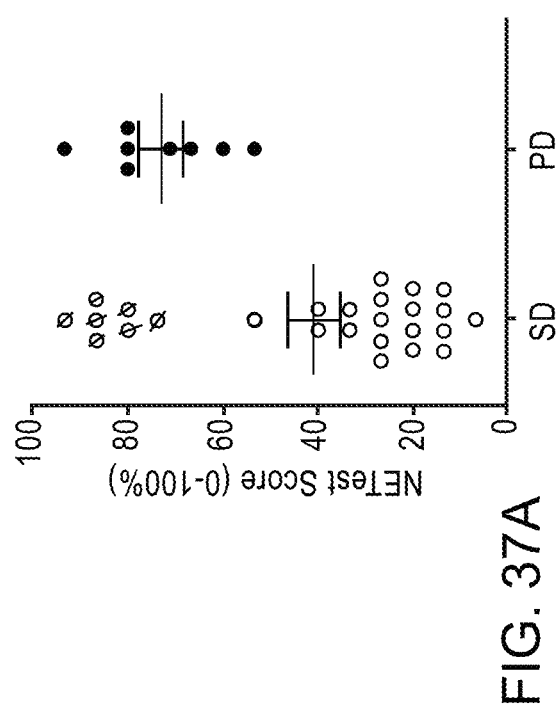

In this prospective sample set, the initial NETest scores were significantly elevated in the PD patients (median: 75%, range 53-94%) compared to the SD patients (median: 26%, range 7-94%; p=0.01) (FIG. 37A). Eight SD patients had levels >40%. Of these 7 developed disease recurrence in a median of 12.2 months (range 3.6-57.7; FIG. 37B). With reference to FIG. 37C, seven of the initial SD patients (with low NETest scores) did not develop recurrent disease. The median follow-up time was 58 months (range: 32-64).

Figure 37D:
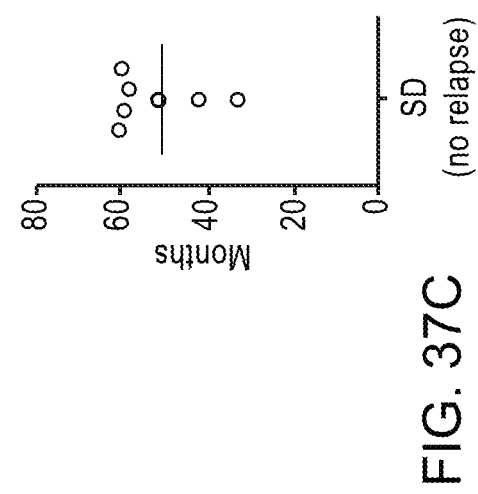
Figure 39D:
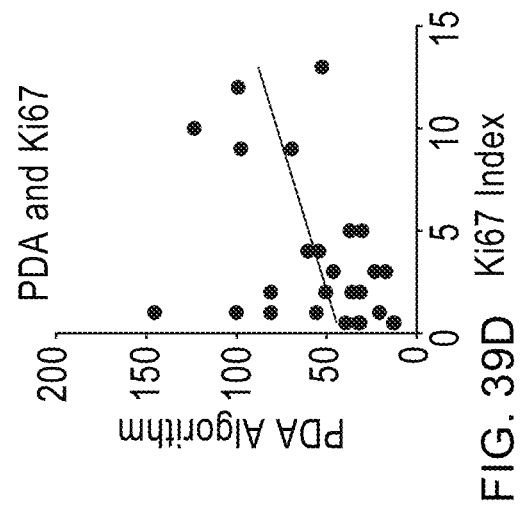
FIGS. 39A-39F are graphs showing the correlations (linear regression) between gene clusters or algorithms, (FIG. 39A) SSTRome and Ki67, (FIG. 39B) TDA and Ki67, (FIG. 39C) Proliferome and Ki67, (FIG. 39D) PDA and Ki67, (FIG. 39E) IDA and Ki67, and (FIG. 39F) PDA and Ki67, each versus the Ki-67 index.
Figure 39F:
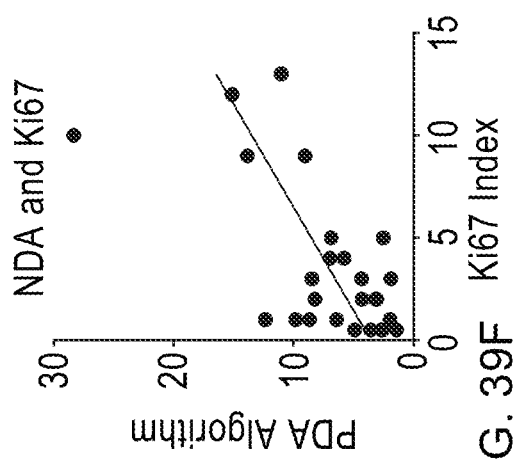
Figure 39C:
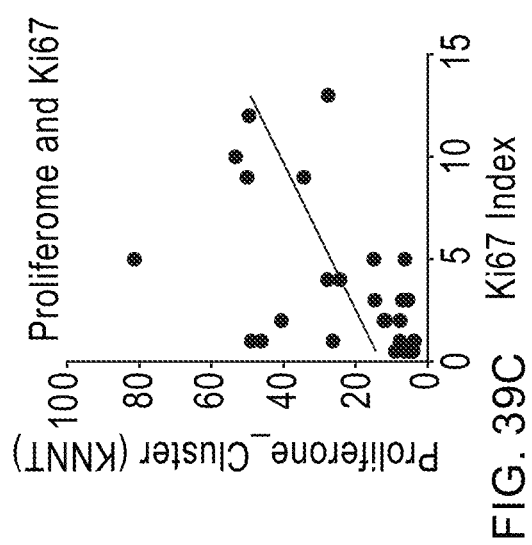
Figure 39E:
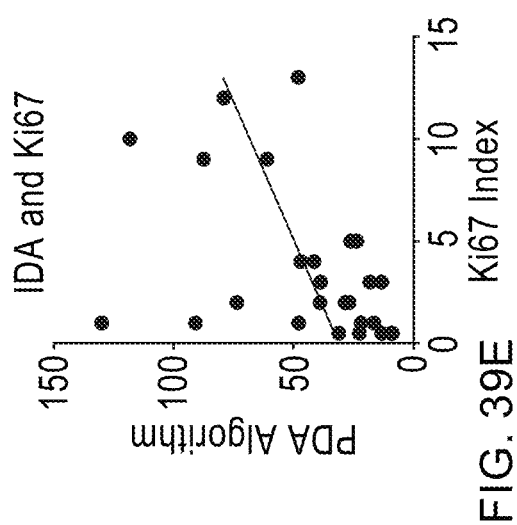
Figure 39A:
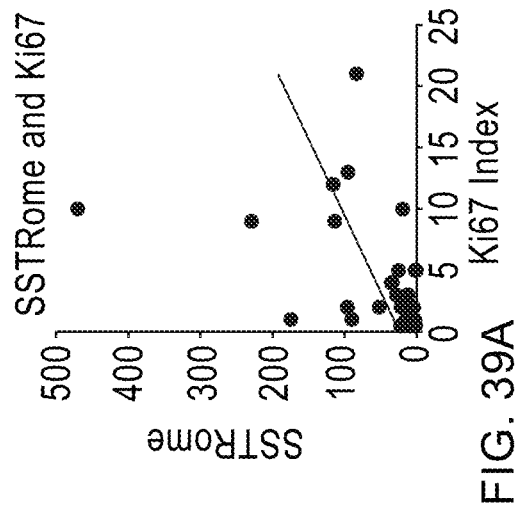
Figure 39B:
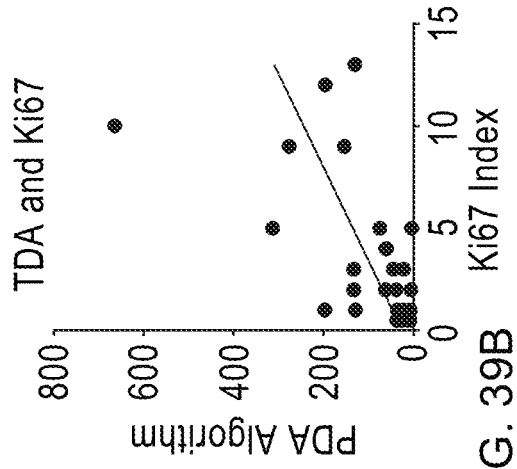

Sixteen events of progressive disease were identified over the time course. Each was associated with elevated NETest (scores >80%). With reference to FIG. 37D, the median time to progression for patients with elevated scores was 13.4 months (range: 3.6-57).

Overall, 23/24 events where the NETest was elevated was associated with development of disease recurrence in median ~13 months. Seven of seven with consistently low scores were disease free (up to 5 years). The accuracy of the test was 97%.

Utility of NET Genes as Surrogate Measure of Tumor Proliferation and Imaging—The utility of NETest genes as well as clusters of genes to function as surrogate markers of histopathological and imaging parameters was evaluated. A particular focus was placed on the Ki-67 index (a marker of tumor proliferation) and on somatostatin-based imaging e.g., $^{68}$Ga-PET. This was undertaken to demonstrate that the NETest and elements thereof could have clinical utility as adjuncts for standard clinical measures. As an example, Ki-67 measurements are tissue based and therefore are invasive. Demonstrating a blood-derived correlate would provide a real-time measure of tumor growth without the need for a biopsy.

These analyses were conducted in two separate datasets: Dataset 1 (n=28) and Dataset 2 (n=22). Dataset 1 included patients who were collected for therapeutic intervention, namely peptide receptor radionucleotide therapy (PRRT). Dataset 2 included patients who exhibited stable disease and were undergoing routine follow-up.

A Surrogate for the Ki-67 Index: Multivariate regression analysis did not identify any significant correlation between individual gene expression and the Ki-67 index (a marker of tumor proliferation) in either of the two groups. With reference to FIGS. 38A and 38B, examination of somatostatin receptor expression identified significant correlations (R=0.9, p=2×10$^{-8}$) with Ki67 in each of the tumor groups.

An examination of all genes in the NETest identified significantly higher correlations with Ki-67 (R=0.93-98, p=10$^{-9}$-10$^{-13}$, FIGS. 38C-38E). The single most informative gene was SSTR4 (FIG. 38D-38F). These data demonstrate firstly, that the NETest as a whole can be used as a liquid biopsy to determine the proliferative index of the tumor i.e., provides a surrogate marker for a tissue-based histopathological measurement. Secondly, expression of circulating somatostatin receptor genes can also be used as a measure of tumor proliferation.

Proliferome+SSTRome algorithm is also referred to as Progressive Diagnostic V; the highly relevant genes (KRAS, SSTR4, and VPS13C) algorithm is also referred to as Progressive Diagnostic VI; the highly relevant genes+ SSTRome algorithm is also referred to as Progressive Diagnostic VII.

With reference to FIGS. 39A-39F, correlations (linear regression) between gene clusters (SSTRome and proliferome) or each of the algorithms and the Ki-67 index, are shown. Examination of individual gene clusters confirmed that the SSTRome and Proliferome correlated with the Ki-67 index (R=0.16-0.25, p<0.05, FIGS. 39A, 39C). Analysis of the algorithms identified that the NDA and TDA algorithms were highly correlated with the Ki-67 index (R=0.34-0.42, p<0.002, FIGS. 39B, 39F) while the PDA and IDA were less well-correlated (R=0.14-0.17, p=0.06, FIGS. 39D, 39E). These results demonstrate that gene clusters and algorithms including biologically relevant tumor information e.g., SSTRome can be utilized as a measure of tumor tissue proliferation.

Figure 40B:
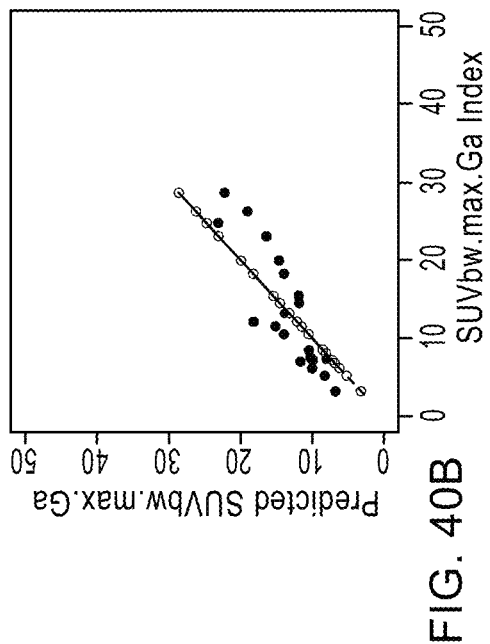
FIGS. 40A-40D are graphs modeling predicted SUVmax (tumor uptake–a measure of receptor density/target availability) for SSTRome (Group I.
Figure 40D:
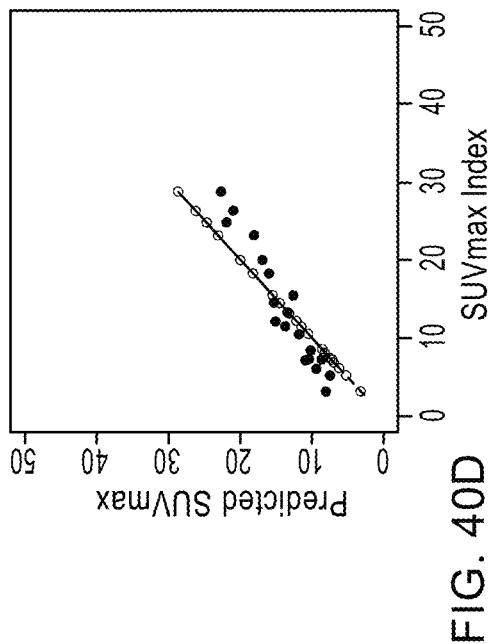
Figure 40A:
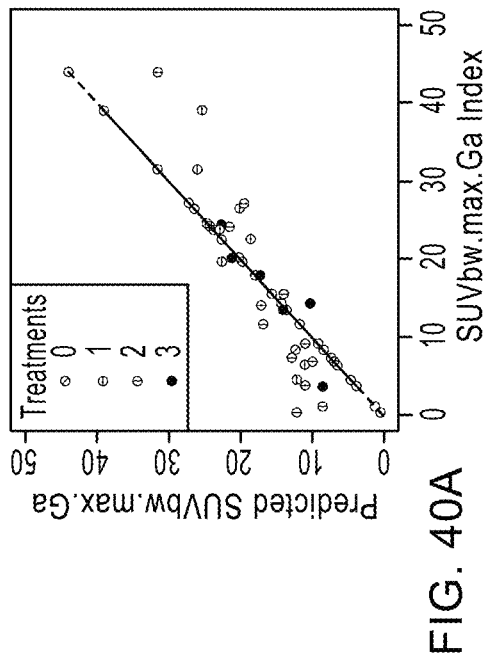
Figure 40C:
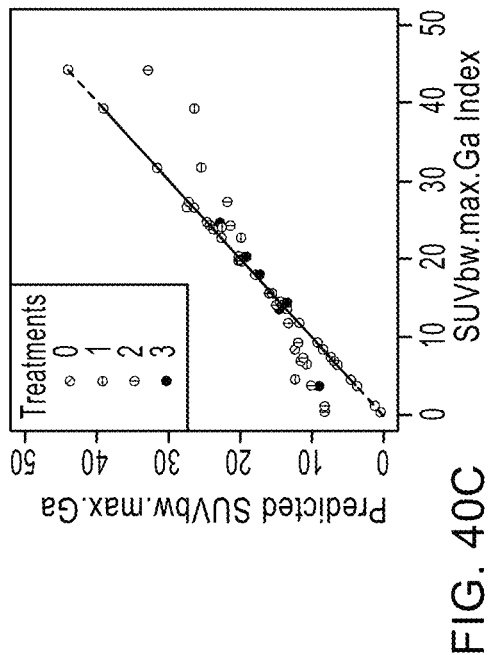

Relationship with Somatostatin-Based Imaging: Next was examined whether genes in the test correlated with two variables from somatostatin-based imaging, the SUVbmax (tumor uptake—a measure of receptor density/target availability) and the MTV (molecular tumor volume—a measure of the tumor burden). Multivariate regression analysis did not identify any single gene to correlate with the SUVmax. However, both the SSTRome as well as the NETest genes as a group were well correlated with the SUVmax. Correlations in both groups ranged between R=0.88-0.94 (p<10$^{-7}$) for the SSTRome (FIGS. 40A-40B) and R=0.97-0.98, p<10$^{-13}$ for the NET gene set (FIGS. 40C-40D).

Multivariate regression analysis identified ZFHX3 as a marker of MTV in Group 1 (R=0.98, FIG. 41A) while TPH1 was correlated with MTV in Group 2 (R=0.76, FIG. 41B).

Similarly to the SUVmax, both the SSTRome as well as the NETest genes as a group were well correlated with the MTV. Correlations in both groups ranged between R=0.72-0.77 (p<10$^{-4}$) for the SSTRome (FIGS. 41C-41E) and R=0.91-0.95, p<10$^{-12}$ for the NET gene set (FIGS. 41D-41F).

These data demonstrate that genes in the NETest correlate and can be used to estimate both the target availability for somatostatin analog-based therapies as well as provide a measure of the tumor burden. Both these aspects are critical for directing therapy as well as measuring the efficacy of therapy.

ZFHX3 as a Marker for Disease Assessment: The identification of ZFHX3 as the best marker for MTV, as shown in FIG. 41A, suggests that expression of this gene may have clinical utility as a measure of tumor burden and changes thereof. ZFHX3 is a zinc finger protein involved in the regulation of neuronal differentiation through the control of cell cycle arrest. Loss of ZFHX3 expression with a subsequent loss of cell cycle arrest therefore is related to tumor proliferation and the development of new lesions and/or progression of disease.

It was examined whether measurements of ZFHX3 may provide a marker of new growth/progression in NETs and if that alteration in ZFHX3 may reflect response to therapy or therapy failure (progression). Expression of this gene was initially assessed in patients who had evidence of new lesions.

Figure 42C:
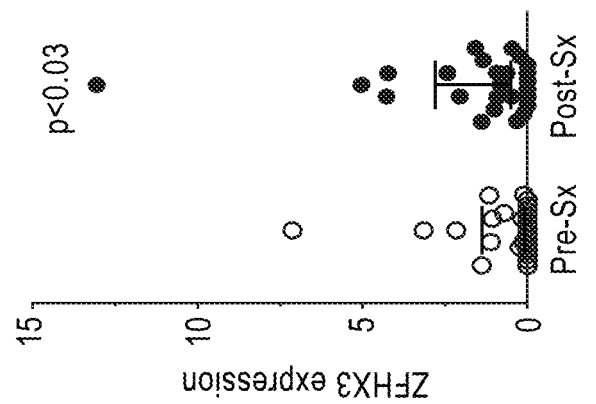
FIGS. 42A-42C are graphs showing ZFHX3 expression in patients identified with (FIG. 42A) new lesions by imaging, with (FIG. 42B) progressive disease by RECIST, and (FIG. 42C) following surgery.
Figure 42B:
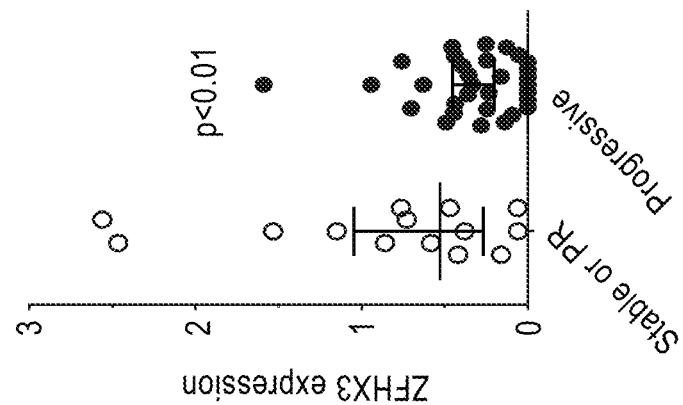
Figure 42A:
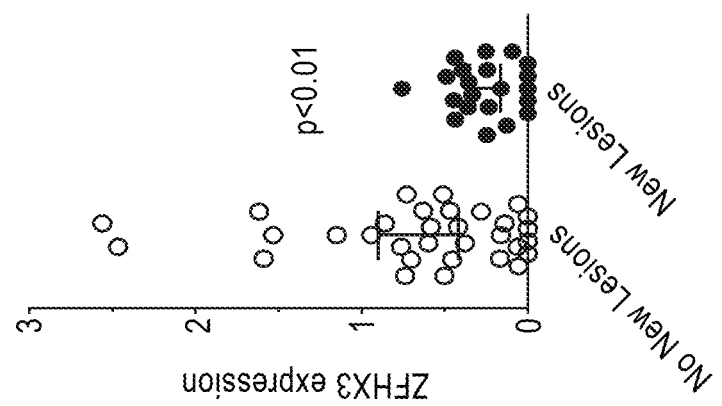

With reference to FIG. 42A, patients who had developed new lesions (identified by imaging) expressed significantly decreased ZFHX3. With reference to FIG. 42B, those patients that were determined as SD also have significantly higher levels than those who were progressive. Moreover, with reference to FIG. 42C, expression of the gene was increased following surgery.

Figure 43B:
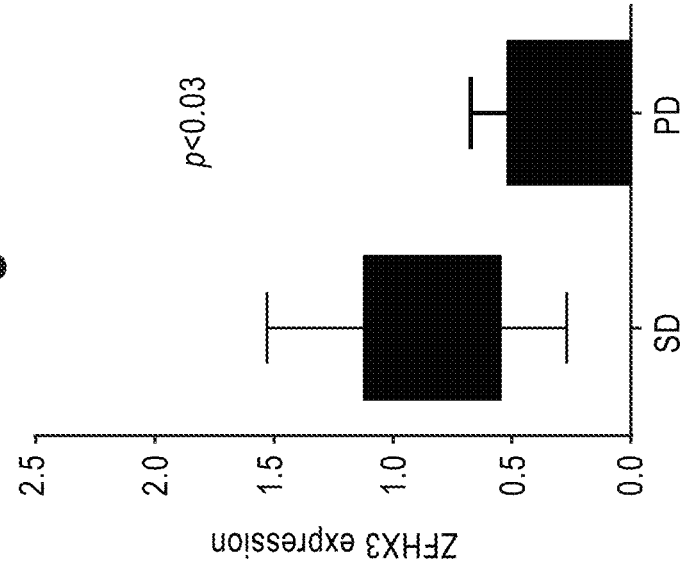
FIGS. 43A-43B are graphs showing ZFHX3 expression in (FIG. 43A) patients who remain in a stable disease state of GEP-NEN versus (FIG. 43B) those who develop a progressive disease state of GEP-NEN.
Figure 43A:
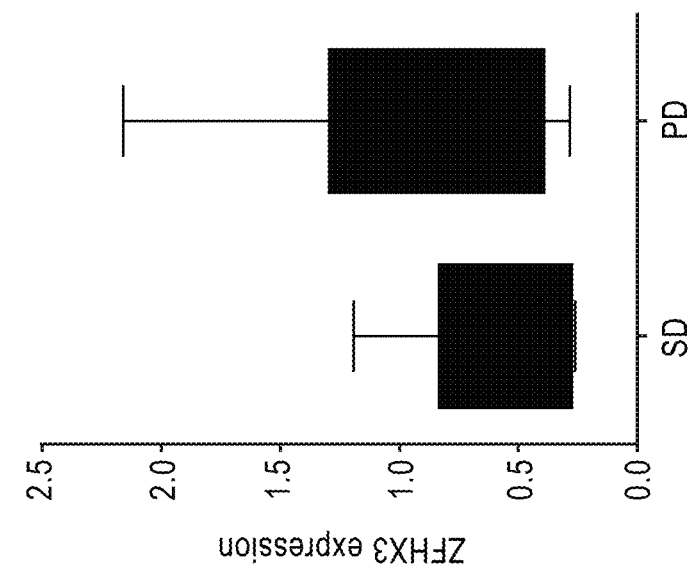

With reference to FIGS. 43A-43B, long-term follow-up (>3 years) in a group identified that patients who remained stable exhibited no changes in ZFHX3 expression over this time period, while patients who developed progressive disease had significantly lower expression levels.

These data demonstrate that ZFHX3 expression correlates with the development of new lesions and a decrease in expression can be used to define disease progression.

Utility of NETEST and Gene Expression for the Prediction of Therapeutic Efficacy—To further evaluate the utility of the NETest in therapy, the relationship between PRRT and clinically defined (per RECIST criteria) outcomes were evaluated. Samples were collected both pre-therapy as well as at follow-up in fifty-four patients. Imaging was available to stage and categorize disease patterns pre- and post-therapy (at 3 and 6 month follow-up).

Figure 44C:
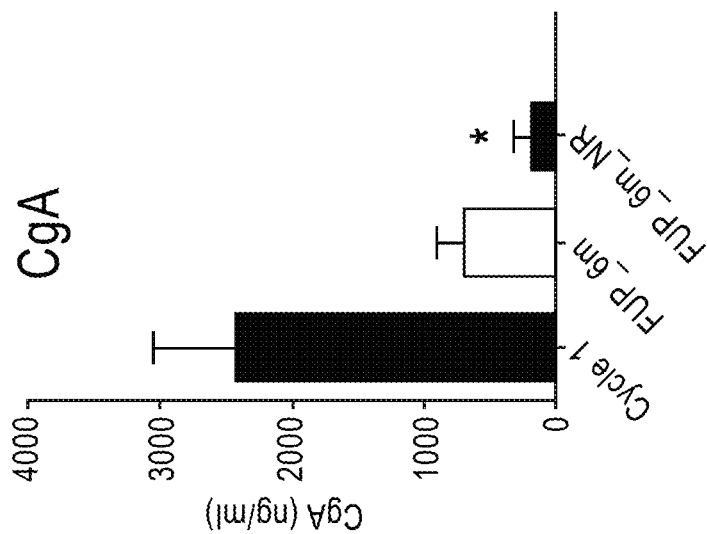
FIGS. 44A-44C are graphs representing (FIG. 44A) the effectiveness of peptide receptor radionucleotide therapy (PRRT), (FIG. 44B) changes in NETest Score versus clinical status at 6M Follow-up (FuP) in responders (R) and non-responders (NR)
Figure 44B:
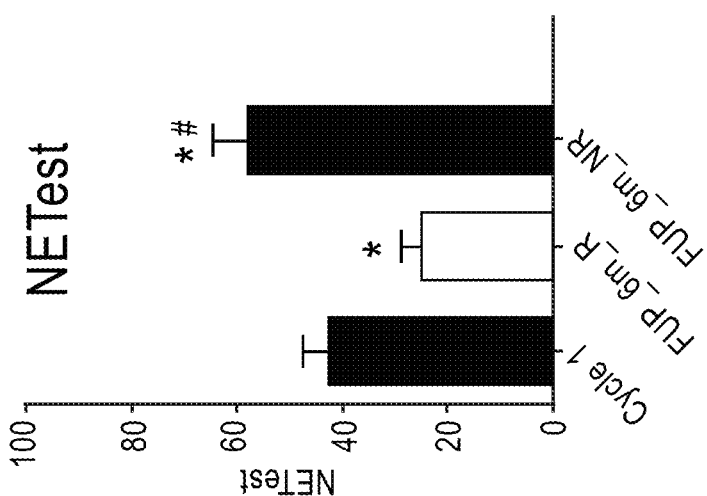
Figure 44A:
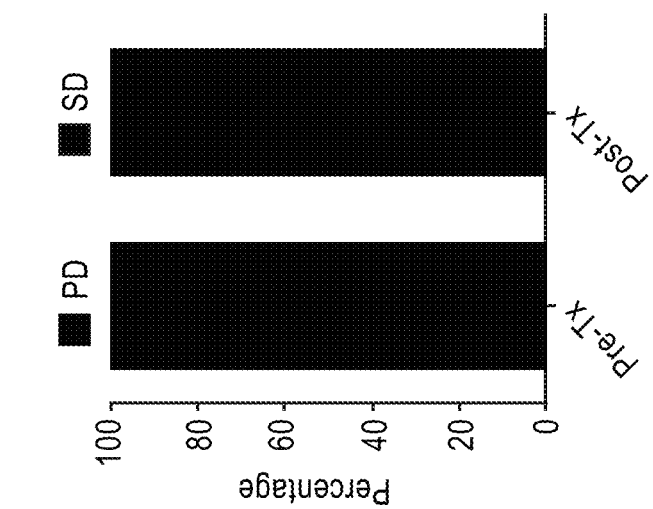
Figure 45:
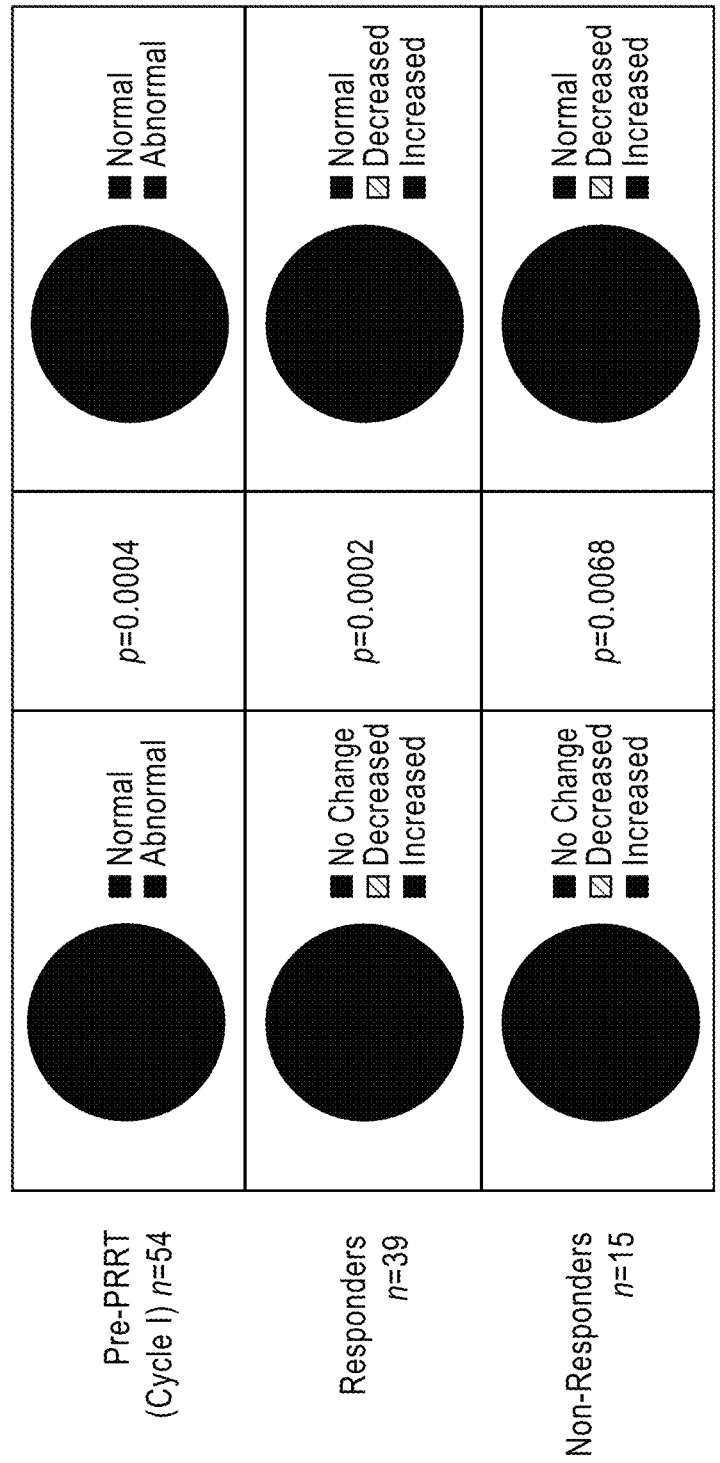
FIG. 45 are graphs showing concordance between the NETest in responders and non-responders prior to and after therapy and in addition the comparison to CgA.

In this prospective sample set, radiotherapy significantly resulted in a reduction in the number of patients with progressive disease (FIG. 44A). Patients who did not respond to therapy i.e., categorized as progressive disease at the 6 month follow-up period exhibited an increase in the NETest score. The score was significantly reduced in patients with SD at this time point (FIG. 44B). No significant alterations were noted for CgA (FIG. 44C). Alterations in NETest paralleled changes in therapeutic responses (FIG. 45). The metrics for biomarkers and outcome identified that the NETest had an accuracy of 89%, sensitivity 75%, specificity 100%, PPV 100% and NPV 83% (FIG. 46A). With reference to FIG. 46B, CgA had an accuracy of 24%, sensitivity 17%, specificity 40%, PPV 40% and NPV 17%. The NETest significantly outperformed CgA (Chi-square=27.4; p=1.2×10⁻⁷).

Pre-treatment NETest scores as well as grading were available and used to identify whether a combination of gene expression and clinical parameters were predictive of outcome, i.e., response to therapy.

Figure 47A:
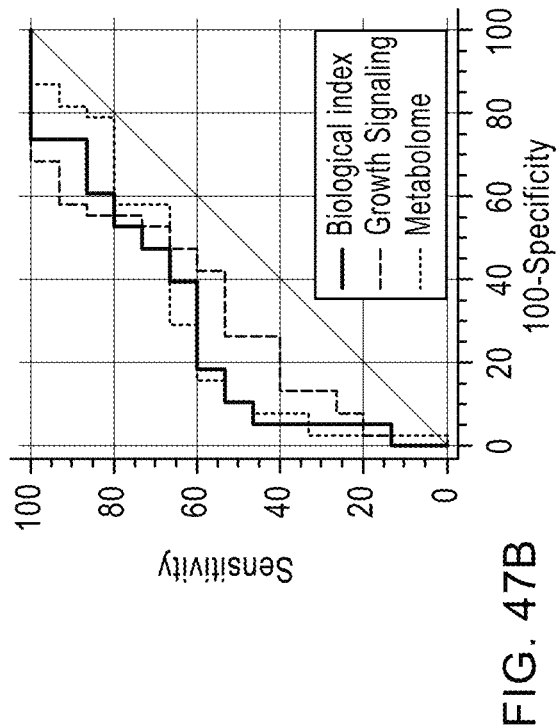
FIG. 47A-47D shows expression of two subsets of NETest genes, the signalome and metabolome in blood samples prior to therapy and the differences between responders (R) and non-responders (NR), the predictive utility of each as well as when combined into a biological index (FIG. 47B), the utility for predicting treatment response alone (Quotient) or as a combination with grade (Combination) (FIG. 47C) and the metrics of the combination for predicting the outcome of PRRT therapy (FIG. 47D).
Figure 47B:
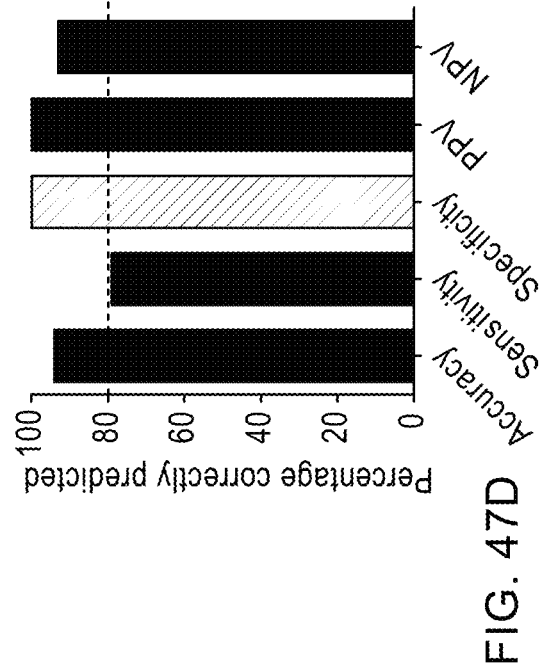

With reference to FIG. 47A, a subset of NETest gene expression levels were significantly different between responders and non-responders prior to therapy. These included genes linked to growth factor signaling (GF signalome: ARAF1, BRAF, KRAS and RAF1) as well as genes linked to metabolism (including A TP6V1H, OAZ2, PANK2, PLD3). Specifically, PRRT-responders exhibited significantly elevated growth factor signaling (9.4±1.3 vs. 5.3±0.7, p=0.05) and significantly elevated metabolomic gene expression (4.37 vs. 2.3±0.6, p=0.0³) prior to PRRT. An integration of the two "clusters" (GF signalome+metabolome) into a "Biological Index" through summation of gene expression enabled prediction of future PRRT-responders from non-responders. A cut-off of 5.9 (normalized gene expression) exhibited >85% specificity for predicting response (>5.9 predicted PRRT responders) and resulted in an AUC of 0.74±0.08 (z-statistic=2.915, p=0.0036) (FIG. 47B).

Figure 47C:
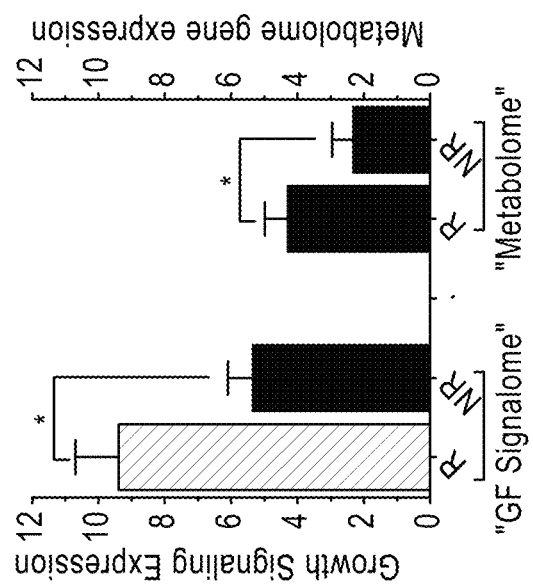

No clinical parameters were predictive of PRRT response except tumor grade. Low grade tumors responded (77%) to therapy while ~50% of high grade lesions were associated with responses. Grading alone was only 65% accurate (p=0.1). In contrast a "Prediction Quotient" which comprised the combination of the Biological Index ("GF signalome"+"metabolome") and the tumor grade was significantly (92%) more accurate. The Prediction Quotient had a significantly better AUC (0.90±0.07) than histological grade alone for predicting treatment response (AUC=0.66, difference between areas 0.23, z-statistic 2.25, p=0.024) (FIG. 47C).

Figure 47D:
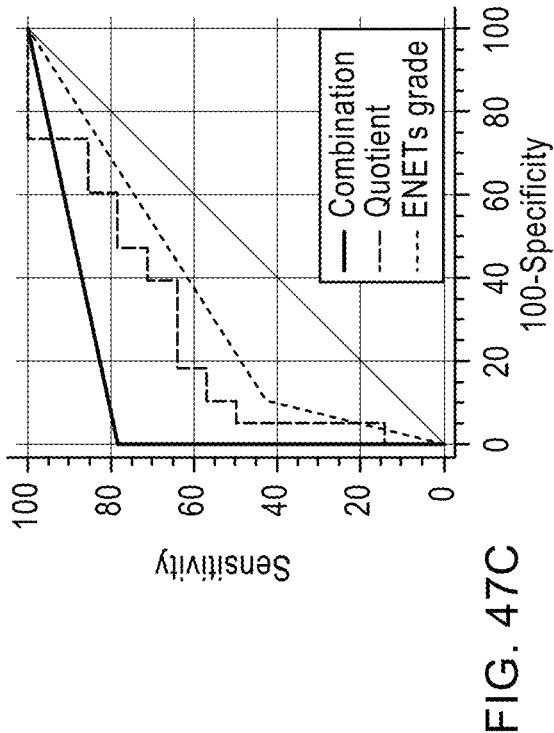

The Prediction Quotient was also clinically useful. Patients could be segregated into Low Grade/High Ome and High Grade/Low Ome groups. The latter had a significantly lower PFS (17 months) than the low grade/high Ome group (PFS not reached, Log-rank: 26.8; p<0.0001: FIG. 47D). The Hazard Ratio was 53.3.

These results demonstrate that alterations in score correlate with treatment responses and that circulating NET transcript measurements prior to therapy are predictive of outcome to PRRT.

What is claimed is:

1. A method for treating a relapsing or reoccurring progressive gastroenteropancreatic neuroendocrine neoplasm (GEP-NEN) in a human subject identified as having an intermediate or high level of risk of developing a relapsing or reoccurring progressive GEP-NEN and that has been administered a first treatment, comprising:
    determining the expression levels of at least 23 biomarkers from a test sample from the human subject by performing reverse transcription polymerase chain reaction (RT-PCR) with a plurality of probes or primers specific to detect the expression of the at least 23 biomarkers, wherein the at least 23 biomarkers comprise APLP2, ARAF, CD59, CTGF, FZD7, KRAS, MKI67/KI67, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, ZFHX3, and ALG9, wherein the test sample is blood, serum, plasma, or neoplastic tissue;
    normalizing the expression levels of APLP2, ARAF, CD59, CTGF, FZD7, KRAS, MKI67/KI67, MORF4L2, NAP1L1, NOL3, PNMA2, RAF1, RSF1, SLC18A2/VMAT2, SPATA7, SSTR1, SSTR3, SSTR4, SSTR5, TPH1, TRMT112, and ZFHX3 to the expression level of ALG9 to obtain normalized expression levels;
    classifying the test sample with respect to the presence or development of a GEP-NEN using the normalized expression levels in a classification system, wherein the classification system is a machine learning system that comprises four different algorithms: Support Vector Machine, Linear Discrimination Analysis, K-Nearest Neighbor, and Naïve Bayes;
    assigning a score based on a result of each of the four different algorithms;
    comparing the score with a predetermined cutoff value;
    determining the presence of a GEP-NEN in the subject by determining that the score is equal to or greater than the predetermined cutoff value, wherein the predetermined cutoff value is 2 on a MAARC-NET scoring system scale of 0-8;
    identifying an intermediate level of risk or high level of risk for the human subject to develop a relapsing or reoccurring progressive GEP-NEN comprising
        (a) identifying an intermediate level of risk for developing a relapsing or reoccurring progressive GEP-NEN by determining that the score is equal to or greater than a predetermined cutoff value of 5 and less than a predetermined cutoff value of 7 on the MAARC-NET scoring system scale of 0-8; or
        (b) identifying a high level of risk for developing a relapsing or reoccurring progressive GEP-NEN when determining that the score is equal to or greater than a predetermined cutoff value of 7 on the MAARC-NET scoring system scale of 0-8; and
    administering a second treatment to the subject identified as having an intermediate level or high level of risk for developing a relapsing or reoccurring progressive GEP-NEN.

2. The method of claim 1, wherein the first treatment comprises a first surgery and the second treatment comprises an at least second surgery, drug therapy or any combination thereof.

3. The method of claim 2, wherein the second treatment comprises drug therapy.

4. The method of claim 3, wherein the drug therapy comprises somatostatin analog treatment, peptide receptor radionuclide therapy (PRRT) or any combination thereof.

5. The method of claim 1, wherein the first treatment comprises a first drug therapy and the second treatment comprises surgery, an at least second drug therapy or any combination thereof.

6. The method of claim 5, wherein the second treatment comprises an at least second drug therapy.

7. The method of claim 6, wherein the first drug therapy comprises a first amount of somatostatin analog treatment.

8. The method of claim 7, wherein the second drug therapy comprises a second amount of somatostatin analog treatment.

9. The method of claim 7, wherein the second drug therapy comprises PRRT.

10. The method of claim 6, wherein the first drug therapy comprises a first amount of PRRT.

11. The method of claim 10, wherein the second drug therapy comprises a second amount of PRRT, wherein the second amount of PRRT is greater than the first amount of PRRT.

12. The method of claim 10, wherein the second drug therapy comprises somatostatin analog treatment.

13. The method of claim 1, wherein the biomarkers are RNA or cDNA.

14. The method of claim 13, wherein when the biomarkers are RNA, the RNA is reverse transcribed to produce cDNA, and the produced cDNA expression level is detected.

15. The method of claim 13, wherein the biomarkers are detected by forming a complex between the RNA or cDNA and a labeled nucleic acid probe or primer.

16. The method of claim 15, wherein the label is a fluorescent label.

17. The method of claim 15, wherein the complex between the RNA or cDNA and the labeled nucleic acid probe or primer is a hybridization complex.

18. The method of claim 1, wherein the expression levels of the biomarkers are detected by forming a complex between the biomarkers and labeled probes or primers.

* * * * *